United States Patent
Delacote et al.

(10) Patent No.: US 9,044,492 B2
(45) Date of Patent: Jun. 2, 2015

(54) METHOD FOR MODULATING THE EFFICIENCY OF DOUBLE-STRAND BREAK-INDUCED MUTAGENESIS

(75) Inventors: Fabien Delacote, Paris (FR); Philippe Duchateau, Livry Gargan (FR); Christophe Perez-Michaut, Paris (FR)

(73) Assignee: CELLECTIS SA, Romainville (FR)

( * ) Notice: Subject to any disclaimer, the term of this patent is extended or adjusted under 35 U.S.C. 154(b) by 407 days.

(21) Appl. No.: 13/367,098

(22) Filed: Feb. 6, 2012

(65) Prior Publication Data

US 2012/0244131 A1    Sep. 27, 2012

Related U.S. Application Data

(60) Provisional application No. 61/439,739, filed on Feb. 4, 2011.

(51) Int. Cl.
| | | |
|---|---|---|
| *C12Q 1/68* | (2006.01) | |
| *A61K 31/7088* | (2006.01) | |
| *C12N 15/10* | (2006.01) | |

(52) U.S. Cl.
CPC .......... *A61K 31/7088* (2013.01); *C12N 15/102* (2013.01); *C12N 15/1086* (2013.01)

(58) Field of Classification Search
USPC .................. 435/6.1, 91.1, 325, 375; 536/24.5
See application file for complete search history.

(56) References Cited

U.S. PATENT DOCUMENTS

| | | |
|---|---|---|
| 7,842,489 B2 | 11/2010 | Arnould et al. |
| 7,897,372 B2 | 3/2011 | Duchateau et al. |
| 8,206,965 B2 | 6/2012 | Arnould et al. |
| 8,211,685 B2 | 7/2012 | Epinat et al. |
| 8,426,177 B2 | 4/2013 | Gouble |
| 8,476,072 B2 | 7/2013 | Cabaniols et al. |
| 8,530,214 B2 | 9/2013 | Arnould et al. |
| 2006/0078552 A1 | 4/2006 | Arnould et al. |
| 2006/0153826 A1 | 7/2006 | Arnould et al. |
| 2006/0206949 A1 | 9/2006 | Arnould et al. |
| 2009/0220476 A1 | 9/2009 | Paques |
| 2009/0222937 A1 | 9/2009 | Arnould et al. |
| 2009/0271881 A1 | 10/2009 | Arnould et al. |
| 2010/0086533 A1 | 4/2010 | Montoya et al. |
| 2010/0146651 A1 | 6/2010 | Smith et al. |
| 2010/0151556 A1 | 6/2010 | Arnould et al. |
| 2010/0167357 A1 | 7/2010 | Fajardo Sanchez et al. |
| 2010/0203031 A1 | 8/2010 | Grizot et al. |
| 2010/0229252 A1 | 9/2010 | Perez-Michaut |

(Continued)

*Primary Examiner* — Terra C Gibbs
(74) *Attorney, Agent, or Firm* — Oblon, McClelland, Maier & Neustadt, L.L.P.

(57) ABSTRACT

A method for modulating double-strand break-induced mutagenesis at a genomic locus of interest in a cell, thereby giving new tools for genome engineering, including therapeutic applications and cell line engineering. A method for modulating double-strand break-induced mutagenesis, concerns the identification of effectors that modulate double-strand break-induced mutagenesis by use of interfering agents; these agents are capable of modulating double-strand break-induced mutagenesis through their respective direct or indirect actions on said effectors. Methods of using these effectors, interfering agents and derivatives, respectively, by introducing them into a cell in order to modulate and more particularly to increase double-strand break-induced mutagenesis. Specific derivatives of identified effectors and interfering agents, vectors encoding them, compositions and kits comprising such derivatives for modulating or increasing double-strand break-induced mutagenesis.

9 Claims, 12 Drawing Sheets

(56) References Cited

U.S. PATENT DOCUMENTS

| | | |
|---|---|---|
| 2011/0072527 A1 | 3/2011 | Duchateau et al. |
| 2011/0091441 A1 | 4/2011 | Gouble et al. |
| 2011/0151539 A1 | 6/2011 | Arnould et al. |
| 2011/0158974 A1 | 6/2011 | Duchateau et al. |
| 2011/0173710 A1 | 7/2011 | Grizot et al. |
| 2011/0179506 A1 | 7/2011 | Grizot |
| 2011/0179507 A1 | 7/2011 | Paques |
| 2011/0191870 A1 | 8/2011 | Paques |
| 2011/0207199 A1 | 8/2011 | Paques et al. |
| 2011/0225664 A1 | 9/2011 | Smith |
| 2011/0239319 A1 | 9/2011 | Danos et al. |
| 2012/0159659 A1 | 6/2012 | Arnould et al. |
| 2012/0171191 A1 | 7/2012 | Choulika et al. |
| 2012/0258537 A1 | 10/2012 | Duchateau et al. |
| 2012/0260356 A1 | 10/2012 | Choulika et al. |
| 2012/0272348 A1 | 10/2012 | Danos et al. |
| 2012/0288941 A1 | 11/2012 | Arnould et al. |
| 2012/0288942 A1 | 11/2012 | Arnould et al. |
| 2012/0288943 A1 | 11/2012 | Arnould et al. |
| 2012/0301456 A1 | 11/2012 | Tremblay et al. |
| 2012/0304321 A1 | 11/2012 | Arnould et al. |
| 2012/0317664 A1 | 12/2012 | Arnould et al. |
| 2012/0322689 A1 | 12/2012 | Epinat et al. |
| 2012/0331574 A1 | 12/2012 | Arnould et al. |
| 2013/0059387 A1 | 3/2013 | Smith et al. |
| 2013/0061341 A1 | 3/2013 | Arnould et al. |
| 2013/0067607 A1 | 3/2013 | Arnould et al. |
| 2013/0203840 A1 | 8/2013 | Arnould et al. |
| 2013/0209437 A1 | 8/2013 | Paques |
| 2013/0227715 A1 | 8/2013 | Danos et al. |
| 2013/0236946 A1 | 9/2013 | Gouble |
| 2013/0326644 A1 | 12/2013 | Paques |
| 2014/0004608 A1 | 1/2014 | Cabaniols et al. |
| 2014/0017731 A1 | 1/2014 | Gouble et al. |

Figure 7
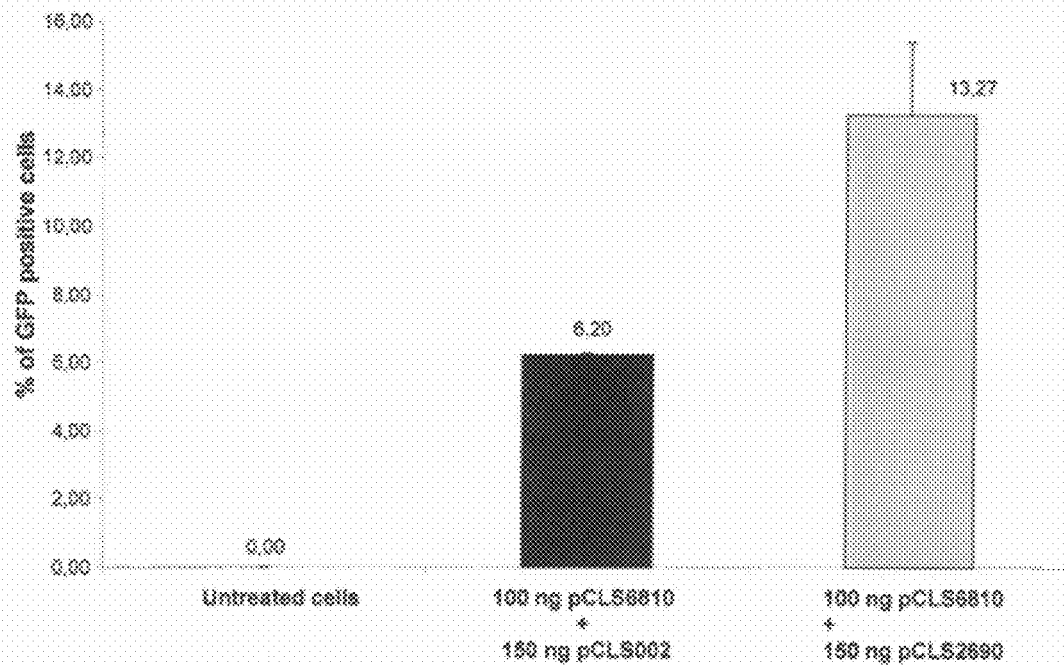
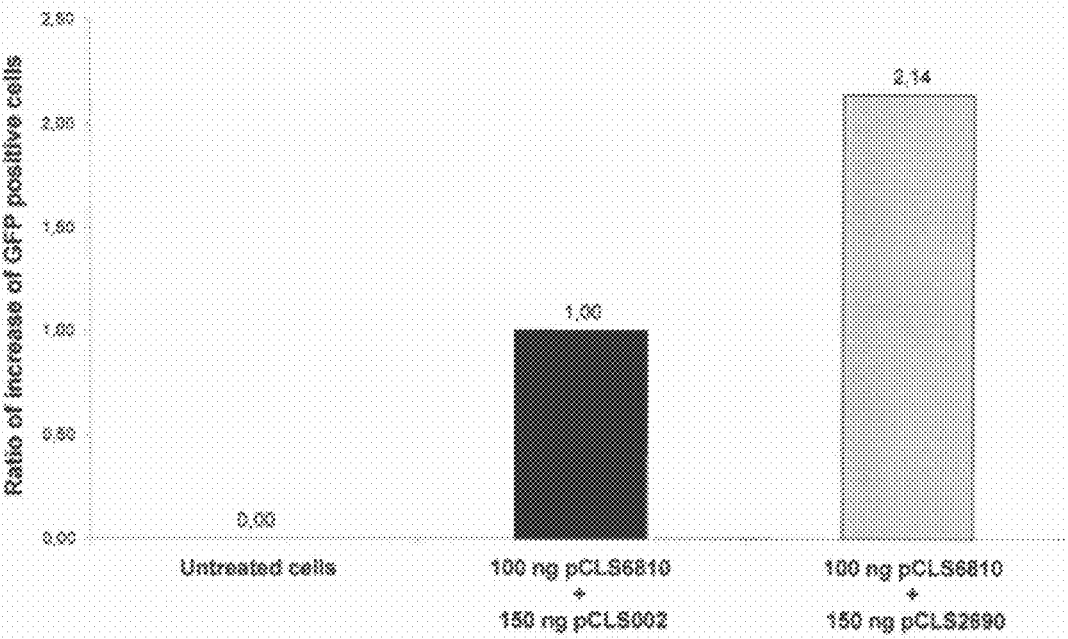

SEQUENCE LISTING

```
<160> NUMBER OF SEQ ID NOS: 1058

<210> SEQ ID NO 1
<211> LENGTH: 12467
<212> TYPE: DNA
<213> ORGANISM: Artificial
<220> FEATURE:
<223> OTHER INFORMATION: pCLS6883

<400> SEQUENCE: 1
atggcagcct atccttatga cgttcctgat tacgctggat ttacctgccc cagggtgaga      60
aagtccaagg aggctccgga tccggcggtt ctggatccgg cggttctggt tccgcagccg     120
aagatgccaa aaacattaag aagggcccag cgccattcta cccactcgaa gacgggaccg     180
ccggcgagca gctgcacaaa gccatgaagc gctacgccct ggtgcccggc accatcgcct     240
ttaccgacgc acatatcgag gtggacatta cctacgccga gtacttcgag atgagcgttc     300
```

```
ggctggcaga agctatgaag cgctatgggc tgaatacaaa ccatcggatc gtggtgtgca      360
gcgagaatag cttgcagttc ttcatgcccg tgttgggtgc cctgttcatc ggtgtggctg      420
tggccccagc taacgacatc tacaacgagc gcgagctgct gaacagcatg ggcatcagcc      480
agcccaccgt cgtattcgtg agcaagaaag ggctgcaaaa gatcctcaac gtgcaaaaga      540
agctaccgat catacaaaag atcatcatca tggatagcaa gaccgactac cagggcttcc      600
aaagcatgta caccttcgtg acttcccatt gccacccggg cttcaacgag tacgacttcg      660
tgcccgagag cttcgaccgg gacaaaacca tcgccctgat catgaacagt agtggcagta      720
ccggattgcc caagggcgta gccctaccgc accgcaccgc ttgtgtccga ttcagtcatg      780
cccgcgaccc catcttcggc aaccagatca tccccgacac cgctatcctc agcgtggtgc      840
catttcacca cggcttcggc atgttcacca cgctgggcta cttgatctgc ggctttcggg      900
tcgtgctcat gtaccgcttc gaggaggagc tattcttgcg cagcttgcaa gactataaga      960
ttcaatctgc cctgctggtg cccacactat ttagcttctt cgctaagagc actctcatcg     1020
acaagtacga cctaagcaac ttgcacgaga tcgccagcgg cggggcgccg ctcagcaagg     1080
aggtaggtga ggccgtggcc aaacgcttcc acctaccagg catccgccag ggctacggcc     1140
tgacagaaac aaccagcgcc attctgatca cccccgaagg ggacgacaag cctggcgcag     1200
taggcaaggt ggtgccccttc ttcgaggcta aggtggtgga cttggacacc ggtaagacac     1260
tgggtgtgaa ccagcgcggc gagctgtgcg tccgtggccc catgatcatg agcggctacg     1320
ttaacaaccc cgaggctaca aacgctctca tcgacaagga cggctggctg cacagcggcg     1380
acatcgccta ctgggacgag gacgagcact tcttcatcgt ggaccggctg aagagcctga     1440
tcaaatacaa gggctaccag gtagccccag ccgaactgga gagcatcctg ctgcaacacc     1500
ccaacatctt cgacgccggg gtcgccggcc tgcccgacga cgatgccggc gagctgcccg     1560
ccgcagtcgt cgtgctggaa cacggtaaaa ccatgaccga aggagatc gtggactatg       1620
tggccagcca ggttacaacc gccaagaagc tgcgcggtgg tgttgtgttc gtggacgagg     1680
tgcctaaagg actgaccggc aagttggacg cccgcaagat ccgcgagatt ctcattaagg     1740
ccaagaaggg cggcaagatc gccgtgtaat aattctagag tcggggcggc cggccgcttc     1800
gagcagacat gataagatac attgatgagt ttggacaaac cacaactaga atgcagtgaa     1860
aaaaatgctt tatttgtgaa atttgtgatg ctattgcttt atttgtaacc attaaaaccc     1920
gctgatcagc ctcgactgtg ccttctagtt gccagccatc tgttgtttgc cctcccccg      1980
tgccttcctt gaccctggaa ggtgccactc ccactgtcct ttcctaataa aatgaggaaa     2040
ttgcatcgca ttgtctgagt aggtgtcatt ctattctggg gggtggggtg gggcaggaca     2100
gcaagggggga ggattgggaa gacaatagca ggcatgctgg ggatgcggtg ggctctatgg     2160
cttctgaggc ggaaagaacg gatccgcagc ctctttccca cccaccttgg gactcagttc     2220
tgccccagat gaaattcagc acccacatat taaattttca gaatggaaat ttaagctgtt     2280
ccgggtgaga tcctttgaaa agacacctga agaagctcaa aaggaaaaga aggattcctt     2340
tgagggaaa ccctctctgg agcaatctcc agcagtcctg acaaggctg atggtcagaa       2400
gccagtccca actcagccat tgttaaaagc ccacctaag ttttcgaaga aatttcacga      2460
caacgagaaa gcaagaggca aagcgatcca tcaagccaac cttcgacatc tctgccgcat     2520
ctgtgggaat tcttttagag ctgatgagca acaggagatatccagtcc atggtcctgt        2580
ggatggtaaa acctaggcc ttttacgaaa gaaggaaaag agagctactt cctggccgga     2640
```

```
cctcattgcc aaggttttcc ggatcgatgt gaaggcagat gttgactcga tccaccccac   2700
tgagttctgc cataactgct ggagcatcat gcacaggaag tttagcagtg ccccatgtga   2760
ggtttacttc ccgaggaacg tgaccatgga gtggcacccc cacacaccat cctgtgacat   2820
ctgcaacact gcccgtcggg gactcaagag gaagagtctt cagccaaact tgcagctcag   2880
caaaaaactc aaaactgtgc ttgaccaagc aagacaagcc cgtcagcaca agagaagagc   2940
tcaggcaagg atcagcagca aggatgtcat gaagaagatc gccaactgca gtaagataca   3000
tcttagtacc aagctccttg cagtggactt cccagagcac tttgtgaaat ccatctcctg   3060
ccagatctgt gaacacattc tggctgaccc tgtggagacc aactgtaagc atgtcttttg   3120
ccgggtctgc attctcagat gcctcaaagt catgggcagc tattgtccct cttgccgata   3180
tccatgcttc cctactgacc tggagagtcc agtgaagtcc tttctgagcg tcttgaattc   3240
cctgatggtg aaatgtccag caaaagagtg caatgaggag gtcagtttgg aaaaatataa   3300
tcaccacatc tcaagtcaca aggaatcaaa agagattttt gtgcacatta ataaaggggg   3360
tcgagtaacg cgtgcaggca tgcaagctgg ccgcaataaa atatctttat tttcattaca   3420
tctgtgtgtt ggttttttgt gtgaatcgta actaacatac gctctccatc aaaacaaaac   3480
gaaacaaaac aaactagcaa aataggctgt ccccagtgca agtgcaggtg ccagaacatt   3540
tctctatcga aggatctgcg atcgctccgg tgcccgtcag tgggcagagc gcacatcgcc   3600
cacagtcccc gagaagttgg ggggaggggt cggcaattga accggtgcct agagaaggtg   3660
gcgcggggta aactgggaaa gtgatgtcgt gtactggctc cgccttttc ccgagggtgg   3720 gggagaaccg tatataagtg cagtagtcgc cgtgaacgtt ctttttcgca cgggtttgc   3780 cgccagaaca cagctgaagc ttcgaggggc tcgcatctct ccttcacgcg cccgccgccc   3840
tacctgaggc cgccatccac gccggttgag tcgcgttctg ccgcctcccg cctgtggtgc   3900
ctcctgaact gcgtccgccg tctaggtaag tttaaagctc aggtcgagac cgggcctttg   3960
tccggcgctc ccttggagcc tacctagact cagccggctc tccacgcttt gcctgaccct   4020
gcttgctcaa ctctacgtct ttgtttcgtt ttctgttctg cgccgttaca gatccaagct   4080
gtgaccggcg cctacgtaag tgatatctac tagatttatc aaaaagagtg ttgacttgtg   4140
agcgctcaca attgatactt agattcatcg agagggacac gtcgactact aaccttcttc   4200
tctttcctac agctgagatc accggcgaag gagggccacc atggcttctt accctggaca   4260
ccagcatgct tctgcctttg accaggctgc cagatccagg ggccactcca acaggagaac   4320
tgccctaaga cccagaagac agcaggaagc cactgaggtg aggcctgagc agaagatgcc   4380
aaccctgctg agggtgtaca ttgatggacc tcatggcatg ggcaagacca ccaccactca   4440
actgctggtg gcactgggct ccagggatga cattgtgtat gtgcctgagc caatgaccta   4500
ctggagagtg ctaggagcct ctgagaccat tgccaacatc tacaccaccc agcacaggct   4560
ggaccaggga gaaatctctg ctggagatgc tgctgtggtg atgacctctg cccagatcac   4620
aatgggaatg cccctatgctg tgactgatgc tgttctggct cctcacattg aggagaggc   4680 tggctcttct catgcccctc cacctgccct gaccctgatc tttgacagac accccattgc   4740
agccctgctg tgctacccag cagcaaggta cctcatgggc tccatgaccc cacaggctgt   4800
gctggctttt gtggccctga tccctccaac cctccctggc accaacattg ttctgggagc   4860
actgcctgaa gacagacaca ttgacaggct ggcaaagagg cagagacctg agagagact   4920 ggaccctggc atgctggctg caatcagaag ggtgtatgga ctgctggcaa acactgtgag   4980
atacctccag tgtggaggct cttggagaga ggactgggga cagctctctg gaacagcagt   5040
```

```
gccccctcaa ggagctgagc cccagtccaa tgctggtcca agaccccaca ttggggacac      5100
cctgttcacc ctgttcagag cccctgagct gctggctccc aatggagacc tgtacaatgt      5160
gtttgcctgg gctctggatg ttctagccaa gaggctgagg tccatgcatg tgttcatcct      5220
ggactatgac cagtcccctg ctggatgcag agatgctctg ctgcaactaa cctctggcat      5280
ggtgcagacc catgtgacca cccctggcag catccccacc atctgtgacc tagccagaac      5340 cttttgccagg gagatgggag aggccaacta aacctgagct agctcgacat gataagatac      5400
attgatgagt ttggacaaac cacaactaga atgcagtgaa aaaaatgctt tatttgtgaa      5460
atttgtgatg ctattgcttt atttgtgaaa tttgtgatgc tattgcttta tttgtaacca      5520
ttataagctg caataaacaa gttaacaaca acaattgcat tcattttatg tttcaggttc      5580 aggggggaggt gtgggaggtt ttttaaagca agtaaaacct ctacaaatgt ggtagatcca      5640
tttttggcgt aatcatggtc atagctgttt cctgtgtgaa attgttatcc gctcacaatt      5700
ccacacaaca tacgagccgg aagcataaag tgtaaagcct ggggtgccta atgagtgagc      5760
taactcacat taattgcgtt gcgctcactg cccgctttcc agtcgggaaa cctgtcgtgc      5820
cagctgcatt aatgaatcgg ccaacgcgcg gggagaggcg gtttgcgtat tgggcgctct      5880
tccgcttcct cgctcactga ctcgctgcgc tcggtcgttc ggctgcggcg agcggtatca      5940
gctcactcaa aggcggtaat acggttatcc acagaatcag gggataacgc aggaaagaac      6000
atgtgagcaa aaggccagca aaaggccagg aaccgtaaaa aggccgcgtt gctggcgttt      6060
ttccataggc tccgcccccc tgacgagcat cacaaaaatc gacgctcaag tcagaggtgg      6120
cgaaacccga caggactata agataccag gcgtttcccc ctggaagctc cctcgtgcgc      6180
tctcctgttc cgaccctgcc gcttaccgga tacctgtccg cctttctccc ttcgggaagc      6240
gtggcgcttt ctcatagctc acgctgtagg tatctcagtt cggtgtaggt cgttcgctcc      6300
aagctgggct gtgtgcacga accccccgtt cagcccgacc gctgcgcctt atccggtaac      6360
tatcgtcttg agtccaaccc ggtaagacac gacttatcgc cactggcagc agccactggt      6420
aacaggatta gcagagcgag gtatgtaggc ggtgctacag agttcttgaa gtggtggcct      6480
aactacggct acactagaag aacagtattt ggtatctgcg ctctgctgaa gccagttacc      6540
ttcggaaaaa gagttggtag ctcttgatcc ggcaaacaaa ccaccgctgg tagcggtggt      6600
tttttgtttt gcaagcagca gattacgcgc agaaaaaaag gatctcaaga agatcctttg      6660
atcttttcta cggggtctga cgctcagtgg aacgaaaact cacgttaagg gattttggtc      6720
atgagattat caaaaaggat cttcacctag atccttttaa attaaaaatg aagttttaaa      6780
tcaatctaaa gtatatatga gtaaacttgg tctgacagtt accaatgctt aatcagtgag      6840
gcacctatct cagcgatctg tctatttcgt tcatccatag ttgcctgact ccccgtcgtg      6900
tagataacta cgatacggga gggcttacca tctggcccca gtgctgcaat gataccgcga      6960
gacccacgct caccggctcc agatttatca gcaataaacc agccagccgg aagggccgag      7020
cgcagaagtg gtcctgcaac tttatccgcc tccatccagt ctattaattg ttgccgggaa      7080
gctagagtaa gtagttcgcc agttaatagt ttgcgcaacg ttgttgccat tgctacaggc      7140
atcgtggtgt cacgctcgtc gtttggtatg gcttcattca gctccggttc caacgatca      7200 aggcgagtta catgatcccc catgttgtgc aaaaaagcgg ttagctcctt cggtcctccg      7260
atcgttgtca gaagtaagtt ggccgcagtg ttatcactca tggttatggc agcactgcat      7320
aattctctta ctgtcatgcc atccgtaaga tgcttttctg tgactggtga gtactcaacc      7380
```

```
aagtcattct gagaatagtg tatgcggcga ccgagttgct cttgcccggc gtcaatacgg   7440
gataataccg cgccacatag cagaacttta aaagtgctca tcattggaaa acgttcttcg   7500
gggcgaaaac tctcaaggat cttaccgctg ttgagatcca gttcgatgta acccactcgt   7560
gcacccaact gatcttcagc atcttttact ttcaccagcg tttctgggtg agcaaaaaca   7620
ggaaggcaaa atgccgcaaa aaagggaata agggcgacac ggaaatgttg aatactcata   7680
ctcttccttt ttcaatatta ttgaagcatt tatcagggtt attgtctcat gagcggatac   7740
atatttgaat gtatttagaa aaataaacaa ataggggttc cgcgcacatt tccccgaaaa   7800
gtgccacctg acgtctaaga aaccattatt atcatgacat taacctataa aaataggcgt   7860
atcacgaggc cctttcgtct cgcgcgtttc ggtgatgacg gtgaaaacct ctgacacatg   7920
cagctcccgg agacggtcac agcttgtctg taagcggatg ccgggagcag acaagcccgt   7980
cagggcgcgt cagcgggtgt tggcgggtgt cggggctggc ttaactatgc ggcatcagag   8040
cagattgtac tgagagtgca ccatatgcgg tgtgaaatac cgcacagatg cgtaaggaga   8100
aaataccgca tcaggcgcca atattaaact tgatgagctc tagagatggt catgcatttt   8160
aaaaagaatt actcaaaata ttgtcttgga ataccagaga gcaagtgctt taagtatagg   8220
ctgggaagta aaatgctaaa ggaatgagaa ggcatttggg gttgagttca acctaagagg   8280
caggggagcc acaggaaaag acctagcacc tgccacagaa gagaattagg aagcagaatt   8340
gaactataag caattttgag gtgttcgttg ggctgcagtt gaaatatttt ttgaggttaa   8400
tgagacattt gaaatggccg tgtattgttt aactcttgca tagtcctgca tagggaacaa   8460
tctaatagga tttctctgtg aatcaagtct tagaaatttg cttttaattt ttatgaaaaa   8520
cgcccatttc tttgtttttg agacagagtc ctgctctgtc atccaggctg ggttgcagtg   8580
gcgtgatctt ggcccactgc aatctctgcc tcctgggttc aggcaatttt cctgtctcag   8640
cctcccgagt agctgggatt tcaagtgcct gccaccatgc ccggctaaat ttttttgtat   8700
ttttggtaca gatggagtat caccatgttg gccaggctgg tctcgaactc ctgacctcaa   8760
gtgattcacc agccttgacc tcccaaagtg ttgggatcac aggcatgagc cactgtgcct   8820
gtgccccaaa acaccaattt ctgatgtgtg atgcatgtaa gatagaacaa acttcagtaa   8880
agcggggact tgaaaagagg cttttggtaac agctgtcagc attaacccct gcccctccgt   8940
acctcctaat cccaccccctg ctcaaagtat gttcatctga aatttgtct ccataactat   9000 gtgactataa aaattctcat cgatttttgtt agttgatcaa ttgagggaaa acatatgtt   9060 acttgatata actggtgggt caaaagaatt aacccaggca aatttgagat aggtggatgg   9120
gatgatggat tgaaaataca gctgctctct ttccaatcat gtactaagta atttgggaaa   9180
gattgatcta attgggtcta gagagtacac ttcacatggc attgtttgac ttttttttctg   9240 catcgctagc gatctgtgca ttacaactca aatcagtcgg gtttcctggc atatgtaatt   9300
gccaatgttt tttaccagaa gagaaacatt actcccacct cttcttatta tgttacaaac   9360
tatagtgcta atgaccatcg accaacagtg actttcagga tgacctgtgt gagttttatc   9420
tgaaaccatg tgaattttc atcttaaaag tcccttagaa tctcagtcta tgtacactca   9480
ggtttgttgc aggtttagag ttccgtgttt tttgtttcta atgtagacac agccttataa   9540
tttacaacag cattcactaa ttaaaattgt aagcataatt actatccacg atacttatta   9600
ttagtttgca ttcataaagc tcaaaattca cttcatcctt tcaagtagtg ataattagt   9660 ttctttgggt ttgcagcttt atcatccttt tatgacccat ttggaagaaa taaacaacca   9720
accccctgga agactgcttt aaaaagctgg aaatacattg tccagctagt acaatgaggc   9780
```

-continued

```
taatacaatg tggaaaatat tacttttctt tgattttagt agcctgttta tctttacatt     9840
tactgaacaa ataactattg agcacctaat gtatactggg acccttgggg aggcaaagat     9900
gaatcaaaga ttctgtcctt aaagacctta agacgcgttg acattgatta ttgactagtt     9960
attaatagta atcaattacg gggtcattag ttcatagccc atatatggag ttccgcgtta    10020
cataacttac ggtaaatggc ccgcctggct gaccgcccaa cgaccccgc ccattgacgt     10080
caataatgac gtatgttccc atagtaacgc caatagggac tttccattga cgtcaatggg    10140
tggagtattt acggtaaact gcccacttgg cagtacatca agtgtatcat atgccaagta    10200
cgccccctat tgacgtcaat gacggtaaat ggcccgcctg gcattatgcc cagtacatga    10260
ccttatggga ctttcctact tggcagtaca tctacgtatt agtcatcgct attaccatgg    10320
tgatgcggtt ttggcagtac atcaatgggc gtggatagcg gtttgactca cggggatttc    10380
caagtctcca ccccattgac gtcaatggga gtttgttttg gcaccaaaat caacgggact    10440
ttccaaaatg tcgtaacaac tccgccccat tgacgcaaat gggcggtagg cgtgtacggt    10500
gggaggtcta tataagcaga gctccccggg agcttgtata tccattttcg gatctgatca    10560
agagacagga tgaggatcgt ttcgcatgat tgaacaagat ggattgcacg caggttctcc    10620
ggccgcttgg gtggagaggc tattcggcta tgactgggca caacagacaa tcggctgctc    10680
tgatgccgcc gtgttccggc tgtcagcgca ggggcgcccg gttcttttg tcaagaccga    10740
cctgtccggt gccctgaatg aactgcagga cgaggcagcg cggctatcgt ggctggccac    10800
gacgggcgtt ccttgcgcag ctgtgctcga cgttgtcact gaagcgggaa gggactggct    10860
gctattgggc gaagtgccgg ggcaggatct cctgtcatct caccttgctc ctgccgagaa    10920
agtatccatc atggctgatg caatgcggcg gctgcatacg cttgatccgg ctacctgccc    10980
attcgaccac caagcgaaac atcgcatcga gcgagcacgt actcggatgg aagccggtct    11040
tgtcgatcag gatgatctgg acgaagagca tcaggggctc gcgccagccg aactgttcgc    11100
caggctcaag gcgcgcatgc ccgacggcga ggatctcgtc gtgacccatg gcgatgcctg    11160
cttgccgaat atcatggtgg aaaatggccg cttttctgga ttcatcgact gtggccggct    11220
gggtgtggcg gaccgctatc aggacatagc gttggctacc cgtgatattg ctgaagagct    11280
tggcggcgaa tgggctgacc gcttcctcgt gctttacggt atcgccgctc ccgattcgca    11340
gcgcatcgcc ttctatcgcc ttcttgacga gttcttctga ttaattaaca ggactgaccg    11400
tgctacgaga tttcgattcc accgccgcct tctatgaaag gttgggcttc ggaatcgttt    11460
tccgggacgc cggctggatg atcctccagc gcggggatct catgctggag ttcttcgccc    11520
accccaactt gtttattgca gcttataatg gttacaaata aagcaatagc atcacaaatt    11580
tcacaaataa agcatttttt tcactgcatt ctagttgtgg tttgtccaaa ctcatcaatg    11640
tatcttatca tgtctgtata ccgtcgacct ctagctagag cttggcgtaa tcatggtcat    11700
agctgtttcc tgtgtgaaat tgttatccgc tcacaattcc acacaacata caggatccac    11760
tagcgatgta cgggccagat atacgcgttg acattgatta ttgactagtt attaatagta    11820
atcaattacg gggtcattag ttcatagccc atatatggag ttccgcgtta cataacttac    11880
ggtaaatggc ccgcctggct gaccgcccaa cgaccccgc ccattgacgt caataatgac    11940
gtatgttccc atagtaacgc caatagggac tttccattga cgtcaatggg tggagtattt    12000
acggtaaact gcccacttgg cagtacatca agtgtatcat atgccaagta cgccccctat    12060
tgacgtcaat gacggtaaat ggcccgcctg gcattatgcc cagtacatga ccttatggga    12120
```

| | |
|---|---|
| ctttcctact tggcagtaca tctacgtatt agtcatcgct attaccatgg tgatgcggtt | 12180 |
| ttggcagtac atcaatgggc gtggatagcg gtttgactca cggggatttc caagtctcca | 12240 |
| ccccattgac gtcaatggga gtttgttttg gcaccaaaat caacgggact ttccaaaatg | 12300 |
| tcgtaacaac tccgccccat tgacgcaaat gggcggtagg cgtgtacggt gggaggtcta | 12360 |
| tataagcaga gctctctggc taactagaga acccactgct tactggctta tcgaaattaa | 12420 |
| tacgactcac tatagggaga cccaagctgg ctagccttag gcgcgcc | 12467 |

<210> SEQ ID NO 2
<211> LENGTH: 12465
<212> TYPE: DNA
<213> ORGANISM: Artificial
<220> FEATURE:
<223> OTHER INFORMATION: pCLS6884

<400> SEQUENCE: 2

| | |
|---|---|
| atggcagcct atccttatga cgttcctgat tacgctggat ttacgctagg gataacaggg | 60 |
| taatatggag gctccggatc cggcggttct ggatccggcg gttctggttc cgcagccgaa | 120 |
| gatgccaaaa acattaagaa gggcccagcg ccattctacc cactcgaaga cgggaccgcc | 180 |
| ggcgagcagc tgcacaaagc catgaagcgc tacgccctgg tgcccggcac catcgccttt | 240 |
| accgacgcac atatcgaggt ggacattacc tacgccgagt acttcgagat gagcgttcgg | 300 |
| ctggcagaag ctatgaagcg ctatgggctg aatacaaacc atcggatcgt ggtgtgcagc | 360 |
| gagaatagct tgcagttctt catgcccgtg ttgggtgccc tgttcatcgg tgtggctgtg | 420 |
| gccccagcta cgacatcta caacgagcgc gagctgctga cagcatggg catcagccag | 480 |
| cccaccgtcg tattcgtgag caagaaaggg ctgcaaaaga tcctcaacgt gcaaaagaag | 540 |
| ctaccgatca tacaaaagat catcatcatg gatagcaaga ccgactacca gggcttccaa | 600 |
| agcatgtaca ccttcgtgac ttcccatttg ccacccggct caacgagta cgacttcgtg | 660 |
| cccgagagct cgaccgggga caaaaccatc gccctgatca tgaacagtag tggcagtacc | 720 |
| ggattgccca agggcgtagc cctaccgcac cgcaccgctt gtgtccgatt cagtcatgcc | 780 |
| cgcgacccca tcttcggcaa ccagatcatc cccgacaccg ctatcctcag cgtggtgcca | 840 |
| tttcaccacg gcttcggcat gttcaccacg ctgggctact tgatctgcgg ctttcgggtc | 900 |
| gtgctcatgt accgcttcga ggaggagcta ttcttgcgca gcttgcaaga ctataagatt | 960 |
| caatctgccc tgctggtgcc cacactattt agcttcttcg ctaagagcac tctcatcgac | 1020 |
| aagtacgacc taagcaactt gcacgagatc gccagcggcg gggcgccgct cagcaaggag | 1080 |
| gtaggtgagg ccgtggccaa acgcttccac ctaccaggca tccgccaggg ctacggcctg | 1140 |
| acagaaacaa ccagcgccat tctgatcacc cccgaagggg acgacaagcc tggcgcagta | 1200 |
| ggcaaggtgg tgcccttctt cgaggctaag gtggtggact ggacaccgg taagacactg | 1260 |
| ggtgtgaacc agcgcggcga gctgtgcgtc cgtggcccca tgatcatgag cggctacgtt | 1320 |
| aacaaccccg aggctacaaa cgctctcatc gacaaggacg gctggctgca cagcggcgac | 1380 |
| atcgcctact gggacgagga cgagcacttc ttcatcgtgg accggctgaa gagcctgatc | 1440 |
| aaatacaagg gctaccaggt agccccagcc gaactggaga gcatcctgct gcaacacccc | 1500 |
| aacatcttcg acgccggggt cgccggcctg cccgacacg atgccggcga gctgcccgcc | 1560 |
| gcagtcgtcg tgctggaaca cggtaaaacc atgaccgaga aggagatcgt ggactatgtg | 1620 |
| gccagccagg ttacaaccgc caagaagctg cgcggtggtg ttgtgttcgt ggacgaggtg | 1680 |
| cctaaaggac tgaccggcaa gttggacgcc cgcaagatcc gcgagattct cattaaggcc | 1740 |

```
aagaagggcg gcaagatcgc cgtgtaataa ttctagagtc ggggcggccg gccgcttcga    1800
gcagacatga taagatacat tgatgagttt ggacaaacca caactagaat gcagtgaaaa    1860
aaatgcttta tttgtgaaat tgtgatgct attgctttat tgtaaccat taaaacccgc     1920 tgatcagcct cgactgtgcc ttctagttgc cagccatctg ttgtttgccc ctcccccgtg    1980
ccttccttga ccctggaagg tgccactccc actgtccttt cctaataaaa tgaggaaatt    2040
gcatcgcatt gtctgagtag gtgtcattct attctggggg gtggggtggg gcaggacagc    2100 aaggggagg attgggaaga caatagcagg catgctgggg atgcggtggg ctctatggct     2160 tctgaggcg aaagaacgga tccgcagcct ctttcccacc caccttggga ctcagttctg     2220
ccccagatga aattcagcac ccacatatta aattttcaga atggaaattt aagctgttcc    2280
gggtgagatc ctttgaaaag cacctgaag aagctcaaaa ggaaaagaag gattcctttg     2340
aggggaaacc ctctctggag caatctccag cagtcctgga caaggctgat ggtcagaagc    2400
cagtcccaac tcagccattg ttaaaagccc accctaagtt ttcgaagaaa tttcacgaca    2460
acgagaaagc aagaggcaaa gcgatccatc aagccaacct tcgacatctc tgccgcatct    2520
gtgggaattc ttttagagct gatgagcaca acaggagata tccagtccat ggtcctgtgg    2580
atggtaaaac cctaggcctt ttacgaaaga aggaaaagag agctacttcc tggccggacc    2640
tcattgccaa ggttttccgg atcgatgtga aggcagatgt tgactcgatc cacccccactg   2700 agttctgcca taactgctgg agcatcatgc acaggaagtt tagcagtgcc ccatgtgagg    2760
tttacttccc gaggaacgtg accatggagt ggcaccccca cacaccatcc tgtgacatct    2820
gcaacactgc ccgtcgggga ctcaagagga agagtcttca gccaaacttg cagctcagca    2880
aaaaactcaa aactgtgctt gaccaagcaa gacaagcccg tcagcacaag agaagagctc    2940
aggcaaggat cagcagcaag gatgtcatga agaagatcgc caactgcagt aagatacatc    3000
ttagtaccaa gctccttgca gtggacttcc cagagcactt tgtgaaatcc atctcctgcc    3060
agatctgtga acacattctg gctgaccctg tggagaccaa ctgtaagcat gtcttttgcc    3120
gggtctgcat tctcagatgc ctcaaagtca tgggcagcta ttgtccctct tgccgatatc    3180
catgcttccc tactgacctg gagagtccag tgaagtcctt tctgagcgtc ttgaattccc    3240
tgatggtgaa atgtccagca aaagagtgca atgaggaggt cagtttggaa aaatataatc    3300
accacatctc aagtcacaag gaatcaaaag agatttttgt gcacattaat aaaggggggtc   3360 gagtaacgcg tgcaggcatg caagctggcc gcaataaaat atctttattt tcattacatc    3420
tgtgtgttgg ttttttgtgt gaatcgtaac taacatacgc tctccatcaa acaaaacga    3480 aacaaaacaa actagcaaaa taggctgtcc ccagtgcaag tgcaggtgcc agaacatttc    3540
tctatcgaag gatctgcgat cgctccggtg cccgtcagtg ggcagagcgc acatcgccca    3600
cagtccccga gaagttgggg ggaggggtcg gcaattgaac cggtgcctag agaaggtggc    3660
gcggggtaaa ctgggaaagt gatgtcgtgt actggctccg cctttttccc gagggtgggg    3720
gagaaccgta tataagtgca gtagtcgccg tgaacgttct ttttcgcaac gggtttgccg    3780
ccagaacaca gctgaagctt cgaggggctc gcatctctcc ttcacgcgcc cgccgcccta    3840 cctgaggcc ccatccacgc cggttgagtc gcgttctgcc gcctcccgcc tgtggtgcct     3900
cctgaactgc gtccgccgtc taggtaagtt taaagctcag gtcgagaccg gcctttgtc     3960 cggcgctccc ttgagccta cctagactca gccggctctc cacgctttgc ctgaccctgc     4020
ttgctcaact ctacgtcttt gtttcgtttt ctgttctgcg ccgttacaga tccaagctgt    4080
```

```
gaccggcgcc tacgtaagtg atatctacta gatttatcaa aaagagtgtt gacttgtgag    4140
cgctcacaat tgatacttag attcatcgag agggacacgt cgactactaa ccttcttctc    4200
tttcctacag ctgagatcac cggcgaagga gggccaccat ggcttcttac cctggacacc    4260
agcatgcttc tgcctttgac caggctgcca gatccagggg ccactccaac aggagaactg    4320
ccctaagacc cagaagacag caggaagcca ctgaggtgag gcctgagcag aagatgccaa    4380
ccctgctgag ggtgtacatt gatggacctc atggcatggg caagaccacc accactcaac    4440
tgctggtggc actgggctcc agggatgaca ttgtgtatgt gcctgagcca atgacctact    4500
ggagagtgct aggagcctct gagaccattg ccaacatcta caccacccag cacaggctgg    4560
accagggaga aatctctgct ggagatgctg ctgtggtgat gacctctgcc cagatcacaa    4620
tgggaatgcc ctatgctgtg actgatgctg ttctggctcc tcacattgga ggagaggctg    4680
gctcttctca tgcccctcca cctgccctga ccctgatctt tgacagacac cccattgcag    4740
ccctgctgtg ctacccagca gcaaggtacc tcatgggctc catgaccccca caggctgtgc    4800
tggcttttgt ggccctgatc cctccaaccc tccctgcac caacattgtt ctgggagcac    4860
tgcctgaaga cagacacatt gacaggctgg caaagaggca gagacctgga gagagactgg    4920
acctggccat gctggctgca atcagaaggg tgtatggact gctggcaaac actgtgagat    4980
acctccagtg tggaggctct tggagagagg actggggaca gctctctgga acagcagtgc    5040
cccctcaagg agctgagccc cagtccaatg ctggtccaag accccacatt ggggacaccc    5100
tgttcaccct gttcagagcc ctgagctgc tggctcccaa tggagacctg tacaatgtgt    5160
ttgcctgggc tctggatgtt ctagccaaga ggctgaggtc catgcatgtg ttcatcctgg    5220
actatgacca gtcccctgct ggatgcagag atgctctgct gcaactaacc tctggcatgg    5280
tgcagaccca tgtgaccacc cctggcagca tccccaccat ctgtgaccta gccagaacct    5340
tgccaggga gatgggagag gccaactaaa cctgagctag ctcgacatga taagatacat    5400
tgatgagttt ggacaaacca caactagaat gcagtgaaaa aaatgcttta tttgtgaaat    5460
ttgtgatgct attgctttat tgtgaaattt gtgatgcta ttgctttatt tgtaaccatt    5520
ataagctgca ataaacaagt taacaacaac aattgcattc atttatgtt tcaggttcag    5580
ggggaggtgt gggaggtttt ttaaagcaag taaaacctct acaaatgtgg tagatccatt    5640
tttgcgtaa tcatggtcat agctgtttcc tgtgtgaaat tgttatccgc tcacaattcc    5700
acacaacata cgagccggaa gcataaagtg taaagcctgg ggtgcctaat gagtgagcta    5760
actcacatta attgcgttgc gctcactgcc cgctttccag tcgggaaacc tgtcgtgcca    5820
gctgcattaa tgaatcggcc aacgcgcggg gagaggcggt ttgcgtattg ggcgctcttc    5880
cgcttcctcg ctcactgact cgctgcgctc ggtcgttcgg ctgcggcgag cggtatcagc    5940
tcactcaaag gcggtaatac ggttatccac agaatcaggg gataacgcag gaaagaacat    6000
gtgagcaaaa ggccagcaaa aggccaggaa ccgtaaaaag gccgcgttgc tggcgttttt    6060
ccataggctc cgcccccctg acgagcatca caaaaatcga cgctcaagtc agaggtggcg    6120
aaacccgaca ggactataaa gataccaggc gtttccccct ggaagctccc tcgtgcgctc    6180
tcctgttccg accctgccgc ttaccggata cctgtccgcc tttctccctt cgggaagcgt    6240
ggcgctttct catagctcac gctgtaggta tctcagttcg gtgtaggtcg ttcgctccaa    6300
gctgggctgt gtgcacgacc ccccgttca gcccgaccgc tgcgccttat ccggtaacta    6360
tcgtcttgag tccaacccgg taagacacga cttatcgcca ctggcagcag ccactggtaa    6420
caggattagc agagcgaggt atgtaggcgg tgctacagag ttcttgaagt ggtggcctaa    6480
```

```
ctacggctac actagaagaa cagtatttgg tatctgcgct ctgctgaagc cagttacctt    6540
cggaaaaaga gttggtagct cttgatccgg caaacaaacc accgctggta gcggtggttt    6600
ttttgtttgc aagcagcaga ttacgcgcag aaaaaaagga tctcaagaag atcctttgat    6660
cttttctacg gggtctgacg ctcagtggaa cgaaaactca cgttaaggga ttttggtcat    6720
gagattatca aaaaggatct tcacctagat ccttttaaat taaaaatgaa gttttaaatc    6780
aatctaaagt atatatgagt aaacttggtc tgacagttac caatgcttaa tcagtgaggc    6840
acctatctca gcgatctgtc tatttcgttc atccatagtt gcctgactcc ccgtcgtgta    6900
gataactacg atacgggagg gcttaccatc tggccccagt gctgcaatga taccgcgaga    6960
cccacgctca ccggctccag atttatcagc aataaaccag ccagccggaa gggccgagcg    7020
cagaagtggt cctgcaactt tatccgcctc catccagtct attaattgtt gccgggaagc    7080
tagagtaagt agttcgccag ttaatagttt gcgcaacgtt gttgccattg ctacaggcat    7140
cgtggtgtca cgctcgtcgt ttggtatggc ttcattcagc tccggttccc aacgatcaag    7200
gcgagttaca tgatccccca tgttgtgcaa aaaagcggtt agctccttcg gtcctccgat    7260
cgttgtcaga agtaagttgg ccgcagtgtt atcactcatg gttatggcag cactgcataa    7320
ttctcttact gtcatgccat ccgtaagatg cttttctgtg actggtgagt actcaaccaa    7380
gtcattctga gaatagtgta tgcggcgacc gagttgctct tgcccggcgt caatacggga    7440
taataccgcg ccacatagca gaactttaaa agtgctcatc attggaaaac gttcttcggg    7500
gcgaaaactc tcaaggatct taccgctgtt gagatccagt tcgatgtaac ccactcgtgc    7560
acccaactga tcttcagcat cttttacttt caccagcgtt tctgggtgag caaaaacagg    7620
aaggcaaaat gccgcaaaaa agggaataag ggcgacacgg aaatgttgaa tactcatact    7680 cttcctttt caatattatt gaagcattta tcagggttat tgtctcatga gcggatacat    7740
atttgaatgt atttagaaaa ataaacaaat aggggttccg cgcacatttc cccgaaaagt    7800
gccacctgac gtctaagaaa ccattattat catgacatta acctataaaa ataggcgtat    7860
cacgaggccc tttcgtctcg cgcgtttcgg tgatgacggt gaaaacctct gacacatgca    7920
gctcccggag acggtcacag cttgtctgta agcggatgcc gggagcagac aagcccgtca    7980
gggcgcgtca gcgggtgttg gcgggtgtcg ggctggctt aactatgcgg catcagagca    8040
gattgtactg agagtgcacc atatgcggtg tgaaataccg cacagatgcg taaggagaaa    8100
ataccgcatc aggcgccaat attaaacttg atgagctcta gagatggtca tgcattttaa    8160
aaagaattac tcaaaatatt gtcttggaat accagagagc aagtgcttta agtataggct    8220
gggaagtaaa atgctaaagg aatgagaagg catttggggt tgagttcaac ctaagaggca    8280
ggggagccac agggaaagac ctagcacctg ccacagaaga gaattaggaa gcagaattga    8340
actataagca attttgaggt gttcgttggg ctgcagttga atatttttt gaggttaatg    8400 agacatttga aatggccgtg tattgtttaa ctcttgcata gtcctgcata gggaacaatc    8460
taataggatt tctctgtgaa tcaagtctta gaaatttgct tttaattttt atgaaaaacg    8520
cccatttctt tgttttgag acagagtcct gctctgtcat ccaggctggg ttgcagtggc    8580
gtgatcttgg cccactgcaa tctctgcctc ctgggttcag gcaattttcc tgtctcagcc    8640
tcccgagtag ctgggatttc aagtgcctgc caccatgccc ggctaaattt ttttgtattt    8700
ttggtacaga tggagtatca ccatgttggc caggctggtc tcgaactcct gacctcaagt    8760
gattcaccag ccttgacctc ccaaagtgtt gggatcacag gcatgagcca ctgtgcctgt    8820
```

```
gccccaaaac accaatttct gatgtgtgat gcatgtaaga tagaacaaac ttcagtaaag    8880
cggggacttg aaaagaggct ttggtaacag ctgtcagcat taacccttgc ccctccgtac    8940
ctcctaatcc caccccctgct caaagtatgt tcatctgaga atttgtctcc ataactatgt   9000
gactataaaa attctcatcg attttgttag ttgatcaatt gagggaaaaa catatgttac    9060
ttgatataac tggtgggtca aaagaattaa cccaggcaaa tttgagatag gtggatggga    9120
tgatggattg aaaatacagc tgctctcttt ccaatcatgt actaagtaat ttgggaaaga    9180
ttgatctaat tgggtctaga gagtacactt cacatggcat tgtttgactt ttttttctgca  9240
tcgctagcga tctgtgcatt acaactcaaa tcagtcgggt ttcctggcat atgtaattgc    9300
caatgttttt taccagaaga gaaacattac tcccacctct tcttattatg ttacaaacta    9360
tagtgctaat gaccatcgac caacagtgac tttcaggatg acctgtgtga gttttatctg    9420
aaaccatgtg aattttctcat cttaaaagtc ccttagaatc tcagtctatg tacactcagg   9480
tttgttgcag gtttagagtt ccgtgttttt tgtttctaat gtagacacag ccttataatt    9540
tacaacagca ttcactaatt aaaattgtaa gcataattac tatccacgat acttattatt    9600
agtttgcatt cataaagctc aaaattcact tcatcctttc aagtagtgaa taattagttt    9660
ctttgggttt gcagctttat catccttta tgacccattt ggaagaaata aacaaccaac     9720
cccctggaag actgctttaa aaagctggaa atacattgtc cagctagtac aatgaggcta    9780
atacaatgtg gaaatatta cttttctttg attttagtag cctgtttatc tttacattta     9840
ctgaacaaat aactattgag cacctaatgt atactgggac ccttggggag gcaaagatga    9900
atcaaagatt ctgtccttaa agaccttaag acgcgttgac attgattatt gactagttat    9960
taatagtaat caattacggg gtcattagtt catagcccat atatggagtt ccgcgttaca   10020
taacttacgg taaatggccc gcctggctga ccgcccaacg accccgccc attgacgtca    10080
ataatgacgt atgttcccat agtaacgcca atagggactt tccattgacg tcaatgggtg   10140
gagtatttac ggtaaactgc ccacttggca gtacatcaag tgtatcatat gccaagtacg   10200
ccccctattg acgtcaatga cggtaaatgg cccgcctggc attatgccca gtacatgacc   10260
ttatgggact ttcctacttg gcagtacatc tacgtattag tcatcgctat taccatggtg   10320
atgcggtttt ggcagtacat caatgggcgt ggatagcggt ttgactcacg gggatttcca   10380
agtctccacc ccattgacgt caatgggagt ttgttttggc accaaaatca acgggacttt   10440
ccaaaatgtc gtaacaactc cgccccattg acgcaaatgg gcggtaggcg tgtacggtgg   10500
gaggtctata taagcagagc tccccggag cttgtatatc cattttcgga tctgatcaag    10560
agacaggatg aggatcgttt cgcatgattg aacaagatgg attgcacgca ggttctccgg   10620
ccgcttgggt ggagaggcta ttcggctatg actgggcaca acagacaatc ggctgctctg   10680
atgccgccgt gttccggctg tcagcgcagg ggcgcccggt tctttttgtc aagaccgacc   10740
tgtccggtgc cctgaatgaa ctgcaggacg aggcagcgcg gctatcgtgg ctggccacga   10800
cgggcgttcc ttgcgcagct gtgctcgacg ttgtcactga agcgggaagg gactggctgc   10860
tattgggcga agtgccgggg caggatctcc tgtcatctca ccttgctcct gccgagaaag   10920
tatccatcat ggctgatgca atgcggcggc tgcatacgct tgatccggct acctgcccat   10980
tcgaccacca agcgaaacat cgcatcgagc gagcacgtac tcggatggaa gccggtcttg   11040
tcgatcagga tgatctggac gaagagcatc aggggctcgc gccagccgaa ctgttcgcca   11100
ggctcaaggc gcgcatgccc gacggcgagg atctcgtcgt gacccatggc gatgcctgct   11160
tgccgaatat catggtggaa aatggccgct tttctggatt catcgactgt ggccggctgg   11220
```

```
gtgtggcgga ccgctatcag gacatagcgt tggctacccg tgatattgct gaagagcttg    11280
gcggcgaatg ggctgaccgc ttcctcgtgc tttacggtat cgccgctccc gattcgcagc    11340
gcatcgcctt ctatcgcctt cttgacgagt tcttctgatt aattaacagg actgaccgtg    11400
ctacgagatt tcgattccac cgccgccttc tatgaaaggt tgggcttcgg aatcgttttc    11460
cgggacgccg gctggatgat cctccagcgc ggggatctca tgctggagtt cttcgcccac    11520
cccaacttgt ttattgcagc ttataatggt tacaaataaa gcaatagcat cacaaatttc    11580
acaaataaag cattttttc actgcattct agttgtggtt tgtccaaact catcaatgta    11640
tcttatcatg tctgtatacc gtcgacctct agctagagct tggcgtaatc atggtcatag    11700
ctgtttcctg tgtgaaattg ttatccgctc acaattccac acaacataca ggatccacta    11760
gcgatgtacg ggccagatat acgcgttgac attgattatt gactagttat taatagtaat    11820
caattacggg gtcattagtt catagcccat atatggagtt ccgcgttaca taacttacgg    11880
taaatggccc gcctggctga ccgcccaacg acccccgccc attgacgtca ataatgacgt    11940
atgttcccat agtaacgcca atagggactt tccattgacg tcaatgggtg gagtatttac    12000
ggtaaactgc ccacttggca gtacatcaag tgtatcatat gccaagtacg ccccctattg    12060
acgtcaatga cggtaaatgg cccgcctggc attatgccca gtacatgacc ttatgggact    12120
ttcctacttg gcagtacatc tacgtattag tcatcgctat taccatggtg atgcggtttt    12180
ggcagtacat caatgggcgt ggatagcggt ttgactcacg gggatttcca agtctccacc    12240
ccattgacgt caatgggagt ttgttttggc accaaaatca acgggacttt ccaaaatgtc    12300
gtaacaactc cgccccattg acgcaaatgg gcggtaggcg tgtacggtgg gaggtctata    12360
taagcagagc tctctggcta actagagaac ccactgctta ctggcttatc gaaattaata    12420
cgactcacta tagggagacc caagctggct agccttaggc gcgcc              12465
```

<210> SEQ ID NO 3
<211> LENGTH: 6101
<212> TYPE: DNA
<213> ORGANISM: Artificial
<220> FEATURE:
<223> OTHER INFORMATION: pCLS2690

<400> SEQUENCE: 3

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
```

```
gtaggcgtgt acggtgggag gtctatataa gcagagctct ctggctaact agagaaccca    840
ctgcttactg gcttatcgaa atgaattccg tcgaccatgg ccaataccaa atataacgaa    900
gagttcctgc tgtacctggc cggctttgtg gacgctgacg gtagcatcat cgctcagatt    960
aaaccaagac agtctcggaa gtttaaacat gagctaagct tgacctttga tgtgactcaa   1020
aagacccagc gccgttggtt tctggacaag ctagtggatg aaattggcgt tggttacgta   1080
tatgattctg gatccgtttc ctattaccag ttaagcgaaa tcaagccgct gcacaacttc   1140
ctgactcaac tgcagccgtt tctggaactg aaacagaaac aggcaaacct ggttctgaaa   1200
attatcgaac agctgccgtc tgcaaaagaa tccccggcca aattcctgga gtttgtacc    1260 tgggtggatc agattgcagc tctgaacgat tctaagacgc gtaaaaccac ttctgaaacc   1320
gttcgtgctg tgctggacag cctgagcgag aagaagaaat cctccccggc ggccggtgga   1380
tctgataagt ataatcaggc tctgtctaaa tacaaccaag cactgtccaa gtacaatcag   1440
gccctgtctg gtgaggcgg ttccaacaaa aagttcctgc tgtatcttgc tggatttgtg   1500
gatggtgatg gctccatcat tgctcagata aaaccacgtc aagggtataa gttcaaacac   1560
cagctctcct tgacttttca ggtcactcag aagacacaaa gaaggtggtt cttggacaaa   1620
ttggttgatc gtattggtgt gggctatgtc gctgaccgtg gctctgtgtc agactaccgc   1680
ctgtctgaaa ttaagcctct tcataacttt ctcacccaac tgcaacccctt cttgaagctc   1740 aaacagaagc aagcaaatct ggttttgaaa atcatcgagc aactgccatc tgccaaggag   1800
tccctggaca gtttcttga agtgtgtact tgggtggatc agattgctgc cttgaatgac   1860
tccaagacca gaaaaaccac ctctgagact gtgagggcag ttctggatag cctctctgag   1920
aagaaaaagt cctctcctta gccatggccc gcggttcgaa ggtaagccta tccctaaccc   1980
tctcctcggt ctcgattcta cgcgtaccgg ttagtaatga gtttaaacgg gggaggctaa   2040
ctgaaacacg gaaggagaca ataccggaag gaacccgcgc tatgacggca ataaaaagac   2100
agaataaaac gcacgggtgt tgggtcgttt gttcataaac gcggggttcg gtcccagggc   2160
tggcactctg tcgataccc accgagaccc cattggggcc aatacgcccg cgtttcttcc   2220
ttttccccac cccacccccc aagttcgggt gaaggcccag ggctcgcagc caacgtcggg   2280
gcggcaggcc ctgccatagc agatctgcgc agctggggct ctaggggta tccccacgcg   2340 ccctgtagcg gcgcattaag cgcggcgggt gtggtggtta cgcgcagcgt gaccgctaca   2400
cttgccagcg ccctagcgcc cgctcctttc gctttcttcc cttcctttct cgccacgttc   2460
gccggctttc cccgtcaagc tctaaatcgg ggcatccctt tagggttccg atttagtgct   2520
ttacggcacc tcgaccccaa aaaacttgat tagggtgatg gttcacgtag tgggccatcg   2580
ccctgataga cggtttttcg ccctttgacg ttggagtcca cgttctttaa tagtggactc   2640
ttgttccaaa ctggaacaac actcaaccct atctcggtct attctttga tttataaggg   2700 attttgggga tttcggccta ttggttaaaa aatgagctga tttaacaaaa atttaacgcg   2760
aattaattct gtggaatgtg tgtcagttag ggtgtggaaa gtccccaggc tccccagcag   2820
gcagaagtat gcaaagcatg catctcaatt agtcagcaac caggtgtgga agtccccag    2880 gctcccagc aggcagaagt atgcaaagca tgcatctcaa ttagtcagca accatagtcc   2940
cgcccctaac tccgcccatc ccgcccctaa ctccgcccag ttccgcccat tctccgcccc   3000
atggctgact aatttttttt atttatgcag aggccgaggc cgcctctgcc tctgagctat   3060
tccagaagta gtgaggaggc ttttttggag gcctaggctt ttgcaaaaag ctcccgggag   3120
cttgtatatc cattttcgga tctgatcagc acgtgttgac aattaatcat cggcatagta   3180
```

```
tatcggcata gtataatacg acaaggtgag gaactaaacc atggccaagc ctttgtctca   3240
agaagaatcc accctcattg aaagagcaac ggctacaatc aacagcatcc ccatctctga   3300
agactacagc gtcgccagcg cagctctctc tagcgacggc cgcatcttca ctggtgtcaa   3360
tgtatatcat tttactgggg gaccttgtgc agaactcgtg gtgctgggca ctgctgctgc   3420
tgcggcagct ggcaacctga cttgtatcgt cgcgatcgga aatgagaaca ggggcatctt   3480
gagcccctgc ggacggtgcc gacaggtgct tctcgatctg catcctggga tcaaagccat   3540
agtgaaggac agtgatggac agccgacggc agttgggatt cgtgaattgc tgccctctgg   3600
ttatgtgtgg gagggctaag cacttcgtgg ccgaggagca ggactgacac gtgctacgag   3660
atttcgattc caccgccgcc ttctatgaaa ggttgggctt cggaatcgtt ttccgggacg   3720
ccggctggat gatcctccag cgcgggatc  tcatgctgga gttcttcgcc cacccaact    3780
tgtttattgc agcttataat ggttacaaat aaagcaatag catcacaaat ttcacaaata   3840
aagcatttt  ttcactgcat tctagttgtg gtttgtccaa actcatcaat gtatcttatc   3900
atgtctgtat accgtcgacc tctagctaga gcttggcgta atcatggtca tagctgtttc   3960
ctgtgtgaaa ttgttatccg ctcacaattc cacacaacat acgagccgga agcataaagt   4020
gtaaagcctg gggtgcctaa tgagtgagct aactcacatt aattgcgttg cgctcactgc   4080
ccgctttcca gtcgggaaac ctgtcgtgcc agctgcatta atgaatcggc caacgcgcgg   4140
ggagaggcgg tttgcgtatt gggcgctctt ccgcttcctc gctcactgac tcgctgcgct   4200
cggtcgttcg gctgcggcga gcggtatcag ctcactcaaa ggcggtaata cggttatcca   4260
cagaatcagg ggataacgca ggaaagaaca tgtgagcaaa aggccagcaa aaggccagga   4320
accgtaaaaa ggccgcgttg ctggcgtttt tccataggct ccgcccccct gacgagcatc   4380
acaaaaatcg acgctcaagt cagaggtggc gaaacccgac aggactataa agataccagg   4440
cgtttccccc tggaagctcc ctcgtgcgct ctcctgttcc gaccctgccg cttaccggat   4500
acctgtccgc ctttctccct tcgggaagcg tggcgctttc tcatagctca cgctgtaggt   4560
atctcagttc ggtgtaggtc gttcgctcca agctgggctg tgtgcacgaa ccccccgttc   4620
agcccgaccg ctgcgcctta tccggtaact atcgtcttga gtccaacccg gtaagacacg   4680
acttatcgcc actggcagca gccactggta acaggattag cagagcgagg tatgtaggcg   4740
gtgctacaga gttcttgaag tggtggccta actacggcta cactagaaga acagtatttg   4800
gtatctgcgc tctgctgaag ccagttacct tcggaaaaag agttggtagc tcttgatccg   4860
gcaaacaaac caccgctggt agcggttttt tgtttgcaa  gcagcagatt acgcgcagaa   4920
aaaaaggatc tcaagaagat cctttgatct tttctacggg gtctgacgct cagtggaacg   4980
aaaactcacg ttaagggatt ttggtcatga gattatcaaa aaggatcttc acctagatcc   5040
ttttaaatta aaaatgaagt tttaaatcaa tctaaagtat atatgagtaa acttggtctg   5100
acagttacca atgcttaatc agtgaggcac ctatctcagc gatctgtcta tttcgttcat   5160
ccatagttgc ctgactcccc gtcgtgtaga taactacgat acgggagggc ttaccatctg   5220
gccccagtgc tgcaatgata ccgcgagacc cacgctcacc ggctccagat ttatcagcaa   5280
taaaccagcc agccggaagg gccgagcgca gaagtggtcc tgcaacttta tccgcctcca   5340
tccagtctat taattgttgc cgggaagcta gagtaagtag ttcgccagtt aatagtttgc   5400
gcaacgttgt tgccattgct acaggcatcg tggtgtcacg ctcgtcgttt ggtatggctt   5460
cattcagctc cggttcccaa cgatcaaggc gagttacatg atcccccatg ttgtgcaaaa   5520
```

-continued

```
aagcggttag ctccttcggt cctccgatcg ttgtcagaag taagttggcc gcagtgttat    5580
cactcatggt tatggcagca ctgcataatt ctcttactgt catgccatcc gtaagatgct    5640
tttctgtgac tggtgagtac tcaaccaagt cattctgaga atagtgtatg cggcgaccga    5700
gttgctcttg cccggcgtca atacgggata ataccgcgcc acatagcaga actttaaaag    5760
tgctcatcat tggaaaacgt tcttcggggc gaaaactctc aaggatctta ccgctgttga    5820
gatccagttc gatgtaaccc actcgtgcac ccaactgatc ttcagcatct tttactttca    5880
ccagcgtttc tgggtgagca aaaacaggaa ggcaaaatgc cgcaaaaaag ggaataaggg    5940
cgacacggaa atgttgaata ctcatactct tcctttttca atattattga agcatttatc    6000
agggttattg tctcatgagc ggatacatat ttgaatgtat ttagaaaaat aaacaaatag    6060
gggttccgcg cacatttccc cgaaaagtgc cacctgacgt c                        6101
```

<210> SEQ ID NO 4
<211> LENGTH: 354
<212> TYPE: PRT
<213> ORGANISM: artificial sequence
<220> FEATURE:
<223> OTHER INFORMATION: SC-GS

<400> SEQUENCE: 4

```
Met Ala Asn Thr Lys Tyr Asn Glu Glu Phe Leu Leu Tyr Leu Ala Gly
1               5                   10                  15

Phe Val Asp Ala Asp Gly Ser Ile Ile Ala Gln Ile Lys Pro Arg Gln
            20                  25                  30

Ser Arg Lys Phe Lys His Glu Leu Ser Leu Thr Phe Asp Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Gln Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Ala Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Gly Asp Gly Ser Ile Ile Ala Gln Ile Lys Pro Arg Gln Gly Tyr
    210                 215                 220

Lys Phe Lys His Gln Leu Ser Leu Thr Phe Val Thr Gln Lys Thr
225                 230                 235                 240

Gln Arg Arg Trp Phe Leu Asp Lys Leu Val Asp Arg Ile Gly Val Gly
                245                 250                 255

Tyr Val Ala Asp Arg Gly Ser Val Ser Asp Tyr Arg Leu Ser Glu Ile
```

```
              260                 265                 270
Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Leu Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 5
<211> LENGTH: 11446
<212> TYPE: DNA
<213> ORGANISM: Artificial
<220> FEATURE:
<223> OTHER INFORMATION: pCLS6810

<400> SEQUENCE: 5
tcatggtcat agctgtttcc tgtgtgaaat tgttatccgc tcacaattcc acacaacata     60
caggatccac tagcgatgta cgggccagat atacgcgttg acattgatta ttgactagtt    120
attaatagta atcaattacg gggtcattag ttcatagccc atatatggag ttccgcgtta    180
cataacttac ggtaaatggc ccgcctggct gaccgcccaa cgaccccgc ccattgacgt    240 caataatgac gtatgttccc atagtaacgc caatagggac tttccattga cgtcaatggg    300
tggagtattt acggtaaact gcccacttgg cagtacatca agtgtatcat atgccaagta    360
cgccccctat tgacgtcaat gacggtaaat ggcccgcctg gcattatgcc cagtacatga    420
ccttatggga ctttcctact tggcagtaca tctacgtatt agtcatcgct attaccatgg    480
tgatgcggtt ttggcagtac atcaatgggc gtggatagcg gtttgactca cggggatttc    540
caagtctcca ccccattgac gtcaatggga gtttgttttg gcaccaaaat caacgggact    600
ttccaaaatg tcgtaacaac tccgccccat tgacgcaaat gggcggtagg cgtgtacggt    660
gggaggtcta taagcagagc tctctggc taactagaga acccactgct tactggctta    720
tcgaaattaa tacgactcac tatagggaga cccaagctgg ctagccttag gcgcgcctcg    780
cgagtttaaa ccgccaccat ggccgcttat ccttatgacg ttcctgatta cgctggattt    840
atagctgccc cagggtgaga aagtccaagg aggctccgga tccggcggtt ctggatccgg    900
cggttctggt tccgccgcta gcggggggcga ggagctgttc gccggcatcg tgcccgtgct    960
gatcgagctg gacggcgacg tgcacggcca aagttcagc gtgcgcggcg agggcgaggg   1020
cgacgccgac tacggcaagc tggagatcaa gttcatctgc accaccggca agctgcccgt   1080
gccctggccc accctggtga ccaccctctg ctacggcatc cagtgcttcg cccgctaccc   1140
cgagcacatg aagatgaacg acttcttcaa gagcgccatg cccgagggct acatccagga   1200
gcgcaccatc cagttccagg acgacggcaa gtacaagacc cgcggcgagg tgaagttcga   1260
gggcgacacc ctggtgaacc gcatcgagct gaagggcaag gacttcaagg aggacggcaa   1320
catcctgggc cacaagctgg agtacagctt caacagccac aacgtgtaca tccgccccga   1380
caaggccaac aacggcctgg aggctaactt caagacccgc cacaacatcg agggcggcgg   1440
cgtgcagctg gccgaccact accagaccaa cgtgccctg ggcgacggcc ccgtgctgat   1500
```

```
ccccatcaac cactacctga gcactcagac caagatcagc aaggaccgca acgaggcccg   1560
cgaccacatg gtgctcctgg agtccttcag cgcctgctgc cacacccacg gcatggacga   1620
gctgtacagg taacccgggg agcggccgct cgagtctaga gggcccgttt aaacccgctg   1680
atcagcctcg actgtgcctt ctagttgcca gccatctgtt gtttgcccct cccccgtgcc   1740
ttccttgacc ctggaaggtg ccactcccac tgtccttttcc taataaaatg aggaaattgc   1800
atcgcattgt ctgagtaggt gtcattctat tctgggggggt ggggtggggc aggacagcaa   1860
gggggaggat tgggaagaca atagcaggca tgctggggat gcggtgggct ctatggcttc   1920
tgaggcggaa agaacggatc cgcagcctct tcccaccca ccttgggact cagttctgcc   1980
ccagatgaaa ttcagcaccc acatattaaa ttttcagaat ggaaatttaa gctgttccgg   2040
gtgagatcct ttgaaaagac acctgaagaa gctcaaaagg aaaagaagga ttcctttgag   2100
gggaaaccct ctctggagca atctccagca gtcctggaca aggctgatgg tcagaagcca   2160
gtcccaactc agccattgtt aaaagcccac cctaagtttt cgaagaaatt tcacgacaac   2220
gagaaagcaa gaggcaaagc gatccatcaa gccaacttc gacatctctg ccgcatctgt   2280
gggaattctt ttagagctga tgagcacaac aggagatatc cagtccatgg tcctgtggat   2340
ggtaaaaccc taggccttttt acgaaagaag gaaaagagag ctacttcctg gccggacctc   2400
attgccaagg ttttccggat cgatgtgaag gcagatgttg actcgatcca ccccactgag   2460
ttctgccata actgctggag catcatgcac aggaagttta gcagtgcccc atgtgaggtt   2520
tacttcccga ggaacgtgac catggagtgg cacccccaca caccatcctg tgacatctgc   2580
aacactgccc gtcggggact caagaggaag agtcttcagc aaaacttgca gctcagcaaa   2640
aaactcaaaa ctgtgcttga ccaagcaaga caagcccgtc agcacaagag aagagctcag   2700
gcaaggatca gcagcaagga tgtcatgaag aagatcgcca actgcagtaa gatacatctt   2760
agtaccaagc tccttgcagt ggacttccca gagcactttg tgaaatccat ctcctgccag   2820
atctgtgaac acattctggc tgaccctgtg agaccaact gtaagcatgt cttttgccgg   2880
gtctgcattc tcagatgcct caaagtcatg ggcagctatt gtccctcttg ccgatatcca   2940
tgcttcccta ctgacctgga gagtccagtg aagtcctttc tgagcgtctt gaattccctg   3000
atggtgaaat gtccagcaaa agagtgcaat gaggaggtca gtttggaaaa atataatcac   3060
cacatctcaa gtcacaagga atcaaaagag atttttgtgc acattaataa agggggtcga   3120
gtaacgcgtg caggcatgca agctggccgc aataaaatat ctttatttc attacatctg   3180 tgtgttggtt ttttgtgtga atcgtaacta acatacgctc tccatcaaaa caaaacgaaa   3240
caaaacaaac tagcaaaata ggctgtcccc agtgcaagtg caggtgccag aacatttctc   3300
tatcgaagga tctgcgatcg ctccggtgcc cgtcagtggg cagagcgcac atcgcccaca   3360
gtccccgaga agttgggggg aggggtcggc aattgaaccg gtgcctagag aaggtggcgc   3420
ggggtaaact gggaaagtga tgtcgtgtac tggctccgcc ttttcccga gggtggggga   3480 gaaccgtata taagtgcagt agtcgccgtg aacgttcttt ttcgcaacgg gtttgccgcc   3540
agaacacagc tgaagcttcg aggggctcgc atctctcctt cacgcgcccg ccgccctacc   3600
tgaggccgcc atcacgccg gttgagtcgc gttctgccgc ctcccgcctg tggtgcctcc   3660
tgaactgcgt ccgccgtcta ggtaagttta agctcaggt cgagaccggg cctttgtccg   3720
gcgctccctt ggagcctacc tagactcagc cggctctcca cgctttgcct gaccctgctt   3780
gctcaactct acgtctttgt ttcgttttct gttctgcgcc gttacagatc caagctgtga   3840
ccggcgccta cgtaagtgat atctactaga tttatcaaaa agagtgttga cttgtgagcg   3900
```

```
ctcacaattg atacttagat tcatcgagag ggacacgtcg actactaacc ttcttctctt    3960
tcctacagct gagatcaccg gcgaaggagg gccaccatgg cttcttaccc tggacaccag    4020
catgcttctg cctttgacca ggctgccaga tccaggggcc actccaacag gagaactgcc    4080
ctaagaccca gaagacagca ggaagccact gaggtgaggc ctgagcagaa gatgccaacc    4140
ctgctgaggg tgtacattga tggacctcat ggcatgggca agaccaccac cactcaactg    4200
ctggtggcac tgggctccag ggatgacatt gtgtatgtgc ctgagccaat gacctactgg    4260
agagtgctag gagcctctga gaccattgcc aacatctaca ccacccagca caggctggac    4320
cagggagaaa tctctgctgg agatgctgct gtggtgatga cctctgccca gatcacaatg    4380
ggaatgccct atgctgtgac tgatgctgtt ctggctcctc acattggagg agaggctggc    4440
tcttctcatg cccctccacc tgccctgacc ctgatctttg acagacaccc cattgcagcc    4500
ctgctgtgct acccagcagc aaggtacctc atgggctcca tgaccccaca ggctgtgctg    4560
gcttttgtgg ccctgatccc tccaaccctc cctggcacca acattgttct gggagcactg    4620
cctgaagaca gacacattga caggctggca aagaggcaga gacctggaga gagactggac    4680
ctggccatgc tggctgcaat cagaagggtg tatggactgc tggcaaacac tgtgagatac    4740
ctccagtgtg gaggctcttg gagagaggac tggggacagc tctctggaac agcagtgccc    4800
cctcaaggag ctgagcccca gtccaatgct ggtccaagac cccacattgg ggacaccctg    4860
ttcaccctgt tcagagcccc tgagctgctg gctcccaatg gagacctgta caatgtgttt    4920
gcctgggctc tggatgttct agccaagagg ctgaggtcca tgcatgtgtt catcctggac    4980
tatgaccagt cccctgctgg atgcagagat gctctgctgc aactaacctc tggcatggtg    5040
cagacccatg tgaccacccc tggcagcatc cccaccatct gtgacctagc cagaaccttt    5100
gccagggaga tgggagaggc caactaaacc tgagctagct cgacatgata agatacattg    5160
atgagtttgg acaaaccaca actagaatgc agtgaaaaaa atgctttatt tgtgaaattt    5220
gtgatgctat tgctttattt gtgaaatttg tgatgctatt gctttatttg taaccattat    5280
aagctgcaat aaacaagtta acaacaacaa ttgcattcat tttatgtttc aggttcaggg    5340
ggaggtgtgg gaggttttt aaagcaagta aaacctctac aaatgtggta gatccatttt    5400
tggcgtaatc atggtcatag ctgtttcctg tgtgaaattg ttatccgctc acaattccac    5460
acaacatacg agccggaagc ataaagtgta agcctggggt gcctaatga gtgagctaac    5520 tcacattaat tgcgttgcgc tcactgcccg ctttccagtc gggaaacctg tcgtgccagc    5580
tgcattaatg aatcggccaa cgcgcgggga gaggcggttt gcgtattggg cgctcttccg    5640
cttcctcgct cactgactcg ctgcgctcgg tcgttcggct gcggcgagcg gtatcagctc    5700
actcaaaggc ggtaatacgg ttatccacag aatcaggggga taacgcagga aagaacatgt    5760
gagcaaaagg ccagcaaaag gccaggaacc gtaaaaaggc cgcgttgctg gcgttttttcc    5820 ataggctccg ccccccctgac gagcatcaca aaaatcgacg ctcaagtcag aggtggcgaa    5880
acccgacagg actataaaga taccaggcgt ttccccctgg aagctccctc gtgcgctctc    5940
ctgttccgac cctgccgctt accggatacc tgtccgcctt tctcccttcg ggaagcgtgg    6000
cgctttctca tagctcacgc tgtaggtatc tcagttcggt gtaggtcgtt cgctccaagc    6060
tgggctgtgt gcacgacccc cccgttcagc ccgaccgctg cgccttatcc ggtaactatc    6120
gtcttgagtc caacccggta agacacgact tatcgccact ggcagcagcc actggtaaca    6180
ggattagcag agcgaggtat gtaggcggtg ctacagagtt cttgaagtgg tggcctaact    6240
```

-continued

```
acggctacac tagaagaaca gtatttggta tctgcgctct gctgaagcca gttaccttcg      6300
gaaaaagagt tggtagctct tgatccggca aacaaaccac cgctggtagc ggtggttttt      6360
ttgtttgcaa gcagcagatt acgcgcagaa aaaaggatc tcaagaagat cctttgatct      6420
tttctacggg gtctgacgct cagtggaacg aaaactcacg ttaagggatt ttggtcatga      6480
gattatcaaa aaggatcttc acctagatcc ttttaaatta aaaatgaagt tttaaatcaa      6540
tctaaagtat atatgagtaa acttggtctg acagttacca atgcttaatc agtgaggcac      6600
ctatctcagc gatctgtcta tttcgttcat ccatagttgc ctgactcccc gtcgtgtaga      6660
taactacgat acgggagggc ttaccatctg gccccagtgc tgcaatgata ccgcgagacc      6720
cacgctcacc ggctccagat ttatcagcaa taaaccagcc agccggaagg gccgagcgca      6780
gaagtggtcc tgcaacttta tccgcctcca tccagtctat taattgttgc cgggaagcta      6840
gagtaagtag ttcgccagtt aatagtttgc gcaacgttgt tgccattgct acaggcatcg      6900
tggtgtcacg ctcgtcgttt ggtatggctt cattcagctc cggttcccaa cgatcaaggc      6960
gagttacatg atcccccatg ttgtgcaaaa aagcggttag ctccttcggt cctccgatcg      7020
ttgtcagaag taagttggcc gcagtgttat cactcatggt tatggcagca ctgcataatt      7080
ctcttactgt catgccatcc gtaagatgct tttctgtgac tggtgagtac tcaaccaagt      7140
cattctgaga atagtgtatg cggcgaccga gttgctcttg cccggcgtca atacgggata      7200
ataccgcgcc acatagcaga actttaaaag tgctcatcat tggaaaacgt tcttcggggc      7260
gaaaactctc aaggatctta ccgctgttga tccagttc gatgtaaccc actcgtgcac      7320
ccaactgatc ttcagcatct tttactttca ccagcgtttc tgggtgagca aaaacaggaa      7380
ggcaaaatgc cgcaaaaaag gaataaggg cgacacggaa atgttgaata ctcatactct      7440
tcctttttca atattattga agcatttatc agggttattg tctcatgagc ggatacatat      7500
ttgaatgtat ttagaaaaat aaacaaatag gggttccgcg cacatttccc cgaaaagtgc      7560
cacctgacgt ctaagaaacc attattatca tgacattaac ctataaaaat aggcgtatca      7620
cgaggccctt tcgtctcgcg cgtttcggtg atgacggtga aaacctctga cacatgcagc      7680
tcccggagac ggtcacagct tgtctgtaag cggatgccgg gagcagacaa gcccgtcagg      7740
gcgcgtcagc gggtgttggc gggtgtcggg gctggcttaa ctatgcggca tcagagcaga      7800
ttgtactgag agtgcaccat atgcggtgtg aaataccgca cagatgcgta aggagaaaat      7860
accgcatcag gcgccaatat taaacttgat gagctctaga gatggtcatg cattttaaaa      7920
agaattactc aaaatattgt cttggaatac cagagagcaa gtgctttaag tataggctgg      7980
gaagtaaaat gctaaaggaa tgagaaggca tttggggttg agttcaacct aagaggcagg      8040
ggagccacag ggaaagacct agcacctgcc acagaagaga attaggaagc agaattgaac      8100
tataagcaat tttgaggtgt tcgttgggct gcagttgaaa tattttttga ggttaatgag      8160
acatttgaaa tggccgtgta ttgttaact cttgcatagt cctgcatagg gaacaatcta      8220
ataggatttc tctgtgaatc aagtcttaga aatttgcttt taattttat gaaaaacgcc      8280 catttctttg ttttgagac agagtcctgc tctgtcatcc aggctgggtt gcagtggcgt      8340
gatcttggcc cactgcaatc tctgcctcct gggttcaggc aattttcctg tctcagcctc      8400
ccgagtagct gggatttcaa gtgcctgcca ccatgcccgg ctaaattttt ttgtattttt      8460
ggtacagatg gagtatcacc atgttggcca ggctggtctc gaactcctga cctcaagtga      8520
ttcaccagcc ttgacctccc aaagtgttgg gatcacaggc atgagccact gtgcctgtgc      8580
cccaaaacac caatttctga tgtgtgatgc atgtaagata gaacaaactt cagtaaagcg      8640
```

```
gggacttgaa aagaggcttt ggtaacagct gtcagcatta acccttgccc ctccgtacct    8700
cctaatccca cccctgctca aagtatgttc atctgagaat ttgtctccat aactatgtga    8760
ctataaaaat tctcatcgat tttgttagtt gatcaattga gggaaaaaca tatgttactt    8820
gatataactg gtgggtcaaa agaattaacc caggcaaatt tgagataggt ggatgggatg    8880
atggattgaa aatacagctg ctctcttttcc aatcatgtac taagtaattt gggaaagatt    8940
gatctaattg ggtctagaga gtacacttca catggcattg tttgactttt tttctgcatc    9000
gctagcgatc tgtgcattac aactcaaatc agtcgggttt cctggcatat gtaattgcca    9060
atgttttta ccagaagaga aacattactc ccacctcttc ttattatgtt acaaactata    9120
gtgctaatga ccatcgacca acagtgactt tcaggatgac ctgtgtgagt tttatctgaa    9180
accatgtgaa ttttcatct taaaagtccc ttagaatctc agtctatgta cactcaggtt    9240
tgttgcaggt ttagagttcc gtgttttttg tttctaatgt agacacagcc ttataattta    9300
caacagcatt cactaattaa aattgtaagc ataattacta tccacgatac ttattattag    9360
tttgcattca taaagctcaa aattcacttc atccttcaa gtagtgaata attagtttct    9420
ttgggtttgc agctttatca tccttttatg acccatttgg aagaaataaa caaccaaccc    9480
cctggaagac tgctttaaaa agctggaaat acattgtcca gctagtacaa tgaggctaat    9540
acaatgtgga aaatattact tttctttgat tttagtagcc tgtttatctt tacatttact    9600
gaacaaataa ctattgagca cctaatgtat actgggaccc ttggggaggc aaagatgaat    9660
caaagattct gtccttaaag accttaagac gcgttgacat tgattattga ctagttatta    9720
atagtaatca attacggggt cattagttca tagcccatat atggagttcc gcgttacata    9780
acttacggta aatggcccgc ctggctgacc gcccaacgac ccccgcccat tgacgtcaat    9840
aatgacgtat gttcccatag taacgccaat agggactttc cattgacgtc aatgggtgga    9900
gtatttacgg taaactgccc acttggcagt acatcaagtg tatcatatgc caagtacgcc    9960
ccctattgac gtcaatgacg gtaaatggcc cgcctggcat tatgcccagt acatgacctt   10020
atgggacttt cctacttggc agtacatcta cgtattagtc atcgctatta ccatggtgat   10080
gcggttttgg cagtacatca atgggcgtgg atagcggttt gactcacggg gatttccaag   10140
tctccacccc attgacgtca atgggagttt gttttggcac caaaatcaac gggactttcc   10200
aaaatgtcgt aacaactccg ccccattgac gcaaatgggc ggtaggcgtg tacggtggga   10260
ggtctatata agcagagctc cccgggagct gtatatcca ttttcggatc tgatcaagag   10320
acaggatgag gatcgtttcg catgattgaa caagatggat tgcacgcagg ttctccggcc   10380
gcttgggtgg agaggctatt cggctatgac tgggcacaac agacaatcgg ctgctctgat   10440
gccgccgtgt tccggctgtc agcgcagggg cgcccggttc ttttgtcaa gaccgacctg   10500
tccggtgccc tgaatgaact gcaggacgag gcagcgcggc tatcgtggct ggccacgacg   10560
ggcgttcctt gcgcagctgt gctcgacgtt gtcactgaag cggaaggga ctggctgcta   10620
ttgggcgaag tgccggggca ggatctcctg tcatctcacc ttgctcctgc cgagaaagta   10680
tccatcatgg ctgatgcaat gcggcggctg catacgcttg atccggctac ctgcccattc   10740
gaccaccaag cgaaacatcg catcgagcga gcacgtactc ggatggaagc cggtcttgtc   10800
gatcaggatg atctggacga agagcatcag gggctcgcgc cagccgaact gttcgccagg   10860
ctcaaggcgc gcatgcccga cggcgaggat ctcgtcgtga cccatggcga tgcctgcttg   10920
ccgaatatca tggtggaaaa tggccgcttt tctggattca tcgactgtgg ccggctgggt   10980
```

```
gtggcggacc gctatcagga catagcgttg gctacccgtg atattgctga agagcttggc    11040
ggcgaatggg ctgaccgctt cctcgtgctt tacggtatcg ccgctcccga ttcgcagcgc    11100
atcgccttct atcgccttct tgacgagttc ttctgattaa ttaacaggac tgaccgtgct    11160
acgagatttc gattccaccg ccgccttcta tgaaaggttg ggcttcggaa tcgttttccg    11220
ggacgccggc tggatgatcc tccagcgcgg ggatctcatg ctggagttct tcgcccaccc    11280
caacttgttt attgcagctt ataatggtta caaataaagc aatagcatca caaatttcac    11340
aaataaagca ttttttttcac tgcattctag ttgtggtttg tccaaactca tcaatgtatc    11400
ttatcatgtc tgtataccgt cgacctctag ctagagcttg gcgtaa                  11446
```

<210> SEQ ID NO 6
<211> LENGTH: 11442
<212> TYPE: DNA
<213> ORGANISM: Artificial
<220> FEATURE:
<223> OTHER INFORMATION: pCLS6663

<400> SEQUENCE: 6

```
tcatggtcat agctgtttcc tgtgtgaaat tgttatccgc tcacaattcc acacaacata     60
caggatccac tagcgatgta cgggccagat atacgcgttg acattgatta ttgactagtt    120
attaatagta atcaattacg ggtcattag ttcatagccc atatatggag ttccgcgtta    180
cataacttac ggtaaatggc ccgcctggct gaccgcccaa cgacccccgc ccattgacgt    240
caataatgac gtatgttccc atagtaacgc caatagggac tttccattga cgtcaatggg    300
tggagtattt acggtaaact gcccacttgg cagtacatca agtgtatcat atgccaagta    360
cgccccctat tgacgtcaat gacggtaaat ggcccgcctg gcattatgcc cagtacatga    420
ccttatggga ctttcctact tggcagtaca tctacgtatt agtcatcgct attaccatgg    480
tgatgcggtt ttggcagtac atcaatgggc gtggatagcg gtttgactca cggggatttc    540
caagtctcca ccccattgac gtcaatggga gtttgttttg gcaccaaaat caacgggact    600
ttccaaaatg tcgtaacaac tccgccccat tgacgcaaat gggcggtagg cgtgtacggt    660
gggaggtcta tataagcaga gctctctggc taactagaga acccactgct tactggctta    720
tcgaaattaa tacgactcac tatagggaga cccaagctgg ctagccttag gcgcgcctcg    780
cgagtttaaa ccgccaccat ggcgcttat ccttatgacg ttcctgatta cgctggattt    840
acgctaggga taacagggta atatggaggc tccggatccg gcggttctgg atccggcggt    900
tctggttccg ccgctagcgg gggcgaggag ctgttcgccg catcgtgcc cgtgctgatc    960 gagctggacg gcgacgtgca cggccacaag ttcagcgtgc gcggcgaggg cgagggcgac   1020
gccgactacg gcaagctgga gatcaagttc atctgcacca ccggcaagct gcccgtgccc   1080
tggcccaccc tggtgaccac cctctgctac ggcatccagt gcttcgcccg ctaccccgag   1140
cacatgaaga tgaacgactt cttcaagagc gccatgcccg agggctacat ccaggagcgc   1200
accatccagt ccaggacga cggcaagtac aagacccgcg cgaggtgaa gttcgagggc   1260 gacaccctgg tgaaccgcat cgagctgaag ggcaaggact tcaaggagga cggcaacatc   1320 ctggggccaca agctggagta cagcttcaac agccacaacg tgtacatccg ccccgacaag   1380
gccaacaacg gcctggaggc taacttcaag acccgccaca acatcgaggg cggcggcgtg   1440
cagctggccg accactacca gaccaacgtg ccctgggcg acggccccgt gctgatcccc   1500
atcaaccact acctgagcac tcagaccaag atcagcaagg accgcaacga ggcccgcgac   1560
cacatggtgc tcctggagtc cttcagcgcc tgctgccaca cccacggcat ggacgagctg   1620
```

```
tacaggtaac ccggggagcg gccgctcgag tctagagggc ccgtttaaac ccgctgatca    1680
gcctcgactg tgccttctag ttgccagcca tctgttgttt gccccctcccc cgtgccttcc    1740 ttgaccctgg aaggtgccac tcccactgtc ctttcctaat aaaatgagga aattgcatcg    1800
cattgtctga gtaggtgtca ttctattctg ggggtgggg tggggcagga cagcaagggg    1860
gaggattggg aagacaatag caggcatgct ggggatgcgg tgggctctat ggcttctgag    1920
gcggaaagaa cggatccgca gcctcttccc cacccaccttt gggactcagt tctgccccag    1980
atgaaattca gcacccacat attaaatttt cagaatggaa atttaagctg ttccgggtga    2040
gatcctttga aaagacacct gaagaagctc aaaaggaaaa gaaggattcc tttgagggga    2100
aaccctctct ggagcaatct ccagcagtcc tggacaaggc tgatggtcag aagccagtcc    2160
caactcagcc attgttaaaa gcccacccta agttttcgaa gaaatttcac gacaacgaga    2220
aagcaagagg caaagcgatc catcaagcca accttcgaca tctctgccgc atctgtggga    2280
attcttttag agctgatgag cacaacagga gatatccagt ccatggtcct gtggatggta    2340
aaaccctagg ccttttacga aagaaggaaa agagagctac ttcctggccg acctcattg    2400 ccaaggtttt ccggatcgat gtgaaggcag atgttgactc gatccacccc actgagttct    2460
gccataactg ctggagcatc atgcacagga gtttagcag tgccccatgt gaggtttact    2520
tcccgaggaa cgtgaccatg gagtggcacc cccacacacc atcctgtgac atctgcaaca    2580
ctgcccgtcg gggactcaag aggaagagtc ttcagccaaa cttgcagctc agcaaaaaac    2640
tcaaaactgt gcttgaccaa gcaagacaag cccgtcagca aagagaaga gctcaggcaa    2700 ggatcagcag caaggatgtc atgaagaaga tcgccaactg cagtaagata catcttagta    2760
ccaagctcct tgcagtggac ttcccagagc actttgtgaa atccatctcc tgccagatct    2820
gtgaacacat tctggctgac cctgtggaga ccaactgtaa gcatgtcttt tgccgggtct    2880
gcattctcag atgcctcaaa gtcatgggca gctattgtcc ctcttgccga tatccatgct    2940
tccctactga cctggagagt ccagtgaagt cctttctgag cgtcttgaat tccctgatgg    3000
tgaaatgtcc agcaaaagag tgcaatgagg aggtcagttt ggaaaaatat aatcaccaca    3060
tctcaagtca caaggaatca aaagagattt ttgtgcacat taataaaggg ggtcgagtaa    3120
cgcgtgcagg catgcaagct ggccgcaata aaatatcttt attttcatta catctgtgtg    3180
ttggtttttt gtgtgaatcg taactaacat acgctctcca tcaaaacaaa acgaaacaaa    3240
acaaactagc aaaataggct gtccccagtg caagtgcagg tgccagaaca tttctctatc    3300
gaaggatctg cgatcgctcc ggtgcccgtc agtgggcaga gcgcacatcg cccacagtcc    3360
ccgagaagtt gggggggggg gtcggcaatt gaaccggtgc ctagagaagg tggcgcgggg    3420
taaactggga aagtgatgtc gtgtactggc tccgcctttt tcccgagggt ggggagaac    3480 cgtatataag tgcagtagtc gccgtgaacg ttcttttcg caacgggttt gccgccagaa    3540
cacagctgaa gcttcgaggg gctcgcatct tccttcacg cgcccgccgc cctacctgag    3600
gccgccatcc acgccggttg agtcgcgttc tgccgcctcc cgcctgtggt gcctcctgaa    3660
ctgcgtccgc cgtctaggta agtttaaagc tcaggtcgag accgggcctt tgtccggcgc    3720
tcccttggag cctacctaga ctcagccggc tctccacgct ttgcctgacc ctgcttgctc    3780
aactctacgt cttgttcgt ttttctgttc tgcgccgtta cagatccaag ctgtgaccgg    3840
cgcctacgta agtgatatct actagattta tcaaaaagag tgttgacttg tgagcgctca    3900
caattgatac ttagattcat cgagagggac acgtcgacta ctaaccttct tctctttcct    3960
```

```
acagctgaga tcaccggcga aggagggcca ccatggcttc ttaccctgga caccagcatg    4020
cttctgcctt tgaccaggct gccagatcca ggggccactc aacaggaga actgccctaa     4080 gacccagaag acagcaggaa gccactgagg tgaggcctga gcagaagatg ccaaccctgc    4140
tgagggtgta cattgatgga cctcatggca tgggcaagac caccaccact caactgctgg    4200
tggcactggg ctccagggat gacattgtgt atgtgcctga gccaatgacc tactggagag    4260
tgctaggagc ctctgagacc attgccaaca tctacaccac ccagcacagg ctggaccagg    4320
gagaaatctc tgctggagat gctgctgtgg tgatgacctc tgcccagatc acaatgggaa    4380
tgccctatgc tgtgactgat gctgttctgg ctcctcacat ggaggagag gctggctctt     4440 ctcatgcccc tccacctgcc ctgaccctga tctttgacag acaccccatt gcagccctgc    4500
tgtgctaccc agcagcaagg tacctcatgg gctccatgac cccacaggct gtgctggctt    4560
ttgtggccct gatccctcca accctccctg gcaccaacat tgttctggga gcactgcctg    4620
aagacagaca cattgacagg ctggcaaaga ggcagagacc tggagagaga ctggacctgg    4680
ccatgctggc tgcaatcaga agggtgtatg gactgctggc aaacactgtg agatacctcc    4740
agtgtggagg ctcttggaga gaggactggg gacagctctc tggaacagca gtgccccctc    4800
aaggagctga gccccagtcc aatgctggtc aagaccccca cattggggac accctgttca    4860
ccctgttcag agcccctgag ctgctggctc ccaatggaga cctgtacaat gtgtttgcct    4920
gggctctgga tgttctagcc aagaggctga ggtccatgca tgtgttcatc ctggactatg    4980
accagtcccc tgctggatgc agagatgctc tgctgcaact aacctctggc atggtgcaga    5040
cccatgtgac caccccctggc agcatcccca ccatctgtga cctagccaga acctttgcca   5100
gggagatggg agaggccaac taaacctgag ctagctcgac atgataagat acattgatga    5160
gtttggacaa accacaacta gaatgcagtg aaaaaaatgc tttatttgtg aaatttgtga    5220
tgctattgct ttatttgtga aatttgtgat gctattgctt tatttgtaac cattataagc    5280
tgcaataaac aagttaacaa caacaattgc attcatttta tgtttcaggt tcagggggag    5340
gtgtgggagg ttttttaaag caagtaaaac ctctacaaat gtggtagatc cattttttggc   5400 gtaatcatgg tcatagctgt ttcctgtgtg aaattgttat ccgctcacaa ttccacacaa    5460
catacgagcc ggaagcataa agtgtaaagc ctggggtgcc taatgagtga gctaactcac    5520
attaattgcg ttgcgctcac tgcccgcttt ccagtcggga aacctgtcgt gccagctgca    5580
ttaatgaatc ggccaacgcg cggggagagg cggtttgcgt attgggcgct cttccgcttc    5640
ctcgctcact gactcgctgc gctcggtcgt tcggctgcgg cgagcggtat cagctcactc    5700
aaaggcggta atacggttat ccacagaatc aggggataac gcaggaaaga acatgtgagc    5760
aaaaggccag caaaaggcca ggaaccgtaa aaaggccgcg ttgctggcgt ttttccatag    5820
gctccgcccc cctgacgagc atcacaaaaa tcgacgctca agtcagaggt ggcgaaaccc    5880
gacaggacta taaagatacc aggcgtttcc cctggaagc tccctcgtgc gctctcctgt     5940
tccgaccctg ccgcttaccg gatacctgtc cgcctttctc ccttcgggaa gcgtggcgct    6000
ttctcatagc tcacgctgta ggtatctcag ttcggtgtag tcgttcgct ccaagctggg     6060 ctgtgtgcac gaccccccg ttcagcccga ccgctgcgcc ttatccggta actatcgtct     6120
tgagtccaac ccggtaagac acgacttatc gccactggca gcagccactg gtaacaggat    6180
tagcagagcg aggtatgtag gcggtgctac agagttcttg aagtggtggc ctaactacgg    6240
ctacactaga agaacagtat ttggtatctg cgctctgctg aagccagtta ccttcggaaa    6300
aagagttggt agctcttgat ccggcaaaca aaccaccgct ggtagcggtg gttttttttgt   6360
```

```
ttgcaagcag cagattacgc gcagaaaaaa aggatctcaa gaagatcctt tgatcttttc   6420 tacgggtct gacgctcagt ggaacgaaaa ctcacgttaa gggattttgg tcatgagatt    6480
atcaaaaagg atcttcacct agatcctttt aaattaaaaa tgaagtttta aatcaatcta   6540
aagtatatat gagtaaactt ggtctgacag ttaccaatgc ttaatcagtg aggcacctat   6600
ctcagcgatc tgtctatttc gttcatccat agttgcctga ctccccgtcg tgtagataac   6660
tacgatacgg gagggcttac catctggccc cagtgctgca atgataccgc gagacccacg   6720
ctcaccggct ccagatttat cagcaataaa ccagccagcc ggaagggccg agcgcagaag   6780
tggtcctgca actttatccg cctccatcca gtctattaat tgttgccggg aagctagagt   6840
aagtagttcg ccagttaata gtttgcgcaa cgttgttgcc attgctacag gcatcgtggt   6900
gtcacgctcg tcgtttggta tggcttcatt cagctccggt tcccaacgat caaggcgagt   6960
tacatgatcc cccatgttgt gcaaaaaagc ggttagctcc ttcggtcctc cgatcgttgt   7020
cagaagtaag ttggccgcag tgttatcact catggttatg gcagcactgc ataattctct   7080
tactgtcatg ccatccgtaa gatgcttttc tgtgactggt gagtactcaa ccaagtcatt   7140
ctgagaatag tgtatgcggc gaccgagttg ctcttgcccg gcgtcaatac gggataatac   7200
cgcgccacat agcagaactt taaaagtgct catcattgga aaacgttctt cggggcgaaa   7260
actctcaagg atcttaccgc tgttgagatc cagttcgatg taacccactc gtgcacccaa   7320
ctgatcttca gcatctttta ctttcaccag cgtttctggg tgagcaaaaa caggaaggca   7380
aaatgccgca aaaagggaa taaggcgac acggaaatgt tgaatactca tactcttcct    7440
ttttcaatat tattgaagca tttatcaggg ttattgtctc atgagcggat acatatttga   7500
atgtatttag aaaaataaac aatagggggt tccgcgcaca tttccccgaa aagtgccacc   7560
tgacgtctaa gaaaccatta ttatcatgac attaacctat aaaaataggc gtatcacgag   7620 gcccttcgt ctcgcgcgtt tcggtgatga cggtgaaaac ctctgacaca tgcagctccc    7680
ggagacggtc acagcttgtc tgtaagcgga tgccgggagc agacaagccc gtcagggcgc   7740
gtcagcgggt gttggcgggt gtcggggctg gcttaactat gcggcatcag agcagattgt   7800
actgagagtg caccatatgc ggtgtgaaat accgcacaga tgcgtaagga gaaaataccg   7860
catcaggcgc caatattaaa cttgatgagc tctagagatg gtcatgcatt ttaaaaagaa   7920
ttactcaaaa tattgtcttg gaataccaga gagcaagtgc tttaagtata ggctgggaag   7980
taaaatgcta aaggaatgag aaggcatttg gggttgagtt caacctaaga ggcaggggag   8040
ccacagggaa agacctagca cctgccacag aagagaatta ggaagcagaa ttgaactata   8100
agcaattttg aggtgttcgt tgggctgcag ttgaaatatt ttttgaggtt aatgagacat   8160
ttgaaatggc cgtgtattgt ttaactcttg catagtcctg catagggaac aatctaatag   8220
gatttctctg tgaatcaagt cttagaaatt tgcttttaat ttttatgaaa aacgcccatt   8280
tctttgtttt tgagacagag tcctgctctg tcatccaggc tgggttgcag tggcgtgatc   8340
ttggcccact gcaatctctg cctcctgggt tcaggcaatt ttcctgtctc agcctcccga   8400
gtagctggga tttcaagtgc ctgccaccat gcccggctaa attttttgt attttttggta   8460 cagatggagt atcaccatgt tggccaggct ggtctcgaac tcctgacctc aagtgattca   8520
ccagccttga cctcccaaag tgttgggatc acaggcatga gccactgtgc ctgtgcccca   8580
aaacaccaat ttctgatgtg tgatgcatgt aagatagaac aaacttcagt aaagcgggga   8640
cttgaaaaga ggctttggta acagctgtca gcattaaccc ttgcccctcc gtacctccta   8700
```

```
atcccacccc tgctcaaagt atgttcatct gagaatttgt ctccataact atgtgactat    8760
aaaaattctc atcgattttg ttagttgatc aattgaggga aaaacatatg ttacttgata    8820
taactggtgg gtcaaaagaa ttaacccagg caaatttgag ataggtggat gggatgatgg    8880
attgaaaata cagctgctct cttttccaatc atgtactaag taatttggga aagattgatc    8940
taattgggtc tagagagtac acttcacatg gcattgtttg actttttttc tgcatcgcta    9000
gcgatctgtg cattacaact caaatcagtc gggtttcctg gcatatgtaa ttgccaatgt    9060
tttttaccag aagagaaaca ttactcccac ctcttcttat tatgttacaa actatagtgc    9120
taatgaccat cgaccaacag tgactttcag gatgacctgt gtgagtttta tctgaaacca    9180
tgtgaatttt tcatcttaaa agtcccttag aatctcagtc tatgtacact caggtttgtt    9240
gcaggtttag agttccgtgt ttttttgtttc taatgtagac acagccttat aatttacaac    9300
agcattcact aattaaaatt gtaagcataa ttactatcca cgatacttat tattagtttg    9360
cattcataaa gctcaaaatt cacttcatcc tttcaagtag tgaataatta gtttctttgg    9420
gtttgcagct ttatcatcct tttatgaccc atttggaaga aataaacaac caacccctg    9480 gaagactgct ttaaaaagct ggaaatacat tgtccagcta gtacaatgag gctaatacaa    9540
tgtggaaaat attactttttc tttgatttta gtagcctgtt tatctttaca tttactgaac    9600
aaataactat tgagcaccta atgtatactg ggacccttgg ggaggcaaag atgaatcaaa    9660
gattctgtcc ttaaagacct taagacgcgt tgacattgat tattgactag ttattaatag    9720
taatcaatta cggggtcatt agttcatagc ccatatatgg agttccgcgt tacataactt    9780
acggtaaatg gcccgcctgg ctgaccgccc aacgaccccc gcccattgac gtcaataatg    9840
acgtatgttc ccatagtaac gccaataggg actttccatt gacgtcaatg ggtggagtat    9900
ttacggtaaa ctgcccactt ggcagtacat caagtgtatc atatgccaag tacgccccct    9960
attgacgtca atgacggtaa atggcccgcc tggcattatg cccagtacat gaccttatgg   10020
gactttccta cttggcagta catctacgta ttagtcatcg ctattaccat ggtgatgcgg   10080 tttttggcagt acatcaatgg gcgtggatag cggtttgact cacggggatt ccaagtctc   10140 caccccattg acgtcaatgg gagtttgttt tggcaccaaa atcaacggga ctttccaaaa   10200
tgtcgtaaca actccgcccc attgacgcaa atgggcggta ggcgtgtacg gtgggaggtc   10260
tatataagca gagctcccccg ggagcttgta tatccatttt cggatctgat caagagacag   10320
gatgaggatc gtttcgcatg attgaacaag atggattgca cgcaggttct ccggccgctt   10380
gggtggagag gctattcggc tatgactggg cacaacagac aatcggctgc tctgatgccg   10440
ccgtgttccg gctgtcagcg caggggcgcc cggttcttttt tgtcaagacc gacctgtccg   10500
gtgccctgaa tgaactgcag gacgaggcag cgcggctatc gtggctggcc acgacgggcg   10560
ttccttgcgc agctgtgctc gacgttgtca ctgaagcggg aagggactgg ctgctattgg   10620
gcgaagtgcc ggggcaggat ctcctgtcat ctcaccttgc tcctgccgag aaagtatcca   10680
tcatggctga tgcaatgcgg cggctgcata cgcttgatcc ggctacctgc ccattcgacc   10740
accaagcgaa acatcgcatc gagcgagcac gtactcggat ggaagccggt cttgtcgatc   10800
aggatgatct ggacgaagag catcaggggc tcgcgccagc cgaactgttc gccaggctca   10860
aggcgcgcat gcccgacggc gaggatctcg tcgtgaccca tggcgatgcc tgcttgccga   10920
atatcatggt ggaaaatggc cgcttttctg gattcatcga ctgtggccgg ctgggtgtgg   10980
cggaccgcta tcaggacata gcgttggcta cccgtgatat tgctgaagag cttggcggcg   11040
aatgggctga ccgcttcctc gtgctttacg gtatcgccgc tcccgattcg cagcgcatcg   11100
```

```
cttctatcg ccttcttgac gagttcttct gattaattaa caggactgac cgtgctacga    11160
gatttcgatt ccaccgccgc cttctatgaa aggttgggct tcggaatcgt tttccgggac    11220
gccggctgga tgatcctcca gcgcggggat ctcatgctgg agttcttcgc ccaccccaac    11280
ttgtttattg cagcttataa tggttacaaa taaagcaata gcatcacaaa tttcacaaat    11340
aaagcatttt tttcactgca ttctagttgt ggtttgtcca aactcatcaa tgtatcttat    11400
catgtctgta taccgtcgac ctctagctag agcttggcgt aa                       11442
```

<210> SEQ ID NO 7
<211> LENGTH: 163
<212> TYPE: PRT
<213> ORGANISM: Chlamydomonas reinhardtii

<400> SEQUENCE: 7

```
Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Thr Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro
```

<210> SEQ ID NO 8
<211> LENGTH: 22
<212> TYPE: DNA
<213> ORGANISM: Artificial
<220> FEATURE:
<223> OTHER INFORMATION: C1221 target

<400> SEQUENCE: 8

```
caaaacgtcg tacgacgttt tg                                              22
```

<210> SEQ ID NO 9
<211> LENGTH: 24
<212> TYPE: DNA
<213> ORGANISM: Artificial
<220> FEATURE:
<223> OTHER INFORMATION: SC-GS target

<400> SEQUENCE: 9

```
ctgccccagg gtgagaaagt ccaa                                            24
```

<210> SEQ ID NO 10

<211> LENGTH: 22
<212> TYPE: DNA
<213> ORGANISM: Artificial
<220> FEATURE:
<223> OTHER INFORMATION: SC-RAG target

<400> SEQUENCE: 10
tgttctcagg tacctcagcc ag                                                    22

<210> SEQ ID NO 11
<211> LENGTH: 354
<212> TYPE: PRT
<213> ORGANISM: artificial sequence
<220> FEATURE:
<223> OTHER INFORMATION: SC-RAG

<400> SEQUENCE: 11

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Asn Pro Asn Gln
            20                  25                  30

Ser Ser Lys Phe Lys His Arg Leu Arg Leu Thr Phe Tyr Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Gln Tyr Val Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Gly Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Arg Gln Ser Asn
    210                 215                 220

Lys Phe Lys His Gln Leu Ser Leu Thr Phe Ala Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Asp Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
              325                 330                 335

Glu Thr Val Arg Ala Val Leu Asp Ser Leu Ser Glu Lys Lys Ser
              340                 345                 350

Ser Pro

<210> SEQ ID NO 12
<211> LENGTH: 6119
<212> TYPE: DNA
<213> ORGANISM: Artificial
<220> FEATURE:
<223> OTHER INFORMATION: pCLS0099

<400> SEQUENCE: 12

| | | | | | | |
|---|---|---|---|---|---|---|
| gacggatcgg | gagatctccc | gatccctat | ggtgcactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggag | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| gtttaaactt | aagcttggta | ccgagctcgg | atccaccggt | cgccaccatg | gtgagcaagg | 960 |
| gcgaggagct | gttcaccggg | gtggtgccca | tcctggtcga | gctggacggc | gacgtaaacg | 1020 |
| gccacaagtt | cagcgtgtcc | ggcgagggcg | agggcgatgc | cacctacggc | aagctgaccc | 1080 |
| tgaagttcat | ctgcaccacc | ggcaagctgc | ccgtgccctg | gcccaccctc | gtgaccaccc | 1140 |
| tgacctacgg | cgtgcagtgc | ttcagccgct | accccgacca | catgaagcag | cacgacttct | 1200 |
| tcaagtccgc | catgcccgaa | ggctacgtcc | aggagcgcac | catcttcttc | aaggacgacg | 1260 |
| gcaactacaa | gacccgcgcc | gaggtgaagt | tcgaggcga | cacctggtg | aaccgcatcg | 1320 |
| agctgaaggg | catcgacttc | aaggaggacg | gcaacatcct | ggggcacaag | ctggagtaca | 1380 |
| actacaacag | ccacaacgtc | tatatcatgg | ccgacaagca | gaagaacggc | atcaaggtga | 1440 |
| acttcaagat | ccgccacaac | atcgaggacg | gcagcgtgca | gctcgccgac | cactaccagc | 1500 |
| agaacacccc | catcggcgac | ggccccgtgc | tgctgcccga | caaccactac | ctgagcaccc | 1560 |
| agtccgccct | gagcaaagac | cccaacgaga | agcgcgatca | catggtcctg | ctggagttcg | 1620 |
| tgaccgccgc | cgggatcact | ctcggcatgg | acgagctgta | caagtaaagc | ggccgcgtcg | 1680 |
| agtctagagg | gcccgtttaa | acccgctgat | cagcctcgac | tgtgccttct | agttgccagc | 1740 |
| catctgttgt | ttgcccctcc | cccgtgcctt | ccttgaccct | ggaaggtgcc | actcccactg | 1800 |

```
tcctttccta ataaaatgag gaaattgcat cgcattgtct gagtaggtgt cattctattc    1860
tgggggggtgg ggtggggcag gacagcaagg gggaggattg ggaagacaat agcaggcatg    1920
ctggggatgc ggtgggctct atggcttctg aggcggaaag aaccagctgg ggctctaggg    1980
ggtatcccca cgcgccctgt agcggcgcat taagcgcggc gggtgtggtg gttacgcgca    2040
gcgtgaccgc tacacttgcc agcgccctag cgcccgctcc tttcgctttc ttcccttcct    2100
ttctcgccac gttcgccggc tttccccgtc aagctctaaa tcgggggctc cctttagggt    2160
tccgatttag tgctttacgg cacctcgacc ccaaaaaact tgattagggt gatggttcac    2220
gtagtgggcc atcgccctga tagacggttt ttcgcccttt gacgttggag tccacgttct    2280
ttaatagtgg actcttgttc caaactggaa caacactcaa ccctatctcg gtctattctt    2340
ttgatttata agggattttg ccgatttcgg cctattggtt aaaaaatgag ctgatttaac    2400
aaaaatttaa cgcgaattaa ttctgtggaa tgtgtgtcag ttagggtgtg gaaagtcccc    2460
aggctcccca gcaggcagaa gtatgcaaag catgcatctc aattagtcag caaccaggtg    2520
tggaaagtcc ccaggctccc cagcaggcag aagtatgcaa agcatgcatc tcaattagtc    2580
agcaaccata gtcccgcccc taactccgcc catcccgccc ctaactccgc ccagttccgc    2640
ccattctccg ccccatggct gactaatttt ttttatttat gcagaggccg aggccgcctc    2700
tgcctctgag ctattccaga agtagtgagg aggcttttttt ggaggcctag gcttttgcaa    2760
aaagctcccg ggagcttgta tatccatttt cggatctgat caagagacag gatgaggatc    2820
gtttcgcatg attgaacaag atggattgca cgcaggttct ccggccgctt gggtggagag    2880
gctattcggc tatgactggg cacaacagac aatcggctgc tctgatgccg ccgtgttccg    2940
gctgtcagcg caggggcgcc cggttctttt tgtcaagacc gacctgtccg gtgccctgaa    3000
tgaactgcag gacgaggcag cgcggctatc gtggctggcc acgacgggcg ttccttgcgc    3060
agctgtgctc gacgttgtca ctgaagcggg aagggactgg ctgctattgg gcgaagtgcc    3120
ggggcaggat ctcctgtcat ctcaccttgc tcctgccgag aaagtatcca tcatggctga    3180
tgcaatgcgg cggctgcata cgcttgatcc ggctacctgc ccattcgacc accaagcgaa    3240
acatcgcatc gagcgagcac gtactcggat ggaagccggt cttgtcgatc aggatgatct    3300
ggacgaagag catcaggggc tcgcgccagc cgaactgttc gccaggctca aggcgcgcat    3360
gcccgacggc gaggatctcg tcgtgaccca tggcgatgcc tgcttgccga atatcatggt    3420
ggaaaatggc cgcttttctg gattcatcga ctgtggccgg ctgggtgtgg cggaccgcta    3480
tcaggacata gcgttggcta cccgtgatat tgctgaagag cttggcggcg aatgggctga    3540
ccgcttcctc gtgctttacg gtatcgccgc tcccgattcg cagcgcatcg ccttctatcg    3600
ccttcttgac gagttcttct gagcgggact ctggggttcg aaatgaccga ccaagcgacg    3660
cccaacctgc catcacgaga tttcgattcc accgccgcct tctatgaaag gttgggcttc    3720
ggaatcgttt tccgggacgc cggctggatg atcctccagc gcggggatct catgctggag    3780
ttcttcgccc accccaactt gtttattgca gcttataatg gttacaaata aagcaatagc    3840
atcacaaatt tcacaaataa agcatttttt tcactgcatt ctagttgtgg tttgtccaaa    3900
ctcatcaatg tatcttatca tgtctgtata ccgtcgacct ctagctagag cttggcgtaa    3960
tcatggtcat agctgttttcc tgtgtgaaat tgttatccgc tcacaattcc acacaacata    4020
cgagccggaa gcataaagtg taaagcctgg ggtgcctaat gagtgagcta actcacatta    4080
attgcgttgc gctcactgcc cgcttttcag tcgggaaacc tgtcgtgcca gctgcattaa    4140
tgaatcggcc aacgcgcggg gagaggcggt ttgcgtattg ggcgctcttc cgcttcctcg    4200
```

```
ctcactgact cgctgcgctc ggtcgttcgg ctgcggcgag cggtatcagc tcactcaaag    4260
gcggtaatac ggttatccac agaatcaggg gataacgcag gaaagaacat gtgagcaaaa    4320
ggccagcaaa aggccaggaa ccgtaaaaag gccgcgttgc tggcgttttt ccataggctc    4380
cgcccccctg acgagcatca caaaaatcga cgctcaagtc agaggtggcg aaacccgaca    4440
ggactataaa gataccaggc gtttccccct ggaagctccc tcgtgcgctc tcctgttccg    4500
accctgccgc ttaccggata cctgtccgcc tttctccctt cgggaagcgt ggcgctttct    4560
catagctcac gctgtaggta tctcagttcg gtgtaggtcg ttcgctccaa gctgggctgt    4620
gtgcacgaac cccccgttca gcccgaccgc tgcgccttat ccggtaacta tcgtcttgag    4680
tccaacccgg taagacacga cttatcgcca ctggcagcag ccactggtaa caggattagc    4740
agagcgaggt atgtaggcgg tgctacagag ttcttgaagt ggtggcctaa ctacggctac    4800
actagaagaa cagtatttgg tatctgcgct ctgctgaagc cagttacctt cggaaaaaga    4860
gttggtagct cttgatccgg caaacaaacc accgctggta gcggtttttt tgtttgcaag    4920
cagcagatta cgcgcagaaa aaaggatctc aagaagatcc tttgatcttt tctacggggt    4980
ctgacgctca gtggaacgaa aactcacgtt aagggatttt ggtcatgag attatcaaaa    5040 aggatcttca cctagatcct tttaaattaa aaatgaagtt ttaaatcaat ctaaagtata    5100
tatgagtaaa cttggtctga cagttaccaa tgcttaatca gtgaggcacc tatctcagcg    5160
atctgtctat ttcgttcatc catagttgcc tgactccccg tcgtgtagat aactacgata    5220
cgggagggct taccatctgg ccccagtgct gcaatgatac cgcgagaccc acgctcaccg    5280
gctccagatt tatcagcaat aaaccagcca gccggaaggg ccgagcgcag aagtggtcct    5340
gcaactttat ccgcctccat ccagtctatt aattgttgcc gggaagctag agtaagtagt    5400
tcgccagtta atagtttgcg caacgttgtt gccattgcta caggcatcgt ggtgtcacgc    5460
tcgtcgtttg gtatggcttc attcagctcc ggttcccaac gatcaaggcg agttacatga    5520
tcccccatgt tgtgcaaaaa agcggttagc tccttcggtc ctccgatcgt tgtcagaagt    5580
aagttggccg cagtgttatc actcatggtt atggcagcac tgcataattc tcttactgtc    5640
atgccatccg taagatgctt ttctgtgact ggtgagtact caaccaagtc attctgagaa    5700
tagtgtatgc ggcgaccgag ttgctcttgc ccggcgtcaa tacgggataa taccgcgcca    5760
catagcagaa ctttaaaagt gctcatcatt ggaaaacgtt cttcggggcg aaaactctca    5820
aggatcttac cgctgttgag atccagttcg atgtaaccca ctcgtgcacc caactgatct    5880
tcagcatctt ttactttcac cagcgtttct gggtgagcaa aaacaggaag gcaaaatgcc    5940
gcaaaaaagg gaataagggc gacacggaaa tgttgaatac tcatactctt ccttttttcaa    6000 tattattgaa gcatttatca gggttattgt ctcatgagcg gatacatatt tgaatgtatt    6060
tagaaaaata acaaataggg gttccgcgca catttccccg aaaagtgcca acctgacgt    6119
```

<210> SEQ ID NO 13
<211> LENGTH: 21
<212> TYPE: DNA
<213> ORGANISM: Artificial
<220> FEATURE:
<223> OTHER INFORMATION: Target sequence in the gene CSNK1D

<400> SEQUENCE: 13
ccggtctagg atcgaaatgt t                                              21

<210> SEQ ID NO 14

```
<211> LENGTH: 21
<212> TYPE: DNA
<213> ORGANISM: Artificial
<220> FEATURE:
<223> OTHER INFORMATION: Target sequence in the gene AK2

<400> SEQUENCE: 14
cggcagaacc cgagtatcct a                                              21

<210> SEQ ID NO 15
<211> LENGTH: 21
<212> TYPE: DNA
<213> ORGANISM: Artificial
<220> FEATURE:
<223> OTHER INFORMATION: Target sequence in the gene AKT2

<400> SEQUENCE: 15
caagcgtggt gaatacatca a                                              21

<210> SEQ ID NO 16
<211> LENGTH: 21
<212> TYPE: DNA
<213> ORGANISM: Artificial
<220> FEATURE:
<223> OTHER INFORMATION: Target sequence in the gene CAMK2G

<400> SEQUENCE: 16
gaggaagaga tctataccct a                                              21

<210> SEQ ID NO 17
<211> LENGTH: 21
<212> TYPE: DNA
<213> ORGANISM: Artificial
<220> FEATURE:
<223> OTHER INFORMATION: Target sequence in the gene GK2

<400> SEQUENCE: 17
tacgttagaa gagcactgta a                                              21

<210> SEQ ID NO 18
<211> LENGTH: 21
<212> TYPE: DNA
<213> ORGANISM: Artificial
<220> FEATURE:
<223> OTHER INFORMATION: Target sequence in the gene PFKFB4

<400> SEQUENCE: 18
cagaaagtgt ctggacttgt a                                              21

<210> SEQ ID NO 19
<211> LENGTH: 21
<212> TYPE: DNA
<213> ORGANISM: Artificial
<220> FEATURE:
<223> OTHER INFORMATION: Target sequence in the gene MAPK12

<400> SEQUENCE: 19
ctggacgtat tcactcctga t                                              21

<210> SEQ ID NO 20
<211> LENGTH: 21
<212> TYPE: DNA
<213> ORGANISM: Artificial
<220> FEATURE:
<223> OTHER INFORMATION: Target sequence in the gene PRKCE

<400> SEQUENCE: 20
```

```
cccgaccatg gtagtgttca a                                              21

<210> SEQ ID NO 21
<211> LENGTH: 21
<212> TYPE: DNA
<213> ORGANISM: Artificial
<220> FEATURE:
<223> OTHER INFORMATION: Target sequence in the gene EIF2AK2

<400> SEQUENCE: 21
cggaaagact tacgttatta a                                              21

<210> SEQ ID NO 22
<211> LENGTH: 21
<212> TYPE: DNA
<213> ORGANISM: Artificial
<220> FEATURE:
<223> OTHER INFORMATION: Target sequence in the gene WEE1

<400> SEQUENCE: 22
cagggtagat tacctcggat a                                              21

<210> SEQ ID NO 23
<211> LENGTH: 21
<212> TYPE: DNA
<213> ORGANISM: Artificial
<220> FEATURE:
<223> OTHER INFORMATION: Target sequence in the gene CDK5R1

<400> SEQUENCE: 23
ccggaaggcc acgctgtttg a                                              21

<210> SEQ ID NO 24
<211> LENGTH: 21
<212> TYPE: DNA
<213> ORGANISM: Artificial
<220> FEATURE:
<223> OTHER INFORMATION: Target sequence in the gene LIG4

<400> SEQUENCE: 24
caccgtttat ttggactcgt a                                              21

<210> SEQ ID NO 25
<211> LENGTH: 21
<212> TYPE: DNA
<213> ORGANISM: Artificial
<220> FEATURE:
<223> OTHER INFORMATION: Target sequence in the gene AKAP1

<400> SEQUENCE: 25
agcgctgaac ttgattggga a                                              21

<210> SEQ ID NO 26
<211> LENGTH: 21
<212> TYPE: DNA
<213> ORGANISM: Artificial
<220> FEATURE:
<223> OTHER INFORMATION: Target sequence in the gene MAP3K6

<400> SEQUENCE: 26
tcagaggagc tgagtaatga a                                              21

<210> SEQ ID NO 27
<211> LENGTH: 21
<212> TYPE: DNA
```

<213> ORGANISM: Artificial
<220> FEATURE:
<223> OTHER INFORMATION: Target sequence in the gene DYRK3

<400> SEQUENCE: 27
tcgacagtac gtggccctaa a					21

<210> SEQ ID NO 28
<211> LENGTH: 21
<212> TYPE: DNA
<213> ORGANISM: Artificial
<220> FEATURE:
<223> OTHER INFORMATION: Target sequence in the gene RPS6KA4

<400> SEQUENCE: 28
cgccaccttc atggcattca a					21

<210> SEQ ID NO 29
<211> LENGTH: 21
<212> TYPE: DNA
<213> ORGANISM: Artificial
<220> FEATURE:
<223> OTHER INFORMATION: Target sequence in the gene STK17A

<400> SEQUENCE: 29
cacactcgtg atgtagttca t					21

<210> SEQ ID NO 30
<211> LENGTH: 21
<212> TYPE: DNA
<213> ORGANISM: Artificial
<220> FEATURE:
<223> OTHER INFORMATION: Target sequence in the gene GNE

<400> SEQUENCE: 30
cccgatcatg tttggcatta a					21

<210> SEQ ID NO 31
<211> LENGTH: 21
<212> TYPE: DNA
<213> ORGANISM: Artificial
<220> FEATURE:
<223> OTHER INFORMATION: Target sequence in the gene ERN2

<400> SEQUENCE: 31
ctggttcggc gggaagttca a					21

<210> SEQ ID NO 32
<211> LENGTH: 21
<212> TYPE: DNA
<213> ORGANISM: Artificial
<220> FEATURE:
<223> OTHER INFORMATION: Target sequence in the gene HUNK

<400> SEQUENCE: 32
cacgggcaaa gtgccctgta a					21

<210> SEQ ID NO 33
<211> LENGTH: 21
<212> TYPE: DNA
<213> ORGANISM: Artificial
<220> FEATURE:
<223> OTHER INFORMATION: Target sequence in the gene SMG1

<400> SEQUENCE: 33
caccatggta ttacaggttc a					21

<210> SEQ ID NO 34
<211> LENGTH: 21
<212> TYPE: DNA
<213> ORGANISM: Artificial
<220> FEATURE:
<223> OTHER INFORMATION: Target sequence in the gene WNK4

<400> SEQUENCE: 34
cagcttgttg ggcgtttcca a                                       21

<210> SEQ ID NO 35
<211> LENGTH: 21
<212> TYPE: DNA
<213> ORGANISM: Artificial
<220> FEATURE:
<223> OTHER INFORMATION: Target sequence in the gene MAGI2

<400> SEQUENCE: 35
caggcccaac ttgggatatc a                                       21

<210> SEQ ID NO 36
<211> LENGTH: 6089
<212> TYPE: DNA
<213> ORGANISM: Artificial
<220> FEATURE:
<223> OTHER INFORMATION: pCLS2222

<400> SEQUENCE: 36

```
atggccaata ccaaatataa cgaagagttc ctgctgtacc tggccggctt tgtggacggt     60
gacggtagca tcatcgctca gattaatcca accagtctt ctaagtttaa acatcgtcta    120
cgtttgacct tttatgtgac tcaaaagacc cagcgccgtt ggtttctgga caaactagtg    180
gatgaaattg gcgttggtta cgtacgtgat tctggatccg tttcccagta cgttttaagc    240
gaaatcaagc cgctgcacaa cttcctgact caactgcagc cgtttctgga actgaaacag    300
aaacaggcaa acctggttct gaaaattatc gaacagctgc cgtctgcaaa agaatccccg    360
gacaaattcc tggaagtttg tacctgggtg atcagattg cagctctgaa cgattctaag    420
acgcgtaaaa ccacttctga aaccgttcgt gctgtgctgg acagcctgag cgggaagaag    480
aaatcctccc cggcggccgg tggatctgat aagtataatc aggctctgtc taaatacaac    540
caagcactgt ccaagtacaa tcaggccctg tctggtggag gcggttccaa caaaagttc    600
ctgctgtatc ttgctggatt tgtggattct gatggctcca tcattgctca gataaaacca    660
cgtcaatcta acaagttcaa acaccagctc tccttgactt ttgcagtcac tcagaagaca    720
caaagaaggt ggttcttgga caaattggtt gataggattg gtgtgggcta tgtctatgac    780
agtggctctg tgtcagacta ccgcctgtct gaaattaagc ctcttcataa ctttctcacc    840
caactgcaac ccttcttgaa gctcaaacag aagcaagcaa atctggtttt gaaaatcatc    900
gagcaactgc catctgccaa ggagtccccc tgacaagtttc ttgaagtgtg tacttgggtg    960
gatcagattg ctgccttgaa tgactccaag accagaaaaa ccacctctga gactgtgagg   1020
gcagttctgg atagcctctc tgagaagaaa agtcctctc cttagtctag agggcccgcg   1080
gttcgaaggt aagcctatcc ctaaccctct cctcggtctc gattctacgc gtaccggtta   1140
gtaatgagtt taacgggggg aggctaactg aaacacggaa ggagacaata ccggaaggaa   1200
cccgcgctat gacggcaata aaaagacaga ataaaacgca cggtgttgg gtcgtttgtt   1260
cataaacgcg gggttcggtc ccagggctgg cactctgtcg atacccacc gagacccat   1320
```

```
tggggccaat acgcccgcgt ttcttccttt tccccacccc acccccccaag ttcgggtgaa    1380
ggcccagggc tcgcagccaa cgtcggggcg gcaggccctg ccatagcaga tctgcgcagc    1440
tggggctcta gggggtatcc ccacgcgccc tgtagcggcg cattaagcgc ggcgggtgtg    1500
gtggttacgc gcagcgtgac cgctacactt gccagcgccc tagcgcccgc tcctttcgct    1560
ttcttcccct cctttctcgc cacgttcgcc ggctttcccc gtcaagctct aaatcggggc    1620
atcccctttag ggttccgatt tagtgcttta cggcacctcg accccaaaaa acttgattag    1680
ggtgatggtt cacgtagtgg gccatcgccc tgatagacgg ttttcgccc tttgacgttg     1740
gagtccacgt tctttaatag tggactcttg ttccaaactg gaacaacact caaccctatc    1800
tcggtctatt cttttgattt ataagggatt ttggggattt cggcctattg gttaaaaaat    1860
gagctgattt aacaaaaatt taacgcgaat taattctgtg gaatgtgtgt cagttagggt    1920
gtggaaagtc cccaggctcc ccagcaggca gaagtatgca aagcatgcat ctcaattagt    1980
cagcaaccag gtgtggaaag tccccaggct ccccagcagg cagaagtatg caaagcatgc    2040
atctcaatta gtcagcaacc atagtcccgc ccctaactcc gcccatcccg ccctaactc    2100
cgcccagttc cgcccattct ccgccccatg gctgactaat ttttttttatt tatgcagagg    2160
ccgaggccgc ctctgcctct gagctattcc agaagtagtg aggaggcttt tttggaggcc    2220
taggcttttg caaaaagctc ccgggagctt gtatatccat tttcggatct gatcagcacg    2280
tgttgacaat taatcatcgg catagtatat cggcatagta taatacgaca aggtgaggaa    2340
ctaaaccatg gccaagcctt tgtctcaaga agaatccacc ctcattgaaa gagcaacggc    2400
tacaatcaac agcatcccca tctctgaaga ctacagcgtc gccagcgcag ctctctctag    2460
cgacggccgc atcttcactg gtgtcaatgt atatcattt actgggggac cttgtgcaga    2520
actcgtggtg ctgggcactg ctgctgctgc ggcagctggc aacctgactt gtatcgtcgc    2580
gatcggaaat gagaacaggg gcatcttgag cccctgcgga cggtgccgac aggtgcttct    2640
cgatctgcat cctgggatca aagccatagt gaaggacagt gatggacagc cgacggcagt    2700
tgggattcgt gaattgctgc cctctggtta tgtgtgggag ggctaagcac ttcgtggccg    2760
aggagcagga ctgacacgtg ctacgagatt tcgattccac cgccgccttc tatgaaaggt    2820
tgggcttcgg aatcgttttc cgggacgccg gctggatgat cctccagcgc ggggatctca    2880
tgctggagtt cttcgcccac cccaacttgt ttattgcagc ttataatggt tacaaataaa    2940
gcaatagcat cacaaatttc acaaataaag catttttttc actgcattct agttgtggtt    3000
tgtccaaact catcaatgta tcttatcatg tctgtatacc gtcgacctct agctagagct    3060
tggcgtaatc atggtcatag ctgtttcctg tgtgaaattg ttatccgctc acaattccac    3120
acaacatacg agccggaagc ataaagtgta aagcctgggg tgcctaatga gtgagctaac    3180
tcacattaat tgcgttgcgc tcactgcccg ctttccagtc gggaaacctg tcgtgccagc    3240
tgcattaatg aatcggccaa cgcgcgggga gaggcggttt gcgtattggg cgctcttccg    3300
cttcctcgct cactgactcg ctgcgctcgg tcgttcggct gcggcgagcg gtatcagctc    3360
actcaaaggc ggtaatacgg ttatccacag aatcagggga taacgcagga aagaacatgt    3420
gagcaaaagg ccagcaaaag gccaggaacc gtaaaaaggc cgcgttgctg gcgttttcc    3480
ataggctccg cccccctgac gagcatcaca aaaatcgacg ctcaagtcag aggtggcgaa    3540
acccgacagg actataaaga taccaggcgt ttccccctgg aagctccctc gtgcgctctc    3600
ctgttccgac cctgccgctt accggatacc tgtccgcctt tctcccttcg ggaagcgtgg    3660
cgctttctca tagctcacgc tgtaggtatc tcagttcggt gtaggtcgtt cgctccaagc    3720
```

-continued

```
tgggctgtgt gcacgaaccc cccgttcagc ccgaccgctg cgccttatcc ggtaactatc   3780
gtcttgagtc caacccggta agacacgact tatcgccact ggcagcagcc actggtaaca   3840
ggattagcag agcgaggtat gtaggcggtg ctacagagtt cttgaagtgg tggcctaact   3900
acggctacac tagaagaaca gtatttggta tctgcgctct gctgaagcca gttaccttcg   3960
gaaaaagagt tggtagctct tgatccggca acaaaccac cgctggtagc ggttttttg    4020 tttgcaagca gcagattacg cgcagaaaaa aaggatctca agaagatcct ttgatctttt   4080
ctacggggtc tgacgctcag tggaacgaaa actcacgtta agggattttg gtcatgagat   4140
tatcaaaaag gatcttcacc tagatccttt taaattaaaa atgaagtttt aaatcaatct   4200
aaagtatata tgagtaaact tggtctgaca gttaccaatg cttaatcagt gaggcaccta   4260
tctcagcgat ctgtctattt cgttcatcca tagttgcctg actccccgtc gtgtagataa   4320
ctacgatacg ggagggctta ccatctggcc ccagtgctgc aatgataccg cgagacccac   4380
gctcaccggc tccagattta tcagcaataa accagccagc cggaagggcc gagcgcagaa   4440
gtggtcctgc aactttatcc gcctccatcc agtctattaa ttgttgccgg gaagctagag   4500
taagtagttc gccagttaat agtttgcgca acgttgttgc cattgctaca ggcatcgtgg   4560
tgtcacgctc gtcgtttggt atggcttcat tcagctccgg ttcccaacga tcaaggcgag   4620
ttacatgatc ccccatgttg tgcaaaaaag cggttagctc cttcggtcct ccgatcgttg   4680
tcagaagtaa gttggccgca gtgttatcac tcatggttat ggcagcactg cataattctc   4740
ttactgtcat gccatccgta agatgctttt ctgtgactgg tgagtactca accaagtcat   4800
tctgagaata gtgtatgcgg cgaccgagtt gctcttgccc ggcgtcaata cgggataata   4860
ccgcgccaca tagcagaact ttaaaagtgc tcatcattgg aaaacgttct cggggcgaa    4920 aactctcaag gatcttaccg ctgttgagat ccagttcgat gtaacccact cgtgcaccca   4980
actgatcttc agcatctttt actttcacca gcgtttctgg gtgagcaaaa acaggaaggc   5040
aaaatgccgc aaaaaaggga ataagggcga cacggaaatg ttgaatactc atactcttcc   5100
tttttcaata ttattgaagc atttatcagg gttattgtct catgagcgga tacatatttg   5160
aatgtattta gaaaaataaa caaatagggg ttccgcgcac atttccccga aaagtgccac   5220
ctgacgtcga cggatcggga gatctcccga tcccctatgg tgcactctca gtacaatctg   5280
ctctgatgcc gcatagttaa gccagtatct gctccctgct tgtgtgttgg aggtcgctga   5340
gtagtgcgcg agcaaaattt aagctacaac aaggcaaggc ttgaccgaca attgcatgaa   5400
gaatctgctt agggttaggc gttttgcgct gcttcgcgat gtacgggcca gatatacgcg   5460
ttgacattga ttattgacta gttattaata gtaatcaatt acgggtcat tagttcatag    5520 cccatatatg gagttccgcg ttacataact tacggtaaat ggcccgcctg gctgaccgcc   5580
caacgacccc cgcccattga cgtcaataat gacgtatgtt cccatagtaa cgccaatagg   5640
gactttccat tgacgtcaat gggtggagta tttacggtaa actgcccact tggcagtaca   5700
tcaagtgtat catatgccaa gtacgccccc tattgacgtc aatgacggta atggcccgc    5760 ctggcattat gcccagtaca tgaccttatg ggactttcct acttggcagt acatctacgt   5820
attagtcatc gctattacca tggtgatgcg gttttggcag tacatcaatg ggcgtggata   5880
gcggtttgac tcacggggat ttccaagtct ccaccccatt gacgtcaatg ggagtttgtt   5940
ttggcaccaa aatcaacggg actttccaaa atgtcgtaac aactccgccc cattgacgca   6000
aatgggcggt aggcgtgtac ggtgggaggt ctatataagc agagctctct ggctaactag   6060
```
agaacccact gcttactggc ttatcgacc        6089

<210> SEQ ID NO 37
<211> LENGTH: 21
<212> TYPE: DNA
<213> ORGANISM: Artificial
<220> FEATURE:
<223> OTHER INFORMATION: Target sequence in the gene WRN

<400> SEQUENCE: 37
cggattgtat acgtaactcc a        21

<210> SEQ ID NO 38
<211> LENGTH: 21
<212> TYPE: DNA
<213> ORGANISM: Artificial
<220> FEATURE:
<223> OTHER INFORMATION: Target sequence in the gene MAPK3

<400> SEQUENCE: 38
cccgtctaat atataaatat a        21

<210> SEQ ID NO 39
<211> LENGTH: 21
<212> TYPE: DNA
<213> ORGANISM: Artificial
<220> FEATURE:
<223> OTHER INFORMATION: Target sequence in the gene FANCD2

<400> SEQUENCE: 39
aagcagctct ctagcaccgt a        21

<210> SEQ ID NO 40
<211> LENGTH: 236
<212> TYPE: PRT
<213> ORGANISM: Saccharomyces cerevisiae

<400> SEQUENCE: 40

Met Ala Lys Asn Ile Lys Lys Asn Gln Val Met Asn Leu Gly Pro Asn
1               5                   10                  15

Ser Lys Leu Leu Lys Glu Tyr Lys Ser Gln Leu Ile Glu Leu Asn Ile
            20                  25                  30

Glu Gln Phe Glu Ala Gly Ile Gly Leu Ile Leu Gly Asp Ala Tyr Ile
        35                  40                  45

Arg Ser Arg Asp Glu Gly Lys Thr Tyr Cys Met Gln Phe Glu Trp Lys
    50                  55                  60

Asn Lys Ala Tyr Met Asp His Val Cys Leu Leu Tyr Asp Gln Trp Val
65                  70                  75                  80

Leu Ser Pro Pro His Lys Lys Glu Arg Val Asn His Leu Gly Asn Leu
                85                  90                  95

Val Ile Thr Trp Gly Ala Gln Thr Phe Lys His Gln Ala Phe Asn Lys
            100                 105                 110

Leu Ala Asn Leu Phe Ile Val Asn Lys Lys Thr Ile Pro Asn Asn
        115                 120                 125

Leu Val Glu Asn Tyr Leu Thr Pro Met Ser Leu Ala Tyr Trp Phe Met
    130                 135                 140

Asp Asp Gly Gly Lys Trp Asp Tyr Asn Lys Asn Ser Thr Asn Lys Ser
145                 150                 155                 160

Ile Val Leu Asn Thr Gln Ser Phe Thr Phe Glu Glu Val Glu Tyr Leu
                165                 170                 175

```
Val Lys Gly Leu Arg Asn Lys Phe Gln Leu Asn Cys Tyr Val Lys Ile
            180                 185                 190

Asn Lys Asn Lys Pro Ile Ile Tyr Ile Asp Ser Met Ser Tyr Leu Ile
        195                 200                 205

Phe Tyr Asn Leu Ile Lys Pro Tyr Leu Ile Pro Gln Met Met Tyr Lys
        210                 215                 220

Leu Pro Asn Thr Ile Ser Ser Glu Thr Phe Leu Lys
225                 230                 235

<210> SEQ ID NO 41
<211> LENGTH: 2686
<212> TYPE: DNA
<213> ORGANISM: Artificial
<220> FEATURE:
<223> OTHER INFORMATION: pCLS0002

<400> SEQUENCE: 41
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt acccggggat    420
cctctagagt cgacctgcag gcatgcaagc ttggcgtaat catggtcata gctgtttcct    480
gtgtgaaatt gttatccgct cacaattcca cacaacatac gagccggaag cataaagtgt    540
aaagcctggg gtgcctaatg agtgagctaa ctcacattaa ttgcgttgcg ctcactgccc    600
gctttccagt cgggaaacct gtcgtgccag ctgcattaat gaatcggcca acgcgcgggg    660
agaggcggtt tgcgtattgg gcgctcttcc gcttcctcgc tcactgactc gctgcgctcg    720
gtcgttcggc tgcggcgagc ggtatcagct cactcaaagg cggtaatacg ttatccaca    780 gaatcagggg ataacgcagg aaagaacatg tgagcaaaag gccagcaaaa ggccaggaac    840
cgtaaaaagg ccgcgttgct ggcgtttttc cataggctcc gcccccctga cgagcatcac    900
aaaaatcgac gctcaagtca gaggtggcga aacccgacag gactataaag ataccaggcg    960
tttccccctg gaagctccct cgtgcgctct cctgttccga ccctgccgct taccggatac   1020
ctgtccgcct ttctcccttc gggaagcgtg gcgctttctc atagctcacg ctgtaggtat   1080
ctcagttcgg tgtaggtcgt tcgctccaag ctgggctgtg tgcacgaacc ccccgttcag   1140
cccgaccgct gcgccttatc cggtaactat cgtcttgagt ccaacccggt aagacacgac   1200
ttatcgccac tggcagcagc cactggtaac aggattagca gagcgaggta tgtaggcggt   1260
gctacagagt tcttgaagtg gtggcctaac tacggctaca ctagaaggac agtatttggt   1320
atctgcgctc tgctgaagcc agttaccttc ggaaaaagag ttggtagctc ttgatccggc   1380
aaacaaacca ccgctggtag cggtggtttt tttgtttgca agcagcagat tacgcgcaga   1440
aaaaaaggat ctcaagaaga tcctttgatc ttttctacgg ggtctgacgc tcagtggaac   1500
gaaaactcac gttaagggat tttggtcatg agattatcaa aaaggatctt cacctagatc   1560
cttttaaatt aaaaatgaag ttttaaatca atctaaagta tatatgagta aacttggtct   1620
gacagttacc aatgcttaat cagtgaggca cctatctcag cgatctgtct atttcgttca   1680
tccatagttg cctgactccc cgtcgtgtag ataactacga tacgggaggg cttaccatct   1740
```

```
ggccccagtg ctgcaatgat accgcgagac ccacgctcac cggctccaga tttatcagca    1800
ataaaccagc cagccggaag ggccgagcgc agaagtggtc ctgcaacttt atccgcctcc    1860
atccagtcta ttaattgttg ccgggaagct agagtaagta gttcgccagt taatagtttg    1920
cgcaacgttg ttgccattgc tacaggcatc gtggtgtcac gctcgtcgtt tggtatggct    1980
tcattcagct ccggttccca acgatcaagg cgagttacat gatccccat gttgtgcaaa     2040 aaagcggtta gctccttcgg tcctccgatc gttgtcagaa gtaagttggc cgcagtgtta    2100
tcactcatgg ttatggcagc actgcataat tctcttactg tcatgccatc cgtaagatgc    2160
ttttctgtga ctggtgagta ctcaaccaag tcattctgag aatagtgtat gcggcgaccg    2220
agttgctctt gcccggcgtc aatacgggat aataccgcgc cacatagcag aactttaaaa    2280
gtgctcatca ttggaaaacg ttcttcgggg cgaaaactct caaggatctt accgctgttg    2340
agatccagtt cgatgtaacc cactcgtgca cccaactgat cttcagcatc ttttactttc    2400
accagcgttt ctgggtgagc aaaaacagga aggcaaaatg ccgcaaaaaa gggaataagg    2460
gcgacacgga aatgttgaat actcatactc ttcctttttc aatattattg aagcatttat    2520
cagggttatt gtctcatgag cggatacata tttgaatgta tttagaaaaa taaacaaata    2580
ggggttccgc gcacatttcc ccgaaaagtg ccacctgacg tctaagaaac cattattatc    2640
atgacattaa cctataaaaa taggcgtatc acgaggccct ttcgtc                   2686

<210> SEQ ID NO 42
<211> LENGTH: 60
<212> TYPE: DNA
<213> ORGANISM: Artificial
<220> FEATURE:
<223> OTHER INFORMATION: Forward Adaptor sequence for Deep sequencing
<220> FEATURE:
<221> NAME/KEY: misc_feature
<222> LOCATION: (27)..(32)
<223> OTHER INFORMATION: n is a, t, c or g

<400> SEQUENCE: 42
ccatctcatc cctgcgtgtc tccgacnnnn nnggcaaaga tgaatcaaag attctgtcct    60

<210> SEQ ID NO 43
<211> LENGTH: 57
<212> TYPE: DNA
<213> ORGANISM: Artificial
<220> FEATURE:
<223> OTHER INFORMATION: Reverse Adaptor sequence for Deep sequencing

<400> SEQUENCE: 43
cctatcccct gtgtgccttg gcagtctcag gatctcaccc ggaacagctt aaatttc       57

<210> SEQ ID NO 44
<211> LENGTH: 21
<212> TYPE: DNA
<213> ORGANISM: Artificial
<220> FEATURE:
<223> OTHER INFORMATION: Target sequence in the gene XRCC6

<400> SEQUENCE: 44
accgagggcg atgaagaagc a                                              21

<210> SEQ ID NO 45
<211> LENGTH: 21
<212> TYPE: DNA
<213> ORGANISM: Artificial
<220> FEATURE:
```

```
<223> OTHER INFORMATION: Target sequence in the gene BRCA1

<400> SEQUENCE: 45
accatacagc ttcataaata a                                              21

<210> SEQ ID NO 46
<211> LENGTH: 21
<212> TYPE: DNA
<213> ORGANISM: Artificial
<220> FEATURE:
<223> OTHER INFORMATION: Target sequence in the gene ATR

<400> SEQUENCE: 46
caggcactaa ttgttcttca a                                              21

<210> SEQ ID NO 47
<211> LENGTH: 21
<212> TYPE: DNA
<213> ORGANISM: Artificial
<220> FEATURE:
<223> OTHER INFORMATION: Target sequence in the gene CSNK1D

<400> SEQUENCE: 47
ctccctgacg attccactgt a                                              21

<210> SEQ ID NO 48
<211> LENGTH: 21
<212> TYPE: DNA
<213> ORGANISM: Artificial
<220> FEATURE:
<223> OTHER INFORMATION: Target sequence in the gene AK2

<400> SEQUENCE: 48
ctgcaagcct accacactca a                                              21

<210> SEQ ID NO 49
<211> LENGTH: 21
<212> TYPE: DNA
<213> ORGANISM: Artificial
<220> FEATURE:
<223> OTHER INFORMATION: Target sequence in the gene AKT2

<400> SEQUENCE: 49
acgggctaaa gtgaccatga a                                              21

<210> SEQ ID NO 50
<211> LENGTH: 21
<212> TYPE: DNA
<213> ORGANISM: Artificial
<220> FEATURE:
<223> OTHER INFORMATION: Target sequence in the gene CAMK2G

<400> SEQUENCE: 50
ccgatgagaa acctcgtgtt a                                              21

<210> SEQ ID NO 51
<211> LENGTH: 21
<212> TYPE: DNA
<213> ORGANISM: Artificial
<220> FEATURE:
<223> OTHER INFORMATION: Target sequence in the gene GK2

<400> SEQUENCE: 51
ctcgggtgtg ccataataat a                                              21
```

```
<210> SEQ ID NO 52
<211> LENGTH: 21
<212> TYPE: DNA
<213> ORGANISM: Artificial
<220> FEATURE:
<223> OTHER INFORMATION: Target sequence in the gene PFKFB4

<400> SEQUENCE: 52
acggagagcg accatcttta a                                              21

<210> SEQ ID NO 53
<211> LENGTH: 21
<212> TYPE: DNA
<213> ORGANISM: Artificial
<220> FEATURE:
<223> OTHER INFORMATION: Target sequence in the gene MAPK12

<400> SEQUENCE: 53
tggaagcgtg ttacttacaa a                                              21

<210> SEQ ID NO 54
<211> LENGTH: 21
<212> TYPE: DNA
<213> ORGANISM: Artificial
<220> FEATURE:
<223> OTHER INFORMATION: Target sequence in the gene PRKCE

<400> SEQUENCE: 54
cacggaaaca cccgtacctt a                                              21

<210> SEQ ID NO 55
<211> LENGTH: 21
<212> TYPE: DNA
<213> ORGANISM: Artificial
<220> FEATURE:
<223> OTHER INFORMATION: Target sequence in the gene EIF2AK2

<400> SEQUENCE: 55
tacataggcc ttatcaatag a                                              21

<210> SEQ ID NO 56
<211> LENGTH: 21
<212> TYPE: DNA
<213> ORGANISM: Artificial
<220> FEATURE:
<223> OTHER INFORMATION: Target sequence in the gene WEE1

<400> SEQUENCE: 56
acaattacga atagaattga a                                              21

<210> SEQ ID NO 57
<211> LENGTH: 21
<212> TYPE: DNA
<213> ORGANISM: Artificial
<220> FEATURE:
<223> OTHER INFORMATION: Target sequence in the gene CDK5R1

<400> SEQUENCE: 57
tgagctggtt tgactcatta a                                              21

<210> SEQ ID NO 58
<211> LENGTH: 21
<212> TYPE: DNA
<213> ORGANISM: Artificial
<220> FEATURE:
<223> OTHER INFORMATION: Target sequence in the gene LIG4
```

<400> SEQUENCE: 58
atctggtaag ctcgcatcta a                                              21

<210> SEQ ID NO 59
<211> LENGTH: 21
<212> TYPE: DNA
<213> ORGANISM: Artificial
<220> FEATURE:
<223> OTHER INFORMATION: Target sequence in the gene AKAP1

<400> SEQUENCE: 59
cacgcagaga tgacagtaca a                                              21

<210> SEQ ID NO 60
<211> LENGTH: 21
<212> TYPE: DNA
<213> ORGANISM: Artificial
<220> FEATURE:
<223> OTHER INFORMATION: Target sequence in the gene MAP3K6

<400> SEQUENCE: 60
caccatccaa atgctgttga a                                              21

<210> SEQ ID NO 61
<211> LENGTH: 21
<212> TYPE: DNA
<213> ORGANISM: Artificial
<220> FEATURE:
<223> OTHER INFORMATION: Target sequence in the gene DYRK3

<400> SEQUENCE: 61
agccaataag cttaaagcta a                                              21

<210> SEQ ID NO 62
<211> LENGTH: 21
<212> TYPE: DNA
<213> ORGANISM: Artificial
<220> FEATURE:
<223> OTHER INFORMATION: Target sequence in the gene RPS6KA4

<400> SEQUENCE: 62
caggctgtgc ctttgacttt a                                              21

<210> SEQ ID NO 63
<211> LENGTH: 21
<212> TYPE: DNA
<213> ORGANISM: Artificial
<220> FEATURE:
<223> OTHER INFORMATION: Target sequence in the gene STK17A

<400> SEQUENCE: 63
tccattgtaa ccgaagagtt a                                              21

<210> SEQ ID NO 64
<211> LENGTH: 21
<212> TYPE: DNA
<213> ORGANISM: Artificial
<220> FEATURE:
<223> OTHER INFORMATION: Target sequence in the gene GNE

<400> SEQUENCE: 64
atggaaatac atatcgaatg a                                              21

<210> SEQ ID NO 65
<211> LENGTH: 21

```
<212> TYPE: DNA
<213> ORGANISM: Artificial
<220> FEATURE:
<223> OTHER INFORMATION: Target sequence in the gene ERN2

<400> SEQUENCE: 65
aaggatgaaa ctggcttcta t                                         21

<210> SEQ ID NO 66
<211> LENGTH: 21
<212> TYPE: DNA
<213> ORGANISM: Artificial
<220> FEATURE:
<223> OTHER INFORMATION: Target sequence in the gene HUNK

<400> SEQUENCE: 66
tcggaccaag atcaaaccaa a                                         21

<210> SEQ ID NO 67
<211> LENGTH: 21
<212> TYPE: DNA
<213> ORGANISM: Artificial
<220> FEATURE:
<223> OTHER INFORMATION: Target sequence in the gene SMG1

<400> SEQUENCE: 67
atcgatgttg ccagactact a                                         21

<210> SEQ ID NO 68
<211> LENGTH: 21
<212> TYPE: DNA
<213> ORGANISM: Artificial
<220> FEATURE:
<223> OTHER INFORMATION: Target sequence in the gene WNK4

<400> SEQUENCE: 68
caggaggagc cagcaccatt a                                         21

<210> SEQ ID NO 69
<211> LENGTH: 21
<212> TYPE: DNA
<213> ORGANISM: Artificial
<220> FEATURE:
<223> OTHER INFORMATION: Target sequence in the gene MAGI2

<400> SEQUENCE: 69
atggaccgat gggagaatca a                                         21

<210> SEQ ID NO 70
<211> LENGTH: 21
<212> TYPE: DNA
<213> ORGANISM: Artificial
<220> FEATURE:
<223> OTHER INFORMATION: Target sequence in the gene XRCC6

<400> SEQUENCE: 70
tttgtactat atactgttaa a                                         21

<210> SEQ ID NO 71
<211> LENGTH: 21
<212> TYPE: DNA
<213> ORGANISM: Artificial
<220> FEATURE:
<223> OTHER INFORMATION: Target sequence in the gene BRCA1

<400> SEQUENCE: 71
```
aacctatcgg aagaaggcaa g                                              21

<210> SEQ ID NO 72
<211> LENGTH: 21
<212> TYPE: DNA
<213> ORGANISM: Artificial
<220> FEATURE:
<223> OTHER INFORMATION: Target sequence in the gene FANCD2

<400> SEQUENCE: 72
cagagtttgc ttcactctct a                                              21

<210> SEQ ID NO 73
<211> LENGTH: 21
<212> TYPE: DNA
<213> ORGANISM: Artificial
<220> FEATURE:
<223> OTHER INFORMATION: Target sequence in the gene WRN

<400> SEQUENCE: 73
tccgctgtag caattggagt a                                              21

<210> SEQ ID NO 74
<211> LENGTH: 21
<212> TYPE: DNA
<213> ORGANISM: Artificial
<220> FEATURE:
<223> OTHER INFORMATION: Target sequence in the gene MAPK3

<400> SEQUENCE: 74
tggaccggat gttaacctt a                                               21

<210> SEQ ID NO 75
<211> LENGTH: 21
<212> TYPE: DNA
<213> ORGANISM: Artificial
<220> FEATURE:
<223> OTHER INFORMATION: Target sequence in the gene PRKDC (PRKDC_5)

<400> SEQUENCE: 75
ctcgtgtatt acagaaggaa a                                              21

<210> SEQ ID NO 76
<211> LENGTH: 21
<212> TYPE: DNA
<213> ORGANISM: Artificial
<220> FEATURE:
<223> OTHER INFORMATION: Target sequence in the gene PRKDC (PRKDC_8)

<400> SEQUENCE: 76
gaccctgttg acagtacttt a                                              21

<210> SEQ ID NO 77
<211> LENGTH: 21
<212> TYPE: DNA
<213> ORGANISM: Artificial sequence
<220> FEATURE:
<223> OTHER INFORMATION: Target sequence in the gene RAD51

<400> SEQUENCE: 77
caggataaag cttccgggaa a                                              21

<210> SEQ ID NO 78
<211> LENGTH: 21
<212> TYPE: DNA
<213> ORGANISM: Artificial sequence

```
<220> FEATURE:
<223> OTHER INFORMATION: Target sequence in the gene LIG4

<400> SEQUENCE: 78
aaggacaata acgtagagga a                                              21

<210> SEQ ID NO 79
<211> LENGTH: 21
<212> TYPE: DNA
<213> ORGANISM: Artificial sequence
<220> FEATURE:
<223> OTHER INFORMATION: Target sequence in the gene Luc2

<400> SEQUENCE: 79
aacgtacgcg gaatacttcg a                                              21

<210> SEQ ID NO 80
<211> LENGTH: 21
<212> TYPE: DNA
<213> ORGANISM: Artificial sequence
<220> FEATURE:
<223> OTHER INFORMATION: Target sequence in the gene LCMT2

<400> SEQUENCE: 80
caggcgcggt acagaacacc a                                              21

<210> SEQ ID NO 81
<211> LENGTH: 21
<212> TYPE: DNA
<213> ORGANISM: Artificial sequence
<220> FEATURE:
<223> OTHER INFORMATION: Target sequence in the gene SNORD115-10

<400> SEQUENCE: 81 gagaaccttga tattgtctga a                                             21

<210> SEQ ID NO 82
<211> LENGTH: 21
<212> TYPE: DNA
<213> ORGANISM: Artificial sequence
<220> FEATURE:
<223> OTHER INFORMATION: Target sequence in the gene WNK4

<400> SEQUENCE: 82
cagcttgttg ggcgtttcca a                                              21

<210> SEQ ID NO 83
<211> LENGTH: 21
<212> TYPE: DNA
<213> ORGANISM: Artificial sequence
<220> FEATURE:
<223> OTHER INFORMATION: Target sequence in the gene HMX2

<400> SEQUENCE: 83
cgggcgcgta ctgtactgta a                                              21

<210> SEQ ID NO 84
<211> LENGTH: 21
<212> TYPE: DNA
<213> ORGANISM: Artificial sequence
<220> FEATURE:
<223> OTHER INFORMATION: Target sequence in the gene TAL1

<400> SEQUENCE: 84
tccgtcaacg ttgtactgta t                                              21
```

```
<210> SEQ ID NO 85
<211> LENGTH: 21
<212> TYPE: DNA
<213> ORGANISM: Artificial sequence
<220> FEATURE:
<223> OTHER INFORMATION: Target sequence in the gene VAV3

<400> SEQUENCE: 85
cacgactttc tcgaacacct a                                             21

<210> SEQ ID NO 86
<211> LENGTH: 21
<212> TYPE: DNA
<213> ORGANISM: Artificial sequence
<220> FEATURE:
<223> OTHER INFORMATION: Target sequence in the gene APOA1BP

<400> SEQUENCE: 86
atgacgattg atgaactgta t                                             21

<210> SEQ ID NO 87
<211> LENGTH: 21
<212> TYPE: DNA
<213> ORGANISM: Artificial sequence
<220> FEATURE:
<223> OTHER INFORMATION: Target sequence in the gene SNORD115-14

<400> SEQUENCE: 87
gagaaactta tattgtctga a                                             21

<210> SEQ ID NO 88
<211> LENGTH: 21
<212> TYPE: DNA
<213> ORGANISM: Artificial sequence
<220> FEATURE:
<223> OTHER INFORMATION: Target sequence in the gene REM1

<400> SEQUENCE: 88
cgctgtggtg ttcgactgta a                                             21

<210> SEQ ID NO 89
<211> LENGTH: 21
<212> TYPE: DNA
<213> ORGANISM: Artificial sequence
<220> FEATURE:
<223> OTHER INFORMATION: Target sequence in the gene MTHFD2L

<400> SEQUENCE: 89
cagcggtata ttagttcagt t                                             21

<210> SEQ ID NO 90
<211> LENGTH: 21
<212> TYPE: DNA
<213> ORGANISM: Artificial sequence
<220> FEATURE:
<223> OTHER INFORMATION: Target sequence in the gene OR8H2

<400> SEQUENCE: 90
ctcaactgtc gtcacaccta a                                             21

<210> SEQ ID NO 91
<211> LENGTH: 21
<212> TYPE: DNA
<213> ORGANISM: Artificial sequence
<220> FEATURE:
<223> OTHER INFORMATION: Target sequence in the gene UBAC2
```

```
<400> SEQUENCE: 91
cacgctggac atccagagac a                                              21

<210> SEQ ID NO 92
<211> LENGTH: 21
<212> TYPE: DNA
<213> ORGANISM: Artificial sequence
<220> FEATURE:
<223> OTHER INFORMATION: Target sequence in the gene HGFAC

<400> SEQUENCE: 92
aaggactgcg gcacagagaa a                                              21

<210> SEQ ID NO 93
<211> LENGTH: 21
<212> TYPE: DNA
<213> ORGANISM: Artificial sequence
<220> FEATURE:
<223> OTHER INFORMATION: Target sequence in the gene GOLT1A

<400> SEQUENCE: 93
cactagctcg atggtctgaa a                                              21

<210> SEQ ID NO 94
<211> LENGTH: 21
<212> TYPE: DNA
<213> ORGANISM: Artificial sequence
<220> FEATURE:
<223> OTHER INFORMATION: Target sequence in the gene FAM24A

<400> SEQUENCE: 94
ctggatggtt gaactgtagc a                                              21

<210> SEQ ID NO 95
<211> LENGTH: 21
<212> TYPE: DNA
<213> ORGANISM: Artificial sequence
<220> FEATURE:
<223> OTHER INFORMATION: Target sequence in the gene NEFH

<400> SEQUENCE: 95
ctcgctggac acgctgagca a                                              21

<210> SEQ ID NO 96
<211> LENGTH: 21
<212> TYPE: DNA
<213> ORGANISM: Artificial sequence
<220> FEATURE:
<223> OTHER INFORMATION: Target sequence in the gene SPRN

<400> SEQUENCE: 96
caggaacatt cccaagcagg a                                              21

<210> SEQ ID NO 97
<211> LENGTH: 21
<212> TYPE: DNA
<213> ORGANISM: Artificial sequence
<220> FEATURE:
<223> OTHER INFORMATION: Target sequence in the gene INTS12

<400> SEQUENCE: 97
caggacctag tggaagtact a                                              21

<210> SEQ ID NO 98
```

```
<211> LENGTH: 21
<212> TYPE: DNA
<213> ORGANISM: Artificial sequence
<220> FEATURE:
<223> OTHER INFORMATION: Target sequence in the gene PAF1

<400> SEQUENCE: 98
ctccactgag ttcaaccgtt a                                        21

<210> SEQ ID NO 99
<211> LENGTH: 21
<212> TYPE: DNA
<213> ORGANISM: Artificial sequence
<220> FEATURE:
<223> OTHER INFORMATION: Target sequence in the gene ALDH8A1

<400> SEQUENCE: 99
ctggataaag caggtgttcc a                                        21

<210> SEQ ID NO 100
<211> LENGTH: 21
<212> TYPE: DNA
<213> ORGANISM: Artificial sequence
<220> FEATURE:
<223> OTHER INFORMATION: Target sequence in the gene ELF2

<400> SEQUENCE: 100
aagcatcagt tcacagcagt a                                        21

<210> SEQ ID NO 101
<211> LENGTH: 21
<212> TYPE: DNA
<213> ORGANISM: Artificial sequence
<220> FEATURE:
<223> OTHER INFORMATION: Target sequence in the gene TSSC1

<400> SEQUENCE: 101
cagctgcgga gacgactgta a                                        21

<210> SEQ ID NO 102
<211> LENGTH: 21
<212> TYPE: DNA
<213> ORGANISM: Artificial sequence
<220> FEATURE:
<223> OTHER INFORMATION: Target sequence in the gene TMEM130

<400> SEQUENCE: 102
cccgctggtg cttactggca a                                        21

<210> SEQ ID NO 103
<211> LENGTH: 21
<212> TYPE: DNA
<213> ORGANISM: Artificial sequence
<220> FEATURE:
<223> OTHER INFORMATION: Target sequence in the gene TMEM130

<400> SEQUENCE: 103
tccgtcaaca gtagttcctt a                                        21

<210> SEQ ID NO 104
<211> LENGTH: 21
<212> TYPE: DNA
<213> ORGANISM: Artificial sequence
<220> FEATURE:
<223> OTHER INFORMATION: Target sequence in the gene SNORD114-17

<400> SEQUENCE: 104
```
atgaatgata tgtgtctgaa a                                              21

<210> SEQ ID NO 105
<211> LENGTH: 21
<212> TYPE: DNA
<213> ORGANISM: Artificial sequence
<220> FEATURE:
<223> OTHER INFORMATION: Target sequence in the gene FGL2

<400> SEQUENCE: 105
caggatcgag gaggtgttca a                                              21

<210> SEQ ID NO 106
<211> LENGTH: 21
<212> TYPE: DNA
<213> ORGANISM: Artificial sequence
<220> FEATURE:
<223> OTHER INFORMATION: Target sequence in the gene DUSP1

<400> SEQUENCE: 106
cacgaacagt gcgctgagct a                                              21

<210> SEQ ID NO 107
<211> LENGTH: 21
<212> TYPE: DNA
<213> ORGANISM: Artificial sequence
<220> FEATURE:
<223> OTHER INFORMATION: Target sequence in the gene MYCL1

<400> SEQUENCE: 107
aaggccttgg aatacttgca a                                              21

<210> SEQ ID NO 108
<211> LENGTH: 21
<212> TYPE: DNA
<213> ORGANISM: Artificial sequence
<220> FEATURE:
<223> OTHER INFORMATION: Target sequence in the gene TAF6

<400> SEQUENCE: 108
ctgggagtgt ccagaagtac a                                              21

<210> SEQ ID NO 109
<211> LENGTH: 21
<212> TYPE: DNA
<213> ORGANISM: Artificial sequence
<220> FEATURE:
<223> OTHER INFORMATION: Target sequence in the gene EIF4A3

<400> SEQUENCE: 109
ccgcatcttg gtgaaacgtg a                                              21

<210> SEQ ID NO 110
<211> LENGTH: 21
<212> TYPE: DNA
<213> ORGANISM: Artificial sequence
<220> FEATURE:
<223> OTHER INFORMATION: Target sequence in the gene CXorf59

<400> SEQUENCE: 110
ctgtgagttc ctgtacacct a                                              21

<210> SEQ ID NO 111
<211> LENGTH: 21
<212> TYPE: DNA

```
<213> ORGANISM: Artificial sequence
<220> FEATURE:
<223> OTHER INFORMATION: Target sequence in the gene TALDO1

<400> SEQUENCE: 111
ccgggccgag tatccacaga a                                              21

<210> SEQ ID NO 112
<211> LENGTH: 21
<212> TYPE: DNA
<213> ORGANISM: Artificial sequence
<220> FEATURE:
<223> OTHER INFORMATION: Target sequence in the gene C16orf59

<400> SEQUENCE: 112
cgggatgaac ctgcagtctg a                                              21

<210> SEQ ID NO 113
<211> LENGTH: 21
<212> TYPE: DNA
<213> ORGANISM: Artificial sequence
<220> FEATURE:
<223> OTHER INFORMATION: Target sequence in the gene H2AFY

<400> SEQUENCE: 113
caagtttgtg atccactgta a                                              21

<210> SEQ ID NO 114
<211> LENGTH: 21
<212> TYPE: DNA
<213> ORGANISM: Artificial sequence
<220> FEATURE:
<223> OTHER INFORMATION: Target sequence in the gene SAMD5

<400> SEQUENCE: 114
ctgctcatag gagttcagta a                                              21

<210> SEQ ID NO 115
<211> LENGTH: 21
<212> TYPE: DNA
<213> ORGANISM: Artificial sequence
<220> FEATURE:
<223> OTHER INFORMATION: Target sequence in the gene PROK2

<400> SEQUENCE: 115
tcgctctgga gtagaaacca a                                              21

<210> SEQ ID NO 116
<211> LENGTH: 21
<212> TYPE: DNA
<213> ORGANISM: Artificial sequence
<220> FEATURE:
<223> OTHER INFORMATION: Target sequence in the gene BCL9L

<400> SEQUENCE: 116
acccacaatt gtaatgtagc a                                              21

<210> SEQ ID NO 117
<211> LENGTH: 21
<212> TYPE: DNA
<213> ORGANISM: Artificial sequence
<220> FEATURE:
<223> OTHER INFORMATION: Target sequence in the gene WDR5

<400> SEQUENCE: 117
aagcagcacc gcagactgta a                                              21
```

<210> SEQ ID NO 118
<211> LENGTH: 21
<212> TYPE: DNA
<213> ORGANISM: Artificial sequence
<220> FEATURE:
<223> OTHER INFORMATION: Target sequence in the gene ADAMTSL5

<400> SEQUENCE: 118
atgcctaacc aggcactgta a                                    21

<210> SEQ ID NO 119
<211> LENGTH: 21
<212> TYPE: DNA
<213> ORGANISM: Artificial sequence
<220> FEATURE:
<223> OTHER INFORMATION: Target sequence in the gene BASP1

<400> SEQUENCE: 119
ttccaagatc cgcgtctgaa a                                    21

<210> SEQ ID NO 120
<211> LENGTH: 21
<212> TYPE: DNA
<213> ORGANISM: Artificial sequence
<220> FEATURE:
<223> OTHER INFORMATION: Target sequence in the gene ALX1

<400> SEQUENCE: 120
tagagctatg gacaactgta a                                    21

<210> SEQ ID NO 121
<211> LENGTH: 21
<212> TYPE: DNA
<213> ORGANISM: Artificial sequence
<220> FEATURE:
<223> OTHER INFORMATION: Target sequence in the gene KLHL34

<400> SEQUENCE: 121
ctcggcagtc gtggaaacca a                                    21

<210> SEQ ID NO 122
<211> LENGTH: 21
<212> TYPE: DNA
<213> ORGANISM: Artificial sequence
<220> FEATURE:
<223> OTHER INFORMATION: Target sequence in the gene CYFIP2

<400> SEQUENCE: 122
cgcccacgtc atggaggtgt a                                    21

<210> SEQ ID NO 123
<211> LENGTH: 21
<212> TYPE: DNA
<213> ORGANISM: Artificial sequence
<220> FEATURE:
<223> OTHER INFORMATION: Target sequence in the gene MID1

<400> SEQUENCE: 123
tagaacgtga tgagtcatca t                                    21

<210> SEQ ID NO 124
<211> LENGTH: 21
<212> TYPE: DNA
<213> ORGANISM: Artificial sequence
<220> FEATURE:

<223> OTHER INFORMATION: Target sequence in the gene SGCD

<400> SEQUENCE: 124
taaatctata gaaacaccta a    21

<210> SEQ ID NO 125
<211> LENGTH: 21
<212> TYPE: DNA
<213> ORGANISM: Artificial sequence
<220> FEATURE:
<223> OTHER INFORMATION: Target sequence in the gene RING1

<400> SEQUENCE: 125
cagggtcaga tcagaccaca a    21

<210> SEQ ID NO 126
<211> LENGTH: 21
<212> TYPE: DNA
<213> ORGANISM: Artificial sequence
<220> FEATURE:
<223> OTHER INFORMATION: Target sequence in the gene CAV3

<400> SEQUENCE: 126
ttgcgttcac ttgtactgta a    21

<210> SEQ ID NO 127
<211> LENGTH: 21
<212> TYPE: DNA
<213> ORGANISM: Artificial sequence
<220> FEATURE:
<223> OTHER INFORMATION: Target sequence in the gene KIAA0280

<400> SEQUENCE: 127
cagcattccc tctgctatct a    21

<210> SEQ ID NO 128
<211> LENGTH: 21
<212> TYPE: DNA
<213> ORGANISM: Artificial sequence
<220> FEATURE:
<223> OTHER INFORMATION: Target sequence in the gene ISCU

<400> SEQUENCE: 128
ctccagcatg tggtgacgta a    21

<210> SEQ ID NO 129
<211> LENGTH: 21
<212> TYPE: DNA
<213> ORGANISM: Artificial sequence
<220> FEATURE:
<223> OTHER INFORMATION: Target sequence in the gene ARVCF

<400> SEQUENCE: 129
aagactattg gtaaacacct a    21

<210> SEQ ID NO 130
<211> LENGTH: 21
<212> TYPE: DNA
<213> ORGANISM: Artificial sequence
<220> FEATURE:
<223> OTHER INFORMATION: Target sequence in the gene BBC3

<400> SEQUENCE: 130
cagcctgtaa gatactgtat a    21

```
<210> SEQ ID NO 131
<211> LENGTH: 21
<212> TYPE: DNA
<213> ORGANISM: Artificial sequence
<220> FEATURE:
<223> OTHER INFORMATION: Target sequence in the gene ZMYND11

<400> SEQUENCE: 131
ccggatgaag tcggaccaca a                                              21

<210> SEQ ID NO 132
<211> LENGTH: 21
<212> TYPE: DNA
<213> ORGANISM: Artificial sequence
<220> FEATURE:
<223> OTHER INFORMATION: Target sequence in the gene PCDHGB5

<400> SEQUENCE: 132
cgggcaaatc tttagtctga a                                              21

<210> SEQ ID NO 133
<211> LENGTH: 21
<212> TYPE: DNA
<213> ORGANISM: Artificial sequence
<220> FEATURE:
<223> OTHER INFORMATION: Target sequence in the gene INTS12

<400> SEQUENCE: 133
aacctgctac ttcgtcagct a                                              21

<210> SEQ ID NO 134
<211> LENGTH: 21
<212> TYPE: DNA
<213> ORGANISM: Artificial sequence
<220> FEATURE:
<223> OTHER INFORMATION: Target sequence in the gene INTS12

<400> SEQUENCE: 134
ctggatggcg ttatgatttc a                                              21

<210> SEQ ID NO 135
<211> LENGTH: 21
<212> TYPE: DNA
<213> ORGANISM: Artificial sequence
<220> FEATURE:
<223> OTHER INFORMATION: Target sequence in the gene NUP35

<400> SEQUENCE: 135
caggacttgg atcaacacct t                                              21

<210> SEQ ID NO 136
<211> LENGTH: 21
<212> TYPE: DNA
<213> ORGANISM: Artificial sequence
<220> FEATURE:
<223> OTHER INFORMATION: Target sequence in the gene OR2M7

<400> SEQUENCE: 136
aagggcaagt ctggagattg a                                              21

<210> SEQ ID NO 137
<211> LENGTH: 21
<212> TYPE: DNA
<213> ORGANISM: Artificial sequence
<220> FEATURE:
<223> OTHER INFORMATION: Target sequence in the gene SLC6A14
```

```
<400> SEQUENCE: 137
accaatagta actcactgta a                                              21

<210> SEQ ID NO 138
<211> LENGTH: 21
<212> TYPE: DNA
<213> ORGANISM: Artificial sequence
<220> FEATURE:
<223> OTHER INFORMATION: Target sequence in the gene CHP2

<400> SEQUENCE: 138
cagggcgaca ataaactgta t                                              21

<210> SEQ ID NO 139
<211> LENGTH: 21
<212> TYPE: DNA
<213> ORGANISM: Artificial sequence
<220> FEATURE:
<223> OTHER INFORMATION: Target sequence in the gene TRIM61

<400> SEQUENCE: 139
tagggtatgt atatgttcct a                                              21

<210> SEQ ID NO 140
<211> LENGTH: 21
<212> TYPE: DNA
<213> ORGANISM: Artificial sequence
<220> FEATURE:
<223> OTHER INFORMATION: Target sequence in the gene AFG3L1

<400> SEQUENCE: 140
cggctggaag tcgtgaacaa a                                              21

<210> SEQ ID NO 141
<211> LENGTH: 21
<212> TYPE: DNA
<213> ORGANISM: Artificial sequence
<220> FEATURE:
<223> OTHER INFORMATION: Target sequence in the gene GTF2I

<400> SEQUENCE: 141
taggtggtcg tgtgatggta a                                              21

<210> SEQ ID NO 142
<211> LENGTH: 21
<212> TYPE: DNA
<213> ORGANISM: Artificial sequence
<220> FEATURE:
<223> OTHER INFORMATION: Target sequence in the gene TMPRSS11A

<400> SEQUENCE: 142
atccacatca atggactgtt a                                              21

<210> SEQ ID NO 143
<211> LENGTH: 21
<212> TYPE: DNA
<213> ORGANISM: Artificial sequence
<220> FEATURE:
<223> OTHER INFORMATION: Target sequence in the gene KRTAP13-3

<400> SEQUENCE: 143
caggactcac atgctctgca a                                              21

<210> SEQ ID NO 144
<211> LENGTH: 21
```

```
<212> TYPE: DNA
<213> ORGANISM: Artificial sequence
<220> FEATURE:
<223> OTHER INFORMATION: Target sequence in the gene ZNF107

<400> SEQUENCE: 144
tacctcggac cagctctgta a                                        21

<210> SEQ ID NO 145
<211> LENGTH: 21
<212> TYPE: DNA
<213> ORGANISM: Artificial sequence
<220> FEATURE:
<223> OTHER INFORMATION: Target sequence in the gene NCOR2

<400> SEQUENCE: 145
aacgagattg ctggaaacca a                                        21

<210> SEQ ID NO 146
<211> LENGTH: 21
<212> TYPE: DNA
<213> ORGANISM: Artificial sequence
<220> FEATURE:
<223> OTHER INFORMATION: Target sequence in the gene NKX2-3

<400> SEQUENCE: 146
caggtacaag tgcaagagac a                                        21

<210> SEQ ID NO 147
<211> LENGTH: 21
<212> TYPE: DNA
<213> ORGANISM: Artificial sequence
<220> FEATURE:
<223> OTHER INFORMATION: Target sequence in the gene NFKBIA

<400> SEQUENCE: 147
cagccagaaa ttgctgaggc a                                        21

<210> SEQ ID NO 148
<211> LENGTH: 21
<212> TYPE: DNA
<213> ORGANISM: Artificial sequence
<220> FEATURE:
<223> OTHER INFORMATION: Target sequence in the gene FAM69B

<400> SEQUENCE: 148
ccggcgggag ctggtactgt t                                        21

<210> SEQ ID NO 149
<211> LENGTH: 21
<212> TYPE: DNA
<213> ORGANISM: Artificial sequence
<220> FEATURE:
<223> OTHER INFORMATION: Target sequence in the gene CARD9

<400> SEQUENCE: 149
cagcgacaac accgacactg a                                        21

<210> SEQ ID NO 150
<211> LENGTH: 21
<212> TYPE: DNA
<213> ORGANISM: Artificial sequence
<220> FEATURE:
<223> OTHER INFORMATION: Target sequence in the gene TMEM105

<400> SEQUENCE: 150
```

```
aacgaggtat ggaactgttc a                                              21

<210> SEQ ID NO 151
<211> LENGTH: 21
<212> TYPE: DNA
<213> ORGANISM: Artificial sequence
<220> FEATURE:
<223> OTHER INFORMATION: Target sequence in the gene LARP6

<400> SEQUENCE: 151
atggtgtctt gtaggaccaa a                                              21

<210> SEQ ID NO 152
<211> LENGTH: 21
<212> TYPE: DNA
<213> ORGANISM: Artificial sequence
<220> FEATURE:
<223> OTHER INFORMATION: Target sequence in the gene VSIG8

<400> SEQUENCE: 152
ccggcgtata ggcgtgatca t                                              21

<210> SEQ ID NO 153
<211> LENGTH: 21
<212> TYPE: DNA
<213> ORGANISM: Artificial sequence
<220> FEATURE:
<223> OTHER INFORMATION: Target sequence in the gene TXNRD1

<400> SEQUENCE: 153
ccgactcaga gtagtagctc a                                              21

<210> SEQ ID NO 154
<211> LENGTH: 21
<212> TYPE: DNA
<213> ORGANISM: Artificial sequence
<220> FEATURE:
<223> OTHER INFORMATION: Target sequence in the gene USP36

<400> SEQUENCE: 154
caagagcgtc tcggacacct a                                              21

<210> SEQ ID NO 155
<211> LENGTH: 21
<212> TYPE: DNA
<213> ORGANISM: Artificial sequence
<220> FEATURE:
<223> OTHER INFORMATION: Target sequence in the gene MYEOV2

<400> SEQUENCE: 155
gtcagcgaag acagcacaat a                                              21

<210> SEQ ID NO 156
<211> LENGTH: 21
<212> TYPE: DNA
<213> ORGANISM: Artificial sequence
<220> FEATURE:
<223> OTHER INFORMATION: Target sequence in the gene NES

<400> SEQUENCE: 156
cgcgccgtcg aggcagagaa a                                              21

<210> SEQ ID NO 157
<211> LENGTH: 21
<212> TYPE: DNA
<213> ORGANISM: Artificial sequence
```

```
<220> FEATURE:
<223> OTHER INFORMATION: Target sequence in the gene PRDX3

<400> SEQUENCE: 157
aaggcgttcc agtatgtaga a                                              21

<210> SEQ ID NO 158
<211> LENGTH: 21
<212> TYPE: DNA
<213> ORGANISM: Artificial sequence
<220> FEATURE:
<223> OTHER INFORMATION: Target sequence in the gene USP39

<400> SEQUENCE: 158
caggctctat ctaatgttcc t                                              21

<210> SEQ ID NO 159
<211> LENGTH: 21
<212> TYPE: DNA
<213> ORGANISM: Artificial sequence
<220> FEATURE:
<223> OTHER INFORMATION: Target sequence in the gene KRT16

<400> SEQUENCE: 159
tacgagcaga tggcagagaa a                                              21

<210> SEQ ID NO 160
<211> LENGTH: 21
<212> TYPE: DNA
<213> ORGANISM: Artificial sequence
<220> FEATURE:
<223> OTHER INFORMATION: Target sequence in the gene HMGA1

<400> SEQUENCE: 160
caccacaact ccaggaagga a                                              21

<210> SEQ ID NO 161
<211> LENGTH: 21
<212> TYPE: DNA
<213> ORGANISM: Artificial sequence
<220> FEATURE:
<223> OTHER INFORMATION: Target sequence in the gene SLCO3A1

<400> SEQUENCE: 161
cagcatcgcc atcgcgctca a                                              21

<210> SEQ ID NO 162
<211> LENGTH: 21
<212> TYPE: DNA
<213> ORGANISM: Artificial sequence
<220> FEATURE:
<223> OTHER INFORMATION: Target sequence in the gene SFN

<400> SEQUENCE: 162
ccgggagaag gtggagactg a                                              21

<210> SEQ ID NO 163
<211> LENGTH: 21
<212> TYPE: DNA
<213> ORGANISM: Artificial sequence
<220> FEATURE:
<223> OTHER INFORMATION: Target sequence in the gene DPP4

<400> SEQUENCE: 163
atcgggaagt ggcgtgttca a                                              21
```

<210> SEQ ID NO 164
<211> LENGTH: 21
<212> TYPE: DNA
<213> ORGANISM: Artificial sequence
<220> FEATURE:
<223> OTHER INFORMATION: Target sequence in the gene SPTBN2

<400> SEQUENCE: 164
cagcgtcaac atcctgctca a                                    21

<210> SEQ ID NO 165
<211> LENGTH: 21
<212> TYPE: DNA
<213> ORGANISM: Artificial sequence
<220> FEATURE:
<223> OTHER INFORMATION: Target sequence in the gene PRRG3

<400> SEQUENCE: 165
aaggtcaacc cttggttctt a                                    21

<210> SEQ ID NO 166
<211> LENGTH: 21
<212> TYPE: DNA
<213> ORGANISM: Artificial sequence
<220> FEATURE:
<223> OTHER INFORMATION: Target sequence in the gene SARM1

<400> SEQUENCE: 166
ctggtggtta agggtagcaa a                                    21

<210> SEQ ID NO 167
<211> LENGTH: 21
<212> TYPE: DNA
<213> ORGANISM: Artificial sequence
<220> FEATURE:
<223> OTHER INFORMATION: Target sequence in the gene GRIN2C

<400> SEQUENCE: 167
cccagctttc actatcggca a                                    21

<210> SEQ ID NO 168
<211> LENGTH: 21
<212> TYPE: DNA
<213> ORGANISM: Artificial sequence
<220> FEATURE:
<223> OTHER INFORMATION: Target sequence in the gene TMEM179

<400> SEQUENCE: 168
cgggccggcc atggcgctca a                                    21

<210> SEQ ID NO 169
<211> LENGTH: 21
<212> TYPE: DNA
<213> ORGANISM: Artificial sequence
<220> FEATURE:
<223> OTHER INFORMATION: Target sequence in the gene TWIST1

<400> SEQUENCE: 169
cacctctgca ttctgataga a                                    21

<210> SEQ ID NO 170
<211> LENGTH: 21
<212> TYPE: DNA
<213> ORGANISM: Artificial sequence
<220> FEATURE:
<223> OTHER INFORMATION: Target sequence in the gene TWIST1

```
<400> SEQUENCE: 170
cccgtctgaa ttcctcagga a                                              21

<210> SEQ ID NO 171
<211> LENGTH: 21
<212> TYPE: DNA
<213> ORGANISM: Artificial sequence
<220> FEATURE:
<223> OTHER INFORMATION: Target sequence in the gene C10orf90

<400> SEQUENCE: 171
cagatccgtc ctgtcgctca a                                              21

<210> SEQ ID NO 172
<211> LENGTH: 21
<212> TYPE: DNA
<213> ORGANISM: Artificial sequence
<220> FEATURE:
<223> OTHER INFORMATION: Target sequence in the gene BTNL9

<400> SEQUENCE: 172
aaggacatta ttagtttgac a                                              21

<210> SEQ ID NO 173
<211> LENGTH: 21
<212> TYPE: DNA
<213> ORGANISM: Artificial sequence
<220> FEATURE:
<223> OTHER INFORMATION: Target sequence in the gene CES2

<400> SEQUENCE: 173
ctgcatgatg ttagttacca a                                              21

<210> SEQ ID NO 174
<211> LENGTH: 21
<212> TYPE: DNA
<213> ORGANISM: Artificial sequence
<220> FEATURE:
<223> OTHER INFORMATION: Target sequence in the gene AOF1

<400> SEQUENCE: 174
atcgatgcgg tatgaaacca a                                              21

<210> SEQ ID NO 175
<211> LENGTH: 21
<212> TYPE: DNA
<213> ORGANISM: Artificial sequence
<220> FEATURE:
<223> OTHER INFORMATION: Target sequence in the gene CPLX2

<400> SEQUENCE: 175
cagataggta gcagagacca a                                              21

<210> SEQ ID NO 176
<211> LENGTH: 21
<212> TYPE: DNA
<213> ORGANISM: Artificial sequence
<220> FEATURE:
<223> OTHER INFORMATION: Target sequence in the gene KCTD15

<400> SEQUENCE: 176
caggataagc cgcctcttca a                                              21

<210> SEQ ID NO 177
```

```
<211> LENGTH: 21
<212> TYPE: DNA
<213> ORGANISM: Artificial sequence
<220> FEATURE:
<223> OTHER INFORMATION: Target sequence in the gene CSH1

<400> SEQUENCE: 177
acgggctgct ctactgcttc a                                              21

<210> SEQ ID NO 178
<211> LENGTH: 21
<212> TYPE: DNA
<213> ORGANISM: Artificial sequence
<220> FEATURE:
<223> OTHER INFORMATION: Target sequence in the gene EDIL3

<400> SEQUENCE: 178
cccaagtttg tcgaagacat t                                              21

<210> SEQ ID NO 179
<211> LENGTH: 21
<212> TYPE: DNA
<213> ORGANISM: Artificial sequence
<220> FEATURE:
<223> OTHER INFORMATION: Target sequence in the gene PAX3

<400> SEQUENCE: 179
aacgcctgac gtggagaaga a                                              21

<210> SEQ ID NO 180
<211> LENGTH: 21
<212> TYPE: DNA
<213> ORGANISM: Artificial sequence
<220> FEATURE:
<223> OTHER INFORMATION: Target sequence in the gene KCNC3

<400> SEQUENCE: 180
cagcggcaag atcgtgatca a                                              21

<210> SEQ ID NO 181
<211> LENGTH: 21
<212> TYPE: DNA
<213> ORGANISM: Artificial sequence
<220> FEATURE:
<223> OTHER INFORMATION: Target sequence in the gene LRRC8C

<400> SEQUENCE: 181
taccttatac tggctgttct a                                              21

<210> SEQ ID NO 182
<211> LENGTH: 21
<212> TYPE: DNA
<213> ORGANISM: Artificial sequence
<220> FEATURE:
<223> OTHER INFORMATION: Target sequence in the gene LOC90586

<400> SEQUENCE: 182
ctgggcatgg gtatgctgta a                                              21

<210> SEQ ID NO 183
<211> LENGTH: 21
<212> TYPE: DNA
<213> ORGANISM: Artificial sequence
<220> FEATURE:
<223> OTHER INFORMATION: Target sequence in the gene LONRF2

<400> SEQUENCE: 183
```
ccgacggata ttagtcatca t          21

<210> SEQ ID NO 184
<211> LENGTH: 21
<212> TYPE: DNA
<213> ORGANISM: Artificial sequence
<220> FEATURE:
<223> OTHER INFORMATION: Target sequence in the gene DDX3X

<400> SEQUENCE: 184
aacgagagag ttggcagtac a          21

<210> SEQ ID NO 185
<211> LENGTH: 21
<212> TYPE: DNA
<213> ORGANISM: Artificial sequence
<220> FEATURE:
<223> OTHER INFORMATION: Target sequence in the gene GNG4

<400> SEQUENCE: 185
ccgaagtcaa cttgactgta a          21

<210> SEQ ID NO 186
<211> LENGTH: 21
<212> TYPE: DNA
<213> ORGANISM: Artificial sequence
<220> FEATURE:
<223> OTHER INFORMATION: Target sequence in the gene SAP30L

<400> SEQUENCE: 186
caagagcgta aggcacctat a          21

<210> SEQ ID NO 187
<211> LENGTH: 21
<212> TYPE: DNA
<213> ORGANISM: Artificial sequence
<220> FEATURE:
<223> OTHER INFORMATION: Target sequence in the gene KCTD15

<400> SEQUENCE: 187
aaccttggag attcacggca a          21

<210> SEQ ID NO 188
<211> LENGTH: 21
<212> TYPE: DNA
<213> ORGANISM: Artificial sequence
<220> FEATURE:
<223> OTHER INFORMATION: Target sequence in the gene LOC165186

<400> SEQUENCE: 188
caacgtctct atagagacca a          21

<210> SEQ ID NO 189
<211> LENGTH: 21
<212> TYPE: DNA
<213> ORGANISM: Artificial sequence
<220> FEATURE:
<223> OTHER INFORMATION: Target sequence in the gene FAM59A

<400> SEQUENCE: 189
aagggcagat ttagcacccg a          21

<210> SEQ ID NO 190
<211> LENGTH: 21
<212> TYPE: DNA

```
<213> ORGANISM: Artificial sequence
<220> FEATURE:
<223> OTHER INFORMATION: Target sequence in the gene ARF5

<400> SEQUENCE: 190
ttcgcggatc ttcgggaaga a                                             21

<210> SEQ ID NO 191
<211> LENGTH: 21
<212> TYPE: DNA
<213> ORGANISM: Artificial sequence
<220> FEATURE:
<223> OTHER INFORMATION: Target sequence in the gene ESSPL

<400> SEQUENCE: 191
cagcctacac tttgaccaca a                                             21

<210> SEQ ID NO 192
<211> LENGTH: 21
<212> TYPE: DNA
<213> ORGANISM: Artificial sequence
<220> FEATURE:
<223> OTHER INFORMATION: Target sequence in the gene SPON1

<400> SEQUENCE: 192
atcgcacgga agggtgaaca a                                             21

<210> SEQ ID NO 193
<211> LENGTH: 21
<212> TYPE: DNA
<213> ORGANISM: Artificial sequence
<220> FEATURE:
<223> OTHER INFORMATION: Target sequence in the gene BCL11B

<400> SEQUENCE: 193
cagaggtggg ttaaactgta a                                             21

<210> SEQ ID NO 194
<211> LENGTH: 21
<212> TYPE: DNA
<213> ORGANISM: Artificial sequence
<220> FEATURE:
<223> OTHER INFORMATION: Target sequence in the gene ZNF826

<400> SEQUENCE: 194
tcagatggtc ctcacaccta a                                             21

<210> SEQ ID NO 195
<211> LENGTH: 21
<212> TYPE: DNA
<213> ORGANISM: Artificial sequence
<220> FEATURE:
<223> OTHER INFORMATION: Target sequence in the gene C21orf62

<400> SEQUENCE: 195
caacctgatg tgcaactgta a                                             21

<210> SEQ ID NO 196
<211> LENGTH: 21
<212> TYPE: DNA
<213> ORGANISM: Artificial sequence
<220> FEATURE:
<223> OTHER INFORMATION: Target sequence in the gene OGFOD1

<400> SEQUENCE: 196
tcggacgctg ttacggaaga a                                             21
```

```
<210> SEQ ID NO 197
<211> LENGTH: 21
<212> TYPE: DNA
<213> ORGANISM: Artificial sequence
<220> FEATURE:
<223> OTHER INFORMATION: Target sequence in the gene LYST

<400> SEQUENCE: 197
cacatcattg tcaacaccta a                                              21

<210> SEQ ID NO 198
<211> LENGTH: 21
<212> TYPE: DNA
<213> ORGANISM: Artificial sequence
<220> FEATURE:
<223> OTHER INFORMATION: Target sequence in the gene LIPJ

<400> SEQUENCE: 198
agggttgttg tatacttgca a                                              21

<210> SEQ ID NO 199
<211> LENGTH: 21
<212> TYPE: DNA
<213> ORGANISM: Artificial sequence
<220> FEATURE:
<223> OTHER INFORMATION: Target sequence in the gene GH2

<400> SEQUENCE: 199
cagctggcat atgacaccta t                                              21

<210> SEQ ID NO 200
<211> LENGTH: 21
<212> TYPE: DNA
<213> ORGANISM: Artificial sequence
<220> FEATURE:
<223> OTHER INFORMATION: Target sequence in the gene PHF21B

<400> SEQUENCE: 200
caccgtggtc agcgtcaaga a                                              21

<210> SEQ ID NO 201
<211> LENGTH: 21
<212> TYPE: DNA
<213> ORGANISM: Artificial sequence
<220> FEATURE:
<223> OTHER INFORMATION: Target sequence in the gene ZFYVE28

<400> SEQUENCE: 201
caagcctgaa acagacgaca a                                              21

<210> SEQ ID NO 202
<211> LENGTH: 21
<212> TYPE: DNA
<213> ORGANISM: Artificial sequence
<220> FEATURE:
<223> OTHER INFORMATION: Target sequence in the gene TMEM183A

<400> SEQUENCE: 202
ctgtacctat aacaccagta a                                              21

<210> SEQ ID NO 203
<211> LENGTH: 21
<212> TYPE: DNA
<213> ORGANISM: Artificial sequence
<220> FEATURE:
```

<223> OTHER INFORMATION: Target sequence in the gene HIST1H2AE

<400> SEQUENCE: 203
atcccgagtc ccagaaacca a                                              21

<210> SEQ ID NO 204
<211> LENGTH: 21
<212> TYPE: DNA
<213> ORGANISM: Artificial sequence
<220> FEATURE:
<223> OTHER INFORMATION: Target sequence in the gene XKRX

<400> SEQUENCE: 204
cacccataat gtagtagact a                                              21

<210> SEQ ID NO 205
<211> LENGTH: 21
<212> TYPE: DNA
<213> ORGANISM: Artificial sequence
<220> FEATURE:
<223> OTHER INFORMATION: Target sequence in the gene CTR9

<400> SEQUENCE: 205
aagggtagtg gcagtgaaca a                                              21

<210> SEQ ID NO 206
<211> LENGTH: 21
<212> TYPE: DNA
<213> ORGANISM: Artificial sequence
<220> FEATURE:
<223> OTHER INFORMATION: Target sequence in the gene POLDIP2

<400> SEQUENCE: 206
cacgtgaggt ttgatcagta a                                              21

<210> SEQ ID NO 207
<211> LENGTH: 21
<212> TYPE: DNA
<213> ORGANISM: Artificial sequence
<220> FEATURE:
<223> OTHER INFORMATION: Target sequence in the gene C5orf3

<400> SEQUENCE: 207
cgcccacgaa tggatcagga a                                              21

<210> SEQ ID NO 208
<211> LENGTH: 21
<212> TYPE: DNA
<213> ORGANISM: Artificial sequence
<220> FEATURE:
<223> OTHER INFORMATION: Target sequence in the gene FGFR3

<400> SEQUENCE: 208
accctacgtt accgtgctca a                                              21

<210> SEQ ID NO 209
<211> LENGTH: 21
<212> TYPE: DNA
<213> ORGANISM: Artificial sequence
<220> FEATURE:
<223> OTHER INFORMATION: Target sequence in the gene DIRAS2

<400> SEQUENCE: 209
cccgacggtg gaagacacct a                                              21

```
<210> SEQ ID NO 210
<211> LENGTH: 21
<212> TYPE: DNA
<213> ORGANISM: Artificial sequence
<220> FEATURE:
<223> OTHER INFORMATION: Target sequence in the gene TM4SF5

<400> SEQUENCE: 210
cgccctcctg ctggtaccta a                                           21

<210> SEQ ID NO 211
<211> LENGTH: 21
<212> TYPE: DNA
<213> ORGANISM: Artificial sequence
<220> FEATURE:
<223> OTHER INFORMATION: Target sequence in the gene CENPH

<400> SEQUENCE: 211
atggataaca tgaaacacct a                                           21

<210> SEQ ID NO 212
<211> LENGTH: 21
<212> TYPE: DNA
<213> ORGANISM: Artificial sequence
<220> FEATURE:
<223> OTHER INFORMATION: Target sequence in the gene NAGK

<400> SEQUENCE: 212
cccggtcttg ttccagggca a                                           21

<210> SEQ ID NO 213
<211> LENGTH: 21
<212> TYPE: DNA
<213> ORGANISM: Artificial sequence
<220> FEATURE:
<223> OTHER INFORMATION: Target sequence in the gene LGI2

<400> SEQUENCE: 213
tacgacgaga gttggaccaa a                                           21

<210> SEQ ID NO 214
<211> LENGTH: 21
<212> TYPE: DNA
<213> ORGANISM: Artificial sequence
<220> FEATURE:
<223> OTHER INFORMATION: Target sequence in the gene TERT

<400> SEQUENCE: 214
ccagaacgtt ccgcagagaa a                                           21

<210> SEQ ID NO 215
<211> LENGTH: 21
<212> TYPE: DNA
<213> ORGANISM: Artificial sequence
<220> FEATURE:
<223> OTHER INFORMATION: Target sequence in the gene PEAR1

<400> SEQUENCE: 215
ctgcacgctg ctcatgtgaa a                                           21

<210> SEQ ID NO 216
<211> LENGTH: 21
<212> TYPE: DNA
<213> ORGANISM: Artificial sequence
<220> FEATURE:
<223> OTHER INFORMATION: Target sequence in the gene FBLIM1
```

```
<400> SEQUENCE: 216
ctccacaatt gttataacca a                                              21

<210> SEQ ID NO 217
<211> LENGTH: 21
<212> TYPE: DNA
<213> ORGANISM: Artificial sequence
<220> FEATURE:
<223> OTHER INFORMATION: Target sequence in the gene PDE7A

<400> SEQUENCE: 217
cagataggtg ctctgatact a                                              21

<210> SEQ ID NO 218
<211> LENGTH: 21
<212> TYPE: DNA
<213> ORGANISM: Artificial sequence
<220> FEATURE:
<223> OTHER INFORMATION: Target sequence in the gene ETV4

<400> SEQUENCE: 218
accggagtca ttgggaagga a                                              21

<210> SEQ ID NO 219
<211> LENGTH: 21
<212> TYPE: DNA
<213> ORGANISM: Artificial sequence
<220> FEATURE:
<223> OTHER INFORMATION: Target sequence in the gene SNORD9

<400> SEQUENCE: 219
ctgtgatgag ttgccatgct a                                              21

<210> SEQ ID NO 220
<211> LENGTH: 21
<212> TYPE: DNA
<213> ORGANISM: Artificial sequence
<220> FEATURE:
<223> OTHER INFORMATION: Target sequence in the gene TMEM25

<400> SEQUENCE: 220
caggcgatga gtctagtagc a                                              21

<210> SEQ ID NO 221
<211> LENGTH: 21
<212> TYPE: DNA
<213> ORGANISM: Artificial sequence
<220> FEATURE:
<223> OTHER INFORMATION: Target sequence in the gene SETD5

<400> SEQUENCE: 221
aacgcgcttg aacaacacct a                                              21

<210> SEQ ID NO 222
<211> LENGTH: 21
<212> TYPE: DNA
<213> ORGANISM: Artificial sequence
<220> FEATURE:
<223> OTHER INFORMATION: Target sequence in the gene SART1

<400> SEQUENCE: 222
cagcatcgag gagactaaca a                                              21

<210> SEQ ID NO 223
<211> LENGTH: 21
```

-continued

```
<212> TYPE: DNA
<213> ORGANISM: Artificial sequence
<220> FEATURE:
<223> OTHER INFORMATION: Target sequence in the gene IL17RB

<400> SEQUENCE: 223
ccgcttgttg aaggccacca a                                                    21

<210> SEQ ID NO 224
<211> LENGTH: 21
<212> TYPE: DNA
<213> ORGANISM: Artificial sequence
<220> FEATURE:
<223> OTHER INFORMATION: Target sequence in the gene NEU1

<400> SEQUENCE: 224
caggtctagt gagctgtaga a                                                    21

<210> SEQ ID NO 225
<211> LENGTH: 21
<212> TYPE: DNA
<213> ORGANISM: Artificial sequence
<220> FEATURE:
<223> OTHER INFORMATION: Target sequence in the gene ST6GALNAC1

<400> SEQUENCE: 225
cccacgacgc agagaaacca a                                                    21

<210> SEQ ID NO 226
<211> LENGTH: 21
<212> TYPE: DNA
<213> ORGANISM: Artificial sequence
<220> FEATURE:
<223> OTHER INFORMATION: Target sequence in the gene KCNIP2

<400> SEQUENCE: 226
cagctgcagg agcaaaccaa a                                                    21

<210> SEQ ID NO 227
<211> LENGTH: 21
<212> TYPE: DNA
<213> ORGANISM: Artificial sequence
<220> FEATURE:
<223> OTHER INFORMATION: Target sequence in the gene PPP3CA

<400> SEQUENCE: 227
tcggcctgta tgggactgta a                                                    21

<210> SEQ ID NO 228
<211> LENGTH: 21
<212> TYPE: DNA
<213> ORGANISM: Artificial sequence
<220> FEATURE:
<223> OTHER INFORMATION: Target sequence in the gene PRPF4

<400> SEQUENCE: 228
tccggtcgtg aagaaaccac a                                                    21

<210> SEQ ID NO 229
<211> LENGTH: 21
<212> TYPE: DNA
<213> ORGANISM: Artificial sequence
<220> FEATURE:
<223> OTHER INFORMATION: Target sequence in the gene SYNGAP1

<400> SEQUENCE: 229
```
cagagcagtg gtaccctgta a                                              21

<210> SEQ ID NO 230
<211> LENGTH: 21
<212> TYPE: DNA
<213> ORGANISM: Artificial sequence
<220> FEATURE:
<223> OTHER INFORMATION: Target sequence in the gene PTBP1

<400> SEQUENCE: 230
gcgcgtgaag atcctgttca a                                              21

<210> SEQ ID NO 231
<211> LENGTH: 21
<212> TYPE: DNA
<213> ORGANISM: Artificial sequence
<220> FEATURE:
<223> OTHER INFORMATION: Target sequence in the gene IGFL4

<400> SEQUENCE: 231
ccagacagtt gtgaggttca a                                              21

<210> SEQ ID NO 232
<211> LENGTH: 21
<212> TYPE: DNA
<213> ORGANISM: Artificial sequence
<220> FEATURE:
<223> OTHER INFORMATION: Target sequence in the gene HES1

<400> SEQUENCE: 232
cacgacaccg gataaaccaa a                                              21

<210> SEQ ID NO 233
<211> LENGTH: 21
<212> TYPE: DNA
<213> ORGANISM: Artificial sequence
<220> FEATURE:
<223> OTHER INFORMATION: Target sequence in the gene UNQ830

<400> SEQUENCE: 233
cacagacgat gttccacagg a                                              21

<210> SEQ ID NO 234
<211> LENGTH: 21
<212> TYPE: DNA
<213> ORGANISM: Artificial sequence
<220> FEATURE:
<223> OTHER INFORMATION: Target sequence in the gene UNQ830

<400> SEQUENCE: 234
ctcgggaaac gtggacgaca a                                              21

<210> SEQ ID NO 235
<211> LENGTH: 21
<212> TYPE: DNA
<213> ORGANISM: Artificial sequence
<220> FEATURE:
<223> OTHER INFORMATION: Target sequence in the gene PLG

<400> SEQUENCE: 235
aagtgcggtg ggagtactgt a                                              21

<210> SEQ ID NO 236
<211> LENGTH: 21
<212> TYPE: DNA
<213> ORGANISM: Artificial sequence

```
<220> FEATURE:
<223> OTHER INFORMATION: Target sequence in the gene IK

<400> SEQUENCE: 236
caggcgcttc aaggaaacca a                                              21

<210> SEQ ID NO 237
<211> LENGTH: 21
<212> TYPE: DNA
<213> ORGANISM: Artificial sequence
<220> FEATURE:
<223> OTHER INFORMATION: Target sequence in the gene UBE2D4

<400> SEQUENCE: 237
ccgaatgaca gtccttacca a                                              21

<210> SEQ ID NO 238
<211> LENGTH: 21
<212> TYPE: DNA
<213> ORGANISM: Artificial sequence
<220> FEATURE:
<223> OTHER INFORMATION: Target sequence in the gene NEK3

<400> SEQUENCE: 238
cagagatatc aagtccaaga a                                              21

<210> SEQ ID NO 239
<211> LENGTH: 21
<212> TYPE: DNA
<213> ORGANISM: Artificial sequence
<220> FEATURE:
<223> OTHER INFORMATION: Target sequence in the gene ATF7IP2

<400> SEQUENCE: 239
taggacgact gaaataacca a                                              21

<210> SEQ ID NO 240
<211> LENGTH: 21
<212> TYPE: DNA
<213> ORGANISM: Artificial sequence
<220> FEATURE:
<223> OTHER INFORMATION: Target sequence in the gene SRRM2

<400> SEQUENCE: 240
cgccacctaa acagaaatct a                                              21

<210> SEQ ID NO 241
<211> LENGTH: 21
<212> TYPE: DNA
<213> ORGANISM: Artificial sequence
<220> FEATURE:
<223> OTHER INFORMATION: Target sequence in the gene SRRM2

<400> SEQUENCE: 241
ctcgatcatc tccggagcta a                                              21

<210> SEQ ID NO 242
<211> LENGTH: 21
<212> TYPE: DNA
<213> ORGANISM: Artificial sequence
<220> FEATURE:
<223> OTHER INFORMATION: Target sequence in the gene FYCO1

<400> SEQUENCE: 242
aagccacgtc atataactca a                                              21
```

```
<210> SEQ ID NO 243
<211> LENGTH: 21
<212> TYPE: DNA
<213> ORGANISM: Artificial sequence
<220> FEATURE:
<223> OTHER INFORMATION: Target sequence in the gene ABHD9

<400> SEQUENCE: 243
cagctcagtg ctactctgaa t                                              21

<210> SEQ ID NO 244
<211> LENGTH: 21
<212> TYPE: DNA
<213> ORGANISM: Artificial sequence
<220> FEATURE:
<223> OTHER INFORMATION: Target sequence in the gene CGB

<400> SEQUENCE: 244
accaaggatg gagatgttcc a                                              21

<210> SEQ ID NO 245
<211> LENGTH: 21
<212> TYPE: DNA
<213> ORGANISM: Artificial sequence
<220> FEATURE:
<223> OTHER INFORMATION: Target sequence in the gene HES5

<400> SEQUENCE: 245
cacgcagatg aagctgctgt a                                              21

<210> SEQ ID NO 246
<211> LENGTH: 21
<212> TYPE: DNA
<213> ORGANISM: Artificial sequence
<220> FEATURE:
<223> OTHER INFORMATION: Target sequence in the gene RAB10

<400> SEQUENCE: 246
aagggacaaa ctagtaggtt t                                              21

<210> SEQ ID NO 247
<211> LENGTH: 21
<212> TYPE: DNA
<213> ORGANISM: Artificial sequence
<220> FEATURE:
<223> OTHER INFORMATION: Target sequence in the gene RAB10

<400> SEQUENCE: 247
cccgttagtg ctacactcat t                                              21

<210> SEQ ID NO 248
<211> LENGTH: 21
<212> TYPE: DNA
<213> ORGANISM: Artificial sequence
<220> FEATURE:
<223> OTHER INFORMATION: Target sequence in the gene BZW2

<400> SEQUENCE: 248
caggagcgtc tttctcagga a                                              21

<210> SEQ ID NO 249
<211> LENGTH: 21
<212> TYPE: DNA
<213> ORGANISM: Artificial sequence
<220> FEATURE:
<223> OTHER INFORMATION: Target sequence in the gene FAM100B
```

```
<400> SEQUENCE: 249
cacgttcttc caagaaacca a                                              21

<210> SEQ ID NO 250
<211> LENGTH: 21
<212> TYPE: DNA
<213> ORGANISM: Artificial sequence
<220> FEATURE:
<223> OTHER INFORMATION: Target sequence in the gene MGC23985

<400> SEQUENCE: 250
accagacaag ccagacgaca a                                              21

<210> SEQ ID NO 251
<211> LENGTH: 21
<212> TYPE: DNA
<213> ORGANISM: Artificial sequence
<220> FEATURE:
<223> OTHER INFORMATION: Target sequence in the gene CSAG2

<400> SEQUENCE: 251
ccagccgaac gaggaactca a                                              21

<210> SEQ ID NO 252
<211> LENGTH: 21
<212> TYPE: DNA
<213> ORGANISM: Artificial sequence
<220> FEATURE:
<223> OTHER INFORMATION: Target sequence in the gene CSAG2

<400> SEQUENCE: 252
ctcctttatc ttccaaacca a                                              21

<210> SEQ ID NO 253
<211> LENGTH: 21
<212> TYPE: DNA
<213> ORGANISM: Artificial sequence
<220> FEATURE:
<223> OTHER INFORMATION: Target sequence in the gene GGA1

<400> SEQUENCE: 253
cccgccatgt gacgacacca a                                              21

<210> SEQ ID NO 254
<211> LENGTH: 21
<212> TYPE: DNA
<213> ORGANISM: Artificial sequence
<220> FEATURE:
<223> OTHER INFORMATION: Target sequence in the gene C10orf53

<400> SEQUENCE: 254
ctggaatgtg gtggaactca t                                              21

<210> SEQ ID NO 255
<211> LENGTH: 21
<212> TYPE: DNA
<213> ORGANISM: Artificial sequence
<220> FEATURE:
<223> OTHER INFORMATION: Target sequence in the gene TBL3

<400> SEQUENCE: 255
ctgcgtcacg tggaacacca a                                              21

<210> SEQ ID NO 256
```

```
<211> LENGTH: 21
<212> TYPE: DNA
<213> ORGANISM: Artificial sequence
<220> FEATURE:
<223> OTHER INFORMATION: Target sequence in the gene EEF1A1

<400> SEQUENCE: 256
cagaatagga acaaggttct a                                              21

<210> SEQ ID NO 257
<211> LENGTH: 21
<212> TYPE: DNA
<213> ORGANISM: Artificial sequence
<220> FEATURE:
<223> OTHER INFORMATION: Target sequence in the gene OTOP3

<400> SEQUENCE: 257
ttgccagtac ttcaccctct a                                              21

<210> SEQ ID NO 258
<211> LENGTH: 21
<212> TYPE: DNA
<213> ORGANISM: Artificial sequence
<220> FEATURE:
<223> OTHER INFORMATION: Target sequence in the gene BANP

<400> SEQUENCE: 258
cagcgacatc caggttcagt a                                              21

<210> SEQ ID NO 259
<211> LENGTH: 21
<212> TYPE: DNA
<213> ORGANISM: Artificial sequence
<220> FEATURE:
<223> OTHER INFORMATION: Target sequence in the gene FOXP2

<400> SEQUENCE: 259
aaggcgacat tcagacaaat a                                              21

<210> SEQ ID NO 260
<211> LENGTH: 21
<212> TYPE: DNA
<213> ORGANISM: Artificial sequence
<220> FEATURE:
<223> OTHER INFORMATION: Target sequence in the gene BAHD1

<400> SEQUENCE: 260
caagaattac ccacttcgta a                                              21

<210> SEQ ID NO 261
<211> LENGTH: 21
<212> TYPE: DNA
<213> ORGANISM: Artificial sequence
<220> FEATURE:
<223> OTHER INFORMATION: Target sequence in the gene ZNF416

<400> SEQUENCE: 261
gaggcctttg ccagagttaa a                                              21

<210> SEQ ID NO 262
<211> LENGTH: 21
<212> TYPE: DNA
<213> ORGANISM: Artificial sequence
<220> FEATURE:
<223> OTHER INFORMATION: Target sequence in the gene VPS4A

<400> SEQUENCE: 262
```
ctcaaagacc gagtgacata a                                              21

<210> SEQ ID NO 263
<211> LENGTH: 21
<212> TYPE: DNA
<213> ORGANISM: Artificial sequence
<220> FEATURE:
<223> OTHER INFORMATION: Target sequence in the gene FAM38B

<400> SEQUENCE: 263
cacctagtga ttctaactca a                                              21

<210> SEQ ID NO 264
<211> LENGTH: 21
<212> TYPE: DNA
<213> ORGANISM: Artificial sequence
<220> FEATURE:
<223> OTHER INFORMATION: Target sequence in the gene LRRC24

<400> SEQUENCE: 264
ccacgagatg ttcgtcatca a                                              21

<210> SEQ ID NO 265
<211> LENGTH: 21
<212> TYPE: DNA
<213> ORGANISM: Artificial sequence
<220> FEATURE:
<223> OTHER INFORMATION: Target sequence in the gene SECISBP2

<400> SEQUENCE: 265
tcccagtatc tttataacca a                                              21

<210> SEQ ID NO 266
<211> LENGTH: 21
<212> TYPE: DNA
<213> ORGANISM: Artificial sequence
<220> FEATURE:
<223> OTHER INFORMATION: Target sequence in the gene C6orf1

<400> SEQUENCE: 266
cagatgtata gtattcagta t                                              21

<210> SEQ ID NO 267
<211> LENGTH: 21
<212> TYPE: DNA
<213> ORGANISM: Artificial sequence
<220> FEATURE:
<223> OTHER INFORMATION: Target sequence in the gene SEMA3G

<400> SEQUENCE: 267 ccctgccta ttgaaactca a                                               21

<210> SEQ ID NO 268
<211> LENGTH: 21
<212> TYPE: DNA
<213> ORGANISM: Artificial sequence
<220> FEATURE:
<223> OTHER INFORMATION: Target sequence in the gene C16orf3

<400> SEQUENCE: 268
ctgggacaac gcagtgttca a                                              21

<210> SEQ ID NO 269
<211> LENGTH: 21
<212> TYPE: DNA

<213> ORGANISM: Artificial sequence
<220> FEATURE:
<223> OTHER INFORMATION: Target sequence in the gene ANKRD12

<400> SEQUENCE: 269
ccggagcgga ttaaaccacc a                                    21

<210> SEQ ID NO 270
<211> LENGTH: 21
<212> TYPE: DNA
<213> ORGANISM: Artificial sequence
<220> FEATURE:
<223> OTHER INFORMATION: Target sequence in the gene TEX28

<400> SEQUENCE: 270
cagcgaagag agaatggcct a                                    21

<210> SEQ ID NO 271
<211> LENGTH: 21
<212> TYPE: DNA
<213> ORGANISM: Artificial sequence
<220> FEATURE:
<223> OTHER INFORMATION: Target sequence in the gene MAPK8IP3

<400> SEQUENCE: 271
cagccgcaac atggaagtac a                                    21

<210> SEQ ID NO 272
<211> LENGTH: 21
<212> TYPE: DNA
<213> ORGANISM: Artificial sequence
<220> FEATURE:
<223> OTHER INFORMATION: Target sequence in the gene FAM9A

<400> SEQUENCE: 272
aaagctcagt tggaagctca a                                    21

<210> SEQ ID NO 273
<211> LENGTH: 21
<212> TYPE: DNA
<213> ORGANISM: Artificial sequence
<220> FEATURE:
<223> OTHER INFORMATION: Target sequence in the gene ACTR8

<400> SEQUENCE: 273
tactaccaac ttagtcatca a                                    21

<210> SEQ ID NO 274
<211> LENGTH: 21
<212> TYPE: DNA
<213> ORGANISM: Artificial sequence
<220> FEATURE:
<223> OTHER INFORMATION: Target sequence in the gene SNHG1

<400> SEQUENCE: 274
cagcgttaca gtaatgttcc a                                    21

<210> SEQ ID NO 275
<211> LENGTH: 21
<212> TYPE: DNA
<213> ORGANISM: Artificial sequence
<220> FEATURE:
<223> OTHER INFORMATION: Target sequence in the gene SNORD114-10

<400> SEQUENCE: 275
atgatgaata catgtctgaa a                                    21

```
<210> SEQ ID NO 276
<211> LENGTH: 21
<212> TYPE: DNA
<213> ORGANISM: Artificial sequence
<220> FEATURE:
<223> OTHER INFORMATION: Target sequence in the gene LYPD1

<400> SEQUENCE: 276
cacggtgaac gttcaagaca t                                              21

<210> SEQ ID NO 277
<211> LENGTH: 21
<212> TYPE: DNA
<213> ORGANISM: Artificial sequence
<220> FEATURE:
<223> OTHER INFORMATION: Target sequence in the gene SSBP1

<400> SEQUENCE: 277
agcctaaaga ttagactgta a                                              21

<210> SEQ ID NO 278
<211> LENGTH: 21
<212> TYPE: DNA
<213> ORGANISM: Artificial sequence
<220> FEATURE:
<223> OTHER INFORMATION: Target sequence in the gene TRIM32

<400> SEQUENCE: 278
cagcactcca ggaatgttca a                                              21

<210> SEQ ID NO 279
<211> LENGTH: 21
<212> TYPE: DNA
<213> ORGANISM: Artificial sequence
<220> FEATURE:
<223> OTHER INFORMATION: Target sequence in the gene POLR3H

<400> SEQUENCE: 279
aacaaacggc acagacacca a                                              21

<210> SEQ ID NO 280
<211> LENGTH: 21
<212> TYPE: DNA
<213> ORGANISM: Artificial sequence
<220> FEATURE:
<223> OTHER INFORMATION: Target sequence in the gene SNORA71B

<400> SEQUENCE: 280
tgcctttgcc ctggtcattg a                                              21

<210> SEQ ID NO 281
<211> LENGTH: 21
<212> TYPE: DNA
<213> ORGANISM: Artificial sequence
<220> FEATURE:
<223> OTHER INFORMATION: Target sequence in the gene KRT6C

<400> SEQUENCE: 281
caagtcaacg tctctgtagt a                                              21

<210> SEQ ID NO 282
<211> LENGTH: 21
<212> TYPE: DNA
<213> ORGANISM: Artificial sequence
<220> FEATURE:
```

<223> OTHER INFORMATION: Target sequence in the gene CYP2A7

<400> SEQUENCE: 282
cccaagctag gtggcattca t         21

<210> SEQ ID NO 283
<211> LENGTH: 21
<212> TYPE: DNA
<213> ORGANISM: Artificial sequence
<220> FEATURE:
<223> OTHER INFORMATION: Target sequence in the gene PTPN22

<400> SEQUENCE: 283
tgggatgtac gttgttacca a         21

<210> SEQ ID NO 284
<211> LENGTH: 21
<212> TYPE: DNA
<213> ORGANISM: Artificial sequence
<220> FEATURE:
<223> OTHER INFORMATION: Target sequence in the gene P2RX5

<400> SEQUENCE: 284
ctgataaaga agggttacca a         21

<210> SEQ ID NO 285
<211> LENGTH: 21
<212> TYPE: DNA
<213> ORGANISM: Artificial sequence
<220> FEATURE:
<223> OTHER INFORMATION: Target sequence in the gene FANCE

<400> SEQUENCE: 285
tcgaatctgg atgatgctaa a         21

<210> SEQ ID NO 286
<211> LENGTH: 21
<212> TYPE: DNA
<213> ORGANISM: Artificial sequence
<220> FEATURE:
<223> OTHER INFORMATION: Target sequence in the gene PLS3

<400> SEQUENCE: 286
aacggattca tttgtgacta t         21

<210> SEQ ID NO 287
<211> LENGTH: 21
<212> TYPE: DNA
<213> ORGANISM: Artificial sequence
<220> FEATURE:
<223> OTHER INFORMATION: Target sequence in the gene HNRNPA1

<400> SEQUENCE: 287
cagggtgatg ccaggttcta t         21

<210> SEQ ID NO 288
<211> LENGTH: 21
<212> TYPE: DNA
<213> ORGANISM: Artificial sequence
<220> FEATURE:
<223> OTHER INFORMATION: Target sequence in the gene CD72

<400> SEQUENCE: 288
atcacctacg agaatgttca a         21

```
<210> SEQ ID NO 289
<211> LENGTH: 21
<212> TYPE: DNA
<213> ORGANISM: Artificial sequence
<220> FEATURE:
<223> OTHER INFORMATION: Target sequence in the gene PRC1

<400> SEQUENCE: 289
tcgagtggag ctggttcagt a                                         21

<210> SEQ ID NO 290
<211> LENGTH: 21
<212> TYPE: DNA
<213> ORGANISM: Artificial sequence
<220> FEATURE:
<223> OTHER INFORMATION: Target sequence in the gene COL5A3

<400> SEQUENCE: 290
cccgggcatc caggtctgaa a                                         21

<210> SEQ ID NO 291
<211> LENGTH: 21
<212> TYPE: DNA
<213> ORGANISM: Artificial sequence
<220> FEATURE:
<223> OTHER INFORMATION: Target sequence in the gene ZNF649

<400> SEQUENCE: 291
aacgctatga acacggaaga a                                         21

<210> SEQ ID NO 292
<211> LENGTH: 21
<212> TYPE: DNA
<213> ORGANISM: Artificial sequence
<220> FEATURE:
<223> OTHER INFORMATION: Target sequence in the gene HCP5

<400> SEQUENCE: 292
taggagggag tcagtactgt t                                         21

<210> SEQ ID NO 293
<211> LENGTH: 21
<212> TYPE: DNA
<213> ORGANISM: Artificial sequence
<220> FEATURE:
<223> OTHER INFORMATION: Target sequence in the gene PXDNL

<400> SEQUENCE: 293
taccgactga atgccacctt a                                         21

<210> SEQ ID NO 294
<211> LENGTH: 21
<212> TYPE: DNA
<213> ORGANISM: Artificial sequence
<220> FEATURE:
<223> OTHER INFORMATION: Target sequence in the gene CDYL2

<400> SEQUENCE: 294
aatgatcatg ttggagagca a                                         21

<210> SEQ ID NO 295
<211> LENGTH: 21
<212> TYPE: DNA
<213> ORGANISM: Artificial sequence
<220> FEATURE:
<223> OTHER INFORMATION: Target sequence in the gene C17orf28
```

<400> SEQUENCE: 295
cccgtggaag ccaccgatga t     21

<210> SEQ ID NO 296
<211> LENGTH: 21
<212> TYPE: DNA
<213> ORGANISM: Artificial sequence
<220> FEATURE:
<223> OTHER INFORMATION: Target sequence in the gene PPP1R13L

<400> SEQUENCE: 296
aaggagtaaa gtctagcagg a     21

<210> SEQ ID NO 297
<211> LENGTH: 21
<212> TYPE: DNA
<213> ORGANISM: Artificial sequence
<220> FEATURE:
<223> OTHER INFORMATION: Target sequence in the gene LINCR

<400> SEQUENCE: 297
ctgggccgtg atggacgtgt a     21

<210> SEQ ID NO 298
<211> LENGTH: 21
<212> TYPE: DNA
<213> ORGANISM: Artificial sequence
<220> FEATURE:
<223> OTHER INFORMATION: Target sequence in the gene PRTN3

<400> SEQUENCE: 298
caactacgac gcggagaaca a     21

<210> SEQ ID NO 299
<211> LENGTH: 21
<212> TYPE: DNA
<213> ORGANISM: Artificial sequence
<220> FEATURE:
<223> OTHER INFORMATION: Target sequence in the gene SLC25A19

<400> SEQUENCE: 299
ctccctgtga tcagttacca a     21

<210> SEQ ID NO 300
<211> LENGTH: 21
<212> TYPE: DNA
<213> ORGANISM: Artificial sequence
<220> FEATURE:
<223> OTHER INFORMATION: Target sequence in the gene C14orf45

<400> SEQUENCE: 300
ttccgtcttc caagttacca a     21

<210> SEQ ID NO 301
<211> LENGTH: 21
<212> TYPE: DNA
<213> ORGANISM: Artificial sequence
<220> FEATURE:
<223> OTHER INFORMATION: Target sequence in the gene PPHLN1

<400> SEQUENCE: 301
caagagatac ttcaccctca a     21

<210> SEQ ID NO 302
<211> LENGTH: 21

```
<212> TYPE: DNA
<213> ORGANISM: Artificial sequence
<220> FEATURE:
<223> OTHER INFORMATION: Target sequence in the gene ENDOGL1

<400> SEQUENCE: 302
aagaagctag aagaactcaa a                                              21

<210> SEQ ID NO 303
<211> LENGTH: 21
<212> TYPE: DNA
<213> ORGANISM: Artificial sequence
<220> FEATURE:
<223> OTHER INFORMATION: Target sequence in the gene SEPT7

<400> SEQUENCE: 303
cagaatctca ttactgcttc a                                              21

<210> SEQ ID NO 304
<211> LENGTH: 21
<212> TYPE: DNA
<213> ORGANISM: Artificial sequence
<220> FEATURE:
<223> OTHER INFORMATION: Target sequence in the gene CHRNB4

<400> SEQUENCE: 304
cagcaagtca tgcgtgacca a                                              21

<210> SEQ ID NO 305
<211> LENGTH: 21
<212> TYPE: DNA
<213> ORGANISM: Artificial sequence
<220> FEATURE:
<223> OTHER INFORMATION: Target sequence in the gene SPACA3

<400> SEQUENCE: 305
aagctctacg gtcgttgtga a                                              21

<210> SEQ ID NO 306
<211> LENGTH: 21
<212> TYPE: DNA
<213> ORGANISM: Artificial sequence
<220> FEATURE:
<223> OTHER INFORMATION: Target sequence in the gene DCI

<400> SEQUENCE: 306
caggtactgc ataggactca a                                              21

<210> SEQ ID NO 307
<211> LENGTH: 21
<212> TYPE: DNA
<213> ORGANISM: Artificial sequence
<220> FEATURE:
<223> OTHER INFORMATION: Target sequence in the gene C6orf136

<400> SEQUENCE: 307
ctcatttgtc gccatcgtct a                                              21

<210> SEQ ID NO 308
<211> LENGTH: 21
<212> TYPE: DNA
<213> ORGANISM: Artificial sequence
<220> FEATURE:
<223> OTHER INFORMATION: Target sequence in the gene CLIC6

<400> SEQUENCE: 308
```
ccgaatctaa ttccgcagga a                                               21

<210> SEQ ID NO 309
<211> LENGTH: 21
<212> TYPE: DNA
<213> ORGANISM: Artificial sequence
<220> FEATURE:
<223> OTHER INFORMATION: Target sequence in the gene RBPJL

<400> SEQUENCE: 309
ctcaaaggtc tccctcttca a                                               21

<210> SEQ ID NO 310
<211> LENGTH: 21
<212> TYPE: DNA
<213> ORGANISM: Artificial sequence
<220> FEATURE:
<223> OTHER INFORMATION: Target sequence in the gene DPY19L2P1

<400> SEQUENCE: 310
gtccattgtc taagtgttct a                                               21

<210> SEQ ID NO 311
<211> LENGTH: 21
<212> TYPE: DNA
<213> ORGANISM: Artificial sequence
<220> FEATURE:
<223> OTHER INFORMATION: Target sequence in the gene C21orf2

<400> SEQUENCE: 311
aagggccgtt tctccacaga a                                               21

<210> SEQ ID NO 312
<211> LENGTH: 21
<212> TYPE: DNA
<213> ORGANISM: Artificial sequence
<220> FEATURE:
<223> OTHER INFORMATION: Target sequence in the gene C1orf76

<400> SEQUENCE: 312
tacggtgatc ctcctctgca t                                               21

<210> SEQ ID NO 313
<211> LENGTH: 21
<212> TYPE: DNA
<213> ORGANISM: Artificial sequence
<220> FEATURE:
<223> OTHER INFORMATION: Target sequence in the gene TBC1D5

<400> SEQUENCE: 313
aggaaggttg ttggccaaca a                                               21

<210> SEQ ID NO 314
<211> LENGTH: 21
<212> TYPE: DNA
<213> ORGANISM: Artificial sequence
<220> FEATURE:
<223> OTHER INFORMATION: Target sequence in the gene TMEM203

<400> SEQUENCE: 314
aacaggtgtc agatactcat a                                               21

<210> SEQ ID NO 315
<211> LENGTH: 21
<212> TYPE: DNA
<213> ORGANISM: Artificial sequence

```
<220> FEATURE:
<223> OTHER INFORMATION: Target sequence in the gene PTPRA

<400> SEQUENCE: 315
ccggagaatg gcagacgaca a                                      21

<210> SEQ ID NO 316
<211> LENGTH: 21
<212> TYPE: DNA
<213> ORGANISM: Artificial sequence
<220> FEATURE:
<223> OTHER INFORMATION: Target sequence in the gene CSNK1A1L

<400> SEQUENCE: 316
ctgcttacct gtgaagacat a                                      21

<210> SEQ ID NO 317
<211> LENGTH: 21
<212> TYPE: DNA
<213> ORGANISM: Artificial sequence
<220> FEATURE:
<223> OTHER INFORMATION: Target sequence in the gene GSTM1L

<400> SEQUENCE: 317
atccttgacc tgaactgtat a                                      21

<210> SEQ ID NO 318
<211> LENGTH: 21
<212> TYPE: DNA
<213> ORGANISM: Artificial sequence
<220> FEATURE:
<223> OTHER INFORMATION: Target sequence in the gene LOXL2

<400> SEQUENCE: 318
ccggagttgc ctgctcagaa a                                      21

<210> SEQ ID NO 319
<211> LENGTH: 21
<212> TYPE: DNA
<213> ORGANISM: Artificial sequence
<220> FEATURE:
<223> OTHER INFORMATION: Target sequence in the gene ACSL5

<400> SEQUENCE: 319
caagggtaca aacgtgttca a                                      21

<210> SEQ ID NO 320
<211> LENGTH: 21
<212> TYPE: DNA
<213> ORGANISM: Artificial sequence
<220> FEATURE:
<223> OTHER INFORMATION: Target sequence in the gene MT4

<400> SEQUENCE: 320
atgcacaacc tgcaactgta a                                      21

<210> SEQ ID NO 321
<211> LENGTH: 21
<212> TYPE: DNA
<213> ORGANISM: Artificial sequence
<220> FEATURE:
<223> OTHER INFORMATION: Target sequence in the gene DNTTIP1

<400> SEQUENCE: 321
ccggcatggt atggaaacca a                                      21
```

<210> SEQ ID NO 322
<211> LENGTH: 21
<212> TYPE: DNA
<213> ORGANISM: Artificial sequence
<220> FEATURE:
<223> OTHER INFORMATION: Target sequence in the gene OR2A14

<400> SEQUENCE: 322
cacctggcca ttgttgacat a                                              21

<210> SEQ ID NO 323
<211> LENGTH: 21
<212> TYPE: DNA
<213> ORGANISM: Artificial sequence
<220> FEATURE:
<223> OTHER INFORMATION: Target sequence in the gene ASB2

<400> SEQUENCE: 323
caagtacggt gctgacatca a                                              21

<210> SEQ ID NO 324
<211> LENGTH: 21
<212> TYPE: DNA
<213> ORGANISM: Artificial sequence
<220> FEATURE:
<223> OTHER INFORMATION: Target sequence in the gene SREBF2

<400> SEQUENCE: 324
ccgcagtgtc ctgtcattcg a                                              21

<210> SEQ ID NO 325
<211> LENGTH: 21
<212> TYPE: DNA
<213> ORGANISM: Artificial sequence
<220> FEATURE:
<223> OTHER INFORMATION: Target sequence in the gene ISG20L1

<400> SEQUENCE: 325
cacgggcact catcagtaga a                                              21

<210> SEQ ID NO 326
<211> LENGTH: 21
<212> TYPE: DNA
<213> ORGANISM: Artificial sequence
<220> FEATURE:
<223> OTHER INFORMATION: Target sequence in the gene SPTBN2

<400> SEQUENCE: 326
ctccgcggat ctagtcatca a                                              21

<210> SEQ ID NO 327
<211> LENGTH: 21
<212> TYPE: DNA
<213> ORGANISM: Artificial sequence
<220> FEATURE:
<223> OTHER INFORMATION: Target sequence in the gene LYNX1

<400> SEQUENCE: 327
caccaggatg aaggtcagta a                                              21

<210> SEQ ID NO 328
<211> LENGTH: 21
<212> TYPE: DNA
<213> ORGANISM: Artificial sequence
<220> FEATURE:
<223> OTHER INFORMATION: Target sequence in the gene LTBR

```
<400> SEQUENCE: 328
tacatctaca atggaccagt a                                              21

<210> SEQ ID NO 329
<211> LENGTH: 21
<212> TYPE: DNA
<213> ORGANISM: Artificial sequence
<220> FEATURE:
<223> OTHER INFORMATION: Target sequence in the gene ZNF295

<400> SEQUENCE: 329
caggttgaag tccataatca g                                              21

<210> SEQ ID NO 330
<211> LENGTH: 21
<212> TYPE: DNA
<213> ORGANISM: Artificial sequence
<220> FEATURE:
<223> OTHER INFORMATION: Target sequence in the gene SOX11

<400> SEQUENCE: 330
ctccgacctg gtgttcacat a                                              21

<210> SEQ ID NO 331
<211> LENGTH: 21
<212> TYPE: DNA
<213> ORGANISM: Artificial sequence
<220> FEATURE:
<223> OTHER INFORMATION: Target sequence in the gene PANK2

<400> SEQUENCE: 331
ctgtgtgtga acttactgta a                                              21

<210> SEQ ID NO 332
<211> LENGTH: 21
<212> TYPE: DNA
<213> ORGANISM: Artificial sequence
<220> FEATURE:
<223> OTHER INFORMATION: Target sequence in the gene RBM47

<400> SEQUENCE: 332
cacggtggct ccaaacgttc a                                              21

<210> SEQ ID NO 333
<211> LENGTH: 21
<212> TYPE: DNA
<213> ORGANISM: Artificial sequence
<220> FEATURE:
<223> OTHER INFORMATION: Target sequence in the gene CCDC13

<400> SEQUENCE: 333
cccaaccggg agcgagaaga a                                              21

<210> SEQ ID NO 334
<211> LENGTH: 21
<212> TYPE: DNA
<213> ORGANISM: Artificial sequence
<220> FEATURE:
<223> OTHER INFORMATION: Target sequence in the gene RTF1

<400> SEQUENCE: 334
accgctcatc acgaacatca t                                              21

<210> SEQ ID NO 335
```

```
<211> LENGTH: 21
<212> TYPE: DNA
<213> ORGANISM: Artificial sequence
<220> FEATURE:
<223> OTHER INFORMATION: Target sequence in the gene ZRANB2

<400> SEQUENCE: 335
cacgatcttc atcacgctca t                                              21

<210> SEQ ID NO 336
<211> LENGTH: 21
<212> TYPE: DNA
<213> ORGANISM: Artificial sequence
<220> FEATURE:
<223> OTHER INFORMATION: Target sequence in the gene FAM83E

<400> SEQUENCE: 336
ctcggcgtct gtcaagcaga a                                              21

<210> SEQ ID NO 337
<211> LENGTH: 21
<212> TYPE: DNA
<213> ORGANISM: Artificial sequence
<220> FEATURE:
<223> OTHER INFORMATION: Target sequence in the gene RCP9

<400> SEQUENCE: 337
gaggaatttc ctcgagaaca a                                              21

<210> SEQ ID NO 338
<211> LENGTH: 21
<212> TYPE: DNA
<213> ORGANISM: Artificial sequence
<220> FEATURE:
<223> OTHER INFORMATION: Target sequence in the gene NMBR

<400> SEQUENCE: 338
cccgcggaca gtaaacttgc a                                              21

<210> SEQ ID NO 339
<211> LENGTH: 21
<212> TYPE: DNA
<213> ORGANISM: Artificial sequence
<220> FEATURE:
<223> OTHER INFORMATION: Target sequence in the gene CPNE2

<400> SEQUENCE: 339
caggacagaa accgcgatca a                                              21

<210> SEQ ID NO 340
<211> LENGTH: 21
<212> TYPE: DNA
<213> ORGANISM: Artificial sequence
<220> FEATURE:
<223> OTHER INFORMATION: Target sequence in the gene PRDM14

<400> SEQUENCE: 340
accggcctca caagtgttct a                                              21

<210> SEQ ID NO 341
<211> LENGTH: 21
<212> TYPE: DNA
<213> ORGANISM: Artificial sequence
<220> FEATURE:
<223> OTHER INFORMATION: Target sequence in the gene U2AF1

<400> SEQUENCE: 341
```
cccgtgacgg acttcagaga a                                               21

<210> SEQ ID NO 342
<211> LENGTH: 21
<212> TYPE: DNA
<213> ORGANISM: Artificial sequence
<220> FEATURE:
<223> OTHER INFORMATION: Target sequence in the gene NRARP

<400> SEQUENCE: 342
ttcgctgttg ctggtgttct a                                               21

<210> SEQ ID NO 343
<211> LENGTH: 21
<212> TYPE: DNA
<213> ORGANISM: Artificial sequence
<220> FEATURE:
<223> OTHER INFORMATION: Target sequence in the gene HNRNPC

<400> SEQUENCE: 343
ctcccgtgta ttcattggga a                                               21

<210> SEQ ID NO 344
<211> LENGTH: 21
<212> TYPE: DNA
<213> ORGANISM: Artificial sequence
<220> FEATURE:
<223> OTHER INFORMATION: Target sequence in the gene GAS2L2

<400> SEQUENCE: 344
ctccggaacc atgtgatggt a                                               21

<210> SEQ ID NO 345
<211> LENGTH: 21
<212> TYPE: DNA
<213> ORGANISM: Artificial sequence
<220> FEATURE:
<223> OTHER INFORMATION: Target sequence in the gene KIFC2

<400> SEQUENCE: 345
agggcggctg ccagaactca a                                               21

<210> SEQ ID NO 346
<211> LENGTH: 21
<212> TYPE: DNA
<213> ORGANISM: Artificial sequence
<220> FEATURE:
<223> OTHER INFORMATION: Target sequence in the gene SFRS7

<400> SEQUENCE: 346
cccgacgtcc ctttgatcca a                                               21

<210> SEQ ID NO 347
<211> LENGTH: 21
<212> TYPE: DNA
<213> ORGANISM: Artificial sequence
<220> FEATURE:
<223> OTHER INFORMATION: Target sequence in the gene FERMT2

<400> SEQUENCE: 347
aagctagatg accagtctga a                                               21

<210> SEQ ID NO 348
<211> LENGTH: 21
<212> TYPE: DNA

```
<213> ORGANISM: Artificial sequence
<220> FEATURE:
<223> OTHER INFORMATION: Target sequence in the gene FRMD4A

<400> SEQUENCE: 348
ctggattctg ttcaactgta a                                              21

<210> SEQ ID NO 349
<211> LENGTH: 21
<212> TYPE: DNA
<213> ORGANISM: Artificial sequence
<220> FEATURE:
<223> OTHER INFORMATION: Target sequence in the gene SNORD13

<400> SEQUENCE: 349
agcgtgatga ttgggtgttc a                                              21

<210> SEQ ID NO 350
<211> LENGTH: 21
<212> TYPE: DNA
<213> ORGANISM: Artificial sequence
<220> FEATURE:
<223> OTHER INFORMATION: Target sequence in the gene TTLL9

<400> SEQUENCE: 350
tgcgtcaacg atcggaagaa a                                              21

<210> SEQ ID NO 351
<211> LENGTH: 21
<212> TYPE: DNA
<213> ORGANISM: Artificial sequence
<220> FEATURE:
<223> OTHER INFORMATION: Target sequence in the gene ZNF691

<400> SEQUENCE: 351
ttgctgctac cttgacctca a                                              21

<210> SEQ ID NO 352
<211> LENGTH: 21
<212> TYPE: DNA
<213> ORGANISM: Artificial sequence
<220> FEATURE:
<223> OTHER INFORMATION: Target sequence in the gene TRAPPC6A

<400> SEQUENCE: 352
ctgtgtgtgt ggaatctgaa a                                              21

<210> SEQ ID NO 353
<211> LENGTH: 21
<212> TYPE: DNA
<213> ORGANISM: Artificial sequence
<220> FEATURE:
<223> OTHER INFORMATION: Target sequence in the gene EIF4A3

<400> SEQUENCE: 353
aaagagcaga tttacgatgt a                                              21

<210> SEQ ID NO 354
<211> LENGTH: 21
<212> TYPE: DNA
<213> ORGANISM: Artificial sequence
<220> FEATURE:
<223> OTHER INFORMATION: Target sequence in the gene PRR16

<400> SEQUENCE: 354
aacctgcaga tttcacctat t                                              21
```

<210> SEQ ID NO 355
<211> LENGTH: 21
<212> TYPE: DNA
<213> ORGANISM: Artificial sequence
<220> FEATURE:
<223> OTHER INFORMATION: Target sequence in the gene RPIA

<400> SEQUENCE: 355
aaccacgtga ggaataacca a                                              21

<210> SEQ ID NO 356
<211> LENGTH: 21
<212> TYPE: DNA
<213> ORGANISM: Artificial sequence
<220> FEATURE:
<223> OTHER INFORMATION: Target sequence in the gene FAM26E

<400> SEQUENCE: 356
ctgccgatct aaagttagct a                                              21

<210> SEQ ID NO 357
<211> LENGTH: 21
<212> TYPE: DNA
<213> ORGANISM: Artificial sequence
<220> FEATURE:
<223> OTHER INFORMATION: Target sequence in the gene C11orf75

<400> SEQUENCE: 357
ccgcgggcag gaataactca a                                              21

<210> SEQ ID NO 358
<211> LENGTH: 21
<212> TYPE: DNA
<213> ORGANISM: Artificial sequence
<220> FEATURE:
<223> OTHER INFORMATION: Target sequence in the gene WBSCR19

<400> SEQUENCE: 358
aaggacttca acagtcagct t                                              21

<210> SEQ ID NO 359
<211> LENGTH: 21
<212> TYPE: DNA
<213> ORGANISM: Artificial sequence
<220> FEATURE:
<223> OTHER INFORMATION: Target sequence in the gene CTSA

<400> SEQUENCE: 359
ccggccctgg ttagtgaagt a                                              21

<210> SEQ ID NO 360
<211> LENGTH: 21
<212> TYPE: DNA
<213> ORGANISM: Artificial sequence
<220> FEATURE:
<223> OTHER INFORMATION: Target sequence in the gene NEK10

<400> SEQUENCE: 360
cagaaggtat ctactctgaa a                                              21

<210> SEQ ID NO 361
<211> LENGTH: 21
<212> TYPE: DNA
<213> ORGANISM: Artificial sequence
<220> FEATURE:

<223> OTHER INFORMATION: Target sequence in the gene WIPF3

<400> SEQUENCE: 361
ctccggatga atataaacca t                                            21

<210> SEQ ID NO 362
<211> LENGTH: 21
<212> TYPE: DNA
<213> ORGANISM: Artificial sequence
<220> FEATURE:
<223> OTHER INFORMATION: Target sequence in the gene TRAFD1

<400> SEQUENCE: 362
ccaggtctct cagtgacata a                                            21

<210> SEQ ID NO 363
<211> LENGTH: 21
<212> TYPE: DNA
<213> ORGANISM: Artificial sequence
<220> FEATURE:
<223> OTHER INFORMATION: Target sequence in the gene

<400> SEQUENCE: 363
ccggttgaac ttatccgcgt t                                            21

<210> SEQ ID NO 364
<211> LENGTH: 21
<212> TYPE: DNA
<213> ORGANISM: Artificial sequence
<220> FEATURE:
<223> OTHER INFORMATION: Target sequence in the gene ZNF658

<400> SEQUENCE: 364
ctcagcccat atagtacatc a                                            21

<210> SEQ ID NO 365
<211> LENGTH: 21
<212> TYPE: DNA
<213> ORGANISM: Artificial sequence
<220> FEATURE:
<223> OTHER INFORMATION: Target sequence in the gene STXBP2

<400> SEQUENCE: 365
cacggacaag gcgaacatca a                                            21

<210> SEQ ID NO 366
<211> LENGTH: 21
<212> TYPE: DNA
<213> ORGANISM: Artificial sequence
<220> FEATURE:
<223> OTHER INFORMATION: Target sequence in the gene TRIM71

<400> SEQUENCE: 366
caggatcgtg gtggctgaca a                                            21

<210> SEQ ID NO 367
<211> LENGTH: 21
<212> TYPE: DNA
<213> ORGANISM: Artificial sequence
<220> FEATURE:
<223> OTHER INFORMATION: Target sequence in the gene CAP1

<400> SEQUENCE: 367
caacacgaca ttgcaaatca a                                            21

```
<210> SEQ ID NO 368
<211> LENGTH: 21
<212> TYPE: DNA
<213> ORGANISM: Artificial sequence
<220> FEATURE:
<223> OTHER INFORMATION: Target sequence in the gene VLDLR

<400> SEQUENCE: 368
caagatcgta ggatagtact a                                              21

<210> SEQ ID NO 369
<211> LENGTH: 21
<212> TYPE: DNA
<213> ORGANISM: Artificial sequence
<220> FEATURE:
<223> OTHER INFORMATION: Target sequence in the gene CREBZF

<400> SEQUENCE: 369
caggaggaga gtcgctacct a                                              21

<210> SEQ ID NO 370
<211> LENGTH: 21
<212> TYPE: DNA
<213> ORGANISM: Artificial sequence
<220> FEATURE:
<223> OTHER INFORMATION: Target sequence in the gene FAM120C

<400> SEQUENCE: 370
ctgcgtgagg ctagcactca t                                              21

<210> SEQ ID NO 371
<211> LENGTH: 21
<212> TYPE: DNA
<213> ORGANISM: Artificial sequence
<220> FEATURE:
<223> OTHER INFORMATION: Target sequence in the gene C4BPA

<400> SEQUENCE: 371
aactcagacg cttacctgta a                                              21

<210> SEQ ID NO 372
<211> LENGTH: 21
<212> TYPE: DNA
<213> ORGANISM: Artificial sequence
<220> FEATURE:
<223> OTHER INFORMATION: Target sequence in the gene TBL3

<400> SEQUENCE: 372
ctgccatgat aaggacatca a                                              21

<210> SEQ ID NO 373
<211> LENGTH: 21
<212> TYPE: DNA
<213> ORGANISM: Artificial sequence
<220> FEATURE:
<223> OTHER INFORMATION: Target sequence in the gene OLFML2A

<400> SEQUENCE: 373
tccagtcata tttagaacaa a                                              21

<210> SEQ ID NO 374
<211> LENGTH: 21
<212> TYPE: DNA
<213> ORGANISM: Artificial sequence
<220> FEATURE:
<223> OTHER INFORMATION: Target sequence in the gene TBC1D8B
```

```
<400> SEQUENCE: 374
gagaagggta ctcacagctt a                                              21

<210> SEQ ID NO 375
<211> LENGTH: 21
<212> TYPE: DNA
<213> ORGANISM: Artificial sequence
<220> FEATURE:
<223> OTHER INFORMATION: Target sequence in the gene ADAMTS7

<400> SEQUENCE: 375
ctgcatcaac ggcatctgta a                                              21

<210> SEQ ID NO 376
<211> LENGTH: 21
<212> TYPE: DNA
<213> ORGANISM: Artificial sequence
<220> FEATURE:
<223> OTHER INFORMATION: Target sequence in the gene BAG4

<400> SEQUENCE: 376
acccaagtac atatcctgta a                                              21

<210> SEQ ID NO 377
<211> LENGTH: 21
<212> TYPE: DNA
<213> ORGANISM: Artificial sequence
<220> FEATURE:
<223> OTHER INFORMATION: Target sequence in the gene GRID2

<400> SEQUENCE: 377
aagcaatgga tcggagaaca a                                              21

<210> SEQ ID NO 378
<211> LENGTH: 21
<212> TYPE: DNA
<213> ORGANISM: Artificial sequence
<220> FEATURE:
<223> OTHER INFORMATION: Target sequence in the gene GDF15

<400> SEQUENCE: 378
ctgggaagat tcgaacaccg a                                              21

<210> SEQ ID NO 379
<211> LENGTH: 21
<212> TYPE: DNA
<213> ORGANISM: Artificial sequence
<220> FEATURE:
<223> OTHER INFORMATION: Target sequence in the gene RASAL2

<400> SEQUENCE: 379
ctcgtgggct gcctaaacta a                                              21

<210> SEQ ID NO 380
<211> LENGTH: 21
<212> TYPE: DNA
<213> ORGANISM: Artificial sequence
<220> FEATURE:
<223> OTHER INFORMATION: Target sequence in the gene UGT2B28

<400> SEQUENCE: 380
cacccaggta atggttagaa a                                              21

<210> SEQ ID NO 381
<211> LENGTH: 21
```

```
<212> TYPE: DNA
<213> ORGANISM: Artificial sequence
<220> FEATURE:
<223> OTHER INFORMATION: Target sequence in the gene FLJ20254

<400> SEQUENCE: 381
cccgattccg tgaatcagct a                                              21

<210> SEQ ID NO 382
<211> LENGTH: 21
<212> TYPE: DNA
<213> ORGANISM: Artificial sequence
<220> FEATURE:
<223> OTHER INFORMATION: Target sequence in the gene DPF2

<400> SEQUENCE: 382
ccggagtagc ccagagcaat t                                              21

<210> SEQ ID NO 383
<211> LENGTH: 21
<212> TYPE: DNA
<213> ORGANISM: Artificial sequence
<220> FEATURE:
<223> OTHER INFORMATION: Target sequence in the gene CNGB1

<400> SEQUENCE: 383
cagaagttac tccggaagaa a                                              21

<210> SEQ ID NO 384
<211> LENGTH: 21
<212> TYPE: DNA
<213> ORGANISM: Artificial sequence
<220> FEATURE:
<223> OTHER INFORMATION: Target sequence in the gene CAPN13

<400> SEQUENCE: 384
acgaaggatg gtcccaaata a                                              21

<210> SEQ ID NO 385
<211> LENGTH: 21
<212> TYPE: DNA
<213> ORGANISM: Artificial sequence
<220> FEATURE:
<223> OTHER INFORMATION: Target sequence in the gene CAP1

<400> SEQUENCE: 385
aagcctggcc cttatgtgaa a                                              21

<210> SEQ ID NO 386
<211> LENGTH: 21
<212> TYPE: DNA
<213> ORGANISM: Artificial sequence
<220> FEATURE:
<223> OTHER INFORMATION: Target sequence in the gene PDIA6

<400> SEQUENCE: 386
acgggattag aggatttcct a                                              21

<210> SEQ ID NO 387
<211> LENGTH: 21
<212> TYPE: DNA
<213> ORGANISM: Artificial sequence
<220> FEATURE:
<223> OTHER INFORMATION: Target sequence in the gene TMEM63A

<400> SEQUENCE: 387
```
cagggactct cttgacgctg a                                                21

<210> SEQ ID NO 388
<211> LENGTH: 21
<212> TYPE: DNA
<213> ORGANISM: Artificial sequence
<220> FEATURE:
<223> OTHER INFORMATION: Target sequence in the gene SMARCC1

<400> SEQUENCE: 388
cagcggattt caaccaagaa t                                                21

<210> SEQ ID NO 389
<211> LENGTH: 21
<212> TYPE: DNA
<213> ORGANISM: Artificial sequence
<220> FEATURE:
<223> OTHER INFORMATION: Target sequence in the gene TBKBP1

<400> SEQUENCE: 389
cactgcttac ggagacatca a                                                21

<210> SEQ ID NO 390
<211> LENGTH: 21
<212> TYPE: DNA
<213> ORGANISM: Artificial sequence
<220> FEATURE:
<223> OTHER INFORMATION: Target sequence in the gene LGALS2

<400> SEQUENCE: 390
caccattgtc tgcaactcat t                                                21

<210> SEQ ID NO 391
<211> LENGTH: 21
<212> TYPE: DNA
<213> ORGANISM: Artificial sequence
<220> FEATURE:
<223> OTHER INFORMATION: Target sequence in the gene CACNG1

<400> SEQUENCE: 391
caccgtctgg atcgagtact a                                                21

<210> SEQ ID NO 392
<211> LENGTH: 21
<212> TYPE: DNA
<213> ORGANISM: Artificial sequence
<220> FEATURE:
<223> OTHER INFORMATION: Target sequence in the gene ZBTB7C

<400> SEQUENCE: 392
gccactggat ctggtcatca a                                                21

<210> SEQ ID NO 393
<211> LENGTH: 21
<212> TYPE: DNA
<213> ORGANISM: Artificial sequence
<220> FEATURE:
<223> OTHER INFORMATION: Target sequence in the gene PREB

<400> SEQUENCE: 393
ccgggctccg ttcccgttgt a                                                21

<210> SEQ ID NO 394
<211> LENGTH: 21
<212> TYPE: DNA
<213> ORGANISM: Artificial sequence

```
<220> FEATURE:
<223> OTHER INFORMATION: Target sequence in the gene CBX8

<400> SEQUENCE: 394
aaggaaagta acacggacca a                                              21

<210> SEQ ID NO 395
<211> LENGTH: 21
<212> TYPE: DNA
<213> ORGANISM: Artificial sequence
<220> FEATURE:
<223> OTHER INFORMATION: Target sequence in the gene RBM8A

<400> SEQUENCE: 395
acacgacaaa ttcgcagaat a                                              21

<210> SEQ ID NO 396
<211> LENGTH: 21
<212> TYPE: DNA
<213> ORGANISM: Artificial sequence
<220> FEATURE:
<223> OTHER INFORMATION: Target sequence in the gene MDM1

<400> SEQUENCE: 396
atgagggtgt aacaaaccat a                                              21

<210> SEQ ID NO 397
<211> LENGTH: 21
<212> TYPE: DNA
<213> ORGANISM: Artificial sequence
<220> FEATURE:
<223> OTHER INFORMATION: Target sequence in the gene TPD52L3

<400> SEQUENCE: 397
caggccaggt cgtcaactca a                                              21

<210> SEQ ID NO 398
<211> LENGTH: 21
<212> TYPE: DNA
<213> ORGANISM: Artificial sequence
<220> FEATURE:
<223> OTHER INFORMATION: Target sequence in the gene C3orf59

<400> SEQUENCE: 398
aagggcaagt aacgtgttca t                                              21

<210> SEQ ID NO 399
<211> LENGTH: 21
<212> TYPE: DNA
<213> ORGANISM: Artificial sequence
<220> FEATURE:
<223> OTHER INFORMATION: Target sequence in the gene LRP5

<400> SEQUENCE: 399
ctggacggac tcagagacca a                                              21

<210> SEQ ID NO 400
<211> LENGTH: 21
<212> TYPE: DNA
<213> ORGANISM: Artificial sequence
<220> FEATURE:
<223> OTHER INFORMATION: Target sequence in the gene DLD

<400> SEQUENCE: 400
cagccgattg atgctgatgt a                                              21
```

<210> SEQ ID NO 401
<211> LENGTH: 21
<212> TYPE: DNA
<213> ORGANISM: Artificial sequence
<220> FEATURE:
<223> OTHER INFORMATION: Target sequence in the gene TCF20

<400> SEQUENCE: 401
caggagttgc acgtagagaa a        21

<210> SEQ ID NO 402
<211> LENGTH: 21
<212> TYPE: DNA
<213> ORGANISM: Artificial sequence
<220> FEATURE:
<223> OTHER INFORMATION: Target sequence in the gene KIAA0644

<400> SEQUENCE: 402
cggcggcaac ttcataacca a        21

<210> SEQ ID NO 403
<211> LENGTH: 21
<212> TYPE: DNA
<213> ORGANISM: Artificial sequence
<220> FEATURE:
<223> OTHER INFORMATION: Target sequence in the gene ARFRP1

<400> SEQUENCE: 403
cggcgtcatc tacgtcattg a        21

<210> SEQ ID NO 404
<211> LENGTH: 21
<212> TYPE: DNA
<213> ORGANISM: Artificial sequence
<220> FEATURE:
<223> OTHER INFORMATION: Target sequence in the gene STAU1

<400> SEQUENCE: 404
ctcggatgca gtccacctat a        21

<210> SEQ ID NO 405
<211> LENGTH: 21
<212> TYPE: DNA
<213> ORGANISM: Artificial sequence
<220> FEATURE:
<223> OTHER INFORMATION: Target sequence in the gene GRIP2

<400> SEQUENCE: 405
caggagtgat ctgctgaaca t        21

<210> SEQ ID NO 406
<211> LENGTH: 21
<212> TYPE: DNA
<213> ORGANISM: Artificial sequence
<220> FEATURE:
<223> OTHER INFORMATION: Target sequence in the gene UHRF1BP1

<400> SEQUENCE: 406
ccgcgtgagg cttgaccact a        21

<210> SEQ ID NO 407
<211> LENGTH: 21
<212> TYPE: DNA
<213> ORGANISM: Artificial sequence
<220> FEATURE:
<223> OTHER INFORMATION: Target sequence in the gene CPNE2

<400> SEQUENCE: 407
cacgatcgtc tccagcaaga a					21

<210> SEQ ID NO 408
<211> LENGTH: 21
<212> TYPE: DNA
<213> ORGANISM: Artificial sequence
<220> FEATURE:
<223> OTHER INFORMATION: Target sequence in the gene ICA1

<400> SEQUENCE: 408
caggatcgat atgctcaaga t					21

<210> SEQ ID NO 409
<211> LENGTH: 21
<212> TYPE: DNA
<213> ORGANISM: Artificial sequence
<220> FEATURE:
<223> OTHER INFORMATION: Target sequence in the gene CDH20

<400> SEQUENCE: 409
tactacgaag tgattatcca a					21

<210> SEQ ID NO 410
<211> LENGTH: 21
<212> TYPE: DNA
<213> ORGANISM: Artificial sequence
<220> FEATURE:
<223> OTHER INFORMATION: Target sequence in the gene BPIL2

<400> SEQUENCE: 410
ccggagtcta ctttaccggt a					21

<210> SEQ ID NO 411
<211> LENGTH: 21
<212> TYPE: DNA
<213> ORGANISM: Artificial sequence
<220> FEATURE:
<223> OTHER INFORMATION: Target sequence in the gene ADRBK1

<400> SEQUENCE: 411
cggctggagg ctcgcaagaa a					21

<210> SEQ ID NO 412
<211> LENGTH: 21
<212> TYPE: DNA
<213> ORGANISM: Artificial sequence
<220> FEATURE:
<223> OTHER INFORMATION: Target sequence in the gene MOG

<400> SEQUENCE: 412
cagagtgata ggaccaagac a					21

<210> SEQ ID NO 413
<211> LENGTH: 21
<212> TYPE: DNA
<213> ORGANISM: Artificial sequence
<220> FEATURE:
<223> OTHER INFORMATION: Target sequence in the gene HOXD3

<400> SEQUENCE: 413
ctcgccataa atcagccgca a					21

<210> SEQ ID NO 414

```
<211> LENGTH: 21
<212> TYPE: DNA
<213> ORGANISM: Artificial sequence
<220> FEATURE:
<223> OTHER INFORMATION: Target sequence in the gene STRA6

<400> SEQUENCE: 414
ctggaagata ctgggactgt t                                      21

<210> SEQ ID NO 415
<211> LENGTH: 21
<212> TYPE: DNA
<213> ORGANISM: Artificial sequence
<220> FEATURE:
<223> OTHER INFORMATION: Target sequence in the gene SNORA40

<400> SEQUENCE: 415
cccagaactc attgttcagt a                                      21

<210> SEQ ID NO 416
<211> LENGTH: 21
<212> TYPE: DNA
<213> ORGANISM: Artificial sequence
<220> FEATURE:
<223> OTHER INFORMATION: Target sequence in the gene GK5

<400> SEQUENCE: 416
taccatcttg tacgagcaat a                                      21

<210> SEQ ID NO 417
<211> LENGTH: 21
<212> TYPE: DNA
<213> ORGANISM: Artificial sequence
<220> FEATURE:
<223> OTHER INFORMATION: Target sequence in the gene LZTR1

<400> SEQUENCE: 417
caagatcaaa tacccacgga a                                      21

<210> SEQ ID NO 418
<211> LENGTH: 21
<212> TYPE: DNA
<213> ORGANISM: Artificial sequence
<220> FEATURE:
<223> OTHER INFORMATION: Target sequence in the gene TRIM42

<400> SEQUENCE: 418
cagcgccatc gccaagttca a                                      21

<210> SEQ ID NO 419
<211> LENGTH: 21
<212> TYPE: DNA
<213> ORGANISM: Artificial sequence
<220> FEATURE:
<223> OTHER INFORMATION: Target sequence in the gene C1orf38

<400> SEQUENCE: 419
aagttgtaag tgactaacca a                                      21

<210> SEQ ID NO 420
<211> LENGTH: 21
<212> TYPE: DNA
<213> ORGANISM: Artificial sequence
<220> FEATURE:
<223> OTHER INFORMATION: Target sequence in the gene ANKRD20A3

<400> SEQUENCE: 420
```
atccctcact gaattcagta a                                                      21

<210> SEQ ID NO 421
<211> LENGTH: 21
<212> TYPE: DNA
<213> ORGANISM: Artificial sequence
<220> FEATURE:
<223> OTHER INFORMATION: Target sequence in the gene ATG9B

<400> SEQUENCE: 421
cagccgcggc ctggcgctca a                                                      21

<210> SEQ ID NO 422
<211> LENGTH: 21
<212> TYPE: DNA
<213> ORGANISM: Artificial sequence
<220> FEATURE:
<223> OTHER INFORMATION: Target sequence in the gene PI4KA

<400> SEQUENCE: 422
aagcggctgc gtgaagacat a                                                      21

<210> SEQ ID NO 423
<211> LENGTH: 21
<212> TYPE: DNA
<213> ORGANISM: Artificial sequence
<220> FEATURE:
<223> OTHER INFORMATION: Target sequence in the gene SDHB

<400> SEQUENCE: 423
ctggtggaac ggagacaaat a                                                      21

<210> SEQ ID NO 424
<211> LENGTH: 21
<212> TYPE: DNA
<213> ORGANISM: Artificial sequence
<220> FEATURE:
<223> OTHER INFORMATION: Target sequence in the gene RAB43

<400> SEQUENCE: 424
ccgagcgtgg gtcccagtct a                                                      21

<210> SEQ ID NO 425
<211> LENGTH: 21
<212> TYPE: DNA
<213> ORGANISM: Artificial sequence
<220> FEATURE:
<223> OTHER INFORMATION: Target sequence in the gene ZNF443

<400> SEQUENCE: 425
aagcattatc tcatcgctca a                                                      21

<210> SEQ ID NO 426
<211> LENGTH: 21
<212> TYPE: DNA
<213> ORGANISM: Artificial sequence
<220> FEATURE:
<223> OTHER INFORMATION: Target sequence in the gene IL17C

<400> SEQUENCE: 426
ccgcgagaca gctgcgctca a                                                      21

<210> SEQ ID NO 427
<211> LENGTH: 21
<212> TYPE: DNA

```
<213> ORGANISM: Artificial sequence
<220> FEATURE:
<223> OTHER INFORMATION: Target sequence in the gene GPR149

<400> SEQUENCE: 427
caccgtgagc gtagcgcaga a                                              21

<210> SEQ ID NO 428
<211> LENGTH: 21
<212> TYPE: DNA
<213> ORGANISM: Artificial sequence
<220> FEATURE:
<223> OTHER INFORMATION: Target sequence in the gene OR56A3

<400> SEQUENCE: 428
aactccgtta ttgtggaaga a                                              21

<210> SEQ ID NO 429
<211> LENGTH: 21
<212> TYPE: DNA
<213> ORGANISM: Artificial sequence
<220> FEATURE:
<223> OTHER INFORMATION: Target sequence in the gene TECTB

<400> SEQUENCE: 429
cagggcaacc ttccaattca a                                              21

<210> SEQ ID NO 430
<211> LENGTH: 21
<212> TYPE: DNA
<213> ORGANISM: Artificial sequence
<220> FEATURE:
<223> OTHER INFORMATION: Target sequence in the gene BLK

<400> SEQUENCE: 430
ctggtaagcg actgtcatca a                                              21

<210> SEQ ID NO 431
<211> LENGTH: 21
<212> TYPE: DNA
<213> ORGANISM: Artificial sequence
<220> FEATURE:
<223> OTHER INFORMATION: Target sequence in the gene ZNF718

<400> SEQUENCE: 431
ccgcaactca atctgttcta a                                              21

<210> SEQ ID NO 432
<211> LENGTH: 21
<212> TYPE: DNA
<213> ORGANISM: Artificial sequence
<220> FEATURE:
<223> OTHER INFORMATION: Target sequence in the gene SEC11B

<400> SEQUENCE: 432
gtgggagaaa tcgctgttct a                                              21

<210> SEQ ID NO 433
<211> LENGTH: 21
<212> TYPE: DNA
<213> ORGANISM: Artificial sequence
<220> FEATURE:
<223> OTHER INFORMATION: Target sequence in the gene FGD2

<400> SEQUENCE: 433
cagggtcatc ttctccaaca t                                              21
```

<210> SEQ ID NO 434
<211> LENGTH: 21
<212> TYPE: DNA
<213> ORGANISM: Artificial sequence
<220> FEATURE:
<223> OTHER INFORMATION: Target sequence in the gene TIFA

<400> SEQUENCE: 434
ctgggtgtgc ccaattgatc a                                        21

<210> SEQ ID NO 435
<211> LENGTH: 21
<212> TYPE: DNA
<213> ORGANISM: Artificial sequence
<220> FEATURE:
<223> OTHER INFORMATION: Target sequence in the gene PRB3

<400> SEQUENCE: 435
aagaaggtgg tcatagctct a                                        21

<210> SEQ ID NO 436
<211> LENGTH: 21
<212> TYPE: DNA
<213> ORGANISM: Artificial sequence
<220> FEATURE:
<223> OTHER INFORMATION: Target sequence in the gene TREML1

<400> SEQUENCE: 436
caggcgtacg tttctcacag a                                        21

<210> SEQ ID NO 437
<211> LENGTH: 21
<212> TYPE: DNA
<213> ORGANISM: Artificial sequence
<220> FEATURE:
<223> OTHER INFORMATION: Target sequence in the gene PHF10

<400> SEQUENCE: 437
atggcagtgt atggaatgta a                                        21

<210> SEQ ID NO 438
<211> LENGTH: 21
<212> TYPE: DNA
<213> ORGANISM: Artificial sequence
<220> FEATURE:
<223> OTHER INFORMATION: Target sequence in the gene PTDSS2

<400> SEQUENCE: 438
ctggtggatg tgcatgatca t                                        21

<210> SEQ ID NO 439
<211> LENGTH: 21
<212> TYPE: DNA
<213> ORGANISM: Artificial sequence
<220> FEATURE:
<223> OTHER INFORMATION: Target sequence in the gene MGC12966

<400> SEQUENCE: 439
caccactgta cttggcgtta a                                        21

<210> SEQ ID NO 440
<211> LENGTH: 21
<212> TYPE: DNA
<213> ORGANISM: Artificial sequence
<220> FEATURE:

<223> OTHER INFORMATION: Target sequence in the gene FAM3D

<400> SEQUENCE: 440
tacgacgatc cagggaccaa a                                              21

<210> SEQ ID NO 441
<211> LENGTH: 21
<212> TYPE: DNA
<213> ORGANISM: Artificial sequence
<220> FEATURE:
<223> OTHER INFORMATION: Target sequence in the gene PDZD7

<400> SEQUENCE: 441
ccggcgcatc gtccacctat a                                              21

<210> SEQ ID NO 442
<211> LENGTH: 21
<212> TYPE: DNA
<213> ORGANISM: Artificial sequence
<220> FEATURE:
<223> OTHER INFORMATION: Target sequence in the gene NOX5

<400> SEQUENCE: 442
ttgccctatt tgactccgat a                                              21

<210> SEQ ID NO 443
<211> LENGTH: 21
<212> TYPE: DNA
<213> ORGANISM: Artificial sequence
<220> FEATURE:
<223> OTHER INFORMATION: Target sequence in the gene CNGA3

<400> SEQUENCE: 443
cccgtccagc aacctgtact a                                              21

<210> SEQ ID NO 444
<211> LENGTH: 21
<212> TYPE: DNA
<213> ORGANISM: Artificial sequence
<220> FEATURE:
<223> OTHER INFORMATION: Target sequence in the gene MTMR6

<400> SEQUENCE: 444
cccggatagc aagcaaacca a                                              21

<210> SEQ ID NO 445
<211> LENGTH: 21
<212> TYPE: DNA
<213> ORGANISM: Artificial sequence
<220> FEATURE:
<223> OTHER INFORMATION: Target sequence in the gene GRAMD1A

<400> SEQUENCE: 445
cacgatctcc atccagctga a                                              21

<210> SEQ ID NO 446
<211> LENGTH: 21
<212> TYPE: DNA
<213> ORGANISM: Artificial sequence
<220> FEATURE:
<223> OTHER INFORMATION: Target sequence in the gene MRLC2

<400> SEQUENCE: 446
gagggtgtaa attgtattga a                                              21

```
<210> SEQ ID NO 447
<211> LENGTH: 21
<212> TYPE: DNA
<213> ORGANISM: Artificial sequence
<220> FEATURE:
<223> OTHER INFORMATION: Target sequence in the gene LOC285908

<400> SEQUENCE: 447
cccgacggcc ttgacagacc a                                          21

<210> SEQ ID NO 448
<211> LENGTH: 21
<212> TYPE: DNA
<213> ORGANISM: Artificial sequence
<220> FEATURE:
<223> OTHER INFORMATION: Target sequence in the gene FAM18B

<400> SEQUENCE: 448
tcagtggacc ttgagctaat a                                          21

<210> SEQ ID NO 449
<211> LENGTH: 21
<212> TYPE: DNA
<213> ORGANISM: Artificial sequence
<220> FEATURE:
<223> OTHER INFORMATION: Target sequence in the gene WDFY2

<400> SEQUENCE: 449
agccaccttc catgacagta a                                          21

<210> SEQ ID NO 450
<211> LENGTH: 21
<212> TYPE: DNA
<213> ORGANISM: Artificial sequence
<220> FEATURE:
<223> OTHER INFORMATION: Target sequence in the gene GAS1

<400> SEQUENCE: 450
atggatttat gaagacactc a                                          21

<210> SEQ ID NO 451
<211> LENGTH: 21
<212> TYPE: DNA
<213> ORGANISM: Artificial sequence
<220> FEATURE:
<223> OTHER INFORMATION: Target sequence in the gene C3orf35

<400> SEQUENCE: 451
atggcccacg tgaaatctga a                                          21

<210> SEQ ID NO 452
<211> LENGTH: 21
<212> TYPE: DNA
<213> ORGANISM: Artificial sequence
<220> FEATURE:
<223> OTHER INFORMATION: Target sequence in the gene DEFB106A

<400> SEQUENCE: 452
taaagggaca tgcaagaaca a                                          21

<210> SEQ ID NO 453
<211> LENGTH: 21
<212> TYPE: DNA
<213> ORGANISM: Artificial sequence
<220> FEATURE:
<223> OTHER INFORMATION: Target sequence in the gene IDS
```

<400> SEQUENCE: 453
cccgaggtcc ctgatggcct a                                              21

<210> SEQ ID NO 454
<211> LENGTH: 21
<212> TYPE: DNA
<213> ORGANISM: Artificial sequence
<220> FEATURE:
<223> OTHER INFORMATION: Target sequence in the gene CCDC19

<400> SEQUENCE: 454
aaggctcgct atcggaccaa a                                              21

<210> SEQ ID NO 455
<211> LENGTH: 21
<212> TYPE: DNA
<213> ORGANISM: Artificial sequence
<220> FEATURE:
<223> OTHER INFORMATION: Target sequence in the gene CCDC19

<400> SEQUENCE: 455
tagattccag ttgatgaaga a                                              21

<210> SEQ ID NO 456
<211> LENGTH: 21
<212> TYPE: DNA
<213> ORGANISM: Artificial sequence
<220> FEATURE:
<223> OTHER INFORMATION: Target sequence in the gene SNORD116-10

<400> SEQUENCE: 456
cagtaccatc atcctcatct a                                              21

<210> SEQ ID NO 457
<211> LENGTH: 21
<212> TYPE: DNA
<213> ORGANISM: Artificial sequence
<220> FEATURE:
<223> OTHER INFORMATION: Target sequence in the gene KIF22

<400> SEQUENCE: 457
caggacatct atgcaggttc a                                              21

<210> SEQ ID NO 458
<211> LENGTH: 21
<212> TYPE: DNA
<213> ORGANISM: Artificial sequence
<220> FEATURE:
<223> OTHER INFORMATION: Target sequence in the gene SNF1LK2

<400> SEQUENCE: 458
caggattaca tccgtttatt a                                              21

<210> SEQ ID NO 459
<211> LENGTH: 21
<212> TYPE: DNA
<213> ORGANISM: Artificial sequence
<220> FEATURE:
<223> OTHER INFORMATION: Target sequence in the gene GTF2A1

<400> SEQUENCE: 459
tccattggtc ttacaagttg a                                              21

<210> SEQ ID NO 460
<211> LENGTH: 21

```
<212> TYPE: DNA
<213> ORGANISM: Artificial sequence
<220> FEATURE:
<223> OTHER INFORMATION: Target sequence in the gene PMF1

<400> SEQUENCE: 460
ctgcggcgcc atgtgcagaa a                                              21

<210> SEQ ID NO 461
<211> LENGTH: 21
<212> TYPE: DNA
<213> ORGANISM: Artificial sequence
<220> FEATURE:
<223> OTHER INFORMATION: Target sequence in the gene MC5R

<400> SEQUENCE: 461
cggcattgtc ttcatcctgt a                                              21

<210> SEQ ID NO 462
<211> LENGTH: 21
<212> TYPE: DNA
<213> ORGANISM: Artificial sequence
<220> FEATURE:
<223> OTHER INFORMATION: Target sequence in the gene CELSR1

<400> SEQUENCE: 462
cgccaacagt gtgattacct a                                              21

<210> SEQ ID NO 463
<211> LENGTH: 21
<212> TYPE: DNA
<213> ORGANISM: Artificial sequence
<220> FEATURE:
<223> OTHER INFORMATION: Target sequence in the gene LRRC32

<400> SEQUENCE: 463
cgccggcaga agtttaacca a                                              21

<210> SEQ ID NO 464
<211> LENGTH: 21
<212> TYPE: DNA
<213> ORGANISM: Artificial sequence
<220> FEATURE:
<223> OTHER INFORMATION: Target sequence in the gene TGM6

<400> SEQUENCE: 464
cagcatcgct ggcaagttca a                                              21

<210> SEQ ID NO 465
<211> LENGTH: 21
<212> TYPE: DNA
<213> ORGANISM: Artificial sequence
<220> FEATURE:
<223> OTHER INFORMATION: Target sequence in the gene EPHA7

<400> SEQUENCE: 465
caggctgcga aggaagtact a                                              21

<210> SEQ ID NO 466
<211> LENGTH: 21
<212> TYPE: DNA
<213> ORGANISM: Artificial sequence
<220> FEATURE:
<223> OTHER INFORMATION: Target sequence in the gene LIMA1

<400> SEQUENCE: 466
```
caggttaaga gtgaggttca a    21

<210> SEQ ID NO 467
<211> LENGTH: 21
<212> TYPE: DNA
<213> ORGANISM: Artificial sequence
<220> FEATURE:
<223> OTHER INFORMATION: Target sequence in the gene PHLDA1

<400> SEQUENCE: 467
aggagcgatg atgtactgta a    21

<210> SEQ ID NO 468
<211> LENGTH: 21
<212> TYPE: DNA
<213> ORGANISM: Artificial sequence
<220> FEATURE:
<223> OTHER INFORMATION: Target sequence in the gene CELSR1

<400> SEQUENCE: 468
cgggatcctg gatgtgatca a    21

<210> SEQ ID NO 469
<211> LENGTH: 21
<212> TYPE: DNA
<213> ORGANISM: Artificial sequence
<220> FEATURE:
<223> OTHER INFORMATION: Target sequence in the gene ETNK1

<400> SEQUENCE: 469
tcgatcgaga tgaggaagta a    21

<210> SEQ ID NO 470
<211> LENGTH: 21
<212> TYPE: DNA
<213> ORGANISM: Artificial sequence
<220> FEATURE:
<223> OTHER INFORMATION: Target sequence in the gene TSPAN14

<400> SEQUENCE: 470
cgggacgata tcgatctgca a    21

<210> SEQ ID NO 471
<211> LENGTH: 21
<212> TYPE: DNA
<213> ORGANISM: Artificial sequence
<220> FEATURE:
<223> OTHER INFORMATION: Target sequence in the gene ANGEL2

<400> SEQUENCE: 471
ctgacgcaat tggcaatgct a    21

<210> SEQ ID NO 472
<211> LENGTH: 21
<212> TYPE: DNA
<213> ORGANISM: Artificial sequence
<220> FEATURE:
<223> OTHER INFORMATION: Target sequence in the gene MTHFD2L

<400> SEQUENCE: 472
tacgtctgat atggttaaag a    21

<210> SEQ ID NO 473
<211> LENGTH: 21
<212> TYPE: DNA
<213> ORGANISM: Artificial sequence

```
<220> FEATURE:
<223> OTHER INFORMATION: Target sequence in the gene B3GALT4

<400> SEQUENCE: 473
atcctgcggt gtcgagcaat a                                              21

<210> SEQ ID NO 474
<211> LENGTH: 21
<212> TYPE: DNA
<213> ORGANISM: Artificial sequence
<220> FEATURE:
<223> OTHER INFORMATION: Target sequence in the gene VKORC1

<400> SEQUENCE: 474
gagggaaggt tctgagcaat a                                              21

<210> SEQ ID NO 475
<211> LENGTH: 21
<212> TYPE: DNA
<213> ORGANISM: Artificial sequence
<220> FEATURE:
<223> OTHER INFORMATION: Target sequence in the gene DCD

<400> SEQUENCE: 475
ctggtctgtg cctatgatcc a                                              21

<210> SEQ ID NO 476
<211> LENGTH: 21
<212> TYPE: DNA
<213> ORGANISM: Artificial sequence
<220> FEATURE:
<223> OTHER INFORMATION: Target sequence in the gene ETHE1

<400> SEQUENCE: 476
cacgattacc atgggttcac a                                              21

<210> SEQ ID NO 477
<211> LENGTH: 21
<212> TYPE: DNA
<213> ORGANISM: Artificial sequence
<220> FEATURE:
<223> OTHER INFORMATION: Target sequence in the gene HOOK1

<400> SEQUENCE: 477
cagggttact tctgttgact a                                              21

<210> SEQ ID NO 478
<211> LENGTH: 21
<212> TYPE: DNA
<213> ORGANISM: Artificial sequence
<220> FEATURE:
<223> OTHER INFORMATION: Target sequence in the gene NDST1

<400> SEQUENCE: 478
cccagcgatg tctgctatct a                                              21

<210> SEQ ID NO 479
<211> LENGTH: 21
<212> TYPE: DNA
<213> ORGANISM: Artificial sequence
<220> FEATURE:
<223> OTHER INFORMATION: Target sequence in the gene COX4I2

<400> SEQUENCE: 479
ctgcacagaa ctcaacgctg a                                              21
```

<210> SEQ ID NO 480
<211> LENGTH: 21
<212> TYPE: DNA
<213> ORGANISM: Artificial sequence
<220> FEATURE:
<223> OTHER INFORMATION: Target sequence in the gene C22orf16

<400> SEQUENCE: 480
cccagatagc tgggattgga a                                              21

<210> SEQ ID NO 481
<211> LENGTH: 21
<212> TYPE: DNA
<213> ORGANISM: Artificial sequence
<220> FEATURE:
<223> OTHER INFORMATION: Target sequence in the gene ACTA2

<400> SEQUENCE: 481
tacgagttgc ctgatgggca a                                              21

<210> SEQ ID NO 482
<211> LENGTH: 21
<212> TYPE: DNA
<213> ORGANISM: Artificial sequence
<220> FEATURE:
<223> OTHER INFORMATION: Target sequence in the gene TNRC18

<400> SEQUENCE: 482
ctcggtcatc cgctcgctca a                                              21

<210> SEQ ID NO 483
<211> LENGTH: 21
<212> TYPE: DNA
<213> ORGANISM: Artificial sequence
<220> FEATURE:
<223> OTHER INFORMATION: Target sequence in the gene HCFC1

<400> SEQUENCE: 483
accgttcact attgtagagt a                                              21

<210> SEQ ID NO 484
<211> LENGTH: 21
<212> TYPE: DNA
<213> ORGANISM: Artificial sequence
<220> FEATURE:
<223> OTHER INFORMATION: Target sequence in the gene PIAS4

<400> SEQUENCE: 484
caccgaatta gtcccacaga a                                              21

<210> SEQ ID NO 485
<211> LENGTH: 21
<212> TYPE: DNA
<213> ORGANISM: Artificial sequence
<220> FEATURE:
<223> OTHER INFORMATION: Target sequence in the gene NPY1R

<400> SEQUENCE: 485
acgacatcag ctgataatca a                                              21

<210> SEQ ID NO 486
<211> LENGTH: 21
<212> TYPE: DNA
<213> ORGANISM: Artificial sequence
<220> FEATURE:
<223> OTHER INFORMATION: Target sequence in the gene DEFB125

<400> SEQUENCE: 486
ctcagacagc tcttactcat a                                              21

<210> SEQ ID NO 487
<211> LENGTH: 21
<212> TYPE: DNA
<213> ORGANISM: Artificial sequence
<220> FEATURE:
<223> OTHER INFORMATION: Target sequence in the gene C1orf128

<400> SEQUENCE: 487
tacgggcaat gtcaagctca a                                              21

<210> SEQ ID NO 488
<211> LENGTH: 21
<212> TYPE: DNA
<213> ORGANISM: Artificial sequence
<220> FEATURE:
<223> OTHER INFORMATION: Target sequence in the gene TAGLN2

<400> SEQUENCE: 488
cagctgagcg ctatggcatt a                                              21

<210> SEQ ID NO 489
<211> LENGTH: 21
<212> TYPE: DNA
<213> ORGANISM: Artificial sequence
<220> FEATURE:
<223> OTHER INFORMATION: Target sequence in the gene TRAPPC6A

<400> SEQUENCE: 489
gacctacgtc ctgcaagaca a                                              21

<210> SEQ ID NO 490
<211> LENGTH: 21
<212> TYPE: DNA
<213> ORGANISM: Artificial sequence
<220> FEATURE:
<223> OTHER INFORMATION: Target sequence in the gene SFTPA2B

<400> SEQUENCE: 490
ctccacgact tcagacatca a                                              21

<210> SEQ ID NO 491
<211> LENGTH: 21
<212> TYPE: DNA
<213> ORGANISM: Artificial sequence
<220> FEATURE:
<223> OTHER INFORMATION: Target sequence in the gene RGS11

<400> SEQUENCE: 491
cccaaggttc ctgaagtctg a                                              21

<210> SEQ ID NO 492
<211> LENGTH: 21
<212> TYPE: DNA
<213> ORGANISM: Artificial sequence
<220> FEATURE:
<223> OTHER INFORMATION: Target sequence in the gene CYFIP2

<400> SEQUENCE: 492
cacgcatcgg ctgctctgta a                                              21

<210> SEQ ID NO 493

-continued

```
<211> LENGTH: 21
<212> TYPE: DNA
<213> ORGANISM: Artificial sequence
<220> FEATURE:
<223> OTHER INFORMATION: Target sequence in the gene MAP6

<400> SEQUENCE: 493
taccaccaag ccagacgaca a                                              21

<210> SEQ ID NO 494
<211> LENGTH: 21
<212> TYPE: DNA
<213> ORGANISM: Artificial sequence
<220> FEATURE:
<223> OTHER INFORMATION: Target sequence in the gene LIG4

<400> SEQUENCE: 494
atctggtaag ctcgcatcta a                                              21

<210> SEQ ID NO 495
<211> LENGTH: 21
<212> TYPE: DNA
<213> ORGANISM: Artificial sequence
<220> FEATURE:
<223> OTHER INFORMATION: Target sequence in the gene TBXA2R

<400> SEQUENCE: 495
cccgcagatg aggtctctga a                                              21

<210> SEQ ID NO 496
<211> LENGTH: 21
<212> TYPE: DNA
<213> ORGANISM: Artificial sequence
<220> FEATURE:
<223> OTHER INFORMATION: Target sequence in the gene OR1L4

<400> SEQUENCE: 496
cactgtagtg gtcctgttct a                                              21

<210> SEQ ID NO 497
<211> LENGTH: 21
<212> TYPE: DNA
<213> ORGANISM: Artificial sequence
<220> FEATURE:
<223> OTHER INFORMATION: Target sequence in the gene UQCRC2

<400> SEQUENCE: 497
tacatccagt ctgacgacaa a                                              21

<210> SEQ ID NO 498
<211> LENGTH: 21
<212> TYPE: DNA
<213> ORGANISM: Artificial sequence
<220> FEATURE:
<223> OTHER INFORMATION: Target sequence in the gene DLL1

<400> SEQUENCE: 498
cacgcagatc aagaacacca a                                              21

<210> SEQ ID NO 499
<211> LENGTH: 21
<212> TYPE: DNA
<213> ORGANISM: Artificial sequence
<220> FEATURE:
<223> OTHER INFORMATION: Target sequence in the gene TAS2R45

<400> SEQUENCE: 499
```
caccgagtgg gtgaagagac a                              21

<210> SEQ ID NO 500
<211> LENGTH: 21
<212> TYPE: DNA
<213> ORGANISM: Artificial sequence
<220> FEATURE:
<223> OTHER INFORMATION: Target sequence in the gene SETBP1

<400> SEQUENCE: 500
cagcgttgct ctgaaggcaa a                              21

<210> SEQ ID NO 501
<211> LENGTH: 21
<212> TYPE: DNA
<213> ORGANISM: Artificial sequence
<220> FEATURE:
<223> OTHER INFORMATION: Target sequence in the gene RND3

<400> SEQUENCE: 501
aacgttaagc ggaacaaatc a                              21

<210> SEQ ID NO 502
<211> LENGTH: 21
<212> TYPE: DNA
<213> ORGANISM: Artificial sequence
<220> FEATURE:
<223> OTHER INFORMATION: Target sequence in the gene C12orf62

<400> SEQUENCE: 502
cagcgccagg ccgcagaaga a                              21

<210> SEQ ID NO 503
<211> LENGTH: 21
<212> TYPE: DNA
<213> ORGANISM: Artificial sequence
<220> FEATURE:
<223> OTHER INFORMATION: Target sequence in the gene CPA5

<400> SEQUENCE: 503
ccgcttatgg cggaagaaca a                              21

<210> SEQ ID NO 504
<211> LENGTH: 21
<212> TYPE: DNA
<213> ORGANISM: Artificial sequence
<220> FEATURE:
<223> OTHER INFORMATION: Target sequence in the gene KCNK15

<400> SEQUENCE: 504
ccggtggaag tccatctgac a                              21

<210> SEQ ID NO 505
<211> LENGTH: 21
<212> TYPE: DNA
<213> ORGANISM: Artificial sequence
<220> FEATURE:
<223> OTHER INFORMATION: Target sequence in the gene GLT8D1

<400> SEQUENCE: 505
tagctggtac agataattca a                              21

<210> SEQ ID NO 506
<211> LENGTH: 21
<212> TYPE: DNA

```
<213> ORGANISM: Artificial sequence
<220> FEATURE:
<223> OTHER INFORMATION: Target sequence in the gene GPR98

<400> SEQUENCE: 506
cagatggttt atcgtgttca a                                              21

<210> SEQ ID NO 507
<211> LENGTH: 21
<212> TYPE: DNA
<213> ORGANISM: Artificial sequence
<220> FEATURE:
<223> OTHER INFORMATION: Target sequence in the gene MAST2

<400> SEQUENCE: 507
caggagtgtg ctgtctggca a                                              21

<210> SEQ ID NO 508
<211> LENGTH: 21
<212> TYPE: DNA
<213> ORGANISM: Artificial sequence
<220> FEATURE:
<223> OTHER INFORMATION: Target sequence in the gene TAF6

<400> SEQUENCE: 508
cagcgtgcag cccatcgtca a                                              21

<210> SEQ ID NO 509
<211> LENGTH: 21
<212> TYPE: DNA
<213> ORGANISM: Artificial sequence
<220> FEATURE:
<223> OTHER INFORMATION: Target sequence in the gene SCT

<400> SEQUENCE: 509
cagcgagcag gacgcagaga a                                              21

<210> SEQ ID NO 510
<211> LENGTH: 21
<212> TYPE: DNA
<213> ORGANISM: Artificial sequence
<220> FEATURE:
<223> OTHER INFORMATION: Target sequence in the gene BAHD1

<400> SEQUENCE: 510
ccgccacggg cgcatcctta a                                              21

<210> SEQ ID NO 511
<211> LENGTH: 21
<212> TYPE: DNA
<213> ORGANISM: Artificial sequence
<220> FEATURE:
<223> OTHER INFORMATION: Target sequence in the gene OR1N1

<400> SEQUENCE: 511
ctgcgttgtt tgtgtgttct a                                              21

<210> SEQ ID NO 512
<211> LENGTH: 21
<212> TYPE: DNA
<213> ORGANISM: Artificial sequence
<220> FEATURE:
<223> OTHER INFORMATION: Target sequence in the gene NPLOC4

<400> SEQUENCE: 512
cagtcgaaat aaggacacct a                                              21
```

<210> SEQ ID NO 513
<211> LENGTH: 21
<212> TYPE: DNA
<213> ORGANISM: Artificial sequence
<220> FEATURE:
<223> OTHER INFORMATION: Target sequence in the gene CDON

<400> SEQUENCE: 513
aagcatgtta ttacagcaga a                                         21

<210> SEQ ID NO 514
<211> LENGTH: 21
<212> TYPE: DNA
<213> ORGANISM: Artificial sequence
<220> FEATURE:
<223> OTHER INFORMATION: Target sequence in the gene FAM46C

<400> SEQUENCE: 514
cagactgatc gccaccaaga a                                         21

<210> SEQ ID NO 515
<211> LENGTH: 21
<212> TYPE: DNA
<213> ORGANISM: Artificial sequence
<220> FEATURE:
<223> OTHER INFORMATION: Target sequence in the gene OR2Z1

<400> SEQUENCE: 515
accacagtcc acagcaggat a                                         21

<210> SEQ ID NO 516
<211> LENGTH: 21
<212> TYPE: DNA
<213> ORGANISM: Artificial sequence
<220> FEATURE:
<223> OTHER INFORMATION: Target sequence in the gene BCL2L1

<400> SEQUENCE: 516
ctgcttggga taaagatgca a                                         21

<210> SEQ ID NO 517
<211> LENGTH: 21
<212> TYPE: DNA
<213> ORGANISM: Artificial sequence
<220> FEATURE:
<223> OTHER INFORMATION: Target sequence in the gene ZFYVE9

<400> SEQUENCE: 517
aactatagtt gggatgatca a                                         21

<210> SEQ ID NO 518
<211> LENGTH: 21
<212> TYPE: DNA
<213> ORGANISM: Artificial sequence
<220> FEATURE:
<223> OTHER INFORMATION: Target sequence in the gene ST6GAL1

<400> SEQUENCE: 518
aaccctcagc ttatgtagct a                                         21

<210> SEQ ID NO 519
<211> LENGTH: 21
<212> TYPE: DNA
<213> ORGANISM: Artificial sequence
<220> FEATURE:

<223> OTHER INFORMATION: Target sequence in the gene FABP6

<400> SEQUENCE: 519
caccatcgga ggcgtgacct a                                              21

<210> SEQ ID NO 520
<211> LENGTH: 21
<212> TYPE: DNA
<213> ORGANISM: Artificial sequence
<220> FEATURE:
<223> OTHER INFORMATION: Target sequence in the gene USF2

<400> SEQUENCE: 520
ccgggagttg cgccagacca a                                              21

<210> SEQ ID NO 521
<211> LENGTH: 21
<212> TYPE: DNA
<213> ORGANISM: Artificial sequence
<220> FEATURE:
<223> OTHER INFORMATION: Target sequence in the gene TSPYL1

<400> SEQUENCE: 521
tagaaccggt tgcaagttca a                                              21

<210> SEQ ID NO 522
<211> LENGTH: 21
<212> TYPE: DNA
<213> ORGANISM: Artificial sequence
<220> FEATURE:
<223> OTHER INFORMATION: Target sequence in the gene SLC35E2

<400> SEQUENCE: 522
ccagcgtccc tttgttgtga a                                              21

<210> SEQ ID NO 523
<211> LENGTH: 21
<212> TYPE: DNA
<213> ORGANISM: Artificial sequence
<220> FEATURE:
<223> OTHER INFORMATION: Target sequence in the gene RFXANK

<400> SEQUENCE: 523
ctcagtcttt gcggacaaga a                                              21

<210> SEQ ID NO 524
<211> LENGTH: 21
<212> TYPE: DNA
<213> ORGANISM: Artificial sequence
<220> FEATURE:
<223> OTHER INFORMATION: Target sequence in the gene PLEKHG2

<400> SEQUENCE: 524
caggttcagc cagaccctca a                                              21

<210> SEQ ID NO 525
<211> LENGTH: 21
<212> TYPE: DNA
<213> ORGANISM: Artificial sequence
<220> FEATURE:
<223> OTHER INFORMATION: Target sequence in the gene FLJ36208

<400> SEQUENCE: 525
cgcaatgtag ttaggtgctc a                                              21

```
<210> SEQ ID NO 526
<211> LENGTH: 21
<212> TYPE: DNA
<213> ORGANISM: Artificial sequence
<220> FEATURE:
<223> OTHER INFORMATION: Target sequence in the gene MEGF11

<400> SEQUENCE: 526
aagaatccgt gtgcagttct a                                              21

<210> SEQ ID NO 527
<211> LENGTH: 21
<212> TYPE: DNA
<213> ORGANISM: Artificial sequence
<220> FEATURE:
<223> OTHER INFORMATION: Target sequence in the gene MLXIP

<400> SEQUENCE: 527
caggacgatg acatgctgta t                                              21

<210> SEQ ID NO 528
<211> LENGTH: 21
<212> TYPE: DNA
<213> ORGANISM: Artificial sequence
<220> FEATURE:
<223> OTHER INFORMATION: Target sequence in the gene TTLL12

<400> SEQUENCE: 528
cacggtgagc tgcccagtac a                                              21

<210> SEQ ID NO 529
<211> LENGTH: 21
<212> TYPE: DNA
<213> ORGANISM: Artificial sequence
<220> FEATURE:
<223> OTHER INFORMATION: Target sequence in the gene ACOT4

<400> SEQUENCE: 529
caaacagtct ctgaacggtt a                                              21

<210> SEQ ID NO 530
<211> LENGTH: 21
<212> TYPE: DNA
<213> ORGANISM: Artificial sequence
<220> FEATURE:
<223> OTHER INFORMATION: Target sequence in the gene VPS33B

<400> SEQUENCE: 530
cagcgttgga tcaacactgt a                                              21

<210> SEQ ID NO 531
<211> LENGTH: 21
<212> TYPE: DNA
<213> ORGANISM: Artificial sequence
<220> FEATURE:
<223> OTHER INFORMATION: Target sequence in the gene LRFN5

<400> SEQUENCE: 531
ctcggttaga tgtgacatca a                                              21

<210> SEQ ID NO 532
<211> LENGTH: 21
<212> TYPE: DNA
<213> ORGANISM: Artificial sequence
<220> FEATURE:
<223> OTHER INFORMATION: Target sequence in the gene CLDN17
```

<400> SEQUENCE: 532
tagtaagacc tccaccagtt a                                              21

<210> SEQ ID NO 533
<211> LENGTH: 21
<212> TYPE: DNA
<213> ORGANISM: Artificial sequence
<220> FEATURE:
<223> OTHER INFORMATION: Target sequence in the gene SCN1A

<400> SEQUENCE: 533
acgcatcaat ctggtgttca t                                              21

<210> SEQ ID NO 534
<211> LENGTH: 21
<212> TYPE: DNA
<213> ORGANISM: Artificial sequence
<220> FEATURE:
<223> OTHER INFORMATION: Target sequence in the gene ZNF521

<400> SEQUENCE: 534
cagcgcttaa atccaagact a                                              21

<210> SEQ ID NO 535
<211> LENGTH: 21
<212> TYPE: DNA
<213> ORGANISM: Artificial sequence
<220> FEATURE:
<223> OTHER INFORMATION: Target sequence in the gene TMEM167

<400> SEQUENCE: 535
ttcagagtct attgactgta a                                              21

<210> SEQ ID NO 536
<211> LENGTH: 21
<212> TYPE: DNA
<213> ORGANISM: Artificial sequence
<220> FEATURE:
<223> OTHER INFORMATION: Target sequence in the gene COPZ2

<400> SEQUENCE: 536
cggtgtgatt ctggagagtg a                                              21

<210> SEQ ID NO 537
<211> LENGTH: 21
<212> TYPE: DNA
<213> ORGANISM: Artificial sequence
<220> FEATURE:
<223> OTHER INFORMATION: Target sequence in the gene CNOT2

<400> SEQUENCE: 537
cagcagcgtt tcataggaag a                                              21

<210> SEQ ID NO 538
<211> LENGTH: 21
<212> TYPE: DNA
<213> ORGANISM: Artificial sequence
<220> FEATURE:
<223> OTHER INFORMATION: Target sequence in the gene NUP210L

<400> SEQUENCE: 538
ctggctgtcc ggcgtcatca a                                              21

<210> SEQ ID NO 539
<211> LENGTH: 21

-continued

```
<212> TYPE: DNA
<213> ORGANISM: Artificial sequence
<220> FEATURE:
<223> OTHER INFORMATION: Target sequence in the gene KCTD17

<400> SEQUENCE: 539
cccgggcctg agaaggaaga a                                              21

<210> SEQ ID NO 540
<211> LENGTH: 21
<212> TYPE: DNA
<213> ORGANISM: Artificial sequence
<220> FEATURE:
<223> OTHER INFORMATION: Target sequence in the gene WDR54

<400> SEQUENCE: 540
cacgctaagg agggtgctgg a                                              21

<210> SEQ ID NO 541
<211> LENGTH: 21
<212> TYPE: DNA
<213> ORGANISM: Artificial sequence
<220> FEATURE:
<223> OTHER INFORMATION: Target sequence in the gene TTC31

<400> SEQUENCE: 541
tgcgatggcg ccgattccaa a                                              21

<210> SEQ ID NO 542
<211> LENGTH: 21
<212> TYPE: DNA
<213> ORGANISM: Artificial sequence
<220> FEATURE:
<223> OTHER INFORMATION: Target sequence in the gene GLTSCR1

<400> SEQUENCE: 542
ccgcatcggg ctcaagctca a                                              21

<210> SEQ ID NO 543
<211> LENGTH: 21
<212> TYPE: DNA
<213> ORGANISM: Artificial sequence
<220> FEATURE:
<223> OTHER INFORMATION: Target sequence in the gene PDLIM3

<400> SEQUENCE: 543
caggacggga actactttga a                                              21

<210> SEQ ID NO 544
<211> LENGTH: 21
<212> TYPE: DNA
<213> ORGANISM: Artificial sequence
<220> FEATURE:
<223> OTHER INFORMATION: Target sequence in the gene KRT78

<400> SEQUENCE: 544
cagcctgttc tgctcgctca a                                              21

<210> SEQ ID NO 545
<211> LENGTH: 21
<212> TYPE: DNA
<213> ORGANISM: Artificial sequence
<220> FEATURE:
<223> OTHER INFORMATION: Target sequence in the gene C6orf81

<400> SEQUENCE: 545
```
caggttcact ccaacttcct a                                              21

<210> SEQ ID NO 546
<211> LENGTH: 21
<212> TYPE: DNA
<213> ORGANISM: Artificial sequence
<220> FEATURE:
<223> OTHER INFORMATION: Target sequence in the gene PTPN23

<400> SEQUENCE: 546
ccgccagatc cttacgctca a                                              21

<210> SEQ ID NO 547
<211> LENGTH: 21
<212> TYPE: DNA
<213> ORGANISM: Artificial sequence
<220> FEATURE:
<223> OTHER INFORMATION: Target sequence in the gene EPC2

<400> SEQUENCE: 547
cagcagttag ttcagatgca a                                              21

<210> SEQ ID NO 548
<211> LENGTH: 21
<212> TYPE: DNA
<213> ORGANISM: Artificial sequence
<220> FEATURE:
<223> OTHER INFORMATION: Target sequence in the gene RBP1

<400> SEQUENCE: 548
taggaactac atcatggact t                                              21

<210> SEQ ID NO 549
<211> LENGTH: 21
<212> TYPE: DNA
<213> ORGANISM: Artificial sequence
<220> FEATURE:
<223> OTHER INFORMATION: Target sequence in the gene 3.8-1

<400> SEQUENCE: 549
ttggatgtct ttgggaacca t                                              21

<210> SEQ ID NO 550
<211> LENGTH: 21
<212> TYPE: DNA
<213> ORGANISM: Artificial sequence
<220> FEATURE:
<223> OTHER INFORMATION: Target sequence in the gene C17orf79

<400> SEQUENCE: 550
ttccttattg acagtgttca a                                              21

<210> SEQ ID NO 551
<211> LENGTH: 21
<212> TYPE: DNA
<213> ORGANISM: Artificial sequence
<220> FEATURE:
<223> OTHER INFORMATION: Target sequence in the gene SYT3

<400> SEQUENCE: 551
tagggcgtag ttggtgctgg a                                              21

<210> SEQ ID NO 552
<211> LENGTH: 21
<212> TYPE: DNA
<213> ORGANISM: Artificial sequence
<220> FEATURE:
<223> OTHER INFORMATION: Target sequence in the gene SAR1B

<400> SEQUENCE: 552
cacattggtt ccaggtctca a                                                    21

<210> SEQ ID NO 553
<211> LENGTH: 21
<212> TYPE: DNA
<213> ORGANISM: Artificial sequence
<220> FEATURE:
<223> OTHER INFORMATION: Target sequence in the gene FLJ40243

<400> SEQUENCE: 553
cactgcgaaa gtgctgacaa a                                                    21

<210> SEQ ID NO 554
<211> LENGTH: 21
<212> TYPE: DNA
<213> ORGANISM: Artificial sequence
<220> FEATURE:
<223> OTHER INFORMATION: Target sequence in the gene SNORA27

<400> SEQUENCE: 554
caaactgggt gtttgtctgt a                                                    21

<210> SEQ ID NO 555
<211> LENGTH: 21
<212> TYPE: DNA
<213> ORGANISM: Artificial sequence
<220> FEATURE:
<223> OTHER INFORMATION: Target sequence in the gene LOC55908

<400> SEQUENCE: 555
ctgggtctct atggccgcac a                                                    21

<210> SEQ ID NO 556
<211> LENGTH: 21
<212> TYPE: DNA
<213> ORGANISM: Artificial sequence
<220> FEATURE:
<223> OTHER INFORMATION: Target sequence in the gene SNX3

<400> SEQUENCE: 556
atcgatgtga gcaacccgca a                                                    21

<210> SEQ ID NO 557
<211> LENGTH: 21
<212> TYPE: DNA
<213> ORGANISM: Artificial sequence
<220> FEATURE:
<223> OTHER INFORMATION: Target sequence in the gene MYO1E

<400> SEQUENCE: 557
cacagacgaa ctcagcttta a                                                    21

<210> SEQ ID NO 558
<211> LENGTH: 21
<212> TYPE: DNA
<213> ORGANISM: Artificial sequence
<220> FEATURE:
<223> OTHER INFORMATION: Target sequence in the gene MEGF9

<400> SEQUENCE: 558
caggatgcca tcagtccttt a                                                    21

```
<210> SEQ ID NO 559
<211> LENGTH: 21
<212> TYPE: DNA
<213> ORGANISM: Artificial sequence
<220> FEATURE:
<223> OTHER INFORMATION: Target sequence in the gene NOC3L

<400> SEQUENCE: 559
aagcatgaac gcattataga t                                               21

<210> SEQ ID NO 560
<211> LENGTH: 21
<212> TYPE: DNA
<213> ORGANISM: Artificial sequence
<220> FEATURE:
<223> OTHER INFORMATION: Target sequence in the gene HHIPL2

<400> SEQUENCE: 560
cccgttcaga ccactcgcca a                                               21

<210> SEQ ID NO 561
<211> LENGTH: 21
<212> TYPE: DNA
<213> ORGANISM: Artificial sequence
<220> FEATURE:
<223> OTHER INFORMATION: Target sequence in the gene ITIH4

<400> SEQUENCE: 561
atggatcgaa gtgaccttca a                                               21

<210> SEQ ID NO 562
<211> LENGTH: 21
<212> TYPE: DNA
<213> ORGANISM: Artificial sequence
<220> FEATURE:
<223> OTHER INFORMATION: Target sequence in the gene DPY19L2

<400> SEQUENCE: 562
ctccgtaatc aatggagcat a                                               21

<210> SEQ ID NO 563
<211> LENGTH: 21
<212> TYPE: DNA
<213> ORGANISM: Artificial sequence
<220> FEATURE:
<223> OTHER INFORMATION: Target sequence in the gene ZNF454

<400> SEQUENCE: 563
ataatccgtt ctagagaata a                                               21

<210> SEQ ID NO 564
<211> LENGTH: 21
<212> TYPE: DNA
<213> ORGANISM: Artificial sequence
<220> FEATURE:
<223> OTHER INFORMATION: Target sequence in the gene TTC21A

<400> SEQUENCE: 564
caaggcggta cagtcttata a                                               21

<210> SEQ ID NO 565
<211> LENGTH: 21
<212> TYPE: DNA
<213> ORGANISM: Artificial sequence
<220> FEATURE:
<223> OTHER INFORMATION: Target sequence in the gene TTC21A
```

<400> SEQUENCE: 565
ctgctactgg gcgatgcctt a                                            21

<210> SEQ ID NO 566
<211> LENGTH: 21
<212> TYPE: DNA
<213> ORGANISM: Artificial sequence
<220> FEATURE:
<223> OTHER INFORMATION: Target sequence in the gene MFSD11

<400> SEQUENCE: 566
cccgcggctc tgactaccga a                                            21

<210> SEQ ID NO 567
<211> LENGTH: 21
<212> TYPE: DNA
<213> ORGANISM: Artificial sequence
<220> FEATURE:
<223> OTHER INFORMATION: Target sequence in the gene MYO1E

<400> SEQUENCE: 567
cagggtaaag catcaagtcg a                                            21

<210> SEQ ID NO 568
<211> LENGTH: 21
<212> TYPE: DNA
<213> ORGANISM: Artificial sequence
<220> FEATURE:
<223> OTHER INFORMATION: Target sequence in the gene ARL5B

<400> SEQUENCE: 568
tagacggtgc tgattgggaa a                                            21

<210> SEQ ID NO 569
<211> LENGTH: 21
<212> TYPE: DNA
<213> ORGANISM: Artificial sequence
<220> FEATURE:
<223> OTHER INFORMATION: Target sequence in the gene SPZ1

<400> SEQUENCE: 569
taccattgcc ttattcgaaa t                                            21

<210> SEQ ID NO 570
<211> LENGTH: 21
<212> TYPE: DNA
<213> ORGANISM: Artificial sequence
<220> FEATURE:
<223> OTHER INFORMATION: Target sequence in the gene MFSD11

<400> SEQUENCE: 570
cagcaactac cttctccttc a                                            21

<210> SEQ ID NO 571
<211> LENGTH: 21
<212> TYPE: DNA
<213> ORGANISM: Artificial sequence
<220> FEATURE:
<223> OTHER INFORMATION: Target sequence in the gene LHX6

<400> SEQUENCE: 571
atgcttgacg ttggcactta a                                            21

<210> SEQ ID NO 572

```
<211> LENGTH: 21
<212> TYPE: DNA
<213> ORGANISM: Artificial sequence
<220> FEATURE:
<223> OTHER INFORMATION: Target sequence in the gene GABARAPL1

<400> SEQUENCE: 572
cagctgctag ttagaaaggt t                                              21

<210> SEQ ID NO 573
<211> LENGTH: 21
<212> TYPE: DNA
<213> ORGANISM: Artificial sequence
<220> FEATURE:
<223> OTHER INFORMATION: Target sequence in the gene OBFC1

<400> SEQUENCE: 573
tcagcttaac ctcacaactt a                                              21

<210> SEQ ID NO 574
<211> LENGTH: 21
<212> TYPE: DNA
<213> ORGANISM: Artificial sequence
<220> FEATURE:
<223> OTHER INFORMATION: Target sequence in the gene BCAS2

<400> SEQUENCE: 574
ctcgcagata ccgacctact a                                              21

<210> SEQ ID NO 575
<211> LENGTH: 21
<212> TYPE: DNA
<213> ORGANISM: Artificial sequence
<220> FEATURE:
<223> OTHER INFORMATION: Target sequence in the gene CCDC62

<400> SEQUENCE: 575
acctacgagt ttgttaatct a                                              21

<210> SEQ ID NO 576
<211> LENGTH: 21
<212> TYPE: DNA
<213> ORGANISM: Artificial sequence
<220> FEATURE:
<223> OTHER INFORMATION: Target sequence in the gene STC1

<400> SEQUENCE: 576
ccagagaatc ttaaggtcta a                                              21

<210> SEQ ID NO 577
<211> LENGTH: 21
<212> TYPE: DNA
<213> ORGANISM: Artificial sequence
<220> FEATURE:
<223> OTHER INFORMATION: Target sequence in the gene TTC23

<400> SEQUENCE: 577
cagggtgata tatgctataa a                                              21

<210> SEQ ID NO 578
<211> LENGTH: 21
<212> TYPE: DNA
<213> ORGANISM: Artificial sequence
<220> FEATURE:
<223> OTHER INFORMATION: Target sequence in the gene NELF

<400> SEQUENCE: 578
```
cgcgtctgta atccagagga a                                    21

<210> SEQ ID NO 579
<211> LENGTH: 21
<212> TYPE: DNA
<213> ORGANISM: Artificial sequence
<220> FEATURE:
<223> OTHER INFORMATION: Target sequence in the gene HSD17B4

<400> SEQUENCE: 579
caggccaatt atagtgctgc a                                    21

<210> SEQ ID NO 580
<211> LENGTH: 21
<212> TYPE: DNA
<213> ORGANISM: Artificial sequence
<220> FEATURE:
<223> OTHER INFORMATION: Target sequence in the gene IL32

<400> SEQUENCE: 580
ccggatgttg aggatcccgc a                                    21

<210> SEQ ID NO 581
<211> LENGTH: 21
<212> TYPE: DNA
<213> ORGANISM: Artificial sequence
<220> FEATURE:
<223> OTHER INFORMATION: Target sequence in the gene TATDN1

<400> SEQUENCE: 581
ctgaccctat gttcagagga a                                    21

<210> SEQ ID NO 582
<211> LENGTH: 21
<212> TYPE: DNA
<213> ORGANISM: Artificial sequence
<220> FEATURE:
<223> OTHER INFORMATION: Target sequence in the gene FAM117A

<400> SEQUENCE: 582
ctcgacctaa tcatagctac a                                    21

<210> SEQ ID NO 583
<211> LENGTH: 21
<212> TYPE: DNA
<213> ORGANISM: Artificial sequence
<220> FEATURE:
<223> OTHER INFORMATION: Target sequence in the gene ZNF710

<400> SEQUENCE: 583
ctcgcccgtg aagccattca a                                    21

<210> SEQ ID NO 584
<211> LENGTH: 21
<212> TYPE: DNA
<213> ORGANISM: Artificial sequence
<220> FEATURE:
<223> OTHER INFORMATION: Target sequence in the gene CABP1

<400> SEQUENCE: 584
cagcagatat gattggtgta a                                    21

<210> SEQ ID NO 585
<211> LENGTH: 21
<212> TYPE: DNA

```
<213> ORGANISM: Artificial sequence
<220> FEATURE:
<223> OTHER INFORMATION: Target sequence in the gene ZNF454

<400> SEQUENCE: 585
tagcactttg cctgtcccta a                                              21

<210> SEQ ID NO 586
<211> LENGTH: 21
<212> TYPE: DNA
<213> ORGANISM: Artificial sequence
<220> FEATURE:
<223> OTHER INFORMATION: Target sequence in the gene CC2D1A

<400> SEQUENCE: 586
cccggcgtcc acgcctacct a                                              21

<210> SEQ ID NO 587
<211> LENGTH: 21
<212> TYPE: DNA
<213> ORGANISM: Artificial sequence
<220> FEATURE:
<223> OTHER INFORMATION: Target sequence in the gene C12orf52

<400> SEQUENCE: 587
tcaggattag tttccagcta a                                              21

<210> SEQ ID NO 588
<211> LENGTH: 21
<212> TYPE: DNA
<213> ORGANISM: Artificial sequence
<220> FEATURE:
<223> OTHER INFORMATION: Target sequence in the gene LOC90826

<400> SEQUENCE: 588
ctggaactgg acagagtaat a                                              21

<210> SEQ ID NO 589
<211> LENGTH: 21
<212> TYPE: DNA
<213> ORGANISM: Artificial sequence
<220> FEATURE:
<223> OTHER INFORMATION: Target sequence in the gene ENPP6

<400> SEQUENCE: 589
caggtcggtg gacgtctaca a                                              21

<210> SEQ ID NO 590
<211> LENGTH: 21
<212> TYPE: DNA
<213> ORGANISM: Artificial sequence
<220> FEATURE:
<223> OTHER INFORMATION: Target sequence in the gene ZNF44

<400> SEQUENCE: 590
caccgggagt gtcatgaata t                                              21

<210> SEQ ID NO 591
<211> LENGTH: 21
<212> TYPE: DNA
<213> ORGANISM: Artificial sequence
<220> FEATURE:
<223> OTHER INFORMATION: Target sequence in the gene HNRPUL1

<400> SEQUENCE: 591
gagagtgact attgaacttg a                                              21
```

<210> SEQ ID NO 592
<211> LENGTH: 21
<212> TYPE: DNA
<213> ORGANISM: Artificial sequence
<220> FEATURE:
<223> OTHER INFORMATION: Target sequence in the gene FAM122A

<400> SEQUENCE: 592
cagccgcttg caccagatca a                                    21

<210> SEQ ID NO 593
<211> LENGTH: 21
<212> TYPE: DNA
<213> ORGANISM: Artificial sequence
<220> FEATURE:
<223> OTHER INFORMATION: Target sequence in the gene KLF16

<400> SEQUENCE: 593
cagcgctagt gagatgcctt a                                    21

<210> SEQ ID NO 594
<211> LENGTH: 21
<212> TYPE: DNA
<213> ORGANISM: Artificial sequence
<220> FEATURE:
<223> OTHER INFORMATION: Target sequence in the gene ACSF2

<400> SEQUENCE: 594
caggagatgt cgccacaatg a                                    21

<210> SEQ ID NO 595
<211> LENGTH: 21
<212> TYPE: DNA
<213> ORGANISM: Artificial sequence
<220> FEATURE:
<223> OTHER INFORMATION: Target sequence in the gene TSHB

<400> SEQUENCE: 595
gagagtgtgc ttattgccta a                                    21

<210> SEQ ID NO 596
<211> LENGTH: 21
<212> TYPE: DNA
<213> ORGANISM: Artificial sequence
<220> FEATURE:
<223> OTHER INFORMATION: Target sequence in the gene ZNF503

<400> SEQUENCE: 596
acggtgtgca ctcctcgcta a                                    21

<210> SEQ ID NO 597
<211> LENGTH: 21
<212> TYPE: DNA
<213> ORGANISM: Artificial sequence
<220> FEATURE:
<223> OTHER INFORMATION: Target sequence in the gene TMEM132D

<400> SEQUENCE: 597
cacgttgagg gcaaaggtga a                                    21

<210> SEQ ID NO 598
<211> LENGTH: 21
<212> TYPE: DNA
<213> ORGANISM: Artificial sequence
<220> FEATURE:

```
<223> OTHER INFORMATION: Target sequence in the gene HEY2

<400> SEQUENCE: 598
taggattccg agagtgccta a                                              21

<210> SEQ ID NO 599
<211> LENGTH: 21
<212> TYPE: DNA
<213> ORGANISM: Artificial sequence
<220> FEATURE:
<223> OTHER INFORMATION: Target sequence in the gene MYO7B

<400> SEQUENCE: 599
accgagctta tttaccgcca a                                              21

<210> SEQ ID NO 600
<211> LENGTH: 21
<212> TYPE: DNA
<213> ORGANISM: Artificial sequence
<220> FEATURE:
<223> OTHER INFORMATION: Target sequence in the gene FLJ45803

<400> SEQUENCE: 600
ctctaggatg tttgccctga a                                              21

<210> SEQ ID NO 601
<211> LENGTH: 21
<212> TYPE: DNA
<213> ORGANISM: Artificial sequence
<220> FEATURE:
<223> OTHER INFORMATION: Target sequence in the gene AZIN1

<400> SEQUENCE: 601
caggttaagc ttgtctggtc a                                              21

<210> SEQ ID NO 602
<211> LENGTH: 21
<212> TYPE: DNA
<213> ORGANISM: Artificial sequence
<220> FEATURE:
<223> OTHER INFORMATION: Target sequence in the gene LOC374920

<400> SEQUENCE: 602
cccgctggag ttcgcctact a                                              21

<210> SEQ ID NO 603
<211> LENGTH: 21
<212> TYPE: DNA
<213> ORGANISM: Artificial sequence
<220> FEATURE:
<223> OTHER INFORMATION: Target sequence in the gene EPAS1

<400> SEQUENCE: 603
cccaatgata agttcaccca a                                              21

<210> SEQ ID NO 604
<211> LENGTH: 21
<212> TYPE: DNA
<213> ORGANISM: Artificial sequence
<220> FEATURE:
<223> OTHER INFORMATION: Target sequence in the gene PGM1

<400> SEQUENCE: 604
caggtacagt ttacactaca a                                              21
```

<210> SEQ ID NO 605
<211> LENGTH: 21
<212> TYPE: DNA
<213> ORGANISM: Artificial sequence
<220> FEATURE:
<223> OTHER INFORMATION: Target sequence in the gene KLHL8

<400> SEQUENCE: 605
caggatattg atggacctac a                                              21

<210> SEQ ID NO 606
<211> LENGTH: 21
<212> TYPE: DNA
<213> ORGANISM: Artificial sequence
<220> FEATURE:
<223> OTHER INFORMATION: Target sequence in the gene FTSJ3

<400> SEQUENCE: 606
cgggtttgag atagtgccta t                                              21

<210> SEQ ID NO 607
<211> LENGTH: 21
<212> TYPE: DNA
<213> ORGANISM: Artificial sequence
<220> FEATURE:
<223> OTHER INFORMATION: Target sequence in the gene
      LOC100137047-PLA2G4B

<400> SEQUENCE: 607
cgccggcaac ctaccagcta a                                              21

<210> SEQ ID NO 608
<211> LENGTH: 21
<212> TYPE: DNA
<213> ORGANISM: Artificial sequence
<220> FEATURE:
<223> OTHER INFORMATION: Target sequence in the gene TIMM8A

<400> SEQUENCE: 608
caggtagagg tgcatgccta a                                              21

<210> SEQ ID NO 609
<211> LENGTH: 21
<212> TYPE: DNA
<213> ORGANISM: Artificial sequence
<220> FEATURE:
<223> OTHER INFORMATION: Target sequence in the gene TMEM117

<400> SEQUENCE: 609
aacgaatcta ctagtgcaac a                                              21

<210> SEQ ID NO 610
<211> LENGTH: 21
<212> TYPE: DNA
<213> ORGANISM: Artificial sequence
<220> FEATURE:
<223> OTHER INFORMATION: Target sequence in the gene LOC124446

<400> SEQUENCE: 610
agccctagaa tgggtgagga a                                              21

<210> SEQ ID NO 611
<211> LENGTH: 21
<212> TYPE: DNA
<213> ORGANISM: Artificial sequence
<220> FEATURE:
<223> OTHER INFORMATION: Target sequence in the gene COPA

```
<400> SEQUENCE: 611
cacacgggtg aagggcaaca a                                              21

<210> SEQ ID NO 612
<211> LENGTH: 21
<212> TYPE: DNA
<213> ORGANISM: Artificial sequence
<220> FEATURE:
<223> OTHER INFORMATION: Target sequence in the gene ZNF785

<400> SEQUENCE: 612
cagcgtttcc ctggagagga a                                              21

<210> SEQ ID NO 613
<211> LENGTH: 21
<212> TYPE: DNA
<213> ORGANISM: Artificial sequence
<220> FEATURE:
<223> OTHER INFORMATION: Target sequence in the gene LOC441108

<400> SEQUENCE: 613
catgacaaga ggagtggata a                                              21

<210> SEQ ID NO 614
<211> LENGTH: 21
<212> TYPE: DNA
<213> ORGANISM: Artificial sequence
<220> FEATURE:
<223> OTHER INFORMATION: Target sequence in the gene NOS2A

<400> SEQUENCE: 614
ctgggccgtg caaaccttca a                                              21

<210> SEQ ID NO 615
<211> LENGTH: 21
<212> TYPE: DNA
<213> ORGANISM: Artificial sequence
<220> FEATURE:
<223> OTHER INFORMATION: Target sequence in the gene CALY

<400> SEQUENCE: 615
ctgcgtgctg atcatgtaca a                                              21

<210> SEQ ID NO 616
<211> LENGTH: 21
<212> TYPE: DNA
<213> ORGANISM: Artificial sequence
<220> FEATURE:
<223> OTHER INFORMATION: Target sequence in the gene FER1L3

<400> SEQUENCE: 616
cacggcgact gtagccctga a                                              21

<210> SEQ ID NO 617
<211> LENGTH: 21
<212> TYPE: DNA
<213> ORGANISM: Artificial sequence
<220> FEATURE:
<223> OTHER INFORMATION: Target sequence in the gene LOC790955

<400> SEQUENCE: 617
ccggaccgag ataccatgcc a                                              21

<210> SEQ ID NO 618
```

```
<211> LENGTH: 21
<212> TYPE: DNA
<213> ORGANISM: Artificial sequence
<220> FEATURE:
<223> OTHER INFORMATION: Target sequence in the gene TAS1R2

<400> SEQUENCE: 618
ccagatcgtc tgcgccttca a                                              21

<210> SEQ ID NO 619
<211> LENGTH: 21
<212> TYPE: DNA
<213> ORGANISM: Artificial sequence
<220> FEATURE:
<223> OTHER INFORMATION: Target sequence in the gene MAPKAPK2

<400> SEQUENCE: 619
cgccatcatc gatgactaca a                                              21

<210> SEQ ID NO 620
<211> LENGTH: 21
<212> TYPE: DNA
<213> ORGANISM: Artificial sequence
<220> FEATURE:
<223> OTHER INFORMATION: Target sequence in the gene KLHL30

<400> SEQUENCE: 620
cagcgtaact gtggccagcc a                                              21

<210> SEQ ID NO 621
<211> LENGTH: 21
<212> TYPE: DNA
<213> ORGANISM: Artificial sequence
<220> FEATURE:
<223> OTHER INFORMATION: Target sequence in the gene PPP1R16B

<400> SEQUENCE: 621
acgggcgaga gtagcagtga a                                              21

<210> SEQ ID NO 622
<211> LENGTH: 21
<212> TYPE: DNA
<213> ORGANISM: Artificial sequence
<220> FEATURE:
<223> OTHER INFORMATION: Target sequence in the gene SPATA17

<400> SEQUENCE: 622
tccatgggag ctgcaattac a                                              21

<210> SEQ ID NO 623
<211> LENGTH: 21
<212> TYPE: DNA
<213> ORGANISM: Artificial sequence
<220> FEATURE:
<223> OTHER INFORMATION: Target sequence in the gene OAZ3

<400> SEQUENCE: 623
cagggtaacc acgaccagct t                                              21

<210> SEQ ID NO 624
<211> LENGTH: 21
<212> TYPE: DNA
<213> ORGANISM: Artificial sequence
<220> FEATURE:
<223> OTHER INFORMATION: Target sequence in the gene CRIPT

<400> SEQUENCE: 624
```
caaggcatag atgtcaactt a                                             21

<210> SEQ ID NO 625
<211> LENGTH: 21
<212> TYPE: DNA
<213> ORGANISM: Artificial sequence
<220> FEATURE:
<223> OTHER INFORMATION: Target sequence in the gene ARSE

<400> SEQUENCE: 625
cggcgtgaag ctgacccaac a                                             21

<210> SEQ ID NO 626
<211> LENGTH: 21
<212> TYPE: DNA
<213> ORGANISM: Artificial sequence
<220> FEATURE:
<223> OTHER INFORMATION: Target sequence in the gene POLR2C

<400> SEQUENCE: 626
ctcggtggag ttcaccctcg a                                             21

<210> SEQ ID NO 627
<211> LENGTH: 21
<212> TYPE: DNA
<213> ORGANISM: Artificial sequence
<220> FEATURE:
<223> OTHER INFORMATION: Target sequence in the gene PNKP

<400> SEQUENCE: 627
cacgtgtgag acagccctga a                                             21

<210> SEQ ID NO 628
<211> LENGTH: 21
<212> TYPE: DNA
<213> ORGANISM: Artificial sequence
<220> FEATURE:
<223> OTHER INFORMATION: Target sequence in the gene KIAA0355

<400> SEQUENCE: 628
aaccgctacc tcagcaaaca a                                             21

<210> SEQ ID NO 629
<211> LENGTH: 21
<212> TYPE: DNA
<213> ORGANISM: Artificial sequence
<220> FEATURE:
<223> OTHER INFORMATION: Target sequence in the gene SLC26A11

<400> SEQUENCE: 629
ctccttcgag gtgactggat a                                             21

<210> SEQ ID NO 630
<211> LENGTH: 21
<212> TYPE: DNA
<213> ORGANISM: Artificial sequence
<220> FEATURE:
<223> OTHER INFORMATION: Target sequence in the gene SNORD22

<400> SEQUENCE: 630
cccagagcct gtaaaggtga a                                             21

<210> SEQ ID NO 631
<211> LENGTH: 21
<212> TYPE: DNA

```
<213> ORGANISM: Artificial sequence
<220> FEATURE:
<223> OTHER INFORMATION: Target sequence in the gene SIM2

<400> SEQUENCE: 631
tagcagctcg tctccagcta a                                              21

<210> SEQ ID NO 632
<211> LENGTH: 21
<212> TYPE: DNA
<213> ORGANISM: Artificial sequence
<220> FEATURE:
<223> OTHER INFORMATION: Target sequence in the gene FAM65A

<400> SEQUENCE: 632
caggaggtga cccgcctaga a                                              21

<210> SEQ ID NO 633
<211> LENGTH: 21
<212> TYPE: DNA
<213> ORGANISM: Artificial sequence
<220> FEATURE:
<223> OTHER INFORMATION: Target sequence in the gene FHDC1

<400> SEQUENCE: 633
aagctcgaga agagattact a                                              21

<210> SEQ ID NO 634
<211> LENGTH: 21
<212> TYPE: DNA
<213> ORGANISM: Artificial sequence
<220> FEATURE:
<223> OTHER INFORMATION: Target sequence of the gene AIG1

<400> SEQUENCE: 634
cagagagatg atatacccga a                                              21

<210> SEQ ID NO 635
<211> LENGTH: 21
<212> TYPE: DNA
<213> ORGANISM: Artificial sequence
<220> FEATURE:
<223> OTHER INFORMATION: Target sequence of the gene EMP1

<400> SEQUENCE: 635
accgtatttc agccatgata a                                              21

<210> SEQ ID NO 636
<211> LENGTH: 21
<212> TYPE: DNA
<213> ORGANISM: Artificial sequence
<220> FEATURE:
<223> OTHER INFORMATION: Target sequence of the gene DMWD

<400> SEQUENCE: 636
cacgcgcgag ggtttctaca a                                              21

<210> SEQ ID NO 637
<211> LENGTH: 21
<212> TYPE: DNA
<213> ORGANISM: Artificial sequence
<220> FEATURE:
<223> OTHER INFORMATION: Target sequence of the gene LPPR2

<400> SEQUENCE: 637
cccgtgtcta agcatgtgca a                                              21
```

<210> SEQ ID NO 638
<211> LENGTH: 21
<212> TYPE: DNA
<213> ORGANISM: Artificial sequence
<220> FEATURE:
<223> OTHER INFORMATION: Target sequence of the gene LYPD4

<400> SEQUENCE: 638
cccgtgcttc atgccctgat a                                              21

<210> SEQ ID NO 639
<211> LENGTH: 21
<212> TYPE: DNA
<213> ORGANISM: Artificial sequence
<220> FEATURE:
<223> OTHER INFORMATION: Target sequence of the gene ARMC6

<400> SEQUENCE: 639
caccaaagcg ttcctggata a                                              21

<210> SEQ ID NO 640
<211> LENGTH: 21
<212> TYPE: DNA
<213> ORGANISM: Artificial sequence
<220> FEATURE:
<223> OTHER INFORMATION: Target sequence of the gene BARHL2

<400> SEQUENCE: 640
tcgccttatt tctatcaccc a                                              21

<210> SEQ ID NO 641
<211> LENGTH: 21
<212> TYPE: DNA
<213> ORGANISM: Artificial sequence
<220> FEATURE:
<223> OTHER INFORMATION: Target sequence of the gene CRTAC1

<400> SEQUENCE: 641
ccgggacatc gcctcaccca a                                              21

<210> SEQ ID NO 642
<211> LENGTH: 21
<212> TYPE: DNA
<213> ORGANISM: Artificial sequence
<220> FEATURE:
<223> OTHER INFORMATION: Target sequence of the gene DES

<400> SEQUENCE: 642
ctgcgagatt gacgccctga a                                              21

<210> SEQ ID NO 643
<211> LENGTH: 21
<212> TYPE: DNA
<213> ORGANISM: Artificial sequence
<220> FEATURE:
<223> OTHER INFORMATION: Target sequence of the gene ARNT2

<400> SEQUENCE: 643
cagaataacc accatgagga a                                              21

<210> SEQ ID NO 644
<211> LENGTH: 21
<212> TYPE: DNA
<213> ORGANISM: Artificial sequence
<220> FEATURE:

<223> OTHER INFORMATION: Target sequence of the gene EPHA10

<400> SEQUENCE: 644
ctcggtgcgc gtctactaca a                                              21

<210> SEQ ID NO 645
<211> LENGTH: 21
<212> TYPE: DNA
<213> ORGANISM: Artificial sequence
<220> FEATURE:
<223> OTHER INFORMATION: Target sequence of the gene EEF1A1

<400> SEQUENCE: 645
caccgagaca tttaggtgaa a                                              21

<210> SEQ ID NO 646
<211> LENGTH: 21
<212> TYPE: DNA
<213> ORGANISM: Artificial sequence
<220> FEATURE:
<223> OTHER INFORMATION: Target sequence of the gene TREML1

<400> SEQUENCE: 646
cagcagagtt tcaggcatga a                                              21

<210> SEQ ID NO 647
<211> LENGTH: 21
<212> TYPE: DNA
<213> ORGANISM: Artificial sequence
<220> FEATURE:
<223> OTHER INFORMATION: Target sequence of the gene COPA

<400> SEQUENCE: 647
ctggcgcatg aatgaatcaa a                                              21

<210> SEQ ID NO 648
<211> LENGTH: 21
<212> TYPE: DNA
<213> ORGANISM: Artificial sequence
<220> FEATURE:
<223> OTHER INFORMATION: Target sequence of the gene MYH14

<400> SEQUENCE: 648
cgcgggcaag gtcgactaca a                                              21

<210> SEQ ID NO 649
<211> LENGTH: 21
<212> TYPE: DNA
<213> ORGANISM: Artificial sequence
<220> FEATURE:
<223> OTHER INFORMATION: Target sequence of the gene MYST1

<400> SEQUENCE: 649
cagatgacca gtatcaccca a                                              21

<210> SEQ ID NO 650
<211> LENGTH: 21
<212> TYPE: DNA
<213> ORGANISM: Artificial sequence
<220> FEATURE:
<223> OTHER INFORMATION: Target sequence of the gene PLD3

<400> SEQUENCE: 650
ccggttctat gacacccgct a                                              21

```
<210> SEQ ID NO 651
<211> LENGTH: 21
<212> TYPE: DNA
<213> ORGANISM: Artificial sequence
<220> FEATURE:
<223> OTHER INFORMATION: Target sequence of the gene EFNA2

<400> SEQUENCE: 651
ccgcgccaac tcggaccgct a                                              21

<210> SEQ ID NO 652
<211> LENGTH: 21
<212> TYPE: DNA
<213> ORGANISM: Artificial sequence
<220> FEATURE:
<223> OTHER INFORMATION: Target sequence of the gene GP9

<400> SEQUENCE: 652
cagacaggag cacctgacca a                                              21

<210> SEQ ID NO 653
<211> LENGTH: 21
<212> TYPE: DNA
<213> ORGANISM: Artificial sequence
<220> FEATURE:
<223> OTHER INFORMATION: Target sequence of the gene ELA2B

<400> SEQUENCE: 653
tggcgtgata tgcacctgca a                                              21

<210> SEQ ID NO 654
<211> LENGTH: 21
<212> TYPE: DNA
<213> ORGANISM: Artificial sequence
<220> FEATURE:
<223> OTHER INFORMATION: Target sequence of the gene DNAI1

<400> SEQUENCE: 654
aagaaggcac atataagcct a                                              21

<210> SEQ ID NO 655
<211> LENGTH: 21
<212> TYPE: DNA
<213> ORGANISM: Artificial sequence
<220> FEATURE:
<223> OTHER INFORMATION: Target sequence of the gene SLK

<400> SEQUENCE: 655
tagcatcttg tgatcaccca a                                              21

<210> SEQ ID NO 656
<211> LENGTH: 21
<212> TYPE: DNA
<213> ORGANISM: Artificial sequence
<220> FEATURE:
<223> OTHER INFORMATION: Target sequence of the gene ZNF74

<400> SEQUENCE: 656
cagggtgcct cctctagtta a                                              21

<210> SEQ ID NO 657
<211> LENGTH: 21
<212> TYPE: DNA
<213> ORGANISM: Artificial sequence
<220> FEATURE:
<223> OTHER INFORMATION: Target sequence of the gene OGDH
```

```
<400> SEQUENCE: 657
caggatcaat cgtgtcaccg a                                              21

<210> SEQ ID NO 658
<211> LENGTH: 21
<212> TYPE: DNA
<213> ORGANISM: Artificial sequence
<220> FEATURE:
<223> OTHER INFORMATION: Target sequence of the gene MMRN1

<400> SEQUENCE: 658
cagggtcgtg atgatgcctt a                                              21

<210> SEQ ID NO 659
<211> LENGTH: 21
<212> TYPE: DNA
<213> ORGANISM: Artificial sequence
<220> FEATURE:
<223> OTHER INFORMATION: Target sequence of the gene AGPAT1

<400> SEQUENCE: 659
tggctccatg ctgcccttca a                                              21

<210> SEQ ID NO 660
<211> LENGTH: 21
<212> TYPE: DNA
<213> ORGANISM: Artificial sequence
<220> FEATURE:
<223> OTHER INFORMATION: Target sequence of the gene CYP3A4

<400> SEQUENCE: 660
ctcgatgcaa tgaacactta a                                              21

<210> SEQ ID NO 661
<211> LENGTH: 21
<212> TYPE: DNA
<213> ORGANISM: Artificial sequence
<220> FEATURE:
<223> OTHER INFORMATION: Target sequence of the gene GNAL

<400> SEQUENCE: 661
atgggtttaa tcccgaggaa a                                              21

<210> SEQ ID NO 662
<211> LENGTH: 21
<212> TYPE: DNA
<213> ORGANISM: Artificial sequence
<220> FEATURE:
<223> OTHER INFORMATION: Target sequence of the gene MYCBP2

<400> SEQUENCE: 662
ctcgatatat tgccataaca a                                              21

<210> SEQ ID NO 663
<211> LENGTH: 21
<212> TYPE: DNA
<213> ORGANISM: Artificial sequence
<220> FEATURE:
<223> OTHER INFORMATION: Target sequence of the gene PSIP1

<400> SEQUENCE: 663
aggcagcaac taaacaatca a                                              21

<210> SEQ ID NO 664
<211> LENGTH: 21
```

```
<212> TYPE: DNA
<213> ORGANISM: Artificial sequence
<220> FEATURE:
<223> OTHER INFORMATION: Target sequence of the gene SLC13A2

<400> SEQUENCE: 664
cccgctaatc ctgggcttca t                                          21

<210> SEQ ID NO 665
<211> LENGTH: 21
<212> TYPE: DNA
<213> ORGANISM: Artificial sequence
<220> FEATURE:
<223> OTHER INFORMATION: Target sequence of the gene HMBS

<400> SEQUENCE: 665
cagcttaacg atgcccatta a                                          21

<210> SEQ ID NO 666
<211> LENGTH: 21
<212> TYPE: DNA
<213> ORGANISM: Artificial sequence
<220> FEATURE:
<223> OTHER INFORMATION: Target sequence of the gene MED14

<400> SEQUENCE: 666
cgggtgaagt ttcgtgttga a                                          21

<210> SEQ ID NO 667
<211> LENGTH: 21
<212> TYPE: DNA
<213> ORGANISM: Artificial sequence
<220> FEATURE:
<223> OTHER INFORMATION: Target sequence of the gene PLXNA4

<400> SEQUENCE: 667
ccgcatcgtc cagacctgca a                                          21

<210> SEQ ID NO 668
<211> LENGTH: 21
<212> TYPE: DNA
<213> ORGANISM: Artificial sequence
<220> FEATURE:
<223> OTHER INFORMATION: Target sequence of the gene TINF2

<400> SEQUENCE: 668
tcctgtggat ttggcctcga a                                          21

<210> SEQ ID NO 669
<211> LENGTH: 21
<212> TYPE: DNA
<213> ORGANISM: Artificial sequence
<220> FEATURE:
<223> OTHER INFORMATION: Target sequence of the gene POLR3C

<400> SEQUENCE: 669
ccggtacatc tatactacca a                                          21

<210> SEQ ID NO 670
<211> LENGTH: 21
<212> TYPE: DNA
<213> ORGANISM: Artificial sequence
<220> FEATURE:
<223> OTHER INFORMATION: Target sequence of the gene POLR2A

<400> SEQUENCE: 670
```
cagcggttga agggcaagga a					21

<210> SEQ ID NO 671
<211> LENGTH: 21
<212> TYPE: DNA
<213> ORGANISM: Artificial sequence
<220> FEATURE:
<223> OTHER INFORMATION: Target sequence of the gene CLDN12

<400> SEQUENCE: 671
ctcctcagtg tgggcgagta a					21

<210> SEQ ID NO 672
<211> LENGTH: 21
<212> TYPE: DNA
<213> ORGANISM: Artificial sequence
<220> FEATURE:
<223> OTHER INFORMATION: Target sequence of the gene ZNF559

<400> SEQUENCE: 672
tcccgagaga tggctaatga a					21

<210> SEQ ID NO 673
<211> LENGTH: 21
<212> TYPE: DNA
<213> ORGANISM: Artificial sequence
<220> FEATURE:
<223> OTHER INFORMATION: Target sequence of the gene WDR3

<400> SEQUENCE: 673
ccgggatgtt atcggcttca a					21

<210> SEQ ID NO 674
<211> LENGTH: 21
<212> TYPE: DNA
<213> ORGANISM: Artificial sequence
<220> FEATURE:
<223> OTHER INFORMATION: Target sequence of the gene KIF2A

<400> SEQUENCE: 674
cagcaagcaa atcaacccga a					21

<210> SEQ ID NO 675
<211> LENGTH: 21
<212> TYPE: DNA
<213> ORGANISM: Artificial sequence
<220> FEATURE:
<223> OTHER INFORMATION: Target sequence of the gene ARHGAP17

<400> SEQUENCE: 675
cagaccagcg atgtgaataa a					21

<210> SEQ ID NO 676
<211> LENGTH: 21
<212> TYPE: DNA
<213> ORGANISM: Artificial sequence
<220> FEATURE:
<223> OTHER INFORMATION: Target sequence of the gene IPO11

<400> SEQUENCE: 676
atgggtcgag ttctactaca a					21

<210> SEQ ID NO 677
<211> LENGTH: 21
<212> TYPE: DNA
<213> ORGANISM: Artificial sequence

```
<220> FEATURE:
<223> OTHER INFORMATION: Target sequence of the gene GYPA

<400> SEQUENCE: 677
accggacatg caggtgaata t                                              21

<210> SEQ ID NO 678
<211> LENGTH: 21
<212> TYPE: DNA
<213> ORGANISM: Artificial sequence
<220> FEATURE:
<223> OTHER INFORMATION: Target sequence of the gene TDGF3

<400> SEQUENCE: 678
ctgcccgttt acatataaca a                                              21

<210> SEQ ID NO 679
<211> LENGTH: 21
<212> TYPE: DNA
<213> ORGANISM: Artificial sequence
<220> FEATURE:
<223> OTHER INFORMATION: Target sequence of the gene INTS4

<400> SEQUENCE: 679
cagatacgtc tcatggtgta a                                              21

<210> SEQ ID NO 680
<211> LENGTH: 21
<212> TYPE: DNA
<213> ORGANISM: Artificial sequence
<220> FEATURE:
<223> OTHER INFORMATION: Target sequence of the gene KRBA1

<400> SEQUENCE: 680
ccgacaaacc gtggcctaca a                                              21

<210> SEQ ID NO 681
<211> LENGTH: 21
<212> TYPE: DNA
<213> ORGANISM: Artificial sequence
<220> FEATURE:
<223> OTHER INFORMATION: Target sequence of the gene KIAA1853

<400> SEQUENCE: 681
cgccagtatc acggcccgca a                                              21

<210> SEQ ID NO 682
<211> LENGTH: 21
<212> TYPE: DNA
<213> ORGANISM: Artificial sequence
<220> FEATURE:
<223> OTHER INFORMATION: Target sequence of the gene TNNT2

<400> SEQUENCE: 682
caggtcgttc atgcccaact t                                              21

<210> SEQ ID NO 683
<211> LENGTH: 21
<212> TYPE: DNA
<213> ORGANISM: Artificial sequence
<220> FEATURE:
<223> OTHER INFORMATION: Target sequence of the gene PLOD1

<400> SEQUENCE: 683
caccatcaac atcgccctga a                                              21
```

<210> SEQ ID NO 684
<211> LENGTH: 21
<212> TYPE: DNA
<213> ORGANISM: Artificial sequence
<220> FEATURE:
<223> OTHER INFORMATION: Target sequence of the gene SERPINA4

<400> SEQUENCE: 684
tcgccacatc ctgcgattca a    21

<210> SEQ ID NO 685
<211> LENGTH: 21
<212> TYPE: DNA
<213> ORGANISM: Artificial sequence
<220> FEATURE:
<223> OTHER INFORMATION: Target sequence of the gene ARID1A

<400> SEQUENCE: 685
caccttggtt acactcgcca a    21

<210> SEQ ID NO 686
<211> LENGTH: 21
<212> TYPE: DNA
<213> ORGANISM: Artificial sequence
<220> FEATURE:
<223> OTHER INFORMATION: Target sequence of the gene EMD

<400> SEQUENCE: 686
tacaatgacg actactatga a    21

<210> SEQ ID NO 687
<211> LENGTH: 21
<212> TYPE: DNA
<213> ORGANISM: Artificial sequence
<220> FEATURE:
<223> OTHER INFORMATION: Target sequence of the gene CXXC4

<400> SEQUENCE: 687
ttcaaggcat ttggaaatga a    21

<210> SEQ ID NO 688
<211> LENGTH: 21
<212> TYPE: DNA
<213> ORGANISM: Artificial sequence
<220> FEATURE:
<223> OTHER INFORMATION: Target sequence of the gene CYP2A6

<400> SEQUENCE: 688
caggcctttc agttgctgca a    21

<210> SEQ ID NO 689
<211> LENGTH: 21
<212> TYPE: DNA
<213> ORGANISM: Artificial sequence
<220> FEATURE:
<223> OTHER INFORMATION: Target sequence of the gene EVI2B

<400> SEQUENCE: 689
taggagtaca ccaggattta t    21

<210> SEQ ID NO 690
<211> LENGTH: 21
<212> TYPE: DNA
<213> ORGANISM: Artificial sequence
<220> FEATURE:
<223> OTHER INFORMATION: Target sequence of the gene UQCRFS1

-continued

```
<400> SEQUENCE: 690
atgctcagtc atacacgcga a                                              21

<210> SEQ ID NO 691
<211> LENGTH: 21
<212> TYPE: DNA
<213> ORGANISM: Artificial sequence
<220> FEATURE:
<223> OTHER INFORMATION: Target sequence of the gene DNAH8

<400> SEQUENCE: 691
ctgcaatatt atgatgagtt a                                              21

<210> SEQ ID NO 692
<211> LENGTH: 21
<212> TYPE: DNA
<213> ORGANISM: Artificial sequence
<220> FEATURE:
<223> OTHER INFORMATION: Target sequence of the gene LMBR1

<400> SEQUENCE: 692
atcggtggaa tacaacataa t                                              21

<210> SEQ ID NO 693
<211> LENGTH: 21
<212> TYPE: DNA
<213> ORGANISM: Artificial sequence
<220> FEATURE:
<223> OTHER INFORMATION: Target sequence of the gene BBOX1

<400> SEQUENCE: 693
aacatggctt gtaccatcca a                                              21

<210> SEQ ID NO 694
<211> LENGTH: 21
<212> TYPE: DNA
<213> ORGANISM: Artificial sequence
<220> FEATURE:
<223> OTHER INFORMATION: Target sequence of the gene FAM86C

<400> SEQUENCE: 694
ccagcgggct cctcaattct a                                              21

<210> SEQ ID NO 695
<211> LENGTH: 21
<212> TYPE: DNA
<213> ORGANISM: Artificial sequence
<220> FEATURE:
<223> OTHER INFORMATION: Target sequence of the gene MST1

<400> SEQUENCE: 695
aaacttcttg tcagacataa a                                              21

<210> SEQ ID NO 696
<211> LENGTH: 21
<212> TYPE: DNA
<213> ORGANISM: Artificial sequence
<220> FEATURE:
<223> OTHER INFORMATION: Target sequence of the gene UBOX5

<400> SEQUENCE: 696
cagacagtaa ctttggtgta a                                              21

<210> SEQ ID NO 697
```

```
<211> LENGTH: 21
<212> TYPE: DNA
<213> ORGANISM: Artificial sequence
<220> FEATURE:
<223> OTHER INFORMATION: Target sequence of the gene POLR2C

<400> SEQUENCE: 697
cagagtgatg tgctaaccat a                                              21

<210> SEQ ID NO 698
<211> LENGTH: 21
<212> TYPE: DNA
<213> ORGANISM: Artificial sequence
<220> FEATURE:
<223> OTHER INFORMATION: Target sequence of the gene PTPDC1

<400> SEQUENCE: 698
cggaatgttg agtgccttca a                                              21

<210> SEQ ID NO 699
<211> LENGTH: 21
<212> TYPE: DNA
<213> ORGANISM: Artificial sequence
<220> FEATURE:
<223> OTHER INFORMATION: Target sequence of the gene TNIK

<400> SEQUENCE: 699
ctggaatata agcgcaaaca a                                              21

<210> SEQ ID NO 700
<211> LENGTH: 21
<212> TYPE: DNA
<213> ORGANISM: Artificial sequence
<220> FEATURE:
<223> OTHER INFORMATION: Target sequence of the gene TSPAN9

<400> SEQUENCE: 700
cgggcgcgga atatcctgga a                                              21

<210> SEQ ID NO 701
<211> LENGTH: 21
<212> TYPE: DNA
<213> ORGANISM: Artificial sequence
<220> FEATURE:
<223> OTHER INFORMATION: Target sequence of the gene POLR2A

<400> SEQUENCE: 701
atggtcgtgt ccggagctaa a                                              21

<210> SEQ ID NO 702
<211> LENGTH: 21
<212> TYPE: DNA
<213> ORGANISM: Artificial sequence
<220> FEATURE:
<223> OTHER INFORMATION: Target sequence of the gene ZBTB40

<400> SEQUENCE: 702
ctcctacgac tcggcctata a                                              21

<210> SEQ ID NO 703
<211> LENGTH: 21
<212> TYPE: DNA
<213> ORGANISM: Artificial sequence
<220> FEATURE:
<223> OTHER INFORMATION: Target sequence of the gene ANKFY1

<400> SEQUENCE: 703
```
gagcgctcag ttgttataca a          21

<210> SEQ ID NO 704
<211> LENGTH: 21
<212> TYPE: DNA
<213> ORGANISM: Artificial sequence
<220> FEATURE:
<223> OTHER INFORMATION: Target sequence of the gene WASH3P

<400> SEQUENCE: 704
ctgctagagt ccatccgcca a          21

<210> SEQ ID NO 705
<211> LENGTH: 21
<212> TYPE: DNA
<213> ORGANISM: Artificial sequence
<220> FEATURE:
<223> OTHER INFORMATION: Target sequence of the gene RGP1

<400> SEQUENCE: 705
caccaggaat cctgcctaca t          21

<210> SEQ ID NO 706
<211> LENGTH: 21
<212> TYPE: DNA
<213> ORGANISM: Artificial sequence
<220> FEATURE:
<223> OTHER INFORMATION: Target sequence of the gene GPR89B

<400> SEQUENCE: 706
cacggatatt ctagccctgg a          21

<210> SEQ ID NO 707
<211> LENGTH: 21
<212> TYPE: DNA
<213> ORGANISM: Artificial sequence
<220> FEATURE:
<223> OTHER INFORMATION: Target sequence of the gene ATP6V0E1

<400> SEQUENCE: 707
cacgttcaga gggaagagcc a          21

<210> SEQ ID NO 708
<211> LENGTH: 21
<212> TYPE: DNA
<213> ORGANISM: Artificial sequence
<220> FEATURE:
<223> OTHER INFORMATION: Target sequence of the gene SULF1

<400> SEQUENCE: 708
tccgtcgaat ttgaaggtga a          21

<210> SEQ ID NO 709
<211> LENGTH: 21
<212> TYPE: DNA
<213> ORGANISM: Artificial sequence
<220> FEATURE:
<223> OTHER INFORMATION: Target sequence of the gene SMOX

<400> SEQUENCE: 709
cccaaggacg tggttgagga a          21

<210> SEQ ID NO 710
<211> LENGTH: 21
<212> TYPE: DNA

<213> ORGANISM: Artificial sequence
<220> FEATURE:
<223> OTHER INFORMATION: Target sequence of the gene RFX2

<400> SEQUENCE: 710
cgggactttc gaagccctga a					21

<210> SEQ ID NO 711
<211> LENGTH: 21
<212> TYPE: DNA
<213> ORGANISM: Artificial sequence
<220> FEATURE:
<223> OTHER INFORMATION: Target sequence of the gene KIFC3

<400> SEQUENCE: 711
cagcgctgcg gagatctaca a					21

<210> SEQ ID NO 712
<211> LENGTH: 21
<212> TYPE: DNA
<213> ORGANISM: Artificial sequence
<220> FEATURE:
<223> OTHER INFORMATION: Target sequence of the gene ATG2B

<400> SEQUENCE: 712
cagtagcgtt gcattggata a					21

<210> SEQ ID NO 713
<211> LENGTH: 21
<212> TYPE: DNA
<213> ORGANISM: Artificial sequence
<220> FEATURE:
<223> OTHER INFORMATION: Target sequence of the gene CCDC81

<400> SEQUENCE: 713
cagagatatc tcatcaccca a					21

<210> SEQ ID NO 714
<211> LENGTH: 21
<212> TYPE: DNA
<213> ORGANISM: Artificial sequence
<220> FEATURE:
<223> OTHER INFORMATION: Target sequence of the gene BSX

<400> SEQUENCE: 714
aaccggcgga tgaagcataa a					21

<210> SEQ ID NO 715
<211> LENGTH: 21
<212> TYPE: DNA
<213> ORGANISM: Artificial sequence
<220> FEATURE:
<223> OTHER INFORMATION: Target sequence of the gene POLR2B

<400> SEQUENCE: 715
cagcgcattg tggcaactct a					21

<210> SEQ ID NO 716
<211> LENGTH: 21
<212> TYPE: DNA
<213> ORGANISM: Artificial sequence
<220> FEATURE:
<223> OTHER INFORMATION: Target sequence of the gene NOS2A

<400> SEQUENCE: 716
ctgggccgtg caaaccttca a					21

<210> SEQ ID NO 717
<211> LENGTH: 21
<212> TYPE: DNA
<213> ORGANISM: Artificial sequence
<220> FEATURE:
<223> OTHER INFORMATION: Target sequence of the gene CCDC128

<400> SEQUENCE: 717
cagaacgaca aggctaaact a                                              21

<210> SEQ ID NO 718
<211> LENGTH: 21
<212> TYPE: DNA
<213> ORGANISM: Artificial sequence
<220> FEATURE:
<223> OTHER INFORMATION: Target sequence of the gene HPSE

<400> SEQUENCE: 718
ctgatgttgg tcagcctcga a                                              21

<210> SEQ ID NO 719
<211> LENGTH: 21
<212> TYPE: DNA
<213> ORGANISM: Artificial sequence
<220> FEATURE:
<223> OTHER INFORMATION: Target sequence of the gene LIMCH1

<400> SEQUENCE: 719
tagcatcgag atcaacataa a                                              21

<210> SEQ ID NO 720
<211> LENGTH: 21
<212> TYPE: DNA
<213> ORGANISM: Artificial sequence
<220> FEATURE:
<223> OTHER INFORMATION: Target sequence of the gene FAM116A

<400> SEQUENCE: 720
aagggtatta tgtaatgcct a                                              21

<210> SEQ ID NO 721
<211> LENGTH: 21
<212> TYPE: DNA
<213> ORGANISM: Artificial sequence
<220> FEATURE:
<223> OTHER INFORMATION: Target sequence of the gene OR4D6

<400> SEQUENCE: 721
cagatacctt gcaatcgcca a                                              21

<210> SEQ ID NO 722
<211> LENGTH: 21
<212> TYPE: DNA
<213> ORGANISM: Artificial sequence
<220> FEATURE:
<223> OTHER INFORMATION: Target sequence of the gene FOXI1

<400> SEQUENCE: 722
cgagatgaac ctctactatg a                                              21

<210> SEQ ID NO 723
<211> LENGTH: 21
<212> TYPE: DNA
<213> ORGANISM: Artificial sequence
<220> FEATURE:

<223> OTHER INFORMATION: Target sequence of the gene COPZ1

<400> SEQUENCE: 723
cccatcggac tgacagtgaa a                                              21

<210> SEQ ID NO 724
<211> LENGTH: 21
<212> TYPE: DNA
<213> ORGANISM: Artificial sequence
<220> FEATURE:
<223> OTHER INFORMATION: Target sequence of the gene ZBTB22

<400> SEQUENCE: 724
cccgcccatt ctactactca a                                              21

<210> SEQ ID NO 725
<211> LENGTH: 21
<212> TYPE: DNA
<213> ORGANISM: Artificial sequence
<220> FEATURE:
<223> OTHER INFORMATION: Target sequence of the gene RNF151

<400> SEQUENCE: 725
cagggccaac ataccttgta a                                              21

<210> SEQ ID NO 726
<211> LENGTH: 21
<212> TYPE: DNA
<213> ORGANISM: Artificial sequence
<220> FEATURE:
<223> OTHER INFORMATION: Target sequence of the gene KCNK4

<400> SEQUENCE: 726
cacggcctcg gccctggatt a                                              21

<210> SEQ ID NO 727
<211> LENGTH: 21
<212> TYPE: DNA
<213> ORGANISM: Artificial sequence
<220> FEATURE:
<223> OTHER INFORMATION: Target sequence of the gene CUBN

<400> SEQUENCE: 727
cacctatgtc atagaggcta a                                              21

<210> SEQ ID NO 728
<211> LENGTH: 21
<212> TYPE: DNA
<213> ORGANISM: Artificial sequence
<220> FEATURE:
<223> OTHER INFORMATION: Target sequence of the gene GABRE

<400> SEQUENCE: 728
cactctaacc atcacaatca a                                              21

<210> SEQ ID NO 729
<211> LENGTH: 21
<212> TYPE: DNA
<213> ORGANISM: Artificial sequence
<220> FEATURE:
<223> OTHER INFORMATION: Target sequence of the gene CHAC2

<400> SEQUENCE: 729
cccggcaagc ctggaagagt t                                              21

```
<210> SEQ ID NO 730
<211> LENGTH: 21
<212> TYPE: DNA
<213> ORGANISM: Artificial sequence
<220> FEATURE:
<223> OTHER INFORMATION: Target sequence of the gene FIG4

<400> SEQUENCE: 730
caggttctta gaaggctatt a                                     21

<210> SEQ ID NO 731
<211> LENGTH: 21
<212> TYPE: DNA
<213> ORGANISM: Artificial sequence
<220> FEATURE:
<223> OTHER INFORMATION: Target sequence of the gene THOC1

<400> SEQUENCE: 731
aacacctgag aatctgatta a                                     21

<210> SEQ ID NO 732
<211> LENGTH: 21
<212> TYPE: DNA
<213> ORGANISM: Artificial sequence
<220> FEATURE:
<223> OTHER INFORMATION: Target sequence of the gene FOXD4

<400> SEQUENCE: 732
cagcggcatc tgcgccttca t                                     21

<210> SEQ ID NO 733
<211> LENGTH: 21
<212> TYPE: DNA
<213> ORGANISM: Artificial sequence
<220> FEATURE:
<223> OTHER INFORMATION: Target sequence of the gene ORAI1

<400> SEQUENCE: 733
ctggcggagt ttgcccgctt a                                     21

<210> SEQ ID NO 734
<211> LENGTH: 21
<212> TYPE: DNA
<213> ORGANISM: Artificial sequence
<220> FEATURE:
<223> OTHER INFORMATION: Target sequence of the gene ZC3H3

<400> SEQUENCE: 734
cagagccttt agtgcccgct a                                     21

<210> SEQ ID NO 735
<211> LENGTH: 21
<212> TYPE: DNA
<213> ORGANISM: Artificial sequence
<220> FEATURE:
<223> OTHER INFORMATION: Target sequence of the gene ATP1A2

<400> SEQUENCE: 735
caaggagatc ccgctcgaca a                                     21

<210> SEQ ID NO 736
<211> LENGTH: 21
<212> TYPE: DNA
<213> ORGANISM: Artificial sequence
<220> FEATURE:
<223> OTHER INFORMATION: Target sequence of the gene KIF6
```

```
<400> SEQUENCE: 736
cagcgttacc atcgatgaca a                                              21

<210> SEQ ID NO 737
<211> LENGTH: 21
<212> TYPE: DNA
<213> ORGANISM: Artificial sequence
<220> FEATURE:
<223> OTHER INFORMATION: Target sequence of the gene C5orf32

<400> SEQUENCE: 737
cagcactatg ggattctaga t                                              21

<210> SEQ ID NO 738
<211> LENGTH: 21
<212> TYPE: DNA
<213> ORGANISM: Artificial sequence
<220> FEATURE:
<223> OTHER INFORMATION: Target sequence of the gene CTSG

<400> SEQUENCE: 738
cacagtgttg ccagagcctt a                                              21

<210> SEQ ID NO 739
<211> LENGTH: 21
<212> TYPE: DNA
<213> ORGANISM: Artificial sequence
<220> FEATURE:
<223> OTHER INFORMATION: Target sequence of the gene UCP2

<400> SEQUENCE: 739
aagcaccgtc aatgcctaca a                                              21

<210> SEQ ID NO 740
<211> LENGTH: 21
<212> TYPE: DNA
<213> ORGANISM: Artificial sequence
<220> FEATURE:
<223> OTHER INFORMATION: Target sequence of the gene CYP4F8

<400> SEQUENCE: 740
caaggacata gtcttctaca a                                              21

<210> SEQ ID NO 741
<211> LENGTH: 21
<212> TYPE: DNA
<213> ORGANISM: Artificial sequence
<220> FEATURE:
<223> OTHER INFORMATION: Target sequence of the gene PRX

<400> SEQUENCE: 741
cccgccgtgg aaattgagga a                                              21

<210> SEQ ID NO 742
<211> LENGTH: 21
<212> TYPE: DNA
<213> ORGANISM: Artificial sequence
<220> FEATURE:
<223> OTHER INFORMATION: Target sequence of the gene FBN2

<400> SEQUENCE: 742
caggattgcc atatgtgcaa a                                              21

<210> SEQ ID NO 743
<211> LENGTH: 21
```

```
<212> TYPE: DNA
<213> ORGANISM: Artificial sequence
<220> FEATURE:
<223> OTHER INFORMATION: Target sequence of the gene GABRR2

<400> SEQUENCE: 743
tacggtcact gccatgtgca a                                              21

<210> SEQ ID NO 744
<211> LENGTH: 21
<212> TYPE: DNA
<213> ORGANISM: Artificial sequence
<220> FEATURE:
<223> OTHER INFORMATION: Target sequence of the gene PAQR4

<400> SEQUENCE: 744
cagcacttgg acagccttca a                                              21

<210> SEQ ID NO 745
<211> LENGTH: 21
<212> TYPE: DNA
<213> ORGANISM: Artificial sequence
<220> FEATURE:
<223> OTHER INFORMATION: Target sequence of the gene NRBP1

<400> SEQUENCE: 745
tcggtggagg agggagtcaa a                                              21

<210> SEQ ID NO 746
<211> LENGTH: 21
<212> TYPE: DNA
<213> ORGANISM: Artificial sequence
<220> FEATURE:
<223> OTHER INFORMATION: Target sequence of the gene RIMBP2

<400> SEQUENCE: 746
cggagaagac atcgtgcctt a                                              21

<210> SEQ ID NO 747
<211> LENGTH: 21
<212> TYPE: DNA
<213> ORGANISM: Artificial sequence
<220> FEATURE:
<223> OTHER INFORMATION: Target sequence of the gene CNTLN

<400> SEQUENCE: 747
ctccggcaaa gtgttactaa t                                              21

<210> SEQ ID NO 748
<211> LENGTH: 21
<212> TYPE: DNA
<213> ORGANISM: Artificial sequence
<220> FEATURE:
<223> OTHER INFORMATION: Target sequence of the gene ZNF79

<400> SEQUENCE: 748
ctcggaaatc ctgaaacctc a                                              21

<210> SEQ ID NO 749
<211> LENGTH: 21
<212> TYPE: DNA
<213> ORGANISM: Artificial sequence
<220> FEATURE:
<223> OTHER INFORMATION: Target sequence of the gene NEUROG3

<400> SEQUENCE: 749
```
cgagcgcaat cgaatgcaca a                                              21

<210> SEQ ID NO 750
<211> LENGTH: 21
<212> TYPE: DNA
<213> ORGANISM: Artificial sequence
<220> FEATURE:
<223> OTHER INFORMATION: Target sequence of the gene ISLR

<400> SEQUENCE: 750
cagcaacgag ctgaccttca t                                              21

<210> SEQ ID NO 751
<211> LENGTH: 21
<212> TYPE: DNA
<213> ORGANISM: Artificial sequence
<220> FEATURE:
<223> OTHER INFORMATION: Target sequence of the gene POLR2F

<400> SEQUENCE: 751
cagaagcgaa tcaccacacc a                                              21

<210> SEQ ID NO 752
<211> LENGTH: 21
<212> TYPE: DNA
<213> ORGANISM: Artificial sequence
<220> FEATURE:
<223> OTHER INFORMATION: Target sequence of the gene CYB561D2

<400> SEQUENCE: 752
caggtgagca atgcctacct a                                              21

<210> SEQ ID NO 753
<211> LENGTH: 21
<212> TYPE: DNA
<213> ORGANISM: Artificial sequence
<220> FEATURE:
<223> OTHER INFORMATION: Target sequence of the gene AIFM1

<400> SEQUENCE: 753
tcggtcgtgc gtgagaggaa a                                              21

<210> SEQ ID NO 754
<211> LENGTH: 21
<212> TYPE: DNA
<213> ORGANISM: Artificial sequence
<220> FEATURE:
<223> OTHER INFORMATION: Target sequence of the gene SLURP1

<400> SEQUENCE: 754
caggaccatt acccgctgca a                                              21

<210> SEQ ID NO 755
<211> LENGTH: 21
<212> TYPE: DNA
<213> ORGANISM: Artificial sequence
<220> FEATURE:
<223> OTHER INFORMATION: Target sequence of the gene SERPINB6

<400> SEQUENCE: 755
ccgcggttta aactagagga a                                              21

<210> SEQ ID NO 756
<211> LENGTH: 21
<212> TYPE: DNA
<213> ORGANISM: Artificial sequence

```
<220> FEATURE:
<223> OTHER INFORMATION: Target sequence of the gene C1orf63

<400> SEQUENCE: 756
caggctaaag ccgcaggtga a                                              21

<210> SEQ ID NO 757
<211> LENGTH: 21
<212> TYPE: DNA
<213> ORGANISM: Artificial sequence
<220> FEATURE:
<223> OTHER INFORMATION: Target sequence of the gene SLC44A5

<400> SEQUENCE: 757
ctccgtattg ctaaacctac a                                              21

<210> SEQ ID NO 758
<211> LENGTH: 21
<212> TYPE: DNA
<213> ORGANISM: Artificial sequence
<220> FEATURE:
<223> OTHER INFORMATION: Target sequence of the gene C1orf64

<400> SEQUENCE: 758
ccaggaggtt cccgaggcta a                                              21

<210> SEQ ID NO 759
<211> LENGTH: 21
<212> TYPE: DNA
<213> ORGANISM: Artificial sequence
<220> FEATURE:
<223> OTHER INFORMATION: Target sequence of the gene ZDHHC11

<400> SEQUENCE: 759
cgcgtggaaa tacattgcct a                                              21

<210> SEQ ID NO 760
<211> LENGTH: 21
<212> TYPE: DNA
<213> ORGANISM: Artificial sequence
<220> FEATURE:
<223> OTHER INFORMATION: Target sequence of the gene RARG

<400> SEQUENCE: 760
cccgtccttg tgccaggtca a                                              21

<210> SEQ ID NO 761
<211> LENGTH: 21
<212> TYPE: DNA
<213> ORGANISM: Artificial sequence
<220> FEATURE:
<223> OTHER INFORMATION: Target sequence of the gene VEGFB

<400> SEQUENCE: 761
ccggatgcag atcctcatga t                                              21

<210> SEQ ID NO 762
<211> LENGTH: 21
<212> TYPE: DNA
<213> ORGANISM: Artificial sequence
<220> FEATURE:
<223> OTHER INFORMATION: Target sequence of the gene GTDC1

<400> SEQUENCE: 762
cgccgacacg atggcagcca a                                              21
```

<210> SEQ ID NO 763
<211> LENGTH: 21
<212> TYPE: DNA
<213> ORGANISM: Artificial sequence
<220> FEATURE:
<223> OTHER INFORMATION: Target sequence of the gene ZER1

<400> SEQUENCE: 763
ctgcgagatg ttcctcaatt t                                            21

<210> SEQ ID NO 764
<211> LENGTH: 21
<212> TYPE: DNA
<213> ORGANISM: Artificial sequence
<220> FEATURE:
<223> OTHER INFORMATION: Target sequence of the gene LHX6

<400> SEQUENCE: 764
ccggtgcggc cgacagatct a                                            21

<210> SEQ ID NO 765
<211> LENGTH: 21
<212> TYPE: DNA
<213> ORGANISM: Artificial sequence
<220> FEATURE:
<223> OTHER INFORMATION: Target sequence of the gene FAM44B

<400> SEQUENCE: 765
ttcggttaca taagagtgca a                                            21

<210> SEQ ID NO 766
<211> LENGTH: 21
<212> TYPE: DNA
<213> ORGANISM: Artificial sequence
<220> FEATURE:
<223> OTHER INFORMATION: Target sequence of the gene PTCD2

<400> SEQUENCE: 766
tacgagttgg atctcgagga a                                            21

<210> SEQ ID NO 767
<211> LENGTH: 21
<212> TYPE: DNA
<213> ORGANISM: Artificial sequence
<220> FEATURE:
<223> OTHER INFORMATION: Target sequence of the gene KIAA1009

<400> SEQUENCE: 767
ttggtgcacc gttgactact a                                            21

<210> SEQ ID NO 768
<211> LENGTH: 21
<212> TYPE: DNA
<213> ORGANISM: Artificial sequence
<220> FEATURE:
<223> OTHER INFORMATION: Target sequence of the gene DYDC2

<400> SEQUENCE: 768
tgggcggtat acagtaaaca a                                            21

<210> SEQ ID NO 769
<211> LENGTH: 21
<212> TYPE: DNA
<213> ORGANISM: Artificial sequence
<220> FEATURE:
<223> OTHER INFORMATION: Target sequence of the gene NAPEPLD

<400> SEQUENCE: 769
ctgctgcacg ccgaattgaa a                                              21

<210> SEQ ID NO 770
<211> LENGTH: 21
<212> TYPE: DNA
<213> ORGANISM: Artificial sequence
<220> FEATURE:
<223> OTHER INFORMATION: Target sequence of the gene PRAP1

<400> SEQUENCE: 770
cccggttgtg ggtgatgcca a                                              21

<210> SEQ ID NO 771
<211> LENGTH: 21
<212> TYPE: DNA
<213> ORGANISM: Artificial sequence
<220> FEATURE:
<223> OTHER INFORMATION: Target sequence of the gene RPS17

<400> SEQUENCE: 771
cggcagtctg tccaaccttc a                                              21

<210> SEQ ID NO 772
<211> LENGTH: 21
<212> TYPE: DNA
<213> ORGANISM: Artificial sequence
<220> FEATURE:
<223> OTHER INFORMATION: Target sequence of the gene SLC5A10

<400> SEQUENCE: 772
cagcaaagcg ggagccctga a                                              21

<210> SEQ ID NO 773
<211> LENGTH: 21
<212> TYPE: DNA
<213> ORGANISM: Artificial sequence
<220> FEATURE:
<223> OTHER INFORMATION: Target sequence of the gene ZNF468

<400> SEQUENCE: 773
ttctatgagt attgtaccga a                                              21

<210> SEQ ID NO 774
<211> LENGTH: 21
<212> TYPE: DNA
<213> ORGANISM: Artificial sequence
<220> FEATURE:
<223> OTHER INFORMATION: Target sequence of the gene PLEK

<400> SEQUENCE: 774
accattgact taggtgcctt a                                              21

<210> SEQ ID NO 775
<211> LENGTH: 21
<212> TYPE: DNA
<213> ORGANISM: Artificial sequence
<220> FEATURE:
<223> OTHER INFORMATION: Target sequence of the gene CTAG1B

<400> SEQUENCE: 775
cagggctgaa tggatgctgc a                                              21

<210> SEQ ID NO 776

```
<211> LENGTH: 21
<212> TYPE: DNA
<213> ORGANISM: Artificial sequence
<220> FEATURE:
<223> OTHER INFORMATION: Target sequence of the gene CLEC1B

<400> SEQUENCE: 776
caggcacaac ttaacatggg a                                              21

<210> SEQ ID NO 777
<211> LENGTH: 21
<212> TYPE: DNA
<213> ORGANISM: Artificial sequence
<220> FEATURE:
<223> OTHER INFORMATION: Target sequence of the gene COL9A1

<400> SEQUENCE: 777
aacggtttgc ctggagctat a                                              21

<210> SEQ ID NO 778
<211> LENGTH: 21
<212> TYPE: DNA
<213> ORGANISM: Artificial sequence
<220> FEATURE:
<223> OTHER INFORMATION: Target sequence of the gene OR11H1

<400> SEQUENCE: 778
catgtacatg ttcctgggaa a                                              21

<210> SEQ ID NO 779
<211> LENGTH: 21
<212> TYPE: DNA
<213> ORGANISM: Artificial sequence
<220> FEATURE:
<223> OTHER INFORMATION: Target sequence of the gene NR4A1

<400> SEQUENCE: 779
cagcaccttc atggacggct a                                              21

<210> SEQ ID NO 780
<211> LENGTH: 21
<212> TYPE: DNA
<213> ORGANISM: Artificial sequence
<220> FEATURE:
<223> OTHER INFORMATION: Target sequence of the gene NPPB

<400> SEQUENCE: 780
ctgaggcggc attaagagga a                                              21

<210> SEQ ID NO 781
<211> LENGTH: 21
<212> TYPE: DNA
<213> ORGANISM: Artificial sequence
<220> FEATURE:
<223> OTHER INFORMATION: Target sequence of the gene OR12D3

<400> SEQUENCE: 781
cacaatcaag ctaaacctac a                                              21

<210> SEQ ID NO 782
<211> LENGTH: 21
<212> TYPE: DNA
<213> ORGANISM: Artificial sequence
<220> FEATURE:
<223> OTHER INFORMATION: Target sequence of the gene PROKR2

<400> SEQUENCE: 782
```

```
ccggaccttc ttcgcagcca a                                              21
```

<210> SEQ ID NO 783
<211> LENGTH: 21
<212> TYPE: DNA
<213> ORGANISM: Artificial sequence
<220> FEATURE:
<223> OTHER INFORMATION: Target sequence of the gene PTPRS

<400> SEQUENCE: 783

```
atggcgtgcc cgaataccca a                                              21
```

<210> SEQ ID NO 784
<211> LENGTH: 21
<212> TYPE: DNA
<213> ORGANISM: Artificial sequence
<220> FEATURE:
<223> OTHER INFORMATION: Target sequence of the gene ZFYVE20

<400> SEQUENCE: 784

```
ctgcgggtct attatgtgca a                                              21
```

<210> SEQ ID NO 785
<211> LENGTH: 21
<212> TYPE: DNA
<213> ORGANISM: Artificial sequence
<220> FEATURE:
<223> OTHER INFORMATION: Target sequence of the gene ZZEF1

<400> SEQUENCE: 785

```
ccgctgcgtt tatatggata a                                              21
```

<210> SEQ ID NO 786
<211> LENGTH: 21
<212> TYPE: DNA
<213> ORGANISM: Artificial sequence
<220> FEATURE:
<223> OTHER INFORMATION: Target sequence of the gene WDR53

<400> SEQUENCE: 786

```
cgggaccatt atggcagtca a                                              21
```

<210> SEQ ID NO 787
<211> LENGTH: 21
<212> TYPE: DNA
<213> ORGANISM: Artificial sequence
<220> FEATURE:
<223> OTHER INFORMATION: Target sequence of the gene LOC198437

<400> SEQUENCE: 787

```
accgccaaga ggtgcagaca a                                              21
```

<210> SEQ ID NO 788
<211> LENGTH: 21
<212> TYPE: DNA
<213> ORGANISM: Artificial sequence
<220> FEATURE:
<223> OTHER INFORMATION: Target sequence of the gene CXCL9

<400> SEQUENCE: 788

```
ccggtggaga tcccacccga a                                              21
```

<210> SEQ ID NO 789
<211> LENGTH: 21
<212> TYPE: DNA

```
<213> ORGANISM: Artificial sequence
<220> FEATURE:
<223> OTHER INFORMATION: Target sequence of the gene JAM2

<400> SEQUENCE: 789
tccgacattt gcaaagaggt a                                              21

<210> SEQ ID NO 790
<211> LENGTH: 21
<212> TYPE: DNA
<213> ORGANISM: Artificial sequence
<220> FEATURE:
<223> OTHER INFORMATION: Target sequence of the gene DDX52

<400> SEQUENCE: 790
ctgaggatga taagccatta t                                              21

<210> SEQ ID NO 791
<211> LENGTH: 21
<212> TYPE: DNA
<213> ORGANISM: Artificial sequence
<220> FEATURE:
<223> OTHER INFORMATION: Target sequence of the gene ZNF582

<400> SEQUENCE: 791
cagatgatca tcagacatga a                                              21

<210> SEQ ID NO 792
<211> LENGTH: 21
<212> TYPE: DNA
<213> ORGANISM: Artificial sequence
<220> FEATURE:
<223> OTHER INFORMATION: Target sequence of the gene IRF8

<400> SEQUENCE: 792
taccgaattg ttcctgagga a                                              21

<210> SEQ ID NO 793
<211> LENGTH: 21
<212> TYPE: DNA
<213> ORGANISM: Artificial sequence
<220> FEATURE:
<223> OTHER INFORMATION: Target sequence of the gene C13orf31

<400> SEQUENCE: 793
ctcacgctgg ttggaaaggt a                                              21

<210> SEQ ID NO 794
<211> LENGTH: 21
<212> TYPE: DNA
<213> ORGANISM: Artificial sequence
<220> FEATURE:
<223> OTHER INFORMATION: Target sequence of the gene RPS24

<400> SEQUENCE: 794
aagatagatc gccatcatga a                                              21

<210> SEQ ID NO 795
<211> LENGTH: 21
<212> TYPE: DNA
<213> ORGANISM: Artificial sequence
<220> FEATURE:
<223> OTHER INFORMATION: Target sequence of the gene HIST3H2BB

<400> SEQUENCE: 795
cctcggcgtc ctgaacccaa a                                              21
```

```
<210> SEQ ID NO 796
<211> LENGTH: 21
<212> TYPE: DNA
<213> ORGANISM: Artificial sequence
<220> FEATURE:
<223> OTHER INFORMATION: Target sequence of the gene ZNF14

<400> SEQUENCE: 796
aggactcgtg ctgcagtgaa a                                              21

<210> SEQ ID NO 797
<211> LENGTH: 21
<212> TYPE: DNA
<213> ORGANISM: Artificial sequence
<220> FEATURE:
<223> OTHER INFORMATION: Target sequence of the gene NDUFS7

<400> SEQUENCE: 797
cgccgtggag atgatgcaca t                                              21

<210> SEQ ID NO 798
<211> LENGTH: 21
<212> TYPE: DNA
<213> ORGANISM: Artificial sequence
<220> FEATURE:
<223> OTHER INFORMATION: Target sequence of the gene LRFN2

<400> SEQUENCE: 798
caaggccttc gtggtcaaca a                                              21

<210> SEQ ID NO 799
<211> LENGTH: 21
<212> TYPE: DNA
<213> ORGANISM: Artificial sequence
<220> FEATURE:
<223> OTHER INFORMATION: Target sequence of the gene DLL3

<400> SEQUENCE: 799
cccggtgaat gccgatgcct a                                              21

<210> SEQ ID NO 800
<211> LENGTH: 21
<212> TYPE: DNA
<213> ORGANISM: Artificial sequence
<220> FEATURE:
<223> OTHER INFORMATION: Target sequence of the gene RAD21

<400> SEQUENCE: 800
ctgggagtag ttcgaatcta t                                              21

<210> SEQ ID NO 801
<211> LENGTH: 21
<212> TYPE: DNA
<213> ORGANISM: Artificial sequence
<220> FEATURE:
<223> OTHER INFORMATION: Target sequence of the gene CD7

<400> SEQUENCE: 801
ctggtcctgg tgacagagga a                                              21

<210> SEQ ID NO 802
<211> LENGTH: 21
<212> TYPE: DNA
<213> ORGANISM: Artificial sequence
<220> FEATURE:
```

<223> OTHER INFORMATION: Target sequence of the gene RAB3B

<400> SEQUENCE: 802
ccggaccatc acaacagcct a                                              21

<210> SEQ ID NO 803
<211> LENGTH: 21
<212> TYPE: DNA
<213> ORGANISM: Artificial sequence
<220> FEATURE:
<223> OTHER INFORMATION: Target sequence of the gene LOR

<400> SEQUENCE: 803
ccgaggtttg caaatccttc a                                              21

<210> SEQ ID NO 804
<211> LENGTH: 21
<212> TYPE: DNA
<213> ORGANISM: Artificial sequence
<220> FEATURE:
<223> OTHER INFORMATION: Target sequence of the gene PRKCSH

<400> SEQUENCE: 804
ctgcaccaac actggctata a                                              21

<210> SEQ ID NO 805
<211> LENGTH: 21
<212> TYPE: DNA
<213> ORGANISM: Artificial sequence
<220> FEATURE:
<223> OTHER INFORMATION: Target sequence of the gene GYG2

<400> SEQUENCE: 805
aacgtagagt atagaaatcc a                                              21

<210> SEQ ID NO 806
<211> LENGTH: 21
<212> TYPE: DNA
<213> ORGANISM: Artificial sequence
<220> FEATURE:
<223> OTHER INFORMATION: Target sequence of the gene OR11H1

<400> SEQUENCE: 806
atcctatact cttgtcctga a                                              21

<210> SEQ ID NO 807
<211> LENGTH: 21
<212> TYPE: DNA
<213> ORGANISM: Artificial sequence
<220> FEATURE:
<223> OTHER INFORMATION: Target sequence of the gene LOC541473

<400> SEQUENCE: 807
cacggtggtg actcaagcct a                                              21

<210> SEQ ID NO 808
<211> LENGTH: 21
<212> TYPE: DNA
<213> ORGANISM: Artificial sequence
<220> FEATURE:
<223> OTHER INFORMATION: Target sequence of the gene ACTL7A

<400> SEQUENCE: 808
caccgctttg agtacgagga a                                              21

-continued

```
<210> SEQ ID NO 809
<211> LENGTH: 21
<212> TYPE: DNA
<213> ORGANISM: Artificial sequence
<220> FEATURE:
<223> OTHER INFORMATION: Target sequence of the gene C9orf75

<400> SEQUENCE: 809
cgggtgcgtg gcagagcttc a                                              21

<210> SEQ ID NO 810
<211> LENGTH: 21
<212> TYPE: DNA
<213> ORGANISM: Artificial sequence
<220> FEATURE:
<223> OTHER INFORMATION: Target sequence of the gene KCNK5

<400> SEQUENCE: 810
caggtcgggc acctactaca a                                              21

<210> SEQ ID NO 811
<211> LENGTH: 21
<212> TYPE: DNA
<213> ORGANISM: Artificial sequence
<220> FEATURE:
<223> OTHER INFORMATION: Target sequence of the gene NETO1

<400> SEQUENCE: 811
aagacagtgc attgaacttt a                                              21

<210> SEQ ID NO 812
<211> LENGTH: 21
<212> TYPE: DNA
<213> ORGANISM: Artificial sequence
<220> FEATURE:
<223> OTHER INFORMATION: Target sequence of the gene PDE6B

<400> SEQUENCE: 812
ccgggaaatt gtcttctaca a                                              21

<210> SEQ ID NO 813
<211> LENGTH: 21
<212> TYPE: DNA
<213> ORGANISM: Artificial sequence
<220> FEATURE:
<223> OTHER INFORMATION: Target sequence of the gene KALRN

<400> SEQUENCE: 813
caggtgttgg actggattga a                                              21

<210> SEQ ID NO 814
<211> LENGTH: 21
<212> TYPE: DNA
<213> ORGANISM: Artificial sequence
<220> FEATURE:
<223> OTHER INFORMATION: Target sequence of the gene PTPN14

<400> SEQUENCE: 814
aagggcgatt acgatgtaca t                                              21

<210> SEQ ID NO 815
<211> LENGTH: 21
<212> TYPE: DNA
<213> ORGANISM: Artificial sequence
<220> FEATURE:
<223> OTHER INFORMATION: Target sequence of the gene RECK
```

<400> SEQUENCE: 815
tcgcgtggca gtcgattact a                                        21

<210> SEQ ID NO 816
<211> LENGTH: 21
<212> TYPE: DNA
<213> ORGANISM: Artificial sequence
<220> FEATURE:
<223> OTHER INFORMATION: Target sequence of the gene LOC388335

<400> SEQUENCE: 816
cccagtccag ccctaaacta a                                        21

<210> SEQ ID NO 817
<211> LENGTH: 21
<212> TYPE: DNA
<213> ORGANISM: Artificial sequence
<220> FEATURE:
<223> OTHER INFORMATION: Target sequence of the gene RPESP

<400> SEQUENCE: 817
cagaccagtg caagcctaca a                                        21

<210> SEQ ID NO 818
<211> LENGTH: 21
<212> TYPE: DNA
<213> ORGANISM: Artificial sequence
<220> FEATURE:
<223> OTHER INFORMATION: Target sequence of the gene MLC1

<400> SEQUENCE: 818
cccggctgag atggattact t                                        21

<210> SEQ ID NO 819
<211> LENGTH: 21
<212> TYPE: DNA
<213> ORGANISM: Artificial sequence
<220> FEATURE:
<223> OTHER INFORMATION: Target sequence of the gene CEND1

<400> SEQUENCE: 819
cacggtgaag aggacgcccg a                                        21

<210> SEQ ID NO 820
<211> LENGTH: 21
<212> TYPE: DNA
<213> ORGANISM: Artificial sequence
<220> FEATURE:
<223> OTHER INFORMATION: Target sequence of the gene UCN3

<400> SEQUENCE: 820
cccacaagtt ctacaaagcc a                                        21

<210> SEQ ID NO 821
<211> LENGTH: 21
<212> TYPE: DNA
<213> ORGANISM: Artificial sequence
<220> FEATURE:
<223> OTHER INFORMATION: Target sequence of the gene ZDHHC12

<400> SEQUENCE: 821
cagatactgc ctggtgctgc a                                        21

<210> SEQ ID NO 822
<211> LENGTH: 21

-continued

```
<212> TYPE: DNA
<213> ORGANISM: Artificial sequence
<220> FEATURE:
<223> OTHER INFORMATION: Target sequence of the gene CNIH2

<400> SEQUENCE: 822
ctggtgcaaa cttgccttct a                                           21

<210> SEQ ID NO 823
<211> LENGTH: 21
<212> TYPE: DNA
<213> ORGANISM: Artificial sequence
<220> FEATURE:
<223> OTHER INFORMATION: Target sequence of the gene NAT9

<400> SEQUENCE: 823
cacgctaggt ctgaccaagt t                                           21

<210> SEQ ID NO 824
<211> LENGTH: 21
<212> TYPE: DNA
<213> ORGANISM: Artificial sequence
<220> FEATURE:
<223> OTHER INFORMATION: Target sequence of the gene DKFZp761E198

<400> SEQUENCE: 824
ctgcacgaac tgggacctac a                                           21

<210> SEQ ID NO 825
<211> LENGTH: 21
<212> TYPE: DNA
<213> ORGANISM: Artificial sequence
<220> FEATURE:
<223> OTHER INFORMATION: Target sequence of the gene GNAQ

<400> SEQUENCE: 825
cacaataagg ctcatgcaca a                                           21

<210> SEQ ID NO 826
<211> LENGTH: 21
<212> TYPE: DNA
<213> ORGANISM: Artificial sequence
<220> FEATURE:
<223> OTHER INFORMATION: Target sequence of the gene BPIL1

<400> SEQUENCE: 826
ctgcacattg ggagccttat a                                           21

<210> SEQ ID NO 827
<211> LENGTH: 21
<212> TYPE: DNA
<213> ORGANISM: Artificial sequence
<220> FEATURE:
<223> OTHER INFORMATION: Target sequence of the gene FLJ13137

<400> SEQUENCE: 827
cccgatgata tggcagccat a                                           21

<210> SEQ ID NO 828
<211> LENGTH: 21
<212> TYPE: DNA
<213> ORGANISM: Artificial sequence
<220> FEATURE:
<223> OTHER INFORMATION: Target sequence of the gene C12orf25

<400> SEQUENCE: 828
```
cagcggagat gggtccagct a    21

<210> SEQ ID NO 829
<211> LENGTH: 21
<212> TYPE: DNA
<213> ORGANISM: Artificial sequence
<220> FEATURE:
<223> OTHER INFORMATION: Target sequence of the gene DPPA2

<400> SEQUENCE: 829
cccgactgtg ctaagaggaa t    21

<210> SEQ ID NO 830
<211> LENGTH: 21
<212> TYPE: DNA
<213> ORGANISM: Artificial sequence
<220> FEATURE:
<223> OTHER INFORMATION: Target sequence of the gene LYPD2

<400> SEQUENCE: 830
caccaacgaa accatgtgca a    21

<210> SEQ ID NO 831
<211> LENGTH: 21
<212> TYPE: DNA
<213> ORGANISM: Artificial sequence
<220> FEATURE:
<223> OTHER INFORMATION: Target sequence of the gene S100A7

<400> SEQUENCE: 831
aaaggacaag aatgaggata a    21

<210> SEQ ID NO 832
<211> LENGTH: 21
<212> TYPE: DNA
<213> ORGANISM: Artificial sequence
<220> FEATURE:
<223> OTHER INFORMATION: Target sequence of the gene SNORA38

<400> SEQUENCE: 832
tgcaggctca tgatcaacca a    21

<210> SEQ ID NO 833
<211> LENGTH: 21
<212> TYPE: DNA
<213> ORGANISM: Artificial sequence
<220> FEATURE:
<223> OTHER INFORMATION: Target sequence of the gene CDH23

<400> SEQUENCE: 833
tacagtcacc acgaccttca a    21

<210> SEQ ID NO 834
<211> LENGTH: 21
<212> TYPE: DNA
<213> ORGANISM: Artificial sequence
<220> FEATURE:
<223> OTHER INFORMATION: Target sequence of the gene SERPINB12

<400> SEQUENCE: 834
tacgatcttg ggtggagttt a    21

<210> SEQ ID NO 835
<211> LENGTH: 21
<212> TYPE: DNA
<213> ORGANISM: Artificial sequence

```
<220> FEATURE:
<223> OTHER INFORMATION: Target sequence of the gene HAS2

<400> SEQUENCE: 835
cagctcgatc taagtgcctt a                                              21

<210> SEQ ID NO 836
<211> LENGTH: 21
<212> TYPE: DNA
<213> ORGANISM: Artificial sequence
<220> FEATURE:
<223> OTHER INFORMATION: Target sequence of the gene MSGN1

<400> SEQUENCE: 836
cctggtagag gtggactaca a                                              21

<210> SEQ ID NO 837
<211> LENGTH: 21
<212> TYPE: DNA
<213> ORGANISM: Artificial sequence
<220> FEATURE:
<223> OTHER INFORMATION: Target sequence of the gene RAD17

<400> SEQUENCE: 837
agggaatata gcacatctat a                                              21

<210> SEQ ID NO 838
<211> LENGTH: 21
<212> TYPE: DNA
<213> ORGANISM: Artificial sequence
<220> FEATURE:
<223> OTHER INFORMATION: Target sequence of the gene EPS8

<400> SEQUENCE: 838
ttggatattg tgagacctcc a                                              21

<210> SEQ ID NO 839
<211> LENGTH: 21
<212> TYPE: DNA
<213> ORGANISM: Artificial sequence
<220> FEATURE:
<223> OTHER INFORMATION: Target sequence of the gene PPP1R3B

<400> SEQUENCE: 839
cccgctagat atgccattca a                                              21

<210> SEQ ID NO 840
<211> LENGTH: 21
<212> TYPE: DNA
<213> ORGANISM: Artificial sequence
<220> FEATURE:
<223> OTHER INFORMATION: Target sequence of the gene SAPS2

<400> SEQUENCE: 840
cagcgaggat ggcgaccaga a                                              21

<210> SEQ ID NO 841
<211> LENGTH: 21
<212> TYPE: DNA
<213> ORGANISM: Artificial sequence
<220> FEATURE:
<223> OTHER INFORMATION: Target sequence of the gene CSMD2

<400> SEQUENCE: 841
cagcgcggat tcagtgccca a                                              21
```

```
<210> SEQ ID NO 842
<211> LENGTH: 21
<212> TYPE: DNA
<213> ORGANISM: Artificial sequence
<220> FEATURE:
<223> OTHER INFORMATION: Target sequence of the gene MUC20

<400> SEQUENCE: 842
ctgcgtgtca ggagaggcta a                                          21

<210> SEQ ID NO 843
<211> LENGTH: 21
<212> TYPE: DNA
<213> ORGANISM: Artificial sequence
<220> FEATURE:
<223> OTHER INFORMATION: Target sequence of the gene CCDC91

<400> SEQUENCE: 843
ctcgatcaag tcatccgcca a                                          21

<210> SEQ ID NO 844
<211> LENGTH: 21
<212> TYPE: DNA
<213> ORGANISM: Artificial sequence
<220> FEATURE:
<223> OTHER INFORMATION: Target sequence of the gene C6orf58

<400> SEQUENCE: 844
ctgcggttga ttctggtgta a                                          21

<210> SEQ ID NO 845
<211> LENGTH: 21
<212> TYPE: DNA
<213> ORGANISM: Artificial sequence
<220> FEATURE:
<223> OTHER INFORMATION: Target sequence of the gene RHOG

<400> SEQUENCE: 845
cacgctgtgc gctacctcga a                                          21

<210> SEQ ID NO 846
<211> LENGTH: 21
<212> TYPE: DNA
<213> ORGANISM: Artificial sequence
<220> FEATURE:
<223> OTHER INFORMATION: Target sequence of the gene NLRP2

<400> SEQUENCE: 846
ttcggcgcag atgggcttca a                                          21

<210> SEQ ID NO 847
<211> LENGTH: 21
<212> TYPE: DNA
<213> ORGANISM: Artificial sequence
<220> FEATURE:
<223> OTHER INFORMATION: Target sequence of the gene LOC390667

<400> SEQUENCE: 847
caactacaac gtgtcctaca a                                          21

<210> SEQ ID NO 848
<211> LENGTH: 21
<212> TYPE: DNA
<213> ORGANISM: Artificial sequence
<220> FEATURE:
<223> OTHER INFORMATION: Target sequence of the gene IGLL3
```

```
<400> SEQUENCE: 848
ctgtgcctag atcacagcct a                                          21

<210> SEQ ID NO 849
<211> LENGTH: 21
<212> TYPE: DNA
<213> ORGANISM: Artificial sequence
<220> FEATURE:
<223> OTHER INFORMATION: Target sequence of the gene HIATL2

<400> SEQUENCE: 849
cagctacctg tggcaggaga a                                          21

<210> SEQ ID NO 850
<211> LENGTH: 21
<212> TYPE: DNA
<213> ORGANISM: Artificial sequence
<220> FEATURE:
<223> OTHER INFORMATION: Target sequence of the gene FLAD1

<400> SEQUENCE: 850
cagcaactac tatcaggtga a                                          21

<210> SEQ ID NO 851
<211> LENGTH: 21
<212> TYPE: DNA
<213> ORGANISM: Artificial sequence
<220> FEATURE:
<223> OTHER INFORMATION: Target sequence of the gene SPC25

<400> SEQUENCE: 851
cgggactaag agatacctac a                                          21

<210> SEQ ID NO 852
<211> LENGTH: 21
<212> TYPE: DNA
<213> ORGANISM: Artificial sequence
<220> FEATURE:
<223> OTHER INFORMATION: Target sequence of the gene MSH2

<400> SEQUENCE: 852
tccaggcatg cttgtgttga a                                          21

<210> SEQ ID NO 853
<211> LENGTH: 21
<212> TYPE: DNA
<213> ORGANISM: Artificial sequence
<220> FEATURE:
<223> OTHER INFORMATION: Target sequence of the gene GPLD1

<400> SEQUENCE: 853
taggaccatg ggagctattg a                                          21

<210> SEQ ID NO 854
<211> LENGTH: 21
<212> TYPE: DNA
<213> ORGANISM: Artificial sequence
<220> FEATURE:
<223> OTHER INFORMATION: Target sequence of the gene PLA2G4D

<400> SEQUENCE: 854
caccgctgtg gttgcagatc a                                          21

<210> SEQ ID NO 855
```

-continued

```
<211> LENGTH: 21
<212> TYPE: DNA
<213> ORGANISM: Artificial sequence
<220> FEATURE:
<223> OTHER INFORMATION: Target sequence of the gene KLRG1

<400> SEQUENCE: 855
ctcctaggga ttgatgccta a                                              21

<210> SEQ ID NO 856
<211> LENGTH: 21
<212> TYPE: DNA
<213> ORGANISM: Artificial sequence
<220> FEATURE:
<223> OTHER INFORMATION: Target sequence of the gene ZER1

<400> SEQUENCE: 856
cacgcacatt ccagcctaca a                                              21

<210> SEQ ID NO 857
<211> LENGTH: 21
<212> TYPE: DNA
<213> ORGANISM: Artificial sequence
<220> FEATURE:
<223> OTHER INFORMATION: Target sequence of the gene TMED7

<400> SEQUENCE: 857
tagctaccct aaagtgattt a                                              21

<210> SEQ ID NO 858
<211> LENGTH: 21
<212> TYPE: DNA
<213> ORGANISM: Artificial sequence
<220> FEATURE:
<223> OTHER INFORMATION: Target sequence of the gene HNRPH3

<400> SEQUENCE: 858
aacattgacg atggactacc a                                              21

<210> SEQ ID NO 859
<211> LENGTH: 21
<212> TYPE: DNA
<213> ORGANISM: Artificial sequence
<220> FEATURE:
<223> OTHER INFORMATION: Target sequence of the gene SRBD1

<400> SEQUENCE: 859
cacgcttgac ttcattcgga a                                              21

<210> SEQ ID NO 860
<211> LENGTH: 21
<212> TYPE: DNA
<213> ORGANISM: Artificial sequence
<220> FEATURE:
<223> OTHER INFORMATION: Target sequence of the gene MYBPC1

<400> SEQUENCE: 860
tgggagatga ctggtgtatc a                                              21

<210> SEQ ID NO 861
<211> LENGTH: 21
<212> TYPE: DNA
<213> ORGANISM: Artificial sequence
<220> FEATURE:
<223> OTHER INFORMATION: Target sequence of the gene ARHGEF18

<400> SEQUENCE: 861
```
ctgacccgct ttagaactta a        21

<210> SEQ ID NO 862
<211> LENGTH: 21
<212> TYPE: DNA
<213> ORGANISM: Artificial sequence
<220> FEATURE:
<223> OTHER INFORMATION: Target sequence of the gene TRMU

<400> SEQUENCE: 862
aagcacgtta agaagcccga a        21

<210> SEQ ID NO 863
<211> LENGTH: 21
<212> TYPE: DNA
<213> ORGANISM: Artificial sequence
<220> FEATURE:
<223> OTHER INFORMATION: Target sequence in the gene SNX8

<400> SEQUENCE: 863
ctcgccgaca aggctgcaca a        21

<210> SEQ ID NO 864
<211> LENGTH: 21
<212> TYPE: DNA
<213> ORGANISM: Artificial sequence
<220> FEATURE:
<223> OTHER INFORMATION: Target sequence in the gene SNX8

<400> SEQUENCE: 864
ttggtctgac atgccctgat a        21

<210> SEQ ID NO 865
<211> LENGTH: 21
<212> TYPE: DNA
<213> ORGANISM: Artificial sequence
<220> FEATURE:
<223> OTHER INFORMATION: Target sequence in the gene SLC45A4

<400> SEQUENCE: 865
ctcgaccgcc tggcaagcct a        21

<210> SEQ ID NO 866
<211> LENGTH: 21
<212> TYPE: DNA
<213> ORGANISM: Artificial sequence
<220> FEATURE:
<223> OTHER INFORMATION: Target sequence in the gene SLC7A8

<400> SEQUENCE: 866
caggcggttg aggaacatat t        21

<210> SEQ ID NO 867
<211> LENGTH: 21
<212> TYPE: DNA
<213> ORGANISM: Artificial sequence
<220> FEATURE:
<223> OTHER INFORMATION: Target sequence in the gene SFRS17A

<400> SEQUENCE: 867
cgggatgaaa ctcatgtaca a        21

<210> SEQ ID NO 868
<211> LENGTH: 21
<212> TYPE: DNA

<213> ORGANISM: Artificial sequence
<220> FEATURE:
<223> OTHER INFORMATION: Target sequence in the gene RAB26

<400> SEQUENCE: 868
ccgcagtgtt acccatgcct a					21

<210> SEQ ID NO 869
<211> LENGTH: 21
<212> TYPE: DNA
<213> ORGANISM: Artificial sequence
<220> FEATURE:
<223> OTHER INFORMATION: Target sequence in the gene LNX1

<400> SEQUENCE: 869
atcatcctcg atagtactca a					21

<210> SEQ ID NO 870
<211> LENGTH: 21
<212> TYPE: DNA
<213> ORGANISM: Artificial sequence
<220> FEATURE:
<223> OTHER INFORMATION: Target sequence in the gene RAB21

<400> SEQUENCE: 870
caggcccgta actgtctact a					21

<210> SEQ ID NO 871
<211> LENGTH: 21
<212> TYPE: DNA
<213> ORGANISM: Artificial sequence
<220> FEATURE:
<223> OTHER INFORMATION: Target sequence in the gene KIF7

<400> SEQUENCE: 871
taccctcact gggatcaaca a					21

<210> SEQ ID NO 872
<211> LENGTH: 21
<212> TYPE: DNA
<213> ORGANISM: Artificial sequence
<220> FEATURE:
<223> OTHER INFORMATION: Target sequence in the gene IL1F10

<400> SEQUENCE: 872
gaggatgtga acattgagga a					21

<210> SEQ ID NO 873
<211> LENGTH: 21
<212> TYPE: DNA
<213> ORGANISM: Artificial sequence
<220> FEATURE:
<223> OTHER INFORMATION: Target sequence in the gene NUP62

<400> SEQUENCE: 873
ccgcgaggtg gagaaggtga a					21

<210> SEQ ID NO 874
<211> LENGTH: 21
<212> TYPE: DNA
<213> ORGANISM: Artificial sequence
<220> FEATURE:
<223> OTHER INFORMATION: Target sequence in the gene HSPG2

<400> SEQUENCE: 874
cgggaagtgc aggcccgtca a					21

<210> SEQ ID NO 875
<211> LENGTH: 21
<212> TYPE: DNA
<213> ORGANISM: Artificial sequence
<220> FEATURE:
<223> OTHER INFORMATION: Target sequence in the gene PPP1R10

<400> SEQUENCE: 875
ctcaaacgtc agagcaacgt a                                              21

<210> SEQ ID NO 876
<211> LENGTH: 21
<212> TYPE: DNA
<213> ORGANISM: Artificial sequence
<220> FEATURE:
<223> OTHER INFORMATION: Target sequence in the gene EPHA1

<400> SEQUENCE: 876
cacctttaat gtggaagccc a                                              21

<210> SEQ ID NO 877
<211> LENGTH: 21
<212> TYPE: DNA
<213> ORGANISM: Artificial sequence
<220> FEATURE:
<223> OTHER INFORMATION: Target sequence in the gene RNF138P1

<400> SEQUENCE: 877
caggcgccag tgcctgattt a                                              21

<210> SEQ ID NO 878
<211> LENGTH: 21
<212> TYPE: DNA
<213> ORGANISM: Artificial sequence
<220> FEATURE:
<223> OTHER INFORMATION: Target sequence in the gene LUZP1

<400> SEQUENCE: 878
cagcgggtgc tgagaattga a                                              21

<210> SEQ ID NO 879
<211> LENGTH: 21
<212> TYPE: DNA
<213> ORGANISM: Artificial sequence
<220> FEATURE:
<223> OTHER INFORMATION: Target sequence in the gene THOC1

<400> SEQUENCE: 879
acctacgaga ataattcgga a                                              21

<210> SEQ ID NO 880
<211> LENGTH: 21
<212> TYPE: DNA
<213> ORGANISM: Artificial sequence
<220> FEATURE:
<223> OTHER INFORMATION: Target sequence in the gene RTN3

<400> SEQUENCE: 880
caggatctac aagtccgtca t                                              21

<210> SEQ ID NO 881
<211> LENGTH: 21
<212> TYPE: DNA
<213> ORGANISM: Artificial sequence
<220> FEATURE:

<223> OTHER INFORMATION: Target sequence in the gene SYNPO2

<400> SEQUENCE: 881
caccgttgtc tcctccatca a                                           21

<210> SEQ ID NO 882
<211> LENGTH: 21
<212> TYPE: DNA
<213> ORGANISM: Artificial sequence
<220> FEATURE:
<223> OTHER INFORMATION: Target sequence in the gene SYNPO2

<400> SEQUENCE: 882
tacctcggga agaaatact a                                            21

<210> SEQ ID NO 883
<211> LENGTH: 21
<212> TYPE: DNA
<213> ORGANISM: Artificial sequence
<220> FEATURE:
<223> OTHER INFORMATION: Target sequence in the gene TNS4

<400> SEQUENCE: 883
cagcaatgac ctcatccgac a                                           21

<210> SEQ ID NO 884
<211> LENGTH: 21
<212> TYPE: DNA
<213> ORGANISM: Artificial sequence
<220> FEATURE:
<223> OTHER INFORMATION: Target sequence in the gene ACTA1

<400> SEQUENCE: 884
cacccacaac gtgcccattt a                                           21

<210> SEQ ID NO 885
<211> LENGTH: 21
<212> TYPE: DNA
<213> ORGANISM: Artificial sequence
<220> FEATURE:
<223> OTHER INFORMATION: Target sequence in the gene INE2

<400> SEQUENCE: 885
tagtcgcttt ctaatctaca a                                           21

<210> SEQ ID NO 886
<211> LENGTH: 21
<212> TYPE: DNA
<213> ORGANISM: Artificial sequence
<220> FEATURE:
<223> OTHER INFORMATION: Target sequence in the gene RPL32

<400> SEQUENCE: 886
cagggttcgt agaagattca a                                           21

<210> SEQ ID NO 887
<211> LENGTH: 21
<212> TYPE: DNA
<213> ORGANISM: Artificial sequence
<220> FEATURE:
<223> OTHER INFORMATION: Target sequence in the gene STAC3

<400> SEQUENCE: 887
cccaccgact ttctagagga a                                           21

```
<210> SEQ ID NO 888
<211> LENGTH: 21
<212> TYPE: DNA
<213> ORGANISM: Artificial sequence
<220> FEATURE:
<223> OTHER INFORMATION: Target sequence in the gene GOT1

<400> SEQUENCE: 888
caagaacttc gggctctaca a                                               21

<210> SEQ ID NO 889
<211> LENGTH: 21
<212> TYPE: DNA
<213> ORGANISM: Artificial sequence
<220> FEATURE:
<223> OTHER INFORMATION: Target sequence in the gene PDZRN3

<400> SEQUENCE: 889
cccggtggtt aacgatttaa t                                               21

<210> SEQ ID NO 890
<211> LENGTH: 21
<212> TYPE: DNA
<213> ORGANISM: Artificial sequence
<220> FEATURE:
<223> OTHER INFORMATION: Target sequence in the gene ZNF467

<400> SEQUENCE: 890
gtggatgatt cggaaggtga a                                               21

<210> SEQ ID NO 891
<211> LENGTH: 21
<212> TYPE: DNA
<213> ORGANISM: Artificial sequence
<220> FEATURE:
<223> OTHER INFORMATION: Target sequence in the gene PMP22

<400> SEQUENCE: 891
cagcctcgtg ttgagcctta a                                               21

<210> SEQ ID NO 892
<211> LENGTH: 21
<212> TYPE: DNA
<213> ORGANISM: Artificial sequence
<220> FEATURE:
<223> OTHER INFORMATION: Target sequence in the gene C5orf40

<400> SEQUENCE: 892
cgcccgcatc atgtagccta a                                               21

<210> SEQ ID NO 893
<211> LENGTH: 21
<212> TYPE: DNA
<213> ORGANISM: Artificial sequence
<220> FEATURE:
<223> OTHER INFORMATION: Target sequence of the gene ST6GALNAC5

<400> SEQUENCE: 893
ttggacctga tgaatgtaca a                                               21

<210> SEQ ID NO 894
<211> LENGTH: 21
<212> TYPE: DNA
<213> ORGANISM: Artificial sequence
<220> FEATURE:
<223> OTHER INFORMATION: Target sequence of the gene SEMA4G
```

<400> SEQUENCE: 894
ccgggccttg tggctactca a					21

<210> SEQ ID NO 895
<211> LENGTH: 21
<212> TYPE: DNA
<213> ORGANISM: Artificial sequence
<220> FEATURE:
<223> OTHER INFORMATION: Target sequence of the gene HDDC2

<400> SEQUENCE: 895
aatcataggc ttgtaaacct a					21

<210> SEQ ID NO 896
<211> LENGTH: 21
<212> TYPE: DNA
<213> ORGANISM: Artificial sequence
<220> FEATURE:
<223> OTHER INFORMATION: Target sequence of the gene DOCK11

<400> SEQUENCE: 896
ctgcagcggg ttcaagattc a					21

<210> SEQ ID NO 897
<211> LENGTH: 21
<212> TYPE: DNA
<213> ORGANISM: Artificial sequence
<220> FEATURE:
<223> OTHER INFORMATION: Target sequence of the gene ZNF347

<400> SEQUENCE: 897
cagatggatg ggaatggatc a					21

<210> SEQ ID NO 898
<211> LENGTH: 21
<212> TYPE: DNA
<213> ORGANISM: Artificial sequence
<220> FEATURE:
<223> OTHER INFORMATION: Target sequence of the gene ZNHIT4

<400> SEQUENCE: 898
cgggacctat caggagggtt a					21

<210> SEQ ID NO 899
<211> LENGTH: 21
<212> TYPE: DNA
<213> ORGANISM: Artificial sequence
<220> FEATURE:
<223> OTHER INFORMATION: Target sequence of the gene KIAA1394

<400> SEQUENCE: 899
cccagttggt acagaccttc a					21

<210> SEQ ID NO 900
<211> LENGTH: 21
<212> TYPE: DNA
<213> ORGANISM: Artificial sequence
<220> FEATURE:
<223> OTHER INFORMATION: Target sequence of the gene ARHGEF10L

<400> SEQUENCE: 900
caggaaggac gtcctcggtg a					21

<210> SEQ ID NO 901
<211> LENGTH: 21

```
<212> TYPE: DNA
<213> ORGANISM: Artificial sequence
<220> FEATURE:
<223> OTHER INFORMATION: Target sequence of the gene ZNF689

<400> SEQUENCE: 901
cagcaccagg tcatccatac a                                              21

<210> SEQ ID NO 902
<211> LENGTH: 21
<212> TYPE: DNA
<213> ORGANISM: Artificial sequence
<220> FEATURE:
<223> OTHER INFORMATION: Target sequence of the gene C19orf43

<400> SEQUENCE: 902
cggcgtgaac ttgttcgcca a                                              21

<210> SEQ ID NO 903
<211> LENGTH: 21
<212> TYPE: DNA
<213> ORGANISM: Artificial sequence
<220> FEATURE:
<223> OTHER INFORMATION: Target sequence of the gene GPR89B

<400> SEQUENCE: 903
atccgaatga gtatgccttt a                                              21

<210> SEQ ID NO 904
<211> LENGTH: 21
<212> TYPE: DNA
<213> ORGANISM: Artificial sequence
<220> FEATURE:
<223> OTHER INFORMATION: Target sequence of the gene ARHGEF11

<400> SEQUENCE: 904
cacaacgact ctcgaccgga a                                              21

<210> SEQ ID NO 905
<211> LENGTH: 21
<212> TYPE: DNA
<213> ORGANISM: Artificial sequence
<220> FEATURE:
<223> OTHER INFORMATION: Target sequence of the gene KIAA1841

<400> SEQUENCE: 905
acacttcgtg atcaaggtga a                                              21

<210> SEQ ID NO 906
<211> LENGTH: 21
<212> TYPE: DNA
<213> ORGANISM: Artificial sequence
<220> FEATURE:
<223> OTHER INFORMATION: Target sequence of the gene MSH5

<400> SEQUENCE: 906
cccgggacta tggctactca a                                              21

<210> SEQ ID NO 907
<211> LENGTH: 21
<212> TYPE: DNA
<213> ORGANISM: Artificial sequence
<220> FEATURE:
<223> OTHER INFORMATION: Target sequence of the gene CWC15

<400> SEQUENCE: 907
```
cagtattcaa gcagagacct a                                              21

<210> SEQ ID NO 908
<211> LENGTH: 21
<212> TYPE: DNA
<213> ORGANISM: Artificial sequence
<220> FEATURE:
<223> OTHER INFORMATION: Target sequence of the gene THAP6

<400> SEQUENCE: 908
agccggcatt tgggagccta a                                              21

<210> SEQ ID NO 909
<211> LENGTH: 21
<212> TYPE: DNA
<213> ORGANISM: Artificial sequence
<220> FEATURE:
<223> OTHER INFORMATION: Target sequence of the gene JAKMIP2

<400> SEQUENCE: 909
aaggaacaag tgcctcgcca a                                              21

<210> SEQ ID NO 910
<211> LENGTH: 21
<212> TYPE: DNA
<213> ORGANISM: Artificial sequence
<220> FEATURE:
<223> OTHER INFORMATION: Target sequence of the gene RABIF

<400> SEQUENCE: 910
ctggcattgc ctagatgaca a                                              21

<210> SEQ ID NO 911
<211> LENGTH: 21
<212> TYPE: DNA
<213> ORGANISM: Artificial sequence
<220> FEATURE:
<223> OTHER INFORMATION: Target sequence of the gene ZNF721

<400> SEQUENCE: 911
ttagtaggtc aagaaacctt a                                              21

<210> SEQ ID NO 912
<211> LENGTH: 21
<212> TYPE: DNA
<213> ORGANISM: Artificial sequence
<220> FEATURE:
<223> OTHER INFORMATION: Target sequence of the gene PSMD4

<400> SEQUENCE: 912
ccaggcggaa tcagcagaca t                                              21

<210> SEQ ID NO 913
<211> LENGTH: 21
<212> TYPE: DNA
<213> ORGANISM: Artificial sequence
<220> FEATURE:
<223> OTHER INFORMATION: Target sequence of the gene RHBDL1

<400> SEQUENCE: 913
ctggaacgtc ttcgcctacg a                                              21

<210> SEQ ID NO 914
<211> LENGTH: 21
<212> TYPE: DNA
<213> ORGANISM: Artificial sequence

```
<220> FEATURE:
<223> OTHER INFORMATION: Target sequence of the gene TAS2R14

<400> SEQUENCE: 914
atgggaatgg cttatccttc a                                              21

<210> SEQ ID NO 915
<211> LENGTH: 21
<212> TYPE: DNA
<213> ORGANISM: Artificial sequence
<220> FEATURE:
<223> OTHER INFORMATION: Target sequence of the gene BMI1

<400> SEQUENCE: 915
cagagttcga cctacttgta a                                              21

<210> SEQ ID NO 916
<211> LENGTH: 21
<212> TYPE: DNA
<213> ORGANISM: Artificial sequence
<220> FEATURE:
<223> OTHER INFORMATION: Target sequence of the gene APOH

<400> SEQUENCE: 916
caagttgtaa agcatcttgt a                                              21

<210> SEQ ID NO 917
<211> LENGTH: 21
<212> TYPE: DNA
<213> ORGANISM: Artificial sequence
<220> FEATURE:
<223> OTHER INFORMATION: Target sequence of the gene RPL36

<400> SEQUENCE: 917
cgggaggagc tgagcaacgt a                                              21

<210> SEQ ID NO 918
<211> LENGTH: 21
<212> TYPE: DNA
<213> ORGANISM: Artificial sequence
<220> FEATURE:
<223> OTHER INFORMATION: Target sequence of the gene OMA1

<400> SEQUENCE: 918
tacaagttaa ccatatagta a                                              21

<210> SEQ ID NO 919
<211> LENGTH: 21
<212> TYPE: DNA
<213> ORGANISM: Artificial sequence
<220> FEATURE:
<223> OTHER INFORMATION: Target sequence of the gene KIAA1632

<400> SEQUENCE: 919
cagcgaacag actttaagga a                                              21

<210> SEQ ID NO 920
<211> LENGTH: 21
<212> TYPE: DNA
<213> ORGANISM: Artificial sequence
<220> FEATURE:
<223> OTHER INFORMATION: Target sequence of the gene CAV2

<400> SEQUENCE: 920
cagcaaatac gtaatgtaca a                                              21
```

<210> SEQ ID NO 921
<211> LENGTH: 21
<212> TYPE: DNA
<213> ORGANISM: Artificial sequence
<220> FEATURE:
<223> OTHER INFORMATION: Target sequence of the gene SLAMF9

<400> SEQUENCE: 921
caggcatgga tatgacctac a                                              21

<210> SEQ ID NO 922
<211> LENGTH: 21
<212> TYPE: DNA
<213> ORGANISM: Artificial sequence
<220> FEATURE:
<223> OTHER INFORMATION: Target sequence of the gene SOD1

<400> SEQUENCE: 922
atggcactta ttatgaggct a                                              21

<210> SEQ ID NO 923
<211> LENGTH: 21
<212> TYPE: DNA
<213> ORGANISM: Artificial sequence
<220> FEATURE:
<223> OTHER INFORMATION: Target sequence of the gene MTMR8

<400> SEQUENCE: 923
cagcccaagc agagtatgct a                                              21

<210> SEQ ID NO 924
<211> LENGTH: 21
<212> TYPE: DNA
<213> ORGANISM: Artificial sequence
<220> FEATURE:
<223> OTHER INFORMATION: Target sequence of the gene NXT2

<400> SEQUENCE: 924
ttccgttagt cctaccttga a                                              21

<210> SEQ ID NO 925
<211> LENGTH: 21
<212> TYPE: DNA
<213> ORGANISM: Artificial sequence
<220> FEATURE:
<223> OTHER INFORMATION: Target sequence of the gene PSMD13

<400> SEQUENCE: 925
aagactcgtg agaaggtgaa a                                              21

<210> SEQ ID NO 926
<211> LENGTH: 21
<212> TYPE: DNA
<213> ORGANISM: Artificial sequence
<220> FEATURE:
<223> OTHER INFORMATION: Target sequence of the gene FLJ40235

<400> SEQUENCE: 926
caagataaac gagccagcta a                                              21

<210> SEQ ID NO 927
<211> LENGTH: 21
<212> TYPE: DNA
<213> ORGANISM: Artificial sequence
<220> FEATURE:
<223> OTHER INFORMATION: Target sequence of the gene C9orf66

```
<400> SEQUENCE: 927
ggcggcgttc ttgcgattca a                                              21

<210> SEQ ID NO 928
<211> LENGTH: 21
<212> TYPE: DNA
<213> ORGANISM: Artificial sequence
<220> FEATURE:
<223> OTHER INFORMATION: Target sequence of the gene PGM1

<400> SEQUENCE: 928
tcggctgtac atcgatagct a                                              21

<210> SEQ ID NO 929
<211> LENGTH: 21
<212> TYPE: DNA
<213> ORGANISM: Artificial sequence
<220> FEATURE:
<223> OTHER INFORMATION: Target sequence of the gene DYNLT3

<400> SEQUENCE: 929
ctgcgacgag gttggcttca a                                              21

<210> SEQ ID NO 930
<211> LENGTH: 21
<212> TYPE: DNA
<213> ORGANISM: Artificial sequence
<220> FEATURE:
<223> OTHER INFORMATION: Target sequence of the gene ATP6V1E2

<400> SEQUENCE: 930
gaagctagtg ttgaaccact a                                              21

<210> SEQ ID NO 931
<211> LENGTH: 21
<212> TYPE: DNA
<213> ORGANISM: Artificial sequence
<220> FEATURE:
<223> OTHER INFORMATION: Target sequence of the gene WDR53

<400> SEQUENCE: 931
ccgaccactc tggattacaa a                                              21

<210> SEQ ID NO 932
<211> LENGTH: 21
<212> TYPE: DNA
<213> ORGANISM: Artificial sequence
<220> FEATURE:
<223> OTHER INFORMATION: Target sequence of the gene TRY6

<400> SEQUENCE: 932
caggattact ctgaacaatg a                                              21

<210> SEQ ID NO 933
<211> LENGTH: 21
<212> TYPE: DNA
<213> ORGANISM: Artificial sequence
<220> FEATURE:
<223> OTHER INFORMATION: Target sequence of the gene PTTG3

<400> SEQUENCE: 933
aggcatcctt gtggctacaa a                                              21

<210> SEQ ID NO 934
```

```
<211> LENGTH: 21
<212> TYPE: DNA
<213> ORGANISM: Artificial sequence
<220> FEATURE:
<223> OTHER INFORMATION: Target sequence of the gene MBD6

<400> SEQUENCE: 934
ttccactgta gtgatgcctt a                                              21

<210> SEQ ID NO 935
<211> LENGTH: 21
<212> TYPE: DNA
<213> ORGANISM: Artificial sequence
<220> FEATURE:
<223> OTHER INFORMATION: Target sequence of the gene OR13C3

<400> SEQUENCE: 935
atgggtgaga ttaaccagac a                                              21

<210> SEQ ID NO 936
<211> LENGTH: 21
<212> TYPE: DNA
<213> ORGANISM: Artificial sequence
<220> FEATURE:
<223> OTHER INFORMATION: Target sequence of the gene OR2T27

<400> SEQUENCE: 936
cacggacaca tcagcctacg a                                              21

<210> SEQ ID NO 937
<211> LENGTH: 21
<212> TYPE: DNA
<213> ORGANISM: Artificial sequence
<220> FEATURE:
<223> OTHER INFORMATION: Target sequence of the gene TNNC1

<400> SEQUENCE: 937
cgccagcatg gatgacatct a                                              21

<210> SEQ ID NO 938
<211> LENGTH: 21
<212> TYPE: DNA
<213> ORGANISM: Artificial sequence
<220> FEATURE:
<223> OTHER INFORMATION: Target sequence of the gene TCP11L2

<400> SEQUENCE: 938
caagctaatc ttataggtca a                                              21

<210> SEQ ID NO 939
<211> LENGTH: 21
<212> TYPE: DNA
<213> ORGANISM: Artificial sequence
<220> FEATURE:
<223> OTHER INFORMATION: Target sequence of the gene APOBEC4

<400> SEQUENCE: 939
taccatattc gaacaggtga a                                              21

<210> SEQ ID NO 940
<211> LENGTH: 21
<212> TYPE: DNA
<213> ORGANISM: Artificial sequence
<220> FEATURE:
<223> OTHER INFORMATION: Target sequence of the gene CPN1

<400> SEQUENCE: 940
```
ccggtggatg cactccttca a    21

<210> SEQ ID NO 941
<211> LENGTH: 21
<212> TYPE: DNA
<213> ORGANISM: Artificial sequence
<220> FEATURE:
<223> OTHER INFORMATION: Target sequence of the gene FRAP1

<400> SEQUENCE: 941
ccggagtgtt agaatatgcc a    21

<210> SEQ ID NO 942
<211> LENGTH: 21
<212> TYPE: DNA
<213> ORGANISM: Artificial sequence
<220> FEATURE:
<223> OTHER INFORMATION: Target sequence of the gene PTBP1

<400> SEQUENCE: 942
cacgcacatt ccgttgcctt a    21

<210> SEQ ID NO 943
<211> LENGTH: 21
<212> TYPE: DNA
<213> ORGANISM: Artificial sequence
<220> FEATURE:
<223> OTHER INFORMATION: Target sequence of the gene LGR5

<400> SEQUENCE: 943
cagcagtatg gacgaccttc a    21

<210> SEQ ID NO 944
<211> LENGTH: 21
<212> TYPE: DNA
<213> ORGANISM: Artificial sequence
<220> FEATURE:
<223> OTHER INFORMATION: Target sequence of the gene ZNF567

<400> SEQUENCE: 944
taccacttcc gtagcctata a    21

<210> SEQ ID NO 945
<211> LENGTH: 21
<212> TYPE: DNA
<213> ORGANISM: Artificial sequence
<220> FEATURE:
<223> OTHER INFORMATION: Target sequence of the gene CHMP4C

<400> SEQUENCE: 945
tggcagcttg ggctacctaa a    21

<210> SEQ ID NO 946
<211> LENGTH: 21
<212> TYPE: DNA
<213> ORGANISM: Artificial sequence
<220> FEATURE:
<223> OTHER INFORMATION: Target sequence of the gene NOL9

<400> SEQUENCE: 946
atccgggttc atcctacatt t    21

<210> SEQ ID NO 947
<211> LENGTH: 21
<212> TYPE: DNA

```
<213> ORGANISM: Artificial sequence
<220> FEATURE:
<223> OTHER INFORMATION: Target sequence of the gene KIAA0831

<400> SEQUENCE: 947
ctcggtgacc tcctggttta a                                              21

<210> SEQ ID NO 948
<211> LENGTH: 21
<212> TYPE: DNA
<213> ORGANISM: Artificial sequence
<220> FEATURE:
<223> OTHER INFORMATION: Target sequence of the gene STRN

<400> SEQUENCE: 948
ctggaatacc actaatccca a                                              21

<210> SEQ ID NO 949
<211> LENGTH: 21
<212> TYPE: DNA
<213> ORGANISM: Artificial sequence
<220> FEATURE:
<223> OTHER INFORMATION: Target sequence of the gene ZNF576

<400> SEQUENCE: 949
cgggctggtg cgactatact a                                              21

<210> SEQ ID NO 950
<211> LENGTH: 21
<212> TYPE: DNA
<213> ORGANISM: Artificial sequence
<220> FEATURE:
<223> OTHER INFORMATION: Target sequence of the gene RPLP0

<400> SEQUENCE: 950
caagaacacc atgatgcgca a                                              21

<210> SEQ ID NO 951
<211> LENGTH: 21
<212> TYPE: DNA
<213> ORGANISM: Artificial sequence
<220> FEATURE:
<223> OTHER INFORMATION: Target sequence of the gene CMTM3

<400> SEQUENCE: 951
ctccatcacg gccatcgcca a                                              21

<210> SEQ ID NO 952
<211> LENGTH: 21
<212> TYPE: DNA
<213> ORGANISM: Artificial sequence
<220> FEATURE:
<223> OTHER INFORMATION: Target sequence of the gene ARHGEF1

<400> SEQUENCE: 952
caccgatcac aaagccttct a                                              21

<210> SEQ ID NO 953
<211> LENGTH: 21
<212> TYPE: DNA
<213> ORGANISM: Artificial sequence
<220> FEATURE:
<223> OTHER INFORMATION: Target sequence of the gene FOXD4

<400> SEQUENCE: 953
cagcggcatc tgcgccttca t                                              21
```

<210> SEQ ID NO 954
<211> LENGTH: 21
<212> TYPE: DNA
<213> ORGANISM: Artificial sequence
<220> FEATURE:
<223> OTHER INFORMATION: Target sequence of the gene P76

<400> SEQUENCE: 954
gtggatgatc gtggactaca a                                             21

<210> SEQ ID NO 955
<211> LENGTH: 21
<212> TYPE: DNA
<213> ORGANISM: Artificial sequence
<220> FEATURE:
<223> OTHER INFORMATION: Target sequence of the gene FTH1

<400> SEQUENCE: 955
cgccatcaac cgccagatca a                                             21

<210> SEQ ID NO 956
<211> LENGTH: 21
<212> TYPE: DNA
<213> ORGANISM: Artificial sequence
<220> FEATURE:
<223> OTHER INFORMATION: Target sequence of the gene C12orf53

<400> SEQUENCE: 956
cacaattacc atctccatca t                                             21

<210> SEQ ID NO 957
<211> LENGTH: 21
<212> TYPE: DNA
<213> ORGANISM: Artificial sequence
<220> FEATURE:
<223> OTHER INFORMATION: Target sequence of the gene RPS11

<400> SEQUENCE: 957
ccgagactat ctgcactaca t                                             21

<210> SEQ ID NO 958
<211> LENGTH: 21
<212> TYPE: DNA
<213> ORGANISM: Artificial sequence
<220> FEATURE:
<223> OTHER INFORMATION: Target sequence of the gene RHBDF2

<400> SEQUENCE: 958
cacggctatt tccatgagga a                                             21

<210> SEQ ID NO 959
<211> LENGTH: 21
<212> TYPE: DNA
<213> ORGANISM: Artificial sequence
<220> FEATURE:
<223> OTHER INFORMATION: Target sequence of the gene ALOX15B

<400> SEQUENCE: 959
ttggacctta tggtcaccca a                                             21

<210> SEQ ID NO 960
<211> LENGTH: 21
<212> TYPE: DNA
<213> ORGANISM: Artificial sequence
<220> FEATURE:

<223> OTHER INFORMATION: Target sequence of the gene UNC13D

<400> SEQUENCE: 960
ctggtgtact gcagccttat a                                              21

<210> SEQ ID NO 961
<211> LENGTH: 21
<212> TYPE: DNA
<213> ORGANISM: Artificial sequence
<220> FEATURE:
<223> OTHER INFORMATION: Target sequence of the gene PLEKHB1

<400> SEQUENCE: 961
cagaccgtgg tgggccttca a                                              21

<210> SEQ ID NO 962
<211> LENGTH: 21
<212> TYPE: DNA
<213> ORGANISM: Artificial sequence
<220> FEATURE:
<223> OTHER INFORMATION: Target sequence of the gene PCNXL2

<400> SEQUENCE: 962
ccgaaggatc ctcatccgct a                                              21

<210> SEQ ID NO 963
<211> LENGTH: 21
<212> TYPE: DNA
<213> ORGANISM: Artificial sequence
<220> FEATURE:
<223> OTHER INFORMATION: Target sequence of the gene DGCR5

<400> SEQUENCE: 963
tacgttctag catccattca a                                              21

<210> SEQ ID NO 964
<211> LENGTH: 21
<212> TYPE: DNA
<213> ORGANISM: Artificial sequence
<220> FEATURE:
<223> OTHER INFORMATION: Target sequence of the gene FARSA

<400> SEQUENCE: 964
ccgcttcaag ccagcctaca a                                              21

<210> SEQ ID NO 965
<211> LENGTH: 21
<212> TYPE: DNA
<213> ORGANISM: Artificial sequence
<220> FEATURE:
<223> OTHER INFORMATION: Target sequence of the gene AGPAT1

<400> SEQUENCE: 965
acgcaacgtc gagaacatga a                                              21

<210> SEQ ID NO 966
<211> LENGTH: 21
<212> TYPE: DNA
<213> ORGANISM: Artificial sequence
<220> FEATURE:
<223> OTHER INFORMATION: Target sequence of the gene C19orf63

<400> SEQUENCE: 966
caagacggtc ctgatgtaca a                                              21

```
<210> SEQ ID NO 967
<211> LENGTH: 21
<212> TYPE: DNA
<213> ORGANISM: Artificial sequence
<220> FEATURE:
<223> OTHER INFORMATION: Target sequence of the gene C18orf51

<400> SEQUENCE: 967
agcgcagcgc gtaaacaaca a                                        21

<210> SEQ ID NO 968
<211> LENGTH: 21
<212> TYPE: DNA
<213> ORGANISM: Artificial sequence
<220> FEATURE:
<223> OTHER INFORMATION: Target sequence of the gene TMEM31

<400> SEQUENCE: 968
cacgtaggac acctacaaca t                                        21

<210> SEQ ID NO 969
<211> LENGTH: 21
<212> TYPE: DNA
<213> ORGANISM: Artificial sequence
<220> FEATURE:
<223> OTHER INFORMATION: Target sequence of the gene TMEM54

<400> SEQUENCE: 969
ccactaggac cctgcaagca a                                        21

<210> SEQ ID NO 970
<211> LENGTH: 21
<212> TYPE: DNA
<213> ORGANISM: Artificial sequence
<220> FEATURE:
<223> OTHER INFORMATION: Target sequence of the gene PML

<400> SEQUENCE: 970
caggagcagg atagtgcctt t                                        21

<210> SEQ ID NO 971
<211> LENGTH: 21
<212> TYPE: DNA
<213> ORGANISM: Artificial sequence
<220> FEATURE:
<223> OTHER INFORMATION: Target sequence of the gene GABRD

<400> SEQUENCE: 971
caccttcatc gtgaacgcca a                                        21

<210> SEQ ID NO 972
<211> LENGTH: 21
<212> TYPE: DNA
<213> ORGANISM: Artificial sequence
<220> FEATURE:
<223> OTHER INFORMATION: Target sequence of the gene UNQ9391

<400> SEQUENCE: 972
cacctcgttg gtgaactaca a                                        21

<210> SEQ ID NO 973
<211> LENGTH: 21
<212> TYPE: DNA
<213> ORGANISM: Artificial sequence
<220> FEATURE:
<223> OTHER INFORMATION: Target sequence of the gene ITGA9
```

```
<400> SEQUENCE: 973
acaggtcact gtctacatca a                                              21

<210> SEQ ID NO 974
<211> LENGTH: 21
<212> TYPE: DNA
<213> ORGANISM: Artificial sequence
<220> FEATURE:
<223> OTHER INFORMATION: Target sequence of the gene PDZD8

<400> SEQUENCE: 974
accgatctcg tagaaccttc a                                              21

<210> SEQ ID NO 975
<211> LENGTH: 21
<212> TYPE: DNA
<213> ORGANISM: Artificial sequence
<220> FEATURE:
<223> OTHER INFORMATION: Target sequence of the gene GPX4

<400> SEQUENCE: 975
gtggatgaag atccaaccca a                                              21

<210> SEQ ID NO 976
<211> LENGTH: 21
<212> TYPE: DNA
<213> ORGANISM: Artificial sequence
<220> FEATURE:
<223> OTHER INFORMATION: Target sequence of the gene GPBAR1

<400> SEQUENCE: 976
caggaccaag atgacgccca a                                              21

<210> SEQ ID NO 977
<211> LENGTH: 21
<212> TYPE: DNA
<213> ORGANISM: Artificial sequence
<220> FEATURE:
<223> OTHER INFORMATION: Target sequence of the gene NME2

<400> SEQUENCE: 977
tacattgacc tgaaagaccg a                                              21

<210> SEQ ID NO 978
<211> LENGTH: 21
<212> TYPE: DNA
<213> ORGANISM: Artificial sequence
<220> FEATURE:
<223> OTHER INFORMATION: Target sequence of the gene ZFP106

<400> SEQUENCE: 978
aggcgacata gtgcacaatt a                                              21

<210> SEQ ID NO 979
<211> LENGTH: 21
<212> TYPE: DNA
<213> ORGANISM: Artificial sequence
<220> FEATURE:
<223> OTHER INFORMATION: Target sequence of the gene TCAM1

<400> SEQUENCE: 979
cacgctcgcc tgcgtcccaa a                                              21

<210> SEQ ID NO 980
<211> LENGTH: 21
```

```
<212> TYPE: DNA
<213> ORGANISM: Artificial sequence
<220> FEATURE:
<223> OTHER INFORMATION: Target sequence of the gene LOC374443

<400> SEQUENCE: 980
cccatcgcat ttggaaatgg a                                              21

<210> SEQ ID NO 981
<211> LENGTH: 21
<212> TYPE: DNA
<213> ORGANISM: Artificial sequence
<220> FEATURE:
<223> OTHER INFORMATION: Target sequence of the gene HRG

<400> SEQUENCE: 981
ttggacttgg aaagcccgaa a                                              21

<210> SEQ ID NO 982
<211> LENGTH: 21
<212> TYPE: DNA
<213> ORGANISM: Artificial sequence
<220> FEATURE:
<223> OTHER INFORMATION: Target sequence of the gene TMEM166

<400> SEQUENCE: 982
atggaggtga ttctgattca a                                              21

<210> SEQ ID NO 983
<211> LENGTH: 21
<212> TYPE: DNA
<213> ORGANISM: Artificial sequence
<220> FEATURE:
<223> OTHER INFORMATION: Target sequence of the gene RICH2

<400> SEQUENCE: 983
caaacgctaa tagaagtgca a                                              21

<210> SEQ ID NO 984
<211> LENGTH: 21
<212> TYPE: DNA
<213> ORGANISM: Artificial sequence
<220> FEATURE:
<223> OTHER INFORMATION: Target sequence of the gene LAMC3

<400> SEQUENCE: 984
atcgcgtatc tcactggaga a                                              21

<210> SEQ ID NO 985
<211> LENGTH: 21
<212> TYPE: DNA
<213> ORGANISM: Artificial sequence
<220> FEATURE:
<223> OTHER INFORMATION: Target sequence of the gene APOC1

<400> SEQUENCE: 985
cagccgcatc aaacagagtg a                                              21

<210> SEQ ID NO 986
<211> LENGTH: 21
<212> TYPE: DNA
<213> ORGANISM: Artificial sequence
<220> FEATURE:
<223> OTHER INFORMATION: Target sequence of the gene OR2G3

<400> SEQUENCE: 986
```
agcactcatc tccatctcct a                                              21

<210> SEQ ID NO 987
<211> LENGTH: 21
<212> TYPE: DNA
<213> ORGANISM: Artificial sequence
<220> FEATURE:
<223> OTHER INFORMATION: Target sequence of the gene PLCXD1

<400> SEQUENCE: 987
cacgatgacg tactgcctga a                                              21

<210> SEQ ID NO 988
<211> LENGTH: 21
<212> TYPE: DNA
<213> ORGANISM: Artificial sequence
<220> FEATURE:
<223> OTHER INFORMATION: Target sequence of the gene FAM83H

<400> SEQUENCE: 988
caggtgctcc ataatgagtc a                                              21

<210> SEQ ID NO 989
<211> LENGTH: 21
<212> TYPE: DNA
<213> ORGANISM: Artificial sequence
<220> FEATURE:
<223> OTHER INFORMATION: Target sequence of the gene TREML2

<400> SEQUENCE: 989
ccgctacttg ctgcaggacg a                                              21

<210> SEQ ID NO 990
<211> LENGTH: 21
<212> TYPE: DNA
<213> ORGANISM: Artificial sequence
<220> FEATURE:
<223> OTHER INFORMATION: Target sequence of the gene PATZ1

<400> SEQUENCE: 990
cccgtctggc tgctacacat a                                              21

<210> SEQ ID NO 991
<211> LENGTH: 21
<212> TYPE: DNA
<213> ORGANISM: Artificial sequence
<220> FEATURE:
<223> OTHER INFORMATION: Target sequence of the gene BANF1

<400> SEQUENCE: 991
ccggaaagga gcgcctacta a                                              21

<210> SEQ ID NO 992
<211> LENGTH: 21
<212> TYPE: DNA
<213> ORGANISM: Artificial sequence
<220> FEATURE:
<223> OTHER INFORMATION: Target sequence of the gene KLHL30

<400> SEQUENCE: 992
ctggcataac agggacagga a                                              21

<210> SEQ ID NO 993
<211> LENGTH: 21
<212> TYPE: DNA
<213> ORGANISM: Artificial sequence

```
<220> FEATURE:
<223> OTHER INFORMATION: Target sequence of the gene CA11

<400> SEQUENCE: 993
ccggctcgga acatcagatc a                                              21

<210> SEQ ID NO 994
<211> LENGTH: 21
<212> TYPE: DNA
<213> ORGANISM: Artificial sequence
<220> FEATURE:
<223> OTHER INFORMATION: Target sequence of the gene ECE2

<400> SEQUENCE: 994
cagacactat gcccaagcct a                                              21

<210> SEQ ID NO 995
<211> LENGTH: 21
<212> TYPE: DNA
<213> ORGANISM: Artificial sequence
<220> FEATURE:
<223> OTHER INFORMATION: Target sequence of the gene TMEM87A

<400> SEQUENCE: 995
agcgctgatt gttacaatga a                                              21

<210> SEQ ID NO 996
<211> LENGTH: 21
<212> TYPE: DNA
<213> ORGANISM: Artificial sequence
<220> FEATURE:
<223> OTHER INFORMATION: Target sequence of the gene PMS2

<400> SEQUENCE: 996
tggatgttga aggtaactta a                                              21

<210> SEQ ID NO 997
<211> LENGTH: 21
<212> TYPE: DNA
<213> ORGANISM: Artificial sequence
<220> FEATURE:
<223> OTHER INFORMATION: Target sequence of the gene TDRD3

<400> SEQUENCE: 997
aagcatcgag gcaagctctt a                                              21

<210> SEQ ID NO 998
<211> LENGTH: 21
<212> TYPE: DNA
<213> ORGANISM: Artificial sequence
<220> FEATURE:
<223> OTHER INFORMATION: Target sequence in the gene SHC1

<400> SEQUENCE: 998
cacctgacca tcagtactat a                                              21

<210> SEQ ID NO 999
<211> LENGTH: 21
<212> TYPE: DNA
<213> ORGANISM: Artificial sequence
<220> FEATURE:
<223> OTHER INFORMATION: Target sequence in the gene DNMT3B

<400> SEQUENCE: 999
ctcacggttc ctggagtgta a                                              21
```

```
<210> SEQ ID NO 1000
<211> LENGTH: 21
<212> TYPE: DNA
<213> ORGANISM: Artificial sequence
<220> FEATURE:
<223> OTHER INFORMATION: Target sequence in the gene ITCH

<400> SEQUENCE: 1000
cacgggcgag tttactatgt a                                          21

<210> SEQ ID NO 1001
<211> LENGTH: 21
<212> TYPE: DNA
<213> ORGANISM: Artificial sequence
<220> FEATURE:
<223> OTHER INFORMATION: Target sequence in the gene MAT1A

<400> SEQUENCE: 1001
ttggctcaca ctcgacatga a                                          21

<210> SEQ ID NO 1002
<211> LENGTH: 21
<212> TYPE: DNA
<213> ORGANISM: Artificial sequence
<220> FEATURE:
<223> OTHER INFORMATION: Target sequence in the gene RALA

<400> SEQUENCE: 1002
cgagctaatg ttgacaaggt a                                          21

<210> SEQ ID NO 1003
<211> LENGTH: 21
<212> TYPE: DNA
<213> ORGANISM: Artificial sequence
<220> FEATURE:
<223> OTHER INFORMATION: Target sequence in the gene DEF6

<400> SEQUENCE: 1003
ctggacgctg acggccaaga a                                          21

<210> SEQ ID NO 1004
<211> LENGTH: 21
<212> TYPE: DNA
<213> ORGANISM: Artificial sequence
<220> FEATURE:
<223> OTHER INFORMATION: Target sequence in the gene TIAM1

<400> SEQUENCE: 1004
aacggaaatg gtagagtttc a                                          21

<210> SEQ ID NO 1005
<211> LENGTH: 21
<212> TYPE: DNA
<213> ORGANISM: Artificial sequence
<220> FEATURE:
<223> OTHER INFORMATION: Target sequence in the gene NPAS3

<400> SEQUENCE: 1005
caccatagct attaatgcca a                                          21

<210> SEQ ID NO 1006
<211> LENGTH: 21
<212> TYPE: DNA
<213> ORGANISM: Artificial sequence
<220> FEATURE:
<223> OTHER INFORMATION: Target sequence in the gene CLEC4M
```

-continued

<400> SEQUENCE: 1006
ctggaacagt ggagaaccca a                                              21

<210> SEQ ID NO 1007
<211> LENGTH: 21
<212> TYPE: DNA
<213> ORGANISM: Artificial sequence
<220> FEATURE:
<223> OTHER INFORMATION: Target sequence in the gene PSEN2

<400> SEQUENCE: 1007
caggagagaa atgagcccat a                                              21

<210> SEQ ID NO 1008
<211> LENGTH: 21
<212> TYPE: DNA
<213> ORGANISM: Artificial sequence
<220> FEATURE:
<223> OTHER INFORMATION: Target sequence in the gene SP140

<400> SEQUENCE: 1008
tcgggtgtga tcctaggcca a                                              21

<210> SEQ ID NO 1009
<211> LENGTH: 21
<212> TYPE: DNA
<213> ORGANISM: Artificial sequence
<220> FEATURE:
<223> OTHER INFORMATION: Target sequence in the gene CENPE

<400> SEQUENCE: 1009
caggttaatc ctaccacaca a                                              21

<210> SEQ ID NO 1010
<211> LENGTH: 21
<212> TYPE: DNA
<213> ORGANISM: Artificial sequence
<220> FEATURE:
<223> OTHER INFORMATION: Target sequence in the gene NTRK3

<400> SEQUENCE: 1010
cacggataac tttatcttgt t                                              21

<210> SEQ ID NO 1011
<211> LENGTH: 21
<212> TYPE: DNA
<213> ORGANISM: Artificial sequence
<220> FEATURE:
<223> OTHER INFORMATION: Target sequence in the gene PTGFRN

<400> SEQUENCE: 1011
ccgattcacg gtttcgtggt a                                              21

<210> SEQ ID NO 1012
<211> LENGTH: 21
<212> TYPE: DNA
<213> ORGANISM: Artificial sequence
<220> FEATURE:
<223> OTHER INFORMATION: Target sequence in the gene PISD

<400> SEQUENCE: 1012
ccgcgtcgtg tgactccttc a                                              21

<210> SEQ ID NO 1013

-continued

<210> SEQ ID NO 1013
<211> LENGTH: 21
<212> TYPE: DNA
<213> ORGANISM: Artificial sequence
<220> FEATURE:
<223> OTHER INFORMATION: Target sequence in the gene HBS1L

<400> SEQUENCE: 1013
tacgttacgg tggttctaca a                                              21

<210> SEQ ID NO 1014
<211> LENGTH: 21
<212> TYPE: DNA
<213> ORGANISM: Artificial sequence
<220> FEATURE:
<223> OTHER INFORMATION: Target sequence in the gene TTC23

<400> SEQUENCE: 1014
ctccggaact gccctacttt a                                              21

<210> SEQ ID NO 1015
<211> LENGTH: 21
<212> TYPE: DNA
<213> ORGANISM: Artificial sequence
<220> FEATURE:
<223> OTHER INFORMATION: Target sequence in the gene C3orf44

<400> SEQUENCE: 1015
cagcgaagag tacctctgga a                                              21

<210> SEQ ID NO 1016
<211> LENGTH: 21
<212> TYPE: DNA
<213> ORGANISM: Artificial sequence
<220> FEATURE:
<223> OTHER INFORMATION: Target sequence in the gene ZNF271

<400> SEQUENCE: 1016
acccatgtaa tcagtgcaat a                                              21

<210> SEQ ID NO 1017
<211> LENGTH: 21
<212> TYPE: DNA
<213> ORGANISM: Artificial sequence
<220> FEATURE:
<223> OTHER INFORMATION: Target sequence in the gene CDGAP

<400> SEQUENCE: 1017
ctgatctggc ctgagattca a                                              21

<210> SEQ ID NO 1018
<211> LENGTH: 21
<212> TYPE: DNA
<213> ORGANISM: Artificial sequence
<220> FEATURE:
<223> OTHER INFORMATION: Target sequence in the gene SBNO1

<400> SEQUENCE: 1018
aaggagctag aatgtggata a                                              21

<210> SEQ ID NO 1019
<211> LENGTH: 21
<212> TYPE: DNA
<213> ORGANISM: Artificial sequence
<220> FEATURE:
<223> OTHER INFORMATION: Target sequence in the gene HIST1H2AE

<400> SEQUENCE: 1019
ccgcaacgac gaggagctaa a                                              21

<210> SEQ ID NO 1020
<211> LENGTH: 21
<212> TYPE: DNA
<213> ORGANISM: Artificial sequence
<220> FEATURE:
<223> OTHER INFORMATION: Target sequence in the gene C1orf41

<400> SEQUENCE: 1020
ccgctactta cttgagattc a                                              21

<210> SEQ ID NO 1021
<211> LENGTH: 21
<212> TYPE: DNA
<213> ORGANISM: Artificial sequence
<220> FEATURE:
<223> OTHER INFORMATION: Target sequence in the gene TTC16

<400> SEQUENCE: 1021
ctggtggact tctatgcctt a                                              21

<210> SEQ ID NO 1022
<211> LENGTH: 21
<212> TYPE: DNA
<213> ORGANISM: Artificial sequence
<220> FEATURE:
<223> OTHER INFORMATION: Target sequence in the gene LCE1D

<400> SEQUENCE: 1022
ttccttctga ttctgcctga a                                              21

<210> SEQ ID NO 1023
<211> LENGTH: 21
<212> TYPE: DNA
<213> ORGANISM: Artificial sequence
<220> FEATURE:
<223> OTHER INFORMATION: Target sequence in the gene BPIL3

<400> SEQUENCE: 1023
cccggacttt ctggccatga a                                              21

<210> SEQ ID NO 1024
<211> LENGTH: 21
<212> TYPE: DNA
<213> ORGANISM: Artificial sequence
<220> FEATURE:
<223> OTHER INFORMATION: Target sequence in the gene SIVA1

<400> SEQUENCE: 1024
cacgccgtgc atggcagcct t                                              21

<210> SEQ ID NO 1025
<211> LENGTH: 21
<212> TYPE: DNA
<213> ORGANISM: Artificial sequence
<220> FEATURE:
<223> OTHER INFORMATION: Target sequence in the gene ARHGEF5

<400> SEQUENCE: 1025
tagccgtatg ttaaacagaa t                                              21

<210> SEQ ID NO 1026
<211> LENGTH: 21
<212> TYPE: DNA

```
<213> ORGANISM: Artificial sequence
<220> FEATURE:
<223> OTHER INFORMATION: Target sequence in the gene PRSS8

<400> SEQUENCE: 1026
acccatcacc ttctcccgct a                                              21

<210> SEQ ID NO 1027
<211> LENGTH: 21
<212> TYPE: DNA
<213> ORGANISM: Artificial sequence
<220> FEATURE:
<223> OTHER INFORMATION: Target sequence in the gene COL9A1

<400> SEQUENCE: 1027
caccgacaga tcagcacatt a                                              21

<210> SEQ ID NO 1028
<211> LENGTH: 21
<212> TYPE: DNA
<213> ORGANISM: Artificial sequence
<220> FEATURE:
<223> OTHER INFORMATION: Target sequence in the gene PKD1L2

<400> SEQUENCE: 1028
ccgtgtttgc tgaatgcaca a                                              21

<210> SEQ ID NO 1029
<211> LENGTH: 21
<212> TYPE: DNA
<213> ORGANISM: Artificial sequence
<220> FEATURE:
<223> OTHER INFORMATION: Target sequence in the gene PHF10

<400> SEQUENCE: 1029
cggacagttc caggaatatt a                                              21

<210> SEQ ID NO 1030
<211> LENGTH: 21
<212> TYPE: DNA
<213> ORGANISM: Artificial sequence
<220> FEATURE:
<223> OTHER INFORMATION: Target sequence in the gene MKS1

<400> SEQUENCE: 1030
accgacgaat ctttacctac a                                              21

<210> SEQ ID NO 1031
<211> LENGTH: 21
<212> TYPE: DNA
<213> ORGANISM: Artificial sequence
<220> FEATURE:
<223> OTHER INFORMATION: Target sequence in the gene ARHGAP27

<400> SEQUENCE: 1031
ccgcagggtg ttcttctaca a                                              21

<210> SEQ ID NO 1032
<211> LENGTH: 21
<212> TYPE: DNA
<213> ORGANISM: Artificial sequence
<220> FEATURE:
<223> OTHER INFORMATION: Target sequence in the gene CXCL17

<400> SEQUENCE: 1032
agcgcccact cttccaatta a                                              21
```

<210> SEQ ID NO 1033
<211> LENGTH: 21
<212> TYPE: DNA
<213> ORGANISM: Artificial sequence
<220> FEATURE:
<223> OTHER INFORMATION: Target sequence in the gene SRGAP2

<400> SEQUENCE: 1033
ctcgctaatg tcagtgccag a                                              21

<210> SEQ ID NO 1034
<211> LENGTH: 21
<212> TYPE: DNA
<213> ORGANISM: Artificial sequence
<220> FEATURE:
<223> OTHER INFORMATION: Target sequence in the gene ACTR6

<400> SEQUENCE: 1034
gacgaccttt gtgctggata a                                              21

<210> SEQ ID NO 1035
<211> LENGTH: 21
<212> TYPE: DNA
<213> ORGANISM: Artificial sequence
<220> FEATURE:
<223> OTHER INFORMATION: Target sequence in the gene MIA

<400> SEQUENCE: 1035
cagcgttcag ggagattact a                                              21

<210> SEQ ID NO 1036
<211> LENGTH: 21
<212> TYPE: DNA
<213> ORGANISM: Artificial sequence
<220> FEATURE:
<223> OTHER INFORMATION: Target sequence in the gene OR8J1

<400> SEQUENCE: 1036
agctattgtg gtttcatctt a                                              21

<210> SEQ ID NO 1037
<211> LENGTH: 21
<212> TYPE: DNA
<213> ORGANISM: Artificial sequence
<220> FEATURE:
<223> OTHER INFORMATION: Target sequence in the gene FLJ44635

<400> SEQUENCE: 1037
aaggccctga gggcaaaggt a                                              21

<210> SEQ ID NO 1038
<211> LENGTH: 21
<212> TYPE: DNA
<213> ORGANISM: Artificial sequence
<220> FEATURE:
<223> OTHER INFORMATION: Target sequence in the gene SLC26A1

<400> SEQUENCE: 1038
cagcctctat acgtccttct t                                              21

<210> SEQ ID NO 1039
<211> LENGTH: 21
<212> TYPE: DNA
<213> ORGANISM: Artificial sequence
<220> FEATURE:

-continued

<223> OTHER INFORMATION: Target sequence in the gene CNN1

<400> SEQUENCE: 1039
aagatcaatg agtcaaccca a    21

<210> SEQ ID NO 1040
<211> LENGTH: 21
<212> TYPE: DNA
<213> ORGANISM: Artificial sequence
<220> FEATURE:
<223> OTHER INFORMATION: Target sequence in the gene C19orf23

<400> SEQUENCE: 1040
cacgacgtgg cagacgagga a    21

<210> SEQ ID NO 1041
<211> LENGTH: 21
<212> TYPE: DNA
<213> ORGANISM: Artificial sequence
<220> FEATURE:
<223> OTHER INFORMATION: Target sequence in the gene TRPM2

<400> SEQUENCE: 1041
caggcctatg tctgtgagga a    21

<210> SEQ ID NO 1042
<211> LENGTH: 10
<212> TYPE: PRT
<213> ORGANISM: Artificial sequence
<220> FEATURE:
<223> OTHER INFORMATION: Glycine stretch

<400> SEQUENCE: 1042

Gly Gly Gly Gly Ser Gly Gly Gly Gly Ser
1               5                   10

<210> SEQ ID NO 1043
<211> LENGTH: 5673
<212> TYPE: DNA
<213> ORGANISM: Artificial sequence
<220> FEATURE:
<223> OTHER INFORMATION: pCLS1853

<400> SEQUENCE: 1043
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag cttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780

```
gtaggcgtgt acggtgggag gtctatataa gcagagctct ctggctaact agagaaccca    840
ctgcttactg gcttatcgaa atgaattcga ctcactgttg ggagacccaa gctggctagt    900
taagctatca acaagtttgt acaaaaaagc aggctggcgc gcctacacag cggccttgcc    960
accatggcca ataccaaata taacaaagag ttcctgctgt acctggccgg ctttgtggac   1020
ggtgacggta gcatcatcgc tcagattaaa ccaaaccagt cttataagtt taaacatcag   1080
ctaagcttga cctttcaggt gactcaaaag acccagcgcc gttggtttct ggacaaacta   1140
gtggatgaaa ttggcgttgg ttacgtacgt gatcgcggat ccgtttccaa ctacatctta   1200
agcgaaatca agccgctgca caacttcctg actcaactgc agccgtttct gaaactgaaa   1260
cagaaacagg caaacctggt tctgaaaatt atcgaacagc tgccgtctgc aaaagaatcc   1320
ccggacaaat tcctggaagt ttgtacctgg gtggatcaga ttgcagctct gaacgattct   1380
aagacgcgta aaaccacttc tgaaaccgtt cgtgctgtgc tggacagcct gagcgagaag   1440
aagaaatcct ccccggcggc cgactgataa ctcgagcgct agcacccagc tttcttgtac   1500
aaagtggtga tctagagggc cgcggttcg aaggtaagcc tatccctaac cctctcctcg   1560
gtctcgattc tacgcgtacc ggttagtaat gagtttaaac gggggaggct aactgaaaca   1620
cggaaggaga cataccggga aggaacccgc gctatgacgg caataaaaag acagaataaa   1680
acgcacgggt gttgggtcgt ttgttcataa acgcggggtt cggtcccagg gctggcactc   1740
tgtcgatacc ccaccgagac cccattgggg ccaatacgcc cgcgtttctt ccttttcccc   1800
accccacccc caagttcgg gtgaaggccc agggctcgca gccaacgtcg gggcggcagg   1860
ccctgccata gcagatctgc gcagctgggg ctctaggggg tatccccacg cgccctgtag   1920
cggcgcatta agcgcggcgg gtgtggtggt tacgcgcagc gtgaccgcta cacttgccag   1980
cgccctagcg cccgctcctt tcgctttctt cccttccttt ctcgccacgt tcgccggctt   2040
tccccgtcaa gctctaaatc ggggcatccc tttagggttc cgatttagtg ctttacggca   2100
cctcgacccc aaaaaacttg attagggtga tggttcacgt agtgggccat cgccctgata   2160
gacggttttt cgccctttga cgttggagtc cacgttcttt aatagtggac tcttgttcca   2220
aactggaaca cactcaacc ctatctcggt ctattctttt gatttataag ggattttggg   2280
gatttcggcc tattggttaa aaaatgagct gatttaacaa aaatttaacg cgaattaatt   2340
ctgtggaatg tgtgtcagtt agggtgtgga aagtccccag gctccccagc aggcagaagt   2400
atgcaaagca tgcatctcaa ttagtcagca accaggtgtg gaaagtcccc aggctcccca   2460
gcaggcagaa gtatgcaaag catgcatctc aattagtcag caaccatagt cccgccccta   2520
actccgccca tcccgcccct aactccgccc agttccgccc attctccgcc ccatggctga   2580
ctaatttttt ttatttatgc agaggccgag gccgcctctg cctctgagct attccagaag   2640
tagtgaggag gcttttttgg aggcctaggc ttttgcaaaa agctcccggg agcttgtata   2700
tccattttcg gatctgatca gcacgtgttg acaattaatc atcggcatag tatatcggca   2760
tagtataata cgacaaggtg aggaactaaa ccatggccaa gcctttgtct caagaagaat   2820
ccaccctcat tgaaagagca acggctacaa tcaacagcat ccccatctct gaagactaca   2880
gcgtcgccag cgcagctctc tctagcgacg gccgcatctt cactggtgtc aatgtatatc   2940
attttactgg gggaccttgt gcagaactcg tggtgctggg cactgctgct gctgcggcag   3000
ctggcaacct gacttgtatc gtcgcgatcg gaaatgagaa caggggcatc ttgagcccct   3060
gcggacggtg ccgacaggtg cttctcgatc tgcatcctgg gatcaaagcc atagtgaagg   3120
acagtgatgg acagccgacg gcagttggga ttcgtgaatt gctgccctct ggttatgtgt   3180
```

```
gggagggcta agcacttcgt ggccgaggag caggactgac acgtgctacg agatttcgat    3240
tccaccgccg ccttctatga aaggttgggc ttcggaatcg ttttccggga cgccggctgg    3300
atgatcctcc agcgcgggga tctcatgctg gagttcttcg cccaccccaa cttgtttatt    3360
gcagcttata atggttacaa ataaagcaat agcatcacaa atttcacaaa taaagcattt    3420
ttttcactgc attctagttg tggtttgtcc aaactcatca atgtatctta tcatgtctgt    3480
ataccgtcga cctctagcta gagccttggcg taatcatggt catagctgtt tcctgtgtga    3540
aattgttatc cgctcacaat tccacacaac atacgagccg aagcataaa gtgtaaagcc    3600 tggggtgcct aatgagtgag ctaactcaca ttaattgcgt tgcgctcact gcccgctttc    3660
cagtcgggaa acctgtcgtg ccagctgcat taatgaatcg gccaacgcgc ggggagaggc    3720
ggtttgcgta ttgggcgctc ttccgcttcc tcgctcactg actcgctgcg ctcggtcgtt    3780
cggctgcggc gagcggtatc agctcactca aaggcggtaa tacggttatc cacagaatca    3840
ggggataacg caggaaagaa catgtgagca aaaggccagc aaaaggccag gaaccgtaaa    3900
aaggccgcgt tgctggcgtt tttccatagg ctccgccccc ctgacgagca tcacaaaaat    3960
cgacgctcaa gtcagaggtg gcgaaacccg acaggactat aaagatacca ggcgtttccc    4020
cctggaagct ccctcgtgcg ctctcctgtt ccgaccctgc cgcttaccgg atacctgtcc    4080
gcctttctcc cttcgggaag cgtggcgctt tctcatagct cacgctgtag gtatctcagt    4140
tcggtgtagg tcgttcgctc caagctgggc tgtgtgcacg aaccccccgt tcagcccgac    4200
cgctgcgcct tatccggtaa ctatcgtctt gagtccaacc cggtaagaca cgacttatcg    4260
ccactggcag cagccactgg taacaggatt agcagagcga ggtatgtagg cggtgctaca    4320
gagttcttga agtggtggcc taactacggc tacactagaa gaacagtatt tggtatctgc    4380
gctctgctga agccagttac cttcggaaaa agagttggta gctcttgatc cggcaaacaa    4440
accaccgctg gtagcggttt ttttgtttgc aagcagcaga ttacgcgcag aaaaaaagga    4500
tctcaagaag atcctttgat cttttctacg gggtctgacg ctcagtggaa cgaaaactca    4560
cgttaaggga ttttggtcat gagattatca aaaaggatct tcacctagat ccttttaaat    4620
taaaaatgaa gttttaaatc aatctaaagt atatatgagt aaacttggtc tgacagttac    4680
caatgcttaa tcagtgaggc acctatctca gcgatctgtc tatttcgttc atccatagtt    4740
gcctgactcc ccgtcgtgta gataactacg atacgggagg gcttaccatc tggccccagt    4800
gctgcaatga taccgcgaga cccacgctca ccggctccag atttatcagc aataaaccag    4860
ccagccggaa gggccgagcg cagaagtggt cctgcaactt tatccgcctc catccagtct    4920
attaattgtt gccgggaagc tagagtaagt agttcgccag ttaatagttt cgcaacgtt    4980 gttgccattg ctacaggcat cgtggtgtca cgctcgtcgt ttggtatggc ttcattcagc    5040
tccggttccc aacgatcaag gcgagttaca tgatccccca tgttgtgcaa aaaagcggtt    5100
agctccttcg gtcctccgat cgttgtcaga agtaagttgg ccgcagtgtt atcactcatg    5160
gttatggcag cactgcataa ttctcttact gtcatgccat ccgtaagatg cttttctgtg    5220
actggtgagt actcaaccaa gtcattctga gaatagtgta tgcggcgacc gagttgctct    5280
tgcccggcgt caatacggga taataccgcg ccacatagca gaactttaaa agtgctcatc    5340
attggaaaac gttcttcggg gcgaaaactc tcaaggatct taccgctgtt gagatccagt    5400
tcgatgtaac ccactcgtgc acccaactga tcttcagcat cttttacttt caccagcgtt    5460
tctgggtgag caaaaacagg aaggcaaaat gccgcaaaaa agggaataag ggcgacacgg    5520
```

```
aaatgttgaa tactcatact cttccttttt caatattatt gaagcattta tcagggttat    5580
tgtctcatga gcggatacat atttgaatgt atttagaaaa ataaacaaat aggggttccg    5640
cgcacatttc cccgaaaagt gccacctgac gtc                                 5673

<210> SEQ ID NO 1044
<211> LENGTH: 20
<212> TYPE: DNA
<213> ORGANISM: Artificial sequence
<220> FEATURE:
<223> OTHER INFORMATION: CMVfor primer

<400> SEQUENCE: 1044
cgcaaatggg cggtaggcgt                                                  20

<210> SEQ ID NO 1045
<211> LENGTH: 24
<212> TYPE: DNA
<213> ORGANISM: Artificial sequence
<220> FEATURE:
<223> OTHER INFORMATION: V5reverse primer

<400> SEQUENCE: 1045
cgtagaatcg agaccgagga gagg                                             24

<210> SEQ ID NO 1046
<211> LENGTH: 6922
<212> TYPE: DNA
<213> ORGANISM: Artificial sequence
<220> FEATURE:
<223> OTHER INFORMATION: pCLS8054

<400> SEQUENCE: 1046
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg    780
gtaggcgtgt acggtgggag gtctatataa gcagagctct ctggctaact agagaaccca    840
ctgcttactg gcttatcgaa atgaattcga ctcactgttg ggagacccaa gctggctagt    900
taagctatca caagttttgta caaaaaagca ggctggcgcg cctacacagc ggccttgcca    960
ccatgggttc cgaggcaccc cgggccgaga cctttgtctt cctggacctg gaagccactg    1020
ggctccccag tgtggagccc gagattgccg agctgtccct ctttgctgtc caccgctcct    1080
ccctggagaa cccggagcac gacgagtctg gtgcccctagt attgccccgg gtcctggaca    1140
agctcacgct gtgcatgtgc ccggagcgcc ccttcactgc caaggccagc gagatcaccg    1200
```

```
gcctgagcag tgagggcctg gcgcgatgcc ggaaggctgg ctttgatggc gccgtggtgc   1260
ggacgctgca ggccttcctg agccgccagg cagggcccat ctgccttgtg gcccacaatg   1320
gctttgatta tgatttcccc ctgctgtgtg ccgagctgcg gcgcctgggt gcccgcctgc   1380
cccgggacac tgtctgcctg gacacgctgc cggccctgcg gggcctggac cgcgcccaca   1440
gccacggcac ccgggcccgg ggcgccagg gttacagcct cggcagcctc ttccaccgct   1500
acttccgggc agagccaagc gcagcccact cagccgaggg cgacgtgcac accctgctcc   1560
tgatcttcct gcaccgcgcc gcagagctgc tcgcctgggc cgatgagcag gcccgtgggt   1620
gggcccacat cgagcccatg tacttgccgc ctgatgaccc cagcctggag gcgggaggtg   1680
gaggttctgg aggtggaggt tccaatacca aatataacga agagttcctg ctgtacctgg   1740
ccggctttgt ggacgctgac ggtagcatca tcgctcagat taaaccaaga cagtctcgga   1800
agtttaaaca tgagctaagc ttgactttg atgtgactca aaagacccag cgccgttggt    1860
ttctggacaa gctagtggat gaaattggcg ttggttacgt atatgattct ggatccgttt   1920
cctattacca gttaagcgaa atcaagccgc tgcacaactt cctgactcaa ctgcagccgt   1980
ttctggaact gaaacagaaa caggcaaacc tggttctgaa aattatcgaa cagctgccgt   2040
ctgcaaaaga tccccggcc aaattcctgg aagtttgtac ctgggtggat cagattgcag    2100
ctctgaacga ttctaagacg cgtaaaacca cttctgaaac cgttcgtgct gtgctggata   2160
gcctgagcga gaagaagaaa tcctccccgg cggccggtgg atctgataag tataatcagg   2220
ctctgtctaa atacaaccaa gcactgtcca agtacaatca ggccctgtct ggtggaggcg   2280
gttccaacaa aaagttcctg ctgtatcttg ctggatttgt ggatggtgat ggctccatca   2340
ttgctcagat aaaaccacgt caagggtata agttcaaaca ccagtctctcc ttgacttttc   2400 aggtcactca gaagacacaa agaaggtggt tcttggacaa attggttgat cgtattggtg   2460
tgggctatgt cgctgaccgt ggctctgtgt cagactaccg cctgtctgaa attaagcctc   2520
ttcataactt tctcacccaa ctgcaaccct tcttgaagct caaacagaag caagcaaatc   2580
tggttttgaa aatcatcgag caactgccat ctgccaagga gtccctggac aagtttcttg   2640
aagtgtgtac ttgggtggat cagattgctg ccttgaatga ctccaagacc agaaaaacca   2700
cctctgagac tgtgagggca gttctggata gcctctctga agagaaaaag tcctctcctt   2760
agccatggcc cgcggttcga aggtaagcct atccctaacc ctctcctcgg tctcgattct   2820
acgcgtaccg gttagtaatg agtttaaacg ggggaggcta actgaaacac ggaaggagac   2880
aataccggaa ggaacccgcg ctatgacggc aataaaaaga cagaataaaa cgcacgggtg   2940
ttgggtcgtt tgttcataaa cgcggggttc ggtcccaggg ctggcactct gtcgataccc   3000
caccgagacc ccattggggc caatacgccc gcgtttcttc cttttcccca ccccaccccc   3060
caagttcggg tgaaggccca gggctcgcag ccaacgtcgg ggcggcaggc cctgccatag   3120
cagatctgcg cagctgggc tctaggggt atccccacgc gccctgtagc ggcgcattaa     3180
gcgcggcggg tgtggtggtt acgcgcagcg tgaccgctac acttgccagc gccctagcgc   3240
ccgctccttt cgctttcttc ccttcctttc tcgccacgtt cgccggcttt ccccgtcaag   3300
ctctaaatcg gggcatccct ttagggttcc gatttagtgc tttacggcac ctcgacccca   3360
aaaaacttga ttagggtgat ggttcacgta gtgggccatc gccctgatag acggtttttc   3420
gccctttgac gttggagtcc acgttcttta atagtggact cttgttccaa actggaacaa   3480
cactcaaccc tatctcggtc tattcttttg atttataagg gattttgggg atttcggcct   3540
```

```
attggttaaa aaatgagctg atttaacaaa aatttaacgc gaattaattc tgtggaatgt    3600
gtgtcagtta gggtgtggaa agtccccagg ctccccagca ggcagaagta tgcaaagcat    3660
gcatctcaat tagtcagcaa ccaggtgtgg aaagtcccca ggctcccccag caggcagaag   3720 tatgcaaagc atgcatctca attagtcagc aaccatagtc ccgcccctaa ctccgcccat    3780 cccgcccta actccgccca gttccgccca ttctccgccc catggctgac taattttttt     3840
tatttatgca gaggccgagg ccgcctctgc ctctgagcta ttccagaagt agtgaggagg    3900
cttttttgga ggcctaggct tttgcaaaaa gctcccggga gcttgtatat ccattttcgg    3960
atctgatcag cacgtgttga caattaatca tcggcatagt atatcggcat agtataatac    4020
gacaaggtga ggaactaaac catggccaag cctttgtctc aagaagaatc caccctcatt    4080
gaaagagcaa cggctacaat caacagcatc cccatctctg aagactacag cgtcgccagc    4140
gcagctctct ctagcgacgg ccgcatcttc actggtgtca atgtatatca ttttactggg    4200
ggaccttgtg cagaactcgt ggtgctgggc actgctgctg ctgcggcagc tgcaacctg     4260 acttgtatcg tcgcgatcgg aaatgagaac aggggcatct tgagcccctg cggacggtgc    4320
cgacaggtgc ttctcgatct gcatcctggg atcaaagcca tagtgaagga cagtgatgga    4380
cagccgacgg cagttgggat tcgtgaattg ctgccctctg gttatgtgtg ggagggctaa    4440
gcacttcgtg gccgaggagc aggactgaca cgtgctacga gatttcgatt ccaccgccgc    4500
cttctatgaa aggttgggct tcggaatcgt tttccgggac gccggctgga tgatcctcca    4560
gcgcggggat tcatgctgg agttcttcgc ccaccccaac ttgtttattg cagcttataa      4620
tggttacaaa taaagcaata gcatcacaaa tttcacaaat aaagcatttt tttcactgca    4680
ttctagttgt ggtttgtcca aactcatcaa tgtatcttat catgtctgta taccgtcgac    4740
ctctagctag agcttggcgt aatcatggtc atagctgttt cctgtgtgaa attgttatcc    4800
gctcacaatt ccacacaaca tacgagccgg aagcataaag tgtaaagcct ggggtgccta    4860
atgagtgagc taactcacat taattgcgtt gcgctcactg cccgctttcc agtcgggaaa    4920
cctgtcgtgc cagctgcatt aatgaatcgg ccaacgcgcg gggagaggcg gtttgcgtat    4980
tgggcgctct tccgcttcct cgctcactga ctcgctgcgc tcggtcgttc ggctgcggcg    5040
agcggtatca gctcactcaa aggcggtaat acggttatcc acagaatcag gggataacgc    5100
aggaaagaac atgtgagcaa aaggccagca aaaggccagg aaccgtaaaa aggccgcgtt    5160
gctggcgttt ttccataggc tccgcccccc tgacgagcat cacaaaaatc gacgctcaag    5220
tcagaggtgg cgaaacccga caggactata aagataccag gcgtttcccc ctggaagctc    5280
cctcgtgcgc tctcctgttc cgaccctgcc gcttaccgga tacctgtccg cctttctccc    5340
ttcgggaagc gtggcgcttt ctcatagctc acgctgtagg tatctcagtt cggtgtaggt    5400
cgttcgctcc aagctgggct gtgtgcacga accccccgtt cagcccgacc gctgcgcctt    5460
atccggtaac tatcgtcttg agtccaaccc ggtaagacac gacttatcgc cactggcagc    5520
agccactggt aacaggatta gcagagcgag gtatgtaggc ggtgctacag agttcttgaa    5580
gtggtggcct aactacggct acactagaag aacagtattt ggtatctgcg ctctgctgaa    5640
gccagttacc ttcggaaaaa gagttggtag ctcttgatcc ggcaaacaaa ccaccgctgg    5700
tagcggtttt tttgtttgca agcagcagat tacgcgcaga aaaaaaggat ctcaagaaga    5760
tcctttgatc ttttctacgg ggtctgacgc tcagtggaac gaaaactcac gttaagggat    5820
tttggtcatg agattatcaa aaaggatctt cacctagatc cttttaaatt aaaaatgaag    5880
ttttaaatca atctaaagta tatatgagta aacttggtct gacagttacc aatgcttaat    5940
```

```
cagtgaggca cctatctcag cgatctgtct atttcgttca tccatagttg cctgactccc    6000
cgtcgtgtag ataactacga tacgggaggg cttaccatct ggccccagtg ctgcaatgat    6060
accgcgagac ccacgctcac cggctccaga tttatcagca ataaaccagc cagccggaag    6120
ggccgagcgc agaagtggtc ctgcaacttt atccgcctcc atccagtcta ttaattgttg    6180
ccgggaagct agagtaagta gttcgccagt taatagtttg cgcaacgttg ttgccattgc    6240
tacaggcatc gtggtgtcac gctcgtcgtt tggtatggct tcattcagct ccggttccca    6300
acgatcaagg cgagttacat gatccccat gttgtgcaaa aaagcggtta gctccttcgg    6360
tcctccgatc gttgtcagaa gtaagttggc cgcagtgtta tcactcatgg ttatggcagc    6420
actgcataat tctcttactg tcatgccatc cgtaagatgc ttttctgtga ctggtgagta    6480
ctcaaccaag tcattctgag aatagtgtat gcggcgaccg agttgctctt gcccggcgtc    6540
aatacgggat aataccgcgc cacatagcag aactttaaaa gtgctcatca ttggaaaacg    6600
ttcttcgggg cgaaaactct caaggatctt accgctgttg agatccagtt cgatgtaacc    6660
cactcgtgca cccaactgat cttcagcatc ttttactttc accagcgttt ctgggtgagc    6720
aaaaacagga aggcaaaatg ccgcaaaaaa gggaataagg gcgacacgga aatgttgaat    6780
actcatactc ttcctttttc aatattattg aagcatttat cagggttatt gtctcatgag    6840
cggatacata tttgaatgta tttagaaaaa taaacaaata ggggttccgc gcacatttcc    6900
ccgaaaagtg ccacctgacg tc                                             6922

<210> SEQ ID NO 1047
<211> LENGTH: 48
<212> TYPE: DNA
<213> ORGANISM: Artificial sequence
<220> FEATURE:
<223> OTHER INFORMATION: Link10GSFor primer

<400> SEQUENCE: 1047
ggaggttctg gaggtggagg ttccaatacc aaatataacg aagagttc                 48

<210> SEQ ID NO 1048
<211> LENGTH: 51
<212> TYPE: DNA
<213> ORGANISM: Artificial sequence
<220> FEATURE:
<223> OTHER INFORMATION: Link10TrexRev primer

<400> SEQUENCE: 1048
acctccacct ccagaacctc cacctcccgc ctccaggctg gggtcatcag g              51

<210> SEQ ID NO 1049
<211> LENGTH: 599
<212> TYPE: PRT
<213> ORGANISM: Artificial sequence
<220> FEATURE:
<223> OTHER INFORMATION: Trex2/SC_GS amino acid sequence

<400> SEQUENCE: 1049
```

Met Gly Ser Glu Ala Pro Arg Ala Glu Thr Phe Val Phe Leu Asp Leu
1               5                   10                  15

Glu Ala Thr Gly Leu Pro Ser Val Glu Pro Glu Ile Ala Glu Leu Ser
            20                  25                  30

Leu Phe Ala Val His Arg Ser Ser Leu Glu Asn Pro Glu His Asp Glu
        35                  40                  45

Ser Gly Ala Leu Val Leu Pro Arg Val Leu Asp Lys Leu Thr Leu Cys

```
            50                  55                  60
Met Cys Pro Glu Arg Pro Phe Thr Ala Lys Ala Ser Glu Ile Thr Gly
 65                  70                  75                  80

Leu Ser Ser Glu Gly Leu Ala Arg Cys Arg Lys Ala Gly Phe Asp Gly
                 85                  90                  95

Ala Val Val Arg Thr Leu Gln Ala Phe Leu Ser Arg Gln Ala Gly Pro
                100                 105                 110

Ile Cys Leu Val Ala His Asn Gly Phe Asp Tyr Asp Phe Pro Leu Leu
            115                 120                 125

Cys Ala Glu Leu Arg Arg Leu Gly Ala Arg Leu Pro Arg Asp Thr Val
130                 135                 140

Cys Leu Asp Thr Leu Pro Ala Leu Arg Gly Leu Asp Arg Ala His Ser
145                 150                 155                 160

His Gly Thr Arg Ala Arg Gly Arg Gln Gly Tyr Ser Leu Gly Ser Leu
                165                 170                 175

Phe His Arg Tyr Phe Arg Ala Glu Pro Ser Ala Ala His Ser Ala Glu
            180                 185                 190

Gly Asp Val His Thr Leu Leu Ile Phe Leu His Arg Ala Ala Glu
            195                 200                 205

Leu Leu Ala Trp Ala Asp Glu Gln Ala Arg Gly Trp Ala His Ile Glu
    210                 215                 220

Pro Met Tyr Leu Pro Pro Asp Pro Ser Leu Glu Ala Gly Gly
225                 230                 235                 240

Gly Ser Gly Gly Gly Ser Asn Thr Lys Tyr Asn Glu Glu Phe Leu
                245                 250                 255

Leu Tyr Leu Ala Gly Phe Val Asp Ala Asp Gly Ser Ile Ile Ala Gln
            260                 265                 270

Ile Lys Pro Arg Gln Ser Arg Lys Phe Lys His Glu Leu Ser Leu Thr
            275                 280                 285

Phe Asp Val Thr Gln Lys Thr Gln Arg Arg Trp Phe Leu Asp Lys Leu
    290                 295                 300

Val Asp Glu Ile Gly Val Gly Tyr Val Tyr Asp Ser Gly Ser Val Ser
305                 310                 315                 320

Tyr Tyr Gln Leu Ser Glu Ile Lys Pro Leu His Asn Phe Leu Thr Gln
                325                 330                 335

Leu Gln Pro Phe Leu Glu Leu Lys Gln Lys Gln Ala Asn Leu Val Leu
            340                 345                 350

Lys Ile Ile Glu Gln Leu Pro Ser Ala Lys Glu Ser Pro Ala Lys Phe
            355                 360                 365

Leu Glu Val Cys Thr Trp Val Asp Gln Ile Ala Ala Leu Asn Asp Ser
    370                 375                 380

Lys Thr Arg Lys Thr Thr Ser Glu Thr Val Arg Ala Val Leu Asp Ser
385                 390                 395                 400

Leu Ser Glu Lys Lys Lys Ser Ser Pro Ala Ala Gly Gly Ser Asp Lys
                405                 410                 415

Tyr Asn Gln Ala Leu Ser Lys Tyr Asn Gln Ala Leu Ser Lys Tyr Asn
            420                 425                 430

Gln Ala Leu Ser Gly Gly Gly Ser Asn Lys Lys Phe Leu Leu Tyr
            435                 440                 445

Leu Ala Gly Phe Val Asp Gly Asp Gly Ser Ile Ile Ala Gln Ile Lys
    450                 455                 460

Pro Arg Gln Gly Tyr Lys Phe Lys His Gln Leu Ser Leu Thr Phe Gln
465                 470                 475                 480
```

Val Thr Gln Lys Thr Gln Arg Arg Trp Phe Leu Asp Lys Leu Val Asp
            485                 490                 495

Arg Ile Gly Val Gly Tyr Val Ala Asp Arg Gly Ser Val Ser Asp Tyr
            500                 505                 510

Arg Leu Ser Glu Ile Lys Pro Leu His Asn Phe Leu Thr Gln Leu Gln
            515                 520                 525

Pro Phe Leu Lys Leu Lys Gln Lys Gln Ala Asn Leu Val Leu Lys Ile
            530                 535                 540

Ile Glu Gln Leu Pro Ser Ala Lys Glu Ser Leu Asp Lys Phe Leu Glu
545                 550                 555                 560

Val Cys Thr Trp Val Asp Gln Ile Ala Ala Leu Asn Asp Ser Lys Thr
            565                 570                 575

Arg Lys Thr Thr Ser Glu Thr Val Arg Ala Val Leu Asp Ser Leu Ser
            580                 585                 590

Glu Lys Lys Lys Ser Ser Pro
            595

<210> SEQ ID NO 1050
<211> LENGTH: 236
<212> TYPE: PRT
<213> ORGANISM: Artificial sequence
<220> FEATURE:
<223> OTHER INFORMATION: 236 amino acids Trex2 functional version

<400> SEQUENCE: 1050

Met Ser Glu Ala Pro Arg Ala Glu Thr Phe Val Phe Leu Asp Leu Glu
1               5                   10                  15

Ala Thr Gly Leu Pro Ser Val Glu Pro Glu Ile Ala Glu Leu Ser Leu
            20                  25                  30

Phe Ala Val His Arg Ser Ser Leu Glu Asn Pro Glu His Asp Glu Ser
            35                  40                  45

Gly Ala Leu Val Leu Pro Arg Val Leu Asp Lys Leu Thr Leu Cys Met
            50                  55                  60

Cys Pro Glu Arg Pro Phe Thr Ala Lys Ala Ser Glu Ile Thr Gly Leu
65                  70                  75                  80

Ser Ser Glu Gly Leu Ala Arg Cys Arg Lys Ala Gly Phe Asp Gly Ala
            85                  90                  95

Val Val Arg Thr Leu Gln Ala Phe Leu Ser Arg Gln Ala Gly Pro Ile
            100                 105                 110

Cys Leu Val Ala His Asn Gly Phe Asp Tyr Asp Phe Pro Leu Leu Cys
            115                 120                 125

Ala Glu Leu Arg Arg Leu Gly Ala Arg Leu Pro Arg Asp Thr Val Cys
            130                 135                 140

Leu Asp Thr Leu Pro Ala Leu Arg Gly Leu Asp Arg Ala His Ser His
145                 150                 155                 160

Gly Thr Arg Ala Arg Gly Arg Gln Gly Tyr Ser Leu Gly Ser Leu Phe
            165                 170                 175

His Arg Tyr Phe Arg Ala Glu Pro Ser Ala Ala His Ser Ala Glu Gly
            180                 185                 190

Asp Val His Thr Leu Leu Leu Ile Phe Leu His Arg Ala Ala Glu Leu
            195                 200                 205

Leu Ala Trp Ala Asp Glu Gln Ala Arg Gly Trp Ala His Ile Glu Pro
            210                 215                 220

Met Tyr Leu Pro Pro Asp Asp Pro Ser Leu Glu Ala
225                 230                 235

<210> SEQ ID NO 1051
<211> LENGTH: 279
<212> TYPE: PRT
<213> ORGANISM: Artificial sequence
<220> FEATURE:
<223> OTHER INFORMATION: Trex2 amino acid sequence

<400> SEQUENCE: 1051

```
Met Gly Arg Ala Gly Ser Pro Leu Pro Arg Ser Ser Trp Pro Arg Met
1               5                   10                  15

Asp Asp Cys Gly Ser Arg Ser Arg Cys Ser Pro Thr Leu Cys Ser Ser
            20                  25                  30

Leu Arg Thr Cys Tyr Pro Arg Gly Asn Ile Thr Met Ser Glu Ala Pro
        35                  40                  45

Arg Ala Glu Thr Phe Val Phe Leu Asp Leu Glu Ala Thr Gly Leu Pro
    50                  55                  60

Ser Val Glu Pro Glu Ile Ala Glu Leu Ser Leu Phe Ala Val His Arg
65                  70                  75                  80

Ser Ser Leu Glu Asn Pro Glu His Asp Glu Ser Gly Ala Leu Val Leu
                85                  90                  95

Pro Arg Val Leu Asp Lys Leu Thr Leu Cys Met Cys Pro Glu Arg Pro
            100                 105                 110

Phe Thr Ala Lys Ala Ser Glu Ile Thr Gly Leu Ser Ser Glu Gly Leu
        115                 120                 125

Ala Arg Cys Arg Lys Ala Gly Phe Asp Gly Ala Val Val Arg Thr Leu
    130                 135                 140

Gln Ala Phe Leu Ser Arg Gln Ala Gly Pro Ile Cys Leu Val Ala His
145                 150                 155                 160

Asn Gly Phe Asp Tyr Asp Phe Pro Leu Leu Cys Ala Glu Leu Arg Arg
                165                 170                 175

Leu Gly Ala Arg Leu Pro Arg Asp Thr Val Cys Leu Asp Thr Leu Pro
            180                 185                 190

Ala Leu Arg Gly Leu Asp Arg Ala His Ser His Gly Thr Arg Ala Arg
        195                 200                 205

Gly Arg Gln Gly Tyr Ser Leu Gly Ser Leu Phe His Arg Tyr Phe Arg
    210                 215                 220

Ala Glu Pro Ser Ala Ala His Ser Ala Glu Gly Asp Val His Thr Leu
225                 230                 235                 240

Leu Leu Ile Phe Leu His Arg Ala Ala Glu Leu Leu Ala Trp Ala Asp
                245                 250                 255

Glu Gln Ala Arg Gly Trp Ala His Ile Glu Pro Met Tyr Leu Pro Pro
            260                 265                 270

Asp Asp Pro Ser Leu Glu Ala
        275
```

<210> SEQ ID NO 1052
<211> LENGTH: 5428
<212> TYPE: DNA
<213> ORGANISM: Artificial sequence
<220> FEATURE:
<223> OTHER INFORMATION: pCLS0003

<400> SEQUENCE: 1052
gacggatcgg gagatctccc gatccctat ggtgcactct cagtacaatc tgctctgatg    60
ccgcatagtt aagccagtat ctgctccctg cttgtgtgtt ggaggtcgct gagtagtgcg   120

```
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattctgc    960
agatatccag cacagtggcg gccgctcgag tctagagggc ccgtttaaac ccgctgatca   1020
gcctcgactg tgccttctag ttgccagcca tctgttgttt gcccctcccc cgtgccttcc   1080
ttgaccctgg aaggtgccac tcccactgtc tttcctaata aaatgagga aattgcatcg   1140
cattgtctga gtaggtgtca ttctattctg gggggtgggg tggggcagga cagcaagggg   1200
gaggattggg aagacaatag caggcatgct ggggatgcgg tgggctctat ggcttctgag   1260
gcggaaagaa ccagctgggg ctctaggggg tatccccacg cgccctgtag cggcgcatta   1320
agcgcggcgg gtgtggtggt tacgcgcagc gtgaccgcta cacttgccag cgccctagcg   1380
cccgctcctt tcgctttctt cccttccttt ctcgccacgt tcgccggctt tccccgtcaa   1440
gctctaaatc gggggctccc tttagggttc cgatttagtg ctttacggca cctcgacccc   1500
aaaaaacttg attagggtga tggttcacgt agtgggccat cgccctgata cggttttt     1560
cgcccttga cgttggagtc acgttctttt aatagtggac tcttgttcca aactggaaca   1620
acactcaacc ctatctcggt ctattctttt gatttataag gattttgcc gatttcggcc   1680
tattggttaa aaaatgagct gatttaacaa aaatttaacg cgaattaatt ctgtggaatg   1740
tgtgtcagtt agggtgtgga agtccccag gctccccagc aggcagaagt atgcaaagca   1800
tgcatctcaa ttagtcagca accaggtgtg gaaagtcccc aggctcccca gcaggcagaa   1860
gtatgcaaag catgcatctc aattagtcag caaccatagt cccgccccta actccgccca   1920
tcccgcccct aactccgccc agttccgccc attctccgcc ccatggctga ctaatttttt   1980
ttatttatgc agaggccgag gccgcctctg cctctgagct attccagaag tagtgaggag   2040
gcttttttgg aggcctaggc ttttgcaaaa agctcccggg agcttgtata tccattttcg   2100
gatctgatca agagacagga tgaggatcgt ttcgcatgat tgaacaagat ggattgcacg   2160
caggttctcc ggccgcttgg gtggagaggc tattcggcta tgactgggca caacagacaa   2220
tcggctgctc tgatgccgcc gtgttccggc tgtcagcgca gggcgcccg gttcttttg   2280
tcaagaccga cctgtccggt gccctgaatg aactgcagga cgaggcagcg cggctatcgt   2340
ggctggccac gacgggcgtt ccttgcgcag ctgtgctcga cgttgtcact gaagcgggaa   2400
gggactggct gctattgggc gaagtgccgg gcaggatct cctgtcatct caccttgctc   2460
ctgccgagaa agtatccatc atggctgatg caatgcggcg gctgcatacg cttgatccgg   2520
```

```
ctacctgccc attcgaccac caagcgaaac atcgcatcga gcgagcacgt actcggatgg    2580
aagccggtct tgtcgatcag gatgatctgg acgaagagca tcaggggctc gcgccagccg    2640
aactgttcgc caggctcaag gcgcgcatgc ccgacggcga ggatctcgtc gtgacccatg    2700
gcgatgcctg cttgccgaat atcatggtgg aaaatggccg cttttctgga ttcatcgact    2760
gtggccggct gggtgtggcg gaccgctatc aggacatagc gttggctacc cgtgatattg    2820
ctgaagagct tggcggcgaa tgggctgacc gcttcctcgt gctttacggt atcgccgctc    2880
ccgattcgca gcgcatcgcc ttctatcgcc ttcttgacga gttcttctga gcgggactct    2940
ggggttcgaa atgaccgacc aagcgacgcc caacctgcca tcgcgagatt cgattccac    3000 cgccgccttc tatgaaaggt tgggcttcgg aatcgttttc cgggacgccg gctggatgat    3060
cctccagcgc ggggatctca tgctggagtt cttcgcccac cccaacttgt ttattgcagc    3120
ttataatggt tacaaataaa gcaatagcat cacaaatttc acaaataaag catttttttc    3180
actgcattct agttgtggtt tgtccaaact catcaatgta tcttatcatg tctgtatacc    3240
gtcgacctct agctagagct tggcgtaatc atggtcatag ctgtttcctg tgtgaaattg    3300
ttatccgctc acaattccac acaacatacg agccggaagc ataaagtgta aagcctgggg    3360
tgcctaatga gtgagctaac tcacattaat tgcgttgcgc tcactgcccg ctttccagtc    3420
gggaaacctg tcgtgccagc tgcattaatg aatcggccaa cgcgcgggga gaggcggttt    3480
gcgtattggg cgctcttccg cttcctcgct cactgactcg ctgcgctcgg tcgttcggct    3540
gcggcgagcg gtatcagctc actcaaaggc ggtaatacgg ttatccacag aatcagggga    3600
taacgcagga aagaacatgt gagcaaaagg ccagcaaaag gccaggaacc gtaaaaaggc    3660
cgcgttgctg gcgttttttcc ataggctccg ccccccctgac gagcatcaca aaaatcgacg    3720
ctcaagtcag aggtggcgaa acccgacagg actataaaga taccaggcgt ttccccctgg    3780
aagctccctc gtgcgctctc ctgttccgac cctgccgctt accggatacc tgtccgcctt    3840
tctcccttcg ggaagcgtgg cgctttctca tagctcacgc tgtaggtatc tcagttcggt    3900
gtaggtcgtt cgctccaagc tgggctgtgt gcacgaaccc cccgttcagc ccgaccgctg    3960
cgccttatcc ggtaactatc gtcttgagtc aacccggta agacacgact tatcgccact    4020
ggcagcagcc actggtaaca ggattagcag agcgaggtat gtaggcggtg ctacagagtt    4080
cttgaagtgg tggcctaact acggctacac tagaagaaca gtatttggta tctgcgctct    4140
gctgaagcca gttaccttcg gaaaaagagt tggtagctct tgatccggca aacaaaccac    4200
cgctggtagc ggttttttttg tttgcaagca gcagattacg cgcagaaaaa aaggatctca    4260
agaagatcct ttgatctttt ctacggggtc tgacgctcag tggaacgaaa actcacgtta    4320
agggattttg gtcatgagat tatcaaaaag gatcttcacc tagatccttt taaattaaaa    4380
atgaagtttt aaatcaatct aaagtatata tgagtaaact tggtctgaca gttaccaatg    4440
cttaatcagt gaggcaccta tctcagcgat ctgtctattt cgttcatcca tagttgcctg    4500
actccccgtc gtgtagataa ctacgatacg ggagggctta ccatctggcc ccagtgctgc    4560
aatgataccg cgagacccac gctcaccggc tccagattta tcagcaataa accagccagc    4620
cggaagggcc gagcgcagaa gtggtcctgc aactttatcc gcctccatcc agtctattaa    4680
ttgttgccgg gaagctagag taagtagttc gccagttaat agtttgcgca acgttgttgc    4740
cattgctaca ggcatcgtgg tgtcacgctc gtcgtttggt atggcttcat tcagctccgg    4800
ttcccaacga tcaaggcgag ttacatgatc ccccatgttg tgcaaaaaag cggttagctc    4860
```

```
cttcggtcct ccgatcgttg tcagaagtaa gttggccgca gtgttatcac tcatggttat    4920
ggcagcactg cataattctc ttactgtcat gccatccgta agatgctttt ctgtgactgg    4980
tgagtactca accaagtcat tctgagaata gtgtatgcgg cgaccgagtt gctcttgccc    5040
ggcgtcaata cgggataata ccgcgccaca tagcagaact ttaaaagtgc tcatcattgg    5100
aaaacgttct cggggcgaaa actctcaag gatcttaccg ctgttgagat ccagttcgat     5160
gtaacccact cgtgcaccca actgatcttc agcatctttt actttcacca gcgtttctgg    5220
gtgagcaaaa acaggaaggc aaaatgccgc aaaaaaggga ataagggcga cacggaaatg    5280
ttgaatactc atactcttcc tttttcaata ttattgaagc atttatcagg gttattgtct    5340
catgagcgga tacatatttg aatgtattta gaaaaataaa caataggggt tccgcgcac    5400 atttccccga aaagtgccac ctgacgtc                                       5428

<210> SEQ ID NO 1053
<211> LENGTH: 64
<212> TYPE: DNA
<213> ORGANISM: Artificial sequence
<220> FEATURE:
<223> OTHER INFORMATION: GS locus specific forward primer
<220> FEATURE:
<221> NAME/KEY: misc_feature
<222> LOCATION: (31)..(40)
<223> OTHER INFORMATION: n at positions 31-40 is a or c or t or g

<400> SEQUENCE: 1053
ccatctcatc cctgcgtgtc tccgactcag nnnnnnnnnn gctctctggc taactagaga    60
accc                                                                 64

<210> SEQ ID NO 1054
<211> LENGTH: 53
<212> TYPE: DNA
<213> ORGANISM: Artificial sequence
<220> FEATURE:
<223> OTHER INFORMATION: GS locus specific reverse primer

<400> SEQUENCE: 1054
cctatcccct gtgtgccttg gcagtctcag tcgatcagca cgggcacgat gcc           53

<210> SEQ ID NO 1055
<211> LENGTH: 7709
<212> TYPE: DNA
<213> ORGANISM: Artificial sequence
<220> FEATURE:
<223> OTHER INFORMATION: pCLS9573

<400> SEQUENCE: 1055
gacggatcgg gagatctccc gatccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
```

```
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa atgaattcga ctcactgttg ggagacccaa gctggctagt    900
taagctatca caagtttgta caaaaaagca ggctggcgcg cctacacagc ggccttgcca    960
ccatgggttc cgaggcaccc cgggccgaga cctttgtctt cctggacctg aagccactg    1020 ggctccccag tgtggagccc gagattgccg agctgtccct ctttgctgtc caccgctcct    1080
ccctggagaa cccggagcac gacgagtctg gtgccctagt attgccccgg gtcctggaca    1140
agctcacgct gtgcatgtgc ccggagcgcc ccttcactgc caaggccagc gagatcaccg    1200
gcctgagcag tgagggcctg gcgcgatgcc ggaaggctgg cttttgatggc gccgtggtgc    1260 ggacgctgca ggccttcctg agccgccagg cagggcccat ctgccttgtg cccacaatg    1320 gctttgatta tgatttcccc ctgctgtgtg ccgagctgcg gcgcctgggt gcccgcctgc    1380
cccgggacac tgtctgcctg gacacgctgc cggccctgcg gggcctggac cgcgcccaca    1440
gccacggcac ccgggcccgg ggccgccagg gttacagcct cggcagcctc ttccaccgct    1500
acttccgggc agagccaagc gcagcccact cagccgaggg cgacgtgcac accctgctcc    1560
tgatcttcct gcaccgcgcc gcagagctgc tcgcctgggc cgatgagcag gcccgtgggt    1620
gggcccacat cgagcccatg tacttgccgc ctgatgaccc cagccggag gcgactcctc    1680 cacagaccgg tctggatgtt ccttactccg aggcaccccg ggccgagacc tttgtcttcc    1740
tggacctgga agccactggg ctccccagtg tggagcccga gattgccgag ctgtccctct    1800
ttgctgtcca ccgctcctcc ctggagaacc cggagcacga cgagtctggt gccctagtat    1860
tgccccgggt cctggacaag ctcacgctgt gcatgtgccc ggagcgcccc ttcactgcca    1920
aggccagcga gatcaccggc ctgagcagtg agggcctggc gcgatgccgg aaggctggct    1980
ttgatggcgc cgtggtgcgg acgctgcagg ccttcctgag ccgccaggca gggcccatct    2040
gccttgtggc ccacaatggc tttgattatg atttccccct gctgtgtgcc gagctgcggc    2100
gcctgggtgc ccgcctgccc cgggacactg tctgcctgga cacgctgccg gccctgcggg    2160
gcctggaccg cgcccacagc cacggcaccc gggcccgggg ccgccagggt tacagcctcg    2220
gcagcctctt ccaccgctac ttccgggcag agccaagcgc agcccactca gccgagggcg    2280
acgtgcacac cctgctcctg atcttcctgc accgcgccgc agagctgctc gcctgggccg    2340
atgagcaggc ccgtgggtgg gcccacatcg agcccatgta cttgccgcct gatgacccca    2400
gcctggaggc ggccgacgga ggtggaggtt ctggaggtgg aggttccaat accaaatata    2460
acgaagagtt cctgctgtac ctggccggct ttgtggacgg tgacggtagc atcatcgctc    2520
agattaatcc aaaccagtct tctaagttta acatcgtct acgtttgacc ttttatgtga    2580
ctcaaaagac ccagcgccgt tggtttctgg acaaactagt ggatgaaatt ggcgttggtt    2640
acgtacgtga ttctggatcc gtttcccagt acgttttaag cgaaatcaag ccgctgcaca    2700
acttcctgac tcaactgcag ccgttctctgg aactgaaaca gaaacaggca aacctggttc    2760
tgaaaattat cgaacagctg ccgtctgcaa agaatccccc ggacaaattc ctggaagttt    2820
gtacctgggt ggatcagatt gcagctctga acgattctaa gacgcgtaaa accacttctg    2880
aaaccgttcg tgctgtgctg gacagcctga gcgggaagaa gaaatcctcc ccggcggccg    2940
```

```
gtggatctga taagtatoat caggctctgt ctaaatacaa ccaagcactg tccaagtaca   3000
atcaggccct gtctggtgga ggcggttcca acaaaaagtt cctgctgtat cttgctggat   3060
ttgtggattc tgatggctcc atcattgctc agataaaacc acgtcaatct aacaagttca   3120
aacaccagct ctccttgact tttgcagtca ctcagaagac acaaagaagg tggttcttgg   3180
acaaattggt tgataggatt ggtgtgggct atgtctatga cagtggctct gtgtcagact   3240
accgcctgtc tgaaattaag cctcttcata actttctcac ccaactgcaa cccttcttga   3300
agctcaaaca gaagcaagca atctggtttt gaaaatcat cgagcaactg ccatctgcca   3360
aggagtcccc tgacaagttt cttgaagtgt gtacttgggt ggatcagatt gctgccttga   3420
atgactccaa gaccagaaaa accacctctg agactgtgag ggcagttctg gatagcctct   3480
ctgagaagaa aaagtcctct ccttagctcg agcgctagca cccagctttc ttgtacaaag   3540
tggtgatcta gagggcccgc ggttcgaagg taagcctatc cctaaccctc tcctcggtct   3600
cgattctacg cgtaccggtt agtaatgagt ttaaacgggg gaggctaact gaaacacgga   3660
aggagacaat accggaagga acccgcgcta tgacggcaat aaaaagacag aataaaacgc   3720
acgggtgttg ggtcgtttgt tcataaacgc ggggttcggt cccagggctg gcactctgtc   3780 gatacccac cgagacccca ttggggccaa tacgcccgcg tttcttcctt ttccccaccc   3840
caccccccaa gttcgggtga aggcccaggg ctcgcagcca acgtcggggc ggcaggccct   3900
gccatagcag atctgcgcag ctgggggctct aggggggtatc cccacgcgcc ctgtagcggc   3960
gcattaagcg cggcgggtgt ggtggttacg cgcagcgtga ccgctacact tgccagcgcc   4020
ctagcgcccg ctcctttcgc tttcttccct tcctttctcg ccacgttcgc cggctttccc   4080
cgtcaagctc taaatcgggg catccctta gggttccgat ttagtgcttt acggcacctc   4140
gaccccaaaa aacttgatta gggtgatggt tcacgtagtg ggccatcgcc ctgatagacg   4200 gttttcgcc ctttgacgtt ggagtccacg ttctttaata gtggactctt gttccaaact   4260
ggaacaacac tcaaccctat ctcggtctat tcttttgatt tataaggat tttggggatt   4320 tcggcctatt ggttaaaaaa tgagctgatt taacaaaaat ttaacgcgaa ttaattctgt   4380
ggaatgtgtg tcagttaggg tgtggaaagt ccccaggctc cccagcaggc agaagtatgc   4440
aaagcatgca tctcaattag tcagcaacca ggtgtggaaa gtccccaggc tccccagcag   4500
gcagaagtat gcaaagcatg catctcaatt agtcagcaac catagtcccg cccctaactc   4560
cgcccatccc gcccctaact ccgcccagtt ccgcccattc tccgccccat ggctgactaa   4620
ttttttttat ttatgcagag gccgaggccg cctctgcctc tgagctattc cagaagtagt   4680
gaggaggctt ttttggaggc ctaggctttt gcaaaaagct cccgggagct gtatatcca   4740 ttttcggatc tgatcagcac gtgttgacaa ttaatcatcg gcatagtata tcggcatagt   4800
ataatacgac aaggtgagga actaaaccat ggccaagcct ttgtctcaag aagaatccac   4860
cctcattgaa agagcaacgg ctacaatcaa cagcatcccc atctctgaag actcagcgt   4920 cgccagcgca gctctctcta gcgacggccg catcttcact ggtgtcaatg tatatcattt   4980
tactggggga ccttgtgcag aactcgtggt gctgggcact gctgctgctg cggcagctgg   5040
caacctgact tgtatcgtcg cgatcggaaa tgagaacagg gcatcttga gcccctgcgg   5100 acggtgccga caggtgcttc tcgatctgca tcctgggatc aaagccatag tgaaggacag   5160
tgatggacag ccgacggcag ttgggattcg tgaattgctg ccctctggtt atgtgtggga   5220
gggctaagca cttcgtggcc gaggagcagg actgacacgt gctacgagat ttcgattcca   5280
ccgccgcctt ctatgaaagg ttgggcttcg gaatcgtttt ccgggacgcc ggctggatga   5340
```

```
tcctccagcg cggggatctc atgctggagt tcttcgccca ccccaacttg tttattgcag    5400
cttataatgg ttacaaataa agcaatagca tcacaaattt cacaaataaa gcattttttt    5460
cactgcattc tagttgtggt ttgtccaaac tcatcaatgt atcttatcat gtctgtatac    5520
cgtcgacctc tagctagagc ttggcgtaat catggtcata gctgtttcct gtgtgaaatt    5580
gttatccgct cacaattcca cacaacatac gagccggaag cataaagtgt aaagcctggg    5640
gtgcctaatg agtgagctaa ctcacattaa ttgcgttgcg ctcactgccc gctttccagt    5700
cgggaaacct gtcgtgccag ctgcattaat gaatcggcca acgcgcgggg agaggcggtt    5760
tgcgtattgg gcgctcttcc gcttcctcgc tcactgactc gctgcgctcg tcgttcggc     5820 tgcggcgagc ggtatcagct cactcaaagg cggtaatacg ttatccaca gaatcagggg     5880 ataacgcagg aaagaacatg tgagcaaaag gccagcaaaa ggccaggaac cgtaaaaagg    5940
ccgcgttgct ggcgtttttc cataggctcc gcccccctga cgagcatcac aaaaatcgac    6000
gctcaagtca gaggtggcga aacccgacag gactataaag ataccaggcg tttccccctg    6060
gaagctccct cgtgcgctct cctgttccga ccctgccgct taccggatac ctgtccgcct    6120
ttctcccttc gggaagcgtg gcgctttctc atagctcacg ctgtaggtat ctcagttcgg    6180
tgtaggtcgt tcgctccaag ctgggctgtg tgcacgaacc ccccgttcag cccgaccgct    6240
gcgccttatc cggtaactat cgtcttgagt ccaacccggt aagacacgac ttatcgccac    6300
tggcagcagc cactggtaac aggattagca gagcgaggta tgtaggcggt gctacagagt    6360
tcttgaagtg gtggcctaac tacggctaca ctagaagaac agtatttggt atctgcgctc    6420
tgctgaagcc agttaccttc ggaaaaagag ttggtagctc ttgatccggc aaacaaacca    6480
ccgctggtag cggtttttt gtttgcaagc agcagattac gcgcagaaaa aaggatctc     6540 aagaagatcc tttgatcttt tctacggggt ctgacgctca gtggaacgaa aactcacgtt    6600
aagggatttt ggtcatgaga ttatcaaaaa ggatcttcac ctagatcctt ttaaattaaa    6660
aatgaagttt taaatcaatc taaagtatat atgagtaaac ttggtctgac agttaccaat    6720
gcttaatcag tgaggcacct atctcagcga tctgtctatt tcgttcatcc atagttgcct    6780
gactccccgt cgtgtagata actacgatac gggagggctt accatctggc cccagtgctg    6840
caatgatacc gcgagaccca cgctcaccgg ctccagattt atcagcaata aaccagccag    6900
ccggaagggc cgagcgcaga agtggtcctg caactttatc cgcctccatc cagtctatta    6960
attgttgccg ggaagctaga gtaagtagtt cgccagttaa tagtttgcgc aacgttgttg    7020
ccattgctac aggcatcgtg gtgtcacgct cgtcgtttgg tatggcttca ttcagctccg    7080
gttcccaacg atcaaggcga gttacatgat cccccatgtt gtgcaaaaaa gcggttagct    7140
ccttcggtcc tccgatcgtt gtcagaagta agttggccgc agtgttatca ctcatggtta    7200
tggcagcact gcataattct cttactgtca tgccatccgt aagatgcttt tctgtgactg    7260
gtgagtactc aaccaagtca ttctgagaat agtgtatgcg gcgaccgagt tgctcttgcc    7320
cggcgtcaat acgggataat accgcgccac atagcagaac tttaaaagtg ctcatcattg    7380
gaaaacgttc ttcggggcga aaactctcaa ggatcttacc gctgttgaga tccagttcga    7440
tgtaacccac tcgtgcaccc aactgatctt cagcatcttt tactttcacc agcgtttctg    7500
ggtgagcaaa aacaggaagg caaaatgccg caaaaaaggg aataagggcg acacggaaat    7560
gttgaatact catactcttc ctttttcaat attattgaag catttatcag ggttattgtc    7620
tcatgagcgg atacatattt gaatgtattt agaaaaataa acaaataggg gttccgcgca    7680
```

-continued catttccccg aaaagtgcca cctgacgtc                                    7709

<210> SEQ ID NO 1056
<211> LENGTH: 847
<212> TYPE: PRT
<213> ORGANISM: Artificial sequence
<220> FEATURE:
<223> OTHER INFORMATION: SCTrex2_SC_RAG amino acid sequence

<400> SEQUENCE: 1056

Met Gly Ser Glu Ala Pro Arg Ala Glu Thr Phe Val Phe Leu Asp Leu
1               5                   10                  15

Glu Ala Thr Gly Leu Pro Ser Val Glu Pro Glu Ile Ala Glu Leu Ser
            20                  25                  30

Leu Phe Ala Val His Arg Ser Ser Leu Glu Asn Pro Glu His Asp Glu
        35                  40                  45

Ser Gly Ala Leu Val Leu Pro Arg Val Leu Asp Lys Leu Thr Leu Cys
    50                  55                  60

Met Cys Pro Glu Arg Pro Phe Thr Ala Lys Ala Ser Glu Ile Thr Gly
65                  70                  75                  80

Leu Ser Ser Glu Gly Leu Ala Arg Cys Arg Lys Ala Gly Phe Asp Gly
                85                  90                  95

Ala Val Val Arg Thr Leu Gln Ala Phe Leu Ser Arg Gln Ala Gly Pro
            100                 105                 110

Ile Cys Leu Val Ala His Asn Gly Phe Asp Tyr Asp Phe Pro Leu Leu
        115                 120                 125

Cys Ala Glu Leu Arg Arg Leu Gly Ala Arg Leu Pro Arg Asp Thr Val
    130                 135                 140

Cys Leu Asp Thr Leu Pro Ala Leu Arg Gly Leu Asp Arg Ala His Ser
145                 150                 155                 160

His Gly Thr Arg Ala Arg Gly Arg Gln Gly Tyr Ser Leu Gly Ser Leu
                165                 170                 175

Phe His Arg Tyr Phe Arg Ala Glu Pro Ser Ala Ala His Ser Ala Glu
            180                 185                 190

Gly Asp Val His Thr Leu Leu Leu Ile Phe Leu His Arg Ala Ala Glu
        195                 200                 205

Leu Leu Ala Trp Ala Asp Glu Gln Ala Arg Gly Trp Ala His Ile Glu
    210                 215                 220

Pro Met Tyr Leu Pro Pro Asp Asp Pro Ser Leu Glu Ala Thr Pro Pro
225                 230                 235                 240

Gln Thr Gly Leu Asp Val Pro Tyr Ser Glu Ala Pro Arg Ala Glu Thr
                245                 250                 255

Phe Val Phe Leu Asp Leu Glu Ala Thr Gly Leu Pro Ser Val Glu Pro
            260                 265                 270

Glu Ile Ala Glu Leu Ser Leu Phe Ala Val His Arg Ser Ser Leu Glu
        275                 280                 285

Asn Pro Glu His Asp Glu Ser Gly Ala Leu Val Leu Pro Arg Val Leu
    290                 295                 300

Asp Lys Leu Thr Leu Cys Met Cys Pro Glu Arg Pro Phe Thr Ala Lys
305                 310                 315                 320

Ala Ser Glu Ile Thr Gly Leu Ser Ser Glu Gly Leu Ala Arg Cys Arg
                325                 330                 335

Lys Ala Gly Phe Asp Gly Ala Val Val Arg Thr Leu Gln Ala Phe Leu
            340                 345                 350

Ser Arg Gln Ala Gly Pro Ile Cys Leu Val Ala His Asn Gly Phe Asp

```
              355                 360                 365
Tyr Asp Phe Pro Leu Leu Cys Ala Glu Leu Arg Arg Leu Gly Ala Arg
370                 375                 380

Leu Pro Arg Asp Thr Val Cys Leu Asp Thr Leu Pro Ala Leu Arg Gly
385                 390                 395                 400

Leu Asp Arg Ala His Ser His Gly Thr Arg Ala Arg Gly Arg Gln Gly
                405                 410                 415

Tyr Ser Leu Gly Ser Leu Phe His Arg Tyr Phe Arg Ala Glu Pro Ser
                420                 425                 430

Ala Ala His Ser Ala Glu Gly Asp Val His Thr Leu Leu Ile Phe
                435                 440                 445

Leu His Arg Ala Ala Glu Leu Leu Ala Trp Ala Asp Glu Gln Ala Arg
                450                 455                 460

Gly Trp Ala His Ile Glu Pro Met Tyr Leu Pro Pro Asp Asp Pro Ser
465                 470                 475                 480

Leu Glu Ala Ala Asp Gly Gly Gly Ser Gly Gly Gly Ser Asn
                485                 490                 495

Thr Lys Tyr Asn Glu Glu Phe Leu Leu Tyr Leu Ala Gly Phe Val Asp
                500                 505                 510

Gly Asp Gly Ser Ile Ile Ala Gln Ile Asn Pro Asn Gln Ser Ser Lys
                515                 520                 525

Phe Lys His Arg Leu Arg Leu Thr Phe Tyr Val Thr Gln Lys Thr Gln
530                 535                 540

Arg Arg Trp Phe Leu Asp Lys Leu Val Asp Glu Ile Gly Val Gly Tyr
545                 550                 555                 560

Val Arg Asp Ser Gly Ser Val Ser Gln Tyr Val Leu Ser Glu Ile Lys
                565                 570                 575

Pro Leu His Asn Phe Leu Thr Gln Leu Gln Pro Phe Leu Glu Leu Lys
                580                 585                 590

Gln Lys Gln Ala Asn Leu Val Leu Lys Ile Ile Glu Gln Leu Pro Ser
                595                 600                 605

Ala Lys Glu Ser Pro Asp Lys Phe Leu Glu Val Cys Thr Trp Val Asp
610                 615                 620

Gln Ile Ala Ala Leu Asn Asp Ser Lys Thr Arg Lys Thr Thr Ser Glu
625                 630                 635                 640

Thr Val Arg Ala Val Leu Asp Ser Leu Ser Gly Lys Lys Lys Ser Ser
                645                 650                 655

Pro Ala Ala Gly Gly Ser Asp Lys Tyr Asn Gln Ala Leu Ser Lys Tyr
                660                 665                 670

Asn Gln Ala Leu Ser Lys Tyr Asn Gln Ala Leu Ser Gly Gly Gly Gly
                675                 680                 685

Ser Asn Lys Lys Phe Leu Leu Tyr Leu Ala Gly Phe Val Asp Ser Asp
                690                 695                 700

Gly Ser Ile Ile Ala Gln Ile Lys Pro Arg Gln Ser Asn Lys Phe Lys
705                 710                 715                 720

His Gln Leu Ser Leu Thr Phe Ala Val Thr Gln Lys Thr Gln Arg Arg
                725                 730                 735

Trp Phe Leu Asp Lys Leu Val Asp Arg Ile Gly Val Gly Tyr Val Tyr
                740                 745                 750

Asp Ser Gly Ser Val Ser Asp Tyr Arg Leu Ser Glu Ile Lys Pro Leu
                755                 760                 765

His Asn Phe Leu Thr Gln Leu Gln Pro Phe Leu Lys Leu Lys Gln Lys
770                 775                 780
```

```
Gln Ala Asn Leu Val Leu Lys Ile Ile Glu Gln Leu Pro Ser Ala Lys
785                 790                 795                 800

Glu Ser Pro Asp Lys Phe Leu Glu Val Cys Thr Trp Val Asp Gln Ile
                805                 810                 815

Ala Ala Leu Asn Asp Ser Lys Thr Arg Lys Thr Thr Ser Glu Thr Val
                820                 825                 830

Arg Ala Val Leu Asp Ser Leu Ser Glu Lys Lys Lys Ser Ser Pro
            835                 840                 845

<210> SEQ ID NO 1057
<211> LENGTH: 68
<212> TYPE: DNA
<213> ORGANISM: Artificial sequence
<220> FEATURE:
<223> OTHER INFORMATION: RAG locus specific forward primer
<220> FEATURE:
<221> NAME/KEY: misc_feature
<222> LOCATION: (31)..(40)
<223> OTHER INFORMATION: n at positions 31-40 is a or c or t or g, and
      up to six of them may be absent

<400> SEQUENCE: 1057
ccatctcatc cctgcgtgtc tccgactcag nnnnnnnnnn ggcaaagatg aatcaaagat    60
tctgtcct                                                            68

<210> SEQ ID NO 1058
<211> LENGTH: 57
<212> TYPE: DNA
<213> ORGANISM: Artificial sequence
<220> FEATURE:
<223> OTHER INFORMATION: RAG locus specific reverse primer

<400> SEQUENCE: 1058
cctatcccct gtgtgccttg gcagtctcag gatctcaccc ggaacagctt aaatttc      57
```

METHOD FOR MODULATING THE EFFICIENCY OF DOUBLE-STRAND BREAK-INDUCED MUTAGENESIS

CROSS-REFERENCE TO RELATED APPLICATION

This application claims priority under 35 U.S.C. §119(e) to U.S. Provisional Application No. U.S. 61/439,739, filed Feb. 4, 2011, which is hereby incorporated by reference in its entirety.

FIELD OF THE INVENTION

The present invention relates to a method for modulating double-strand break-induced mutagenesis at a genomic locus of interest in a cell, thereby giving new tools for genome engineering, including therapeutic applications and cell line engineering. More specifically, the method of the present invention for modulating double-strand break-induced mutagenesis (DSB-induced mutagenesis), concerns the identification of effectors that modulate said DSB-induced mutagenesis by uses of interfering agents; these agents are capable of modulating DSB-induced mutagenesis through their respective direct or indirect actions on said effectors. The present invention also concerns the uses of these effectors, interfering agents and derivatives, respectively, by introducing them into a cell in order to modulate and more particularly to increase DSB-induced mutagenesis. The present invention also relates to specific derivatives of identified effectors and interfering agents, vectors encoding them, compositions and kits comprising such derivatives in order to modulate and more particularly to increase DSB-induced mutagenesis.

BACKGROUND OF THE INVENTION

Mutagenesis is induced by physical and chemical means provoking DNA damages when incorrectly repaired leading to mutations. Several chemicals are known to cause DNA lesions and are routinely used. Radiomimetic agents work through free radical attack on the sugar moieties of DNA (Povirk 1996). A second group of drugs inducing DNA damage includes inhibitors of topoisomerase I (TopoI) and II (TopoII) (Teicher 2008) (Burden and N. 1998). Other classes of chemicals bind covalently to the DNA and form bulky adducts that are repaired by the nucleotide excision repair (NER) system (Nouspikel 2009). Chemicals inducing DNA damage have a diverse range of applications and are widely used. However, although certain agents are more commonly applied in studying a particular repair pathway (e.g. cross-linking agents are favored for NER studies), most drugs simultaneously provoke a variety of lesions (Nagy and Soutoglou 2009). The physical means to generate mutagenesis is through the exposure of cells to ionizing radiation of one of three classes—X-rays, gamma rays, or neutrons (Green and Roderick 1966). However, using these classical, strategies, the overall yield of induced mutations is quite low, and the DNA damage leading to mutagenesis cannot be targeted to precise genomic DNA sequence.

The most widely used in vivo site-directed mutagenesis strategy is gene targeting (GT) via homologous recombination (HR). Efficient GT procedures have been available for more than 20 years in yeast (Rothstein 1991) and mouse (Capecchi 1989). Successful GT has also been achieved in Arabidopsis and rice plants (Hanin, Volrath et al. 2001; Terada, Urawa et al. 2002; Endo, Osakabe et al. 2006; Endo, Osakabe et al. 2007). Typically, GT events occur in a fairly small proportion of treated mammalian while GT efficiency is extremely low in higher plant cells and range between 0.01-0.1% of the total number of random integration events (Terada, Johzuka-Hisatomi et al. 2007). The low GT frequencies reported in various organisms are thought to result from competition between HR and non homologous end joining (NHEJ) for repair of dsDNA breaks (DSBs). As a consequence, the ends of a donor molecule are likely to be joined by NHEJ rather than participating in HR, thus reducing GT frequency. There is extensive data indicating that DSBs repair by NHEJ is error-prone. Often, DSBs are repaired by end-joining processes that generate insertions and/or deletions (Britt 1999). Thus, these NHEJ-based strategies might be more effective than HR-based strategies for targeted mutagenesis into cells. Indeed, expression of I-Sce I, a rare cutting restriction enzyme, has been shown to introduce mutations at I-Sce I cleavage sites in Arabidopsis and tobacco (Kirik, Salomon et al. 2000). Nevertheless, the use of restriction enzymes is limited to rarely occurring natural recognition sites or to artificial target sites. To overcome this problem, meganucleases with engineered specificity towards a chosen sequence have been developed. Meganucleases show high specificity to their DNA target, these proteins being able to cleave a unique chromosomal sequence and therefore do not affect global genome integrity. Natural meganucleases are essentially represented by homing endonucleases, a widespread class of proteins found in eukaryotes, bacteria and archae (Chevalier and Stoddard 2001). Early studies of the I-Sce I and HO homing endonucleases have illustrated how the cleavage activity of these proteins can be used to initiate HR events in living cells and have demonstrated the recombinogenie properties of chromosomal DSBs (Dujon, Colleaux et al. 1986; Haber 1995). Since then, meganuclease-induced HR has been successfully used for genome engineering purposes in bacteria (Posfai, Kolisnychenko et al. 1.999), mammalian cells (Sargent, Brenneman et al. 1997; Cohen-Tannoudji, Robine et al. 1998; Donoho, Jasin et al. 1998), mice (Cbuble, Smith et al. 2006) and plants (Puchta, Dujon et al. 1996; Siebert and Puchta 2002). Meganucleases have emerged as scaffolds of choice for deriving genome engineering tools cutting a desired target sequence (Paques and Duchateau 2007).

Combinatorial assembly processes allowing to engineer meganucleases with modified specificities has been described by Arnould et al. (Arnould, Chames et al. 2006; Smith, Grizot et al. 2006; Arnould, Perez et al. 2007; Grizot, Smith et al. 2009). Briefly, these processes rely on the identifications of locally engineered variants with a substrate specificity that differs from the substrate specificity of the wild-type meganuclease by only a few nucleotides. An other type of specific endonucleases is based on Zinc finger nuclease. ZFNs are chimeric proteins composed of a synthetic zinc finger-based DNA binding domain and a DNA cleavage domain. By modification of the zinc finger DNA binding domain, ZFNs can be specifically designed to cleave virtually any long stretch of dsDNA sequence (Kim, Cha et al. 1996; Cathomen and Joung 2008). An NHEJ-based targeted mutagenesis strategy was developed recently in several organisms by using synthetic ZFNs to generate DSBs at specific genomic sites (Lloyd, Plaisier et al. 2005; Beumer, Trautman et al. 2008; Doyon, McCammon et al. 2008; Meng, Noyes et al. 2008). Subsequent repair of the DSBs by NHEJ frequently produces deletions and/or insertions at the joining site. For examples, in zebrafish embryos, the injection of mRNA coding for engineered ZFN led to animals carrying the desired heritable mutations (Doyon, McCammon et al. 2008). In plant, same NHEJ-based targeted-mutagenesis has also been successful (Lloyd, Plaisier et al. 2005). Although these powerful tools are available, there is still a need to further improved double-strand break-induced mutagenesis.

As mentioned above, two mechanisms for the repair of DSBs have been described, involving either homologous recombination or non-homologous end-joining (NHEJ). NHEJ consists of at least two genetically and biochemically distinct process (Feldmann, Schmiemann et al. 2000). The major and best characterized "classic" end-joining pathway (C-NHEJ) involves rejoining of what remains of the two DNA ends through direct, relegation (Critchlow and Jackson 1998). A scheme for this pathway is shown in FIG. 1. NHEJ can be divided in three major steps: detection and protection of DNA ends, DNA end-processing and finally DNA ligation, Detection and protection of DNA ends are mediated by DNA-PK which is composed of Ku70 and Ku80 proteins that form an heterodimer (Ku) binding DNA ends and recruiting DNA-PK catalytic subunit (DNA-PKcs). This interaction DNA-PKcs-Ku-DSB stimulates DNA-PKcs kinase activity, maintains the broken ends in close proximity and prevents from extended degradation. Ku also recruits other components of C-NHEJ repair process. Candidates for DNA end processing are Artemis DNA polymerase mu ($\mu$) and lamda ($\lambda$), polynucleotide kinase (PNK) and Werner's syndrome helicase (WRN) (for review (Mahaney, Meek et al, 2009)). The ligation process is mediated by DNA ligase IV and its cofactors XRCC4 and XLF/Cernnunos. Finally, other proteins or complex modulating NHEJ activity have been described such as BRCA1, Rad50-Mre11-Nbs (Williams, Williams et al. 2007; Shrivastav, De Haro et al. 2008) complex, CtIP or FANCD2 (Bau, Man et al. 2006; Pace, Mosedale et al. 2010)). NHEJ is thought to be effective at all times in the cell cycle ((Essers, van Steeg et al. 2000); (Takata, Sasaki et al. 1998)). NHEJ also plays an important role in DSB repair during V(D)J recombination (Blunt, Finnie et al. 1995) (Taccioli, Rathbun et al. 1993).

The second mechanism, referred as microhomology mediated end joining (MMEJ) or alternative NHEJ (A-NHEJ) or back up NHEJ (B-NHEJ) is associated with significant 5'-3' resection of the end and uses microhomologies to anneal DNA allowing repair. Little is known about the components of this machinery. DNA ligase3 with XRCC1 proteins are candidate for the ligase activity (Audebert, Salles et al. 2004; Wang, Rosidi et al. 2005). PARP seems also to be an important factor of this mechanism (Audebert, Salles et al. 2004) (Wang, Wu et al. 2006).

Theoretically, both classical and alternative NHEJ could lead to mutagenesis, although A-NHEJ mechanism would represent the main pathway to favour when one wants to increase DSB-induced mutagenesis. Several methods have been described in order to modulate NHEJ. For example, US 2004/029130 A1 concerns a method of stimulating NHEJ of DNA the method comprising performing NHEJ of DNA in the presence of inositol hexakisphosphate (IP6) or other stimulatory inositol phosphate. The invention also provides screening assays for compounds which may modulate NHEJ and DNA-PK and related protein kinases and which may be therapeutically useful. WO 98/30902 relates to modulation of the NHEJ system via regulation (using protein and/or natural or synthetic compounds) of the interactions of XRCC4 and DNA ligase IV, and XRCC4 and DNA-PK to effect cellular DNA repair activity. It also relates to screens for individuals predisposed to conditions in which XRCC4 and/or DNA ligase IV are deficient, Sarkaria et al. (Sarkaria, Tibbetts et al. 1998) describes the inhibition of phosphoinositide 3-kinase related kinases (such as DNA-dependent protein kinase, ATR and ATM) by the radiosensitizing agent, wortmannin.

In an attempt to define in molecular detail the mechanism of NHEJ, an in vitro system for end-joining was recently developed (Baumarm and West 1998). The reactions exhibited an apparent requirement for DNA-PKS, Ku70/80, XRCC4 and DNA ligase IV, consistent with the in vivo requirements. Preliminary fractionation and complementation assays, however, revealed that these factors were not sufficient for efficient end-joining, and that other components of the reaction remained to be identified.

RNA interference is an endogenous gene silencing pathway that responds to dsRNAs by silencing homologous genes (Meister and Tuschl 2004). First described in *Caenorhabditis elegans* by Fire et al. the RNAi pathway functions in a broad range of eukaryotic organisms (Hannon 2002). Silencing in these initial experiments was triggered by introduction of long dsRNA. The enzyme Dicer cleaves these long dsRNAs into short-interfering RNAs (siRNAs) of approximately 21-23 nucleotides. One of the two siRNA strands is then incorporated into an RNA-induced silencing complex (RISC). RISC compares these "guide RNAs" to RNAs in the cell and efficiently cleaves target RNAs containing sequences that are perfectly, or nearly perfectly complementary to the guide RNA.

For many years it was unclear whether the RNAi pathway was functional in cultured mammalian cells and in whole mammals. However, Elbashir S. M. et al, 2001 (Elbashir, Harborth et al. 2001), triggered RNAi in cultured mammalian cells by transfecting them with 21 nucleotide synthetic RNA duplexes that mimicked endogenous siRNAs. McCaffrey et al. (McCaffrey, Meuse et al, 2002), also demonstrated that siRNAs and shRNAs could efficiently silence genes in adult mice.

Introduction of chemically synthetized siRNAs can effectively mediate post-transcriptional gene silencing in mammalian cells without inducing interferon responses. Synthetic siRNAs, targeted against a variety of genes have been successfully used in mammalian cells to prevent expression of target mRNA (Harborth, Elbashir et al. 2001). These discoveries of RNAi and siRNA-mediated gene silencing has led to a spectrum of opportunities for functional genomics, target validation, and the development of siRNA-based therapeutics, making it a potentially powerful tool for therapeutics and in vivo studies.

The authors of the present invention have developed a new approach to increase the efficiency of DSB-induced mutagenesis. This new approach relates through, the identification of new effectors that modulate said DSB-induced mutagenesis by uses of interfering agents in an in vivo assay. These agents being capable of modulate DSB-induced mutagenesis through their respective direct or indirect actions on respective effectors, introduction of these interfering agents and/or derivatives into a cell, respectively, will lead to a cell wherein said DSB-induced mutagenesis is modulated.

BRIEF SUMMARY OF THE INVENTION

The present invention relates to a method for modulating DSB-induced mutagenesis at a genomic locus of interest in a cell, thereby giving new tools for genome engineering, including therapeutic applications and cell line engineering.

More specifically, in a first aspect, the present invention concerns a method for identifying effectors that modulate DSB-induced mutagenesis, thereby allowing the increase or decrease of DSB-induced mutagenesis in a cell. As described elsewhere, this method allows screening of interfering agents libraries covering an unlimited number of molecules. As a non-limiting example, the method of the present invention allows screening for interfering RNAs, which in turn allow identifying the genes which they silence, through their capacities to stimulate or to inhibit DSB-induced mutagenesis, based on at least one reporter system.

In a second aspect, the present invention concerns a method for modulating DSB-induced mutagenesis in a cell by using interfering agents.

In a third aspect, the present invention concerns specific interfering agents, their derivatives such as polynucleotide derivatives or other molecules as non-limiting examples.

In a fourth aspect, the present invention further encompasses cells in which. DSB-induced mutagenesis is modulated. It refers, as non-limiting example, to an isolated cell, obtained and/or obtainable by the method according to the present invention.

In a fifth aspect, the present invention also relates to compositions and kits comprising the interfering agents, polynucleotides derivatives, vectors and cells according to the present invention.

In a sixth aspect, the present invention concerns the uses of specific interfering agents, their derivatives such as polynucleotide derivatives or other molecules as non-limiting examples, for modulating DSB-induced mutagenesis.

The above objects highlight certain aspects of the invention. Additional objects, aspects and embodiments of the invention are found in the following detailed description of the invention.

BRIEF DESCRIPTION OF THE FIGURES

In addition to the preceding features, the invention further comprises other features which will emerge from the description which follows, as well as to the appended drawings. A more complete appreciation of the invention and many of the attendant advantages thereof will be readily obtained as the same becomes better understood by reference to the following Figures in conjunction with the detailed description below.

FIG. 7: Extrachromosomal transfection assay in 293H cell line to validate induction of NHEJ repair events of the EGFP reporter gene of the pCLS6810 (SEQ ID NO: 5) plasmid with the expression vector pCLS2690 (SEQ ID NO: 3) for the SC_GS meganuclease in comparison with a control vector pCLS002 (SEQ ID NO: 41).

DETAILED DESCRIPTION OF THE INVENTION

Figure 1:
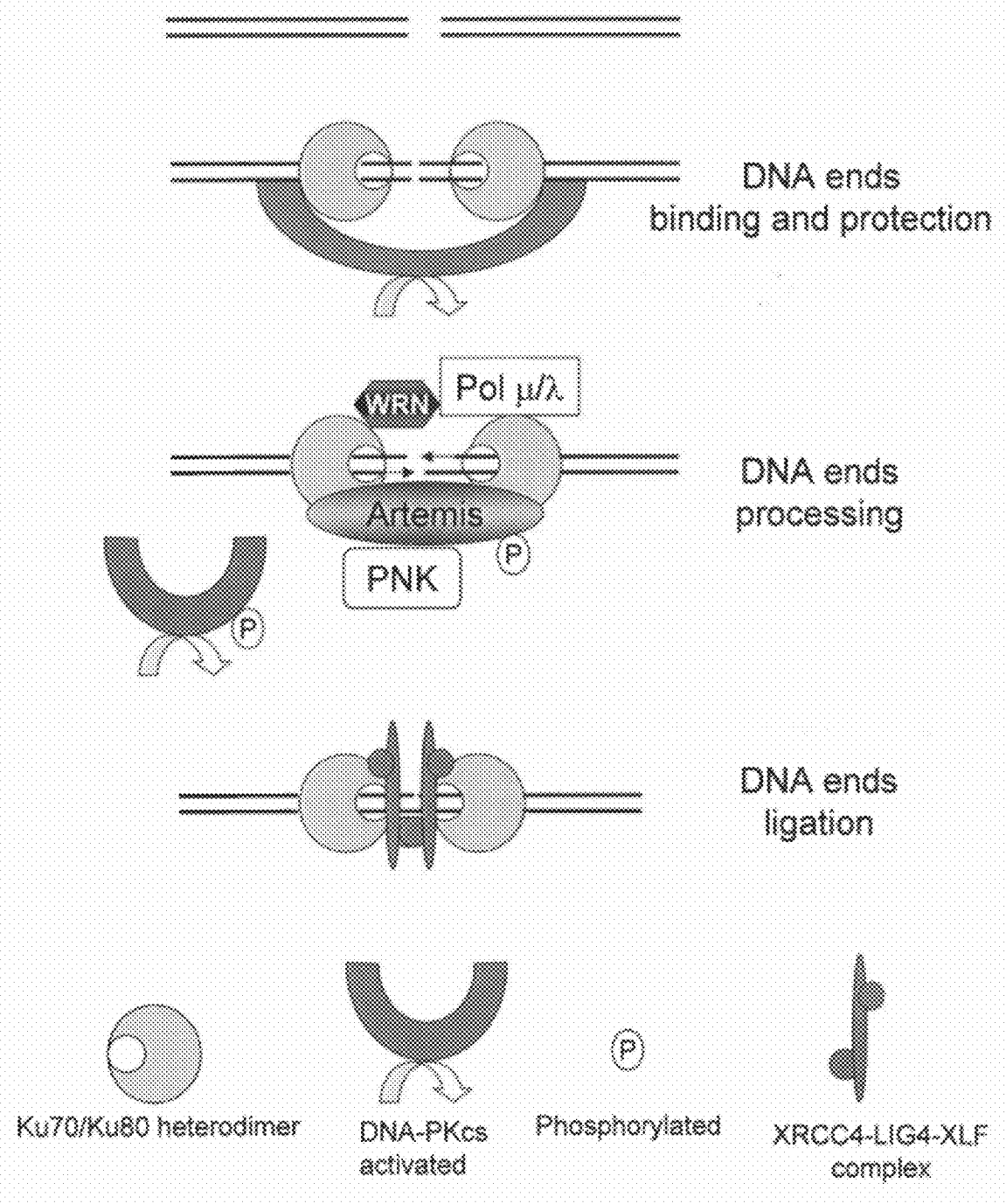
FIG. 1: Scheme of the "classic" end-joining pathway (C-NHEJ).

Unless specifically defined herein below, all technical and scientific terms used herein have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The practice of the present invention will employ, unless otherwise indicated, conventional techniques of cell, biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M, J. Gait ed., 1984); Mullis et al. U.S. Pat. No. 4,683,195; Nucleic Acid Hybridization (B. D. Harries & S. J. Higgins eds. 1984): Transcription And Translation (B. D. Hames & S. J. Higgins eds. 1984); Culture Of Animal Cells (R, I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J, Abeison and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds. Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

In a first aspect, the present invention concerns a method for identifying effectors that modulate double-strand break-induced mutagenesis, thereby allowing the increase or decrease of double-strand break-induced mutagenesis in a cell. As described elsewhere, this method allows screening of interfering agents libraries covering an unlimited number of molecules. As a non-limiting example, the method of the present invention allows screening for interfering RNAs, which in turn allow identifying the genes which they silence, through their capacities to stimulate or to inhibit double-strand break-induced mutagenesis, based on at least one reporter system.

This first aspect of the method of the invention is based on two successive screening steps.

The first screening step is a highly sensitive high-throughput assay measuring double-strand break-induced mutagenesis based on a compatible reporter gene, for example the luciferase gene. This method allows, in a few runs, to screen several thousands of interfering agents for their capacities to modulate double-strand break-induced mutagenesis (compared to negative, neutral or positive interfering agents taken as controls) by measuring the restoration of a functional reporter gene originally rendered inactive by a frameshift introduced via a double-strand break creating agent target site. It is easily understandable that the target sequence for double-strand break-induced mutagenesis can be as a non limiting example, any double-strand break-induced mutagenesis site. For this identification step, said interfering agents are co-transfected with a delivery vector containing said reporter gene rendered inactive by a frameshift mutation inserted via a double-strand break-induced target site and a delivery vector containing a double-strand break creating agent; said double-strand break creating agent provokes a mutagenic double-strand break that can be repaired by NHEJ leading to the restoration of said reporter gene and to the increase in said reporter signal.

Interfering agents that modulate double-strand break-induced mutagenesis can be divided in candidates that stimulate or inhibit said double-strand break-induced mutagenesis. Effectors whose interfering agents increase or decrease the expression of reporter gene detected and thus double-strand break-induced mutagenesis can also be classified as effectors stimulating or inhibiting double-strand break-induced mutagenesis.

In the second screening step of this aspect of the invention, a similar system as in the first screening step is used, except for the reporter gene employed. In this second step, the reporter gene is preferably selected to allow a qualitative and/or quantitative measurement of the modulation seen during the first screening step.

The invention therefore relates to a method for identifying effectors that modulate double-strand break-induced mutagenesis in a cell comprising the steps of:

(a) providing a cell expressing a reporter gene rendered inactive by a frameshift in its coding sequence, due to the introduction in said sequence of a DSB-creating agent target site;
(b) providing an interfering agent;
(c) contacting said cell with:
  i. an interfering agent;
  ii. a delivery vector comprising a double-strand break creating agent, wherein said double-strand break creating agent provokes a mutagenic double-strand break that can be repaired by NHEJ leading to a functional restoration of said reporter gene;
(d) detecting expression of the functional reporter gene in the cell obtained at the end of step (c);
(e) repeating steps (c) and (d) at least one time for each interfering agent;
(f) identifying effectors whose interfering agent increases or decreases the expression of the reporter gene detected at step (d) as compared to a negative control; and
(g) for the effectors identified at step (f), repeating steps (a), (c), (d) and (f) with a cell line expressing a different inactive reporter gene than the inactive reporter gene previously used;

whereby the effectors identified at the end of step (f) are effectors that modulate double-stranded break-induced mutagenesis in a cell.

In a preferred embodiment, the present invention concerns a method for identifying effector genes that modulates endonuclease-induced mutagenesis, thereby allowing the increase or decrease of double-strand break-induced mutagenesis in a cell. As elsewhere described, this method allows screening of an interfering agents library, wherein in a non limitative example, this library is an interfering RNA library covering an unlimited number of genes. The method of the present invention allows screening for interfering RNAs, which in turn allow identifying the genes which they silence, through their capacities to stimulate or to inhibit endonuclease-induced mutagenesis, based on at least one reporter system.

In this preferred embodiment, the method of the invention is based on two successive screening steps.

The first screening step is a highly sensitive high-throughput assay measuring endonuclease-induced mutagenesis based on a compatible reporter gene, for example the luciferase gene. This method allows, in a few runs, to screen several thousands of interfering RNAs for their capacities to modulate the reparation of an endonuclease-induced mutagenesis substrate coupled to said reporter system, compared to negative, neutral or positive interfering RNAs taken as controls. Said endonuclease-induced mutagenesis substrate is rendered inactive by a frameshift in its coding sequence due to the introduction in said sequence of an endonuclease-specific target site, like an I-SceI or an engineered meganuclease target site. It is easily understandable that the endonuclease-specific target site can be any endonuclease-specific target site. For this identification step, said interfering RNAs are co-transfected with a delivery vector containing said reporter gene rendered inactive by a frameshift mutation due to the insertion of a double-strand break-induced target site and a delivery vector containing an endonuclease expression cassette; said endonuclease provokes a mutagenic double-strand break, that can be repaired by NHEJ leading to the functional restoration of said reporter gene and to the increase in said reporter gene-associated signal.

Interfering RNAs that modulate endonuclease-induced mutagenesis can be divided in candidates that stimulate or inhibit said endonuclease-induced mutagenesis. Genes from which these interfering RNAs are derived can also be classified as genes stimulating or inhibiting endonuclease-induced mutagenesis. Therefore, genes related to interfering RNAs that stimulate endonuclease-induced mutagenesis can be classified as genes whose products inhibit double-strand break-induced mutagenesis. Conversely, genes related to interfering RNAs that, inhibit endonuclease-induced mutagenesis can be classified as genes whose products are necessary or stimulate double-strand break-induced mutagenesis.

In the second screening step of this aspect of the invention, a similar system as in the first screening step is used, except for the reporter gene used. In this second step, the reporter gene is preferably selected to allow a qualitative and/or quantitative measurement of the modulation seen during the first screening step, such as the gene encoding the Green Fluorescent Protein (GFP) as non-limiting example.

The invention therefore relates to a method for identifying genes that modulate endonuclease-induced mutagenesis in a cell comprising the steps of:
(a) providing a cell expressing a reporter gene rendered inactive by a frameshift in its coding sequence, due to the introduction in said sequence of a target sequence for an endonuclease;
(b) providing an interfering RNA comprised in an interfering RNA library;
(c) transiently co-transfecting said cell with:
  i. said interfering RNA;
  ii. a delivery vector comprising an endonuclease expression cassette wherein said endonuclease provokes a mutagenic double-strand break that can be repaired by NHEJ leading to a functional restoration of said reporter gene;
(d) detecting the signal emitted by the reporter gene in the co-transfected cell obtained at the end of step (c);
(e) repeating step (c) and (d) at least, one time for each interfering RNA of said interfering RNA library;
(f) identifying genes whose silencing through RNA interference increases or decreases the signal detected at step (d) as compared to a negative control; and
(g) optionally, for the genes identified at step (f), providing an interfering RNA capable of silencing said gene, and repeating steps (a), (c), (d) and (f) with a cell line expressing a different inactive reporter gene than the inactive reporter gene previously used;
whereby the genes identified at the end of step (i) and/or (g) are genes that modulate endonuclease-induced mutagenesis in a cell.

The eukaryotic cell line used at step (a) can be constructed by stably transfecting a cell line with a vector (hereafter referred to as the first vector) comprising an inactive reporter gene, i.e. a reporter gene rendered inactive by a frameshift mutation in its coding sequence, said frameshift mutation being due to the introduction in said sequence of a target sequence for an endonuclease. In other terms, such inactive reporter gene is not capable of emitting any relevant detectable signal upon transfection into a cell. On the vector, the inactive reporter gene is placed under the control of expression signals allowing its expression. Thus, upon stable transfection of the cell line with the first vector, the cell line expresses the inactive reporter gene which is integrated in its genome.

This first vector can for example consist of, or be derived from, the pCLS6883 vector of SEQ ID NO: 1, or of the pCLS6884 vector of SEQ ID NO: 2.

The interfering RNA library used in the frame of this method is preferably representative of an entire eukaryotic transcriptome. In addition, it preferably comprises at least two different interfering RNAs for each gene of the eukaryotic transcriptome. Most preferably, it is constituted by iRNAs capable of targeting human genes, although it may also be constituted by iRNAs capable of targeting genes form common animal models such as mice, rats or monkeys. In a preferred embodiment, the interfering RNA library used in the frame of the present invention, can be restricted to a part of an eukaryotic transcriptome. Said restricted interfering RNA library can be focused and representative of certain classes of genes, such as genes encoding for protein kinases as a non-limiting example.

At step (c), in addition to being transfected with the iRNA, the eukaryotic cell is transfected with a second vector.

The second, vector comprises an endonuclease expression cassette (i.e. an endonuclease under the control of expression signals allowing its expression upon transfection into the cell). Therefore, a functional copy of the reporter gene (and thus a detectable signal) can only be obtained upon endonuclease-induced mutagenesis in the transfected eukaryotic cell.

The second vector can for example consist of, or be derived from, the pCLS2690 vector of SEQ ID NO: 3. The second vector can also for example encode for I-SceI meganuclease (SEQ ID NO: 40).

The endonuclease present in the second vector can for example correspond to a a homing endonuclease such as I-SceI, I-CreI, I-CeuI, I-MsoI, and I-DmoI. It may be a wild-type or a variant endonuclease. In a preferred embodiment, the endonuclease is an engineered meganuclease such as, in a non-limiting example, an engineered SC_GS meganuclease (SEQ ID NO: 4).

The first and second vectors may further comprise selection markers such as genes conferring resistance to an antibiotic in order to select cells co-transfected with both vectors.

In a preferred embodiment, the reporter gene used at step (c) is a high throughput screening-compatible reporter gene such as e.g. the gene encoding luciferase (including variants of this gene such as firefly or *renilla luciferase* genes) or other reporter genes that allow measuring a defined parameter in a large number of samples (relying on the use of multiwell plates, typically with 96, 384 or 1536 wells) as quickly as possible. Other reporter genes include in a non limitative way, the beta-galactosidase and the phosphatase alkaline genes, which are well-known in the art.

In step (d), the signal emitted by the reporter gene in the co-transfected cell is detected using assays well-known in the art.

Step (e) comprises repeating steps (c) and (d) at least one time for each interfering RNA of the interfering RNA library. For example, if the iRNA library comprises two different interfering RNAs for each gene of the eukaryotic transcriptome, each gene of the transcriptome will be tested twice.

At step (f), genes whose silencing through RNA interference increases or decreases, preferably significantly increases or decreases, the signal detected at step (d) as compared to a negative control are identified. In particular, the signal detected at step (d) is compared with the signal detected in the same conditions with at least one interfering RNA taken as a negative control. The interfering RNA taken as a negative control corresponds to a iRNA known not to hybridize and thus not to be involved in endonuclease-induced mutagenesis such as e.g. the "All Star" (AS) iRNA (Qiagen #1027280). For example, if a two-fold increase of the signal detected upon transfection with an iRNA targeting a given gene, compared to the signal detected with a negative control, said given gene is identified as a gene that modulates endonuclease-induced mutagenesis in said cell.

In a preferred embodiment, the method of the present invention further comprises supplementary steps of selection. In other terms, the interfering RNAs identified at step (f) are further selected through another succession of steps (a), (c), (d) and (t), wherein inactive reporter gene is different from the one previously used.

In a most preferred embodiment, steps (a) to (f) the above methods are first carried out using a cell line expressing an inactive luciferase reporter gene. This cell line can for example correspond to a cell line obtained through stable transfection of a cell line with pCLS6883 vector of SEQ ID NO: 1, or of the pCLS6884 vector of SEQ ID NO: 2 or plasmids derived from those. This cell line is then co-transfected with iRNAs and pCLS2690 vector of SEQ ID NO: 3, Once genes whose silencing through. RNA interference increases or decreases the signal detected at step (d) as compared to a negative control are identified, steps (a), (c), (d) and (f) may then be repeated with iRNAs silencing these genes. The cell line used at the second selection round may for example express an inactive GFP reporter gene (due to a frameshift mutation after insertion of an endonuclease target site), and may e.g. be obtained through stable transfection of a cell line with the pCLS inactive GFP-encoding vector (pCLS6810 of SEQ ID NO: 5 or pCLS6663 of SEQ ID NO: 6. The pCLS2690 vector of SEQ ID NO: 3 and the pCLS inactive GFP-encoding vector of SEQ ID NO: 5 can then be used for co-transfection with iRNAs. This second screening allows confirming that the genes identified at step (f) are genes that modulate endonuclease-induced mutagenesis in a cell.

In the second screening, the reporter gene used can be a gene that when active, confers resistance to an antibiotic such as the neomycin phosphotransferase resistant gene nptl, the hygromycin phosphotransferase resistant gene hph, the puromycin N-acetyl transferase gene pac, the blasticidin S deaminase resistant gene bsr and the bleomycin resistant, gene sh ble, as non-limiting examples.

In this second screening, the reporter gene is preferably a gene allowing an accurate detection of the signal and a precise qualitative and/or quantitative measurement of the endonuclease-induced mutagenesis modulation, such as e.g. the genes encoding the Green Fluorescent Protein (GFP), the Red Fluorescent Protein (RFP), the Yellow Fluorescent Protein (YFP) and the Cyano Fluorescent Protein (CFP), respectively. The reporter gene of the second screening can also be any protein antigen that can be detected using a specific antibody conjugated to a fluorescence-emitting probe or tagged by such a fluorescent probe usable in Fluorescent Activated Cell Sorting (FACS). For example cell surface expressing molecule like CD4 can be used as an expression reporter molecule detectable with a specific anti-CD4 antibody conjugated to a fluorescent protein. FACS technology and derivated applications to measure expression of reporter genes are well known in the art.

As shown in Examples 1 to 4, the above method according to the invention was successfully applied to identify several genes that modulate endonuclease-induced mutagenesis in a cell.

In a second aspect, the present invention concerns a method for modulating double-strand break-induced mutagenesis in a cell by using interfering agents. The information obtained when carrying out the above method for identifying effectors that modulate double-strand break-induced mutagenesis in a cell can be used to increase or decrease mutagenesis in cells. Depending on the envisioned application, interfering agents that increase or interfering agents that decrease double-strand break-induced mutagenesis in a cell can be used.

Indeed, interfering agents that modulate double-strand break-induced mutagenesis through their respective effectors can be used directly. For a given interfering agent, it is easily understood that other interfering agents derived from said given interfering agent (equivalent interfering RNAs) can be synthetized and used with the same objectives and results.

Interfering agents or derivatives can be used to modulate double-strand break-induced mutagenesis in a cell by introducing them with at least, one delivery vector containing at least one double-strand break creating agent expression cassette. It is easily understood that these interfering agents or derivatives can be introduced by all methods known in the art, as part or not of a vector, unique or not, under the control of an inducible promoter or not. Therefore, the effects of these interfering agents or derivatives in the cell can be permanent or transitory.

Therefore, the second aspect of the invention pertains to a method for modulating double-strand break-induced mutagenesis in a cell, comprising the steps of:
 (a) identifying an effector that is capable of modulating double-strand break-induced mutagenesis in a cell by a method according to the first aspect of the invention; and
 (b) introducing into a cell:
  i. at least one interfering agent capable of modulating said effector;
  ii. at least one delivery vector comprising at least one double-strand break creating agent;
thereby obtaining a cell in which double-strand break-induced mutagenesis is modulated.

Therefore, in the second aspect of the invention is comprised a method for increasing double-strand break-induced mutagenesis in a cell, comprising the steps of:
 (a) identifying a gene that is capable of stimulating double-strand break-induced mutagenesis in a cell by a method according to the first aspect of the invention or providing a gene selected from the group of genes listed in table I or II; and
 (b) Introducing into a eukaryotic cell:
  i. at least one interfering agent, wherein said interfering agent is a polynucleotide silencing or encoding said gene, wherein said polynucleotide is an interfering RNA capable of silencing said gene if the signal detected at step (d) of the method according to claim 1 is increased as compared to the negative control, and is a cDNA transcribed from said gene if the signal detected at step (d) of the method according to claim 1 is decreased as compared to the negative control;
  ii. at least one delivery vector comprising at least one double-strand break creating agent;
thereby obtaining a eukaryotic cell in which double-strand break-induced mutagenesis is increased.

In another embodiment, is a method for increasing double-strand break-induced mutagenesis in a cell comprising the steps of introducing into said cell:
 i. at least one interfering agent, wherein said interfering agent is a polynucleotide silencing at least one gene selected from the group of genes listed in tables I, II, IV and VII;
 ii. at least one delivery vector comprising at least one double-strand break creating agent;
thereby obtaining a eukaryotic cell in which double-strand break-induced mutagenesis is increased.

More preferably, the interfering RNA used according to the present invention for increasing double-strand break-induced mutagenesis in a cell targets a sequence selected from the group consisting of SEQ ID NO: 13-35, SEQ ID NO: 37-39, SEQ ID NO: 44-76 and SEQ ID NO: 80-555. More preferably, the interfering RNA targets used according to the present invention for increasing double-strand break-induced mutagenesis in a cell targets a sequence selected from the group consisting of SEQ ID NO: 106, 15, 16, 20, 33, 45, 80, 83, 85, 89, 96, 97, 98, 102, 103, 104, 108, 109, 110, 111, 113, 114, 115, 118, 121, 122, 126, 127, 128, 135, 137, 138, 139, 140, 141, 143, 146, 149, 151, 153, 162, 163, 167, 168, 174, 175, 177, 178, 180, 181, 184, 185, 186, 187, 188, 189, 193, 195, 196, 198, 201, 203, 204, 215, 221, 222, 223, 225, 226, 227, 228, 229, 232, 233, 235, 236, 237, 238, 239, 243, 244, 247, 249, 250, 251, 252, 254, 256, 257, 258, 265, 267, 268, 269, 271, 277, 278, 282, 283, 285, 299, 308, 309, 315, 328, 331, 335, 338, 340, 353, 367, 368, 385, 399, 416.

In the above methods, "at least one interfering agent" means that only one interfering agent but also more than one interfering agent, can be used. In a preferred embodiment, 2 interfering RNAs can be used at the same time in the above methods; in a most preferred embodiment, 3, 4, 5, 6, 7, 8, 9 or 10 interfering RNAs can be used at the same time; in another most preferred embodiment, more than 10 interfering RNAs can be used. When several interfering RNAs are used in the above methods, they can be mixed or not, i.e. introduced into the cell at the same moment or not. In another embodiment, more than one interfering agent means 2 different interfering agents as described in the "Definitions" paragraph below; as non-limiting example, one interfering RNA targeting one gene can be used at the same time than one cDNA overexpressing another gene. As another non-limiting example of using different kinds of interfering agents (as described in the "Definitions" paragraph below), at least one interfering RNA can be used at the same time than at least one small compound.

In the above methods, the endonuclease encoded by the vector comprising at least one endonuclease expression cassette may either be the same endonuclease as the one used in the method for identifying genes that modulate endonuclease-induced homologous recombination, or a different endonuclease. This endonuclease can correspond to any of the endonucleases described in the "Definitions" paragraph below. It may for example be a homing endonuclease such as I-SceI, I-CreI, I-CeuI, I-MsoI, and I-DmoI. It may be a wild-type or a variant endonuclease. In a preferred embodiment, the endonuclease is a variant I-CreI endonuclease.

By increasing double-strand break-induced mutagenesis is understood the increase of its efficiency, ie any statistically significant increase of double-strand break-induced mutagenesis in a cell when compared to an appropriate control, including for example, at least 5%, 10%, 20%, 30%, 40%, 50%, 60%, 70%, 80%, 90%, 100%, 200%, 300%, 500% or greater increase in the efficiency of a double-strand break-induced mutagenesis event for a polynucleotide of interest (i.e. a transgene).

In a preferred embodiment according to the invention, the gene that modulates endonuclease-induced mutagenesis is a gene that decreases endonuclease-induced mutagenesis efficiency. In such a case, an interfering RNA capable of silencing said gene, introduced into said considered cell, is able to increase endonuclease-induced mutagenesis. The interfering RNA may for example be a siRNA, a miRNA or a shRNA.

In an extrachromosomal assay transiently expressing the vectors of the above method of the invention in a eukaryotic cell, the inventors have found that the genes listed in table I herebelow are capable of decreasing endonuclease-induced mutagenesis, particularly GS engineered meganuclease-induced mutagenesis (see Example 2). Indeed, siRNAs respectively targeting those genes (sequences listed in Table I) are able to stimulate GS engineered meganuclease-induced mutagenesis. Therefore, a gene that is capable of modulating endonuclease-induced mutagenesis in a eukaryotic cell can be selected from the group of genes listed in Table I below.

TABLE I siRNA hits stimulating GS_SC-induced luciferase signal.

| Gene targeted | Gene ID | siRNA target sequence | SEQ ID NO: | Mean Z Score | Std | Stimulation factor |
|---|---|---|---|---|---|---|
| CSNK1D | 1453 | CCGGTCTAGGATCGAAATGTT | 13 | 3.14 | 0.75 | 3.40 |
| AK2 | 204 | CGGCAGAACCCGAGTATCCTA | 14 | 5.51 | 0.20 | 5.08 |
| AKT2 | 208 | CAAGCGTGGTGAATACATCAA | 15 | 3.65 | 0.23 | 2.94 |
| CAMK2G | 818 | GAGGAAGAGATCTATACCCTA | 16 | 5.01 | 0.23 | 3.66 |
| GK2 | 2712 | TACGTTAGAAGAGCACTGTAA | 17 | 3.33 | 1.49 | 2.75 |
| PFKFB4 | 5210 | CAGAAAGTGTCTGGACTTGTA | 18 | 3.92 | 1.14 | 2.18 |
| MAPK12 | 6300 | CTGGACGTATTCACTCCTGAT | 19 | 3.84 | 0.06 | 3.22 |
| PRKCE | 5581 | CCCGACCATGGTAGTGTTCAA | 20 | 4.00 | 0.43 | 2.91 |
| EIF2AK2 | 5610 | CGGAAAGACTTACGTTATTAA | 21 | 4.50 | 0.22 | 3.15 |
| WEE1 | 7465 | CAGGGTAGATTACCTCGGATA | 22 | 3.20 | 0.08 | 5.01 |
| CDK5R1 | 8851 | CCGGAAGGLCACGCTGTTTGA | 23 | 4.01 | 0.26 | 6.03 |
| LIG4 | 3981 | CACCGTTTATTTGGACTCGTA | 24 | 4.11 | 0.41 | 6.15 |
| AKAP1 | 8165 | AGCGCTGAACTTGATTGGGAA | 25 | 4.97 | 0.32 | 7.24 |
| MAP3K6 | 9064 | TCAGAGGAGCTGAGTAATGAA | 26 | 5.99 | 0.22 | 5.41 |
| DYRK3 | 8444 | TCGACAGTACGTGGCCCTAAA | 27 | 3.54 | 0.22 | 3.61 |

TABLE I-continued siRNA hits stimulating GS_SC-induced luciferase signal.

| Gene targeted | Gene ID | siRNA target sequence | SEQ ID NO: | Mean Z Score | Std | Stimulation factor |
|---|---|---|---|---|---|---|
| RPS6KA4 | 8986 | CGCCACCTTCATGGCATTCAA | 28 | 3.56 | 0.73 | 3.61 |
| STK17A | 9263 | CACACTCGTGATGTAGTTCAT | 29 | 3.26 | 0.43 | 2.07 |
| GNE | 10020 | CCCGATCATGTTTGGCATTAA | 30 | 3.31 | 0.25 | 2.20 |
| ERN2 | 10595 | CTGGTTCGGCGGGAAGTTCAA | 31 | 3.47 | 1.47 | 2.30 |
| HUNK | 30811 | CACGGGCAAAGTGCCCTGTAA | 32 | 3.63 | 1.30 | 1.97 |
| SMG1 | 23049 | CACCATGGTATTACAGGTTCA | 33 | 3.22 | 0.46 | 2.05 |
| WNK4 | 65266 | CAGCTTGTTGGGCGTTTCCAA | 34 | 5.58 | 0.70 | 4.15 |
| MAGI2 | 9863 | CAGGCCCAACTTGGGATATCA | 35 | 3.07 | 0.63 | 2.07 |

More preferably, the interfering RNA targets used in the frame of the method according to the present invention target a sequence selected from the group consisting of SEQ ID NO: 13-35, SEQ ID NO: 37-39, SEQ ID NO: 44-76 and SEQ ID NO: 80-1041. More preferably, the interfering RNA targets used in the frame of the method according to the present invention target a sequence selected from the group consisting of SEQ ID NO: 13-35, SEQ ID NO: 37-39, SEQ ID NO: 44-76 and SEQ ID NO: 80-555. More preferably, the interfering RNA targets used in the frame of the method according to the present invention target a sequence selected from the group consisting of SEQ ID NO: 106, 15, 16, 20, 33, 45, 80, 83, 85, 89, 96, 97, 98, 102, 103, 104, 108, 109, 110, 111, 113, 114, 115, 118, 121, 122, 126, 127, 128, 135, 137, 138, 139, 140, 141, 143, 146, 149, 151, 153, 162, 163, 167, 168, 174, 175, 177, 178, 180, 181, 184, 185, 186, 187, 188, 189, 193, 195, 196, 198, 201, 203, 204, 215, 221, 222, 223, 225, 226, 227, 228, 229, 232, 233, 235, 236, 237, 238, 239, 243, 244, 247, 249, 250, 251, 252, 254, 256, 257, 258, 265, 267, 268, 269, 271, 277, 278, 282, 283, 285, 299, 308, 309, 315, 328, 331, 335, 338, 340, 353, 367, 368, 385, 399, 416.

As shown in example 3, the above method according to the invention was successfully applied to stimulate endonuclease-induced mutagenesis in a cellular model stably expressing at an endogenous locus (RAG1) the construction that allows to measure GS engineered meganuclease-induced mutagenesis. Indeed, siRNAs targeting genes involved in NHEJ (LIG4; SEQ ID NO: 24) or in NHEJ and other DNA repair pathway (WRN; SEQ ID NO: 37) or in DNA repair (FANCD2, SEQ ID NO: 39) or in DNA repair regulation (MAPK3, SEQ ID NO: 38) were able to increase GS engineered meganuclease-induced luciferase signal. Moreover, 8 siRNAs identified with the extrachromosomal assay of example 2, targeting CAMK2G (SEQ ID NO: 16), SMG1 (SEQ ID NO: 33), PRKCE (SEQ ID NO: 20), CSNK1D (SEQ ID NO: 13), AK2 (SEQ ID NO: 14), AKT2 (SEQ ID NO: 15), MAPK12 (SEQ ID NO: 19) and EIF2AK2 (SEQ ID NO: 21) genes and also two siRNAs targeting PRKDC gene (PRKDC_5, SEQ ID NO: 75 and PRKDC_8, SEQ ID NO: 76) involved in DNA repair regulation were able to increase GS engineered meganuclease-induced luciferase signal. As shown in example 4, the above method according to the invention was successfully applied to stimulate endonuclease-induced mutagenesis at an endogenous locus (RAG1).

SiRNAs targeting XRCC6 (SEQ ID NO: 44), BRCA1 (SEQ ID NO: 45), FANCD2 (SEQ ID NO: 39), WRN (SEQ ID NO: 37) and MAPK3 (SEQ ID NO: 38) were able to enhance the percentage of mutagenic NHEJ repair as measured by Deep Sequencing analysis at the endogenous RAG1 locus (see Table II below)

TABLE II siRNA stimulating endonuclease-induced mutagenesis at RAG1 locus.

| Gene targeted | Gene ID | siRNA target sequence | SEQ ID NO: | NHEJ Stimulation factor |
|---|---|---|---|---|
| XRCC6 | 2547 | ACCGAGGGCGATGAAGAAGCA | 44 | 1.6 |
| BRCA1 | 672 | ACCATACAGCTTCATAAATAA | 45 | 2.1 |
| FANCD2 | 2177 | AAGCAGCTCTCTAGCACCGTA | 39 | 2.5 |
| WRN | 7486 | CGGATTGTATACGTAACTCCA | 37 | 2.4 |
| MAPK3 | 5595 | CCCGTCTAATATATAAATATA | 38 | 1.9 |

As also shown in example 3, the screen of a siRNA collection from Qiagen led to the identification of 481 siRNA hits that stimulate SC-GS-induced mutagenesis as listed in table IV (SEQ ID NO: 80-555) and to the identification of 486 siRNA hits that inhibit SC-GS-induced mutagenesis as listed in table V (SEQ ID NO: 556-1041). Interfering RNA capable of silencing a given gene can easily be obtained by the skilled in the art. Such iRNAs may for example be purchased from a provider. Alternatively, commercially available tools allow designing iRNAs targeting a given gene.

Useful interfering RNAs can be designed with a number of software program, e.g., the OligoEngine siRNA design tool available at the oligoengine.com world wide website. Database RNAi Codex (available at the codex.cshl.edu website) publishes available RNAi resources, and provides the most complete access to this growing resource.

The iRNAs used in the frame of the present invention can for example be a shRNA. shRNAs can be produced using a wide variety of well-known RNAi techniques. ShRNAs that are synthetically produced as well as miRNA that are found, in nature can for example be redesigned to function as synthetic silencing shRNAs. DNA vectors that express perfect complementary shRNAs are commonly used to generate functional siRNAs.

iRNAs can be produced by chemical synthesis (e.g. in the case of siRNAs) or can be produced by recombinant technologies through an expression vector (e.g. in the case of shRNAs).

The iRNAs according to the invention may optionally be chemically modified.

In another preferred embodiment according to the invention, the gene that modulates endonuclease-induced mutagenesis is a gene that increases endonuclease-induced mutagenesis (i.e. the presence of which increases double-strand break-induced mutagenesis in a cell). In such a case, a cDNA leading to increased expression of said gene is introduced into said cell.

cDNA usually refers to a double-stranded DNA that is derived from mRNA which can be obtained from prokaryotes or eukaryotes by reverse transcription. cDNA is a more convenient way to work with the coding sequence than mRNA because RNA is very easily degraded by omnipresent RNases. Methods and advantages to work with cDNA are well known in the art (1989, Molecular cloning: a laboratory manual, $2^{nd}$ edition and further ones, Cold Spring Harbor Laboratory Press, Cold Spring Harbor, N.Y.). Particularly in the context of the present invention the availability of a cDNA clone allows the corresponding protein to be expressed in a variety of contexts. The cDNA can be inserted into a variety of expression vectors for different purposes. Perhaps the most obvious use of such an approach in the present invention is to drive the expression of a defined protein involved, in a protein transduction cascade to levels that allow higher frequency of endonuclease-induced mutagenesis and so, mutagenesis events. As well-known in the art, one can express not only the wild type protein but also mutant proteins, said particular mutations having consequences in structure-function relationships within a protein itself (improved catalytic activity) or for association with another endogenous protein.

As used herein, the term "cDNA" encompasses both full-length cDNAs naturally transcribed from the gene and biologically active fragments thereof, such as e.g. cDNAs encoding the mature protein encoded by the gene or biologically active fragments thereof. The biologically active fragments thereof can for example code for maturation products of the protein encoded by the gene.

In a third aspect, the present invention concerns specific interfering agents, their derivatives such as polynucleotides derivatives or other molecules as non-limiting examples. In this aspect, the present invention concerns specific interfering agents for modulating double-(strand break-induced mutagenesis in a cell, wherein said interfering agents modulate effectors representative of an entire eukaryotic transcriptome. In a preferred embodiment, said interfering agents modulate effectors which are part of a restricted library representative of certain classes of effectors. In a most preferred embodiment, said interfering agents modulate effectors from the group listed in Table I and Table II. In a preferred embodiment of this third aspect, the present invention concerns specific polynucleotide derivatives identified for effector genes, which increase endonuclease-induced mutagenesis.

In a preferred embodiment of this aspect of the invention, these polynucleotide derivatives are interfering RNAs, more preferably siRNAs or shRNAs.

As indicated in the definitions hereabove, the siRNAs according to the invention are double-stranded RNAs, each RNA of the duplex comprising for example between 17 and 29 nucleotides, e.g. 17, 18, 19, 20, 21, 22, 23, 24, 25, 26, 27, 28 or 29 nucleotides.

Such siRNAs can be formed from two RNA molecules that hybridize together or can alternatively be generated from a single RNA molecule that includes a self-hybridizing portion, referred to as shRNAs. The duplex portion of a siRNA can include one or more impaired and/or mismatched nucleotides in one or both strand of the duplex (bulges) or can contain one or more noncomplementary nucleotides pairs. Duplex of a siRNA is composed of a sense strand and of an antisense strand. Given a target transcript, only one strand of the siRNA duplex is supposed to hybridize with one strand of said target transcript, in certain embodiments, one strand (either sense, either antisense) is perfectly complementary with a region of the target transcript, either on the entire length of the considered siRNA strand (comprised between 17 and 29 nucleotides, including 17, 18, 19, 20, 21, 22, 23, 24, 25, 26, 27, 28, and 29 nucleotides), either on only a part of the considered siRNA strand, 17 to 29 or 19 to 29 nucleotides matching for example, or 18, 19, 20, 21, 22, 23, 24, 25, 26, 27, 28 from 29 nucleotides. In one embodiment it is intended that the considered strand of the siRNA duplex (either sense, either antisense) hybridizes the target transcript without a single mismatch over that length. In another embodiment, one or more mismatches between the considered strand of the siRNA duplex (either sense, either antisense) can exist.

Therefore, an aspect of the invention is drawn to an interfering RNA for increasing endonuclease-induced mutagenesis in a cell, wherein said interfering RNA comprises a sense RNA nucleic acid and an antisense RNA nucleic acid, and wherein said interfering RNA down-regulates the expression (most preferably silences the expression) of gene transcripts part of library representative of an entire transcriptome. In a preferred embodiment, the interfering RNA library used in the frame of the present invention can be representative of only a part of an eukaryotic transcriptome. Said restricted interfering RNA library can be representative of certain classes of transcripts, such as those encoding for kinases as a non-limiting example. In a preferred embodiment, said interfering RNA library can be obtained from a provider; as a non limiting-example, said interfering RNA library can be a library purchased from Qiagen and covering 19121 genes with two different siRNAs per gene. In a preferred embodiment of this aspect of the invention, interfering RNA targets a gene selected from this library. In a most preferred embodiment of this aspect of the invention, interfering RNA targets a gene selected from the group of genes listed in Table I, II, IV and Table VII. More preferably, the interfering RNA according to the invention targets a sequence selected from the group consisting of SEQ ID NO: 13-35, SEQ ID NO: 37-39, SEQ ID NO: 44-76 and SEQ ID NO: 80-1041. More preferably, the interfering RNA targets used in the frame of the method according to the present invention target a sequence selected from the group consisting of SEQ ID NO: 13-35, SEQ ID NO: 37-39, SEQ ID NO: 44-76 and SEQ ID NO: 80-555. More preferably, the interfering RNA targets used in the frame of the method according to the present invention target a sequence selected from the group consisting of SEQ ID NO: 106, 15, 16, 20, 33, 45, 80, 83, 85, 89, 96, 97, 98, 102, 103, 104, 108, 109, 110, 111, 113, 114, 115, 118, 121, 122, 126, 127, 128, 135, 137, 138, 139, 140, 141, 143, 146, 149, 151, 153, 162, 163, 167, 168, 174, 175, 177, 178, 180, 181, 184, 185, 186, 187, 188, 189, 193, 195, 196, 198, 201, 203, 204, 215, 221, 222, 223, 225, 226, 227, 228, 229, 232, 233, 235, 236, 237, 238, 239, 243, 244, 247, 249, 250, 251, 252, 254, 256, 257, 258, 265, 267, 268, 269, 271, 277, 278, 282, 283, 285, 299, 308, 309, 315, 328, 331, 335, 338, 340, 353, 367, 368, 385, 399, 416.

In other terms, one strand of this iRNA (either sense, either antisense) comprises a sequence hybridizing to a sequence selected from the group consisting of SEQ ID NO: 13-35, SEQ ID NO: 37-39, SEQ ID NO: 44-76 and SEQ ID NO: 80-1041, more preferably from the group consisting of SEQ ID NO: 13-35, SEQ ID NO: 37-39, SEQ ID NO: 44-76 and SEQ ID NO: 80-555, again more preferably from the group consisting of SEQ ID NO: 106, 15, 16, 20, 33, 45, 80, 83, 85, 89, 96, 97, 98, 102, 103, 104, 108, 109, 110, 111, 113, 114, 115, 118, 121, 122, 126, 127, 128, 135, 137, 138, 139, 140, 141, 143, 146, 149, 151, 153, 162, 163, 167, 168, 174, 175, 177, 178, 180, 181, 184, 185, 186, 187, 188, 189, 193, 195, 196, 198, 201, 203, 204, 215, 221, 222, 223, 225, 226, 227, 228, 229, 232, 233, 235, 236, 237, 238, 239, 243, 244, 247, 249, 250, 251, 252, 254, 256, 257, 258, 265, 267, 268, 269, 271, 277, 278, 282, 283, 285, 299, 308, 309, 315, 328, 331, 335, 338, 340, 353, 367, 368, 385, 399, 416 with or without mismatch. Preferably, there is no mismatch, meaning that one strand of this iRNA (either sense, either antisense) comprises or consists of the RNA sequence corresponding to a DNA sequence selected from the group consisting of SEQ ID NO: 13-35, SEQ ID NO: 37-39, SEQ ID NO: 44-76 and SEQ ID NO: 80-1041.

In the iRNAs according to the invention, the sense RNA nucleic acid may for example have a length comprised between 19 and 29.

In the frame of the present invention, the interfering RNA according to the invention may further comprising a hairpin sequence, wherein the sense RNA nucleic acid and the antisense RNA nucleic acid are covalently linked by the hairpin sequence to produce a shRNA molecule.

In a preferred embodiment according to the invention, the interfering RNA according to the invention as defined hereabove down-regulates the expression (most preferably silences the expression) of the genes listed in Table I, Table II, Table IV, Table V and Table VII. Indeed, as respectively shown in examples 2 and 4, introducing such an iRNA selected from the group consisting of SEQ ID NO: 13-35, SEQ ID NO: 37-39, SEQ ID NO: 44-46 and SEQ ID NO: 75-76 in a cell leads to approximately a 2 to 7 fold increase of the endonuclease-induced mutagenesis signal of an extrachromosomal reporter assay in this cell and to a 1.6 to 2.5 increase of the endonuclease-induced mutagenesis events at an endogenous locus of this cell. Other results and fold increase are shown in example 3 and 5 for iRNA listed in Tables IV, V and VII.

In a preferred embodiment, these iRNA down-regulating the expression of their respective targeted genes comprise a sense RNA nucleic acid consisting of a sequence at least 70%, 75%, 80%, 85%, 90%, 95%, 99% or 100% identical to a fragment of at least 17 consecutive nucleotides of the respective mRNA sequences of the genes listed in Tables I, II, IV, V and VII. These fragments of at least 17 consecutive nucleotides of the respective mRNA sequences of the genes listed in Tables I and II may for example include 17, 18, 19, 20, 21, 22, 23, 24, 25, 26, 27, 28, and 29 consecutive nucleotides of the respective mRNA sequences of the genes listed in Tables I, II, IV, V and VII.

The antisense RNA nucleic acid of such an iRNA above from the mRNA sequence of a given gene listed in Tables I, II, IV and V may as a non-limiting example consist of a sequence at least 70%, 75%, 80%, 85%, 90%, 95%, 99% or 100% identical to a fragment complementary to at least 17 consecutive nucleotides of the considered mRNA sequence. This fragment of at least 17 consecutive nucleotides complementary of the respective mRNA sequences of the genes listed in Tables I, II, IV, V and VII may for example include 17, 18, 19, 20, 21, 22, 23, 24, 25, 26, 27, 28, and 29 consecutive nucleotides complementary of this sequence.

The iRNAs down-regulating the expression of a given gene listed in Tables I and II may correspond to a different sequence targeting the same given genes listed in Table III below.

TABLE III

Other siRNAs target sequences for targeted genes of Tables I and II

| Gene targeted | Gene ID | siRNA target sequence | SEQ ID NO: |
|---|---|---|---|
| CSNK1D | 1453 | CTCCCTGACGATTCCACTGTA | 47 |
| AK2 | 204 | CTGCAAGCCTACCACACTCAA | 48 |
| AKT2 | 208 | ACGGGCTAAAGTGACCATGAA | 49 |
| CAMK2G | 818 | CCGATGAGAAACCTCGTGTTA | 50 |
| GK2 | 2712 | CTCGGGTGTGCCATAATAATA | 51 |
| PFKFB4 | 5210 | ACGGAGAGCGACCATCTTTAA | 52 |
| MAPK12 | 6300 | TGGAAGCGTGTTACTTACAAA | 53 |
| PRKCE | 5581 | CACGGAAACACCCGTACCTTA | 54 |
| EIF2AK2 | 5610 | TACATAGGCCTTATCAATAGA | 55 |
| WEE1 | 7465 | ACAATTACGAATAGAATTGAA | 56 |
| CDK5R1 | 8851 | TGAGCTGGTTTGACTCATTAA | 57 |
| LIG4 | 3981 | ATCTGGTAAGCTCGCATCTAA | 58 |
| AKAP1 | 8165 | CACGCAGAGATGACAGTACAA | 59 |
| MAP3K6 | 9064 | CACCATCCAAATGCTGTTGAA | 60 |
| DYRK3 | 8444 | AGCCAATAAGCTTAAAGCTAA | 61 |
| RPS6KA4 | 8986 | CAGGCTGTGCCTTTGACTTTA | 62 |
| STK17A | 9263 | TCCATTGTAACCGAAGAGTTA | 63 |
| GNE | 10020 | ATGGAAATACATATCGAATGA | 64 |
| ERN2 | 10595 | AAGGATGAAACTGGCTTCTAT | 65 |
| HUNK | 30811 | TCGGACCAAGATCAAACCAAA | 66 |
| SMG1 | 23049 | ATCGATGTTGCCAGACTACTA | 67 |
| WNK4 | 65266 | CAGGAGGAGCCAGCACCATTA | 68 |
| MAGI2 | 9863 | ATGGACCGATGGGAGAATCAA | 69 |
| XRCC6 | 2547 | TTTGTACTATATACTGTTAAA | 70 |
| BRCA1 | 672 | AACCTATCGGAAGAAGGCAAG | 71 |
| FANCD2 | 2177 | CAGAGTTTGCTTCACTCTCTA | 72 |
| WRN | 7486 | TCCGCTGTAGCAATTGGAGTA | 73 |
| MAPK3 | 5595 | TGGACCGGATGTTAACCTTTA | 74 |

The iRNA clown-regulating the expression of the MAPK3 gene (Gene ID 5595) may for example target a sequence consisting of SEQ ID NO: 38 and/or SEQ ID NO: 74. In other terms, one strand of this iRNA (either sense, either antisense)

comprises a sequence hybridizing to a sequence selected from the group consisting of SEQ ID NO: 38 and/or SEQ ID NO: 74, with or without mismatch. Preferably, there is no mismatch, meaning that one strand of this iRNA (either sense, either antisense) comprises or consists of the RNA sequence corresponding to a DNA sequence selected from the group consisting of SEQ ID NO: 38 and/or SEQ ID NO: 74. In a preferred embodiment, two interfering RNAs can be used at the same time in the methods of the present invention; in a preferred embodiment, these iRNAs are siRNAs; in a most preferred embodiment, combinations of two siRNAs used at the same time in the methods of the present invention encompass siRNAs targeting CAMK2G (SEQ ID NO: 16), SMG1 (SEQ ID NO: 33), PRKCE (SEQ ID NO: 20), FANCD2 (SEQ ID NO: 39) and LIG4 (SEQ ID NO: 24) genes. In another most preferred embodiment, the combinations of two siRNAs that are used in the present invention are selected from the group consisting of CAMK2G+SMG1, CAMK2G+PRKCE, CAMK2G+FANCD2, CAMK2G+LIG4, SMG1+PRKCE, SMG1+FANCD2, SMG1+LIG4, PRKCE+FANCD2, PRKCE+LIG4, FANCD2+LIG4. In another preferred embodiment, several combinations of two siRNAs, i.e. 2, 3, 4, 5, 6, 7, 8, 9 or 10 combinations of two interfering RNAs can be used at the same time; in another most preferred embodiment, more than 10 combinations of two interfering RNAs can be used. When several combinations of two interfering RNAs are used in the above methods, they can be mixed or not, i.e. introduced into the cell at the same moment or not. In another embodiment, one combination of two interfering RNA can be used at the same time than one cDNA overexpressing another gene. In another embodiment, one combination of two interfering RNA can be used at the same time than at least one small compound.

The invention further pertains to viral vector for producing the interfering RNA according to the invention, wherein said viral vector comprises a polynucleotide sequence encoding the sense RNA nucleic acid of said interfering RNA and a polynucleotide sequence encoding the antisense RNA nucleic acid of said interfering RNA.

In such vectors, the polynucleotide sequence encoding the sense RNA nucleic acid may under the control of a first promoter, and the polynucleotide sequence encoding the antisense RNA nucleic acid may be under the control of a second promoter. These promoters may for example be selected from the group consisting of an inducible promoter, a tissue specific promoter and a RNA polymerase III promoter.

Alternatively, when the sense and the antisense nucleic acids are covalently linked by a hairpin sequence to produce a shRNA molecule, they are under the control of a single promoter.

Another aspect of the invention is drawn to an isolated DNA polynucleotide coding for the interfering RNA according to the invention, wherein said DNA polynucleotide comprises a polynucleotide sequence encoding the sense RNA nucleic acid of said interfering RNA and a polynucleotide sequence encoding the antisense RNA nucleic acid of said interfering RNA. In such a DNA polynucleotide, the sense and the antisense nucleic acids may be covalently linked by a hairpin sequence to produce a shRNA molecule upon transcription.

Still another aspect of the invention relates to a plasmidic vector comprising the DNA polynucleotide according to the invention.

Such a plasmidic vector preferably comprises a promoter, wherein the polynucleotide sequence encoding the sense RNA nucleic acid is under control of said promoter. Said promoter may for example be selected from the group consisting of an inducible promoter, a tissue specific promoter and a RNA polymerase III promoter.

In a fourth main aspect of the present invention, is encompassed cells in which double-strand break-induced mutagenesis is modulated. It refers, as non-limiting example, to an isolated cell, obtained and/or obtainable by the method according to the present invention. Cells in which double-strand break-induced mutagenesis is increased are useful for genome engineering, including therapeutic applications and cell line engineering.

The invention therefore relates to an isolated cell obtained and/or obtainable by the methods according to the invention as defined in the above paragraphs. As shown in example 3, a cellular model has been established which stably expresses at an endogenous locus (RAG1) the construction that allows to measure GS engineered meganuclease-induced mutagenesis. Moreover, in this cell line, different siRNAs were shown to increase GS engineered meganuclease-induced mutagenesis via a reporter signal. According to this fourth aspect of the invention, a cell in which endonuclease-induced mutagenesis is increased can be directly or indirectly be derived from this cellular model.

The invention further relates to a cell, wherein said cell is stably transformed with at least one interfering RNA, viral vector, isolated DNA polynucleotide or plasmidic vector as described in the previous paragraphs.

The eukaryotic cell can be any type of cell such as e.g. a CHO cell (for example a CHO-K1 or a CHO-S cell), a HEK293 cell, a Caco2 cell, an U2-OS cell, a NIH 3T3 cell, a NSO cell, a SP2 cell, and a DG44 cell.

In a preferred embodiment, the cell is a cell suitable for production of recombinant proteins.

Said cell is preferably an immortalized and/or a transformed cell, although primary cells are contemplated by the present invention, in particular in the frame of gene therapy.

In a fifth main aspect, the present invention also relates to compositions and kits comprising the interfering agents, polynucleotides derivatives, vectors and cells according to the present invention.

The invention further pertains to compositions and kits comprising the iRNAs, DNA polynucleotides, cDNAs, vectors and cells according to the invention described hereabove.

In this aspect of the invention, the present invention concerns a composition for modulating double-strand break-induced mutagenesis in a cell, wherein said composition comprises at least an interfering agent that modulate an effector from a group of effectors representative of an entire eukaryotic transcriptome. In a preferred embodiment, said interfering agent modulates an effector which is part of a restricted library representative of certain classes of effectors. In a most preferred embodiment, said interfering agent modulates an effector from the group listed in Table I, Table II, Table IV, Table V and Table VII.

In a preferred embodiment of this aspect of the invention, the invention pertains to a composition for increasing mutagenesis and/or endonuclease-induced mutagenesis in a cell comprising at least one interfering RNA, viral vector, isolated DNA polynucleotide or plasmidic vector as defined in the above paragraphs, and/or an isolated cell as defined in the above paragraphs.

The composition preferably further comprises a carrier. The carrier can for example be a buffer, such as e.g. a buffer allowing storage of the iRNAs, DNA polynucleotides, vectors and cells according to the invention, or a pharmaceutically acceptable carrier.

In another aspect of the invention, the present invention concerns a kit for modulating double-strand break-induced mutagenesis in a cell, wherein said composition comprises at least an interfering agent that modulate an effector from a group of effectors representative of an entire eukaryotic transcriptome. In a preferred embodiment, said interfering agent modulate an effector which are part of a restricted library representative of certain classes of effectors. In a most preferred embodiment, said interfering agent modulate an effector from the group listed in Table I, II, IV, V and VII.

In a preferred embodiment of this aspect of the invention, the invention also pertains to a kit for increasing mutagenesis and/or endonuclease-induced mutagenesis in a cell, wherein said kit comprises at least one interfering RNA, viral vector, isolated DNA polynucleotide or plasmidic vector as defined in the above paragraphs, and/or an isolated eukaryotic cell as defined in the above paragraphs.

The kit may further comprise instructions for use in increasing mutagenesis efficiency and/or for use in increasing endonuclease-induced mutagenesis.

In a sixth main aspect, the present invention concerns the uses of specific interfering agents for modulating double-strand break-induced mutagenesis in a cell, wherein said interfering agent modulates an effector from a group of effectors representative of an entire eukaryotic transcriptome. In a preferred embodiment, said interfering agent modulates an effector which is part of a restricted library representative of certain classes of effectors. In a most preferred embodiment, said interfering agent modulates an effector from the group listed in Tables I, II, IV, V and VII. In a preferred embodiment of this sixth aspect, the present invention concerns the uses of specific polynucleotide derivatives identified for effector genes, which increase double-strand break-induced mutagenesis efficiency.

Indeed, the polynucleotides derivatives according to the invention, which include the iRNAs, DNA polynucleotides, cDNAs and vectors described hereabove, can be used to increase mutagenesis in a cell and/or to increase double-strand break-induced mutagenesis in a cell.

Therefore, an aspect, of the invention is directed to an in vitro or ex vivo use of at least one interfering agent, such as but non-limited to interfering RNA, DNA polynucleotide, viral vector or plasmidic vector as defined in the above paragraphs for increasing mutagenesis in a cell and/or endonuclease-induced mutagenesis in a cell, tissue or organ.

Modulating double-strand break-induced mutagenesis is also useful in animal models, for which it is often desired to construct knock-in or knock-out animals, as a non limiting example.

Therefore, the invention relates to the use of specific interfering agents for modulating double-strand break-induced mutagenesis in a non-human model, wherein said interfering agent modulates an effector from a group of effectors representative of an entire eukaryotic transcriptome. In a preferred embodiment, said interfering agent modulates an effector which is part of a restricted library representative of certain classes of effectors. In a most preferred embodiment, said interfering agent modulate an effector from the group listed in Tables I, II, IV, V and VII. The invention also relates to the use of an interfering RNA according to the invention for increasing mutagenesis efficiency and/or endonuclease-induced mutagenesis in a non-human animal model. The animal models thus obtained are also part of the invention.

It is further desirable to modulate double-strand break-induced mutagenesis or endonuclease-induced mutagenesis in the frame of treatments of subjects by therapy.

Therefore, the invention further pertains to an interfering agent according to the invention for use as a medicament.

A preferred embodiment of the invention is drawn to an interfering agent or an interfering RNA according to the invention for use as an adjuvant in the treatment of a genetic disease by gene therapy. For purposes of therapy, an interfering agent or an interfering RNA according to the invention can be administered with a DSB-creating agent with a pharmaceutically acceptable excipient in a therapeutically effective amount. Such a combination is said to be administered in a "therapeutically effective amount" if the amount administered, is physiologically significant. An agent is physiologically significant if its presence results in a detectable change in the physiology of the recipient. In the present context, an agent, is physiologically significant if its presence results in a decrease in the severity of one or more symptoms of the targeted disease and in a genome correction of the lesion or abnormality. (See Current Protocols in Human Genetics: Chapter 12 "Vectors For Gene Therapy" & Chapter 13 "Delivery Systems for Gene Therapy"). In other words, the term adjuvant refers to a compound administered in addition to the active principle aiming at treating the patient, said adjuvant increasing the efficiency of the treatment. In a preferred embodiment, said interfering agent according to the invention can be administered at the same time than a DSB-creating agent. In another preferred embodiment, said interfering agent according to the invention can be administered before a DSB-creating agent in another preferred embodiment, said, interfering agent, according to the invention can be administered after a DSB-creating agent.

Gene therapy is a technique for the treatment of genetic disorders in man whereby the absent or faulty gene is replaced by a working gene, so that the body can make the correct enzyme or protein and consequently eliminate the root cause of the disease.

In the present case, the interfering agent such as but non-limited to an interfering RNA modulates the endonuclease-induced mutagenesis to increase the efficiency of the treatment by gene therapy.

Examples of genetic disorders that can be treated by gene therapy include but are not limited to the Lesch-Nyhan syndrome, retinoblastoma, thalassaemia, the sickle cell disease, adenosine deaminase-deficiency, severe combined immune deficiency (SCID), Huntington's disease, adrenoleukodystrophy, the Angelman syndrome, the Canavan disease, the Celiac disease, the Charcot-Marie-Tooth disease, color blindness, Cystic fibrosis, the Down syndrome, Duchenne muscular dystrophy, Haemophilia, the Klinefelter's syndrome, Neurofibromatosis, Phenylketonuria, the Prader-Willi syndrome, the Sickle-cell disease, the Tay-Sachs disease and the Turner syndrome.

As non-limiting example, an interfering agent according to the invention can be used to modulate the endonuclease-induced mutagenesis in the treatment of a genetic disorder where a dominant non functional allele is targeted by at least one DSB-creating agent to knock such dominant non functional allele; in this case, an interfering agent according to the invention is used to increase the endonuclease-induced mutagenesis in the treatment of a genetic disorder.

As another non-limiting example, an interfering agent according to the invention can be used to modulate the endonuclease-induced mutagenesis in the treatment of a genetic disorder where an absent or faulty gene is targeted by at least one DSB-creating agent and replaced by a working gene via gene targeting for example; in this case, an interfering agent according to the invention is used to decrease the endonuclease-induced mutagenesis in the treatment of a genetic disorder.

An interfering agent according to the present invention may also be used in cancer therapy. A way to improve cancer cells killing can be to increase their mutagenesis rate using an interfering agent according to the invention either in association with radiotherapy, as a non-limiting example, either by increasing endonuclease-induced mutagenesis according to the invention. As known in the art, radiotherapy is also called radiation therapy. This approach allows the treatment of cancers and other diseases with ionizing radiation that injures or destroy cancer cells in the area being treated by damaging their genetic material. The approach according to the present invention allows to improve such radio therapeutic treatments by increasing the mutagenesis rate in the cells of the treated area, either by adding in the treated cells an interfering agent according to the invention and/or targeting a gene with a specific endonuclease, thereby obtaining cancer cells with increased rate of mutagenesis and increased rate of mortality. In a parallel approach, an interfering agent according to the present invention may also be used to improve cancer treatment by chemotherapy.

Definitions

The terms "effector" and "effectors" refer to any cellular target, from nucleic or protein origin that can be targeted to directly or indirectly modulate double-strand break-induced mutagenesis; it encompasses any molecule that binds to nucleic acid to modulate gene transcription or protein translation, any molecule that bind to another protein to alter or modify at least one property of that protein, such as its activity, or any gene or gene products that could play a role directly or indirectly in the process of double-strand break-induced mutagenesis.

The term "interfering agent" or "interfering agents" refer to any molecule and compound, likely to interact with effectors. It encompasses small chemicals, small molecules, or small compounds, composite chemicals or molecules, from synthetic or natural origin, encompassing amino acids or nucleic acid derivatives, synthons, Active Pharmaceutical Ingredients, any chemical of industrial interest, used in the manufacturing of drugs, industrial chemicals or agricultural products. These interfering agents are part or not of molecular libraries dedicated to particular screening, commercially available or not. These interfering agents encompass polynucleotides derivatives as a non limiting example.

The term "endonuclease" refers to any wild-type or variant enzyme capable of catalyzing the hydrolysis (cleavage) of bonds between nucleic acids within of a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site of about 12-45 base pairs (bp) in length, more preferably of 14-45 bp. Rare-cutting endonucleases significantly increase HR by inducing DNA double-strand breaks (DSBs) at a defined locus (Rouet, Smih et al. 1994; Rouet, Smih et al. 1994; Choulika, Perrin et al. 1995; Pingoud and Silva 2007). Rare-cutting endonucleases can for example be a homing endonuclease (Paques and Duchateau 2007), a chimeric Zinc-Finger nuclease (ZFN) resulting from the fusion of engineered zinc-finger domains with the catalytic domain of a restriction enzyme such as FokI (Porteus and Carroll 2005) or a chemical endonuclease (Eisenschmidt, Lanio et al. 2005; Arimondo, Thomas et al. 2006; Simon, Cannata et al. 2008). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer 2005). Such chemical endonucleases are comprised in the term "endonuclease" according to the present invention. Rare-cutting endonucleases can also be for example TALENs, a new class of chimeric nucleases using a FokI catalytic domain and a DNA binding domain derived from Transcription Activator Like Effector (TALE), a family of proteins used in the infection process by plant pathogens of the *Xanthomonas* genus (Boch, Scholze et al. 2009; Moscou and Bogdanove 2009; Christian, Cermak et al, 2010; Li, Huang et al. 2010).

Rare-cutting endonuclease can be a homing endonuclease, also known under the name of meganuclease. Such homing endonucleases are well-known to the art (Stoddard 2005). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease.

In the wild, meganucleases are essentially represented by homing endonucleases. Homing Endonucleases (HEs) are a widespread family of natural meganucleases including hundreds of proteins families (Chevalier and Stoddard 2001). These proteins are encoded by mobile genetic elements which propagate by a process called "homing": the endonuclease cleaves a cognate allele from which the mobile element is absent, thereby stimulating a homologous recombination event that duplicates the mobile DNA into the recipient locus. Given their exceptional cleavage properties in terms of efficacy and specificity, they could represent ideal scaffolds to derive novel, highly specific endonucleases. HEs belong to four major families. The LAGLIDADG family, named after a conserved peptidic motif involved in the catalytic center, is the most widespread and the best characterized group. Seven structures are now available. Whereas most proteins from this family are monomeric and display two LAGLIDADG motifs, a few have only one motif, and thus dimerize to cleave palindromic or pseudo-palindromic target sequences.

Although the LAGLIDADG peptide is the only conserved region among members of the family, these proteins share a very similar architecture. The catalytic core is flanked by two DNA-binding domains with a perfect two-fold symmetry for homodimers such as I-CreI (Chevalier, Monnat et al. 2001), I-MsoI (Chevalier, Turmel et al. 2003) and I-CreI (Spiegel, Chevalier et al, 2006) and with a pseudo symmetry for monomers such as I-SceI (Moure, Gimble et al. 2003), I-DmoI (Silva, Dalgaard et al. 1999) or I-AniI (Bolduc, Spiegel et al. 2003). Both monomers and both domains (for monomeric proteins) contribute to the catalytic core, organized around divalent cations. Just above the catalytic core, the two LAGLIDADG peptides also play an essential role in the dimerization interface. DNA binding depends on two typical saddle-shaped αββαββα folds, sitting on the DNA major groove. Other domains can be found, for example in inteins such as PI-PfuI (Ichiyanagi, Ishino et al. 2000) and PI-SceI (Moure, Gimble et al. 2002), whose protein splicing domain is also involved in DNA binding.

The making of functional chimeric meganucleases, by fusing the N-terminal I-DmoI domain with an I-CreI monomer (Chevalier, Kortemme et al. 2002; Epinat, Arnould et al.

2003); International PCT Application WO 03/078619 (Cellectis) and WO 2004/031346 (Fred Hutchinson Cancer Research Center, Stoddard et al)) have demonstrated the plasticity of LAGLIDADG proteins.

Different groups have also used a semi-rational approach to locally alter the specificity of the I-CreI (Seligman, Stephens et al. 1997; Sussman, Chadsey et al. 2004); International PCT Applications WO 2006/097784, WO 2006/097853, WO 2007/060495 and WO 2007/049156 (Cellectis); (Arnould, Chames et al. 2006; Rosen, Morrison et al. 2006; Smith, Grizot et al. 2006), I-SceI (Doyon, Pattanayak et al. 2006), PI-SceI (Gimble, Moure et al. 2003) and I-MsoI (Ashworth, Havranek et al. 2006).

In addition, hundreds of I-CreI derivatives with locally altered specificity were engineered by combining the semi-rational approach and High Throughput Screening:

Residues Q44, R68 and R70 or Q44, R68, D75 and I77 of I-CreI were mutagenized and a collection of variants with altered specificity at positions ±3 to 5 of the DNA target (5NNN DNA target) were identified by screening (international PCT Applications WO 2006/097784 and WO 2006/097853 (Cellectis); (Arnould, Chames et al. 2006; Smith, Grizot et al. 2006).

Residues K28, N30 and Q38 or K28, Y33, Q38 and S40 of I-CreI were mutagenized and a collection of variants with altered specificity at positions ±8 to 10 of the DNA target (10NNN DNA target) were identified by screening (Arnould, Chames et al. 2006; Smith, Grizot et al, 2006); International PCT Applications WO 2007/060495 and WO 2007/049156 (Cellectis)).

Two different variants were combined and assembled in a functional heterodimeric endonuclease able to cleave a chimeric target resulting from the fusion of two different halves of each variant DNA target sequence ((Arnould, Chames et al. 2006; Smith, Grizot et al. 2006); International PCT Applications WO 2006/097854 and WO 2007/034262).

Furthermore, residues 28 to 40 and 44 to 77 of I-CreI were shown to form two partially separable functional subdomains, able to bind distinct parts of a homing endonuclease target half-site (Smith, Grizot et al. 2006); International PCT Applications WO 2007/049095 and WO 2007/057781 (Cellectis).

The combination of mutations from the two subdomains of I-CreI within, the same monomer allowed the design of novel chimeric molecules (homodimers) able to cleave a palindromic combined DNA target sequence comprising the nucleotides at positions ±3 to 5 and ±8 to 10 which are bound by each subdomain (Smith, Grizot et al. 2006); International PCT Applications WO 2007/049095 and WO 2007/057781 (Cellectis).

The method for producing meganuclease variants and the assays based on cleavage-induced recombination in mammal or yeast cells, which are used for screening variants with altered specificity are described in the International PCT Application WO 2004/067736; (Epinat, Arnould et al. 2003; Chames, Epinat et al. 2005; Arnould, Chames et al. 2006). These assays result in a functional LacZ reporter gene which can be monitored by standard methods.

The combination of the two former steps allows a larger combinatorial approach, involving four different subdomains. The different subdomains can be modified separately and combined to obtain an entirely redesigned meganuclease variant (heterodimer or single-chain molecule) with chosen specificity. In a first step, couples of novel meganucleases are combined in new molecules ("half-meganucleases") cleaving palindromic targets derived from the target one wants to cleave. Then, the combination of such "half-meganucleases" can result in a heterodimeric species cleaving the target of interest. The assembly of four sets of mutations into heterodimeric endonucleases cleaving a model target sequence or a sequence from different genes has been described in the following Cellectis International patent applications; XPC gene (WO2007/093918), RAG gene (WO2008/010093), HPRT gene (WO200S/059382), beta-2 microglobulin gene (WO2008/102274), Rosa26 gene (WO2008/152523), Human hemoglobin beta gene (WO2009/13622) and Human interleukin-2 receptor gamma chain gene (WO2009019614).

These variants can be used to cleave genuine chromosomal sequences and have paved the way for novel perspectives in several fields, including gene therapy.

Examples of such endonuclease include I-Sce I, I-Chu I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pju I, PI-Rma I, PI-Spb I, PI-Ssp I, PI-Fac I, PI-Mja I, PI-Pho I, PI-Tag I, PI-Thy I, PI-Tko I, PI-Tsp I, I-MsoI.

A homing endonuclease can be a LAGLIDADG endonuclease such as I-SceI, I-CreI, I-CeuI, I-MsoI, and I-DmoI.

Said LAGLIDADG endonuclease can be I-Sce I, a member of the family that contains two LAGLIDADG motifs and functions as a monomer, its molecular mass being approximately twice the mass of other family members like I-CreI which contains only one LAGLIDADG motif and functions as homodimers.

Endonucleases mentioned in the present application encompass both wild-type (naturally-occurring) and variant endonucleases. Endonucleases according to the invention can be a "variant" endonuclease, i.e. an endonuclease that does not naturally exist in nature and that is obtained by genetic engineering or by random mutagenesis, i.e. an engineered endonuclease. This variant endonuclease can for example be obtained by substitution of at least one residue in the amino acid sequence of a wild-type, naturally-occurring, endonuclease with a different amino acid. Said substitutions) can for example be introduced by site-directed mutagenesis and/or by random mutagenesis. In the frame of the present invention, such variant endonucleases remain functional, i.e. they retain the capacity of recognizing and specifically cleaving a target sequence to initiate gene targeting process.

The variant endonuclease according to the invention cleaves a target sequence that is different from the target sequence of the corresponding wild-type endonuclease. Methods for obtaining such variant endonucleases with novel specificities are well-known in the art.

Endonucleases variants may be homodimers (meganuclease comprising two identical monomers) or heterodimers (meganuclease comprising two non-identical monomers). It is understood that the scope of the present invention also encompasses endonuclease variants per se, including heterodimers (WO2006097854), obligate heterodimers (WO2008093249) and single chain meganucleases (WO03307861.9 and WO2009095793) as non limiting examples, able to cleave one target of interest in a polynucleotide sequence or in a genome. The invention also encompasses hybrid variant per se composed of two monomers from different origins (WO03078619).

Endonucleases with novel specificities can be used in the method according to the present invention for gene targeting and thereby integrating a transgene of interest into a genome at a predetermined location.

Endonucleases according to the invention or rare-cutting endonucleases according to the invention can be mentioned or defined as one double-strand break creating agent amongst other double-strand break creating agents well-known in the art. Double-strand break creating agent means any agent or chemical or molecule able to create DNA (or double-stranded nucleic acids) double-strand breaks (DSBs). As previously mentioned, endonucleases can be considered as double-strand break creating agent targeting specific DNA sequences, in other terms, a double-strand break creating agent targeting a double-strand break creating agent target site. Under "double-strand break creating agent" is also encompassed variants or derivatives of endonucleases such as engineered variants or engineered derivatives of meganucleases, zinc-finger nucleases or TALENs; these variants or derivatives can be chimeric rare-cutting endonucleases, i.e. fusion proteins comprising additional protein catalytic domains, displaying one or several enzymatic activities amongst nuclease, endonuclease or exonuclease, or a fusion protein with a polymerase activity, a kinase activity, a phosphatase activity, a methylase activity, a topoisomerase activity, an integrase activity, a transposase activity, a ligase activity, a helicase activity, or a recombinase activity, as non-limiting examples or fusion proteins with other proteins implicated in DNA processing. In a more precise non-limiting example, said "double-strand break creating agent" according to the present invention can be a fusion protein between a single-chain meganuclease obtained according to previously published methods (Grizot et al. 2009) and an exonuclease Trex2 as shown in example 4.

Other agents or chemicals or molecules are double-strand break creating agents whom DNA sequence targets are non-specific or non-predictable such as, in a non limiting list, alkylating agents (Methyl Methane Sulfonate or dimethane sulfonates family and analogs), zeocyn, enzyme inhibitors such as toposiomerase inhibitors (types I and II such as non limiting examples quinolones, fluoroquinolones, ciprofloxacin, irinotecan, lamellarin D, doxorubicin, etoposide) and ionizing radiations (x-rays, Ultraviolet, gamma-rays).

The term "reporter gene", as used herein, refers to a nucleic acid sequence whose product can be easily assayed, for example, colorimetrically as an enzymatic reaction product, such as the lacZ gene which encodes for β-galactosidase. Examples of widely-used reporter molecules include enzymes such, as β-galactosidase, β-glucoronidase, β-glucosidase; luminescent molecules such as green fluorescent protein and firefly luciferase; and auxotrophic markers such as His3p and Ura3p. (See, e.g., Chapter 9 in Ausubel, F. M., et al. Current Protocols in Molecular Biology, John Wiley & Sons, Inc. (1998)). The expressions "inactive reporter gene" or "reporter gene rendered inactive" refers to a reporter gene wherein one part of said reporter gene has been replaced for the purpose of the present invention, in this inactive state, said inactive reporter gene is not capable of emitting any relevant detectable signal upon, transfection in a cell. In the present invention, reporter genes such as Luciferase and Green Fluorescent Protein genes have been rendered inactive by, respectively, the introduction of a frameshift mutation in their respective coding sequence. Said frameshift mutation can be due, as a non-limiting example, to the introduction in said coding sequence of a target, sequence for an endonuclease. Upon cellular co-transfection of said inactive reporter gene and endonuclease, said endonuclease provokes a double strand break in its target that is repaired by NHEJ, leading to a functional restoration of said reporter gene. The expressions "functional restoration" of a reporter gene or "functional reporter gene" refer to the recovering of a reporter gene capable of emitting a relevant detectable signal upon transfection in a cell. "RNA interference" refers to a sequence-specific post transcriptional gene silencing mechanism triggered by dsRNA, during which process the target RNA is degraded. RNA degradation occurs in a sequence-specific manner rather than by a sequence-independent dsRNA response, like PKR response.

The terms "interfering RNA" and "iRNA" refer to double stranded RNAs capable of triggering RNA interference of a gene. The gene thus silenced is defined as the gene targeted by the iRNA. Interfering RNAs include, e.g., siRNAs and shRNAs; an interfering RNA is also an interfering agent as described above.

"iRNA-expressing construct" and "iRNA construct" are generic terms which include small interfering RNAs (siRNAs), shRNAs and other RNA species, and which can be cleaved in vivo to form siRNAs. As mentioned before, it has been shown that the enzyme Dicer cleaves long dsRNAs into short-interfering RNAs (siRNAs) of approximately 21-23 nucleotides. One of the two siRNA strands is then incorporated into an RNA-induced silencing complex (RISC). RISC compares these "guide RNAs" to RNAs in the cell and efficiently cleaves target RNAs containing sequences that are perfectly, or nearly perfectly complementary to the guide RNA. "iRNA construct" also includes nucleic acid preparation designed to achieve an RNA interference effect, such as expression vectors able of giving rise to transcripts which form dsRNAs or hairpin RNA in cells, and or transcripts which can produce siRNAs in vivo.

A "short interfering RNA" or "siRNA" comprises a RNA duplex (double-stranded region) and can further comprises one or two single-stranded overhangs, 3' or 5' overhangs. Each molecule of the duplex can comprise between 17 and 29 nucleotides, including 17, 18, 19, 20, 21, 22, 23, 24, 25, 26, 27, 28, and 29 nucleotides. siRNAs can additionally be chemically modified.

"MicroRNAs" or "miRNAs" are endogenously encoded RNAs that are about 22-nucleotide-long, that post-transcriptionally regulate target genes and are generally expressed in a highly tissue-specific or developmental-stage-specific fashion. At least more than 200 distinct miRNAs have been identified in plants and animals. These small regulatory RNAs are believed to serve important biological functions by two predominant modes of action: (1) by repressing the translation of target mRNAs, and (2) through RNA interference, that means cleavage and degradation of mRNAs. In this latter case, miRNAs function analogously to siRNAs. miRNAs are first transcribed as part as a long, largely single-stranded primary transcript (pri-miRNA) (Lee, Jeon et al. 2002). This pri-miRNA transcript is generally and possibly invariably, synthetized by RNA polymerase II and therefore is polyadenylated and may be spliced. It contains an about 80-nucleotides long hairpin structure that encodes the mature about 22-nucleotides miRNA part of one arm of the stem. In animal cells, this primary transcript is cleaved by a nuclear RNaseIII-type enzyme called Drosha (Lee et al, 2003, Nature 425:415-419) to liberate a hairpin mRNA precursor, or pre-miRNA of about-65 nucleotides long. This pre-miRNA is then exported to the cytoplasm by exportin-5 and the GTP-bound form, of the Ran cofactor (Yi, Qin et al. 2003). Once in the cytoplasm, the pre-miRNA is further processed by Dicer, another RNaseIII enzyme to produce a duplex of about-22 nucleotides base pairs long that is structurally identical to a siRNA duplex (Hutvagner, McLachlan et al. 2001). The binding of protein components of the RISC, or RISC cofactors, to the duplex results in incorporation of the mature, single-stranded miRNA into a RISC or RISC-like protein complex, while the other strand of the duplex is degraded (Bartel et al, 2004, Cell 116: 281-297).

Thus, one can design and express artificial miRNAs based on the features of existing miRNA genes. The miR-30 (microRNA 30) architecture can be used to express miRNAs (or siRNAs) from RNA polymerase II promoter-based expression plasmids (Zeng, Cai et al. 2005). In some instances the precursor miRNA molecules may include more than one stem-loop structure. The multiple stem-loop structures may be linked to one another through a linker, such as, for example, a nucleic acid, linker, a miRNA flanking sequence, other molecules, or some combination thereof.

A "short hairpin RNA (shRNA)" refers to a segment of RNA that is complementary to a portion of a target gene (complementary to one or more transcripts of a target gene), and has a stem-loop (hairpin) structure, and which can be used to silence gene expression.

A "stem-loop structure" refers to a nucleic acid having a secondary structure that includes a region of nucleotides which are blown or predicted to form a double strand (stem portion) that is linked on one side by a region of predominantly single-stranded nucleotides (loop portion). The terms "hairpin" is also used herein to refer to stem-loop structures.

By "double-strand break-induced target sequence" or "double-strand break creating agent target site", or "DSB creating agent target site" is intended a sequence that is recognized by any double strand break creating agent.

The expression "polynucleotide derivatives" refers to polynucleotide sequences that can be deduced and constructed from the respective sequence or a part of the respective sequence of identified-effector genes according to the present invention. These derivatives can refer to mRNAs, siRNAs, dsRNAs, miRNAs, cDNAs. These derivatives can be used directly or as part of a delivery vector or vector/plasmid/construct, by introducing them in an eukaryotic cell to increase gene targeting efficiency and/or endonuclease-induced homologous recombination.

"Transfection" means "introduction" into a live cell, either in vitro or in vivo, of certain nucleic acid construct, preferably into a desired cellular location of a cell, said nucleic acid construct being functional once in the transfected cell. Such presence of the introduced nucleic acid may be stable or transient. Successful transfection will have an intended effect or a combination of effects on the transfected cell, such as silencing and/or enhancing a gene target and/or triggering target physiological event, like enhancing the frequency of mutagenesis following an endonuclease-induced DSB as a non-limiting example.

"Modulate" or "modulation" is used to qualify the up- or down-regulation of a pathway like NHEJ consecutive to an endonuclease-induced DSB in particular conditions or not, compared to a control condition, the level of this modulation being measured by an appropriate method. More broadly, it can refer to any phenomenon "modulation" is associated with, like the expression level of a gene, a polynucleotide or derivative thereof (DNA, cDNA, plasmids, RNA, mRNA, interfering RNA), polypeptides, etc.

"Amino acid residues" in a polypeptide sequence are designated herein according to the one-letter code, in which, for example, Q means Gln or Glutamine residue, R means Arg or Arginine residue and D means Asp or Aspartic acid residue.

"Amino acid substitution" means the replacement of one amino acid residue with another, for instance the replacement of an Arginine residue with a Glutamine residue in a peptide sequence is an amino acid substitution.

"Altered/enhanced/increased/improved cleavage activity", refers to an increase in the detected level of meganuclease cleavage activity, see below, against a target DNA sequence by a second meganuclease in comparison to the activity of a first meganuclease against the target DNA sequence. Normally the second meganuclease is a variant of the first and comprise one or more substituted amino acid residues in comparison to the first meganuclease.

"Nucleotides" are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

By "meganuclease", is intended an endonuclease having a double-stranded DNA target sequence of 12 to 45 bp, more preferably 22 to 24 bp when said meganuclease is an I-CreI variant. Said meganuclease is either a dimeric enzyme, wherein each domain is on a monomer or a monomeric enzyme comprising the two domains on a single polypeptide.

By "meganuclease domain" is intended the region which interacts with one half of the DNA target of a meganuclease and is able to associate with the other domain of the sane meganuclease which interacts with the other half of the DNA target to form a functional meganuclease able to cleave said DNA target.

By "meganuclease variant" or "variant." it is intended a meganuclease variant or a "DSB-creating agent" variant, a rare-cutting endonuclease" variant, a "chimeric rare-cutting endonuclease" variant obtained, by replacement of at least one residue in the amino acid sequence of the parent meganuclease or parent "DSB-creating agent", parent rare-cutting endonuclease", parent "chimeric rare-cutting endonuclease" with a different amino acid.

By "peptide linker" it is intended to mean a peptide sequence of at least 10 and preferably at least 17 amino acids which links the C-terminal amino acid residue of the first monomer to the N-terminal residue of the second monomer and which allows the two variant monomers to adopt the correct conformation for activity and which does not alter the specificity of either of the monomers for their targets.

By "subdomain" it is intended the region of a LAGLIDADG homing endonuclease core domain which interacts with a distinct part of a homing endonuclease DNA target half-site.

By "selection or selecting" it is intended to mean the isolation of one or more meganuclease variants based upon an observed specified phenotype, for instance altered cleavage activity. This selection can be of the variant in a peptide form upon which the observation is made or alternatively the selection can be of a nucleotide coding for selected meganuclease variant.

By "screening" it is intended to mean the sequential or simultaneous selection of one or more meganuclease variant(s) which exhibits a specified phenotype such as altered cleavage activity.

By "derived from" it is intended to mean a "DSB-creating agent" variant, a rare-cutting endonuclease" variant, a "chimeric rare-cutting endonuclease" variant or a meganuclease variant which is created from a parent "DSB-creating agent", rare-cutting endonuclease", "chimeric rare-cutting endonuclease" or meganuclease and hence the peptide sequence of the resulting "DSB-creating agent" variant, rare-cutting endonuclease" variant, "chimeric rare-cutting endonuclease" variant or meganuclease variant is related to (primary sequence level) but derived from (mutations) the sequence peptide sequence of the parent meganuclease. By "I-CreI" is intended the wild-type I-CreI having the sequence of pdb accession code 1g9y, corresponding to the sequence SEQ ID NO: 7 in the sequence listing.

By "I-CreI variant with novel specificity" is intended a variant having a pattern of cleaved targets different from that of the parent meganuclease. The terms "novel specificity", "modified specificity", "novel cleavage specificity", "novel substrate specificity" which are equivalent and used indifferently, refer to the specificity of the variant towards the nucleotides of the DNA target sequence. In the present patent application all the I-CreI variants described comprise an additional Alanine after the first Methionine of the wild type I-CreI sequence (SEQ ID NO: 7). These variants also comprise two additional Alanine residues and an Aspartic Acid residue after the final Proline of the wild type I-CreI sequence. These additional residues do not affect the properties of the enzyme and to avoid confusion these additional residues do not affect the numeration of the residues in I-CreI or a variant referred in the present patent application, as these references exclusively refer to residues of the wild type I-CreI enzyme (SEQ ID NO: 7) as present in the variant, so for instance residue 2 of I-CreI is in fact residue 3 of a variant which comprises an additional Alanine after the first Methionine.

By "I-CreI site" is intended a 22 to 24 bp double-stranded DNA sequence which is cleaved by I-CreI. I-CreI sites include the wild-type non-palindromic I-CreI homing site and the derived palindromic sequences such as the sequence $5'-t_{-12}c_{-11}a_{-10}a_{-9}a_{-8}a_{-7}c_{-6}g_{-5}t_{-4}c_{-3}g_{-2}t_{-1}a_{+1}c_{+2}g_{+3}a_{+4}c_{+5}g_{+6}t_{+7}t_{+8}t_{+9}t_{+10}g_{+11}a_{+12}$ (SEQ ID NO: 8), also called C1221.

By "domain" or "core domain" is intended the "LAGLIDADG homing endonuclease core domain" which is the characteristic $\alpha\beta\beta\alpha\beta\beta\alpha$ fold of the homing endonucleases of the LAGLIDADG family, corresponding to a sequence of about one hundred amino acid residues. Said domain comprises four beta-strands ($\beta_1\beta_2\beta_3\beta_4$) folded in an anti-parallel beta-sheet which interacts with one half of the DNA target. This domain is able to associate with another LAGLIDADG homing endonuclease core domain which interacts with the other half of the DNA target to form a functional endonuclease able to cleave said DNA target. For example, in the case of the dimeric homing endonuclease I-CreI (163 amino acids), the LAGLIDADG homing endonuclease core domain corresponds to the residues 6 to 94.

By "beta-hairpin" is intended two consecutive beta-strands of the antiparallel beta-sheet of a LAGLIDADG homing endonuclease core domain ($\beta_1\beta_2$ or $\beta_3\beta_4$) which are connected by a loop or a turn, By "single-chain meganuclease", "single-chain chimeric meganuclease", "single-chain meganuclease derivative", "single-chain chimeric meganuclease derivative" or "single-chain derivative" is intended a meganuclease comprising two LAGLIDADG homing endonuclease domains or core domains linked by a peptidic spacer as described in WO03078619 and WO2009095793. The single-chain meganuclease is able to cleave a chimeric DNA target sequence comprising one different half of each parent meganuclease target sequence. —By "SC-GS meganuclease" or "engineered SC-GS meganuclease" is meant an engineered single chain meganuclease as described in WO03078619 and WO2009095793 capable of cleaving a target sequence according to SEQ ID NO: 9, and having a polypeptidic sequence corresponding as a non-limiting example to SEQ ID NO: 4. —By "SC-RAG meganuclease" or "meganuclease SC-RAG" or "SC-RAG" is meant an engineered single chain meganuclease as described in WO03078619 and WO2009095793 capable of cleaving a target sequence according to SEQ ID NO: 10, and having a polypeptidic sequence corresponding as a non-limiting example to SEQ ID NO: 11.

By "DNA target", "DNA target sequence", "target sequence", "target-site", "target", "site", "site of interest", "recognition site", "polynucleotide recognition site", "recognition sequence", "homing recognition site", "homing site", "cleavage site", "endonuclease-specific target site" is intended a 20 to 24 bp double-stranded palindromic, partially palindromic (pseudo-palindromic) or non-palindromic polynucleotide sequence that is recognized and cleaved by a LAGLIDADG homing endonuclease such as I-CreI, or a variant, or a single-chain chimeric meganuclease derived from I-CreI. Said DNA target sequence is qualified of "cleavable" by an endonuclease, when recognized within a genomic sequence and known to correspond to the DNA target sequence of a given endonuclease or a variant of such endonuclease. These terms refer to a distinct DNA location, preferably a genomic location, at which a double stranded break (cleavage) is to be induced by the meganuclease. The DNA target is defined by the 5' to 3' sequence of one strand of the double-stranded polynucleotide, as indicate above for C1221. Cleavage of the DNA target occurs at the nucleotides at positions +2 and −2, respectively for the sense and the antisense strand. Unless otherwise indicated, the position at which cleavage of the DNA target by an I-Cre I meganuclease variant occurs, corresponds to the cleavage site on the sense strand of the DNA target. By "an I-SceI target site" is meant a target sequence for the endonuclease I-SceI; by "an engineered meganuclease target site" is meant a target sequence for a variant endonuclease that has been engineered as previously mentioned and as described in WO2006097854, WO2008093249, WO03078619, WO2009095793, WO03078619 and WO 2004/067736.

By "DNA target half-site", "half cleavage site" or half-site" is intended the portion of the DNA target which is bound by each LAGLIDADG homing endonuclease core domain.

By "chimeric DNA target" or "hybrid DNA target" is intended the fusion of different halves of two parent meganuclease target sequences. In addition at least one half of said target may comprise the combination of nucleotides which are bound by at least two separate subdomains (combined DNA target).

By "parent meganuclease" it is intended to mean a wild type meganuclease or a variant of such a wild type meganuclease with identical properties or alternatively a meganuclease with some altered characteristic in comparison to a wild type version of the same meganuclease.

By "delivery vector" or "delivery vectors" is intended any delivery vector which can be used in the present invention to put into cell contact or deliver inside cells or subcellular compartments agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound, contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid, molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e.g. adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g. Herpes Simplex virus types 1 and 2, Epstein-Barr virus, cytomegalovirus), and poxvirus (e.g., vaccinia, fowl pox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication. In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells.

By "integrative lentiviral vectors (or LV)", is meant such vectors as non limiting example, that are able to integrate the genome of a target cell. At the opposite by "non integrative lentiviral vectors (or NILV)" is meant efficient gene delivery vectors that do not integrate the genome of a target cell through the action of the virus integrase.

One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors. A vector according to the present invention comprises, but is not limited to, a YAC (yeast artificial chromosome), a BAG (bacterial artificial), a baculovirus vector, a phage, a phagemid, a cosmid, a viral vector, a plasmid, a RNA vector or a linear or circular DNA or RNA molecule which may consist of chromosomal, non chromosomal, semi-synthetic or synthetic DNA. In general, expression vectors of utility in recombinant DNA techniques are often in the form of "plasmids" which refer generally to circular double stranded DNA loops which, in their vector form are not bound to the chromosome. Large numbers of suitable vectors are known to those of skill in the art. Vectors can comprise selectable markers, for example: neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for *S. cerevisiae*; tetracycline rifampicin or ampicillin resistance in *E. coli*. Preferably said vectors are expression vectors, wherein a sequence encoding a polypeptide of interest is placed under control of appropriate transcriptional and translational control elements to permit production or synthesis of said polypeptide. Therefore, said polynucleotide is comprised in an expression cassette. More particularly, the vector comprises a replication origin, a promoter operatively linked to said encoding polynucleotide, a ribosome binding site, a RNA-splicing site (when genomic DNA is used), a polyadenylation site and a transcription termination site. It also can comprise an enhancer or silencer elements. Selection of the promoter will depend upon the cell in which the polypeptide is expressed. Suitable promoters include tissue specific and/or inducible promoters. Examples of inducible promoters are: eukaryotic metallothionine promoter which is induced by increased levels of heavy metals, prokaryotic lacZ promoter which is induced in response to isopropyl-β-D-thiogalacto-pyranoside (IPTG) and eukaryotic heat shock promoter which is induced by increased temperature. Examples of tissue specific promoters are skeletal muscle creatine kinase, prostate-specific antigen (PSA), α-antitrypsin protease, human surfactant (SP) A and B proteins, β-casein and acidic whey protein genes.

Inducible promoters may be induced by pathogens or stress, more preferably by stress like cold, heat, UV light, or high ionic concentrations (reviewed in (Potenza, Aleman et al, 2004)). Inducible promoter may be induced by chemicals (reviewed in (Moore, Samalova et al. 2006); (Padidam 2003); (Wang, Zhou et al. 2003); (Zuo and Chua 2000).

Delivery vectors and vectors can be associated or combined with any cellular permeabilization techniques such as sonoporation or electroporation or derivatives of these techniques.

By "cell" or "cells" is intended any prokaryotic or eukaryotic living cells, cell lines derived from these organisms for in vitro cultures, primary cells from animal or plant origin.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines. These cells thus represent a more valuable model to the in vivo state they refer to.

In the frame of the present invention, "eukaryotic cells" refer to a fungal, plant or animal cell or a cell line derived from the organisms listed below and established for in vitro culture. More preferably, the fungus is of the genus *Aspergillus, Penicillium, Acremonium, Trichoderma, Chrysoporium, Mortierella, Kluyveromyces* or *Pichia*; More preferably, the fungus is of the species *Aspergillus niger, Aspergillus nidulans, Aspergillus oryzae, Aspergillus terreus, Penicillium chrysogenum, Penicillium citrinum, Acremonium Chrysogenum, Trichoderma reesei, Mortierella alpine, Chrysosporium lucknowense, Kiuyverornyces lactis, Pichia pastoris* or *Pichia ciferrii.*

More preferably the plant is of the genus *Arabidospis, Nicotiana, Solanum, Iactuca, Brassica, Oryza, Asparagus, Pisum, Medicago, Zea, Hordeum, Secale, Triticum, Capsicum, Cucumis, Cucurbita, Citrullis, Citrus, Sorghum*; More preferably, the plant is of the species *Arabidospis thaliana, Nicotiana tabaccum, Solanum lycopersicum, Solanum*

*tuberosum, Solanum melongena, Solanum esculentum, Lactuca saliva, Brassica napus, Brassica oleracea, Brassica rapa, Oryza glaberrima, Oryza saliva, Asparagus officinalis, Pisum sativum, Medieago saliva, zea mays, Hordeum vulgare, Secale cereal, Triticum aestivum, Triticum durum, Capsicum sativus, Cucurbita pepo, Citrullus lanatus, Cucumis melo, Citrus aurantifolia, Citrus maxima, Citrus medica, Citrus reticulata.*

More preferably the animal cell is of the genus *Homo, Rattus, Mus, Sus, Bos, Danio, Canis, Fells, Equus, Salmo, Oncorhynchus, Gallus, Meleagris, Drosophila, Caenorhabditis*; more preferably, the animal cell is of the species *Homo sapiens, Rattus norvegicus, Mus musculus, Sus scrofa, Bos taurus, Danio rerio, Canis lupus, Felis catus, Equus caballus, Salmo salar, Oncorhynchus mykiss, Gallus gallus, Meleagris gallopavo, Drosophila melanogaster, Caenorhabditis elegans.*

By "homologous" is intended a sequence with enough identity to another one to lead to homologous recombination between sequences, more particularly having at least 95% identity, preferably 97% identity and more preferably 99%.

"Identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. By a polynucleotide having a sequence at least, for example, 95% "identical" to a query sequence of the present invention, it is intended that the sequence of the polynucleotide is identical to the query sequence except that the sequence may include up to five nucleotide alterations per each 100 nucleotides of the query sequence. In other words, to obtain a polynucleotide having a sequence at least 95% identical to a query sequence, up to 5% (5 of 100) of the nucleotides of the sequence may be inserted, deleted, or substituted with another nucleotide. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. The <<needle>> program, which uses the Needleman-Wunsch global alignment algorithm (Needleman and Wunseh 1970) to find the optimum alignment (including gaps) of two sequences when considering their entire length, may for example be used. The needle program is for example available on the ebi.ac.uk world wide web site. The percentage of identity in accordance with the invention is preferably calculated using the EMBOSS::needle (global) program with a "Gap Open" parameter equal to 10.0, a "Gap Extend" parameter equal to 0.5, and a Blosum62 matrix.

By "mutation" is intended the substitution, deletion, insertion of one or more nucleotides/amino acids in a polynucleotide (cDNA, gene) or a polypeptide sequence. Said mutation can affect the coding sequence of a gene or its regulatory sequence. It may also affect the structure of the genomic sequence or the structure/stability of the encoded mRNA. By "frameshift mutation" is intended a genetic mutation caused by insertions or deletions in a DNA sequence of a number of nucleotides that is not evenly divisible by three. Due to the triplet nature of the genetic code, such insertions or deletions can change the reading frame of the considered gene, resulting in a completely different translation of this gene. For the purpose of the present invention, such frameshift mutations have been inserted in the coding sequence of a reporter gene, leading to a inactive reporter gene that can only be restored after an NHEJ event. In the frame of the present invention, the expression "double-strand break-induced mutagenesis" (DSB-induced mutagenesis) refers to a mutagenesis event consecutive to an NHEJ event following an endonuclease-induced DSB, leading to insertion/deletion at the cleavage site of an endonuclease.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

As used herein, the term "transgene" refers to a sequence encoding a polypeptide. Preferably, the polypeptide encoded by the transgene is either not expressed, or expressed but not biologically active, in the cell, tissue or individual in which the transgene is inserted. Most preferably, the transgene encodes a therapeutic polypeptide useful for the treatment of an individual.

The term, "gene of interest" or "GOI" refers to any nucleotide sequence encoding a known or putative gene product.

As used herein, the term "locus" is the specific physical location of a DNA sequence (e.g. of a gene) on a chromosome. The term, "locus" usually refers to the specific physical location of an endonuclease's target sequence on a chromosome. Such a locus, which comprises a target sequence that is recognized and cleaved by an endonuclease according to the invention, is referred to as "locus according to the invention". Also, the expression "genomic locus of interest" is used to qualify a nucleic acid sequence in a genome that can be a putative target for a double-strand break according to the invention. By "endogenous genomic locus of interest" is intended a native nucleic acid sequence in a genome, i.e., a sequence or allelic variations of this sequence that is naturally present at this genomic locus. It is understood that the considered genomic locus of interest of die present invention can be between two overlapping genes the considered endonuclease's target sequences are located in two different genes. "Genomic locus of interest" in the present application, encompasses nuclear genetic material but also a portion of genetic material that can exist independently to the main body of genetic material, such as plasmids, episomes, virus, transposons or in organelles such as mitochondria or chloroplasts as non-limiting examples, at which a double stranded break (cleavage) can be induced by the DSB-creating agent, i.e endonuclease, rare-cutting endonuclease and/or chimeric rare-cutting endonuclease of the invention.

By "RAG1 locus" is intended the RAG1 gene position in a mammalian genome. For example, the human RAG1 gene is available in the NCBI database, under the accession number NC 000011.8 (GeneID:5896) and its locus is positioned from position 36546139 to 36557877.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Example 1

Constructions Monitoring Meganuclease-Induced Mutagenesis

Plasmids measuring meganuclease-induced mutagenesis at their target site were constructed. They are based on activation of a reporter gene after cleavage of a target by a meganuclease followed by a mutagenic repair of this double strand break (DSB). The present invention uses Luciferase reporter gene and I-SceI and GS meganucleases but other reporter gene such as GFP and other meganucleases can be used.

a) Materials and Methods
Cell Culture

Cell line 293H was cultured at 37° C. with 5% $CO_2$ in Dulbecco's modified Eagle's medium (DMEM) Glutamax supplemented with 10% fetal calf serum, 2 mM L-glutamme, 100 UI/ml penicilline, 100 µg/ml streptomycine, 0.25 µg/m amphotericine B (Fongizone).

Transient Transfection in 96 Well Plate Format

Figure 2:
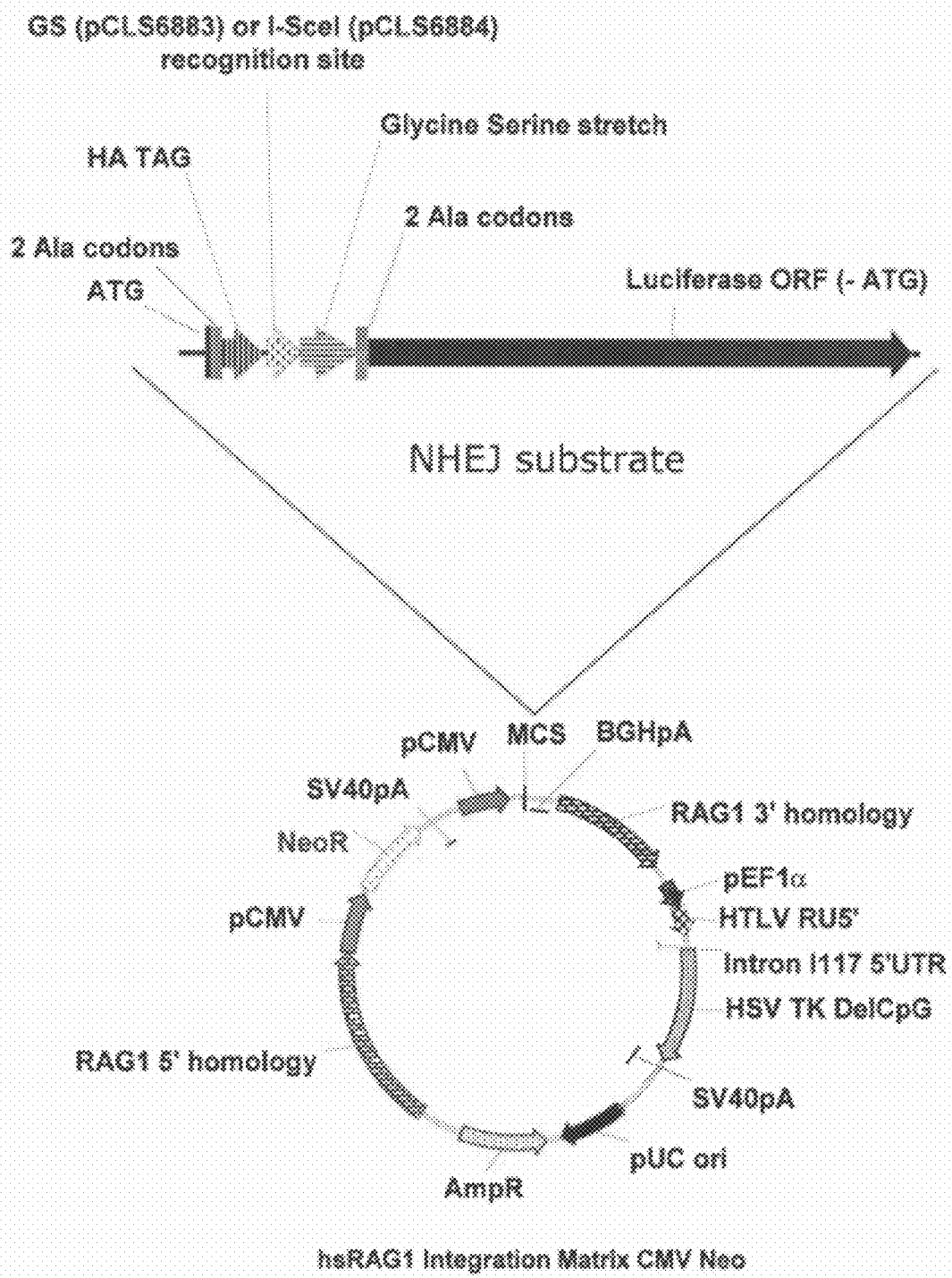
FIG. 2: Plasmid construction maps to quantify NHEJ repair events by SC_GS (pCLS6883; SEQ ID NO: 1) or I-SceI (pCLS6884 SEQ ID NO: 2); these constructions can be targeted to RAG1 locus.

Twenty thousand cells per well were seeded in white 96 well plates one day before transfection. Per well, cells were transfected with 200 ng of total DNA with 100 ng pCLS6883 (SEQ ID NO: 1) and either 100 ng of pCLS2690 (SEQ ID NO: 3) or 100 ng of pCLS0099 (SEQ ID NO: 12) using 1.35 µl of Polyfect transfection reagent (QIAGEN). Ninety-six hours post transfection 50 µl per well of ONEGlo (Promega) were added, cells were incubated in dark for 3 minutes before luciferase activity analysis (1 second/well) using PHERAStar luminometer (BMG Labtech).

b) Results;

The plasmids pCLS6883 (SEQ ID NO: 1) and pCLS6884 (SEQ ID NO:2) were constructed to quantify NHEJ repair events induced by SC_GS or I-SceI respectively. These constructions can be targeted at RAG1 site locus and are presented in FIG. 2.

The sequence used to measure meganuclease-induced mutagenesis is made of an ATG start codon followed by i) 2 codons for alanine ii) the tag HA sequence iii) GS or I-SceI recognition site iv) a glycine serine stretch v) the same 2 codons for alanine as in i) and finally vi) luciferase reporter gene lacking its ATG start codon. Luciferase reporter gene is inactive due to a frame-shift introduced by GS or I-SceI recognition site. Thus induction of a DNA double strand break (DSB) by SC_GS (SEQ ID NO: 4) encoded by vector pCLS2690 (SEQ ID NO: 3) or I-SecI meganuclease (SEQ ID NO: 40) followed by a mutagenic DSB repair by NHEJ can lead to the restoration of Luciferase gene in frame with ATG start codon.

These sequences were placed in a plasmid used to target the final construct at RAG1 locus using hsRAG1 Integration Matrix CMV Neo from cGPS® Custom Human Full Kit DD (Cellectis Bioresearch).

The plasmid pCLS6883 (SEQ ID NO: 1) was tested in an extrachromosomal assay by co transfection with either pCLS2690 (SEQ ID NO: 3) encoding SC_GS meganuclease or pCLS0099 (SEQ ID NO: 12) encoding GFP. Luciferase signal was analysed 72 hours post transfection. Co transfection with pCLS6883 (SEQ ID NO: 1) and pCLS0099 (SEQ ID NO: 12) led to a 1,800 R.L.U. signal whereas co transfection with pCLS6883 (SEQ ID NO: 1) and pCLS2690 (SEQ ID NO: 3) led to a 20,000 R.L.U signal. This result demonstrates that the presence of meganuclease SC_GS induced luciferase by a factor of 11 and that pCLS6883 (SEQ ID NO: 1) construe is thus measuring mutagenic NHEJ DSB-repair induced by SC_GS.

Example 2

Screening with Extrachromosomal Assay of siRNAs Targeting Genes Coding for Kinases The construct measuring SC_GS induced mutagenesis at GS locus with Luciferase reporter gene (pCLS6883, SEQ ID NO: 1) was used to screen in an extrachromosomal assay siRNAs targeting genes coding for kinases. This screen identified 23 siRNAs that led to stimulation of Luciferase signal induced by meganuclease SC_GS.

a) Materials and Methods
Extrachromosomal Screening

Twenty thousand of 293H cells per well were seeded in white 96 well plates one day before transfection. Per well, cells were transfected with 200 ng of total DNA with 100 ng pCLS6883 (SEQ ID NO: 1) and either 100 ng of pCLS2690 (SEQ ID NO: 3) or 100 ng of pCLS0099 (SEQ ID NO: 12) and with siRNA at 33 nM final concentration using 1.35 µl of Polyfect transfection reagent (QIAGEN). The siRNAs kinase set (QIAGEN) is targeting 696 genes with 2 siRNAs per gene. Ninety-six hours post transfection 50 µl per well of ONEGlo (Promega) were added, cells were incubated in dark for 3 minutes before luciferase activity analysis (1 second/well) using PHERAStar luminometer (BMG Labtech).

b) Results

Each plate from siRNA kinase set was co-transfected in duplicate in presence of SC_GS (pCLS2690, SEQID NO: 1), induced condition) or in simplicate in presence of GFP (pCLS0099, SEQ ID NO: 12, not induced condition). Induction by SC_GS was monitored by comparison of the Luciferase signal obtained with pCLS2690 (SEQID NO: 1) over the one obtained with pCLS0099 (SEQ ID NO: 12). The induction varied from 2 to 11 depending on the transfection.

Figure 3:
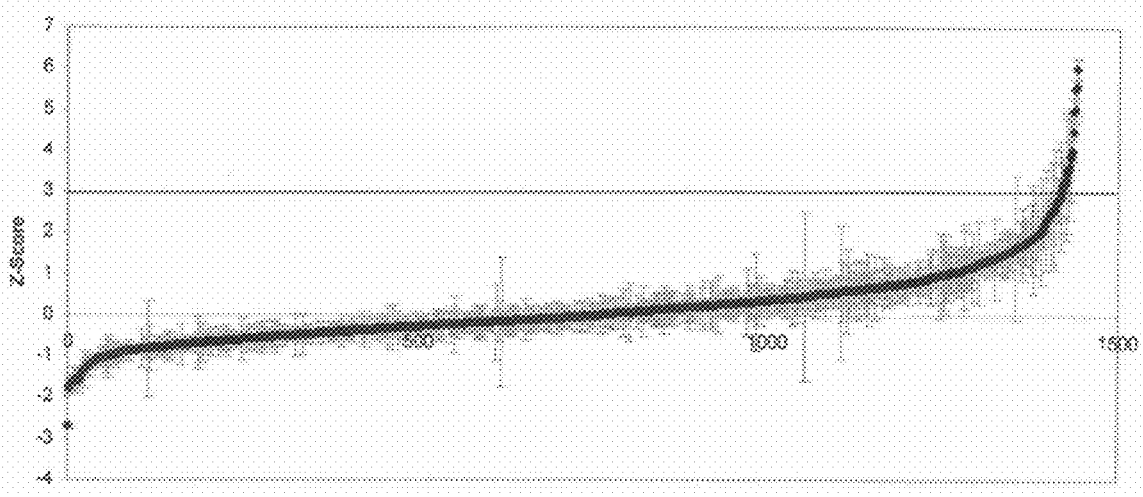
FIG. 3: Z-score values of an extrachromosomal assay screening of si RNA targeting 696 genes coding for kinases.

To normalize the different transfections, Z score was calculated for each plate with, the following equation $Z=(x-\mu)/\sigma$ were x is the R.L.U. value of a given siRNA, µ, is the median R.L.U. value of the plate and σ its standard deviation. A siRNA was considered as a stimulating hit when its Z score value was higher than 3 (FIG. 3).

This screen led to the identification of 23 positive hits that stimulate luciferase signal by a factor ranging from 2 to 7 (cf. Table I below).

TABLE I siRNA hits stimulating GS_SC-induced luciferase signal.

| Gene targeted | Gene siRNA ID | siRNA target sequence | SEQ ID NO: | Mean Z Score | Std | Stimulation factor |
|---|---|---|---|---|---|---|
| CSNK1D | 1453 | CCGGTCTAGGATCGAAATGTT | 13 | 3.14 | 0.75 | 3.40 |
| AK2 | 204 | CGGCAGAACCCGAGTATCCTA | 14 | 5.51 | 0.20 | 5.08 |
| AKT2 | 208 | CAAGCGTGGTGAATACATCAA | 15 | 3.65 | 0.23 | 2.94 |
| CAMK2G | 818 | GAGGAAGAGATCTATACCCTA | 16 | 5.01 | 0.23 | 3.66 |
| GK2 | 2712 | TACGTTAGAAGAGCACTGTAA | 17 | 3.33 | 1.49 | 2.75 |
| PFKFB4 | 5210 | CAGAAAGTGTCTGGACTTGTA | 18 | 3.92 | 1.14 | 2.18 |
| MAPK12 | 6300 | CTGGACGTATTCACTCCTGAT | 19 | 3.84 | 0.06 | 3.22 |
| PRKCE | 5581 | CCCGACCATGGTAGTGTTCAA | 20 | 4.00 | 0.43 | 2.91 |
| EIF2AK2 | 5610 | CGGAAAGACTTACGTTATTAA | 21 | 4.50 | 0.22 | 3.15 |
| WEE1 | 7465 | CAGGGTAGATTACCTCGGATA | 22 | 3.20 | 0.08 | 5.01 |
| CDK5R1 | 8851 | CCGGAAGGCCACGCTGTTTGA | 23 | 4.01 | 0.26 | 6.03 |
| LIG4 | 3981 | CACCGTTTATTTGGACTCGTA | 24 | 4.11 | 0.41 | 6.15 |
| AKAP1 | 8165 | AGCGCTGAACTTGATTGGGAA | 25 | 4.97 | 0.32 | 7.24 |
| MAP3K6 | 9064 | TCAGAGGAGCTGAGTAATGAA | 26 | 5.99 | 0.22 | 5.41 |
| DYRK3 | 8444 | TCGACAGTACGTGGCCCTAAA | 27 | 3.54 | 0.22 | 3.61 |
| RPS6KA4 | 8986 | CGCCACCTTCATGGCATTCAA | 28 | 3.56 | 0.73 | 3.61 |
| STK17A | 9263 | CACACTCGTGATGTAGTTCAT | 29 | 3.26 | 0.43 | 2.07 |
| GNE | 10020 | CCCGATCATGTTTGGCATTAA | 30 | 3.31 | 0.25 | 2.20 |
| ERN2 | 10595 | CTGGTTCGGCGGGAAGTTCAA | 31 | 3.47 | 1.47 | 2.30 |
| HUNK | 30811 | CACGGGCAAAGTGCCCTGTAA | 32 | 3.63 | 1.30 | 1.97 |
| SMG1 | 23049 | CACCATGGTATTACAGGTTCA | 33 | 3.22 | 0.46 | 2.05 |
| WNK4 | 65266 | CAGCTTGTTGGGCGTTTCCAA | 34 | 5.58 | 0.70 | 4.15 |
| MAGI2 | 9863 | CAGGCCCAACTTGGGATATCA | 35 | 3.07 | 0.63 | 2.07 |

Example 3

Establishment of Cellular Model Measuring Meganuclease-Induced Mutagenesis

Stable cell lines measuring meganuclease-induced mutagenesis at targeted locus were established. The different constructions were introduced at RAG1 locus in a single copy using cGPS kit. The cell line measuring SC_GS-induced mutagenesis can be used to screen an siRNA collection covering 19,121 genes to identify new genes regulating mutagenic DSB repair.

a) Materials and Methods
Cell Culture

Cell line 293H was cultured at 37° C. with 5% $CO_2$ in Dulbecco's modified Eagle's medium (DMEM) Glutamax supplemented with 10% fetal calf serum, 2 mM L-glutamine, 100 UI/ml penicilline, 100 µg/ml streptomycine, 0.25 µg/ml amphotericine B (Fongizone). The clones measuring meganuclease-induced mutagenesis were maintained with 200 µg/ml of G418 (Invitrogen).

Stable Transfection to Generate Cell Line Measuring I-Meganuclease-Induced Mutagenic NHEJ Repair One million of 293H cells were seeded one day prior to transfection, 3 µg of SC_RAG encoding vector (pCLS2222, SEQID NO: 36) and 2 µg of plasmid measuring SC_GS-induced mutagenic NHEJ repair (pCLS6883, SEQID NO: 1) were co-transfected on cells using 25 µl of lipofectamine (Invitrogen) according to the manufacturer's instructions. Three days following transfection, 2000 cells were seeded in 10 cm petri. One week after seeding 400 µg/ml of G418 (Invitrogen) were added on cells. Neomycin resistant clones were transferred in 96 well plate using ClonePix (Genetix) and cultured in presence of 400 µg/ml of G418 (Invitrogen) and 50 µM of Gancyclovir (Sigma). Genomic DNA of Neomycin and Gancyclovir resistant clones were extracted in order to perform a PGR specific of RAG1 targeted integration (cGPS® Custom Human Full Kit DD, Cellectis Rioresearch).

Transient Transfection in 96 Well Plate Format for siRNA Screening

Twenty thousand cells per well were seeded in white 96 well plates one day before transfection. Per well, cells were transfected with 200 ng of DNA (SC_GS encoding vector pCLS2690, SEQID NO: 3 or GFP encoding vector pCLS0099, SEQID NO: 12) and with or without 33 nM final concentration of siRNA using 1.35 µl of Polyfect transfection reagent (QIAGEN). Seventy two to ninety six hours post transfection 50 µl per well of ONEGlo (Promega) were added, cells were incubated in dark for 3 minutes before luciferase activity analysis (1 second/well) using PHERAStar luminometer (BMG Labtech). siRNAs targeting the gene WEN (SEQID NO: 37), MAPK3 (SEQID NO: 38), FANCD2 (SEQID NO: 39), PRKDC (PRKDC_5, CTCGTGTATTACAGAAGGAAA=SEQ ID NO: 75 and PRKDC_8, GACCCTGTTGACAGTACTTTA=SEQ ID NO: 76) and LIG4 (SEQID NO: 24) were used to extinct genes involved in DNA repair or regulation in order to analyze their potential for mutagenic NHEJ stimulation. Moreover, 8 siRNAs identified with an extrachromosomal assay and targeting CAMK2G (SEQ ID NO: 16), SMG1 (SEQ ID NO: 33), PRKCE (SEQ ID NO: 20), CSNK1D (SEQ ID NO: 13), AK2 (SEQ ID NO: 14), AKT2 (SEQ ID NO: 15), MAPK12 (SEQ ID NO: 19) and E1F2AK2 (SEQ ID NO: 21) genes were used. All experiments carried out in 96-well plates (cell seeding, cell transfection, incubation and luciferase detection) were performed with a Velocity 11 robot (Velocity, Palo Alto, Calif.).

b) Results:

A cell line measuring mutagenic NHEJ repair induced by SC_GS was created. This cell line contains a single copy of the reporter system integrated at RAG1 locus and was validated by comparison of Luciferase signal obtained after transfection with GFP encoding vector pCLS0099, SEQID NO: 12 to SC_GS encoding vector pCLS2690, SEQID NO: 3 (see FIG. 4A). Indeed, transfection with GFP (SEQ ID NO: 12) encoding vector gave similar 60 R.L.U. luciferase signal than untreated cells whereas transfection with SC_GS encoding vector (SEQ ID NO: 3) with no sRNA or with siRNA control AS induced a 600 R.L.U. luciferase signal. Moreover siRNAs targeting genes involved in classical NHEJ (LIG4) or in classical NHEJ and other DNA repair pathway (WRN and FANCD2) or in DNA repair regulation (MAPK3) increased SC_GS-induced luciferase signal from 725 up to 1,200 R.L.U (see FIG. 4A). Moreover, 8 siRNAs identified with an extra-chromosomal assay, targeting CAMK2G (SEQ ID NO: 16), SMG1 (SEQ ID NO: 33), PRKCE (SEQ ID NO: 20), CSNK1D (SEQ ID NO: 13), AK2 (SEQ ID NO: 14), AKT2 (SEQ ID NO: 15), MARK. 12 (SEQ ID NO: 19) and E1F2AK2 (SEQ ID NO: 21) genes and also two siRNAs targeting PRKDC gene (siRNA target sequence PRKDC_5, CTCGTGTATTACAGAAGGAAA=SEQ ID NO: 75 and siRNA target sequence PRKDC_8, GACCCTGTTGACAGTACTTTA=SEQ ID NO: 76) involved in DNA repair regulation increased SC_GS-induced luciferase signal from 6,000 up to 14,000 R.L.U (see FIG. 4B). This result demonstrates that inhibition of these genes stimulate SC_GS-induced mutagenic NHEJ repair signal.

HTS Screening Measuring SC_GS-Induced Non Homologous End Joining Repair Activity:

Screening of a siRNA collection covering 19,121 genes (Qiagen with two siRNAs targeting each gene) using this cell line will lead, to identification of other siRNAs that could, modulate SC_GS-induced mutagenic NHEJ repair. For that purpose, a high-throughput screening was set up to cotransfect each siRNA of the collection with pCLS2690 (SEQID NO: 3) in duplicate. This screen led to identification of 481 and 486 hits stimulating and inhibiting the luciferase signal respectively.

a) Materials and Methods siRNA Dilation

The siRNA collection from QIAGEN was received in 96 well plate format in solution at 10 µM concentration. On each plate columns 1 and 12 were empty allowing controls addition. During dilution process of siRNA, siRNA AS (Qiagen #1027280), a negative control, siRNA RAD51 (SEQ ID NO: 77) and siRNA LIG4 (SEQ ID NO: 78), two siRNAs targeting proteins involved in recombination process and siRNA Luc2 (SEQ ID NO: 79) targeting the expression of the reporter gene used were added at 333 nM final concentration.

Fourteen thousand cells per well were seeded in white 96 well plates one day before transfection. Per well cells were co-transfected with 200 ng of DNA pCLS2690 (SEQID NO: 3) and with 33 nM final concentration of siRNA using 1.35 µl of Polyfect transfection reagent (QIAGEN) per well. Seventy two hours post transfection 50 µl per well of ONEGlo (Promega) were added, cells were incubated in dark for 3 minutes before analysis of luciferase activity (1 second/well) using PHERAStar luminometer (BMG Labtech).

b) Results:

Seventeen runs were performed to screen the entire collection. For each run the mean luciferase intensity of the all run and of siRNA Luc2 (SEQ ID NO: 79) and their standard deviations were calculated. A siRNA hit stimulating luciferase signal was defined for each run when its luciferase intensity was above the run mean intensity plus 2.5 times the run standard deviation. A siRNA hit inhibiting luciferase signal was defined as follows: its luciferase signal is less than the mean luciferase activity obtained with siRNA Luc2 (SEQ ID NO: 79) plus 0.5 times its standard deviation. On each run SC_GS-induced mutagenic NHEJ repair was checked by comparison of induced luciferase signal between co-transfection of pCLS2690 (SEQ ID No. 3) with either the siRNA control AS (Qiagen #1027280) or with the siRNA screened. Effect of siRNA was also verified by analyzing the decrease of luciferase signal with co-transfection of pCLS2690 (SEQ ID No. 3) with siRNA Luc2 (SEQ ID NO: 79)

Figure 12:
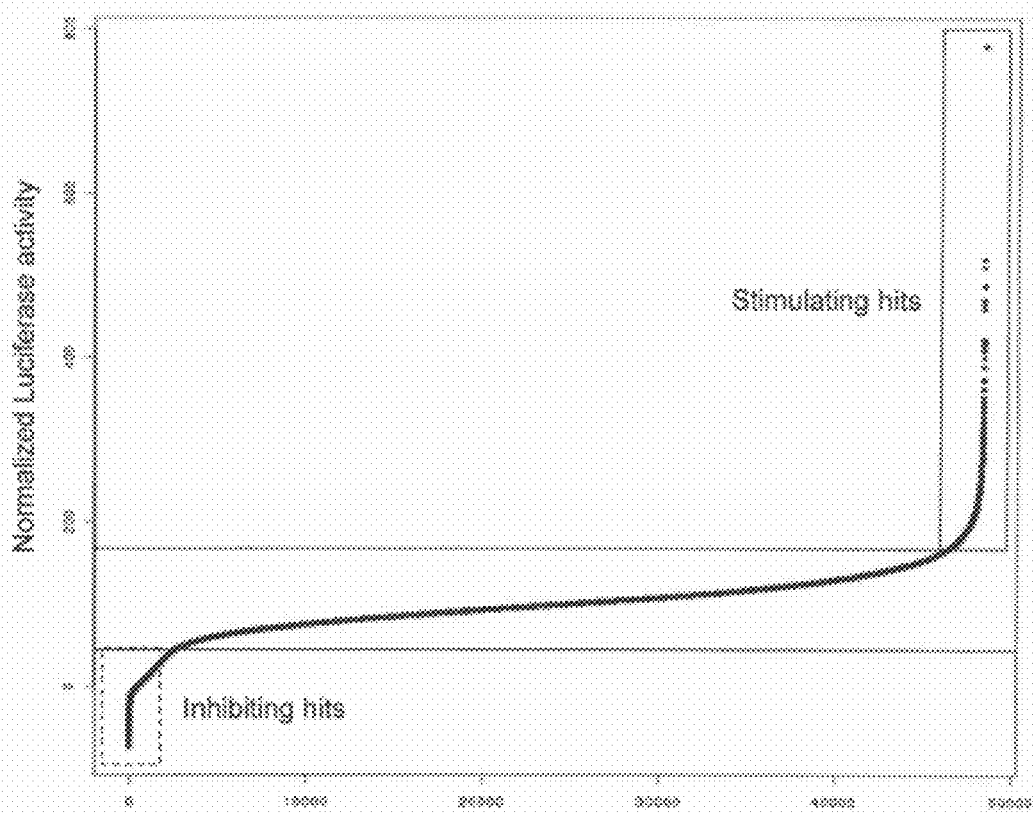
FIG. 12: Normalized Luciferase activity of the High-throughput screening of the sRNA library. Hits stimulating or inhibiting the SC_GS-induced Non Homologous End Joining repair activity are indicated by plain or hatched squares respectively.

To compare the screen form run to run, normalization was applied on each run to get the run mean luciferase signal equal to 100 R.L.U. FIG. 12 represents data of all runs after normalization and shows the hits stimulating (with at least a normalized luciferase activity superior to 183) or hits inhibiting (with at least a normalized luciferase activity inferior to 37.5) SC_GS-induced mutagenic NHEJ repair luciferase signal.

As indicated in Table IV below, this screen led to the identification of 481 siRNAs hits that stimulate SC_GS-induced mutagenic NHEJ repair luciferase signal with at least a stimulation factor of 1.83.

TABLE IV siRNA hits stimulating GS_SC-induced luciferase signal with at least a fold increase of increase of 1.83

| Gene Targeted | Gene ID | siRNA target sequence | SEQ ID NO |
|---|---|---|---|
| LCMT2 | 9836 | CAGGCGCGGTACAGAACACCA | 80 |
| SNORD115-10 | 100033447 | GAGAACCTTATATTGTCTGAA | 81 |
| WNK4 | 65266 | CAGCTTGTTGGGCGTTTCCAA | 82 |
| HMX2 | 3167 | CGGGCGCGTACTGTACTGTAA | 83 |

TABLE IV-continued siRNA hits stimulating GS_SC-induced luciferase signal with at least a fold increase of increase of 1.83

| Gene Targeted | Gene ID | siRNA target sequence | SEQ ID NO |
|---|---|---|---|
| TAL1 | 6886 | TCCGTCAACGTTGTACTGTAT | 84 |
| VAV3 | 10451 | CACGACTTTCTCGAACACCTA | 85 |
| APOA1BP | 128240 | ATGACGATTGATGAACTGTAT | 86 |
| SNORD115-14 | 100033451 | GAGAAACTTATATTGTCTGAA | 87 |
| REM1 | 28954 | CGCTGTGGTGTTCGACTGTAA | 88 |
| MTHFD2L | 441024 | CAGCGGTATATTAGTTCAGTT | 89 |
| OR8H2 | 390151 | CTCAACTGTCGTCACACCTAA | 90 |
| UBAC2 | 337867 | CACGCTGGACATCCAGAGACA | 91 |
| HGFAC | 3083 | AAGGACTGCGGCACAGAGAAA | 92 |
| GOLT1A | 127845 | CACTAGCTCGATGGTCTGAAA | 93 |
| FAM24A | 118670 | CTGGATGGTTGAACTGTAGCA | 94 |
| NEFH | 4744 | CTCGCTGGACACGCTGAGCAA | 95 |
| SPRN | 503542 | CAGGAACATTCCCAAGCAGGA | 96 |
| INTS12 | 57117 | CAGGACCTAGTGGAAGTACTA | 97 |
| PAF1 | 54623 | CTCCACTGAGTTCAACCGTTA | 98 |
| ALDH8A1 | 64577 | CTGGATAAAGCAGGTGTTCCA | 99 |
| ELF2 | 1998 | AAGCATCAGTTCACAGCAGTA | 100 |
| TSSC1 | 7260 | CAGCTGCGGAGACGACTGTAA | 101 |
| TMEM130 | 222865 | CCCGCTGGTGCTTACTGGCAA | 102 |
|  |  | TCCGTCAACAGTAGTTCCTTA | 103 |
| SNORD114-17 | 767595 | ATGAATGATATGTGTCTGAAA | 104 |
| FGL2 | 10875 | CAGGATCGAGGAGGTGTTCAA | 105 |
| DUSP1 | 1843 | CACGAACAGTGCGCTGAGCTA | 106 |
| MYCL1 | 4610 | AAGGCCTTGGAATACTTGCAA | 107 |
| TAF6 | 6878 | CTGGGAGTGTCCAGAAGTACA | 108 |
| EIF4A3 | 9775 | CCGCATCTTGGTGAAACGTGA | 109 |
| CXorf59 | 286464 | CTGTGAGTTCCTGTACACCTA | 110 |
| TALDO1 | 6888 | CCGGGCCGAGTATCCACAGAA | 111 |
| C16orf59 | 80178 | CGGGATGAACCTGCAGTCTGA | 112 |
| H2AFY | 9555 | CAAGTTTGTGATCCACTGTAA | 113 |
| SAMD5 | 389432 | CTGCTCATAGGAGTTCAGTAA | 114 |
| PROK2 | 60675 | TCGCTCTGGAGTAGAAACCAA | 115 |
| BCL9L | 283149 | ACCCACAATTGTAATGTAGCA | 116 |
| WDR5 | 11091 | AAGCAGCACCGCAGACTGTAA | 117 |
| ADAMTSL5 | 339366 | ATGCCTAACCAGGCACTGTAA | 118 |
| BASP1 | 10409 | TTCCAAGATCCGCGTCTGAAA | 119 |
| ALX1 | 8092 | TAGAGCTATGGACAACTGTAA | 120 |
| KLHL34 | 257240 | CTCGGCAGTCGTGGAAACCAA | 121 |
| CYFIP2 | 26999 | CGCCCACGTCATGGAGGTGTA | 122 |
| MID1 | 4281 | TAGAACGTGATGAGTCATCAT | 123 |
| SGCD | 6444 | TAAATCTATAGAAACACCTAA | 124 |
| RING1 | 6015 | CAGGGTCAGATCAGACCACAA | 125 |
| CAV3 | 859 | TTGCGTTCACTTGTACTGTAA | 126 |
| KIAA0280 | 23201 | CAGCATTCCCTCTGCTATCTA | 127 |
| ISCU | 23479 | CTCCAGCATGTGGTGACGTAA | 128 |
| ARVCF | 421 | AAGACTATTGGTAAACACCTA | 129 |
| BBC3 | 27113 | CAGCCTGTAAGATACTGTATA | 130 |
| ZMYND11 | 10771 | CCGGATGAAGTCGGACCACAA | 131 |
| PCDHGB5 | 56101 | CGGGCAAATCTTTAGTCTGAA | 132 |
| INTS12 | 57117 | AACCTGCTACTTCGTCAGCTA | 133 |
|  |  | CTGGATGGCGTTATGATTTCA | 134 |
| NUP35 | 129401 | CAGGACTTGGATCAACACCTT | 135 |
| OR2M7 | 391196 | AAGGGCAAGTCTGGAGATTGA | 136 |
| SLC6A14 | 11254 | ACCAATAGTAACTCACTGTAA | 137 |
| CHP2 | 63928 | CAGGGCGACAATAAACTGTAT | 138 |
| TRIM61 | 391712 | TAGGGTATGTATATGTTCCTA | 139 |
| AFG3L1 | 172 | CGGCTGGAAGTCGTGAACAAA | 140 |
| GTF2I | 2969 | TAGGTGGTCGTGTGATGGTAA | 141 |
| TMPRSS11A | 339967 | ATCCACATCAATGGACTGTTA | 142 |
| KRTAP13-3 | 337960 | CAGGACTCACATGCTCTGCAA | 143 |
| ZNF107 | 51427 | TACCTCGGACCAGCTCTGTAA | 144 |
| NCOR2 | 9612 | AACGAGATTGCTGGAAACCAA | 145 |
| SMG1 | 23049 | CACCATGGTATTACAGGTTCA | 33 |
| NKX2-3 | 159296 | CAGGTACAAGTGCAAGAGACA | 146 |
| NFKBIA | 4792 | CAGCCAGAAATTGCTGAGGCA | 147 |
| FAM69B | 138311 | CCGGCGGGAGCTGGTACTGTT | 148 |
| CARD9 | 64170 | CAGCGACAACACCGACACTGA | 149 |
| TMEM105 | 284186 | AACGAGGTATGGAACTGTTCA | 150 |
| LARP6 | 55323 | ATGGTGTCTTGTAGGACCAAA | 151 |
| VSIG8 | 391123 | CCGGCGTATAGGCGTGATCAT | 152 |
| TXNRD1 | 7296 | CCGACTCAGAGTAGTAGCTCA | 153 |
| USP36 | 57602 | CAAGAGCGTCTCGGACACCTA | 154 |

TABLE IV-continued siRNA hits stimulating GS_SC-induced luciferase signal with at least a fold increase of increase of 1.83

| Gene Targeted | Gene ID | siRNA target sequence | SEQ ID NO |
|---|---|---|---|
| MYEOV2 | 150678 | GTCAGCGAAGACAGCACAATA | 155 |
| NES | 10763 | CGCGCCGTCGAGGCAGAGAAA | 156 |
| PRDX3 | 10935 | AAGGCGTTCCAGTATGTAGAA | 157 |
| USP39 | 10713 | CAGGCTCTATCTAATGTTCCT | 158 |
| KRT16 | 3868 | TACGAGCAGATGGCAGAGAAA | 159 |
| MAGA1 | 3159 | CACCACAACTCCAGGAAGGAA | 160 |
| SLCO3A1 | 28232 | CAGCATCGCCATCGCGCTCAA | 161 |
| SFN | 2810 | CCGGGAGAAGGTGGAGACTGA | 162 |
| DPP4 | 1803 | ATCGGGAAGTGGCGTGTTCAA | 163 |
| SPTBN2 | 6712 | CAGCGTCAACATCCTGCTCAA | 164 |
| PRR3 | 79057 | AAGGTCAACCCTTGGTTCTTA | 165 |
| SARM1 | 23098 | CTGGTGGTTAAGGGTAGCAAA | 166 |
| GRIN2C | 2905 | CCCAGCTTTCACTATCGGCAA | 167 |
| TMEM179 | 388021 | CGGGCCGGCCATGGCGCTCAA | 168 |
| TWIST1 | 7291 | CACCTCTGCATTCTGATAGAA | 169 |
|  |  | CCCGTCTGAATTCCTCAGGAA | 170 |
| C10orf90 | 118611 | CAGATCCGTCCTGTCGCTCAA | 171 |
| BTNL9 | 153579 | AAGGACATTATTAGTTTGACA | 172 |
| CES2 | 8824 | CTGCATGATGTTAGTTACCAA | 173 |
| AOF1 | 221656 | ATCGATGCGGTATGAAACCAA | 174 |
| CPLX2 | 10814 | CAGATAGGTAGCAGAGACCAA | 175 |
| CAMK2G | 818 | GAGGAAGAGATCTATACCCTA | 16 |
| KCTD15 | 79047 | CAGGATAAGCCGCCTCTTCAA | 176 |
| CSH1 | 1442 | ACGGGCTGCTCTACTGCTTCA | 177 |
| EDIL3 | 10085 | CCCAAGTTTGTCGAAGACATT | 178 |
| PAX3 | 5077 | AACGCCTGACGTGGAGAAGAA | 179 |
| KCNC3 | 3748 | CAGCGGCAAGATCGTGATCAA | 180 |
| LRRC8C | 84230 | TACCTTATACTGGCTGTTCTA | 181 |
| LOC90586 | 90586 | CTGGGCATGGGTATGCTGTAA | 182 |
| LONRF2 | 164832 | CCGACGGATATTAGTCATCAT | 183 |
| DDX3X | 1654 | AACGAGAGAGTTGGCAGTACA | 184 |
| GNG4 | 2786 | CCGAAGTCAACTTGACTGTAA | 185 |
| SAP30L | 79685 | CAAGAGCGTAAGGCACCTATA | 186 |
| KCTD15 | 79047 | AACCTTGGAGATTCACGGCAA | 187 |
| LOC165186 | 165186 | CAACGTCTCTATAGAGACCAA | 188 |
| FAM59A | 64762 | AAGGGCAGATTTAGCACCCGA | 189 |
| ARF5 | 381 | TTCGCGGATCTTCGGGAAGAA | 190 |
| ESSPL | 345062 | CAGCCTACACTTTGACCACAA | 191 |
| SPON1 | 10418 | ATCGCACGGAAGGGTGAACAA | 192 |
| BCL11B | 64919 | CAGAGGTGGGTTAAACTGTAA | 193 |
| ZNF826 | 664701 | TCAGATGGTCCTCACACCTAA | 194 |
| C2lorf62 | 56245 | CAACCTGATGTGCAACTGTAA | 195 |
| OGFOD1 | 55239 | TCGGACGCTGTTACGGAAGAA | 196 |
| LYST | 1130 | CACATCATTGTCAACACCTAA | 197 |
| LIPJ | 142910 | AGGGTTGTTGTATACTTGCAA | 198 |
| GH2 | 2689 | CAGCTGGCATATGACACCTAT | 199 |
| PHF21B | 112885 | CACCGTGGTCAGCGTCAAGAA | 200 |
| ZFYVE28 | 57732 | CAAGCCTGAAACAGACGACAA | 201 |
| TMEM183A | 92703 | CTGTACCTATAACACCAGTAA | 202 |
| HIST1H2AE | 3012 | ATCCCGAGTCCCAGAAACCAA | 203 |
| XKRX | 402415 | CACCCATAATGTAGTAGACTA | 204 |
| CTR9 | 9646 | AAGGGTAGTGGCAGTGAACAA | 205 |
| POLDIP2 | 26073 | CACGTGAGGTTTGATCAGTAA | 206 |
| C5orf3 | 10827 | CGCCCACGAATGGATCAGGAA | 207 |
| FGFR3 | 2261 | ACCCTACGTTACCGTGCTCAA | 208 |
| DIRAS2 | 54769 | CCCGACGGTGGAAGACACCTA | 209 |
| TM4SF5 | 9032 | CGCCCTCCTGCTGGTACCTAA | 210 |
| CENPH | 64946 | ATGGATAACATGAAACACCTA | 211 |
| NAGK | 55577 | CCCGGTCTTGTTCCAGGGCAA | 212 |
| LGI2 | 55203 | TACGACGAGAGTTGGACCAAA | 213 |
| TERT | 7015 | CCAGAACGTTCCGCAGAGAAA | 214 |
| PEAR1 | 375033 | CTGCACGCTGCTCATGTGAAA | 215 |
| FBLIM1 | 54751 | CTCCACAATTGTTATAACCAA | 216 |
| PDE7A | 5150 | CAGATAGGTGCTCTGATACTA | 217 |
| ETV4 | 2118 | ACCGGAGTCATTGGGAAGGAA | 218 |
| SNORD9 | 692053 | CTGTGATGAGTTGCCATGCTA | 219 |
| TMEM25 | 84866 | CAGGCGATGAGTCTAGTAGCA | 220 |
| SETD5 | 55209 | AACGCGCTTGAACAACACCTA | 221 |
| SART1 | 9092 | CAGCATCGAGGAGACTAACAA | 222 |
| IL17RB | 55540 | CCGCTTGTTGAAGGCCACCAA | 223 |
| NEU1 | 4758 | CAGGTCTAGTGAGCTGTAGAA | 224 |
| ST6GALNAC1 | 55808 | CCCACGACGCAGAGAAACCAA | 225 |

TABLE IV-continued siRNA hits stimulating GS_SC-induced luciferase signal with at least a fold increase of increase of 1.83

| Gene Targeted | Gene ID | siRNA target sequence | SEQ ID NO |
|---|---|---|---|
| KCNIP2 | 30819 | CAGCTGCAGGAGCAAACCAAA | 226 |
| PPP3CA | 5530 | TCGGCCTGTATGGGACTGTAA | 227 |
| PRPF4 | 9128 | TCCGGTCGTGAAGAAACCACA | 228 |
| SYNGAP1 | 8831 | CAGAGCAGTGGTACCCTGTAA | 229 |
| PTBP1 | 5725 | GCGCGTGAAGATCCTGTTCAA | 230 |
| IGFL4 | 444882 | CCAGACAGTTGTGAGGTTCAA | 231 |
| HES1 | 3280 | CACGACACCGGATAAACCAAA | 232 |
| UNQ830 | 389084 | CACAGACGATGTTCCACAGGA | 233 |
|  |  | CTCGGGAAACGTGGACGACAA | 234 |
| PLG | 5340 | AAGTGCGGTGGGAGTACTGTA | 235 |
| IK | 3550 | CAGGCGCTTCAAGGAAACCAA | 236 |
| UBE2D4 | 51619 | CCGAATGACAGTCCTTACCAA | 237 |
| NEK3 | 4752 | CAGAGATATCAAGTCCAAGAA | 238 |
| ATF7IP2 | 80063 | TAGGACGACTGAAATAACCAA | 239 |
| SRRM2 | 23524 | CGCCACCTAAACAGAAATCTA | 240 |
| SRRM2 | 23524 | CTCGATCATCTCCGGAGCTAA | 241 |
| FYCO1 | 79443 | AAGCCACGTCATATAACTCAA | 242 |
| ABHD9 | 79852 | CAGCTCAGTGCTACTGTGAAT | 243 |
| CGB | 1082 | ACCAAGGATGGAGATGTTCCA | 244 |
| HES5 | 388585 | CACGCAGATGAAGCTGCTGTA | 245 |
| RAB10 | 10890 | AAGGGACAAACTAGTAGGTTT | 246 |
|  |  | CCCGTTAGTGCTACACTCATT | 247 |
| BZW2 | 28969 | CAGGAGCGTCTTTCTCAGGAA | 248 |
| FAM100B | 283991 | CACGTTCTTCCAAGAAACCAA | 249 |
| MGC23985 | 389336 | ACCAGACAAGCCAGACGACAA | 250 |
| CSAG2 | 728461 | CCAGCCGAACGAGGAACTCAA | 251 |
|  |  | CTCCTTTATCTTCCAAACCAA | 252 |
| GGA1 | 26088 | CCCGCCATGTGACGACACCAA | 253 |
| C10orf53 | 282966 | CTGGAATGTGGTGGAACTCAT | 254 |
| TBL3 | 10607 | CTGCGTCACGTGGAACACCAA | 255 |
| EEF1A1 | 1915 | CAGAATAGGAACAAGGTTCTA | 256 |
| OTOP3 | 347741 | TTGCCAGTACTTCACCCTCTA | 257 |
| BANP | 54971 | CAGCGACATCCAGGTTCAGTA | 258 |
| FOXP2 | 93986 | AAGGCGACATTCAGACAAATA | 259 |
| BAHD1 | 22893 | CAAGAATTACCCACTTCGTAA | 260 |
| ZNF416 | 55659 | GAGGCCTTTGCCAGAGTTAAA | 261 |
| VPS4A | 27183 | CTCAAAGACCGAGTGACATAA | 262 |
| FAM38B | 63895 | CACCTAGTGATTCTAACTCAA | 263 |
| LRRC24 | 441381 | CCACGAGATGTTCGTCATCAA | 264 |
| PRKCE | 5581 | CCCGACCATGGTAGTGTTCAA | 20 |
| SECISBP2 | 79048 | TCCCAGTATCTTTATAACCAA | 265 |
| C6orf1 | 221491 | CAGATGTATAGTATTCAGTAT | 266 |
| SEMA3G | 56920 | CCCTGCCCTATTGAAACTCAA | 267 |
| C16orf3 | 750 | CTGGGACAACGCAGTGTTCAA | 268 |
| ANKRD12 | 23253 | CCGGAGCGGATTAAACCACCA | 269 |
| TEX28 | 1527 | CAGCGAAGAGAATGGCCTA | 270 |
| MAPK8IP3 | 23162 | CAGCCGCAACATGGAAGTACA | 271 |
| FAM9A | 171482 | AAAGCTCAGTTGGAAGCTCAA | 272 |
| ACTR8 | 93973 | TACTACCAACTTAGTCATCAA | 273 |
| SNHG1 | 23642 | CAGCGTTACAGTAATGTTCCA | 274 |
| SNORD114-10 | 767588 | ATGATGAATACATGTCTGAAA | 275 |
| LYPD1 | 116372 | CACGGTGAACGTTCAAGACAT | 276 |
| SSBP1 | 6742 | AGCCTAAAGATTAGACTGTAA | 277 |
| TRIM32 | 22954 | CAGCACTCCAGGAATGTTCAA | 278 |
| POLR3H | 171568 | AACAAACGGCACAGACACCAA | 279 |
| SNORA71B | 26776 | TGCCTTTGCCCTGGTCATTGA | 280 |
| KRT6C | 286887 | CAAGTCAACGTCTCTGTAGTA | 281 |
| CYP2A7 | 1549 | CCCAAGCTAGGTGGCATTCAT | 282 |
| PTPN22 | 26191 | TGGGATGTACGTTGTTACCAA | 283 |
| P2RX5 | 5026 | CTGATAAAGAAGGGTTACCAA | 284 |
| FANCE | 2178 | TCGAATCTGGATGATGCTAAA | 285 |
| PLS3 | 5358 | AACGGATTCATTTGTGACTAT | 286 |
| HNRNPA1 | 3178 | CAGGGTGATGCCAGGTTCTAT | 287 |
| CD72 | 971 | ATCACCTACGAGAATGTTCAA | 288 |
| PRC1 | 9055 | TCGAGTGGAGCTGGTTCAGTA | 289 |
| COL5A3 | 50509 | CCCGGGCATCCAGGTCTGAAA | 290 |
| ZNF649 | 65251 | AACGCTATGAACACGGAAGAA | 291 |
| HCP5 | 10866 | TAGGAGGGAGTCAGTACTGTT | 292 |
| PXDNL | 137902 | TACCGACTGAATGCCACCTTA | 293 |
| CDYL2 | 124359 | AATGATCATGTTGGAGAGCAA | 294 |
| C17orf28 | 283987 | CCCGTGGAAGCCACCGATGAT | 295 |
| PPP1R13L | 10848 | AAGGAGTAAAGTCTAGCAGGA | 296 |

TABLE IV-continued siRNA hits stimulating GS_SC-induced luciferase signal with at least a fold increase of increase of 1.83

| Gene Targeted | Gene ID | siRNA target sequence | SEQ ID NO |
|---|---|---|---|
| LINCR | 93082 | CTGGGCCGTGATGGACGTGTA | 297 |
| PRTN3 | 5657 | CAACTACGACGCGGAGAACAA | 298 |
| SLC25A19 | 60386 | CTCCCTGTGATCAGTTACCAA | 299 |
| C14orf45 | 80127 | TTCCGTCTTCCAAGTTACCAA | 300 |
| PPHLN1 | 51535 | CAAGAGATACTTCACCCTCAA | 301 |
| ENDOGL1 | 9941 | AAGAAGCTAGAAGAACTCAAA | 302 |
| SEPT7 | 989 | CAGAATCTCATTACTGCTTCA | 303 |
| CHRNB4 | 1143 | CAGCAAGTCATGCGTGACCAA | 304 |
| SPACA3 | 124912 | AAGCTCTACGGTCGTTGTGAA | 305 |
| DCI | 1632 | CAGGTACTGCATAGGACTCAA | 306 |
| C6orf136 | 221545 | CTCATTTGTCGCCATCGTCTA | 307 |
| CLIC6 | 54102 | CCGAATCTAATTCCGCAGGAA | 308 |
| RBPJL | 11317 | CTCAAAGGTCTCCCTCTTCAA | 309 |
| DPY19L2P1 | 554236 | GTCCATTGTCTAAGTGTTCTA | 310 |
| C21orf2 | 755 | AAGGGCCGTTTCTCCACAGAA | 311 |
| C1orf76 | 148753 | TACGGTGATCCTCCTCTGCAT | 312 |
| TBC1D5 | 9779 | AGGAAGGTTGTTGGCCAACAA | 313 |
| TMEM203 | 94107 | AACAGGTGTCAGATACTCATA | 314 |
| PTPRA | 5786 | CCGGAGAATGGCAGACGACAA | 315 |
| CSNK1A1L | 122011 | CTGCTTACCTGTGAAGACATA | 316 |
| GSTM1L | 2945 | ATCCTTGACCTGAACTGTATA | 317 |
| LOXL2 | 4017 | CCGGAGTTGCCTGCTCAGAAA | 318 |
| ACSL5 | 51703 | CAAGGGTACAAACGTGTTCAA | 319 |
| MT4 | 84560 | ATGCACAACCTGCAACTGTAA | 320 |
| DNTTIP1 | 116092 | CCGGCATGGTATGGAAACCAA | 321 |
| OR2A14 | 135941 | CACCTGGCCATTGTTGACATA | 322 |
| ASB2 | 51676 | CAAGTACGGTGCTGACATCAA | 323 |
| SREBF2 | 6721 | CCGCAGTGTCCTGTCATTCGA | 324 |
| ISG20L1 | 64782 | CACGGGCACTCATCAGTAGAA | 325 |
| SPTBN2 | 6712 | CTCCGCGGATCTAGTCATCAA | 326 |
| LYNX1 | 66004 | CACCAGGATGAAGGTCAGTAA | 327 |
| LTBR | 4055 | TACATCTACAATGGACCAGTA | 328 |
| ZNF295 | 49854 | CAGGTTGAAGTCCATAATCAG | 329 |
| SOX11 | 6664 | CTCCGACCTGGTGTTCACATA | 330 |
| PANK2 | 80025 | CTGTGTGTGAACTTACTGTAA | 331 |
| RBM47 | 54502 | CACGGTGGCTCCAAACGTTCA | 332 |
| CCDC13 | 152206 | CCCAACCGGGAGCGAGAAGAA | 333 |
| RTF1 | 23168 | ACCGCTCATCACGAACATCAT | 334 |
| ZRANB2 | 9406 | CACGATCTTCATCACGCTCAT | 335 |
| FAM83E | 54854 | CTCGGCGTCTGTCAAGCAGAA | 336 |
| RCP9 | 27297 | GAGGAATTTCCTCGAGAACAA | 337 |
| NMBR | 4829 | CCCGCGGACAGTAAACTTGCA | 338 |
| CPNE2 | 221184 | CAGGACAGAAACCGCGATCAA | 339 |
| XRCC6 | 2547 | GAGGATCATGCTGTTCACCAA | 44 |
| PRDM14 | 63978 | ACCGGCCTCACAAGTGTTCTA | 340 |
| U2AF1 | 7307 | CCCGTGACGGACTTCAGAGAA | 341 |
| NRARP | 441478 | TTCGCTGTTGCTGGTGTTCTA | 342 |
| HNRNPC | 3183 | CTCCCGTGTATTCATTGGGAA | 343 |
| GAS2L2 | 246176 | CTCCGGAACCATGTGATGGTA | 344 |
| KIFC2 | 90990 | AGGGCGGCTGCCAGAACTCAA | 345 |
| SFRS7 | 6432 | CCCGACGTCCCTTTGATCCAA | 346 |
| FERMT2 | 10979 | AAGCTAGATGACCAGTCTGAA | 347 |
| FRMD4A | 55691 | CTGGATTCTGTTCAACTGTAA | 348 |
| SNORD13 | 692084 | AGCGTGATGATTGGGTGTTCA | 349 |
| TTLL9 | 164395 | TGCGTCAACGATCGGAAGAAA | 350 |
| ZNF691 | 51058 | TTGCTGCTACCTTGACCTCAA | 351 |
| TRAPPC6A | 79090 | CTGTGTGTGTGGAATCTGAAA | 352 |
| EIF4A3 | 9775 | AAAGAGCAGATTTACGATGTA | 353 |
| PRR16 | 51334 | AACCTGCAGATTTCACCTATT | 354 |
| RPIA | 22934 | AACCACGTGAGGAATAACCAA | 355 |
| FAM26E | 254228 | CTGCCGATCTAAAGTTAGCTA | 356 |
| C11orf75 | 56935 | CCGCGGGCAGGAATAACTCAA | 357 |
| WBSCR19 | 285955 | AAGGACTTCAACAGTCAGCTT | 358 |
| CTSA | 5476 | CCGGCCCTGGTTAGTGAAGTA | 359 |
| NEK10 | 152110 | CAGAAGGTATCTACTCTGAAA | 360 |
| WIPF3 | 644150 | CTCCGGATGAATATAAACCAT | 361 |
| TRAFD1 | 10906 | CCAGGTCTCTCAGTGACATAA | 362 |
| TH1L | 51497 | CCGGTTGAACTTATCCGCGTT | 363 |
| ZNF658 | 26149 | CTCAGCCCATATAGTACATCA | 364 |
| STXBP2 | 6813 | CACGGACAAGGCGAACATCAA | 365 |
| TRIM71 | 131405 | CAGGATCGTGGTGGCTGACAA | 366 |
| CAP1 | 10487 | CAACACGACATTGCAAATCAA | 367 |

TABLE IV-continued siRNA hits stimulating GS_SC-induced luciferase signal with at least a fold increase of increase of 1.83

| Gene Targeted | Gene ID | siRNA target sequence | SEQ ID NO |
|---|---|---|---|
| BRCA1 | 672 | CTGCAGATAGTTCTACCAGTA | 45 |
| VLDLR | 7436 | CAAGATCGTAGGATAGTACTA | 368 |
| CREBZF | 58487 | CAGGAGGAGAGTCGCTACCTA | 369 |
| FAM120C | 54954 | CTGCGTGAGGCTAGCACTCAT | 370 |
| C4BPA | 722 | AACTCAGACGCTTACCTGTAA | 371 |
| TBL3 | 10607 | CTGCCATGATAAGGACATCAA | 372 |
| OLFML2A | 169611 | TCCAGTCATATTTAGAACAAA | 373 |
| TBC1D8B | 54885 | GAGAAGGGTACTCACAGCTTA | 374 |
| ADAMTS7 | 11173 | CTGCATCAACGGCATCTGTAA | 375 |
| BAG4 | 9530 | ACCCAAGTACATATCCTGTAA | 376 |
| GRID2 | 2895 | AAGCAATGGATCGGAGAACAA | 377 |
| GDF15 | 9518 | CTGGGAAGATTCGAACACCGA | 378 |
| RASAL2 | 9462 | CTCGTGGGCTGCCTAAACTAA | 379 |
| UGT2B28 | 54490 | CACCCAGGTAATGGTTAGAAA | 380 |
| FLJ20254 | 54867 | CCCGATTCCGTGAATCAGCTA | 381 |
| DPF2 | 5977 | CCGGAGTAGCCCAGAGCAATT | 382 |
| CNGB1 | 1258 | CAGAAGTTACTCCGGAAGAAA | 383 |
| CAPN13 | 92291 | ACGAAGGATGGTCCCAAATAA | 384 |
| CAP1 | 10487 | AAGCCTGGCCCTTATGTGAAA | 385 |
| PDIA6 | 10130 | ACGGGATTAGAGGATTTCCTA | 386 |
| TMEM63A | 9725 | CAGGGACTCTCTTGACGCTGA | 387 |
| SMARCC1 | 6599 | CAGCGGATTTCAACCAAGAAT | 388 |
| TBKBP1 | 9755 | CACTGCTTACGGAGACATCAA | 389 |
| LGALS2 | 3957 | CACCATTGTCTGCAACTCATT | 390 |
| CACNG1 | 786 | CACCGTCTGGATCGAGTACTA | 391 |
| ZBTB7C | 201501 | GCCACTGGATCTGGTCATCAA | 392 |
| PREB | 10113 | CCGGGCTCCGTTCCCGTTGTA | 393 |
| CBX8 | 57332 | AAGGAAAGTAACACGGACCAA | 394 |
| RBM8A | 9939 | ACACGACAAATTCGCAGAATA | 395 |
| MDM1 | 56890 | ATGAGGGTGTAACAAACCATA | 396 |
| TPD52L3 | 89882 | CAGGCCAGGTCGTCAACTCAA | 397 |
| C3orf59 | 151963 | AAGGGCAAGTAACGTGTTCAT | 398 |
| LRP5 | 4041 | CTGGACGGACTCAGAGACCAA | 399 |
| DLD | 1738 | CAGCCGATTGATGCTGATGTA | 400 |
| TCF20 | 6942 | CAGGAGTTGCACGTAGAGAAA | 401 |
| KIAA0644 | 9865 | CGGCGGCAACTTCATAACCAA | 402 |
| ARFRP1 | 10139 | CGGCGTCATCTACGTCATTGA | 403 |
| STAU1 | 6780 | CTCGGATGCAGTCCACCTATA | 404 |
| GRIP2 | 80852 | CAGGAGTGATCTGCTGAACAT | 405 |
| UHRF1BP1 | 54887 | CCGCGTGAGGCTTGACCACTA | 406 |
| CPNE2 | 221184 | CACGATCGTCTCCAGCAAGAA | 407 |
| ICA1 | 3382 | CAGGATCGATATGCTCAAGAT | 408 |
| CDH20 | 28316 | TACTACGAAGTGATTATCCAA | 409 |
| BPIL2 | 254240 | CCGGAGTCTACTTTACCGGTA | 410 |
| ADRBK1 | 156 | CGGCTGGAGGCTCGCAAGAAA | 411 |
| MOG | 4340 | CAGAGTGATAGGACCAAGACA | 412 |
| HOXD3 | 3232 | CTCGCCATAAATCAGCCGCAA | 413 |
| STRA6 | 64220 | CTGGAAGATACTGGGACTGTT | 414 |
| SNORA40 | 677822 | CCCAGAACTCATTGTTCAGTA | 415 |
| GK5 | 256356 | TACCATCTTGTACGAGCAATA | 416 |
| LZTR1 | 8216 | CAAGATCAAATACCCACGGAA | 417 |
| TRIM42 | 287015 | CAGCGCCATCGCCAAGTTCAA | 418 |
| C1orf38 | 9473 | AAGTTGTAAGTGACTAACCAA | 419 |
| ANKRD20A3 | 441425 | ATCCCTCACTGAATTCAGTAA | 420 |
| ATG9B | 285973 | CAGCCGCGGCCTGGCGCTCAA | 421 |
| PI4KA | 5297 | AAGCGGCTGCGTGAAGACATA | 422 |
| SDHB | 6390 | CTGGTGGAACGGAGACAAATA | 423 |
| RAB43 | 339122 | CCGAGCGTGGGTCCCAGTCTA | 424 |
| ZNF443 | 10224 | AAGCATTATCTCATCGCTCAA | 425 |
| IL17C | 27189 | CCGCGAGACAGCTGCGCTCAA | 426 |
| GPR149 | 344758 | CACCGTGAGCGTAGCGCAGAA | 427 |
| OR56A3 | 390083 | AACTCCGTTATTGTGGAAGAA | 428 |
| TECTB | 6975 | CAGGGCAACCTTCCAATTCAA | 429 |
| BLK | 640 | CTGGTAAGCGACTGTCATCAA | 430 |
| ZNF718 | 255403 | CCGCAACTCAATCTGTTCTAA | 431 |
| SEC11B | 157708 | GTGGGAGAAATCGCTGTTCTA | 432 |
| FGD2 | 221472 | CAGGGTCATCTTCTCCAACAT | 433 |
| TIFA | 92610 | CTGGGTGTGCCCAATTGATCA | 434 |
| PRB3 | 5544 | AAGAAGGTGGTCATAGCTCTA | 435 |
| TREML1 | 340205 | CAGGCGTACGTTTCTCACAGA | 436 |
| PHF10 | 55274 | ATGGCAGTGTATGGAATGTAA | 437 |
| PTDSS2 | 81490 | CTGGTGGATGTGCATGATCAT | 438 |

TABLE IV-continued siRNA hits stimulating GS_SC-induced luciferase signal with at least a fold increase of increase of 1.83

| Gene Targeted | Gene ID | siRNA target sequence | SEQ ID NO |
|---|---|---|---|
| MGC12966 | 84792 | CACCACTGTACTTGGCGTTAA | 439 |
| FAM3D | 131177 | TACGACGATCCAGGGACCAAA | 440 |
| PDZD7 | 79955 | CCGGCGCATCGTCCACCTATA | 441 |
| NOX5 | 79400 | TTGCCCTATTTGACTCCGATA | 442 |
| CNGA3 | 1261 | CCCGTCCAGCAACCTGTACTA | 443 |
| MTMR6 | 9107 | CCCGGATAGCAAGCAAACCAA | 444 |
| GRAMD1A | 57655 | CACGATCTCCATCCAGCTGAA | 445 |
| MRLC2 | 103910 | GAGGGTGTAAATTGTATTGAA | 446 |
| LOC285908 | 285908 | CCCGACGGCCTTGACAGACCA | 447 |
| FAM18B | 51030 | TCAGTGGACCTTGAGCTAATA | 448 |
| WDFY2 | 115825 | AGCCACCTTCCATGACAGTAA | 449 |
| GAS1 | 2619 | ATGGATTATGAAGACACTCA | 450 |
| C3orf35 | 339883 | ATGGCCCACGTGAAATCTGAA | 451 |
| DEFB106A | 245909 | TAAAGGGACATGCAAGAACAA | 452 |
| ID5 | 3423 | CCCGAGGTCCCTGATGGCCTA | 453 |
| CCDC19 | 25790 | AAGGCTCGCTATCGGACCAAA | 454 |
|  |  | TAGATTCCAGTTGATGAAGAA | 455 |
| SNORD116-10 | 100033422 | CAGTACCATCATCCTCATCTA | 456 |
| KIF22 | 3835 | CAGGACATCTATGCAGGTTCA | 457 |
| SNF1LK2 | 23235 | CAGGATTACATCCGTTTATTA | 458 |
| GTF2A1 | 2957 | TCCATTGGTCTTACAAGTTGA | 459 |
| PMF1 | 11243 | CTGCGGCGCCATGTGCAGAAA | 460 |
| MC5R | 4161 | CGGCATTGTCTTCATCCTGTA | 461 |
| CELSR1 | 9620 | CGCCAACAGTGTGATTACCTA | 462 |
| LRRC32 | 2615 | CGCCGGCAGAAGTTTAACCAA | 463 |
| TGM6 | 343641 | CAGCATCGCTGGCAAGTTCAA | 464 |
| EPHA7 | 2045 | CAGGCTGCGAAGGAAGTACTA | 465 |
| LIMA1 | 51474 | CAGGTTAAGAGTGAGGTTCAA | 466 |
| PHLDA1 | 22822 | AGGAGCGATGATGTACTGTAA | 467 |
| CELSR1 | 9620 | CGGGATCCTGGATGTGATCAA | 468 |
| ETNK1 | 55500 | TCGATCGAGATGAGGAAGTAA | 469 |
| TSPAN14 | 81619 | CGGGACGATATCGATCTGCAA | 470 |
| ANGEL2 | 90806 | CTGACGCAATTGGCAATGCTA | 471 |
| MTHFD2L | 441024 | TACGTCTGATATGGTTAAAGA | 472 |
| B3GALT4 | 8705 | ATCCTGCGGTGTCGAGCAATA | 473 |
| VKORC1 | 79001 | GAGGGAAGGTTCTGAGCAATA | 474 |
| DCD | 117159 | CTGGTCTGTGCCTATGATCCA | 475 |
| ETHE1 | 23474 | CACGATTACCATGGGTTCACA | 476 |
| HOOK1 | 51361 | CAGGGTTACTTCTGTTGACTA | 477 |
| NDST1 | 3340 | CCCAGCGATGTCTGCTATCTA | 478 |
| COX4I2 | 84701 | CTGCACAGAACTCAACGCTGA | 479 |
| C22orf16 | 400916 | CCCAGATAGCTGGGATTGGAA | 480 |
| ACTA2 | 59 | TACGAGTTGCCTGATGGGCAA | 481 |
| TNRC18 | 84629 | CTCGGTCATCCGCTCGCTCAA | 482 |
| HCFC1 | 3054 | ACCGTTCACTATTGTAGAGTA | 483 |
| PIAS4 | 51588 | CACCGAATTAGTCCCACAGAA | 484 |
| NPY1R | 4886 | ACGACATCAGCTGATAATCAA | 485 |
| DEFB125 | 245938 | CTCAGACAGCTCTTACTCATA | 486 |
| C1orf128 | 57095 | TACGGGCAATGTCAAGCTCAA | 487 |
| TAGLN2 | 8407 | CAGCTGAGCGCTATGGCATTA | 488 |
| TRAPPC6A | 79090 | GACCTACGTCCTGCAAGACAA | 489 |
| SFTPA2B | 6436 | CTCCACGACTTCAGACATCAA | 490 |
| RGS11 | 8786 | CCCAAGGTTCCTGAAGTCTGA | 491 |
| CYFIP2 | 26999 | CACGCATCGGCTGCTCTGTAA | 492 |
| MAP6 | 4135 | TACCACCAAGCCAGACGACAA | 493 |
| LIG4 | 3981 | ATCTGGTAAGCTCGCATCTAA | 494 |
| TBXA2R | 6915 | CCCGCAGATGAGGTCTCTGAA | 495 |
| OR1L4 | 254973 | CACTGTAGTGGTCCTGTTCTA | 496 |
| UQCRC2 | 7385 | TACATCCAGTCTGACGACAAA | 497 |
| DLL1 | 28514 | CACGCAGATCAAGAACACCAA | 498 |
| TAS2R45 | 259291 | CACCGAGTGGGTGAAGAGACA | 499 |
| SETBP1 | 26040 | CAGCGTTGCTCTGAAGGCAAA | 500 |
| RND3 | 390 | AACGTTAAGCGGAACAAATCA | 501 |
| C12orf62 | 84987 | CAGCGCCAGGCCGCAGAAGAA | 502 |
| CPA5 | 93979 | CCGCTTATGGCGGAAGAACAA | 503 |
| KCNK15 | 60598 | CCGGTGGAAGTCCATCTGACA | 504 |
| GLT8D1 | 55830 | TAGCTGGTACAGATAATTCAA | 505 |
| GPR98 | 84059 | CAGATGGTTTATCGTGTTCAA | 506 |
| MAST2 | 23139 | CAGGAGTGTGCTGTCTGGCAA | 507 |
| TAF6 | 6878 | CAGCGTGCAGCCCATCGTCAA | 508 |
| SCT | 6343 | CAGCGAGCAGGACGCAGAGAA | 509 |
| BAHD1 | 22893 | CCGCCACGGGCGCATCCTTAA | 510 |

TABLE IV-continued siRNA hits stimulating GS_SC-induced luciferase signal with at least a fold increase of increase of 1.83

| Gene Targeted | Gene ID | siRNA target sequence | SEQ ID NO |
|---|---|---|---|
| OR1N1 | 138883 | CTGCGTTGTTTGTGTGTTCTA | 511 |
| NPLOC4 | 55666 | CAGTCGAAATAAGGACACCTA | 512 |
| CDON | 50937 | AAGCATGTTATTACAGCAGAA | 513 |
| FAM46C | 54855 | CAGACTGATCGCCACCAAGAA | 514 |
| OR2Z1 | 284383 | ACCACAGTCCACAGCAGGATA | 515 |
| BCL2L1 | 598 | CTGCTTGGGATAAAGATGCAA | 516 |
| ZFYVE9 | 9372 | AACTATAGTTGGGATGATCAA | 517 |
| ST6GAL1 | 6480 | AACCCTCAGCTTATGTAGCTA | 518 |
| FABP6 | 2172 | CACCATCGGAGGCGTGACCTA | 519 |
| USF2 | 7392 | CCGGGAGTTGCGCCAGACCAA | 520 |
| TSPYL1 | 7259 | TAGAACCGGTTGCAAGTTCAA | 521 |
| SLC35E2 | 9906 | CCAGCGTCCCTTTGTTGTGAA | 522 |
| RFXANK | 8625 | CTCAGTCTTTGCGGACAAGAA | 523 |
| PLEKHG2 | 64857 | CAGGTTCAGCCAGACCCTCAA | 524 |
| FLJ36208 | 283948 | CGCAATGTAGTTAGGTGCTCA | 525 |
| MEGF11 | 84465 | AAGAATCCGTGTGCAGTTCTA | 526 |
| MLXIP | 22877 | CAGGACGATGACATGCTGTAT | 527 |
| TTLL12 | 23170 | CACGGTGAGCTGCCCAGTACA | 528 |
| ACOT4 | 122970 | CAAACAGTCTCTGAACGGTTA | 529 |
| VPS33B | 26276 | CAGCGTTGGATCAACACTGTA | 530 |
| LRFN5 | 145581 | CTCGGTTAGATGTGACATCAA | 531 |
| CLDN17 | 26285 | TAGTAAGACCTCCACCAGTTA | 532 |
| SCN1A | 6323 | ACGCATCAATCTGGTGTTCAT | 533 |
| ZNF521 | 25925 | CAGCGCTTAAATCCAAGACTA | 534 |
| TMEM167 | 153339 | TTCAGAGTCTATTGACTGTAA | 535 |
| COPZ2 | 51226 | CGGTGTGATTCTGGAGAGTGA | 536 |
| CNOT2 | 4848 | CAGCAGCGTTTCATAGGAAGA | 537 |
| NUP210L | 91181 | CTGGCTGTCCGGCGTCATCAA | 538 |
| KCTD17 | 79734 | CCCGGGCCTGAGAAGGAAGAA | 539 |
| WDR54 | 84058 | CACGCTAAGGAGGGTGCTGGA | 540 |
| TTC31 | 64427 | TGCGATGGCGCCGATTCCAAA | 541 |
| GLTSCR1 | 29998 | CCGCATCGGGCTCAAGCTCAA | 542 |
| PDLIM3 | 27295 | CAGGACGGGAACTACTTTGAA | 543 |
| KRT78 | 196374 | CAGCCTGTTCTGCTCGCTCAA | 544 |
| C6orf81 | 221481 | CAGGTTCACTCCAACTTCCTA | 545 |
| PTPN23 | 25930 | CCGCCAGATCCTTACGCTCAA | 546 |
| EPC2 | 26122 | CAGCAGTTAGTTCAGATGCAA | 547 |
| RBP1 | 5947 | TAGGAACTACATCATGGACTT | 548 |
| 3.8-1 | 352961 | TTGGATGTCTTTGGGAACCAT | 549 |
| C17orf79 | 55352 | TTCCTTATTGACAGTGTTCAA | 550 |
| SYT3 | 84258 | TAGGGCGTAGTTGGTGCTGGA | 551 |
| SAR1B | 51128 | CACATTGGTTCCAGGTCTCAA | 552 |
| FLJ40243 | 133558 | CACTGCGAAAGTGCTGACAAA | 553 |
| SNORA27 | 619499 | CAAACTGGGTGTTTGTCTGTA | 554 |
| LOC55908 | 55908 | CTGGGTCTCTATGGCCGCACA | 555 |

This screen led also to the identification of 486 siRNAs hits that inhibit SC_GS-induced mutagenic NHEJ repair luciferase signal to at least a normalized luciferase activity inferior to 37,5 (see Table V below).

TABLE V siRNA hits inhibiting GS_SC-induced lusiferase signal to at least a normalized luciferase activity inferior to 37, 5

| Gene Targeted | Gene ID | siRNA target sequence | SEQ ID NO |
|---|---|---|---|
| SNX3 | 8724 | ATCGATGTGAGCAACCCGCAA | 556 |
| MYO1E | 4643 | CACAGACGAACTCAGCTTTAA | 557 |
| MEGF9 | 1955 | CAGGATGCCATCAGTCCTTTA | 558 |
| NOC3L | 64318 | AAGCATGAACGCATTATAGAT | 559 |
| HHIPL2 | 79802 | CCCGTTCAGACCACTCGCCAA | 560 |
| ITIH4 | 3700 | ATGGATCGAAGTGACCTTCAA | 561 |
| DPY19L2 | 283417 | CTCCGTAATCAATGGAGCATA | 562 |

TABLE V-continued siRNA hits inhibiting GS_SC-induced lusiferase signal to at least a normalized luciferase activity inferior to 37, 5

| Gene Targeted | Gene ID | siRNA target sequence | SEQ ID NO |
|---|---|---|---|
| ZNF454 | 285676 | ATAATCCGTTCTAGAGAATAA | 563 |
| TTC21A | 199223 | CAAGGCGGTACAGTCTTATAA | 564 |
| TTC21A | 199223 | CTGCTACTGGGCGATGCCTTA | 565 |
| MFSD11 | 79157 | CCCGCGGCTCTGACTACCGAA | 566 |
| MYO1E | 4643 | CAGGGTAAAGCATCAAGTCGA | 567 |
| ARL5B | 221079 | TAGACGGTGCTGATTGGGAAA | 568 |
| SPZ1 | 84654 | TACCATTGCCTTATTCGAAAT | 569 |
| MFSD11 | 79157 | CAGCAACTACCTTCTCCTTCA | 570 |
| LHX6 | 26468 | ATGCTTGACGTTGGCACTTAA | 571 |
| GABARAPL1 | 23710 | CAGCTGCTAGTTAGAAAGGTT | 572 |
| OBFC1 | 79991 | TCAGCTTAACCTCACAACTTA | 573 |
| BCAS2 | 10286 | CTCGCAGATACCGACCTACTA | 574 |
| CCDC62 | 84660 | ACCTACGAGTTTGTTAATCTA | 575 |
| STC1 | 6781 | CCAGAGAATCTTAAGGTCTAA | 576 |
| TTC23 | 64927 | CAGGGTGATATATGCTATAAA | 577 |
| NELF | 26012 | CGCGTCTGTAATCCAGAGGAA | 578 |
| HSD17B4 | 3295 | CAGGCCAATTATAGTGCTGCA | 579 |
| IL32 | 9235 | CCGGATGTTGAGGATCCCGCA | 580 |
| TATDN1 | 83940 | CTGACCCTATGTTCAGAGGAA | 581 |
| FAM117A | 81558 | CTCGACCTAATCATAGCTACA | 582 |
| ZNF710 | 374655 | CTCGCCCGTGAAGCCATTCAA | 583 |
| CABP1 | 9478 | CAGCAGATATGATTGGTGTAA | 584 |
| ZNF454 | 285676 | TAGCACTTTGCCTGTCCCTAA | 585 |
| CC2D1A | 54862 | CCCGGCGTCCACGCCTACCTA | 586 |
| C12orf52 | 84934 | TCAGGATTAGTTTCCAGCTAA | 587 |
| LOC90826 | 90826 | CTGGAACTGGACAGAGTAATA | 588 |
| ENPP6 | 133121 | CAGGTCGGTGGACGTCTACAA | 589 |
| ZNF44 | 51710 | CACCGGGAGTGTCATGAATAT | 590 |
| HNRPUL1 | 11100 | GAGAGTGACTATTGAACTTGA | 591 |
| FAM122A | 116224 | CAGCCGCTTGCACCAGATCAA | 592 |
| KLF16 | 83855 | CAGCGCTAGTGAGATGCCTTA | 593 |
| ACSF2 | 80221 | CAGGAGATGTCGCCACAATGA | 594 |
| TSHC | 7252 | GAGAGTGTGCTTATTGCCTAA | 595 |
| ZNF503 | 84858 | ACGGTGTGCACTCCTCGCTAA | 596 |
| TMEM132D | 121256 | CACGTTGAGGGCAAAGGTGAA | 597 |
| HEY2 | 23493 | TAGGATTCCGAGAGTGCCTAA | 598 |
| MYO7B | 4648 | ACCGAGCTTATTTACCGCCAA | 599 |
| FLJ45803 | 399948 | CTCTAGGATGTTTGCCCTGAA | 600 |

TABLE V-continued siRNA hits inhibiting GS_SC-induced lusiferase signal to at least a normalized luciferase activity inferior to 37, 5

| Gene Targeted | Gene ID | siRNA target sequence | SEQ ID NO |
|---|---|---|---|
| AZIN1 | 51582 | CAGGTTAAGCTTGTCTGGTCA | 601 |
| LOC374920 | 374920 | CCCGCTGGAGTTCGCCTACTA | 602 |
| EPAS1 | 2034 | CCCAATGATAAGTTCACCCAA | 603 |
| PGM1 | 5236 | CAGGTACAGTTTACACTACAA | 604 |
| KLHL8 | 57563 | CAGGATATTGATGGACCTACA | 605 |
| FTSI3 | 117246 | CGGGTTTGAGATAGTGCCTAT | 606 |
| LOC100137047-PLA2G4B | 8681 | CGCCGGCAACCTACCAGCTAA | 607 |
| TIMM8A | 1678 | CAGGTAGAGGTGCATGCCTAA | 608 |
| TMEM117 | 84216 | AACGAATCTACTAGTGCAACA | 609 |
| LOC124446 | 128446 | AGCCCTAGAATGGGTGAGGAA | 610 |
| COPA | 1314 | CACACGGGTGAAGGGCAACAA | 611 |
| ZNF785 | 146540 | CAGCGTTTCCCTGGAGAGGAA | 612 |
| LOC441108 | 441108 | CATGACAAGAGGAGTGGATAA | 613 |
| NOS2A | 4843 | CTGGGCCGTGCAAACCTTCAA | 614 |
| CALY | 50632 | CTGCGTGCTGATCATGTACAA | 615 |
| FER1L3 | 26509 | CACGGCGACTGTAGCCCTGAA | 616 |
| LOC790955 | 790955 | CCGGACCGAGATACCATGCCA | 617 |
| TAS1R2 | 80834 | CCAGATCGTCTGCGCCTTCAA | 618 |
| MAPKAPK2 | 9261 | CGCCATCATCGATGACTACAA | 619 |
| KLHL30 | 377007 | CAGCGTAACTGTGGCCAGCCA | 620 |
| PPP1R16B | 26051 | ACGGGCGAGAGTAGCAGTGAA | 621 |
| SPATA17 | 128153 | TCCATGGGAGCTGCAATTACA | 622 |
| OAZ3 | 51686 | CAGGGTAACCACGACCAGCTT | 623 |
| CRIPT | 9419 | CAAGGCATAGATGTCAACTTA | 624 |
| ARSE | 415 | CGGCGTGAAGCTGACCCAACA | 625 |
| POLR2C | 5432 | CTCGGTGGAGTTCACCCTCGA | 626 |
| PNKP | 11284 | CACGTGTGAGACAGCCCTGAA | 627 |
| KIAA0355 | 9710 | AACCGCTACCTCAGCAAACAA | 628 |
| SLC26A11 | 284129 | CTCCTTCGAGGTGACTGGATA | 629 |
| SNORD22 | 9304 | CCCAGAGCCTGTAAAGGTGAA | 630 |
| SIM2 | 6493 | TAGCAGCTCGTCTCCAGCTAA | 631 |
| FAM65A | 79567 | CAGGAGGTGACCCGCCTAGAA | 632 |
| FHDC1 | 85462 | AAGCTCGAGAAGAGATTACTA | 633 |
| AIG1 | 51390 | CAGAGAGATGATATACCCGAA | 634 |
| EMP1 | 2012 | ACCGTATTTCAGCCATGATAA | 635 |
| DMWD | 1762 | CACGCGCGAGGGTTTCTACAA | 636 |
| LPPR2 | 64748 | CCCGTGTCTAAGCATGTGCAA | 637 |

TABLE V-continued siRNA hits inhibiting GS_SC-induced lusiferase signal to at least a normalized luciferase activity inferior to 37, 5

| Gene Targeted | Gene ID | siRNA target sequence | SEQ ID NO |
|---|---|---|---|
| LYPD4 | 147719 | CCCGTGCTTCATGCCCTGATA | 638 |
| ARMC6 | 93436 | CACCAAAGCGTTCCTGGATAA | 639 |
| BARHL2 | 343472 | TCGCCTTATTTCTATCACCCA | 640 |
| CRTAC1 | 55118 | CCGGGACATCGCCTCACCCAA | 641 |
| DES | 1674 | CTGCGAGATTGACGCCCTGAA | 642 |
| ARNT2 | 9915 | CAGAATAACCACCATGAGGAA | 643 |
| EPHA10 | 284656 | CTCGGTGCGCGTCTACTACAA | 644 |
| EEF1A1 | 1915 | CACCGAGACATTTAGGTGAAA | 645 |
| TREML1 | 340205 | CAGCAGAGTTTCAGGCATGAA | 646 |
| COPA | 1314 | CTGGCGCATGAATGAATCAAA | 647 |
| MYH14 | 79784 | CGCGGGCAAGGTCGACTACAA | 648 |
| MYST1 | 84148 | CAGATGACCAGTATCACCCAA | 649 |
| PLD3 | 23646 | CCGGTTCTATGACACCCGCTA | 650 |
| EFNA2 | 1943 | CCGCGCCAACTCGGACCGCTA | 651 |
| GP9 | 2815 | CAGACAGGAGCACCTGACCAA | 652 |
| ELA28 | 51032 | TGGCGTGATATGCACCTGCAA | 653 |
| DNAI1 | 27019 | AAGAAGGCACATATAAGCCTA | 654 |
| SLK | 9748 | TAGCATCTTGTGATCACCCAA | 655 |
| ZNF74 | 7625 | CAGGGTGCCTCCTCTAGTTAA | 656 |
| OGDH | 4967 | CAGGATCAATCGTGTCACCGA | 657 |
| MMRN1 | 22915 | CAGGGTCGTGATGATGCCTTA | 658 |
| AGPAT1 | 10554 | TGGCTCCATGCTGCCCTTCAA | 659 |
| CYP3A4 | 1576 | CTCGATGCAATGAACACTTAA | 660 |
| GNAL | 2774 | ATGGGTTTAATCCCGAGGAAA | 661 |
| MYCBP2 | 23077 | CTCGATATATTGCCATAACAA | 662 |
| PSIP1 | 11168 | AGGCAGCAACTAAACAATCAA | 663 |
| SLC13A2 | 9058 | CCCGCTAATCCTGGGCTTCAT | 664 |
| HMBS | 3145 | CAGCTTAACGATGCCCATTAA | 665 |
| MED14 | 9282 | CGGGTGAAGTTTCGTGTTGAA | 666 |
| PLXNA4 | 91584 | CCGCATCGTCCAGACCTGCAA | 667 |
| TINF2 | 26277 | TCCTGTGGATTTGGCCTCGAA | 668 |
| POLR3C | 10623 | CCGGTACATCTATACTACCAA | 669 |
| POLR2A | 5430 | CAGCGGTTGAAGGGCAAGGAA | 670 |
| CLDN12 | 9069 | CTCCTCAGTGTGGGCGAGTAA | 671 |
| ZNF559 | 84527 | TCCCGAGAGATGGCTAATGAA | 672 |
| WDR3 | 10885 | CCGGGATGTTATCGGCTTCAA | 673 |
| K1F2A | 3796 | CAGCAAGCAAATCAACCCGAA | 674 |
| ARHGAP17 | 55114 | CAGACCAGCGATGTGAATAAA | 675 |

TABLE V-continued siRNA hits inhibiting GS_SC-induced lusiferase signal to at least a normalized luciferase activity inferior to 37, 5

| Gene Targeted | Gene ID | siRNA target sequence | SEQ ID NO |
|---|---|---|---|
| IPO11 | 51194 | ATGGGTCGAGTTCTACTACAA | 676 |
| GYPA | 2993 | ACCGGACATGCAGGTGAATAT | 677 |
| TDGF3 | 6998 | CTGCCCGTTTACATATAACAA | 678 |
| INTS4 | 92105 | CAGATACGTCTCATGGTGTAA | 679 |
| KRBA1 | 84626 | CCGACAAACCGTGGCCTACAA | 680 |
| KIAA1853 | 84530 | CGCCAGTATCACGGCCCGCAA | 681 |
| TNNT2 | 7139 | CAGGTCGTTCATGCCCAACTT | 682 |
| PLOD1 | 5351 | CACCATCAACATCGCCCTGAA | 683 |
| SERP1NA4 | 5267 | TCGCCACATCCTGCGATTCAA | 684 |
| ARID1A | 8289 | CACCTTGGTTACACTCGCCAA | 685 |
| EMD | 2010 | TACAATGACGACTACTATGAA | 686 |
| CXXC4 | 80319 | TTCAAGGCATTTGGAAATGAA | 687 |
| CYP2A6 | 1548 | CAGGCCTTTCAGTTGCTGCAA | 688 |
| EVI2B | 2124 | TAGGAGTACACCAGGATTTAT | 689 |
| UQCRFS1 | 7386 | ATGCTCAGTCATACACGCGAA | 690 |
| DNAH8 | 1769 | CTGCAATATTATGATGAGTTA | 691 |
| LMBR1 | 64327 | ATCGGTGGAATACAACATAAT | 692 |
| BBOX1 | 8424 | AACATGGCTTGTACCATCCAA | 693 |
| FAM86C | 55199 | CCAGCGGGCTCCTCAATTCTA | 694 |
| MST1 | 4485 | AAACTTCTTGTCAGACATAAA | 695 |
| UBOX5 | 22888 | CAGACAGTAACTTTGGTGTAA | 696 |
| POLR2C | 5432 | CAGAGTGATGTGCTAACCATA | 697 |
| PTPDC1 | 138639 | CGGAATGTTGAGTGCCTTCAA | 698 |
| TNIK | 23043 | CTGGAATATAAGCGCAAACAA | 699 |
| TSPAN9 | 10867 | CGGGCGCGGAATATCCTGGAA | 700 |
| POLR2A | 5430 | ATGGTCGTGTCCGGAGCTAAA | 701 |
| ZBTB40 | 9923 | CTCCTACGACTCGGCCTATAA | 702 |
| ANKFY1 | 51479 | GAGCGCTCAGTTGTTATACAA | 703 |
| WASH3P | 374666 | CTGCTAGAGTCCATCCGCCAA | 704 |
| RGP1 | 9827 | CACCAGGAATCCTGCCTACAT | 705 |
| GPR89B | 51463 | CACGGATATTCTAGCCCTGGA | 706 |
| ATP6V0E1 | 8992 | CACGTTCAGAGGGAAGAGCCA | 707 |
| SULF1 | 23213 | TCCGTCGAATTTGAAGGTGAA | 708 |
| SMOX | 54498 | CCCAAGGACGTGGTTGAGGAA | 709 |
| RFX2 | 5990 | CGGGACTTTCGAAGCCCTGAA | 710 |
| KIFC3 | 3801 | CAGCGCTGCGGAGATCTACAA | 711 |
| ATG2B | 55102 | CAGTAGCGTTGCATTGGATAA | 712 |

TABLE V-continued siRNA hits inhibiting GS_SC-induced lusiferase signal to at least a normalized luciferase activity inferior to 37, 5

Figure 4:
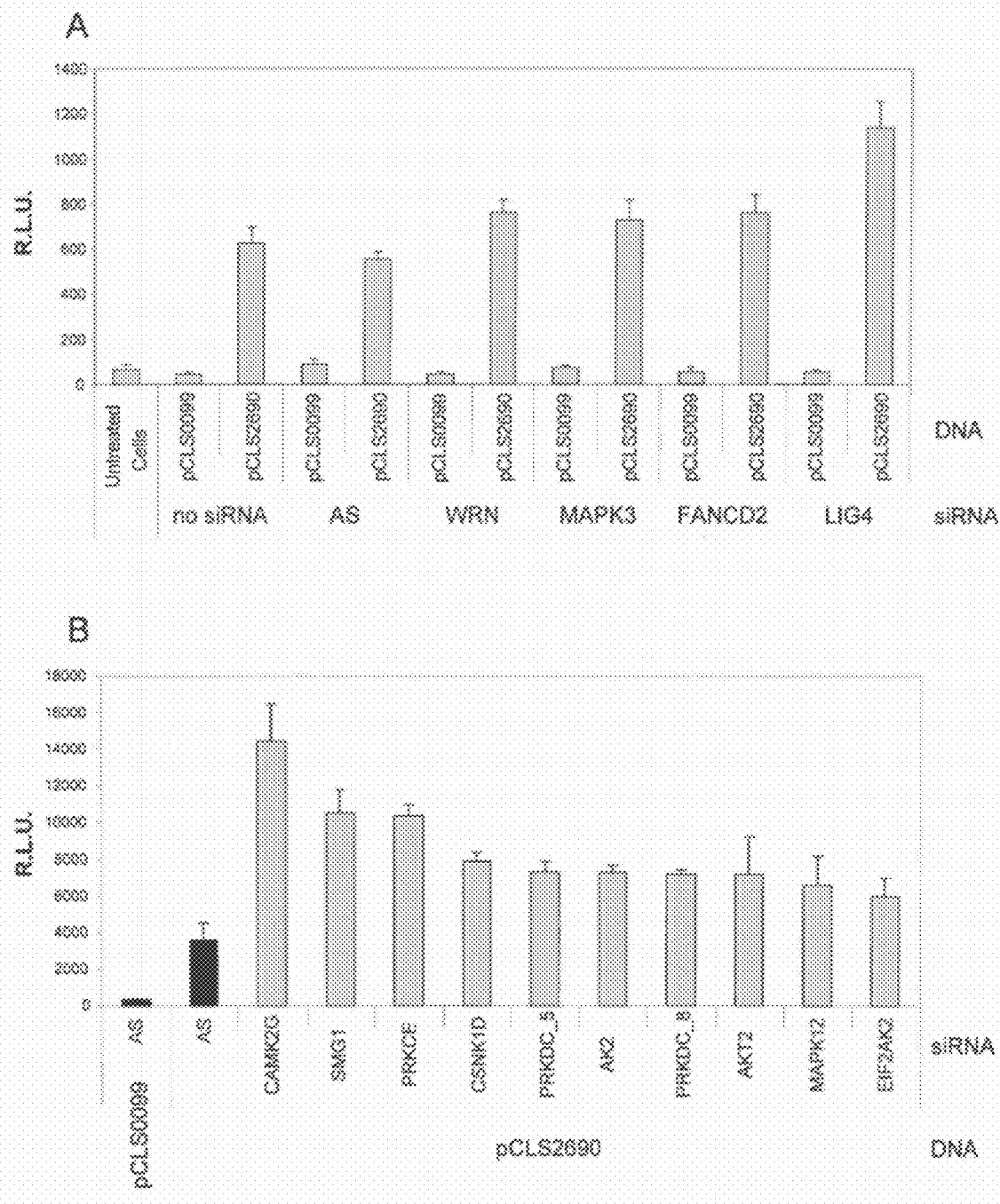
FIG. 4: Validation, of a stable cellular model to quantify NHEJ repair events induced by SC_GS via a luciferase reporter gene, after integration of pCLS6883 (SEQ ID NO: 1) at RAG1 locus of 293H cells; Panel 4A: Examples of four siRNAs increasing NHEJ repair events induced by SC_GS at RAG1 locus of 293H cells after targeting WRN, MAPK3, FANCD2 and LIG4 genes. Panel 4B: Examples of 10 siRNAs increasing NHEJ repair events induced by SC_GS at RAG1 locus of 293H cells (8 siRNAs identified with an extrachromosomal assay targeting CAMK2G, SMG1, PRKCE, CSNK1D, AK2, AKT2, MAPK12 and EIF2AK2 genes and two siRNAs targeting PRKDC gene).

| Gene Targeted | Gene ID | siRNA target sequence | SEQ ID NO |
|---|---|---|---|
| CCDC81 | 60494 | CAGAGATATCTCATCACCCAA | 713 |
| BSX | 390259 | AACCGGCGGATGAAGCATAAA | 714 |
| POLR2B | 5431 | CAGCGCATTGTGGCAACTCTA | 715 |
| NOS2A | 4843 | CTGGGCCGTGCAAACCTTCAA | 716 |
| CCDC128 | 129285 | CAGAACGACAAGGCTAAACTA | 717 |
| HPSE | 10855 | CTGATGTTGGTCAGCCTCGAA | 718 |
| LIMCH1 | 22998 | TAGCATCGAGATCAACATAAA | 719 |
| FAM116A | 201627 | AAGGGTATTATGTAATGCCTA | 720 |
| OR4D6 | 219983 | CAGATACCTTGCAATCGCCAA | 721 |
| FOXI1 | 2299 | CGAGATGAACCTCTACTATGA | 722 |
| COPZ1 | 22818 | CCCATCGGACTGACAGTGAAA | 723 |
| ZBTB22 | 9278 | CCCGCCCATTCTACTACTCAA | 724 |
| RNF151 | 146310 | CAGGGCCAACATACCTTGTAA | 725 |
| KCNK4 | 50801 | CACGGCCTCGGCCCTGGATTA | 726 |
| CUBN | 8029 | CACCTATGTCATAGAGGCTAA | 727 |
| GABRE | 2564 | CACTCTAACCATCACAATCAA | 728 |
| CHAC2 | 494143 | CCCGGCAAGCCTGGAAGAGTT | 729 |
| FIG4 | 9896 | CAGGTTCTTAGAAGGCTATTA | 730 |
| THOC1 | 9984 | AACACCTGAGAATCTGATTAA | 731 |
| FOXD4 | 2298 | CAGCGGCATCTGCGCCTTCAT | 732 |
| ORAI1 | 84876 | CTGGCGGAGTTTGCCCGCTTA | 733 |
| ZC3H3 | 23144 | CAGAGCCTTTAGTGCCCGCTA | 734 |
| ATP1A2 | 477 | CAAGGAGATCCCGCTCGACAA | 735 |
| KIF6 | 221458 | CAGCGTTACCATCGATGACAA | 736 |
| C5orf32 | 84418 | CAGCACTATGGGATTCTAGAT | 737 |
| CTSG | 1511 | CACAGTGTTGCCAGAGCCTTA | 738 |
| UCP2 | 7351 | AAGCACCGTCAATGCCTACAA | 739 |
| CYP4F8 | 11283 | CAAGGACATAGTCTTCTACAA | 740 |
| PRX | 57716 | CCCGCCGTGGAAATTGAGGAA | 741 |
| FBN2 | 2201 | CAGGATTGCCATATGTGCAAA | 742 |
| GABBR2 | 2570 | TACGGTCACTGCCATGTGCAA | 743 |
| PAQR4 | 124222 | CAGCACTTGGACAGCCTTCAA | 744 |
| NRBP1 | 29959 | TCGGTGGAGGAGGGAGTCAAA | 745 |
| RIMBP2 | 23504 | CGGAGAAGACATCGTGCCTTA | 746 |
| CNTLN | 54875 | CTCCGGCAAAGTGTTACTAAT | 747 |
| ZNF79 | 7633 | CTCGGAAATCCTGAAACCTCA | 748 |
| NEUROG3 | 50674 | CGAGCGCAATCGAATGCACAA | 749 |
| ISLR | 3671 | CAGCAACGAGCTGACCTTCAT | 750 |

TABLE V-continued siRNA hits inhibiting GS_SC-induced lusiferase signal to at least a normalized luciferase activity inferior to 37, 5

| Gene Targeted | Gene ID | siRNA target sequence | SEQ ID NO |
| --- | --- | --- | --- |
| POLR2F | 5435 | CAGAAGCGAATCACCACACCA | 751 |
| CYB561D2 | 11068 | CAGGTGAGCAATGCCTACCTA | 752 |
| AIFM1 | 9131 | TCGGTCGTGCGTGAGAGGAAA | 753 |
| SLURP1 | 57152 | CAGGACCATTACCCGCTGCAA | 754 |
| SERPINB6 | 5269 | CCGCGGTTTAAACTAGAGGAA | 755 |
| C1orf63 | 57035 | CAGGCTAAAGCCGCAGGTGAA | 756 |
| SLC44A5 | 204962 | CTCCGTATTGCTAAACCTACA | 757 |
| C1orf64 | 149563 | CCAGGAGGTTCCCGAGGCTAA | 758 |
| ZDHHC11 | 79844 | CGCGTGGAAATACATTGCCTA | 759 |
| RARG | 5916 | CCCGTCCTTGTGCCAGGTCAA | 760 |
| VEGFB | 7423 | CCGGATGCAGATCCTCATGAT | 761 |
| GTDC1 | 79712 | CGCCGACACGATGGCAGCCAA | 762 |
| ZER1 | 10444 | CTGCGAGATGTTCCTCAATTT | 763 |
| LHX6 | 26468 | CCGGTGCGGCCGACAGATCTA | 764 |
| FAM44B | 91272 | TTCGGTTACATAAGAGTGCAA | 765 |
| PTCD2 | 79810 | TACGAGTTGGATCTCGAGGAA | 766 |
| KIAA1009 | 22832 | TTGGTGCACCGTTGACTACTA | 767 |
| DYDC2 | 84332 | TGGGCGGTATACAGTAAACAA | 768 |
| NAPEPLD | 222236 | CTGCTGCACGCCGAATTGAAA | 769 |
| PRAP1 | 118471 | CCCGGTTGTGGGTGATGCCAA | 770 |
| RPS17 | 6218 | CGGCAGTCTGTCCAACCTTCA | 771 |
| SLC5A10 | 125206 | CAGCAAAGCGGGAGCCCTGAA | 772 |
| ZNF468 | 90333 | TTCTATGAGTATTGTACCGAA | 773 |
| PLEK | 5341 | ACCATTGACTTAGGTGCCTTA | 774 |
| CTAG1B | 1485 | CAGGGCTGAATGGATGCTGCA | 775 |
| CLEC1B | 51266 | CAGGCACAACTTAACATGGGA | 776 |
| COL9A1 | 1297 | AACGGTTTGCCTGGAGCTATA | 777 |
| OR11H1 | 81061 | CATGTACATGTTCCTGGGAAA | 778 |
| NR4A1 | 3164 | CAGCACCTTCATGGACGGCTA | 779 |
| NPPB | 4879 | CTGAGGCGGCATTAAGAGGAA | 780 |
| OR12D3 | 81797 | CACAATCAAGCTAAACCTACA | 781 |
| PROKR2 | 128674 | CCGGACCTTCTTCGCAGCCAA | 782 |
| PTPRS | 5802 | ATGGCGTGCCCGAATACCCAA | 783 |
| ZFYVE20 | 64145 | CTGCGGGTCTATTATGTGCAA | 784 |
| ZZEF1 | 23140 | CCGCTGCGTTTATATGGATAA | 785 |
| WDR53 | 348793 | CGGGACCATTATGGCAGTCAA | 786 |
| LOC198437 | 198437 | ACCGCCAAGAGGTGCAGACAA | 787 |

TABLE V-continued siRNA hits inhibiting GS_SC-induced lusiferase signal to at least a normalized luciferase activity inferior to 37, 5

| Gene Targeted | Gene ID | siRNA target sequence | SEQ ID NO |
|---|---|---|---|
| CXCL9 | 4283 | CCGGTGGAGATCCCACCCGAA | 788 |
| JAM2 | 58494 | TCCGACATTTGCAAAGAGGTA | 789 |
| DDX52 | 11056 | CTGAGGATGATAAGCCATTAT | 790 |
| ZNF582 | 147948 | CAGATGATCATCAGACATGAA | 791 |
| IRF8 | 3394 | TACCGAATTGTTCCTGAGGAA | 792 |
| C13orf31 | 144811 | CTCACGCTGGTTGGAAAGGTA | 793 |
| RPS24 | 6229 | AAGATAGATCGCCATCATGAA | 794 |
| HIST3H2BB | 128312 | CCTCGGCGTCCTGAACCCAAA | 795 |
| ZNF14 | 7561 | AGGACTCGTGCTGCAGTGAAA | 796 |
| NDUFS7 | 374291 | CGCCGTGGAGATGATGCACAT | 797 |
| LRFN2 | 57497 | CAAGGCCTTCGTGGTCAACAA | 798 |
| DLL3 | 10683 | CCCGGTGAATGCCGATGCCTA | 799 |
| RAD21 | 5885 | CTGGGAGTAGTTCGAATCTAT | 800 |
| CD7 | 924 | CTGGTCCTGGTGACAGAGGAA | 801 |
| RAB3B | 5865 | CCGGACCATCACAACAGCCTA | 802 |
| LOR | 4014 | CCGAGGTTTGCAAATCCTTCA | 803 |
| PRKCSH | 5589 | CTGCACCAACACTGGCTATAA | 804 |
| GYG2 | 8908 | AACGTAGAGTATAGAAATCCA | 805 |
| OR11H1 | 81061 | ATCCTATACTCTTGTCCTGAA | 806 |
| LOC541473 | 541473 | CACGGTGGTGACTCAAGCCTA | 807 |
| ACTL7A | 10881 | CACCGCTTTGAGTACGAGGAA | 808 |
| C9orf75 | 286262 | CGGGTGCGTGGCAGAGCTTCA | 809 |
| KCNK5 | 8645 | CAGGTCGGGCACCTACTACAA | 810 |
| NETO1 | 81832 | AAGACAGTGCATTGAACTTTA | 811 |
| PDE6B | 5158 | CCGGGAAATTGTCTTCTACAA | 812 |
| KALRN | 8997 | CAGGTGTTGGACTGGATTGAA | 813 |
| PTPN14 | 5784 | AAGGGCGATTACGATGTACAT | 814 |
| RECK | 8434 | TCGCGTGGCAGTCGATTACTA | 815 |
| LOC388335 | 388335 | CCCAGTCCAGCCCTAAACTAA | 816 |
| RPESP | 157869 | CAGACCAGTGCAAGCCTACAA | 817 |
| MLC1 | 23209 | CCCGGCTGAGATGGATTACTT | 818 |
| CEND1 | 51286 | CACGGTGAAGAGGACGCCCGA | 819 |
| UCN3 | 114131 | CCCACAAGTTCTACAAAGCCA | 820 |
| ZDHHC12 | 84885 | CAGATACTGCCTGGTGCTGCA | 821 |
| CNIH2 | 254263 | CTGGTGCAAACTTGCCTTCTA | 822 |
| NAT9 | 26151 | CACGCTAGGTCTGACCAAGTT | 823 |
| DKFZp761E198 | 91056 | CTGCACGAACTGGGACCTACA | 824 |
| GNAQ | 2776 | CACAATAAGGCTCATGCACAA | 825 |

TABLE V-continued siRNA hits inhibiting GS_SC-induced lusiferase signal to at least a normalized luciferase activity inferior to 37, 5

| Gene Targeted | Gene ID | siRNA target sequence | SEQ ID NO |
|---|---|---|---|
| BPIL1 | 80341 | CTGCACATTGGGAGCCTTATA | 826 |
| FLJ13137 | 400793 | CCCGATGATATGGCAGCCATA | 827 |
| C12orf25 | 84070 | CAGCGGAGATGGGTCCAGCTA | 828 |
| DPPA2 | 151871 | CCCGACTGTGCTAAGAGGAAT | 829 |
| LYPD2 | 137797 | CACCAACGAAACCATGTGCAA | 830 |
| S100A7 | 6278 | AAAGGACAAGAATGAGGATAA | 831 |
| SNORA38 | 677820 | TGCAGGCTCATGATCAACCAA | 832 |
| CDH23 | 64072 | TACAGTCACCACGACCTTCAA | 833 |
| SERPINB12 | 89777 | TACGATCTTGGGTGGAGTTTA | 834 |
| HAS2 | 3037 | CAGCTCGATCTAAGTGCCTTA | 835 |
| MSGN1 | 343930 | CCTGGTAGAGGTGGACTACAA | 836 |
| RAD17 | 5884 | AGGGAATATAGCACATCTATA | 837 |
| EPS8 | 2059 | TTGGATATTGTGAGACCTCCA | 838 |
| PPP1R3B | 79660 | CCCGCTAGATATGCCATTCAA | 839 |
| SAPS2 | 9701 | CAGCGAGGATGGCGACCAGAA | 840 |
| CSMD2 | 114784 | CAGCGCGGATTCAGTGCCCAA | 841 |
| MUC20 | 200958 | CTGCGTGTCAGGAGAGGCTAA | 842 |
| CCDC91 | 55297 | CTCGATCAAGTCATCCGCCAA | 843 |
| C6orf58 | 352999 | CTGCGGTTGATTCTGGTGTAA | 844 |
| RHOG | 391 | CACGCTGTGCGCTACCTCGAA | 845 |
| NLRP2 | 55655 | TTCGGCGCAGATGGGCTTCAA | 846 |
| LOC390667 | 390667 | CAACTACAACGTGTCCTACAA | 847 |
| IGLL3 | 91353 | CTGTGCCTAGATCACAGCCTA | 848 |
| HIATL2 | 84278 | CAGCTACCTGTGGCAGGAGAA | 849 |
| FLAD1 | 80308 | CAGCAACTACTATCAGGTGAA | 850 |
| SPC25 | 57405 | CGGGACTAAGAGATACCTACA | 851 |
| MSH2 | 4436 | TCCAGGCATGCTTGTGTTGAA | 852 |
| GPLD1 | 2822 | TAGGACCATGGGAGCTATTGA | 853 |
| PLA2G4D | 283748 | CACCGCTGTGGTTGCAGATCA | 854 |
| KLRG1 | 10219 | CTCCTAGGGATTGATGCCTAA | 855 |
| ZER1 | 10444 | CACGCACATTCCAGCCTACAA | 856 |
| TMED7 | 51014 | TAGCTACCCTAAAGTGATTTA | 857 |
| HNRPH3 | 3189 | AACATTGACGATGGACTACCA | 858 |
| SRBD1 | 55133 | CACGCTTGACTTCATTCGGAA | 859 |
| MYBPC1 | 4604 | TGGGAGATGACTGGTGTATCA | 860 |
| ARHGEF18 | 23370 | CTGACCCGCTTTAGAACTTAA | 861 |
| TRMU | 55687 | AAGCACGTTAAGAAGCCCGAA | 862 |

TABLE V-continued siRNA hits inhibiting GS_SC-induced lusiferase signal to at least a normalized luciferase activity inferior to 37, 5

| Gene Targeted | Gene ID | siRNA target sequence | SEQ ID NO |
|---|---|---|---|
| SNX8 | 29886 | CTCGCCGACAAGGCTGCACAA | 863 |
|  |  | TTGGTCTGACATGCCCTGATA | 864 |
| SLC45A4 | 57210 | CTCGACCGCCTGGCAAGCCTA | 865 |
| SLC7A8 | 23428 | CAGGCGGTTGAGGAACATATT | 866 |
| SFRS17A | 8227 | CGGGATGAAACTCATGTACAA | 867 |
| RAB26 | 25837 | CCGCAGTGTTACCCATGCCTA | 868 |
| LNX1 | 84708 | ATCATCCTCGATAGTACTCAA | 869 |
| RAB21 | 23011 | CAGGCCCGTAACTGTCTACTA | 870 |
| KIF7 | 374654 | TACCCTCACTGGGATCAACAA | 871 |
| IL1F10 | 84639 | GAGGATGTGAACATTGAGGAA | 872 |
| NUP62 | 23636 | CCGCGAGGTGGAGAAGGTGAA | 873 |
| HSPG2 | 3339 | CGGGAAGTGCAGGCCCGTCAA | 874 |
| PPP1R10 | 5514 | CTCAAACGTCAGAGCAACGTA | 875 |
| EPHA1 | 2041 | CACCTTTAATGTGGAAGCCCA | 876 |
| RNF138P1 | 379013 | CAGGCGCCAGTGCCTGATTTA | 877 |
| LUZP1 | 7798 | CAGCGGGTGCTGAGAATTGAA | 878 |
| THOC1 | 9984 | ACCTACGAGAATAATTCGGAA | 879 |
| RTN3 | 10313 | CAGGATCTACAAGTCCGTCAT | 880 |
| SYNPO2 | 171024 | CACCGTTGTCTCCTCCATCAA | 881 |
|  |  | TACCTCGGGAAAGAAATACTA | 882 |
| TNS4 | 84951 | CAGCAATGACCTCATCCGACA | 883 |
| ACTA1 | 58 | CACCCACAACGTGCCCATTTA | 884 |
| INE2 | 8551 | TAGTCGCTTTCTAATCTACAA | 885 |
| RPL32 | 6161 | CAGGGTTCGTAGAAGATTCAA | 886 |
| STAC3 | 246329 | CCCACCGACTTTCTAGAGGAA | 887 |
| GOT1 | 2805 | CAAGAACTTCGGGCTCTACAA | 888 |
| PDZRN3 | 23024 | CCCGGTGGTTAACGATTTAAT | 889 |
| ZNF467 | 168544 | GTGGATGATTCGGAAGGTGAA | 890 |
| PMP22 | 5376 | CAGCCTCGTGTTGAGCCTTAA | 891 |
| C5ofr40 | 408263 | CGCCCGCATCATGTAGCCTAA | 892 |
| ST6GALNAC5 | 81849 | TTGGACCTGATGAATGTACAA | 893 |
| SEMA4G | 57715 | CCGGGCCTTGTGGCTACTCAA | 894 |
| HDDC2 | 51020 | AATCATAGGCTTGTAAACCTA | 895 |
| DOCK11 | 139818 | CTGCAGCGGGTTCAAGATTCA | 896 |
| ZNF347 | 84671 | CAGATGGATGGGAATGGATCA | 897 |
| ZNHIT4 | 83444 | CGGGACCTATCAGGAGGGTTA | 898 |
| KIAA1394 | 57571 | CCCAGTTGGTACAGACCTTCA | 899 |
| ARHGEF10L | 55160 | CAGGAAGGACGTCCTCGGTGA | 900 |

TABLE V-continued siRNA hits inhibiting GS_SC-induced lusiferase signal to at least a normalized luciferase activity inferior to 37, 5

| Gene Targeted | Gene ID | siRNA target sequence | SEQ ID NO |
| --- | --- | --- | --- |
| ZNF689 | 115509 | CAGCACCAGGTCATCCATACA | 901 |
| C19orf43 | 79002 | CGGCGTGAACTTGTTCGCCAA | 902 |
| GPR89B | 51463 | ATCCGAATGAGTATGCCTTTA | 903 |
| ARHGEF11 | 9826 | CACAACGACTCTCGACCGGAA | 904 |
| KIAA1841 | 84542 | ACACTTCGTGATCAAGGTGAA | 905 |
| MSH5 | 4439 | CCCGGGACTATGGCTACTCAA | 906 |
| CWC15 | 51503 | CAGTATTCAAGCAGAGACCTA | 907 |
| THAP6 | 152815 | AGCCGGCATTTGGGAGCCTAA | 908 |
| JAKMIP2 | 9832 | AAGGAACAAGTGCCTCGCCAA | 909 |
| RABIF | 5877 | CTGGCATTGCCTAGATGACAA | 910 |
| ZNF721 | 170960 | TTAGTAGGTCAAGAAACCTTA | 911 |
| PSMD4 | 5710 | CCAGGCGGAATCAGCAGACAT | 912 |
| RHBDL1 | 9028 | CTGGAACGTCTTCGCCTACGA | 913 |
| TAS2R14 | 50840 | ATGGGAATGGCTTATCCTTCA | 914 |
| BMI1 | 648 | CAGAGTTCGACCTACTTGTAA | 915 |
| APOH | 350 | CAAGTTGTAAAGCATCTTGTA | 916 |
| RPL36 | 25873 | CGGGAGGAGCTGAGCAACGTA | 917 |
| OMA1 | 115209 | TACAAGTTAACCATATAGTAA | 918 |
| KIAA1632 | 57724 | CAGCGAACAGACTTTAAGGAA | 919 |
| CAV2 | 858 | CAGCAAATACGTAATGTACAA | 920 |
| SLAMF9 | 89886 | CAGGCATGGATATGACCTACA | 921 |
| SOD1 | 6647 | ATGGCACTTATTATGAGGCTA | 922 |
| MTMR8 | 55613 | CAGCCCAAGCAGAGTATGCTA | 923 |
| NXT2 | 55916 | TTCCGTTAGTCCTACCTTGAA | 924 |
| PSMD13 | 5719 | AAGACTCGTGAGAAGGTGAAA | 925 |
| FU40235 | 284369 | CAAGATAAACGAGCCAGCTAA | 926 |
| C9orf66 | 157983 | GGCGGCGTTCTTGCGATTCAA | 927 |
| PGM1 | 5236 | TCGGCTGTACATCGATAGCTA | 928 |
| DYNLT3 | 6990 | CTGCGACGAGGTTGGCTTCAA | 929 |
| ATP6V1E2 | 90423 | GAAGCTAGTGTTGAACCACTA | 930 |
| WDR53 | 348793 | CCGACCACTCTGGATTACAAA | 931 |
| TRY6 | 154754 | CAGGATTACTCTGAACAATGA | 932 |
| PTTG3 | 26255 | AGGCATCCTTGTGGCTACAAA | 933 |
| MBD6 | 114785 | TTCCACTGTAGTGATGCCTTA | 934 |
| OR13C3 | 138803 | ATGGGTGAGATTAACCAGACA | 935 |
| OR2T27 | 403239 | CACGGACACATCAGCCTACGA | 936 |
| TNNC1 | 7134 | CGCCAGCATGGATGACATCTA | 937 |

TABLE V-continued siRNA hits inhibiting GS_SC-induced lusiferase signal to at least a normalized luciferase activity inferior to 37, 5

| Gene Targeted | Gene ID | siRNA target sequence | SEQ ID NO |
|---|---|---|---|
| TCP11L2 | 255394 | CAAGCTAATCTTATAGGTCAA | 938 |
| APOBEC4 | 403314 | TACCATATTCGAACAGGTGAA | 939 |
| CPN1 | 1369 | CCGGTGGATGCACTCCTTCAA | 940 |
| FRAP1 | 2475 | CCGGAGTGTTAGAATATGCCA | 941 |
| PTBP1 | 5725 | CACGCACATTCCGTTGCCTTA | 942 |
| LGR5 | 8549 | CAGCAGTATGGACGACCTTCA | 943 |
| ZNF567 | 163081 | TACCACTTCCGTAGCCTATAA | 944 |
| CHMP4C | 92421 | TGGCAGCTTGGGCTACCTAAA | 945 |
| NOL9 | 79707 | ATCCGGGTTCATCCTACATTT | 946 |
| KIAA0831 | 22863 | CTCGGTGACCTCCTGGTTTAA | 947 |
| STRN | 6801 | CTGGAATACCACTAATCCCAA | 948 |
| ZNF576 | 79177 | CGGGCTGGTGCGACTATACTA | 949 |
| RPLP0 | 6175 | CAAGAACACCATGATGCGCAA | 950 |
| CMTM3 | 123920 | CTCCATCACGGCCATCGCCAA | 951 |
| ARHGEF1 | 9138 | CACCGATCACAAAGCCTTCTA | 952 |
| FOXD4 | 2298 | CAGCGGCATCTGCGCCTTCAT | 953 |
| P76 | 196463 | GTGGATGATCGTGGACTACAA | 954 |
| FTH1 | 2495 | CGCCATCAACCGCCAGATCAA | 955 |
| C12orf53 | 196500 | CACAATTACCATCTCCATCAT | 956 |
| RPS11 | 6205 | CCGAGACTATCTGCACTACAT | 957 |
| RHBDF2 | 79651 | CACGGCTATTTCCATGAGGAA | 958 |
| ALOX15B | 247 | TTGGACCTTATGGTCACCCAA | 959 |
| UNC13D | 201294 | CTGGTGTACTGCAGCCTTATA | 960 |
| PLEKHB1 | 58473 | CAGACCGTGGTGGGCCTTCAA | 961 |
| PCNXL2 | 80003 | CCGAAGGATCCTCATCCGCTA | 962 |
| DGCR5 | 26220 | TACGTTCTAGCATCCATTCAA | 963 |
| FARSA | 2193 | CCGCTTCAAGCCAGCCTACAA | 964 |
| AGPAT1 | 10554 | ACGCAACGTCGAGAACATGAA | 965 |
| C19orf63 | 284361 | CAAGACGGTCCTGATGTACAA | 966 |
| C18orf51 | 125704 | AGCGCAGCGCGTAAACAACAA | 967 |
| TMEM31 | 203562 | CACGTAGGACACCTACAACAT | 968 |
| TMEM54 | 113452 | CCACTAGGACCCTGCAAGCAA | 969 |
| PML | 5371 | CAGGAGCAGGATAGTGCCTTT | 970 |
| GABRD | 2563 | CACCTTCATCGTGAACGCCAA | 971 |
| UNQ9391 | 203074 | CACCTCGTTGGTGAACTACAA | 972 |
| ITGA9 | 3680 | ACAGGTCACTGTCTACATCAA | 973 |
| PDZD8 | 118987 | ACCGATCTCGTAGAACCTTCA | 974 |
| GPX4 | 2879 | GTGGATGAAGATCCAACCCAA | 975 |

TABLE V-continued siRNA hits inhibiting GS_SC-induced lusiferase signal to at least a normalized luciferase activity inferior to 37, 5

| Gene Targeted | Gene ID | siRNA target sequence | SEQ ID NO |
|---|---|---|---|
| GPBAR1 | 151306 | CAGGACCAAGATGACGCCCAA | 976 |
| NME2 | 4831 | TACATTGACCTGAAAGACCGA | 977 |
| ZFP106 | 64397 | AGGCGACATAGTGCACAATTA | 978 |
| TCAM1 | 146771 | CACGCTCGCCTGCGTCCCAAA | 979 |
| LOC374443 | 374443 | CCCATCGCATTTGGAAATGGA | 980 |
| HRG | 3273 | TTGGACTTGGAAAGCCCGAAA | 981 |
| TMEM166 | 84141 | ATGGAGGTGATTCTGATTCAA | 982 |
| RICH2 | 9912 | CAAACGCTAATAGAAGTGCAA | 983 |
| LAMC3 | 10319 | ATCGCGTATCTCACTGGAGAA | 984 |
| APOC1 | 341 | CAGCCGCATCAAACAGAGTGA | 985 |
| OR2G3 | 81469 | AGCACTCATCTCCATCTCCTA | 986 |
| PLCXD1 | 55344 | CACGATGACGTACTGCCTGAA | 987 |
| FAM83H | 286077 | CAGGTGCTCCATAATGAGTCA | 988 |
| TREML2 | 79865 | CCGCTACTTGCTGCAGGACGA | 989 |
| PATZ1 | 23598 | CCCGTCTGGCTGCTACACATA | 990 |
| BANF1 | 8815 | CCGGAAAGGAGCGCCTACTAA | 991 |
| KLHL30 | 377007 | CTGGCATAACAGGGACAGGAA | 992 |
| CA11 | 770 | CCGGCTCGGAACATCAGATCA | 993 |
| ECE2 | 9718 | CAGACACTATGCCCAAGCCTA | 994 |
| TMEM87A | 25963 | AGCGCTGATTGTTACAATGAA | 995 |
| PMS2 | 5395 | TGGATGTTGAAGGTAACTTAA | 996 |
| TDRD3 | 81550 | AAGCATCGAGGCAAGCTCTTA | 997 |
| SHC1 | 6464 | CACCTGACCATCAGTACTATA | 998 |
| DNMT3B | 1789 | CTCACGGTTCCTGGAGTGTAA | 999 |
| ITCH | 83737 | CACGGGCGAGTTTACTATGTA | 1000 |
| MAT1A | 4143 | TTGGCTCACACTCGACATGAA | 1001 |
| RALA | 5898 | CGAGCTAATGTTGACAAGGTA | 1002 |
| DEF6 | 50619 | CTGGACGCTGACGGCCAAGAA | 1003 |
| TIAM1 | 7074 | AACGGAAATGGTAGAGTTTCA | 1004 |
| NPAS3 | 64067 | CACCATAGCTATTAATGCCAA | 1005 |
| CLEC4M | 10332 | CTGGAACAGTGGAGAACCCAA | 1006 |
| PSEN2 | 5664 | CAGGAGAGAAATGAGCCCATA | 1007 |
| SP140 | 11262 | TCGGGTGTGATCCTAGGCCAA | 1008 |
| CENPE | 1062 | CAGGTTAATCCTACCACACAA | 1009 |
| NTRK3 | 4916 | CACGGATAACTTTATCTTGTT | 1010 |
| PTGFRN | 5738 | CCGATTCACGGTTTCGTGGTA | 1011 |
| PISD | 23761 | CCGCGTCGTGTGACTCCTTCA | 1012 |

TABLE V-continued siRNA hits inhibiting GS_SC-induced lusiferase signal to at least a normalized luciferase activity inferior to 37, 5

| Gene Targeted | Gene ID | siRNA target sequence | SEQ ID NO |
|---|---|---|---|
| HBSIL | 10767 | TACGTTACGGTGGTTCTACAA | 1013 |
| TTC23 | 64927 | CTCCGGAACTGCCCTACTTTA | 1014 |
| C3orf44 | 131831 | CAGCGAAGAGTACCTCTGGAA | 1015 |
| ZNF271 | 10778 | ACCCATGTAATCAGTGCAATA | 1016 |
| CDGAP | 57514 | CTGATCTGGCCTGAGATTCAA | 1017 |
| SBNO1 | 55206 | AAGGAGCTAGAATGTGGATAA | 1018 |
| HIST1H2AE | 3012 | CCGCAACGACGAGGAGCTAAA | 1019 |
| C1orf41 | 51668 | CCGCTACTTACTTGAGATTCA | 1020 |
| TTC16 | 158248 | CTGGTGGACTTCTATGCCTTA | 1021 |
| LCE1D | 353134 | TTCCTTCTGATTCTGCCTGAA | 1022 |
| BPIL3 | 128859 | CCCGGACTTTCTGGCCATGAA | 1023 |
| SIVA1 | 10572 | CACGCCGTGCATGGCAGCCTT | 1024 |
| ARHGEF5 | 7984 | TAGCCGTATGTTAAACAGAAT | 1025 |
| PRSS8 | 5652 | ACCCATCACCTTCTCCCGCTA | 1026 |
| COL9A1 | 1297 | CACCGACAGATCAGCACATTA | 1027 |
| PKD1L2 | 114780 | CCGTGTTTGCTGAATGCACAA | 1028 |
| PHF10 | 55274 | CGGACAGTTCCAGGAATATTA | 1029 |
| MKS1 | 54903 | ACCGACGAATCTTTACCTACA | 1030 |
| ARHGAP27 | 201176 | CCGCAGGGTGTTCTTCTACAA | 1031 |
| CXCL17 | 284340 | AGCGCCCACTCTTCCAATTAA | 1032 |
| SRGAP2 | 23380 | CTCGCTAATGTCAGTGCCAGA | 1033 |
| ACTR6 | 64431 | GACGACCTTAGTGCTGGATAA | 1034 |
| MIA | 8190 | CAGCGTTCAGGGAGATTACTA | 1035 |
| OR8J1 | 219477 | AGCTATTGTGGTTTCATCTTA | 1036 |
| FLJ44635 | 392490 | AAGGCCCTGAGGGCAAAGGTA | 1037 |
| SLC26A1 | 10861 | CAGCCTCTATACGTCCTTCTT | 1038 |
| CNN1 | 1264 | AAGATCAATGAGTCAACCCAA | 1039 |
| C19orf23 | 148046 | CACGACGTGGCAGACGAGGAA | 1040 |
| TRPM2 | 7226 | CAGGCCTATGTCTGTGAGGAA | 1041 |

Example 4

Figure 6:
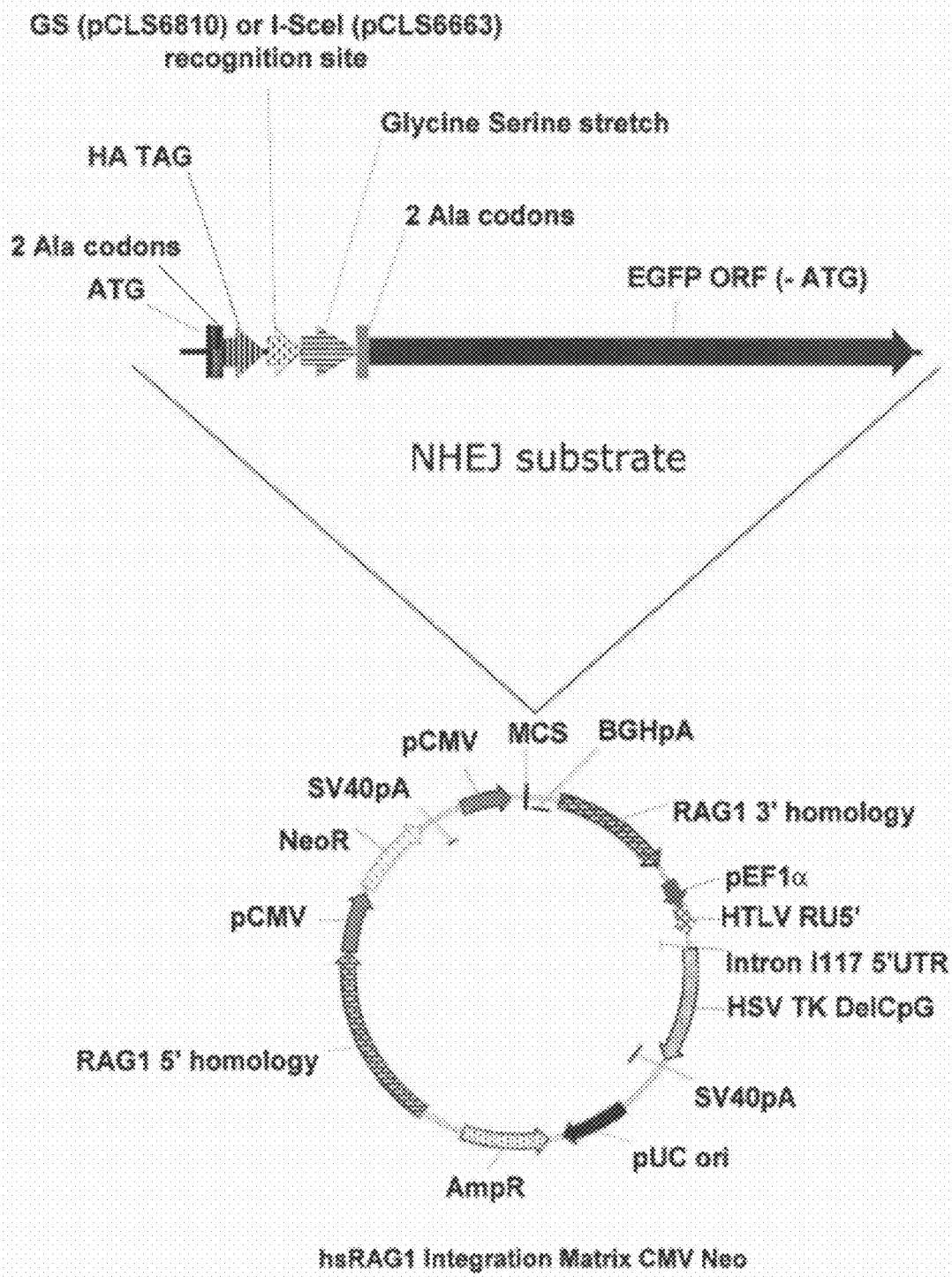
FIG. 6: EGFP plasmid construction maps to monitor a frequency of NHEJ repair events induced by SC_GS (pCLS6810, SEQ ID NO: 5) or I-Sce I (pCLS6663, SEQ ID NO: 6) meganucleases. The vectors can be targeted at RAG1 endogenous locus to obtain an established cell line
Figure 8:
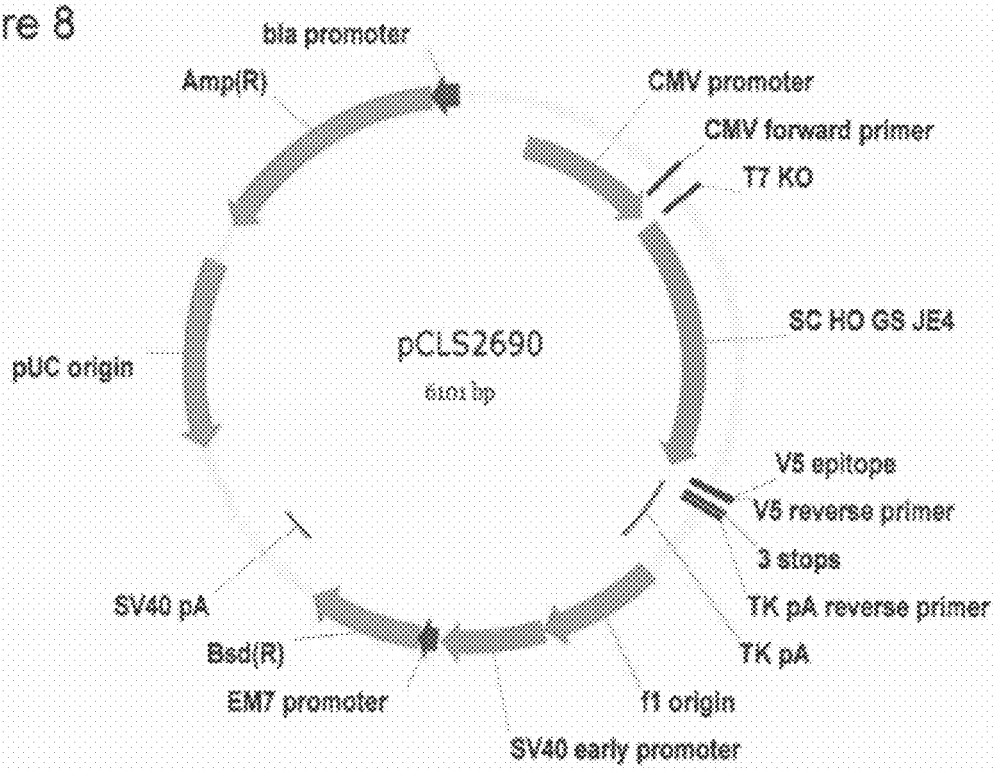
FIG. 8: Vector map of pCLS2690.
Figure 9:
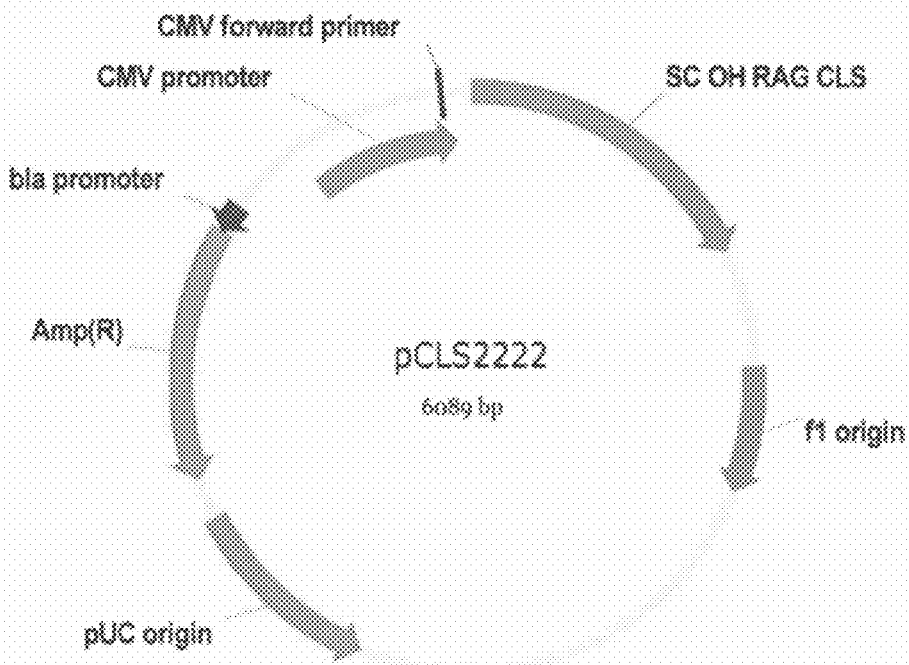
FIG. 9: Vector map of pCLS2222.
Figure 10:
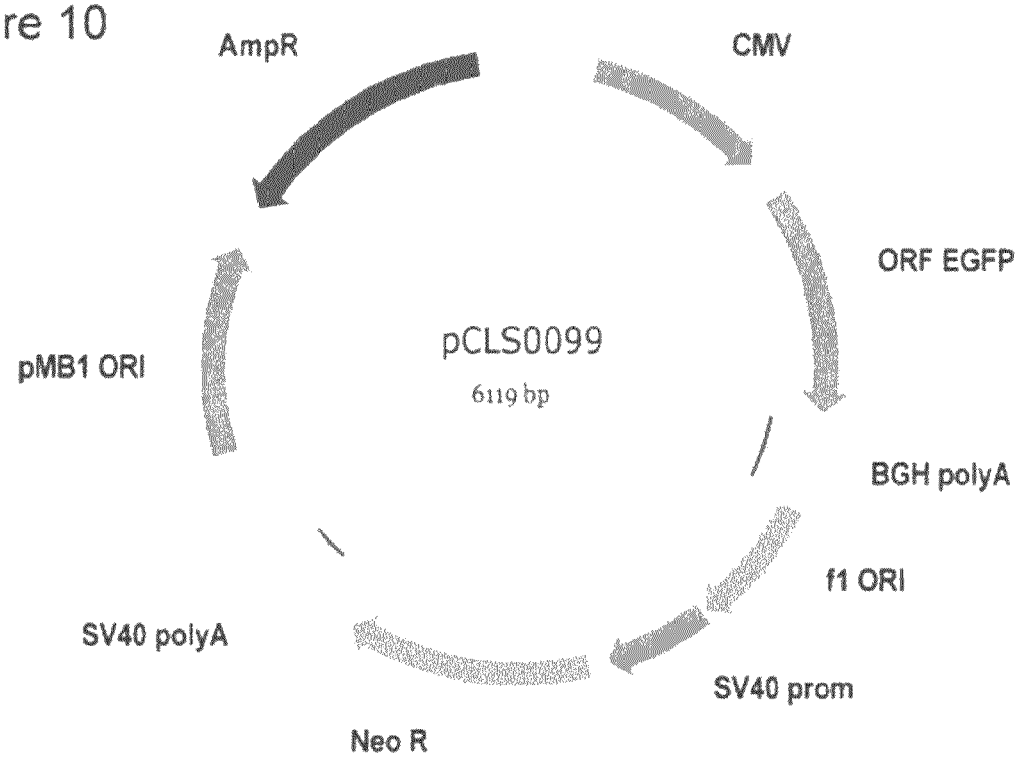
FIG. 10: Vector map of pCLS0099.
Figure 11:
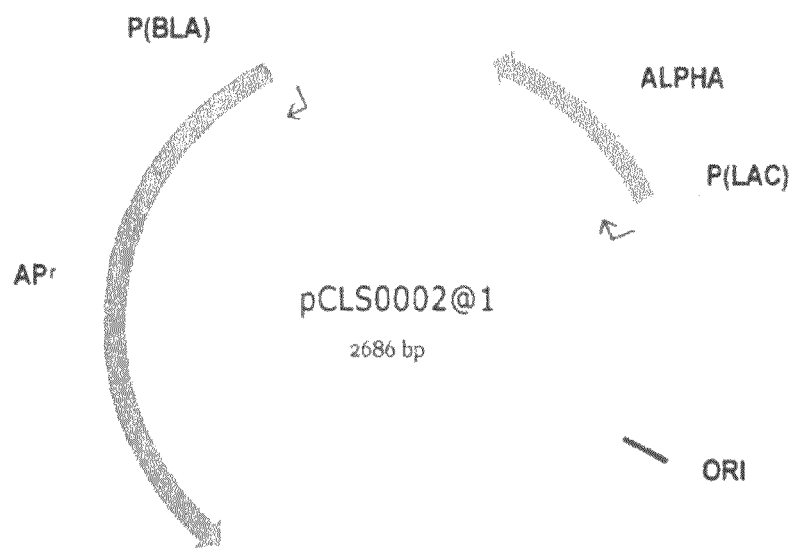
FIG. 11: Vector map of pCLS0002.

NHEJ GFP Reporter Gene Based Model in HEK293 Cell Line in order to validate the siRNAs hits issued from the primary high-throughput screening using the detection of a luciferase signal, it was also useful to derive a new construct based on a different reporter gene allowing the establishment of a correlation between the efficiency of the NHEJ activity induced by a meganuclease and the effect of the siRNAs hits. After it's functional validation in a transient transfection assay in 293H cell line, such plasmid may be further used to establish a cellular model with a single copy of the substrate for NHEJ recombination at the RAG1 locus to measure at a chromosomal location the frequency of SC_GS_induced mutagenesis and validate novel effectors increasing NHEJ efficiency.
a) Material and Methods
Design and Construction of Vector Monitoring GFP Meganuclease Induced NHEJ Mutagenesis The plasmids pCLS6810 (SEQ ID NO: 5) and pCLS6663 (SEQ ID NO: 6) were designed to quantify NHEJ repair frequency induced by SC_GS or I-SceI meganucleases respectively. These plasmids depicted in FIG. 6 are derived from the hsRAG1 Integration Matrix CMV Neo used in cGPS® Custom Human Full Kit DD of Cellectis Bioresearch.

pCLS6810 (SEQ ID NO: 5) and pCLS6663 (SEQ ID NO: 6) contain all the characteristics to obtain by homologous recombination a highly efficient insertion event of a transgene DNA sequence of interest at the RAG1 natural endogenous locus. They are composed of two homology arms of 1.8 kb and 1.2 kb separated by i) an expression cassette of neomycin resistance gene driven by mammalian CMV promoter and ii) an expression, cassette for the substrate of recombination monitoring NHEJ of GFP reporter gene driven also by CMV promoter. As for the vectors pCLS6883 (SEQ ID NO: 1) and pCLS6884 (SEQ ID NO: 2) described in FIG. 2 the sequence used to measure meganuclease-induced mutagenesis is made of an ATG start codon followed by i) 2 codons for alanine ii) the tag HA sequence iii) GS or I-SceI recognition sites iv) a glycine serine stretch, v) the same 2 codons for alanine as in i) and finally vi) a GFP reporter gene lacking its ATG start codon. Since by itself GFP reporter gene is inactive due to a frame-shift introduced by GS or I-SceI recognition sites, creation of a DNA double strand break (DSB) by SC_GS or I-SceI meganuclease (SEQ ID NO: 4 and SEQ ID NO: 40 respectively) followed by a mutagenic DSB repair event of NHEJ can lead to restoration of GFP gene expression in frame with the ATG start codon.

Cell Culture

Cell line 293H was cultured at 37° C. with 5% $CO_2$ in Dulbecco's modified Eagle's medium (DMEM) Glutamax supplemented with 10% fetal calf serum, 2 mM L-glutamine, 100 UI/ml penicilline, 100 µg/ml streptomycine, 0.25 µg/ml amphotericine B (Fongizone).

Cellular Transient Transfection for Functional Validation of NHEJ GFP Reporter Plasmid One day prior transfection the 293H cell line was seeded in 96 well plate at the density of 15000 cells per well in 100 µl. The next day, cells were transfected with Polyfect transfection reagent (Qiagen), Briefly a quantity of total DNA of 200 ng or 250 ng was diluted in 30 µl of water RNAse free. On the other hand 1.33 µl of Polyfect was resuspended in 20 µl of DMEM without serum. Then the DNA was added to the Polyfect mix and incubated for 20 min. at room temperature. After the incubation period the total transfection mix (50 µl) was added over plated, cells. After 96 h of incubation at 37° C., cells were trypsinized and the percentage of EGFP positive cells was monitored by flow cytometry analysis (Guava Instrument) and corrected by the transfection efficiency.

Stable Transfection to Generate 293H Based Cellular Model Measuring Efficiency of Chromosomal Meganuclease-Induced Mutagenic NHEJ Repair One day prior to transfection, 293H cells are seeded in 10 cm tissue culture dishes ($10^6$ cells per dish) in complete medium. The next day 3 µg of SC_RAG encoding vector pCLS2222 (SEQ ID NO: 36) and 2 µg of plasmid measuring SC_GS_induced GFP mutagenic NHEJ repair (pCLS6810 SEQ ID NO: 5) are co_transfected using 25 ul of Lipofectamine 2000 reagent (Invitrogen) during 6 hours according to the instructions of the manufacturer. Three days following transfection, 2000 cells are seeded and G418 selection was added at 400 ug/ml one week after seeding. Neomycin resistant clones were transferred in 96 well plate using Clone Fix (Genetix) and cultured in presence of 400 ug/ml of G418 and 50 uM of Gancyclovir (Sigma). Genomic DNA of Neomycin and Ganclovir resistant clones is extracted and targeted integration of a single copy of the transgene at the RAG1 locus identified by specific PGR amplification. (cGPS® Custom Human Full Kit DD, Cellectis Bioresearch).

b) Results

A) Extrachromosomal Validation of the NHEJ GFP Reporter Vector

In order to test the ability of the vector pCLS6810 (SeqID NO: 5) to achieve efficiently NHEJ mutagenesis of GFP reporter gene induced by SC_GS expression plasmid transient transfections in 96 well plate format were set up. FIGS. 7A and B present the functional assays corresponding to cotransfections of 100 ng of pCLS6810 (SEQID NO: 5) with 150 ng of the SC_GS expression vector pCLS2690 (SEQID NO: 3) or the pCLS0002 (SEQID NO: 41) control plasmid. As presented in FIGS. 7A and B, we get a measurable increase of the percentage of EGFP positive cells with the pCLS2690 (SEQ ID NO: 3) expression plasmid in comparison with the transfection performed with the vector control pCLS0002 (SEQ ID NO: 41). In fact, we get a percentage of EGFP positive cells of 13.3% vs 6.2% with a fold increase ratio of 2.1 obtained. These data imply that pCLS6810 can be used to further establish a cellular model allowing testing the potential effect of different siRNAs hits issued from the high-throughput Lueiferase primary screening on the modulation of the efficiency of the NHEJ repair mechanism induced by a custom meganuclease.

B) Functional Validation of the siRNAs Hits on the NHEJ GFP Reporter Gene Based HEK293 Cell Line The high-throughput screening of the siRNA human genome wide library has allowed the identification of several hundreds of potential hits (cf Table IV) able to increase SC_GS-induced mutagenic NHEJ repair of a luciferase reporter gene. To correlate such effect to an improvement of the frequency of the NHEJ activity, siRNAs were tested in a new cellular model described in this example with the read out of a different reporter gene EGFP.

Material and Methods:

a) Culture Conditions of the NHEJ GFP Reporter Gene Based HEK293 Cell Model

Same protocol as for the culture of the 293H cell line except that the complete culture medium DMEM Glutamax medium with penicilline (100 UI/ml), streptomycine (100 µg/ml), amphotericine B (Fongizone) (0.25 µg/ml), 10% FBS is supplemented with 0.25 mg/ml of G418 sulfate (Invitrogen-Life Science).

b) Making of Trex2/SC_GS Fusion Protein

Figure 13:
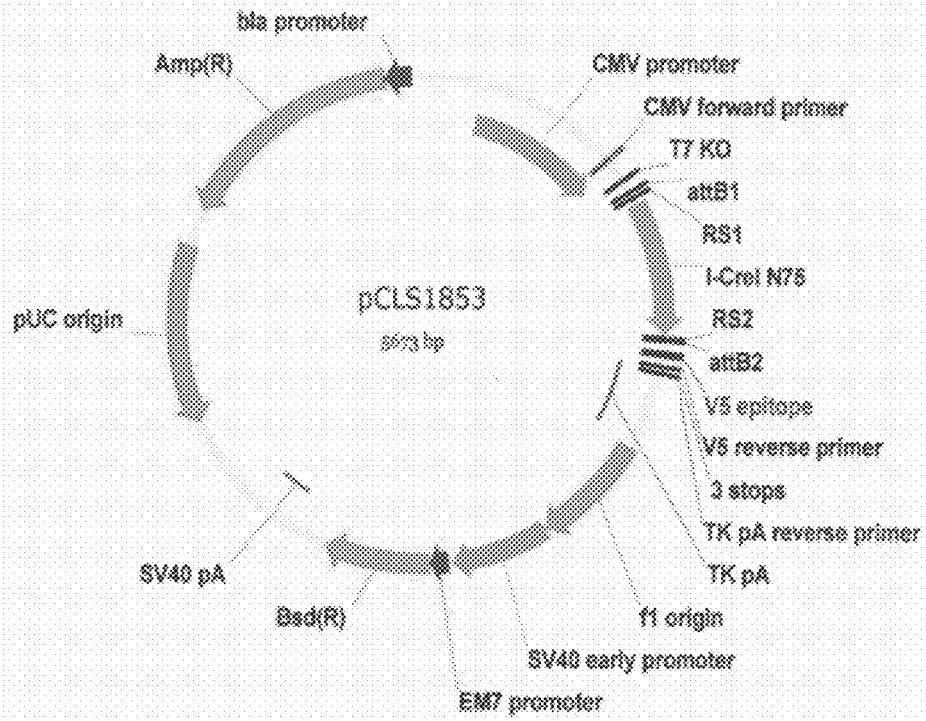
FIG. 13: Vector map of pCLS1853
Figure 14:
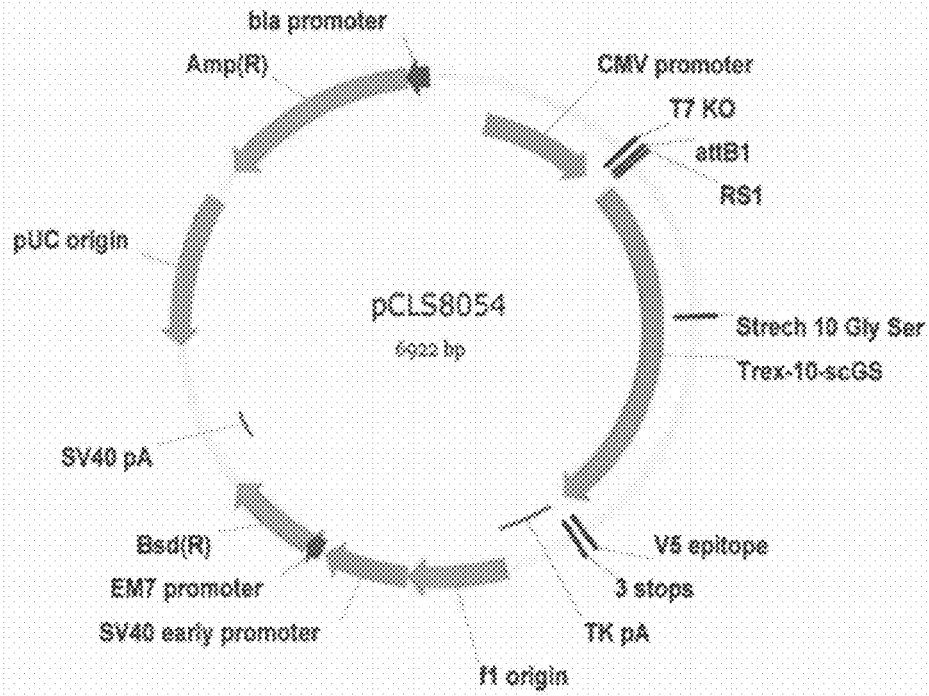
FIG. 14: Vector map of pCLS8054

The Trex2 protein was fused to the SC_GS meganuclease to its N-terminus using a ten amino acids glycin stretch $(GGGGS)_2$ (SEQ ID NO: 1042) as linker. Both SC_GS and Trex2 were initially cloned into the AscI/XhoI restriction sites of the pCLS1853 (FIG. 13, SEQ ID NO: 1043), a derivative of the pcDNA3.1 (Invitrogen), which drives the expression of a gene of interest under the control of the CMV promoter. The fusion protein construct was obtained by amplifying separately the two ORFs using a specific primer and the primer CMVfor (5'-CGCAAATGGGCGGTAG-GCGT-3'; SEQ ID NO: 1044) or V5reverse (5'-CGTA-GAATCGAGACCGAGGAGAGG-3'; SEQ ID NO: 1045), which are located on the plasmid backbone. Then, after a gel purification of the two PCR fragments, a PGR assembly was performed using the CMVfor/V5reverse oligonucleotides. The final PCR product was then digested by AscI and XhoI and ligated into the pCLS18S3 digested with these same enzymes to generate the pCLS8054 (FIG. 14, SEQ ID NO: 1046) expression vector encoding the fused protein Trex2_SC_GS (SEQ ID NO: 1049). The following table VI gives the oligonucleotides that were used to create the construct.

TABLE VI

Oligonucleotides used to create the Trex2/SC_GS construct

| Construct | Amplified ORF | Forward primer | SEQ ID NO: | Reverse primer | SEQ ID NO: |
|---|---|---|---|---|---|
| Trex2/SC_GS | Trex2 | CMVfor | 1044 | Link10TrexRev | 1048 |
|  | SC_GS | Link10GSFor | 1047 | V5reverse | 1045 | b) Cellular Transfection in 96 Well Format for Functional Validation of the siRNAs Hits Same protocol of cotransfection with polyfect as described in example 3 with 200 ng of pCLS2690 DNA (SEQ ID NO: 3) or pCLS8054 (SEQ ID NO: 1046) plasmids and siRNA at a final concentration of 33 nM. After, 96 h of incubation at 37° C., cells were trypsinized and the percentage of EGFP positive cells was monitored by flow cytometry analysis (Guava Instrument) and corrected by the transfection efficiency.
Results:

The new cell line containing a single copy of the GFP reporter system integrated at RAG1 locus was first validated by comparing the frequency of the EGFP positive cells obtained after transfection with the empty vector pCLS0002 (SEQ ID NO: 41) to the one obtained with the SC_GS encoding vector pCLS2690 (SEQ ID NO: 3). Typically, transfection with pCLS0002 (SEQ ID NO: 41) gave no EGFP positive cells as for untreated cells whereas transfections with SC_GS encoding vector (SEQ ID NO: 3) with no siRNA or with siRNA control AS led to detection of 0.5%+/−0.1 of EGFP positive cells (data not shown). This result, implies that, in comparison with the high-throughput cellular model monitoring the effect of the siRNAs hits using the detection of a luciferase signal, this NHEJ GFP new cell line is useful to establish a correlation between a percentage of GFP+ cells and a frequency of the NHEJ mutagenesis induced by SC_GS in presence of different siRNAs.

In this example, the effect of 223 different siRNAs (220 siRNAs identified with the high-throughput screening (cf Example 3) and three siRNAs issued from the results of the extrachromosomal screening (cf Example 3) and targeting the genes FANCD2 (SEQ ID NO: 39), AKT2 (SEQ ID NO: 15) and LIG4 (SEQ ID NO: 24) were monitored using the same siRNAs as those used, during the primary screening. They were chosen based on the high luciferase signal stimulation obtained. Co-transfections with SC_GS encoding vector (SEQ ID NO: 3) were performed in 96w format at least in triplicates and the potential effect of siRNAs hits was assessed using the statistical Student test analysis to eliminate such siRNAs that do not have a robust effect. The ratio of EGFP positive cells percentage calculated between a siRNA hit and siRNA control AS leads to determine the stimulation factor of each siRNA.

In parallel, using the same functional assay and the statistical analysis method as described previously, functional validation of the 223 siRNAs was also performed in the context of a cotransfection with an expression vector pCLS8054 (FIG. 14, SEQ ID NO: 1046) encoding for the Trex2/SC_GS (Seq ID NO: 1049) protein consisting to N-terminus fusion between the meganuclease SC_GS (Seq ID NO: 4) and a 236 amino acid functional version (SEQ ID NO: 1050) of the exonuclease Trex2 (SEQ ID NO: 1051). In fact, human Trex2 protein (SEQ ID NO: 1051) was choosen since it's known to exhibit a 3' to 5' non processive exonuclease activity (Mazur and Perrino, 2001) that might be compatible with the degradation of the 3' DNA overhangs generated by the meganuclease GS and with an improvement of it's NHEJ mutagenesis in presence or not of siRNAs. In comparison with the transfection of the NHEJ GFP reporter cell line with SC_GS expression vector pCLS2690 (SEQ ID NO: 3) quantification of the percentage of EGFP+ cells induced by the fused meganuclease Trex2/SC_GS encoded by pCLS8054 (SEQ ID NO: 1046) was typically enhanced from 0.5%+A 0.1 to 1.8%+/− 0.7 (data not shown) demonstrating the increased efficiency (3.6 fold induction) of the fusion protein Trex2/SC_GS to obtain mutagenic repair of the reporter gene.

As indicated in Table VII below, among the 223 hits tested, 115 siRNAs are able to increase the percentage of EGFP positive cells induced by SC_GS (SEQ ID NO: 4) or Trex2/SC_GS (SEQ ID NO: 1046) expression vectors with at least a stimulation factor of 2. Moreover, a group of 15 siRNAs corresponding to the ClassI have specifically an effect detected in the context of a transfection with SC_GS meganuclease, whereas another group of 63 siRNAs corresponding to ClassII have an activity detected only in presence of the Trex2/SC_GS fused meganuclease. Finally, the ClassIII concerns a group of 37 siRNAs that increase the percentage of GFP+ cells in the presence of either SC_GS or Trex2/SC_GS meganucleases.

Altogether, such data confirm the pertinence of the potential hits identified with the cellular model based on detection of luciferase signal confirming the robustness of the methodology applied to determine the cellular genes able to increase the efficiency of double-strand break-induced mutagenesis by a meganuclease.

TABLE VII

Validation of siRNAs hits stimulating SC_GS or Trex2/SC_GS-induced EGFP activity with at least a 2 fold increase

| Gene Targeted | Gene ID | siRNA target sequence | SEQ ID NO | Effect with SC_GS | Effect with Trex2/SC_GS | Class of Hits |
|---|---|---|---|---|---|---|
| AFG3L1P | 172 | CGGCTGGAAGTCGTGAACAAA | 140 | (−) | (+) | II |
| AKT2 | 208 | CAAGCGTGGTGAATACATCAA | 15 | (−) | (+) | II |
| BRCA1 | 672 | CTGCAGATAGTTCTACCAGTA | 45 | (+) | (+) | III |
| C16orf3 | 750 | CTGGGACAACGCAGTGTTCAA | 268 | (+) | (+) | III |
| CAMK2G | 818 | GAGGAAGAGATCTATACCCTA | 16 | (+) | (+) | III |
| CAV3 | 859 | TTGCGTTCACTTGTACTGTAA | 126 | (−) | (+) | II |
| CSH1 | 1442 | ACGGGCTGCTCTACTGCTTCA | 177 | (+) | (+) | III |

TABLE VII-continued

Validation of siRNAs hits stimulating SC_GS or Trex2/SC_GS-induced EGFP activity with at least a 2 fold increase

| Gene Targeted | Gene ID | siRNA target sequence | SEQ ID NO | Effect with SC_GS | Effect with Trex2/SC_GS | Class of Hits |
|---|---|---|---|---|---|---|
| CYP2A7 | 1549 | CCCAAGCTAGGTGGCATTCAT | 282 | (−) | (+) | II |
| DDX3X | 1654 | AACGAGAGAGTTGGCAGTACA | 184 | (−) | (+) | II |
| DPP4 | 1803 | ATCGGGAAGTGGCGTGTTCAA | 163 | (+) | (+) | III |
| DUSP1 | 1843 | CACGAACAGTGCGCTGAGCTA | 106 | (+) | (+) | III |
| EEF1A1 | 1915 | CAGAATAGGAACAAGGTTCTA | 256 | (−) | (+) | II |
| FANCE | 2178 | TCGAATCTGGATGATGCTAAA | 285 | (−) | (+) | II |
| GNG4 | 2786 | CCGAAGTCAACTTGACTGTAA | 185 | (−) | (+) | II |
| SFN | 2810 | CCGGGAGAAGGTGGAGACTGA | 162 | (+) | (−) | I |
| GRIN2C | 2905 | CCCAGCTTTCACTATCGGCAA | 167 | (+) | (−) | I |
| GTF2I | 2969 | TAGGTGGTCGTGTGATGGTAA | 141 | (−) | (+) | II |
| HIST1H2AE | 3012 | ATCCCGAGTCCCAGAAACCAA | 203 | (+) | (+) | III |
| HMX2 | 3167 | CGGGCGCGTACTGTACTGTAA | 83 | (−) | (+) | II |
| HES1 | 3280 | CACGACACCGGATAAACCAAA | 232 | (−) | (+) | II |
| IK | 3550 | CAGGCGCTTCAAGGAAACCAA | 236 | (−) | (+) | II |
| KCNC3 | 3748 | CAGCGGCAAGATCGTGATCAA | 180 | (−) | (+) | II |
| LRP5 | 4041 | CTGGACGGACTCAGAGACCAA | 399 | (−) | (+) | II |
| LTBR | 4055 | TACATCTACAATGGACCAGTA | 328 | (+) | (+) | I |
| NEK3 | 4752 | CAGAGATATCAAGTCCAAGAA | 238 | (+) | (+) | III |
| NMBR | 4829 | CCCGCGGACAGTAAACTTGCA | 338 | (+) | (+) | III |
| PLG | 5340 | AAGTGCGGTGGGAGTACTGTA | 235 | (−) | (+) | II |
| PPP3CA | 5530 | TCGGCCTGTATGGGACTGTAA | 227 | (−) | (+) | II |
| PRKCE | 5581 | CCCGACCATGGTAGTGTTCAA | 20 | (−) | (+) | II |
| PTPRA | 5786 | CCGGAGAATGGCAGACGACAA | 315 | (+) | (+) | III |
| SSBP1 | 6742 | AGCCTAAAGATTAGACTGTAA | 277 | (−) | (+) | II |
| TAF6 | 6878 | CTGGGAGTGTCCAGAAGTACA | 108 | (−) | (+) | II |
| TALDO1 | 6888 | CCGGGCCGAGTATCCACAGAA | 111 | (+) | (+) | III |
| TXNRD1 | 7296 | CCGACTCAGAGTAGTAGCTCA | 153 | (−) | (+) | II |
| VLDLR | 7436 | CAAGATCGTAGGATAGTACTA | 368 | (−) | (+) | II |
| SYNGAP1 | 8831 | CAGAGCAGTGGTACCCTGTAA | 229 | (−) | (+) | II |
| SART1 | 9092 | CAGCATCGAGGAGACTAACAA | 222 | (+) | (+) | III |
| PRPF4 | 9128 | TCCGGTCGTGAAGAAACCACA | 228 | (+) | (+) | III |
| ZRANB2 | 9406 | CACGATCTTCATCACGCTCAT | 335 | (+) | (−) | I |
| H2AFY | 9555 | CAAGTTTGTGATCCACTGTAA | 113 | (−) | (+) | II |
| EIF4A3 | 9775 | CCGCATCTTGGTGAAACGTGA | 109 | (−) | (+) | II |
| EIF4A3 | 9775 | AAAGAGCAGATTTACGATGTA | 353 | (−) | (+) | II |
| LCMT2 | 9836 | CAGGCGCGGTACAGAACACCA | 80 | (+) | (−) | I |
| EDIL3 | 10085 | CCCAAGTTTGTCGAAGACATT | 178 | (−) | (+) | II |

TABLE VII-continued

Validation of siRNAs hits stimulating SC_GS or Trex2/SC_GS-induced EGFP activity with at least a 2 fold increase

| Gene Targeted | Gene ID | siRNA target sequence | SEQ ID NO | Effect with SC_GS | Effect with Trex2/SC_GS | Class of Hits |
|---|---|---|---|---|---|---|
| VAV3 | 10451 | CACGACTTTCTCGAACACCTA | 85 | (+) | (-) | I |
| CAP1 | 10487 | AAGCCTGGCCCTTATGTGAAA | 385 | (+) | (-) | I |
| CAP1 | 10487 | CAACACGACATTGCAAATCAA | 367 | (+) | (+) | III |
| CPLX2 | 10814 | CAGATAGGTAGCAGAGACCAA | 175 | (-) | (+) | II |
| SLC6A14 | 11254 | ACCAATAGTAACTCACTGTAA | 137 | (-) | (+) | II |
| RBPJL | 11317 | CTCAAAGGTCTCCCTCTTCAA | 309 | (-) | (+) | II |
| TRIM32 | 22954 | CAGCACTCCAGGAATGTTCAA | 278 | (-) | (+) | II |
| SMG1 | 23049 | CACCATGGTATTACAGGTTCA | 33 | (-) | (+) | II |
| MAPK8IP3 | 23162 | CAGCCGCAACATGGAAGTCAC | 271 | (-) | (+) | II |
| FAM168A | 23201 | CAGCATTCCCTCTGCTATCTA | 127 | (-) | (+) | II |
| ANKRD12 | 23253 | CCGGAGCGGATTAAACCACCA | 269 | (-) | (+) | II |
| ISCU | 23479 | CTCCAGCATGTGGTGACGTAA | 128 | (-) | (+) | II |
| PTPN22 | 26191 | TGGGATGTACGTTGTTACCAA | 283 | (-) | (+) | II |
| CYFIP2 | 26999 | CGCCCACGTCATGGAGGTGTA | 122 | (-) | (+) | II |
| KCNIP2 | 30819 | CAGCTGCAGGAGCAAACCAAA | 226 | (-) | (+) | II |
| UBE2D4 | 51619 | CCGAATGACAGTCCTTACCAA | 237 | (+) | (+) | III |
| CLIC6 | 54102 | CCGAATCTAATTCCGCAGGAA | 308 | (-) | (+) | II |
| PAF1 | 54623 | CTCCACTGAGTTCAACCGTTA | 98 | (-) | (+) | II |
| BANP | 54971 | CAGCGACATCCAGGTTCAGTA | 258 | (-) | (+) | II |
| SETD5 | 55209 | AACGCGCTTGAACAACACCTA | 221 | (+) | (-) | I |
| OGFOD1 | 55239 | TCGGACGCTGTTACGGAAGAA | 196 | (+) | (+) | III |
| LARP6 | 55323 | ATGGTGTCTTGTAGGACCAAA | 151 | (-) | (+) | II |
| IL17RB | 55540 | CCGCTTGTTGAAGGCCACCAA | 223 | (-) | (+) | II |
| TMEM130 | 55769 | TCCGTCAACAGTAGTTCCTTA | 103 | (-) | (+) | II |
| ST6GALNAC1 | 55808 | CCCACGACGCAGAGAAACCAA | 225 | (+) | (+) | III |
| C12orf62 | 56245 | CAACCTGATGTGCAACTGTAA | 195 | (-) | (+) | II |
| SEMA3G | 56920 | CCCTGCCCTATTGAAACTCAA | 267 | (-) | (+) | II |
| INTS12 | 57117 | CAGGACCTAGTGGAAGTACTA | 97 | (-) | (+) | II |
| ZFYVE28 | 57732 | CAAGCCTGAAACAGACGACAA | 201 | (+) | (+) | III |
| SLC25A19 | 60386 | CTCCCTGTGATCAGTTACCAA | 299 | (+) | (-) | I |
| PROK2 | 60675 | TCGCTCTGGAGTAGAAACCAA | 115 | (+) | (+) | III |
| CHP2 | 63928 | CAGGGCGACAATAAACTGTAT | 138 | (-) | (+) | II |
| PRDM14 | 63978 | ACCGGCCTCACAAGTGTTCTA | 340 | (+) | (-) | I |
| CARD9 | 64170 | CAGCGACAACACCGACACTGA | 149 | (+) | (+) | III |
| FAM59A | 64762 | AAGGGCAGATTTAGCACCCGA | 189 | (+) | (-) | I |
| BCL11B | 64919 | CAGAGGTGGGTTAAACTGTAA | 193 | (-) | (+) | II |
| KCTD15 | 79047 | AACCTTGGAGATTCACGGCAA | 187 | (-) | (+) | II |

TABLE VII-continued

Validation of siRNAs hits stimulating SC_GS or Trex2/SC_GS-induced EGFP activity with at least a 2 fold increase

| Gene Targeted | Gene ID | siRNA target sequence | SEQ ID NO | Effect with SC_GS | Effect with Trex2/SC_GS | Class of Hits |
|---|---|---|---|---|---|---|
| SECISBP2 | 79048 | TCCCAGTATCTTTATAACCAA | 265 | (+) | (+) | III |
| SAP30L | 79685 | CAAGAGCGTAAGGCACCTATA | 186 | (−) | (+) | II |
| EPHX3 | 79852 | CAGCTCAGTGCTACTCTGAAT | 243 | (+) | (−) | I |
| PANK2 | 80025 | CTGTGTGTGAACTTACTGTAA | 331 | (+) | (−) | I |
| ATF7IP2 | 80063 | TAGGACGACTGAAATAACCAA | 239 | (+) | (+) | III |
| LRRC8C | 84230 | TACCTTATACTGGCTGTTCTA | 181 | (+) | (+) | III |
| CGB | 94027 | ACCAAGGATGGAGATGTTCCA | 244 | (+) | (+) | III |
| NUP35 | 129401 | CAGGACTTGGATCAACACCTT | 135 | (+) | (−) | I |
| LIPJ | 142910 | AGGGTTGTTGTATACTTGCAA | 198 | (−) | (+) | II |
| CSAG2 | 152667 | CTCCTTTATCTTCCAAACCAA | 252 | (+) | (+) | III |
| NKX2-3 | 159296 | CAGGTACAAGTGCAAGAGACA | 146 | (−) | (+) | II |
| FAM179A | 165186 | CAACGTCTCTATAGAGACCAA | 188 | (−) | (+) | II |
| KDM1B | 221656 | ATCGATGCGGTATGAAACCAA | 174 | (−) | (+) | II |
| TMEM130 | 222865 | CCCGCTGGTGCTTACTGGCAA | 102 | (−) | (+) | II |
| GK5 | 256356 | TACCATCTTGTACGAGCAATA | 416 | (−) | (+) | II |
| KLHL34 | 257240 | CTCGGCAGTCGTGGAAACCAA | 121 | (+) | (+) | III |
| C10orf53 | 282966 | CTGGAATGTGGTGGAACTCAT | 254 | (+) | (+) | III |
| FAM100B | 283991 | CACGTTCTTCCAAGAAACCAA | 249 | (+) | (+) | III |
| CXorf59 | 286464 | CTGTGAGTTCCTGTACACCTA | 110 | (−) | (+) | II |
| KRTAP13-3 | 337960 | CAGGACTCACATGCTCTGCAA | 143 | (−) | (+) | II |
| ADAMTSL5 | 339366 | ATGCCTAACCAGGCACTGTAA | 118 | (−) | (+) | II |
| OTOP3 | 347741 | TTGCCAGTACTTCACCCTCTA | 257 | (−) | (+) | II |
| PEAR1 | 375033 | CTGCACGCTGCTCATGTGAAA | 215 | (+) | (+) | III |
| TMEM179 | 388021 | CGGGCCGGCCATGGCGCTCAA | 168 | (+) | (−) | I |
| C2orf82 | 389084 | CACAGACGATGTTCCACAGGA | 233 | (+) | (+) | III |
| C5orf46 | 389336 | ACCAGACAAGCCAGACGACAA | 250 | (+) | (+) | III |
| SAMD5 | 389432 | CTGCTCATAGGAGTTCAGTAA | 114 | (+) | (+) | III |
| TRIM61 | 391712 | TAGGGTATGTATATGTTCCTA | 139 | (+) | (+) | III |
| RAM10 | 401123 | CCCGTTAGTGCTACACTCATT | 247 | (−) | (+) | II |
| XKRX | 402415 | CACCCATAATGTAGTAGACTA | 204 | (+) | (+) | III |
| MTHFD2L | 441024 | CAGCGGTATATTAGTTCAGTT | 89 | (+) | (+) | III |
| SPRN | 503542 | CAGGAACATTCCCAAGCAGGA | 96 | (−) | (+) | II |
| CSAG2 | 728461 | CCAGCCGAACGAGGAACTCAA | 251 | (+) | (+) | III |
| SNORD114-17 | 767595 | ATGAATGATATGTGTCTGAAA | 104 | (+) | (+) | III |

(+) indicates detection of at least a 2 fold increase of the percentage of GFP+ cells
(−) indicates absence of detection of at least a 2 fold increase of the percentage of GFP+ cells
siRNAs ClassI: effect detected with meganuclease SC_GS
siRNAs ClassII: effect detected with meganuclease Trex2/SC_GS
siRNAs ClassIII: effect detected with meganuclease SC_GS and Trex2/SC_GS C) Effect of the siRNAs on the NHEJ Repair Mutagenesis Induced by the SC_GS and Trex2/SC_GS Meganucleases In order to correlate the increase of the EGFP+ cells induced by SC_GS or Trex2/SC_GS in presence of siRNAs hits identified precedently (cf Table VII) with an increase of the frequency of the NHEJ repair activity of the reporter gene, deep sequencing analysis was performed to quantify the frequency of mutagenesis occurring at the site of the meganuclease after it's cleavage.

Material and Methods:
Transfection in the Cellular Model NHEJ EGFP Monitoring Meganuclease-Induced Mutagenesis One million of cells of the NHEJ GFP model were seeded one day prior transfection. Cells were cotransfected with either 3 ug of plasmid encoding SC_GS (pCLS2690, SEQ ID NO: 3) or Trex2/SC_GS (pCLS8054, SEQ ID NO: 1046) in 5 µg of total DNA by complementation with an empty vector pCLS0003 (SEQ ID NO: 1052) in presence or not of siRNAs at final concentrations of 5 nM, 10 nM or 20 nM depending on the siRNA used and 25 ul of lipofectamine (Invitrogen) according to the manufacturer's instructions.

Three to four days following transfection, cells were harvested for flow cytometry analysis using Guava instrumentation and for genomic DNA extraction. Locus specific PCR around the GS target site was performed using the following primers: 5'-CCATCTCATCCCTGCGTGTCTCCGACT-CAGNNNNNNNNNNGCTCTCTCTG-GCTAACTAGAGAACCC-3' (SEQ ID NO: 1053) (containing a forward adaptor sequence and a transgenic locus specific forward sequence, separated by a sequence of ten variable nucleotides needed for PCR product identification) and 5'-CCTATCCCCTGTGTGCCTTGGCAGTCT-CAGTCGATCAGCACGGGCACGATGCC-3' (SEQ ID NO: 1054) (containing a reverse adaptor sequence and a transgenic locus specific reverse sequence). PCR products were sequenced by a 454 sequencing system (454 Life Sciences). Approximately 10,000 sequences were obtained per PCR product and then analyzed for the presence of site-specific insertion or deletion events.

Results
This example is focused on testing if siRNAs hits known to stimulate the percentage of EGFP+ cells induced by SC_GS or Trex2/SC_GS are also able to increase the frequency of the NHEJ mutagenic repair of the reporter gene. For that purpose, the cell line described in this example was co-transfected either with the plasmid pCLS2690 expressing SC_GS (SEQ ID NO: 3) and the siRNAs control AS and those targeting the genes CAP1 (SEQ ID NO: 367), TALDO1 (SEQ ID NO: 111) and DUSP1 (SEQ ID NO: 106) or with the expressing vector pCLS8054 encoding Trex2/SC_GS (SEQ ID NO: 1046) and the siRNAs control AS and those targeting the genes TALDO1 (SEQ ID NO: 111), DUSP1 (SEQ ID NO: 106) and PTPN22 (SEQ ID NO: 283). Quantification of the percentage of GFP+ cells was determined by flow cytometry 4 days post transfection and frequency of mutagenesis determined by deep sequencing analysis.

As shown in table VIII the percentages of 0.96% and 8.86% of GFP+ cells induced by SC_GS or Trex2/SC_GS respectively in presence of the siRNA control AS were increased with the different siRNAs tested. In the case of the transfection with SC_GS, percentage of GFP+ cells was stimulated to 1.47%, 1.85% and 1.45% with the siRNAs targeting respectively the genes CAP1 (SEQ ID NO: 367), TALDO1 (SEQ ID NO: 111) and DUSP1 (SEQ ID NO: 106) corresponding to stimulations factors of the GFP+ cells of 1.53, 1.93 and 1.51. Besides, comparatively to the co-transfection with Trex2/SC_GS and the siRNA control AS, we also observed an increase of the percentage of GFP+ cells to 18.06%, 15.07% and 16.04% with the siRNAs targeting respectively the genes TALDO1 (SEQ ID NO: 111), DUSP1 (SEQ ID NO: 106) and PTPN22 (SEQ ID NO: 283) leading to stimulations factors of the GFP+ cells of 2.04, 1.70 and 1.82.

This phenotypic stimulation of GFP+ cells was also confirmed at a molecular level (cf Table VIII). In fact, SC_GS (SEQ ID NO: 4) led to 4.7% of targeted mutagenesis whereas co-transfection of SC_GS expressing plasmid with the siRNAs CAP1 (SEQ ID NO: 367), TALDO1 (SEQ ID NO: 111) and DUSP1 (SEQ ID NO: 106) stimulate this mutagenic DSB repair to 5.9%, 8.8% and 6.2% respectively. A similar result was obtained with the transfection with Trex2/SC_GS (SEQ ID NO: 1049). In this case, the frequency of mutagenesis of 19.3% with the siRNA control AS was increased repectively to 32.6%, 30%, and 37% with the siRNAs TALDO1 (SEQ ID NO: 111), DUSP1 (SEQ ID NO: 106) and PTPN22 (SEQ ID NO: 283).

Figure 15:
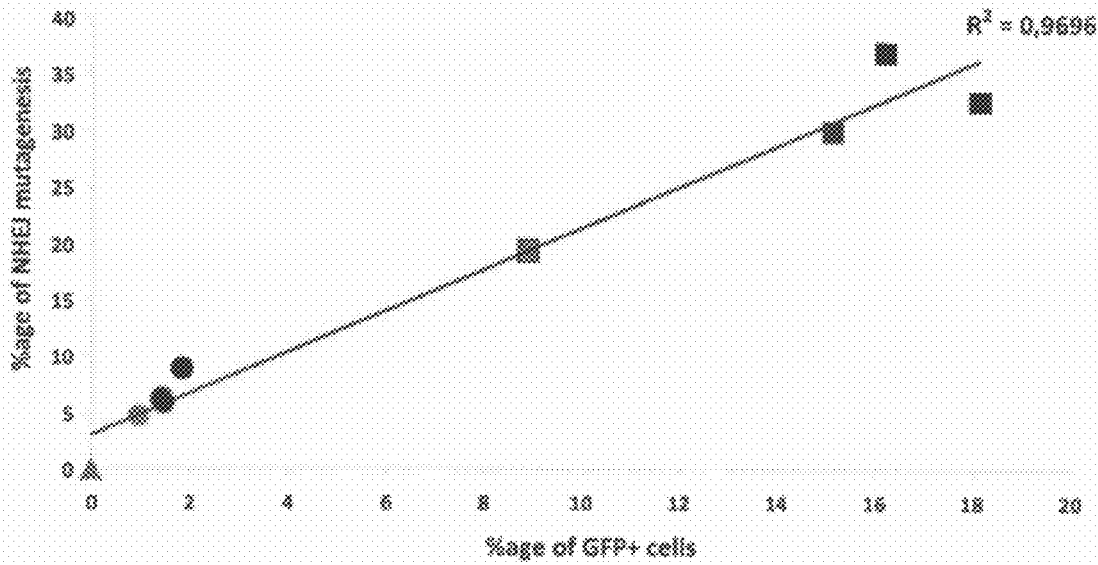
FIG. 15: Graph correlation between the percentage of GFP+ cells induced by the meganucleases SC_GS and Trex2_SC_GS and the frequency of NHEJ mutagenesis analyzed by deep sequencing. Striated triangle: negative control of transfection with pCLS0002 (SEQ ID NO: 41). Striated circle: cotransfection of SC_GS (SEQ ID NO: 4) with siRNA control AS. Dark circles: cotransfections of SC_GS with siRNAs CAP1 (SEQ ID NO: 367), TALDO1 (SEQ ID NO: 111) and DUSP1 (SEQ ID NO: 106). Striated square: cotransfection of Trex2/SC_GS (SEQ ID NO: 1049) with siRNA control AS. Dark squares: cotransfections of SC_GS with siRNAs TALDO1 (SEQ ID NO: 111), DUSP1 (SEQ ID NO: 106) and PTPN22 (SEQ ID NO: 283).

Altogether these data and the result presented in FIG. 15 demonstrate that after transfection of this NHEJ GFP cell line by SC_GS or Trex2/SC_GS meganuclease expressing plasmids with siRNAs hits, the percentage of GFP positive cells is increased and directly correlated to the mutagenic NHEJ repair frequency at the meganuclease targeted site implying that siRNAs hits may be useful to improve targeted mutagenesis at different chromosomal locus cleaved by distinct custom meganucleases.

TABLE VIII

Deep sequencing analysis of the effect of siRNAs hits on NHEJ repair mutagenesis induced by the SC_GS and Trex2/SC_GS meganucleases.

| Meganuclease used | siRNA tested | Seq ID NO | % age GFP+ cells | Stimulation factor of GFP+ cells | % age of NHEJ mutagenesis | Stimulation factor of NHEJ mutagenesis |
|---|---|---|---|---|---|---|
| Ctrl (pCLS0002) | | | 0.01 | 0.01 | 0.00 | 0.00 |
| SC_GS (pCLS2690) | Ctrl AS | — | 0.96 | 1.00 | 4.70 | 1.00 |
| | CAP1 | 367 | 1.47 | 1.53 | 5.86 | 1.25 |
| | TALDO1 | 111 | 1.85 | 1.93 | 8.77 | 1.87 |
| | DUSP1 | 106 | 1.45 | 1.51 | 6.19 | 1.32 |
| Trex2/SC_GS (pCLS8054) | Ctrl AS | — | 8.86 | 1.00 | 19.26 | 1.00 |
| | TALDO1 | 111 | 18.06 | 2.04 | 32.60 | 1.69 |
| | DUSP1 | 106 | 15.07 | 1.70 | 30.00 | 1.56 |
| | PTPN22 | 283 | 16.14 | 1.82 | 37.01 | 1.92 |

Example 5

Figure 16:
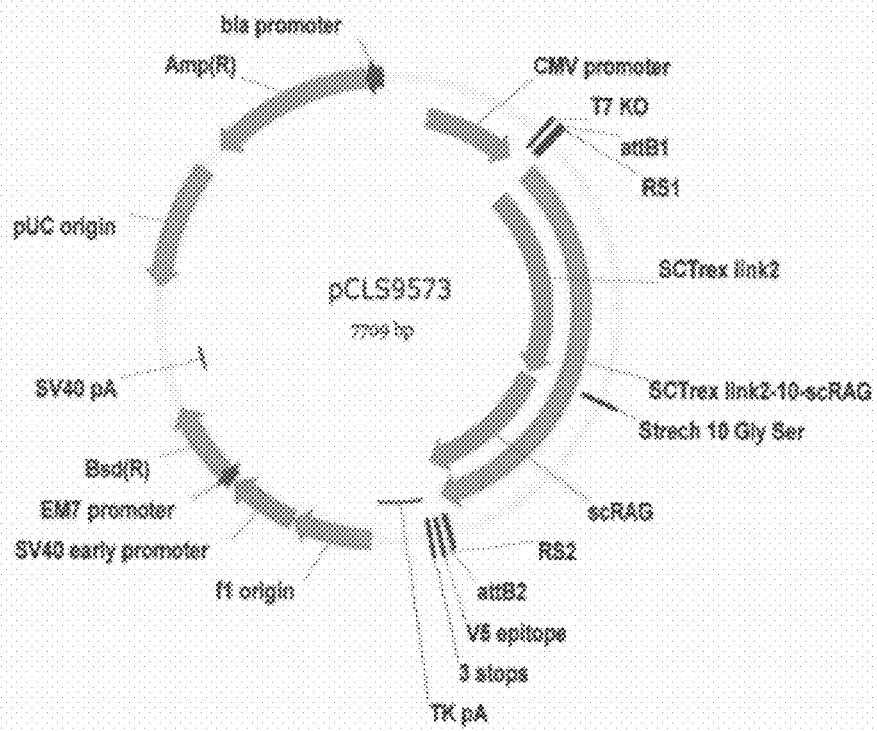
FIG. 16 Vector map of pCLS9573

Stimulation of Meganuclease-Induced Mutagenesis at an Endogenous Locus Using siRNAs Targeting Specific Genes In order to verify that a define siRNA could stimulate mutagenic DSB repair at an endogenous locus, siRNAs targeting genes involved in DSB repair or siRNAs identified during the screenings with the two cellular models were co-transfected in 293H cells with meganuclease SC_RAG (SEQ ID NO: 11 encoded by pCLS2222, SEQ ID NO: 36), or SCTrex2/SC_RAG (SEQ ID NO: 1056 encoded by pCLS9573, FIG. 16 and SEQ ID NO: 1055) plasmid encoding for the meganuclease SC_RAG fused at it's N terminus to a single chain version of Trex2 exonuclease. Mutagenic DSB repair was monitored at molecular level by Deep Sequencing.

Materials and Methods

Cellular Transfection of 293H Cell Line and PCR Analysis of Mutagenic DSB Repair 293H cell line was plated at a density of $1\times10^6$ cells per 10 cm dish in complete medium (DMEM supplemented with 2 mM L-glutamine, penicillin (100 IU/ml), streptomycin (100 mg/ml), amphotericin B (Fongizone: 0.25 mg/ml, Invitrogen-Life Science) and 10% FBS). The next day, cells were transfected in the presence of 25 µl of lipofectamine reagent (Invitrogen) according to the manufacturer's protocol. Typically cells were co-transfected with 2 µg of empty vector pCLS0002 (SEQ ID NO: 41), and 3 µg of meganuclease expression vectors pCLS2222 (SEQ ID NO: 36) or pCLS9573 (SEQ ID NO: 1055) in presence of siRNAs at a final concentration of 1 nM, 7.5 nM, 10 nM or 20 nM depending on the siRNA used. After 48 h to 72 h of incubation at 37° C., cells were harvested for genomic DNA extraction with the Blood and Cell culture DNA midi kit (QIAGEN) according to the manufacturer's protocol. PCR amplification reactions were performed using primers to obtain a fragment of RAG1 locus flanked by specific adaptor sequences. The forward primer contains the following sequence: 5'-CCATCTCATC-CCTGCGTGTCTCCGACT-CAGNNNNNNNNNNGGCAAAGATGAAT-CAAAGATTCTGTCCT-3' (SEQ ID NO: 1057) (containing a forward adaptor sequence and a RAG1 locus specific sequence, separated by a sequence of four to ten variable nucleotides needed for PCR product identification) and the reverse primer contains the following sequence, 5'-CCTATC-CCCTGTGTGCCTTGGCAGTCTCAG-GATCTCACCCGGAACAGCTTAAATTTC-3' (SEQ ID NO: 1058) (containing a reverse adaptor sequence and a RAG1 locus specific sequence). The sequence of four to ten variable nucleotides is a fixed sequence of different lengths ranging from four to ten nucleotides (depending on the protocol of the manufacturer) included in the primer used to perform the PCR amplification and that allows to identify each sequence issued from a deep sequencing reaction with a mix of different PCR fragments corresponding to different experimental conditions. PCR products were sequenced by a 454 sequencing system (454 Life Sciences). Approximately 10,000 exploitable sequences were obtained per PCR pool and then analyzed for the presence of site-specific insertion or deletion events.

a) Results:

siRNAs targeting genes known to be involved in DSB repair mechanism or regulation were tested to estimate their potential for increasing mutagenic DSB repair by NHEJ. 293H cell lines were co-transfected with 3 µg of SC_RAG meganuclease encoding vector (pCLS2222, SEQ ID NO: 36), 2 µg of empty vector (pCLS0002, SEQ ID: 41) and 1 nM of siRNA targeting XRCC6 (SEQID NO: 44), BRCA1 (SEQID NO: 45), ATR (SEQID NO: 46), FANCD2 (SEQID NO: 39), WRN (SEQ ID NO: 37), MAPK3 (SEQ ID NO: 38) or AS (a siRNA control with no known human targets). Those genes were chosen because of their implication in classical NHEJ (XRCC6) or in NHEJ and other DNA repair pathways (BRCA1, FANCD2, WRN) or in DNA repair pathway (ATR) or in DNA repair regulation (MAPK3). Genomic DNA was extracted 2-3 days after transfection and was used to perform a PCR with primer allowing 454 sequencing technology. Sequences obtained per PCR were analyzed to determine the frequency and the nature of mutagenic DSB repair (insertion and or deletion) at RAG1 locus.

Figure 5:
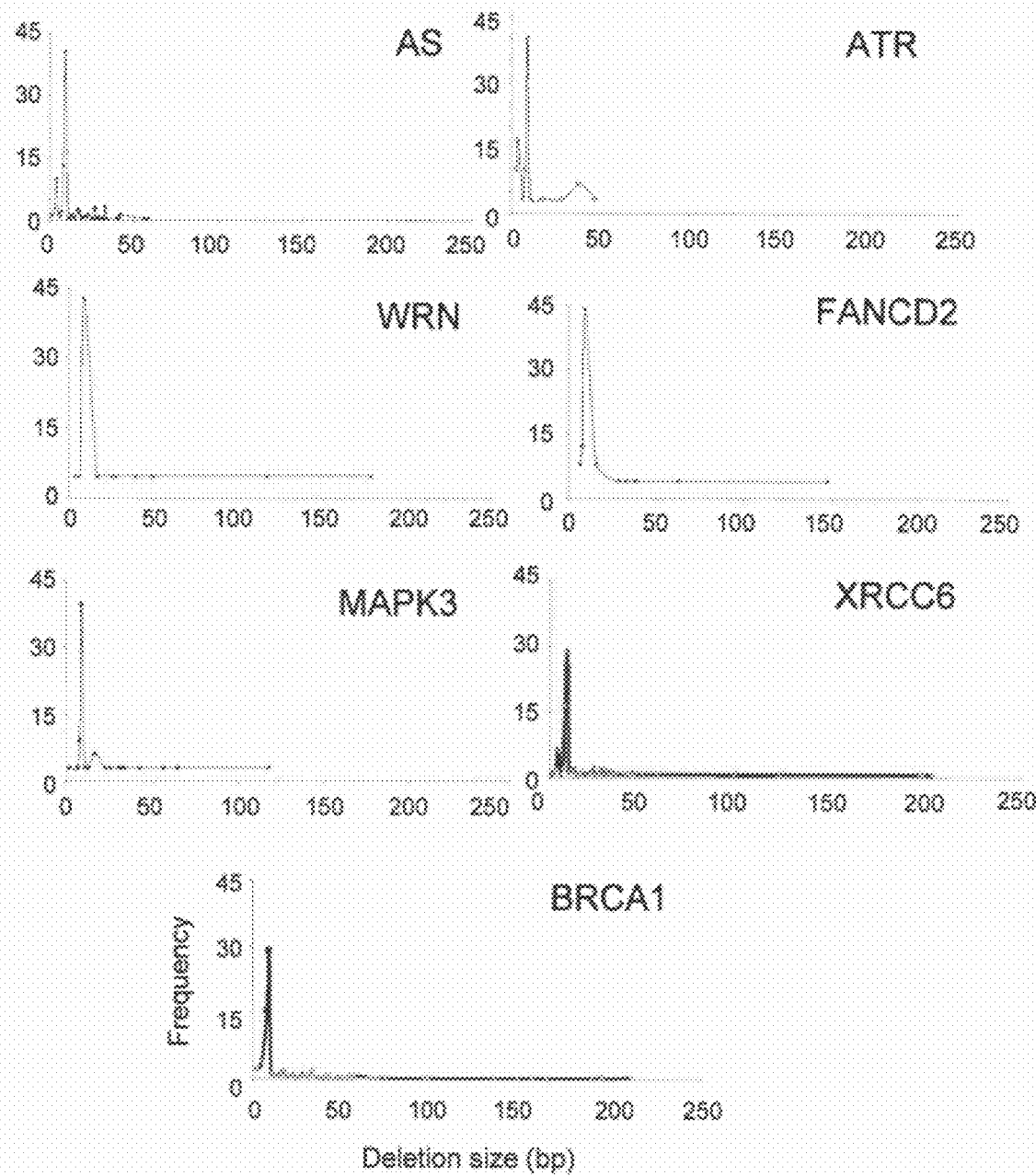
FIG. 5: DeepSequencing experiment for monitoring of NHEJ repair events induced by SC-RAG meganuclease at endogenous RAG1 locus of 293H cells in the presence or not of siRNAs targeting WRN, MAPK3, FANCD2, ATR, BRCA1 and XRCC6 genes.

Mutagenic DSB repair at RAG1 locus in presence of siRNA AS appeared in 0.66%+/−0.13 of events analyzed. When siRNA (SEQ ID NO: 46) targeting ATR gene (Gene ID N°545) was added, percentage of NHEJ was in the same range as with siRNA AS: 0.81%. The presence of siRNAs XRCC6 (SEQ ID NO: 44), BRCA1 (SEQ ID NO: 45), FANCD2 (SEQ ID NO: 39), WRN (SEQ ID NO: 37) or MAPK3 (SEQ ID NO: 38) enhanced the percentage of mutagenic NHEJ repair up to 1.13%, 1.88%, 2.06% 2.15% and 1.6%, respectively corresponding to stimulations factors of 1.7, 2.8, 3.1, 3.2, 2.4 (Table IX). Moreover the nature of the deletions was also modified for all those stimulating siRNAs since they all presented larger deletion events (superior to 100 bp) than the deletion observed with the other siRNAs (the control AS and the siRNA ATR cf. FIG. 5). Altogether these results demonstrate that siRNAs targeting genes involved in DNA repair mechanism or regulation can be used to increase and modulate the efficiency and the nature of mutagenic NHEJ repair induced by I-CreI meganuclease with a modified specificity and at a natural locus (cf. Table IX below).

TABLE IX siRNA stimulating endonuclease-induced mutagenesis at RAG1 locus.

| Gene targeted | Gene ID | siRNA target sequence | SEQ ID NO: | NHEJ Stimulation factor |
|---|---|---|---|---|
| XRCC6 | 2547 | ACCGAGGGCGATGAAGAAGCA | 44 | 1, 7 |
| BRCA1 | 672 | ACCATACAGCTTCATAAATAA | 45 | 2, 8 |
| FANCD2 | 2177 | AAGCAGCTCTCTAGCACCGAT | 39 | 3, 1 |
| WRN | 7486 | CGGATTGTATACGTAACTCCA | 37 | 3, 2 |
| MAPK3 | 5595 | CCCGTCTAATATATAAATATA | 38 | 2, 4 |

Moreover, the siRNAs CAP1 (SEQ ID NO: 367), VAV3 (SEQ ID NO: 85), PTPN22 (SEQ ID NO: 283), MTHFD2L (SEQ ID NO: 89), TALDO1 (SEQ ID NO: 111) and DUSP1 (SEQ ID NO: 106) identified with the screenings of the two cellular-models and belonging to three different classes of siRNAs defined in Table VII were also tested for their capacity to increase the frequency of mutagenic repair at the endogenous locus RAG. As previously described in this example, 293H cell line was cotransfected with the expression plasmids pCLS 2222 (Seq ID NO: 36) or pCLS9573 (SEQ ID NO: 1055) encoding for the meganucleases SC_RAG (SEQ ID NO: 11) and SCTrex2/SC_RAG (SEQ ID NO: 1056) in presence of the siRNA control AS or the different siRNAs tested. Frequency of mutagenesis at RAG locus was analyzed by deep sequencing to monitor the efficiency of each siRNA to increase the mutagenic repair induced by each type of meganuclease.

As shown in Table X below, in agreement with their belonging to different classes defined in Table VII die two siRNAs CAP1 (SEQ ID NO: 367) and VAV3 (SEQ ID NO: 85) are able to increase the frequency of mutagenesis of SC_RAG meganuclease with respectively stimulation factors of 1.43, 1.25 while the siRNA PTPN22 (SEQ ID NO: 283) enhances the NHEJ mutagenic repair of the SCTrex2/SC_RAG meganuclease with a 1.39 fold increase. Moreover, the three siRNAs MTHFD2L (SEQ ID NO: 89), TALDO1 (SEQ ID NO: 111) and DUSP1 (SEQ ID NO: 106), known to have an effect with SC_GS or Trex2/SC/GS are also able to increase the targeted mutagenesis induced by the meganucleases SC_RAG (SEQ ID NO: 11 encoded by pCLS2222, SEQ ID NO: 36) or SCTrex2/SC_RAG (SEQ ID NO: 1056 encoded by pCLS9573, SEQ ID NO: 1055) with stimulations factors of respectively 1.22, 1.23 and 1.43

Altogether, these data imply that siRNAs targeting genes involved in double strand break repair or other cellular process can be useful effectors to enhance the efficiency of NHEJ mutagenesis at natural endogenous locus targeted with distinct custom meganucleases fused or not to the Trex2 exonuclease.

TABLE X

| siRNA Class | siRNA tested | Seq ID NO | Stimulation factor of NHEJ mutagenesis | |
|---|---|---|---|---|
| | | | SC_RAG (Seq ID NO: 11) | SCTrex_SC_RAG (Seq ID NO: 1056) |
| | Ctrl AS | — | 1.00 | 1.00 |
| I | CAP1 | 367 | 1.43 | ND |
| I | VAV3 | 85 | 1.25 | ND |
| II | PTPN22 | 283 | ND | 1.39 |
| III | MTHFD2L | 89 | 1.22 | ND |
| III | TALDO1 | 111 | ND | 1.23 |
| III | DUSP1 | 106 | ND | 1.43 |

Effect of siRNAs hits on NHEJ repair mutagenesis induced by the SC_RAG and SCTrex2/SC_RAG meganucleases; ND: non determined.

List of Cited References

Arimondo, P. B., C. J. Thomas, et al. (2008), "Exploring the cellular activity of camptothecin-triple-helix-forming oligonucleotide conjugates," Mol Cell Biol 28(1): 324-33.

Arnould, S., P. Chames, et al. (2006). "Engineering of large numbers of highly specific homing endonucleases that induce recombination on novel DNA targets," J Mol Biol 355(3): 443-58, Arnould, S., C. Perez, et al. {2007}. "Engineered I-CreI derivatives cleaving sequences from the human XPC gene can induce highly efficient gene correction in mammalian cells." J Mol Biol 371(1): 49-65.

Ashworth, J., J. J. Havranek, et al. (2006). "Computational redesign of endonuclease DNA binding and cleavage specificity." Nature 441(7093): 656-9.

Audebert, M., B. Salles, et al. (2004). "involvement of poly (ADP-ribose) polymerase-1 and XRCC1/DNA ligase III in an alternative route for DNA double-strand breaks rejoining." J Biol Chem 279(53): 55117-26.

Bau, D. T., Y. C. Mau, et al. (2006). "The role of BRCA1 in non-homologous end-joining," Cancer Lett 240(1): 1-8.

Baumann, P. and S. C. West (1998). "DNA end-joining catalyzed by human cell-free extracts." Proc Natl Acad Sci USA 95(24): 14066-70.

Beumer, K. J., J. K. Trautman, et al. (2008). "Efficient gene targeting in Drosophila by direct embryo injection with zinc-finger nucleases," Proc Natl Acad Sci USA 105(50): 19821-6.

Blunt, T., N. J. Finnie, et al. (1995). "Defective DMA-dependent protein kinase activity is linked to V(D)J recombination and DNA repair defects associated with the murine scid mutation." Cell 80(5): 813-23.

Boch, J., H. Scholze, et al. (2009). "Breaking the code of DNA binding specificity of TAL-type III effectors." Science 328(5959); 1509-12.

Bolduc, J. M., P. C. Spiegel, et al. (2003). "Structural and biochemical analyses of DNA and RNA binding by a bifunctional homing endonuclease and group I intron splicing factor." Genes Dev 17(23): 2875-88.

Britt, A. B. (1999). "Molecular genetics of DNA repair in higher plants." Trends Plant Sci 4(1): 20-25.

Burden and O. N. (1998). "Mechanism of action of eukaryotic topoisomerase II and drugs targeted to the enzyme." Biochim Biophys Acta. 1400(1-3): 139-154.

Capecchi, M. R. (1989). "The new mouse genetics: altering the genome by gene targeting." Trends Genet 5(3): 70-6.

Cathomen, T. and J. K. Joung (2008). "Zinc-finger nucleases: the next generation emerges." Mol Ther 16(7): 1200-7.

Chames, P., J. C. Epinat, et al. (2005), "In vivo selection of engineered homing endonucleases using double-strand break induced homologous recombination." Nucleic Acids Res 33(20): e178.

Chevalier, B., M. Turmel, et al. (2003). "Flexible DNA target site recognition by divergent homing endonuclease isoschizomers I-CreI and I-MsoI." J Mol Biol 329(2): 253-69.

Chevalier, B. S., T. Kortemme, et al. (2002). "Design, activity, and structure of a highly specific artificial endonuclease." Mol Cell 10(4): 895-905.

Chevalier, B. S., R. J. Monnat, Jr., et al. (2001). "The homing endonuclease I-CreI uses three metals, one of which is shared between the two active sites." Nat Struct Biol 8(4): 312-6.

Chevalier, B. S. and B. L. Stoddard (2001). "Homing endonucleases: structural and functional insight into the catalysts of intron/intein mobility." Nucleic Acids Res 29(18): 3757-74.

Choulika, A., A. Perrin, et al. (1995). "Induction of homologous recombination in mammalian chromosomes by using the I-SceI system of Saccharomyces cerevisiae." Mol Cell Biol 15(4): 1968-73.

Christian, M., T. Cermak, et al. (2010). "Targeting DNA double-strand breaks with TAL effector nucleases," Genetic 186(2): 757-61.

Cohen-Tannoudji, M., S. Robine, et al. (1998), "I-SceI-induced gene replacement at a natural locus in embryonic stem cells," Mol Cell Biol 18(3): 1444-8.

Critchlow, S. E. and S. P. Jackson (1998). "DNA end-joining: from yeast to man," Trends Biochem Sci 23(10): 394-8.

Donoho, G., M. Jasin, et al. (1998). "Analysis of gene targeting and intrachromosomal homologous recombination stimulated by genomic double-strand breaks in mouse embryonic stem cells."Mol Cell Biol 18(7): 4070-8.

Doyon, J. B., V. Pattanayak, et al. (2006), "Directed evolution and substrate specificity profile of homing endonuclease I-SceI." J Am Chem Soc 128(7): 2477-84.

Doyon, Y., J. M. McCammon, et al. (2008). "Heritable targeted gene disruption in zebrafish using designed zinc-finger nucleases." Nat Biotechnol 28(6): 702-8.

Dujon, B., L. Colleaux, et al. (1988). "Mitochondrial introns as mobile genetic elements: the role of intron-encoded proteins." Basic Life Sci 40: 5-27.

Eisenschmidt, K., T. Lanio, et al. (2005). "Developing a programmed restriction endonuclease for highly specific DMA cleavage." Nucleic Acids Res 33(22): 7039-47.

Elbashir, S. M., J. Harborth, et al. (2001). "Duplexes of 21-nucleotide RNAs mediate RNA interference in cultured mammalian cells." *Nature* 411(6836): 494-8.

Endo, M., K. Osakabe, et al. (2005). "Molecular characterisation of true and ectopic gene targeting events at the acetolactate synthase gene in *Arabidopsis*." *Plant Cell Physiol* 47(3): 372-9.

Endo, M., K. Osakabe, et al. (2007). "Molecular breeding of a novel herbicide-tolerant rice by gene targeting," *Plant J* 52(1): 157-66, Epinat, J. C., S. Arnould, et al. (2003), "A novel engineered meganuclease induces homologous recombination in yeast and mammalian cells," *Nucleic Acids Res* 31(11): 2952-62.

Essers, J., H. van Steeg, et al. (2000). "Homologous and non-homologous recombination differentially affect DMA damage repair in mice." *Embo J* 19(7): 1703-10, Feldmann, E., V. Schmiemann, et al. (2000), "DMA double-strand break repair in cell-free extracts from Ku80-deficient cells: implications for Ku serving as an alignment factor in non-homologous DNA end joining," *Nucleic Acids Res* 28(13): 2585-96.

Gimble, F. S., C. M. Moure, et al. (2003). "Assessing the plasticity of DNA target site recognition of the PI-SceI homing endonuclease using a bacterial two-hybrid selection system," *J Mol Biol* 334(5): 993-1008, Gouble, A., J. Smith, et al. (2006). "Efficient in toto targeted recombination in mouse liver by meganuclease-induced double-strand break." *J Gene Med* 8(5): 616-22.

Green, E. L. and T. H. Roderick (1966). "Radiation Genetics." *In Biology of the Laboratory Mouse* Green, E. L., eds. ((McGraw-Hill, New York)): 165-185.

Grizot, S., J. Smith, et al. (2009). "Efficient targeting of a SCID gene by an engineered single-chain homing endonuclease." *Nucleic Acid Res* 37(18): 5405-19, Haber, J. E. (1995). "In vivo biochemistry: physical monitoring of recombination induced by site-specific endonucleases." *Bioessays* 17(7): 809-20.

Hanin, M., S. Volrath, et al. (2001), "Gene targeting in *Arabidopsis*," *Plant J* 28(8): 671-7, Hannon, G. J. (2002). "RNA interference." *Nature* 418(6894): 244-51.

Harborth, J., S. M. Elbashir, et al. (2001). "Identification of essential genes in cultured mammalian cells using small interfering RNAs." *J Cell Sci* 114(Pt 24): 4557-65.

Hutvagner, G., J. McLachlan, et al. (2001). "A cellular function for the RNA-interference enzyme Dicer in the maturation of the let-7 small temporal RNA." *Science* 293(5531): 834-8, Ichiyanagi, K., Y. Ishino, et al. (2000). "Crystal structure of an archaeal intein-encoded homing endonuclease PI-PfuI." *J Mol Biol* 300(4): 889-901.

Kalish, J. M. and P. M. Glazer (2005), "Targeted genome modification via triple helix formation." *Ann N Y Acad Sci* 1058: 151-61.

Kim, Y. G., J. Cha, et al. (1996). "Hybrid restriction enzymes: zinc finger fusions to Fok I cleavage domain." *Proc Natl Acad Sci USA* 3(3): 1156-60.

Kirik, A., S. Salomon, et al. (2000). "Species-specific double-strand break repair and genome evolution in plants." *Embo J* 19(20): 5562-6.

Lee, Y., K. Jeon, et al. (2002). "MicroRNA maturation: stepwise processing and subcellular localization," *Embo J* 21(17): 4663-70.

Li, T., S. Huang, et al. (2010). "TAL nucleases (TALNs): hybrid proteins composed of TAL effectors and FokI DNA-cleavage domain." Nucleic Acids Res 39(1): 359-72, Lloyd, A., C. L. Plaisier, et al. (2005), "Targeted mutagenesis using zinc-finger nucleases in *Arabidopsis*." *Proc Natl Acad Sci USA* 102(6): 2232-7.

Mahaney, B. L., K. Meek, et al. (2009). "Repair of ionizing radiation-induced DNA double-strand breaks by non-homologous end-joining." *Biochem J* 417(3): 639-50.

Mazur, D. J., and Perrino, F. W. (2001). "Excision of 3' termini by the Trex1 and TREX2 3'->5' exonucleases. Characterization of the recombinant proteins" *J Biol Chem.* 276(20):17022-9

McCaffrey, A. P., L. Meuse, et al. (2002). "RNA interference in adult mice." *Nature* 418(6893): 38-9.

Meister, G. and T. Tuschl (2004). "Mechanisms of gene silencing by double-stranded RNA." *Nature* 431(7006): 343-9.

Meng, X., M. B. Noyes, et al. (2008). "Targeted gene inactivation in zebrafish using engineered zinc-finger nucleases." *Nat Biotechnol* 26(6): 695-701.

Moore, I., M. Samalova, et al. (2006). "Transactivated and chemically inducible gene expression in plants." *Plant J* 45(4): 651-83.

Moscou, M. J. and A. J. Bogdanove (2009). "A simple cipher governs DNA recognition by TAL effectors." *Science* 326 (5959): 1501.

Moure, C. M., F. S. Gimble, et al. (2002). "Crystal structure of the intein homing endonuclease PI-SceI bound to its recognition sequence." *Nat Struct Biol* 9(10): 764-70.

Moure, C. M., F. S. Gimble, et al. (2003). "The crystal structure of the gene targeting homing endonuclease I-SceI reveals the origins of its target site specificity." *J Mol Biol* 334(4): 685-95.

Nagy, Z. and E. Soutoglou (2009). "DNA repair: easy to visualize, difficult to elucidate." *Trends Cell Biol* 19(11): 617-29.

Needleman, S. B. and C. D. Wunsch (1970). "A general method applicable to the search for similarities in the amino acid sequence of two proteins." *J Mol Biol* 48(3): 443-53.

Nouspikel, T. (2009). "DNA repair in mammalian cells: Nucleotide excision repair: variations on versatility." *Cell Mol Life Sci* 66(6): 994-1009.

Pace, P., G. Mosedale, et al. (2010). "Ku70 corrupts DNA repair in the absence of the Fanconi anemia pathway," *Science* 329(5988): 219-23, Padidam, M. (2003). "Chemically regulated gene expression in plants." *Curr Opin Plant Biol* 6(2): 169-77.

Paques, F. and P. Duchateau (2007). "Meganucleases and DNA double-strand break-induced recombination: perspectives for gene therapy." *Curr Gene Ther* 7(1): 49-66.

Pingoud, A. and G. H. Silva (2007). "Precision genome surgery." *Nat Biotechnol* 25(7): 743-4.

Porteus, M. H. and D. Carroll (2005). "Gene targeting using zinc finger nucleases." *Nat Biotechnol* 23(8): 967-73.

Postal, G., V. Kolisnychenko, et al. (1999). "Markerless gene replacement in *Escherichia coli* stimulated by a double-strand break in the chromosome." *Nucleic Acids Res* 27(22): 4409-15.

Potenza, C. L. Aleman, et al. (2004). "Targeting transgene expression in research, agricultural, and environmental applications: Promoters used in plant transformation." *In vitro cellular & developmental biology—plant* 40(1): 1-22.

Povirk, L. F. (1996). "DNA damage and mutagenesis by radiomimetic DNA-cleaving agents: bleomycin, neocarzinostatin and other enediynes." *Mutat Res* 355(1-2): 71-89.

Puchta, H., B. Dujon, et al. (1996). "Two different but related mechanisms are used in plants for the repair of genomic double-strand breaks by homologous recombination." *Proc Natl Acad Sci USA* 93(10): 5055-60.

Rosen, L. E., H. A. Morrison, et al. (2006). "Homing endonuclease I-CreI derivatives with novel DNA target specificities." *Nucleic Acids Res.*

Rothstein, R. (1991). "Targeting, disruption, replacement, and allele rescue: integrative DNA transformation in yeast." *Methods Enzymol* 194: 281-301.

Rouet, P., F. Smih, et al. (1994). "Expression of a site-specific endonuclease stimulates homologous recombination in mammalian cells." *Proc Natl Acad Sci USA* 91(13): 6064-8.

Rouet, P., F. Smih, et al. (1994). "Introduction of double-strand breaks into the genome of mouse cells by expression of a rare-cutting endonuclease." *Mol Cell Biol* 14(12): 8096-106.

Sargent, R. G., M. A. Brenneman, et al. (1997). "Repair of site-specific double-strand breaks in a mammalian chromosome by homologous and illegitimate recombination." *Mol Cell Biol* 17(1): 267-77.

Sarkaria, J. N., R. S. Tibbetts, et al. (1998). "inhibition of phosphoinositide 3-kinase related kinases by the radiosensitizing agent wortmannin." *Cancer Res* 58(19): 4375-82.

Seligman, L. M., K. M. Stephens, et al. (1997). "Genetic analysis of the *Chlamydomonas* reinhardtti I-CreI mobile intron homing system in *Escherichia coli.*" *Genetics* 147(4): 1653-64.

Shrivastav, M., L. P. De Haro, et ah (2008). "Regulation of DNA double-strand break repair pathway choice." *Cell Res* 18(1): 134-47.

Siebert, R. and H. Puchta (2002). "Efficient Repair of Genomic Double-Strand Breaks by Homologous Recombination between Directly Repeated Sequences in the Plant Genome." *Plant Cell* 14(5): 1121-31.

Silva, G. H., J. Z. Dalgaard, et al. (1999). "Crystal structure of the thermostable archaeal intron-encoded endonuclease I-DmoI." *J Mol Biol* 286(4): 1123-36.

Simon, P., F. Cannata, et al. (2008). "Sequence-specific DNA cleavage mediated by bipyridine polyamide conjugates." *Nucleic Acids Res* 38(11): 3531-8.

Smith, J., S. Grizot, et al. (2006). "A combinatorial approach to create artificial homing endonucleases cleaving chosen sequences." *Nucleic Acids Res* 34(22): e149, Spiegel, P. C., B. Chevalier, et al. (2006). "The structure of I-CeuI homing endonuclease: Evolving asymmetric DNA recognition from a symmetric protein scaffold." *Structure* 14(5): 869-80.

Stoddard, B. L. (2005). "Homing endonuclease structure and function." *Q Rev Biophvs* 38(1): 49-95.

Sussman, D., M. Chadsey, et al. (2004). "Isolation and characterization of new homing endonuclease specificities at individual target site positions." *J Mol Biol* 342(1): 31-41.

Taccioii, G. E., G. Rathbun, et al. (1993), "Impairment of V(D)J recombination in double-strand break repair mutants." *Science* 280(5105): 207-10, Takata, M., M. S. Sasaki, et al. (1998), "Homologous recombination and non-homologous end-joining pathways of DNA double-strand break repair have overlapping roles in the maintenance of chromosomal integrity in vertebrate cells." *Embo J* 17(18): 5497-508.

Teicher, B. A. (2008). "Next generation topoisomerase I inhibitors: Rationale and biomarker strategies." *Biochem Pharmacol* 75(6): 1262-71.

Terada, R., Y. Johzuka-Hisatomi, et al. (2007). "Gene targeting by homologous recombination as a biotechnological tool for rice functional genomics." *Plant Physiol* 144(2): 846-56.

Terada, R., H. Urawa, et al. (2002). "Efficient gene targeting by homologous recombination in rice." *Nat Biotechnol* 20(10): 1030-4.

Wang, H., B. Rosidi, et al. (2005). "DNA ligase III as a candidate component of backup pathways of nonhomologous end joining." *Cancer Res* 65(10): 4020-30, Wang, M., W. Wu, et al (2006), "PARP-1 and Ku compete for repair of DNA double strand breaks by distinct NHEJ pathways." *Nucleic Acids Res* 34(21): 6170-82.

Wang, R., X. Zhou, et al, (2003). "Chemically regulated expression systems and their applications in transgenic plants." *Transgenic Res* 12(5): 529-40.

Williams, R. S., J. S. Williams, et al. (2007). "Mre11-Rad50-Nbs1 is a keystone complex connecting DNA repair machinery, double-strand break signaling, and the chromatin template." *Biochem Cell Biol* 85(4): 509-20.

Yi, R., Y. Qin, et al. (2.003), "Exportin-5 mediates the nuclear export of pre-microRNAs and short hairpin RNAs." *Genes Dev* 17(24): 3011-6.

Zeng, Y., X. Cai, et al. (2005). "Use of RNA polymerase II to transcribe artificial microRNAs." *Methods Enzymol* 392: 371-80.

Zuo, J. and N. H. Chua (2000). "Chemical-inducible systems for regulated expression of plant genes." *Curr Opin Biotechnol* 11(2): 146-51.

The invention claimed is:

1. A method for increasing double-strand break-induced mutagenesis in a cell comprising introducing into said cell:
   i. at least one interfering agent, wherein said at least one interfering agent targets the sequence of SEQ ID NO: 106;
   ii. at least one delivery vector comprising at least one double-strand break creating agent;

thereby obtaining a eukaryotic cell in which double-strand break-induced mutagenesis is increased.

2. The method according to claim 1, wherein said interfering agent is identified by a method for determining an ability to increase double-strand break-induced mutagenesis in a cell wherein said method comprises:
   (a) providing a cell expressing a reporter gene, rendered inactive by a frameshift in its coding sequence, due to the introduction in said sequence of a double-strand break creating agent target site;
   (b) providing an interfering agent;
   (c) contacting said cell with:
      i. an interfering agent;
      ii. a delivery vector comprising a double-strand break creating agent wherein said double-strand break creating agent provokes a mutagenic double-strand break that can be repaired by non homologous end joining leading to a functional restoration of said reporter gene;
   (d) detecting expression of the functional reporter gene in the cell obtained at the end of step (c);
   (e) determining whether said interfering agent increases the expression of the reporter gene detected at step (d) as compared to a negative control; and
   (f) for the interfering agent identified at step (e) to increase the expression of the reporter gene, repeating steps (a), (c), (d) and (e) with a cell line expressing a different inactive reporter gene than the inactive reporter gene previously used;
   whereby the interfering agent identified at the end of step (f) is an interfering agent capable of increasing double-strand break-induced mutagenesis in a cell.

3. The method according to claim 2, wherein said reporter gene used at step (a) is a high throughput screening-compatible reporter gene selected from the group consisting of a gene encoding Luciferase, a gene encoding beta-galactosidase or a gene encoding phosphatase alkaline.

4. The method according to claim 2, wherein said interfering agent is an interfering RNA.

5. The method according to claim 1, wherein said double-strand break creating agent is an endonuclease capable of cleaving a target sequence located in a locus of interest of said eukaryotic cells.

6. The method according to claim 1, wherein the interfering agent is an interfering RNA.

7. The method according to claim 6, wherein the interfering RNA is a siRNA.

8. The method according to claim 6, wherein the interfering RNA is a miRNA.

9. The method according to claim 6, wherein the interfering RNA is a shRNA.

* * * * *